United States Patent
Masuda et al.

(10) Patent No.: US 8,957,219 B2
(45) Date of Patent: Feb. 17, 2015

(54) ACETIC ACID AMIDE DERIVATIVE HAVING INHIBITORY ACTIVITY ON ENDOTHELIAL LIPASE

(75) Inventors: Koji Masuda, Osaka (JP); Shiro Kida, Osaka (JP); Kyohei Hayashi, Osaka (JP); Manabu Katou, Osaka (JP); Naoki Yoshikawa, Osaka (JP); Akira Kugimiya, Osaka (JP); Mado Nakajima, Osaka (JP); Nobuyuki Tanaka, Osaka (JP)

(73) Assignee: Shionogi & Co., Ltd., Osaka-shi (JP)

( * ) Notice: Subject to any disclaimer, the term of this patent is extended or adjusted under 35 U.S.C. 154(b) by 271 days.

(21) Appl. No.: 13/124,788

(22) PCT Filed: Oct. 15, 2009

(86) PCT No.: PCT/JP2009/067845
§ 371 (c)(1),
(2), (4) Date: Apr. 18, 2011

(87) PCT Pub. No.: WO2010/044441
PCT Pub. Date: Apr. 22, 2010

(65) Prior Publication Data
US 2011/0251386 A1     Oct. 13, 2011

(30) Foreign Application Priority Data
Oct. 17, 2008    (JP) .................................. 2008-268208

(51) Int. Cl.
*A61K 31/426*     (2006.01)
*A61K 31/428*     (2006.01)
*C07D 513/02*     (2006.01)
(Continued)

(52) U.S. Cl.
CPC .......... *C07D 235/16* (2013.01); *A61K 31/4184* (2013.01); *A61K 31/423* (2013.01); *A61K 31/428* (2013.01); *A61K 31/429* (2013.01); *A61K 31/437* (2013.01); *A61K 31/4439* (2013.01); *A61K 31/4709* (2013.01); *A61K 31/496* (2013.01); *A61K 31/506* (2013.01); *A61K 31/5377* (2013.01); *C07D 263/56* (2013.01); *C07D 417/04* (2013.01); *C07D 417/12* (2013.01); *C07D 513/04* (2013.01)
USPC ........... 548/159; 548/178; 548/180; 548/204; 548/217; 514/367; 514/374

(58) Field of Classification Search
USPC .......... 548/159, 178, 180, 204, 217; 514/367, 514/374
See application file for complete search history.

(56) References Cited

U.S. PATENT DOCUMENTS 3,985,763 A    10/1976   Harnisch
5,834,499 A *   11/1998   Iwaoka et al. ................. 514/366
(Continued)

FOREIGN PATENT DOCUMENTS

DE      2 232 449      1/1974
EP      0 254 545      1/1988
(Continued)

OTHER PUBLICATIONS

Fourtillan et al. (AN 2008:223787, CAPLUS:DN 148:285385 abstract of FR 2904973, 892 reference).*
(Continued)

*Primary Examiner* — Sabiha N Qazi
(74) *Attorney, Agent, or Firm* — Oblon, Spivak, McClelland, Maier & Neustadt, L.L.P.

(57) ABSTRACT

Disclosed is a compound which is useful as an endothelial lipase inhibitor.
A pharmaceutical composition having inhibitory activity on endothelial lipase comprising a compound represented by the formula:

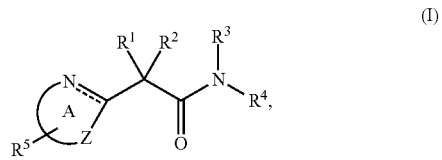

its pharmaceutically acceptable salt, or a solvate thereof, wherein
Ring A is nitrogen-containing hetero ring,
Ring A may be substituted with a substituent other than a group represented by the formula: —C($R^1R^2$)—C(=O)—$NR^3R^4$ and a group represented by the formula: —$R^5$,
a broken line represents the presence or the absence of a bond,
Z is —$NR^6$—, =N—, —O—, or —S—,
$R^6$ is halogen, substituted or unsubstituted alkyl or the like,
$R^1$ and $R^2$ are each independently hydrogen, halogen, hydroxy, cyano, nitro, carboxy or substituted or unsubstituted alkyl,
$R^3$ is hydrogen or substituted or unsubstituted alkyl,
$R^4$ is hydrogen, substituted or unsubstituted alkyl or the like,
$R^3$ and $R^4$ taken together with the adjacent nitrogen atom to which they are attached may form a substituted or unsubstituted ring,
$R^5$ is hydrogen, halogen, hydroxy, cyano, nitro, carboxy, substituted or unsubstituted alkyl, substituted or unsubstituted alkenyl, substituted or unsubstituted alkynyl or the like.

14 Claims, No Drawings

(51) Int. Cl.

| | | |
|---|---|---|
| C07D 513/04 | (2006.01) | |
| C07D 235/16 | (2006.01) | |
| A61K 31/4184 | (2006.01) | |
| A61K 31/423 | (2006.01) | |
| A61K 31/429 | (2006.01) | |
| A61K 31/437 | (2006.01) | |
| A61K 31/4439 | (2006.01) | |
| A61K 31/4709 | (2006.01) | |
| A61K 31/496 | (2006.01) | |
| A61K 31/506 | (2006.01) | |
| A61K 31/5377 | (2006.01) | |
| C07D 263/56 | (2006.01) | |
| C07D 417/04 | (2006.01) | |
| C07D 417/12 | (2006.01) | |

(56) References Cited

U.S. PATENT DOCUMENTS

| | | | |
|---|---|---|---|
| 6,060,462 A * | 5/2000 | Galemmo et al. | 514/64 |
| 6,727,362 B1 | 4/2004 | Lai et al. | |
| 7,086,205 B2 * | 8/2006 | Pervan | 52/403.1 |
| 7,087,610 B2 * | 8/2006 | Wang et al. | 514/254.02 |
| 2005/0282805 A1 | 12/2005 | Hangeland et al. | |
| 2006/0116409 A1 | 6/2006 | Eacho et al. | |
| 2006/0149070 A1 | 7/2006 | Rohde et al. | |
| 2006/0211755 A1 | 9/2006 | Eacho et al. | |
| 2006/0217375 A1 | 9/2006 | Barker et al. | |
| 2006/0276522 A1 | 12/2006 | Eacho et al. | |
| 2008/0070892 A1 | 3/2008 | Harris et al. | |
| 2008/0076750 A1 | 3/2008 | Aslanian et al. | |
| 2008/0090867 A1 | 4/2008 | Zoller et al. | |
| 2008/0161370 A1 | 7/2008 | Zoller et al. | |
| 2008/0167339 A1 | 7/2008 | Zoller et al. | |
| 2008/0167355 A1 | 7/2008 | Zoller et al. | |
| 2008/0287448 A1 | 11/2008 | Zoller et al. | |
| 2008/0287503 A1 | 11/2008 | Petry et al. | |
| 2009/0030011 A1 | 1/2009 | Petry et al. | |
| 2009/0054478 A1 | 2/2009 | Zoller et al. | |
| 2009/0076068 A1 | 3/2009 | Zoller et al. | |
| 2010/0173961 A1 | 7/2010 | Zoller et al. | |
| 2010/0190801 A1 | 7/2010 | Petry et al. | |
| 2010/0286133 A1 | 11/2010 | Zoller et al. | |
| 2011/0039883 A1 | 2/2011 | Zoller et al. | |

FOREIGN PATENT DOCUMENTS

| | | |
|---|---|---|
| FR | 2 904 973 | 2/2008 |
| GB | 829 832 | 3/1960 |
| JP | 50 19937 | 3/1975 |
| JP | 2001 097979 | 4/2001 |
| JP | 2003-231633 A | 8/2003 |
| WO | 2004 093872 | 11/2004 |
| WO | 2004 094393 | 11/2004 |
| WO | 2004 094394 | 11/2004 |
| WO | 2005 025554 | 3/2005 |
| WO | 2005 120508 | 12/2005 |
| WO | 2005 123050 | 12/2005 |
| WO | 2006 053250 | 5/2006 |
| WO | 2006 067224 | 6/2006 |
| WO | 2006 074330 | 7/2006 |
| WO | 2006 111321 | 10/2006 |
| WO | 2006 131231 | 12/2006 |
| WO | 2006 131232 | 12/2006 |
| WO | 2006 131233 | 12/2006 |
| WO | 2007 042178 | 4/2007 |
| WO | 2007 045392 | 4/2007 |
| WO | 2007 045393 | 4/2007 |
| WO | 2007 110215 | 10/2007 |
| WO | 2007 110216 | 10/2007 |
| WO | 2007 146066 | 12/2007 |
| WO | 2008 033460 | 3/2008 |
| WO | 2008 033465 | 3/2008 |

OTHER PUBLICATIONS

Galemo et al. (WO 95/09634, 1995:605714, CAPLUS, DN 123:957).*
Fourtillan et al. (AN 2008:223787, CAPLUS:DN 148:285385 abstract of FR 2904973, Feb. 22, 2008).*
Galemo et al. (WO 95/09634, 1995:605714, CAPLUS, DN 123:957, Apr. 13, 1995).*
U.S. Appl. No. 13/516,441, filed Jun. 15, 2012, Masuda, et al.
Supplementary European Search Report issued Jul. 17, 2012, in European Patent Application No. 09 82 0 619.
Laila M. Chabaka, et al., "Amino Acid Derivatives in Organic Synthesis, Part 4 [1]: Facile Synthesis of Heterocycles Containing a Glycine Residue", Chemical Sciences, vol. 55, No. 1, 2000, pp. 104-108.
Galal A. M. Nawwar, et al., "Synthesis of 2-Substituted Benzothiazoles Containing Amino Acid, Imino or Heteroaryl Moieties With Anticipated Fungicidal Activity", Collection of Czechoslovak Chemical Communications, vol. 60, No. 12, 1995, pp. 2200-2208.
Galal A. M. Nawwar, et al., "Amino Acid Derivatives in Organic Synthesis: New Synthetic Routes to Heterocycles containing Amino Acid Residues", Journal of Chemical Research, Synopsis, vol. 7, 1993, pp. 258-259.
Herbert Bartsch, et al., "Studies on the Chemistry of O.N- and S.N- Containing Heterocycles, 8[1)] —Synthesis and Reactivity of 1,5-Benzoxazepine-2,4(3H,5H)-dione", Liebigs Annalen Der Chemie, vol. 2, 1989, pp. 177-179 (with English Abstract).
Moustafa, H.M., et al., "Studies on Organophosphorus Compounds: Synthesis and Reactions of [1, 2, 4, 3] Triaza-phospholo [4,5-a]Quinoxaline Derivative," Heteroatom Chemistry, vol. 19, No. 5, pp. 520-529, (2008).
Yakout, El-Sayed M.A., et al., "Simple Syntheses of Benzothiazol-2-ylazoles," Heteroatom Chemistry, vol. 10, No. 3, pp. 177-182, (1999).
Broedl, U.C., et al., "Endothelial Lipase: A Modulator of Lipoprotein Metabolism Upregulated by Inflammation," Trends Cardiovasc. Med., vol. 14, No. 5, pp. 202-206, (2004).
Ishida, T., et al., "Endothelial Lipase Modulates Susceptibility to Atherosclerosis in Apolipoprotein-E-deficient Mice," The Journal of Biological Chemistry, vol. 279, No. 43, pp. 45085-45092, (Aug. 9, 2004).
Aotsuka, T., et al., "Benzothiazol-2-Ylcarboxylic Acids with Diverse Spacers: A Novel Class of Potent, Orally Active Aldose Reductase Inhibitors," Bioorganic & Medicinal Chemistry Letters, vol. 7, No. 13, pp. 1677-1682, (1997).
International Search Report issued Nov. 24, 2009 in PCT/JP09/067845 filed Oct. 15, 2009.

* cited by examiner

ACETIC ACID AMIDE DERIVATIVE HAVING INHIBITORY ACTIVITY ON ENDOTHELIAL LIPASE

FIELD OF THE INVENTION

The present invention relates to a pharmaceutically useful compound having inhibitory activity on endothelial lipase (hereinafter, referred to as EL).

BACKGROUND ART

Endothelial Lipase (EL) is a Triglyceride Lipase family on a par with Lipoprotein Lipase (LPL) and Hepatic Lipase (HL). Studies in the knockout mouse and transgenic mouse have indicated that Endothelial Lipase (EL) is associated with the metabolism of HDLc by the strong phospholipase activity, and Endothelial Lipase (EL) is accepted as a factor which regulates plasma HDLc levels (Non-Patent Document 1).

Plasma HDLc levels are accepted as an inverse correlate of coronary artery disease (CAD) risk. HDLc is supposed that an anti-arteriosclerosis action is shown through an anti-oxidization action, an antiinflammatory effect, a cholesterol reverse transmission action or the like, and low HDLc levels are accepted as one of the risk-factors of CAD.

Therefore, an EL inhibitor serves as a CAD therapeutic agent through the increase of HDLc, and increase of a HDLc and reduction of an arteriosclerosis pathological change part is reported by studies in EL knockout clinical mouse (Non-Patent Document 2).

These facts suggest the possibility of a selective inhibitor of EL as a therapeutic agent in lipid metabolism abnormality and arteriosclerosis.

Patent Document 1, 2 and 3 disclose various compounds having inhibitory activity on hepatic lipase and/or endothelial lipase, but acetic acid amide derivative such as the present compound has not been disclosed.

Patent Document 4 discloses a compound having inhibitory activity on triglyceride lipase, lipoprotein lipase, hepatic lipase, pancreatic lipase or endothelial lipase, but acetic acid amide derivative such as the present compound has not been disclosed.

Patent Document 5 to 13 disclose various compounds having inhibitory activity on EL, but acetic acid amide derivative such as the present compound has not been disclosed.

Patent Document 14 discloses a compound having inhibitory activity on MIF (Macrophage Migration Inhibitory Factor), but does not describe the inhibitory activity on EL and the increasing activity of HDLc.

Patent Document 15 discloses a derivative in which 2-position of benzothiazole or benzoxazole is substituted with acetic acid amide group as a compound useful for sleep disorders, but does not describe the inhibitory activity on EL.

PRIOR ART DOCUMENT

Patent Document

[Patent Document 1] WO2004/093872
[Patent Document 2] WO2004/094393
[Patent Document 3] WO2004/094394
[Patent Document 4] WO2006/053250
[Patent Document 5] WO2007/042178
[Patent Document 6] WO2007/045392
[Patent Document 7] WO2007/045393
[Patent Document 8] WO2007/110216
[Patent Document 9] WO2007/110215
[Patent Document 10] WO2007/131231
[Patent Document 11] WO2007/131232
[Patent Document 12] WO2007/131233
[Patent Document 13] WO2006/111321 pamphlet
[Patent Document 14] JP2001-097979
[Patent Document 15] FR2904973

Non-Patent Document

[Non-Patent Document 1] TCM, Vol. 14, No. 5, 2004, p. 202-206
[Non-Patent Document 2] The Journal of Biological Chemistry Vol. 279, No. 43, Issue of Oct. 22, 45085-45092, 2004

DISCLOSURE OF INVENTION

Problems to be Solved by the Invention

The present invention provides a useful endothelial lipase inhibitor.

Means to Solve the Problems

The present inventors have intensively studied to synthesize the excellent compounds having inhibitory activity on endothelial lipase.

The present invention includes:
(1)
A pharmaceutical composition having inhibitory activity on endothelial lipase comprising a compound represented by the formula (I):

[Formula 1]

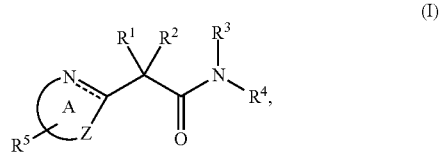

its pharmaceutically acceptable salt, or a solvate thereof, wherein
Ring A is nitrogen-containing hetero ring,
Ring A may be substituted with a substituent other than a group represented by the formula: —C($R^1R^2$)—C(=O)—$NR^3R^4$ and a group represented by the formula: —$R^5$,
a broken line represents the presence or the absence of a bond,
Z is —$NR^6$—, —N—, —O—, or —S—,
$R^6$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl or substituted or unsubstituted heterocycle,
$R^1$ and $R^2$ are each independently hydrogen, halogen, cyano, nitro, carboxy or substituted or unsubstituted alkyl,
$R^3$ is hydrogen or substituted or unsubstituted alkyl,
$R^4$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle or substituted or unsubstituted amino, R$^3$ and R$^4$ taken together with the adjacent nitrogen atom to which they are attached may form a substituted or unsubstituted ring, R$^5$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl, substituted or unsubstituted acyl, substituted or unsubstituted carbamoyl or substituted or unsubstituted amino, with the proviso that compounds wherein Ring A is thiazolopyrimidine and R$^3$ and R$^4$ taken together with the adjacent nitrogen atom to which they are attached may form a substituted or unsubstituted ring are excluded, (2)
The pharmaceutical composition having inhibitory activity on endothelial lipase comprising the compound according to the above (1), its pharmaceutically acceptable salt, or a solvate thereof, wherein Z is —S—, (3)
The pharmaceutical composition having inhibitory activity on endothelial lipase comprising the compound according to the above (1) or (2), its pharmaceutically acceptable salt, or a solvate thereof, wherein Ring A is monocyclic nitrogen-containing aromatic hetero ring, (4)
The pharmaceutical composition having inhibitory activity on endothelial lipase comprising the compound according to the above (1) or (2), its pharmaceutically acceptable salt, or a solvate thereof, wherein Ring A is bicyclic nitrogen-containing aromatic hetero ring, (5)
The pharmaceutical composition having inhibitory activity on endothelial lipase comprising the compound according to any one of the above (1) to (4), its pharmaceutically acceptable salt, or a solvate thereof, wherein R$^5$ is substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl or substituted or unsubstituted amino, (6)
The pharmaceutical composition having inhibitory activity on endothelial lipase comprising the compound according to any one of the above (1) to (5), its pharmaceutically acceptable salt, or a solvate thereof, wherein R$^5$ is substituted or unsubstituted aryl, substituted or unsubstituted heteroaryl, substituted or unsubstituted aryloxy, substituted or unsubstituted heteroaryloxy, substituted or unsubstituted arylthio, substituted or unsubstituted heteroarylthio, substituted or unsubstituted arylsulfonyl, substituted or unsubstituted heteroarylsulfonyl or substituted or unsubstituted amino, (7)
The pharmaceutical composition having inhibitory activity on endothelial lipase comprising the compound according to any one of the above (1) to (6), its pharmaceutically acceptable salt, or a solvate thereof, wherein R$^4$ is substituted or unsubstituted alkyl, wherein substituted or unsubstituted alkyl is substituted or unsubstituted arylalkyl or substituted or unsubstituted heteroarylalkyl, (8)
A compound represented by the formula (II):

[Formula 2]

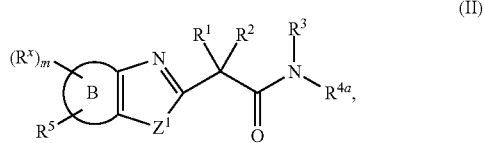

its pharmaceutically acceptable salt, or a solvate thereof, wherein

Z$^1$ is —O— or —S—,

Ring B is aromatic carbocycle, aromatic hetero ring, nonaromatic carbocycle or nonaromatic hetero ring, R$^1$ and R$^2$ are each independently hydrogen, halogen, cyano, nitro, carboxy or substituted or unsubstituted alkyl, R$^3$ is hydrogen or substituted or unsubstituted alkyl, R$^{4a}$ is substituted or unsubstituted arylalkyl, substituted or unsubstituted heteroarylalkyl, substituted or unsubstituted cycloalkylalkyl, substituted or unsubstituted cycloalkenylalkyl, substituted or unsubstituted heterocyclealkyl, a group represented by the formula: —(CR$^7$R$^8$)n-C(=O)—R$^9$, wherein R$^7$ and R$^8$ are each independently hydrogen, halogen, hydroxy, carboxy, substituted or unsubstituted alkyl, substituted or unsubstituted alkyloxy, substituted or unsubstituted aryl, substituted or unsubstituted heteroaryl, substituted or unsubstituted cycloalkyl, substituted or unsubstituted cycloalkenyl or substituted or unsubstituted heterocycle, n is an integer of 1 to 10, R$^9$ is —OR$^{10}$ or —NR$^{11}$R$^{12}$, R$^{10}$ is hydrogen, substituted or unsubstituted alkyl, substituted or unsubstituted aryl, substituted or unsubstituted heteroaryl, substituted or unsubstituted cycloalkyl, substituted or unsubstituted cycloalkenyl or substituted or unsubstituted heterocycle, R$^{11}$ and R$^{12}$ are each independently hydrogen, substituted or unsubstituted alkyl, substituted or unsubstituted alkyloxy, substituted or unsubstituted aryloxy, substituted or unsubstituted heteroaryloxy, substituted or unsubstituted alkylsulfonyl, substituted or unsubstituted aryl, substituted or unsubstituted heteroaryl, substituted or unsubstituted cycloalkyl, substituted or unsubstituted cycloalkenyl or substituted or unsubstituted heterocycle or a group represented by the formula: —C(R$^7$R$^8$)n-O—R$^{13}$, wherein R$^7$, R$^8$ and n are as defined in the above, R$^{13}$ is hydrogen or substituted or unsubstituted alkyl, R$^3$ and R$^{4a}$ taken together with the adjacent nitrogen atom to which they are attached may form a substituted or unsubstituted ring, R$^5$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl, substituted or unsubstituted acyl, substituted or unsubstituted carbamoyl or substituted or unsubstituted amino, $R^X$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl, substituted or unsubstituted acyl, substituted or unsubstituted carbamoyl or substituted or unsubstituted amino, m is an integer of 0 to 3, with the proviso that compounds, wherein $Z^1$ is —S—, Ring B is pyrimidine and $R^3$ and $R^{4a}$ taken together with the adjacent nitrogen atom to which they are attached may form a substituted or unsubstituted ring, compounds, wherein $Z^1$ is —O—, Ring B is benzene, $R^5$ is methyl, m is 0 and $R^3$ and $R^{4a}$ taken together with the adjacent nitrogen atom to which they are attached may form a substituted or unsubstituted ring, compounds, wherein $Z^1$ is —O—, Ring B is benzene, $R^5$ is hydrogen, m is 1, $R^X$ is methyl, and $R^3$ and $R^{4a}$ taken together with the adjacent nitrogen atom to which they are attached may form a substituted or unsubstituted ring and the compounds shown as follows are excluded:

[Formula 3]

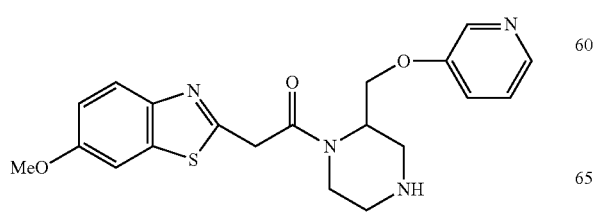

-continued

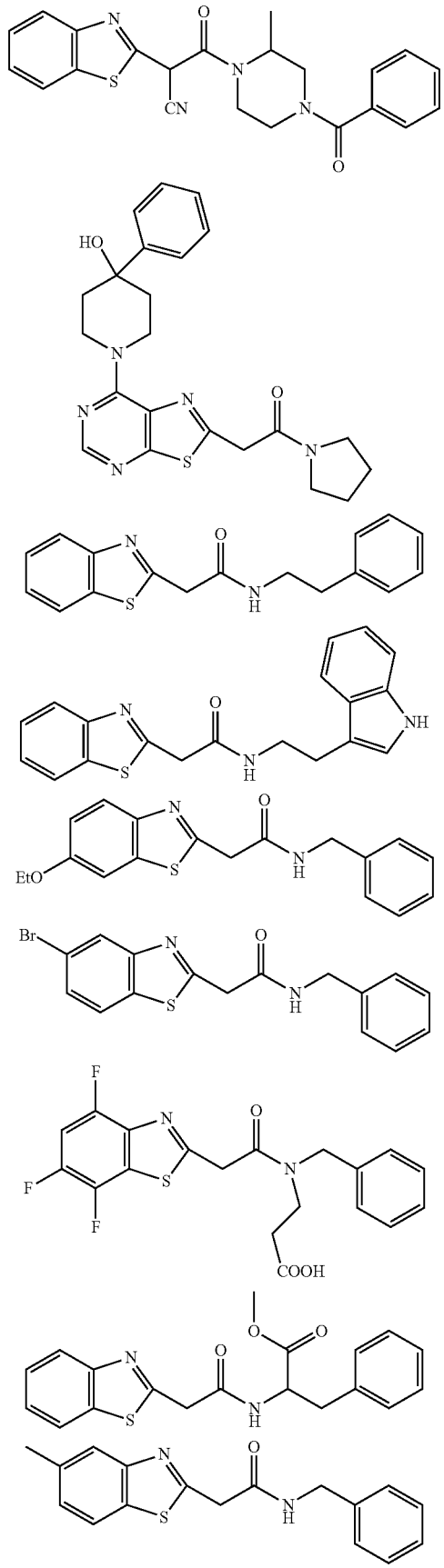

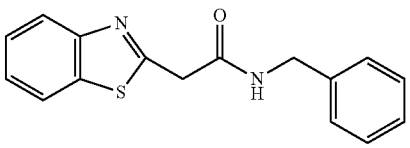
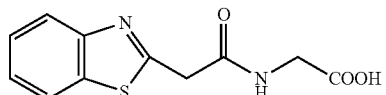
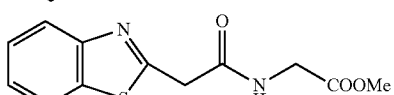
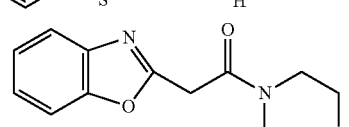
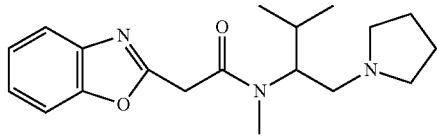
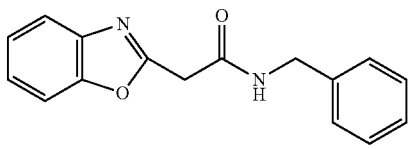
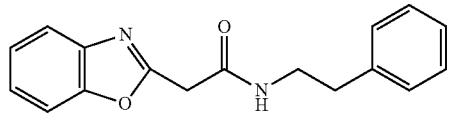
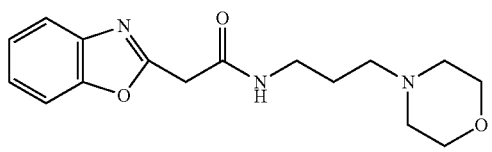
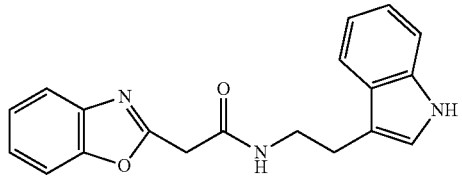
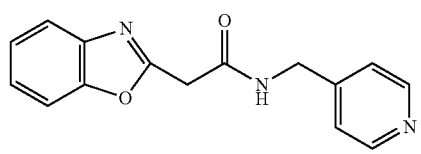
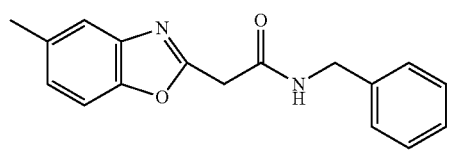
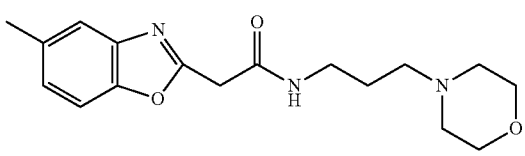

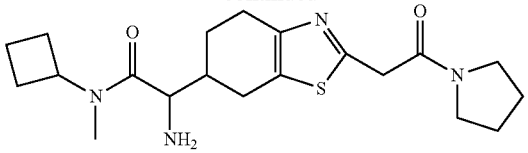
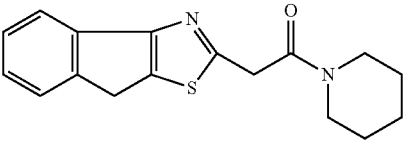

(9)
The compound according to the above (8), its pharmaceutically acceptable salt, or a solvate thereof, wherein $Z^1$ is —S—,

(10)
The compound according to the above (8) or (9), its pharmaceutically acceptable salt, or a solvate thereof, wherein Ring B is aromatic carbocycle,

(11)
The compound according to any one of the above (8) to (10), its pharmaceutically acceptable salt, or a solvate thereof, wherein Ring B is benzene,

(12)
The compound according to the above (8) or (9), its pharmaceutically acceptable salt, or a solvate thereof, wherein Ring B is monocyclic aromatic hetero ring,

(13)
The compound according to any one of the above (9) to (12), its pharmaceutically acceptable salt, or a solvate thereof, wherein the compound represented by the formula (II) is a compound represented by the formula (III):

[Formula 4]

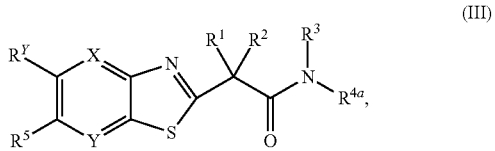

(III)

wherein X and Y are each independently —CR$^X$═, —CH═, or —N═, R$^Y$ is hydrogen or R$^X$, R$^1$, R$^2$, R$^3$, R$^{4a}$, R$^5$ and R$^X$ are as defined in the above (8),

(14)
The compound according to any one of the above (9) to (12), its pharmaceutically acceptable salt, or a solvate thereof, wherein the compound represented by the formula (II) is a compound represented by the formula (IV):

[Formula 5]

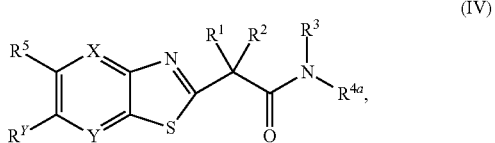

(IV)

wherein X and Y are each independently —CR$^X$═, —CH═, or —N═, R$^Y$ is hydrogen or R$^X$, R$^1$, R$^2$, R$^3$, R$^{4a}$, R$^5$ and R$^X$ are as defined in the above (8),

(15)
The compound according to the above (13) or (14), its pharmaceutically acceptable salt, or a solvate thereof, wherein X and Y are each independently —CR$^X$═ or —CH═,
(16)
The compound according to any one of the above (8) to (15), its pharmaceutically acceptable salt, or a solvate thereof, wherein R$^{4a}$ is substituted or unsubstituted arylalkyl or substituted or unsubstituted heteroarylalkyl,
(17)
The compound according to any one of the above (8) to (16), its pharmaceutically acceptable salt, or a solvate thereof, wherein R$^{4a}$ is substituted or unsubstituted arylalkyl,
(18)
The compound according to any one of the above (8) to (16), its pharmaceutically acceptable salt, or a solvate thereof, wherein R$^{4a}$ is

[Formula 6]

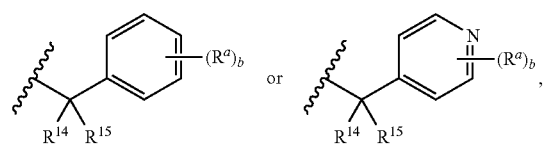

wherein R$^a$ is halogen, hydroxy, carboxy, nitro, cyano, azide, substituted or unsubstituted alkyl, substituted or unsubstituted alkenyl, substituted or unsubstituted alkynyl, substituted or unsubstituted aryl, substituted or unsubstituted cycloalkyl, substituted or unsubstituted cycloalkenyl, substituted or unsubstituted heteroaryl, substituted or unsubstituted heterocycle, substituted or unsubstituted alkyloxy, substituted or unsubstituted aryloxy, substituted or unsubstituted silyloxy, substituted or unsubstituted amino, substituted or unsubstituted carbamoyl, substituted or unsubstituted carbamoyloxy, substituted or unsubstituted acyl, substituted or unsubstituted alkylsulfonyl, substituted or unsubstituted arylsulfonyl, substituted or unsubstituted sulfamoyl or substituted or unsubstituted alkyloxycarbonyl, R$^{14}$ and R$^{15}$ are each independently hydrogen, halogen, hydroxy, cyano, nitro, carboxy, substituted or unsubstituted alkyl, substituted or unsubstituted alkenyl or substituted or unsubstituted alkynyl, b is an integer of 0 to 3,
(19)
The compound according to the above (18), its pharmaceutically acceptable salt, or a solvate thereof, wherein R$^{4a}$ is

[Formula 7]

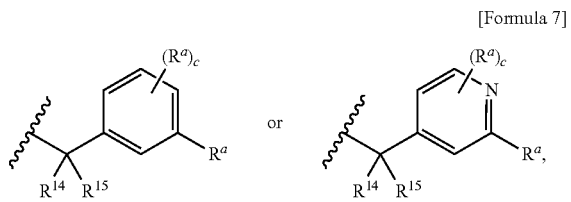

wherein R$^a$, R$^{14}$ and R$^{15}$ are as defined in the above (18), c is an integer of 0 to 2,
(20)
The compound according to any one of the above (8) to (15), its pharmaceutically acceptable salt, or a solvate thereof, wherein R$^{4a}$ is a group represented by the formula: —(CR$^7$R$^8$)n-C(═O)—R$^9$, wherein R$^7$, R$^8$, R$^9$ and n are as defined in the above (8),
(21)
The compound according to the above (20), its pharmaceutically acceptable salt, or a solvate thereof, wherein R$^9$ is —OR$^{10}$,
(22)
The compound according to the above (20), its pharmaceutically acceptable salt, or a solvate thereof, wherein R$^9$ is —NR$^{11}$R$^{12}$,
(23)
The compound according to the above (22), its pharmaceutically acceptable salt, or a solvate thereof, wherein R$^{12}$ is substituted or unsubstituted alkyl,
(24)
The compound according to the above (22) or (23), its pharmaceutically acceptable salt, or a solvate thereof, wherein R$^{11}$ is hydrogen,
(25)
The compound according to any one of the above (20) to (24), its pharmaceutically acceptable salt, or a solvate thereof, wherein n is 1,
(26)
The compound according to any one of the above (20) to (25), its pharmaceutically acceptable salt, or a solvate thereof, wherein R$^7$ and R$^8$ are hydrogen,
(27)
The compound according to any one of the above (8) to (26), its pharmaceutically acceptable salt, or a solvate thereof, wherein R$^1$ and R$^2$ are hydrogen,
(28)
The compound according to any one of the above (8) to (27), its pharmaceutically acceptable salt, or a solvate thereof, wherein R$^3$ is hydrogen,
(29)
The compound according to any one of the above (8) to (28), its pharmaceutically acceptable salt, or a solvate thereof, wherein R$^5$ is substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl or substituted or unsubstituted amino,
(30)
The compound according to any one of the above (8) to (29), its pharmaceutically acceptable salt, or a solvate thereof, wherein R$^5$ is substituted or unsubstituted aryl, substituted or unsubstituted heteroaryl, substituted or unsubstituted aryloxy, substituted or unsubstituted heteroaryloxy, substituted or unsubstituted arylthio, substituted or unsubstituted heteroarylthio, substituted or unsubstituted arylsulfonyl, substituted or unsubstituted heteroarylsulfonyl or substituted or unsubstituted amino,
(31)
The compound according to any one of the above (8) to (28), its pharmaceutically acceptable salt, or a solvate thereof, wherein R⁵ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocycle, substituted or unsubstituted alkyloxy, substituted or unsubstituted aryloxy, substituted or unsubstituted arylsulfonyl or substituted or unsubstituted acyl, (32)

A compound represented by the formula (V):

[Formula 8]

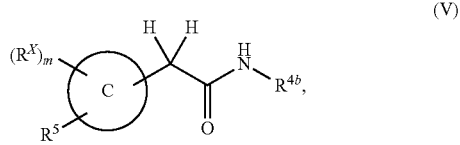

(V)

its pharmaceutically acceptable salt, or a solvate thereof, wherein

Ring C is monocyclic or bicyclic hetero ring, $R^{4b}$ is substituted arylalkyl, wherein a substituent on a ring of the substituted arylalkyl is carboxy, substituted or unsubstituted carbamoyl, substituted or unsubstituted alkylsulfonyl or substituted or unsubstituted sulfamoyl, substituted heteroarylalkyl, wherein a substituent on a ring of the substituted heteroarylalkyl is carboxy, substituted or unsubstituted carbamoyl, substituted or unsubstituted alkylsulfonyl or substituted or unsubstituted sulfamoyl, substituted cycloalkylalkyl, wherein a substituent on a ring of the substituted cycloalkylalkyl is carboxy, substituted or unsubstituted carbamoyl, substituted or unsubstituted alkylsulfonyl or substituted or unsubstituted sulfamoyl, substituted cycloalkenylalkyl, wherein a substituent on a ring of the substituted cycloalkenylalkyl is carboxy, substituted or unsubstituted carbamoyl, substituted or unsubstituted alkylsulfonyl or substituted or unsubstituted sulfamoyl, substituted heterocyclealkyl, wherein a substituent on a ring of the substituted heterocyclealkyl is carboxy, substituted or unsubstituted carbamoyl, substituted or unsubstituted alkylsulfonyl or substituted or unsubstituted sulfamoyl or a group represented by the formula: —(CR⁷R⁸)n-C(=O)—R⁹, wherein R⁷ and R⁸ are each independently hydrogen, halogen, hydroxy, carboxy, substituted or unsubstituted alkyl, substituted or unsubstituted alkyloxy, substituted or unsubstituted aryl, substituted or unsubstituted heteroaryl, substituted or unsubstituted cycloalkyl, substituted or unsubstituted cycloalkenyl or substituted or unsubstituted heterocycle, n is an integer of 1 to 10, R⁹ is —OR¹⁰ or —NR¹¹R¹², R¹⁰ is hydrogen, substituted or unsubstituted alkyl, substituted or unsubstituted aryl, substituted or unsubstituted heteroaryl, substituted or unsubstituted cycloalkyl, substituted or unsubstituted cycloalkenyl or substituted or unsubstituted heterocycle, R¹¹ and R¹² are each independently hydrogen, substituted or unsubstituted alkyl, substituted or unsubstituted alkyloxy, substituted or unsubstituted aryloxy, substituted or unsubstituted heteroaryloxy, substituted or unsubstituted alkylsulfonyl, substituted or unsubstituted aryl, substituted or unsubstituted heteroaryl, substituted or unsubstituted cycloalkyl, substituted or unsubstituted cycloalkenyl or substituted or unsubstituted heterocycle, R⁵ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl, substituted or unsubstituted acyl, substituted or unsubstituted carbamoyl or substituted or unsubstituted amino, $R^X$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl, substituted or unsubstituted acyl, substituted or unsubstituted carbamoyl or substituted or unsubstituted amino, m is an integer of 0 to 3, with the proviso that the compounds shown as follows are excluded:

[Formula 9]

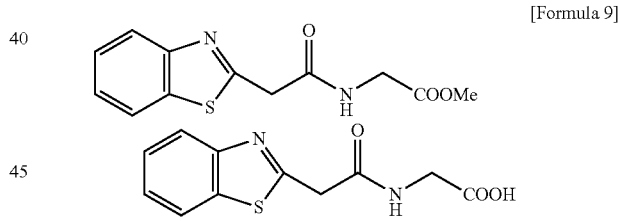

(33)

The compound according to the above (32), its pharmaceutically acceptable salt, or a solvate thereof, wherein Ring C is bicycle, (34)

A pharmaceutical composition comprising the compound according to any one of the above (8) to (33), its pharmaceutically acceptable salt, or a solvate thereof, (35)

A pharmaceutical composition comprising the compound according to any one of the above (8) to (33), its pharmaceutically acceptable salt, or a solvate thereof, which has an inhibitory activity on endothelial lipase, (36)

The pharmaceutical composition according to any one of the above (1) to (7) or (34) for treating and/or preventing lipid metabolism abnormality, (37)

The pharmaceutical composition according to any one of the above (1) to (7) or (34) for treating and/or preventing hyperlipidemia, (38)

The pharmaceutical composition according to any one of the above (1) to (7) or (34) for treating and/or preventing arteriosclerosis, (39)

A method for preventing or treating lipid metabolism abnormality, comprising administering the compound according to any one of the above (1) to (33), its pharmaceutically acceptable salt, or a solvate thereof, (40)

A method for preventing or treating hyperlipidemia, comprising administering the compound according to any one of the above (1) to (33), its pharmaceutically acceptable salt, or a solvate thereof, (41)

A method for preventing or treating arteriosclerosis, comprising administering the compound according to any one of the above (1) to (33), its pharmaceutically acceptable salt, or a solvate thereof, (42)

A use of the compound according to any one of the above (1) to (33), its pharmaceutically acceptable salt, or a solvate thereof for manufacturing a medicament of treatment and/or prevention of lipid metabolism abnormality, (43)

A use of the compound according to any one of the above (1) to (33), its pharmaceutically acceptable salt, or a solvate thereof for manufacturing a medicament of treatment and/or prevention of hyperlipidemia, (44)

A use of the compound according to any one of the above (1) to (33), its pharmaceutically acceptable salt, or a solvate thereof for manufacturing a medicament of treatment and/or prevention of arteriosclerosis, (45)

The compound according to any one of the above (1) to (33), its pharmaceutically acceptable salt, or a solvate thereof for the treatment and/or prevention of lipid metabolism abnormality, (46)

The compound according to any one of the above (1) to (33), its pharmaceutically acceptable salt, or a solvate thereof for the treatment and/or prevention of hyperlipidemia, (47)

The compound according to any one of the above (1) to (33), its pharmaceutically acceptable salt, or a solvate thereof for the treatment and/or prevention of arteriosclerosis.

Further, the present invention includes:

(A1)

A pharmaceutical composition having inhibitory activity on endothelial lipase comprising a compound represented by the formula (I):

[Formula 10]

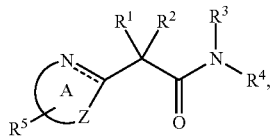

(I)

its pharmaceutically acceptable salt, or a solvate thereof, wherein

Ring A is nitrogen-containing hetero ring,

Ring A may be substituted with a substituent other than a group represented by the formula: —C($R^1R^2$)—C(=O)—$NR^3R^4$ and a group represented by the formula: —$R^5$, a broken line represents the presence or the absence of a bond, Z is —$NR^6$—, =N—, —O—, or —S—, $R^6$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl or substituted or unsubstituted heterocycle, $R^1$ and $R^2$ are each independently hydrogen, halogen, hydroxy, cyano, nitro, carboxy or substituted or unsubstituted alkyl, $R^3$ is hydrogen or substituted or unsubstituted alkyl, $R^4$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle or substituted or unsubstituted amino, $R^3$ and $R^4$ taken together with the adjacent nitrogen atom to which they are attached may form a substituted or unsubstituted ring, $R^5$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted cycloalkyloxy, substituted or unsubstituted aryloxy, substituted or unsubstituted heteroaryloxy, substituted or unsubstituted heterocycleoxy, substituted or unsubstituted alkylthio, substituted or unsubstituted cycloalkylthio, substituted or unsubstituted cycloalkenylthio, substituted or unsubstituted arylthio, substituted or unsubstituted heteroarylthio, substituted or unsubstituted heterocyclethio, substituted or unsubstituted alkylsulfonyl, substituted or unsubstituted cycloalkylsulfonyl, substituted or unsubstituted cycloalkenylsulfonyl, substituted or unsubstituted arylsulfonyl, substituted or unsubstituted heteroarylsulfonyl, substituted or unsubstituted heterocyclesulfonyl, substituted or unsubstituted acyl or substituted or unsubstituted amino, (A2)

The pharmaceutical composition having inhibitory activity on endothelial lipase comprising the compound according to the above (A1), its pharmaceutically acceptable salt, or a solvate thereof, wherein Z is —S—, (A3)

The pharmaceutical composition having inhibitory activity on endothelial lipase comprising the compound according to the above (A1) or (A2), its pharmaceutically acceptable salt, or a solvate thereof, wherein Ring A is monocyclic nitrogen-containing aromatic hetero ring, (A4)

The pharmaceutical composition having inhibitory activity on endothelial lipase comprising the compound according to the above (A1) or (A2), its pharmaceutically acceptable salt, or a solvate thereof, wherein Ring A is bicyclic nitrogen-containing aromatic hetero ring, (A5)

The pharmaceutical composition having inhibitory activity on endothelial lipase comprising the compound according to any one of the above (A1) to (A4), its pharmaceutically acceptable salt, or a solvate thereof, wherein $R^4$ is substituted or unsubstituted alkyl, wherein substituted or unsubstituted alkyl is substituted or unsubstituted arylalkyl or substituted or unsubstituted heteroarylalkyl, (A6)

A compound represented by the formula (II):

[Formula 11]

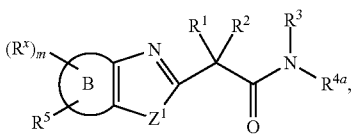

(II)

its pharmaceutically acceptable salt, or a solvate thereof, wherein $Z^1$ is —O— or —S—, Ring B is aromatic carbocycle, aromatic hetero ring, non-aromatic carbocycle or nonaromatic hetero ring, $R^1$ and $R^2$ are each independently hydrogen, halogen, hydroxy, cyano, nitro, carboxy or substituted or unsubstituted alkyl, $R^3$ is hydrogen or substituted or unsubstituted alkyl, $R^{4a}$ is substituted or unsubstituted arylalkyl, substituted or unsubstituted heteroarylalkyl, substituted or unsubstituted cycloalkylalkyl, substituted or unsubstituted cycloalkenylalkyl, substituted or unsubstituted heterocyclealkyl, a group represented by the formula: —$(CR^7R^8)$n-C(=O)—$R^9$, wherein $R^7$ and $R^8$ are each independently hydrogen, carboxy, substituted or unsubstituted alkyl, substituted or unsubstituted aryl, substituted or unsubstituted heteroaryl, substituted or unsubstituted cycloalkyl, substituted or unsubstituted cycloalkenyl or substituted or unsubstituted heterocycle, n is an integer of 1 to 10, $R^9$ is —$OR^{10}$ or —$NR^{11}R^{12}$, $R^{10}$, $R^{11}$ and $R^{12}$ are each independently hydrogen or substituted or unsubstituted alkyl or a group represented by the formula: —$C(R^7R^8)$n-O—$R^{13}$, wherein $R^7$, $R^8$ and n are as defined in the above, $R^{13}$ is hydrogen or substituted or unsubstituted alkyl, $R^3$ and $R^{4a}$ taken together with the adjacent nitrogen atom to which they are attached may form a substituted or unsubstituted ring, $R^5$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted cycloalkyloxy, substituted or unsubstituted aryloxy, substituted or unsubstituted heteroaryloxy, substituted or unsubstituted heterocycleoxy, substituted or unsubstituted alkylthio, substituted or unsubstituted cycloalkylthio, substituted or unsubstituted cycloalkenylthio, substituted or unsubstituted arylthio, substituted or unsubstituted heteroarylthio, substituted or unsubstituted heterocyclethio, substituted or unsubstituted alkylsulfonyl, substituted or unsubstituted cycloalkylsulfonyl, substituted or unsubstituted cycloalkenylsulfonyl, substituted or unsubstituted arylsulfonyl, substituted or unsubstituted heteroarylsulfonyl, substituted or unsubstituted heterocyclesulfonyl, substituted or unsubstituted acyl or substituted or unsubstituted amino, $R^x$ is halogen, hydroxy, cyano, nitro, carboxy, substituted or unsubstituted alkyl, substituted or unsubstituted alkenyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted amino or substituted or unsubstituted carbamoyl, m is an integer of 0 to 3, with the proviso that compounds, wherein $Z^1$ is —O—, Ring B is benzene, $R^5$ is methyl, m is 0 and $R^3$ and $R^{4a}$ taken together with the adjacent nitrogen atom to which they are attached may form a substituted or unsubstituted ring and the compounds shown as follows are excluded:

[Formula 12]

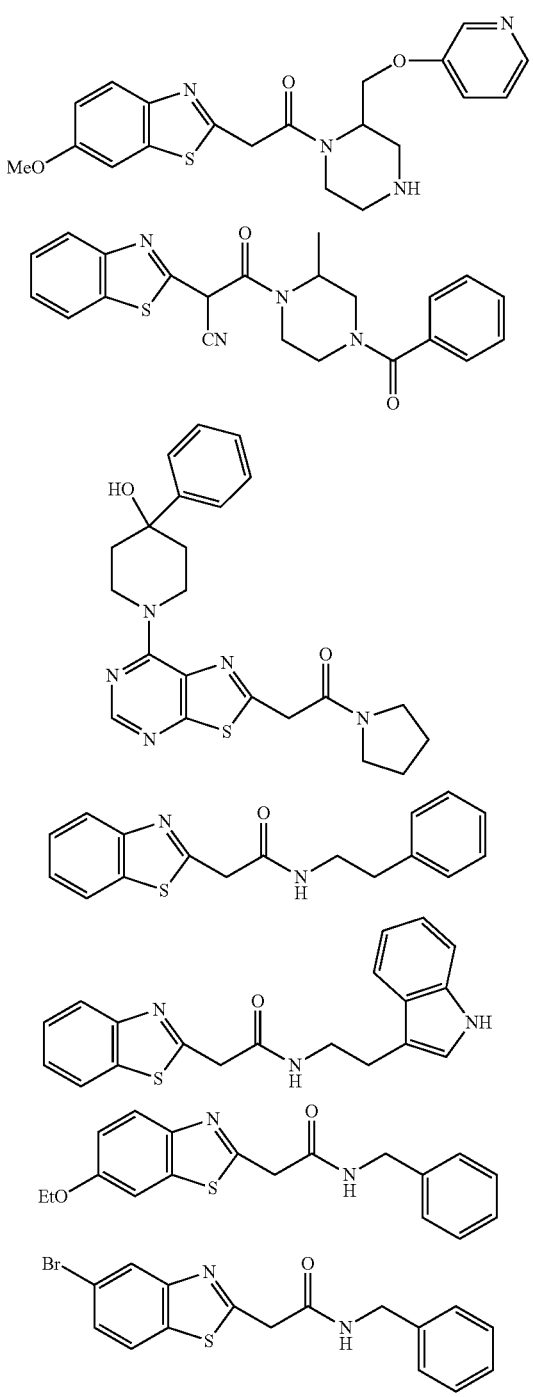

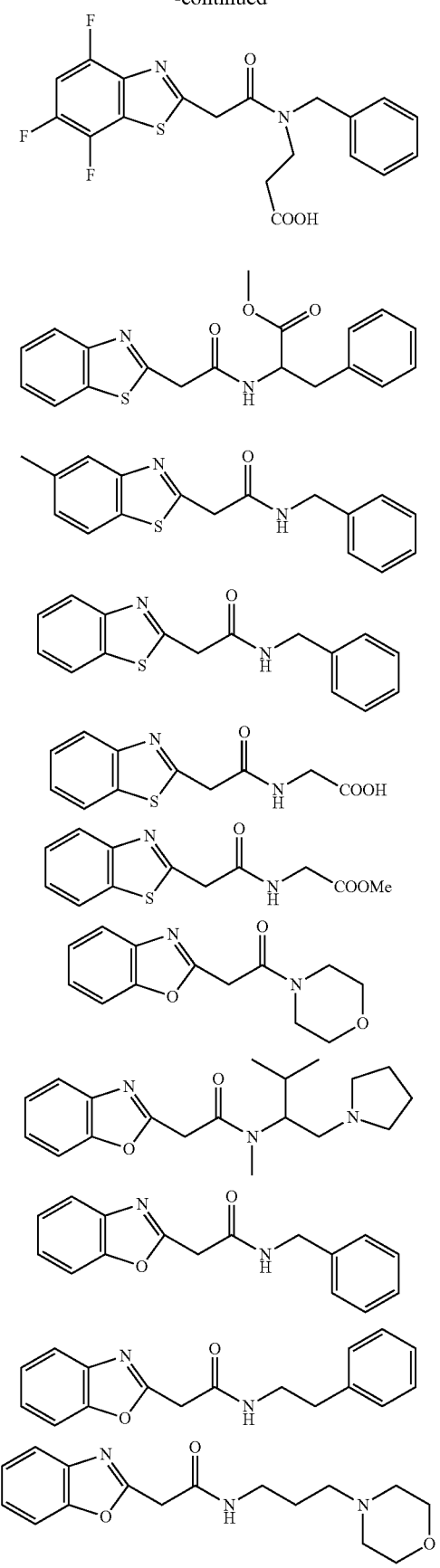
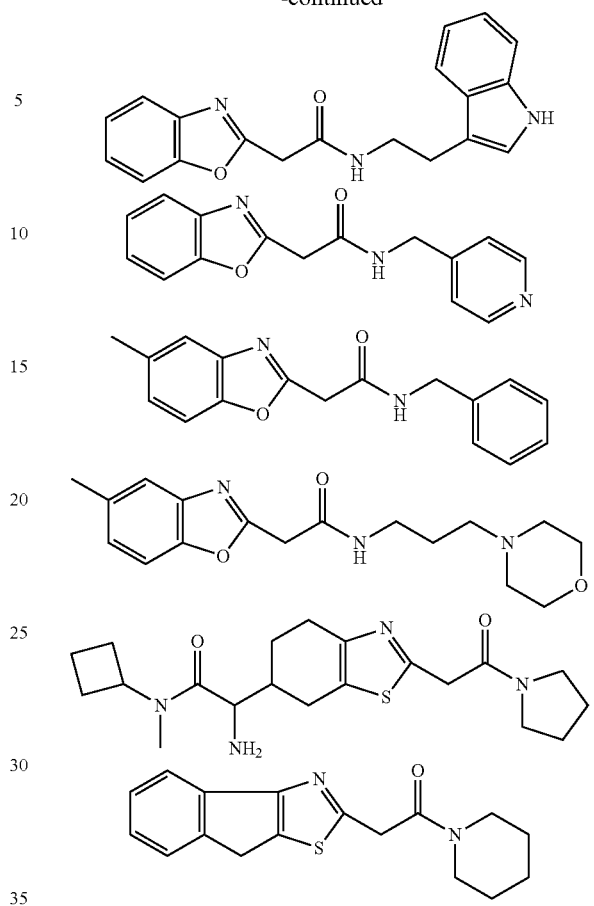

(A7)
The compound according to the above (A6), its pharmaceutically acceptable salt, or a solvate thereof, wherein $Z^1$ is —S—, (A8)
The compound according to the above (A6) or (A7), its pharmaceutically acceptable salt, or a solvate thereof, wherein Ring B is aromatic carbocycle, (A9)
The compound according to any one of the above (A6) to (A8), its pharmaceutically acceptable salt, or a solvate thereof, wherein Ring B is benzene, (A10)
The compound according to the above (A6) or (A7), its pharmaceutically acceptable salt, or a solvate thereof, wherein Ring B is monocyclic aromatic hetero ring, (A11)
The compound according to any one of the above (A6) to (A10), its pharmaceutically acceptable salt, or a solvate thereof, wherein $R^{4a}$ is substituted or unsubstituted arylalkyl or substituted or unsubstituted heteroarylalkyl, (A12)
The compound according to any one of the above (A6) to (A11), its pharmaceutically acceptable salt, or a solvate thereof, wherein $R^{4a}$ is substituted or unsubstituted arylalkyl, (A13)
The compound according to any one of the above (A6) to (A11), its pharmaceutically acceptable salt, or a solvate thereof, wherein $R^{4a}$ is

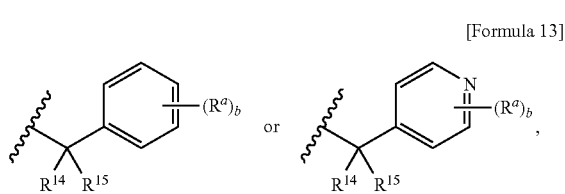

wherein $R^a$ is halogen, hydroxy, carboxy, nitro, cyano, azide, substituted or unsubstituted alkyl, substituted or unsubstituted alkenyl, substituted or unsubstituted alkynyl, substituted or unsubstituted aryl, substituted or unsubstituted cycloalkyl, substituted or unsubstituted cycloalkenyl, substituted or unsubstituted heteroaryl, substituted or unsubstituted heterocycle, substituted or unsubstituted alkyloxy, substituted or unsubstituted aryloxy, substituted or unsubstituted silyloxy, substituted or unsubstituted amino, substituted or unsubstituted carbamoyl, substituted or unsubstituted carbamoyloxy, substituted or unsubstituted acyl, substituted or unsubstituted alkylsulfonyl, substituted or unsubstituted arylsulfonyl, substituted or unsubstituted sulfamoyl or substituted or unsubstituted alkyloxycarbonyl, $R^{14}$ and $R^{15}$ are each independently hydrogen, halogen, hydroxy, cyano, nitro, carboxy, substituted or unsubstituted alkyl, substituted or unsubstituted alkenyl or substituted or unsubstituted alkynyl, b is an integer of 0 to 3, (A14)

The compound according to the above (A13), its pharmaceutically acceptable salt, or a solvate thereof, wherein $R^{4a}$ is

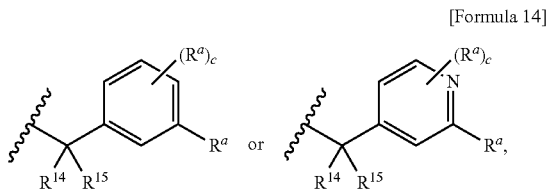

wherein $R^a$, $R^{14}$ and $R^{15}$ are as defined in the above (A13), c is an integer of 0 to 2, (A15)

The compound according to any one of the above (A6) to (A14), its pharmaceutically acceptable salt, or a solvate thereof, wherein $R^1$ and $R^2$ are each independently hydrogen, hydroxy or substituted or unsubstituted alkyl, (A16)

The compound according to any one of the above (A6) to (A15), its pharmaceutically acceptable salt, or a solvate thereof, wherein $R^3$ is hydrogen, (A17)

The compound according to any one of the above (A6) to (A16), its pharmaceutically acceptable salt, or a solvate thereof, wherein $R^5$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocycle, substituted or unsubstituted alkyloxy, substituted or unsubstituted aryloxy, substituted or unsubstituted arylsulfonyl or substituted or unsubstituted acyl, (A18)

A pharmaceutical composition comprising the compound according to any one of the above (A6) to (A17), its pharmaceutically acceptable salt, or a solvate thereof, (A19)

A pharmaceutical composition comprising the compound according to any one of the above (A6) to (A17), its pharmaceutically acceptable salt, or a solvate thereof, which has an inhibitory activity on endothelial lipase, (A20)

The pharmaceutical composition according to the above (A18) for treating and/or preventing lipid metabolism abnormality, (A21)

The pharmaceutical composition according to the above (A18) for treating and/or preventing hyperlipidemia, (A22)

The pharmaceutical composition according to the above (A18) for treating and/or preventing arteriosclerosis, (A23)

A method for preventing or treating lipid metabolism abnormality, comprising administering the compound according to any one of the above (A6) to (A17), its pharmaceutically acceptable salt, or a solvate thereof, (A24)

A method for preventing or treating hyperlipidemia, comprising administering the compound according to any one of the above (A6) to (A17), its pharmaceutically acceptable salt, or a solvate thereof, (A25)

A method for preventing or treating arteriosclerosis, comprising administering the compound according to any one of the above (A6) to (A17), its pharmaceutically acceptable salt, or a solvate thereof, (A26)

A use of the compound according to any one of the above (A6) to (A17), its pharmaceutically acceptable salt, or a solvate thereof for manufacturing a medicament of treatment and/or prevention of lipid metabolism abnormality, (A27)

A use of the compound according to any one of the above (A6) to (A17), its pharmaceutically acceptable salt, or a solvate thereof for manufacturing a medicament of treatment and/or prevention of hyperlipidemia, (A28)

A use of the compound according to any one of the above (A6) to (A17), its pharmaceutically acceptable salt, or a solvate thereof for manufacturing a medicament of treatment and/or prevention of arteriosclerosis, (A29)

The compound according to any one of the above (A6) to (A17), its pharmaceutically acceptable salt, or a solvate thereof for the treatment and/or prevention of lipid metabolism abnormality, (A30)

The compound according to any one of the above (A6) to (A17), its pharmaceutically acceptable salt, or a solvate thereof for the treatment and/or prevention of hyperlipidemia, (A31)

The compound according to any one of the above (A6) to (A17), its pharmaceutically acceptable salt, or a solvate thereof for the treatment and/or prevention of arteriosclerosis.

Effect of the Invention

Since the present compound has inhibitory activity on endothelial lipase, pharmaceutical compositions comprising the present compound are very useful as medicaments, especially, as medicaments for treatment and/or prevention of lipid metabolism abnormality, hyperlipidemia, arterio sclerosis, atherosclerosis, hypercholesterolemia, hypertriglyceridemia, diabetes, obesity and/or syndrome X.

Moreover, the present compound selectively inhibits endothelial lipase, and has high selectivity to Hepatic Lipase (HL) and Lipoprotein Lipase (LPL). The present compound is a compound having other utility as a medicament. Here, the utility as a medicament includes high metabolic stability, a weak drug-metabolizing enzyme induction, a weak inhibition of drug metabolizing enzyme that metabolizes other drug, a high oral absorption, a low clearance, a long half-life period enough to exhibit drug efficacy and so on.

BEST MODE FOR CARRYING OUT THE INVENTION

In the following, meanings of terms used in the present specification will be explained. Each term has the same meaning when used alone or in combination with other term in this description.

"Halogen" includes fluorine, chlorine, bromine or iodine.

"Alkyl" means a C1 to C10 straight or branched alkyl group, and example includes methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl or the like. Preferable is C1 to C6 or C1 to C4 alkyl, and example includes methyl, ethyl, n-propyl, isopropyl, n-butyl, isobutyl, sec-butyl, tert-butyl, n-pentyl, isopentyl, neopentyl, n-hexyl or isohexyl.

"Alkenyl" means C2 to C8 straight or branched alkenyl having one or more double bond(s) in the above "alkyl", and example includes vinyl, 1-propenyl, 2-propenyl, 1-butenyl, 2-butenyl, 3-butenyl, 1,3-butadienyl, 3-methyl-2-butenyl or the like.

"Alkynyl" means C2 to C8 straight or branched alkynyl having one or more triple bond(s) in the above "alkyl", and example includes ethynyl, propinyl, butynyl or the like. Furthermore, "Alkynyl" may have a double bond.

"Cycloalkyl" means a C3 to C15 cyclic saturated hydrocarbon group, and example includes cyclopropyl, cyclobutyl, cyclopentyl, cyclohexyl, cycloheptyl, cyclooctyl, bridged cyclic hydrocarbon group, Spiro hydrocarbon group or the like. Preferable is cyclopropyl, cyclobutyl, cyclopentyl, cyclohexyl or bridged cyclic hydrocarbon group.

"Bridged cyclic hydrocarbon group" includes a group which is derived by excluding one hydrogen from a C5 to C8 aliphatic cycle which consists of two or more rings that share two or more atoms. Example includes bicyclo[2.1.0]pentyl, bicyclo[2.2.1]heptyl, bicyclo[2.2.2]octyl, bicyclo[3.2.1]octyl, tricyclo[2.2.1.0]heptyl or the like.

"Spiro hydrocarbon group" includes a group which is derived by excluding one hydrogen from a cycle which consists of two hydrocarbon rings that share one carbon atom. Example includes spiro[3.4]octyl or the like.

"Cycloalkenyl" means C3 to C10 cyclic unsaturated aliphatic hydrocarbon group, and example includes cyclopropenyl (e.g.: 1-cyclopropenyl), cyclobutenyl (e.g.: 1-cyclobutenyl), cyclopentenyl (e.g.: 1-cyclopenten-1-yl, 2-cyclopenten-1-yl or 3-cyclopenten-1-yl), cyclohexenyl (e.g.: 1-cyclohexen-1-yl, 2-cyclohexen-1-yl or 3-cyclohexen-1-yl), cycloheptenyl (e.g.: 1-cycloheptenyl), cyclooctenyl (e.g.: 1-cyclooctenyl) or the like. Preferable is cyclopropenyl, cyclobutenyl, cyclopentenyl or cyclohexenyl. Cycloalkenyl also includes bridged cyclic hydrocarbon group and spiro hydrocarbon group which have an unsaturated bond in the ring.

"Aryl" means a monocyclic aromatic hydrocarbon group (e.g.: phenyl) and a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl). Preferable is phenyl or naphthyl (1-naphthyl or 2-naphthyl).

"Heteroaryl" means a monocyclic aromatic heterocyclic group or a fused aromatic heterocyclic group. The monocyclic aromatic heterocyclic group means a group derived from a 5- to 8-membered aromatic ring which may contain 1 to 4 oxygen, sulfur and/or nitrogen atom(s) in the ring, and may have a bond at a substitutable arbitrary position.

The fused aromatic heterocyclic group means a group in which a 5- to 8-membered aromatic ring optionally containing 1 to 4 oxygen, sulfur and/or nitrogen atom(s) in the ring is fused with 1 to 4 of 5- to 8-membered aromatic carbocycle(s) or other 5- to 8-membered aromatic heterocycle(s), and which may have a bond at a substitutable arbitrary position.

Example of the "heteroaryl" includes furyl (e.g.: 2-furyl or 3-furyl), thienyl (e.g.: 2-thienyl or 3-thienyl), pyrrolyl (e.g.: 1-pyrrolyl, 2-pyrrolyl or 3-pyrrolyl), imidazolyl (e.g.: 1-imidazolyl, 2-imidazolyl or 4-imidazolyl), pyrazolyl (e.g.: 1-pyrazolyl, 3-pyrazolyl or 4-pyrazolyl), triazolyl (e.g.: 1,2,4-triazole-1-yl, 1,2,4-triazole-3-yl or 1,2,4-triazole-4-yl), tetrazolyl (e.g.: 1-tetrazolyl, 2-tetrazolyl or 5-tetrazolyl), oxazolyl (e.g.: 2-oxazolyl, 4-oxazolyl or 5-oxazolyl), isoxazolyl (e.g.: 3-isoxazolyl, 4-isoxazolyl or 5-isoxazolyl), thiazolyl (e.g.: 2-thiazolyl, 4-thiazolyl or 5-thiazolyl), thiadiazolyl, isothiazolyl (e.g.: 3-isothiazolyl, 4-isothiazolyl or 5-isothiazolyl), pyridyl (e.g.: 2-pyridyl, 3-pyridyl or 4-pyridyl), pyridazinyl (e.g.: 3-pyridazinyl or 4-pyridazinyl), pyrimidinyl (e.g.: 2-pyrimidinyl, 4-pyrimidinyl or 5-pyrimidinyl), furazanyl (e.g.: 3-furazanyl), pyrazinyl (e.g.: 2-pyrazinyl), oxadiazolyl (e.g.: 1,3,4-oxadiazole-2-yl), benzofuryl (e.g.: 2-benzo[b]furyl, 3-benzo[b]furyl, 4-benzo[b]furyl, 5-benzo[b]furyl, 6-benzo[b]furyl or 7-benzo[b]furyl), benzothienyl (e.g.: 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g.: 1-benzimidazolyl, 2-benzimidazolyl, 4-benzimidazolyl or 5-benzimidazolyl), dibenzofuryl, benzoxazolyl, benzothiazolyl, quinoxalinyl (e.g.: 2-quinoxalinyl, 5-quinoxalinyl or 6-quinoxalinyl), cinnolinyl (e.g.: 3-cinnolinyl, 4-cinnolinyl, 5-cinnolinyl, 6-cinnolinyl, 7-cinnolinyl or 8-quinazolinyl (e.g.: 2-quinazolinyl, 4-quinazolinyl, 5-quinazolinyl, 6-quinazolinyl, 7-quinazolinyl or 8-quinazolinyl), quinolyl (e.g.: 2-quinolyl, 3-quinolyl, 4-quinolyl, 5-quinolyl, 6-quinolyl, 7-quinolyl or 8-quinolyl), phthalazinyl (e.g.: 1-phthalazinyl, 5-phthalazinyl or 6-phthalazinyl), isoquinolyl (e.g.: 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g.: 2-pteridinyl, 4-pteridinyl, 6-pteridinyl or 7-pteridinyl), carbazolyl, phenanthridinyl, acridinyl (e.g.: 1-acridinyl, 2-acridinyl, 3-acridinyl, 4-acridinyl or 9-acridinyl), indolyl (e.g.: 1-indolyl, 2-indolyl, 3-indolyl, 4-indolyl, 5-indolyl, 6-indolyl or 7-indolyl), isoindolyl, phenadinyl (e.g.: 1-phenadinyl or 2-phenadinyl), phenothiadinyl (e.g.: 1-phenothiadinyl, 2-phenothiadinyl, 3-phenothiadinyl or 4-phenothiadinyl) or the like.

"Heterocycle" means a nonaromatic heterocyclic group which contains at least one nitrogen, oxygen or sulfur atom(s) in the ring, and may have a bond at a substitutable arbitrary position. Moreover, the nonaromatic heterocyclic group can be bridged with a C1 to C4 alkyl chain, or can be fused with cycloalkane (5- to 6-membered ring is preferable) or benzene ring. "Nonaromatic heterocyclic group" can be saturated or unsaturated as long as it is non-aromatic. Preferable is a 5- to 8-membered ring. Example includes 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperadinyl, 2-piperadinyl, 2-morpholinyl, 3-morpholinyl, morpholino, tetrahydropyranyl, the following groups or the like.

"Acyl" means formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl or substituted or unsubstituted heterocyclecarbonyl.

The alkyl part of "substituted or unsubstituted alkyloxy", "substituted or unsubstituted alkylthio", "substituted or unsubstituted alkylsulfonyl", "substituted or unsubstituted arylalkyl", "substituted or unsubstituted heteroarylalkyl", "substituted or unsubstituted cycloalkylalkyl", "substituted or unsubstituted cycloalkenylalkyl", "substituted or unsubstituted heterocyclealkyl" and "substituted or unsubstituted alkyloxycarbonyl" means the above "alkyl".

The cycloalkyl part of "substituted or unsubstituted cycloalkyloxy", "substituted or unsubstituted cycloalkylthio", "substituted or unsubstituted cycloalkylsulfonyl" and "substituted or unsubstituted cycloalkylalkyl" means the above "cycloalkyl".

The cycloalkenyl part of "substituted or unsubstituted cycloalkenylthio", "substituted or unsubstituted cycloalkenylsulfonyl", "substituted or unsubstituted cycloalkenyloxy" and "substituted or unsubstituted cycloalkenylalkyl" means the above "cycloalkenyl".

The aryl part of "substituted or unsubstituted aryloxy", "substituted or unsubstituted arylthio", "substituted or unsubstituted arylsulfonyl" and "substituted or unsubstituted arylalkyl" means the above "aryl".

The heteroaryl part of "substituted or unsubstituted heteroaryloxy", "substituted or unsubstituted heteroarylthio", "substituted or unsubstituted heteroarylsulfonyl" and "substituted or unsubstituted heteroarylalkyl" means the above "heteroaryl".

The heterocycle part of "substituted or unsubstituted heterocycleoxy", "substituted or unsubstituted heterocyclethio", "substituted or unsubstituted heterocyclesulfonyl" and "substituted or unsubstituted heterocyclealkyl" means the above "heterocycle."

"Hetero ring" means a ring which contains one or more heteroatom(s) selected from the group consisting of N, O and S in the ring. The ring includes a monocycle or a fused ring (bicyclic ring is preferable), and includes an aromatic hetero ring or a nonaromatic hetero ring. As the "hetero ring", for example, the following examples are included:

[Formula 15]

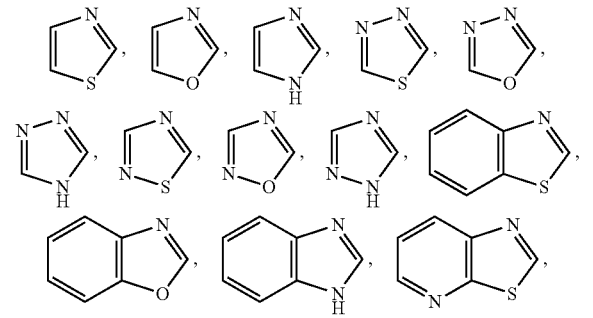

[Formula 16]

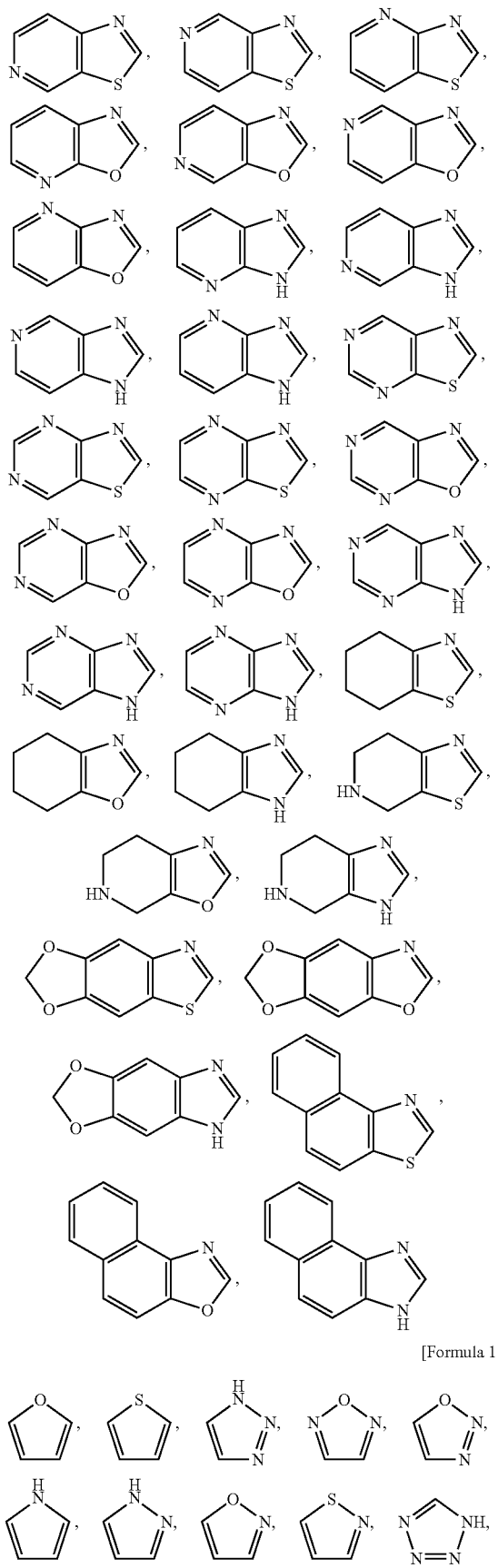

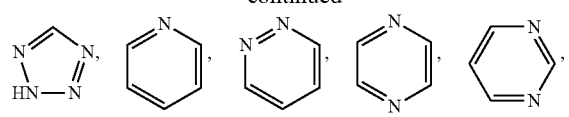
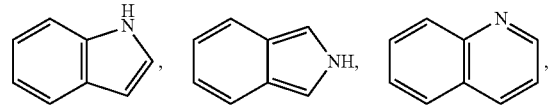
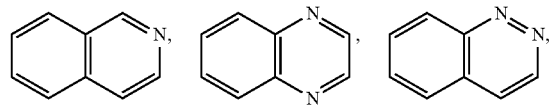
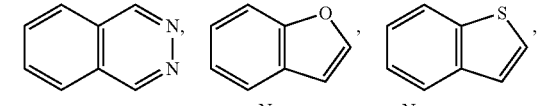
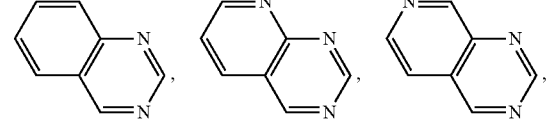
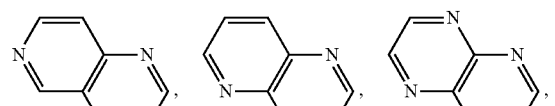
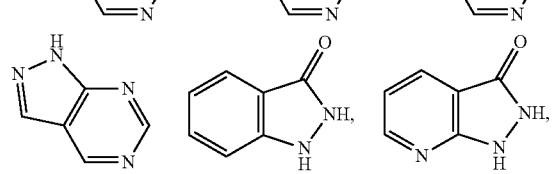
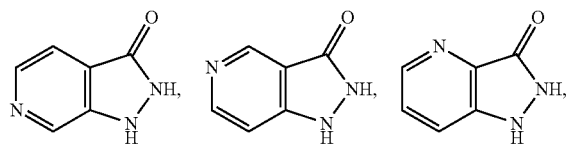
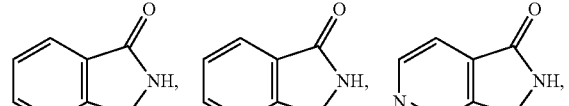
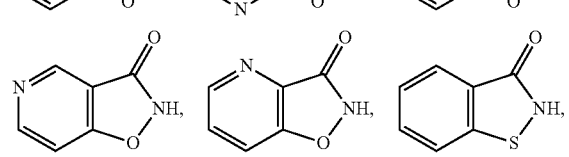
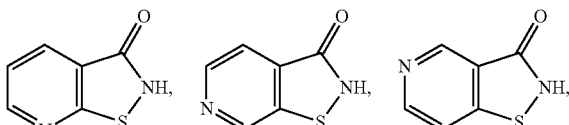
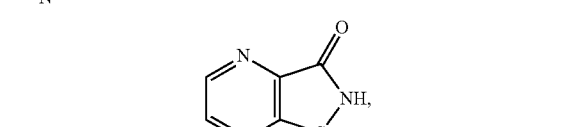
[Formula 17]
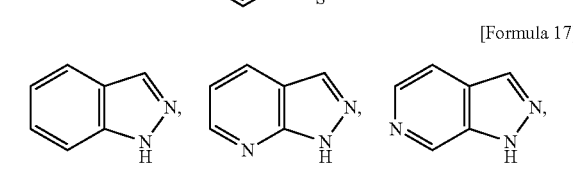
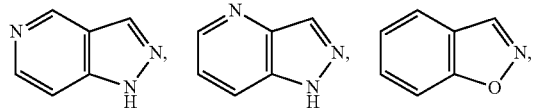
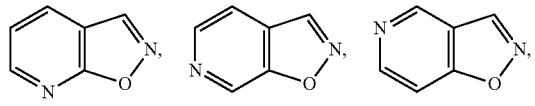
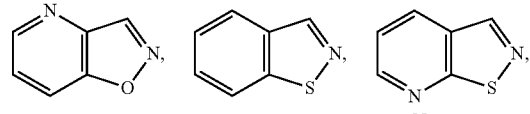
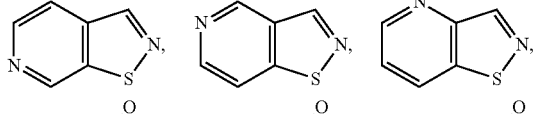
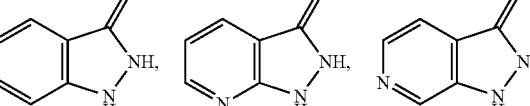
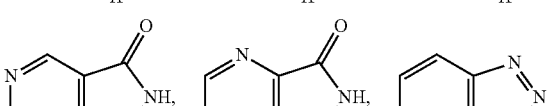
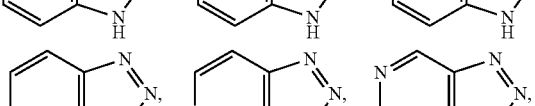
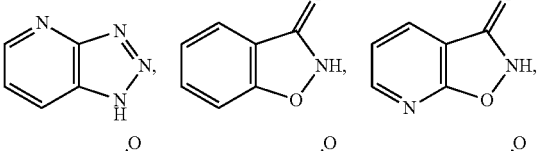
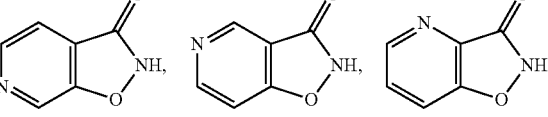
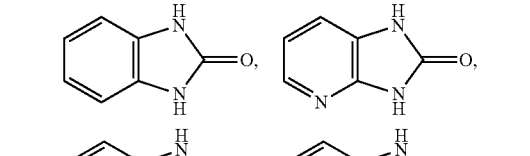
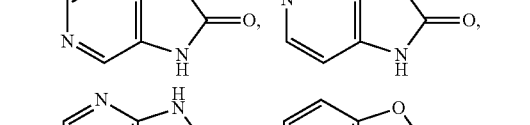
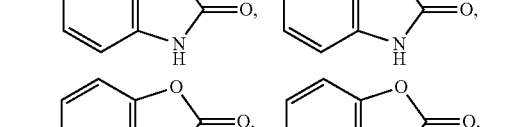
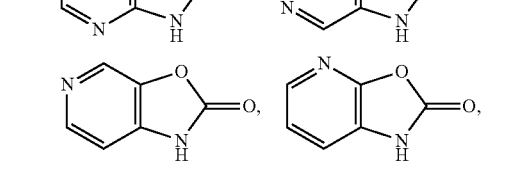

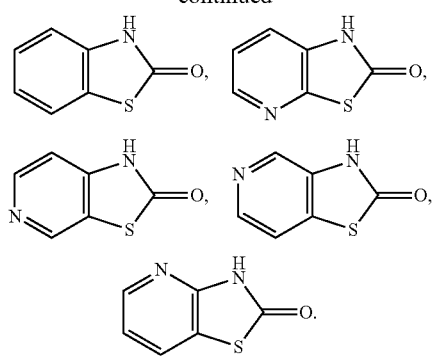

When the above "hetero ring" has a substituent, a substitutable arbitrary position may be substituted and hydrogen of —NH— may be replaced.

"Nitrogen-containing hetero ring" means a ring which contains at least one N in the ring, and moreover may contain O, S or N(R⁶). The ring includes a monocycle or a fused ring, and may include an aromatic hetero ring or a nonaromatic hetero ring. For example, the following examples are included:

[Formula 18]

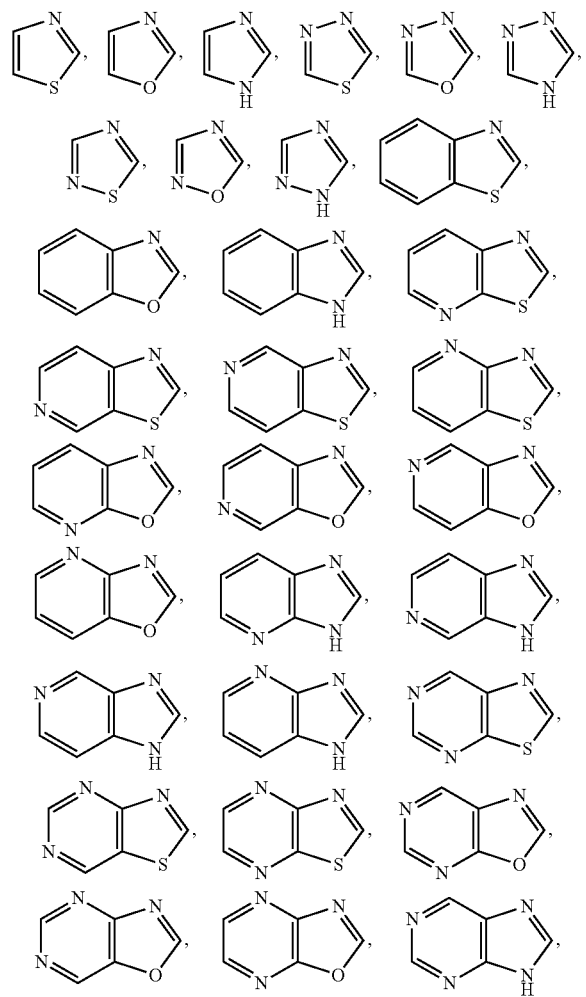

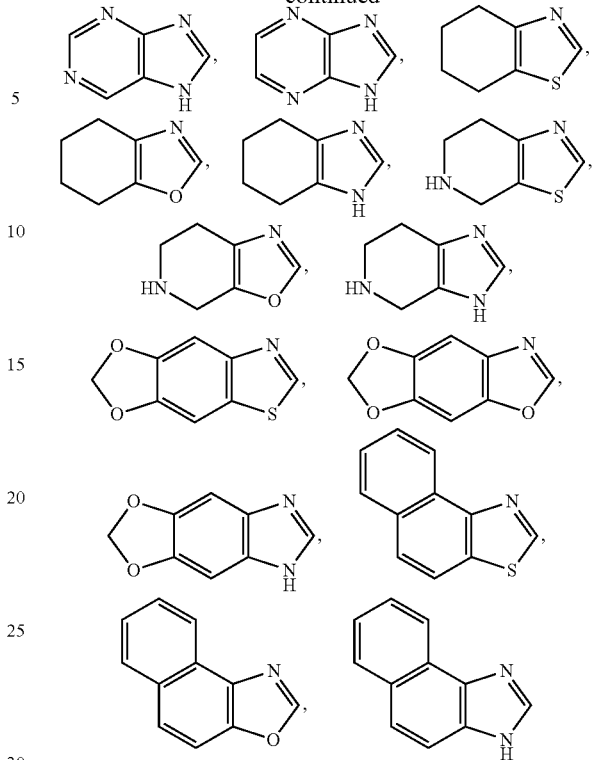

When the above "nitrogen-containing hetero ring" has a substituent, a substitutable arbitrary position may be substituted and hydrogen of —NH— may be replaced.

"substituted or unsubstituted alkyl", "substituted or unsubstituted alkenyl", "substituted or unsubstituted alkynyl", "substituted or unsubstituted aryl", "substituted or unsubstituted heteroaryl", "substituted or unsubstituted cycloalkyl", "substituted or unsubstituted cycloalkenyl", "substituted or unsubstituted heterocycle", "substituted or unsubstituted alkyloxy", "substituted or unsubstituted cycloalkyloxy", "substituted or unsubstituted aryloxy", "substituted or unsubstituted heteroaryloxy", "substituted or unsubstituted heterocycleoxy", "substituted or unsubstituted alkylthio", "substituted or unsubstituted cycloalkylthio", "substituted or unsubstituted cycloalkenylthio", "substituted or unsubstituted arylthio", "substituted or unsubstituted heteroarylthio", "substituted or unsubstituted heterocyclethio", "substituted or unsubstituted alkylsulfonyl", "substituted or unsubstituted cycloalkylsulfonyl", "substituted or unsubstituted cycloalkenylsulfonyl", "substituted or unsubstituted arylsulfonyl", "substituted or unsubstituted heteroarylsulfonyl", "substituted or unsubstituted heterocyclesulfonyl", "substituted or unsubstituted acyl", "substituted or unsubstituted arylalkyl", "substituted or unsubstituted heteroarylalkyl", "substituted or unsubstituted cycloalkylalkyl", "substituted or unsubstituted cycloalkenylalkyl", "substituted or unsubstituted heterocyclealkyl", "substituted or unsubstituted carbamoyl", "substituted or unsubstituted silyloxy", "substituted or unsubstituted carbamoyloxy", "substituted or unsubstituted sulfamoyl", "substituted or unsubstituted alkyloxycarbonyl", "a ring formed by taking together $R^3$ and $R^4$ with the adjacent nitrogen atom to which they are attached" or "a ring formed by taking together $R^3$ and $R^{4a}$ with the adjacent nitrogen atom to which they are attached" may be substituted with 1 to 4 substituent(s) selected from a group consisting of, for example, halogen, hydroxy, carboxy, nitro, cyano, substituted or unsubstituted alkyl (example of a substituent of substituted alkyl includes halogen, hydroxy, carboxy, cyano, amino, alkyl, aryl, cycloalkyl, heteroaryl, heterocycle, alkyloxycarbonyl, alkyloxycarbonylamino or carbamoyl. e.g.: methyl, ethyl, isopropyl, tert-butyl, $CF_3$, $CH_2OH$, $CH_2COOCH_3$, $CH_2NH_2$, benzyl, cyclopentylmethyl, tert-butoxycarbonylaminomethyl or methoxycarbonylmethyl), substituted or unsubstituted alkenyl (example of a substituent of substituted alkenyl includes halogen, carboxy, alkyl, aryl, cycloalkyl, heteroaryl or heterocycle. e.g.: vinyl), substituted or unsubstituted alkynyl (example of a substituent of substituted alkynyl includes halogen, alkyl, aryl, cycloalkyl, heteroaryl or heterocycle. e.g.: ethynyl), substituted or unsubstituted aryl (example of a substituent of substituted aryl includes halogen, alkyl, aryl, cycloalkyl, heteroaryl or heterocycle. e.g.: phenyl or naphthyl), substituted or unsubstituted cycloalkyl (example of a substituent of substituted cycloalkyl includes halogen, alkyl, aryl, cycloalkyl, heteroaryl or heterocycle. e.g.: cyclopropyl), substituted or unsubstituted cycloalkenyl (example of a substituent of substituted cycloalkenyl includes halogen, alkyl, aryl, cycloalkyl, heteroaryl or heterocycle. e.g.: cyclopropenyl), substituted or unsubstituted heteroaryl (example of a substituent of substituted heteroaryl includes halogen, alkyl, aryl, cycloalkyl, heteroaryl or heterocycle. e.g.: tetrazolyl, indolyl or pyrazolyl), substituted or unsubstituted heterocycle (example of a substituent of substituted heterocycle includes halogen, alkyl, aryl, cycloalkyl, heteroaryl or heterocycle. e.g.: pyrrolidinyl, morpholinyl, piperazinyl or piperidyl), substituted or unsubstituted alkyloxy (example of a substituent of substituted alkyloxy includes halogen, carboxy, cyano, alkyl, aryl, cycloalkyl, heteroaryl or heterocycle. e.g.: methoxy, ethoxy, propoxy, butoxy or $OCF_3$), substituted or unsubstituted aryloxy (example of a substituent of substituted aryloxy includes halogen, alkyl, aryl, cycloalkyl, heteroaryl or heterocycle. e.g.: phenyloxy), substituted or unsubstituted silyloxy, substituted or unsubstituted amino (e.g.: alkylamino (e.g.: methylamino, ethylamino or dimethylamino), acylamino (e.g.: acetylamino or benzoylamino), arylalkylamino (e.g.: benzylamino or tritylamino), hydroxyamino, alkylaminoalkyl (e.g.: diethylaminomethyl), alkyloxycarbonylamino, alkylsulfonylamino, carbamoylamino, heterocyclecarbonylamino, arylsulfonylamino, heteroarylsulfonylamino), substituted or unsubstituted carbamoyl (example of a substituent of substituted carbamoyl includes hydroxy, cyano, substituted or unsubstituted alkyl, alkyloxy or alkylsulfonyl. e.g.: alkylcarbamoyl (e.g.: methylcarbamoyl, ethylcarbamoyl, dimethylcarbamoyl, phenylethylcarbamoyl, dimethylaminoethylcarbamoyl, isopropylcarbamoyl or hydroxyethylcarbamoyl), alkylsulfonylcarbamoyl, heteroarylalkylcarbamoyl or substituted or unsubstituted alkyloxycarbamoyl), substituted or unsubstituted carbamoyloxy (example of a substituent of substituted carbamoyloxy includes halogen, alkyl, aryl, cycloalkyl, heteroaryl or heterocycle), substituted or unsubstituted acyl (example of a substituent of substituted acyl includes halogen, alkyl, aryl, cycloalkyl, heteroaryl or heterocycle. e.g.: alkylcarbonyl, arylcarbonyl, heteroarylcarbonyl, heterocyclecarbonyl, formyl or acetyl), substituted or unsubstituted alkylsulfonyl (example of a substituent of substituted alkylsulfonyl includes halogen, alkyl, aryl, cycloalkyl, heteroaryl or heterocycle. e.g.: methanesulfonyl or ethanesulfonyl), substituted or unsubstituted arylsulfonyl, substituted or unsubstituted heteroarylsulfonyl (example of a substituent of substituted heteroarylsulfonyl includes halogen, alkyl, aryl, cycloalkyl, heteroaryl or heterocycle), substituted or unsubstituted sulfamoyl, substituted or unsubstituted alkyloxycarbonyl (example of a substituent of substituted alkyloxycarbonyl includes halogen, alkyl, aryl, cycloalkyl, heteroaryl or heterocycle. e.g.: methoxycarbonyl, ethoxycarbonyl or tort-butoxycarbonyl), aryloxycarbonyl, heteroaryloxycarbonyl, heterocycleoxycarbonyl, cycloalkylsulfonyl, heteroarylsulfonyl, heterocyclesulfonyl, alkylsulfinyl, cycloalkylsulfinyl, arylsulfinyl, heteroarylsulfinyl, heterocyclesulfinyl, nitroso, alkenyloxy (e.g.: vinyloxy or allyloxy), arylalkyloxy (e.g.: benzyloxy), azide, isocyano, isocyanato, thiocyanato, isothiocyanato, mercapto, alkylthio (e.g.: methylthio), formyloxy, haloformyl, oxalo, thioformyl, thiocarboxy, dithiocarboxy, thiocarbamoyl, sulfino, sulfo, sulfoamino, hydrazino, ureide, amidino, guanidino, phthalimide, oxo and the like.

Example of a substituent of "substituted or unsubstituted amino", "substituted or unsubstituted carbamoyl", "substituted or unsubstituted carbamoyloxy" or "substituted or unsubstituted sulfamoyl" includes alkyl, alkenyl, substituted or unsubstituted aryl (example of a substituent of substituted aryl includes carboxy, alkyloxy or sulfamoyl), heteroaryl, alkylcarbonyl, arylcarbonyl, heteroarylcarbonyl, heterocyclecarbonyl, alkyloxycarbonyl, aryloxycarbonyl, heteroaryloxycarbonyl, heterocycleoxycarbonyl, sulfamoyl, alkylsulfonyl, carbamoyl, cycloalkylsulfonyl, arylsulfonyl, heteroarylsulfonyl, heterocyclesulfonyl, acyl, hydroxy, alkylsulfinyl, cycloalkylsulfinyl, arylsulfinyl, heteroarylsulfinyl, heterocyclesulfinyl, amino or the like.

The alkyl part of "alkyloxycarbonyl", "alkyloxycarbonylamino", "alkylamino", "arylalkylamino", "alkylaminoalkyl", "alkyloxycarbonylamino", "alkylsulfonylamino", "alkylcarbamoyl", "alkylsulfonylcarbamoyl", "substituted or unsubstituted alkyloxycarbamoyl", "alkylcarbonyl", "alkylsulfinyl", "arylalkyloxy", "alkylthio" and "alkylsulfonyl" means the above "alkyl".

The alkenyl part of "alkenyloxy" means the above "alkenyl".

The aryl part of "arylalkylamino", "arylsulfonylamino", "arylcarbonyl", "aryloxycarbonyl", "arylsulfinyl", "arylalkyloxy" and "arylsulfonyl" means the above "aryl".

The heteroaryl part of "heteroarylcarbonyl", "heteroaryloxycarbonyl", "heteroarylsulfonyl" and "heteroarylsulfinyl" means the above "heteroaryl".

The heterocycle part of "heterocyclecarbonyl", "heterocyclecarbonylamino", "heterocycleoxycarbonyl", "heterocyclesulfonyl" and "heterocyclesulfinyl" means the above "heterocycle."

The cycloalkyl part of "cycloalkylsulfonyl" and "cycloalkylsulfinyl" means the above "cycloalkyl".

Among the present compound, the following embodiments are preferable.

Ring A in the formula (I) is nitrogen-containing hetero ring in which one atom neighboring to the carbon atom binding to a group represented by the formula: —C($R^1R^2$)—C(=O)—

NR³R⁴ is nitrogen atom and the other atom is heteroatom. The broken line in the formula (I) means the presence or absence of a bond.

Ring A is not only a monocycle but also a fused ring (2 to 3 fused ring), and especially a monocycle or a bicycle is preferable. Ring A may include a heteroatom other than the nitrogen atom shown in the above formula (I) and the constituent atom of the Ring A includes carbon atom, oxygen atom, nitrogen atom or sulfur atom. The bond constructing the Ring A includes a single bond or a double bond.

Ring A may be substituted with a substituent other than a group represented by the formula: —C(R¹R²)—C(=O)—NR³R⁴ and a group represented by the formula: —R⁵.

For example, as the group represented by the formula:

[Formula 19]

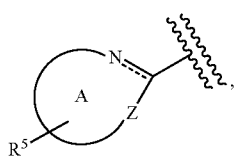

the following rings are included:

[Formula 20]

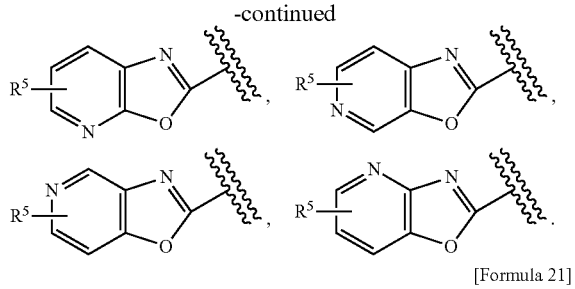

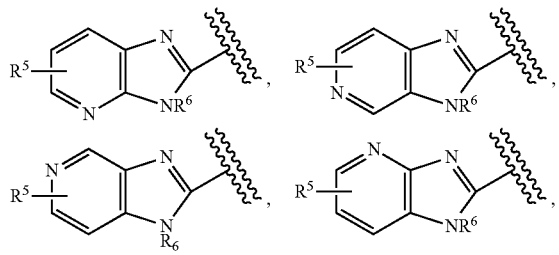

-continued

[Formula 21]

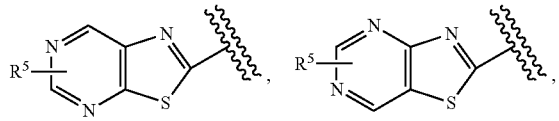

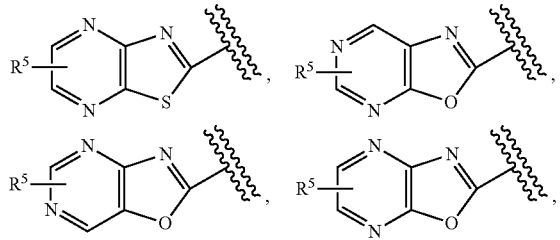

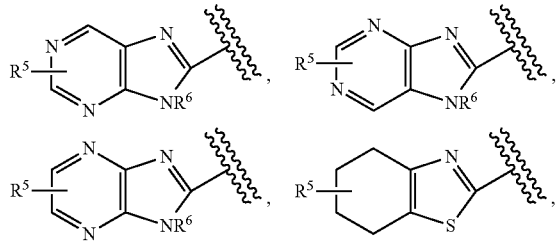

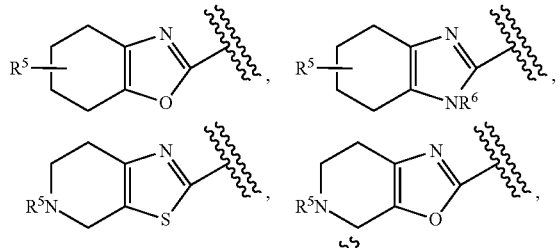

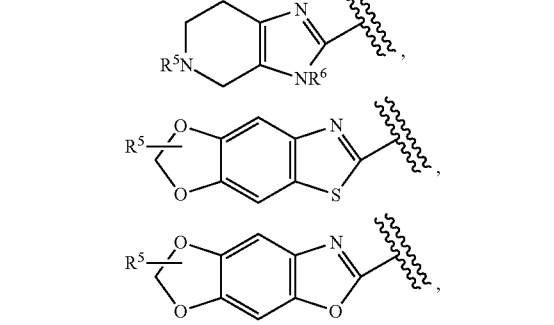

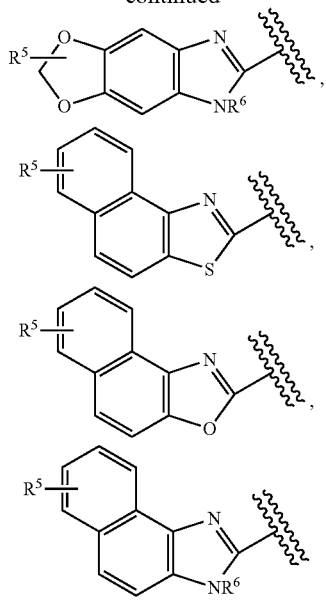

wherein $R^5$ and $R^6$ have the same meaning as the above. In the above formula, a substitutable arbitrary position in Ring A may be substituted with $R^5$. A constituent atom of the Ring A other than a position which is substituted with $R^5$ and $R^6$ may be substituted with a substituent other than $R^5$ and $R^6$.

Preferably, the following rings are included:

[Formula 22]

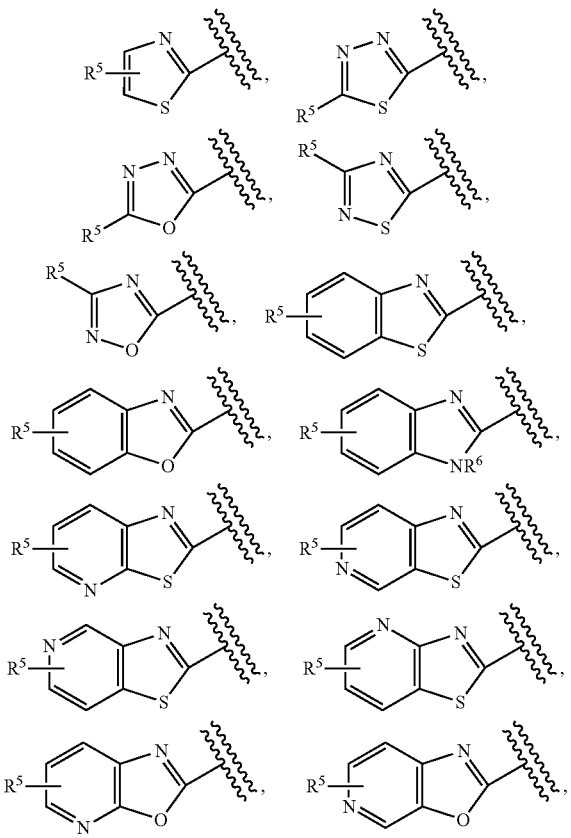

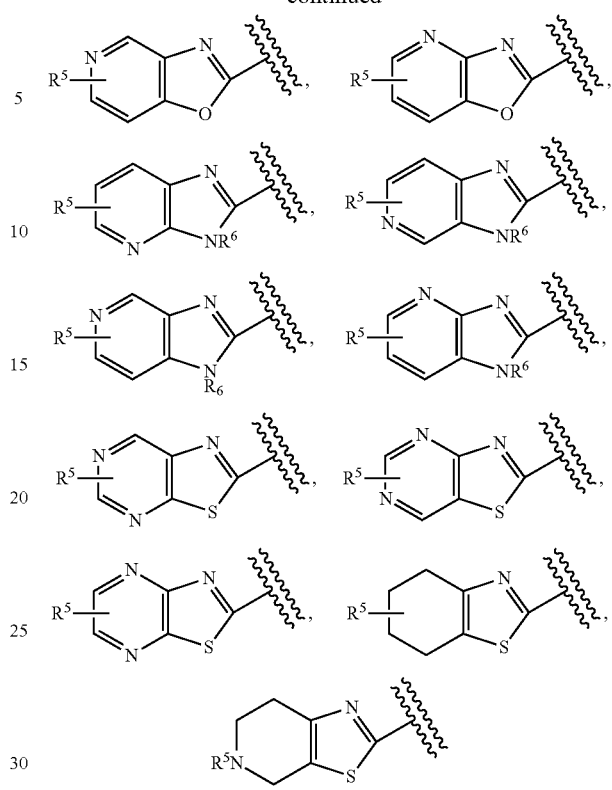

More preferably, the following rings are included:

[Formula 23]

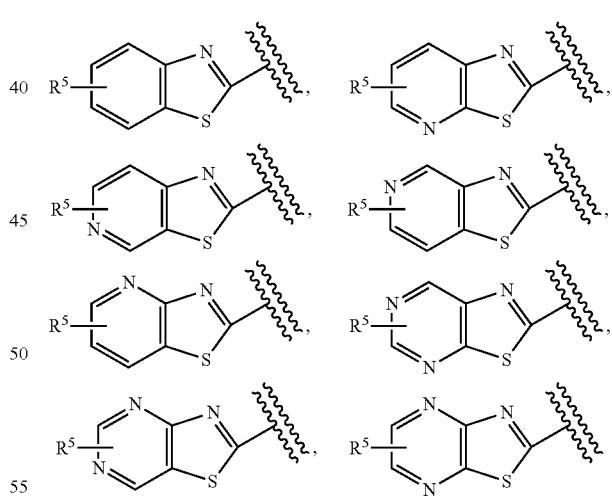

Particular preferably, the following rings are included:

[Formula 24]

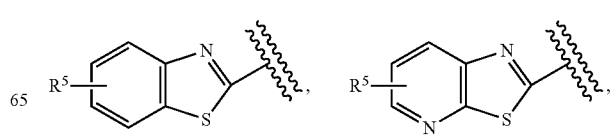

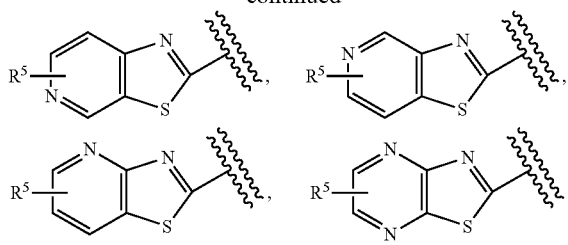

In the above Ring A, a substitutable arbitrary position may be substituted with a substituent other than $R^5$ and $R^6$.

As a substituent other than a group represented by the formula: —C($R^1R^2$)—C(=O)—$NR^3R^4$ and a group represented by the formula: —$R^5$, example includes halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl, substituted or unsubstituted acyl, substituted or unsubstituted carbamoyl, substituted or unsubstituted amino or the like. Ring A may be substituted with 1 to 3 of the substituent(s).

Z is —$NR^6$—, =N—, —O—, or —S—. Preferable is —O— or —S— and more preferable is —S—.

$R^6$ of —$NR^6$— in Z is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl or substituted or unsubstituted heterocycle. Preferable is hydrogen or substituted or unsubstituted alkyl.

$R^1$ and $R^2$ are each independently hydrogen, halogen, cyano, nitro, carboxy or substituted or unsubstituted alkyl. Preferable is hydrogen or substituted or unsubstituted alkyl. More preferable is hydrogen.

$R^3$ is hydrogen or substituted or unsubstituted alkyl. Preferable is hydrogen.

$R^4$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle or substituted or unsubstituted amino.

Preferable is substituted or unsubstituted alkyl, substituted or unsubstituted aryl, substituted or unsubstituted heteroaryl, substituted or unsubstituted cycloalkyl, substituted or unsubstituted heterocycle or substituted or unsubstituted amino.

More preferable is substituted or unsubstituted alkyl.

$R^5$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl, substituted or unsubstituted acyl, substituted or unsubstituted carbamoyl or substituted or unsubstituted amino.

Preferable is substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl or substituted or unsubstituted amino.

More preferable is substituted or unsubstituted aryl, substituted or unsubstituted heteroaryl, substituted or unsubstituted aryloxy, substituted or unsubstituted heteroaryloxy, substituted or unsubstituted arylthio, substituted or unsubstituted heteroarylthio, substituted or unsubstituted arylsulfonyl, substituted or unsubstituted heteroarylsulfonyl or substituted or unsubstituted amino.

$Z^1$ is —O— or —S—. Preferable is —S—.

Ring B in the formula (II) is aromatic carbocycle, aromatic hetero ring, nonaromatic carbocycle or nonaromatic hetero ring which is fused with the adjacent 5 membered ring. A substitutable arbitrary position in Ring B is substituted with $R^5$ (including hydrogen), a substitutable arbitrary position other than a position which is substituted with $R^5$ may be substituted with 0 to 3 of $R^x$.

"Aromatic carbocycle" means a monocyclic aromatic carbocycle (e.g.: benzene ring) or a fused aromatic carbocycle. Herein, as the "fused aromatic carbocycle", example includes C10 to C14 fused aromatic carbocycle or the like. Example includes naphthalene, phenanthrene, anthracene or the like.

"Aromatic hetero ring" means a aromatic ring which contains one or more heteroatom(s) selected from the group consisting of nitrogen atom, sulfur atom and oxygen atom other than the carbon atom in the ring. The ring includes a monocycle or a fused ring.

"Nonaromatic carbocycle" means a 5 to 10 membered nonaromatic carbocycle which may have a saturated or an unsaturated bond partially and may be fused with aryl or heteroaryl.

"Nonaromatic hetero ring" means a nonaromatic ring which contains one or more heteroatom(s) selected from the group consisting of nitrogen atom, sulfur atom and oxygen atom other than the carbon atom in the ring. The ring means a 5 to 10 membered ring which may have a saturated or an unsaturated bond partially and may be fused with aryl or aromatic hetero ring.

As the Ring B, for example, the following rings are included. In the following rings, a substitutable arbitrary position other than a position which is substituted with $R^5$ (including hydrogen) may be substituted with 0 to 3 of $R^x$.

[Formula 25]

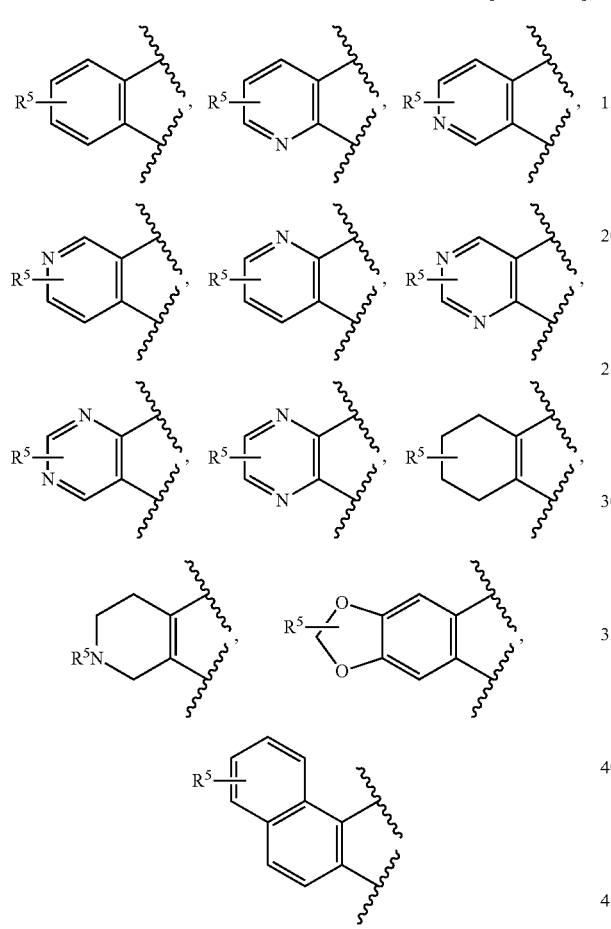

Herein, $R^5$ has the same meaning as the above.
Preferably, the following rings are included:

[Formula 26]

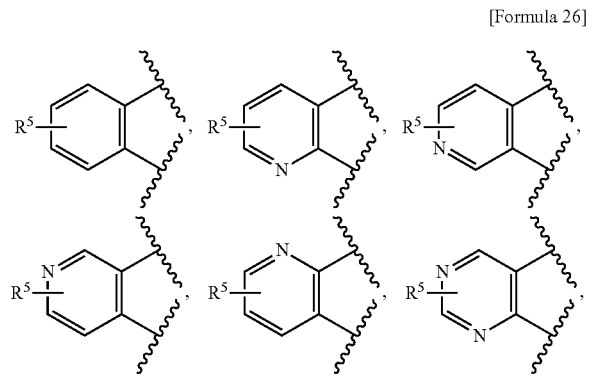

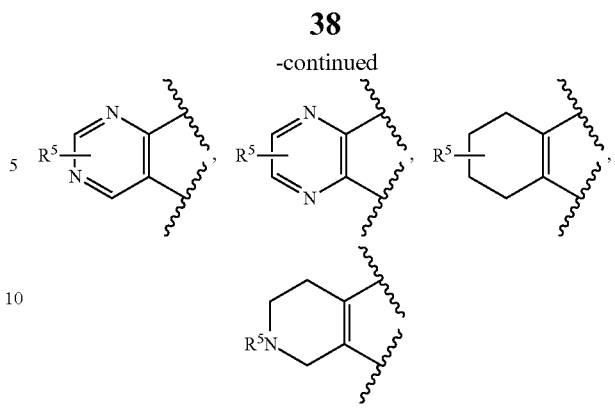

More preferably, the following rings are included:

[Formula 27]

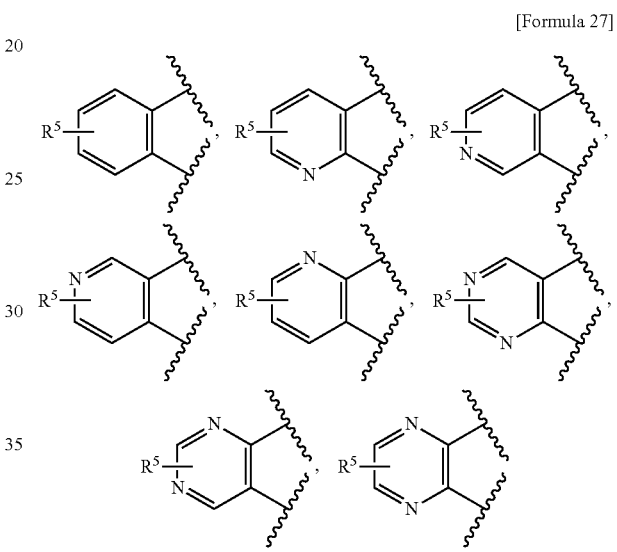

Particular preferably, the following rings are included:

[Formula 28]

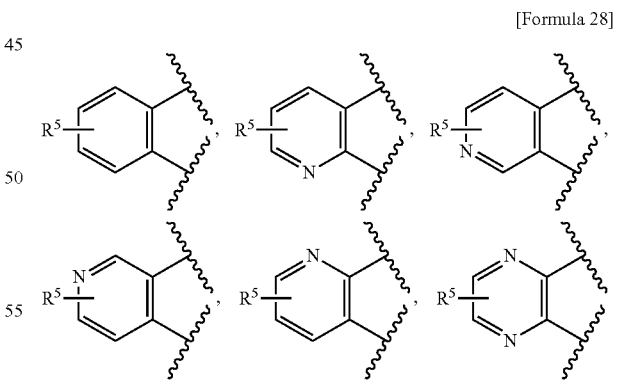

$R^{4a}$ is substituted or unsubstituted arylalkyl, substituted or unsubstituted heteroarylalkyl, substituted or unsubstituted cycloalkylalkyl, substituted or unsubstituted cycloalkenylalkyl, substituted or unsubstituted heterocyclealkyl,
a group represented by the formula: —$(CR^7R^8)n$-C(=O)—$R^9$, wherein $R^7$ and $R^8$ are each independently hydrogen, halogen, hydroxy, carboxy, substituted or unsubstituted alkyl, substituted or unsubstituted alkyloxy, substituted or unsubstituted aryl, substituted or unsubstituted heteroaryl, substituted or unsubstituted cycloalkyl, substituted or unsubstituted cycloalkenyl or substituted or unsubstituted heterocycle, n is an integer of 1 to 10, $R^9$ is —$OR^{10}$ or —$NR^{11}R^{12}$, $R^{10}$ is hydrogen, substituted or unsubstituted alkyl, substituted or unsubstituted aryl, substituted or unsubstituted heteroaryl, substituted or unsubstituted cycloalkyl, substituted or unsubstituted cycloalkenyl or substituted or unsubstituted heterocycle, $R^{11}$ and $R^{12}$ are each independently hydrogen, substituted or unsubstituted alkyl, substituted or unsubstituted alkyloxy, substituted or unsubstituted aryloxy, substituted or unsubstituted heteroaryloxy, substituted or unsubstituted alkylsulfonyl, substituted or unsubstituted aryl, substituted or unsubstituted heteroaryl, substituted or unsubstituted cycloalkyl, substituted or unsubstituted cycloalkenyl or substituted or unsubstituted heterocycle or a group represented by the formula: —$C(R^7R^8)n$-O—$R^{13}$, wherein $R^7$, $R^8$ and n are as defined in the above, $R^{13}$ is hydrogen or substituted or unsubstituted alkyl.

Preferable is substituted or unsubstituted arylalkyl, substituted or unsubstituted heteroarylalkyl or a group represented by the formula: —$(CR^7R^8)n$-C(=O)—$R^9$.

Especially as the substituted or unsubstituted arylalkyl or substituted or unsubstituted heteroarylalkyl in $R^{4a}$, the following groups are preferably included:

[Formula 29]

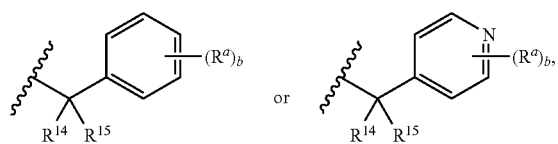

wherein $R^a$, $R^{14}$, and $R^{15}$ are as defined in the above (18).

b is an integer of 0 to 3. Preferable is 1 or 2.

As the substituted or unsubstituted arylalkyl or substituted or unsubstituted heteroarylalkyl in $R^{4a}$, the following groups are more preferably included:

[Formula 30]

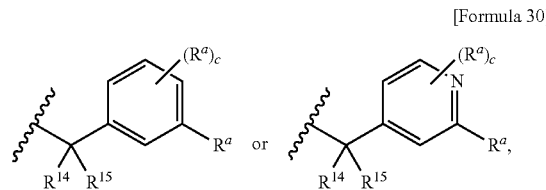

wherein $R^a$, $R^{14}$, and $R^{15}$ are as defined in the above (18).

c is an integer of 0 to 2.

$R^a$ is halogen, hydroxy, carboxy, nitro, cyano, azide, substituted or unsubstituted alkyl, substituted or unsubstituted alkenyl, substituted or unsubstituted alkynyl, substituted or unsubstituted aryl, substituted or unsubstituted cycloalkyl, substituted or unsubstituted cycloalkenyl, substituted or unsubstituted heteroaryl, substituted or unsubstituted heterocycle, substituted or unsubstituted alkyloxy, substituted or unsubstituted aryloxy, substituted or unsubstituted silyloxy, substituted or unsubstituted amino, substituted or unsubstituted carbamoyl, substituted or unsubstituted carbamoyloxy, substituted or unsubstituted acyl, substituted or unsubstituted alkylsulfonyl, substituted or unsubstituted arylsulfonyl, substituted or unsubstituted heterocyclesulfonyl, substituted or unsubstituted sulfamoyl or substituted or unsubstituted alkyloxycarbonyl.

Preferable is carboxy, cyano, substituted or unsubstituted heteroaryl, substituted or unsubstituted amino, substituted or unsubstituted carbamoyl, substituted or unsubstituted carbamoyloxy, substituted or unsubstituted alkylsulfonyl or substituted or unsubstituted sulfamoyl.

More preferable is carboxy, substituted or unsubstituted heteroaryl, substituted or unsubstituted carbamoyl, substituted or unsubstituted carbamoyloxy, substituted or unsubstituted alkylsulfonyl or substituted or unsubstituted sulfamoyl.

$R^7$ and $R^8$ are each independently hydrogen, halogen, hydroxy, carboxy, substituted or unsubstituted alkyl, substituted or unsubstituted alkyloxy, substituted or unsubstituted aryl, substituted or unsubstituted heteroaryl, substituted or unsubstituted cycloalkyl, substituted or unsubstituted cycloalkenyl or substituted or unsubstituted heterocycle.

Preferable is hydrogen.

n is an integer of 1 to 10. Preferable is an integer of 1 to 3. More preferable is 1.

$R^{10}$ is hydrogen, substituted or unsubstituted alkyl, substituted or unsubstituted aryl, substituted or unsubstituted heteroaryl, substituted or unsubstituted cycloalkyl, substituted or unsubstituted cycloalkenyl or substituted or unsubstituted heterocycle.

Preferable is hydrogen or substituted or unsubstituted alkyl.

$R^{11}$ and $R^{12}$ are each independently hydrogen, substituted or unsubstituted alkyl, substituted or unsubstituted alkyloxy, substituted or unsubstituted aryloxy, substituted or unsubstituted heteroaryloxy, substituted or unsubstituted alkylsulfonyl, substituted or unsubstituted aryl, substituted or unsubstituted heteroaryl, substituted or unsubstituted cycloalkyl, substituted or unsubstituted cycloalkenyl or substituted or unsubstituted heterocycle.

$R^{11}$ is preferably hydrogen.

$R^{12}$ is preferably substituted or unsubstituted alkyl, substituted or unsubstituted alkyloxy, substituted or unsubstituted aryloxy, substituted or unsubstituted heteroaryloxy, substituted or unsubstituted alkylsulfonyl, substituted or unsubstituted aryl, substituted or unsubstituted heteroaryl, substituted or unsubstituted cycloalkyl, substituted or unsubstituted cycloalkenyl or substituted or unsubstituted heterocycle.

"A ring formed by taking together $R^3$ and $R^4$ with the adjacent nitrogen atom to which they are attached" and "a ring formed by taking together $R^3$ and $R^{4a}$ with the adjacent nitrogen atom to which they are attached" mean 3- to 15-membered nonaromatic hetero ring which may contain 1 to 4 oxygen, sulfur, and/or nitrogen atom(s) besides the above nitrogen atom in the ring. Moreover, the nonaromatic hetero ring can be bridged with a C1 to C4 alkyl chain, or can be fused with cycloalkane (5- to 6-membered ring is preferable) or benzene ring. The ring can be saturated or unsaturated partially as long as it is nonaromatic. Preferable is a 5- to 8-membered ring. For example, the following groups are exemplified.

[Formula 31]

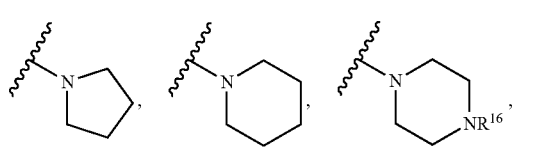

-continued

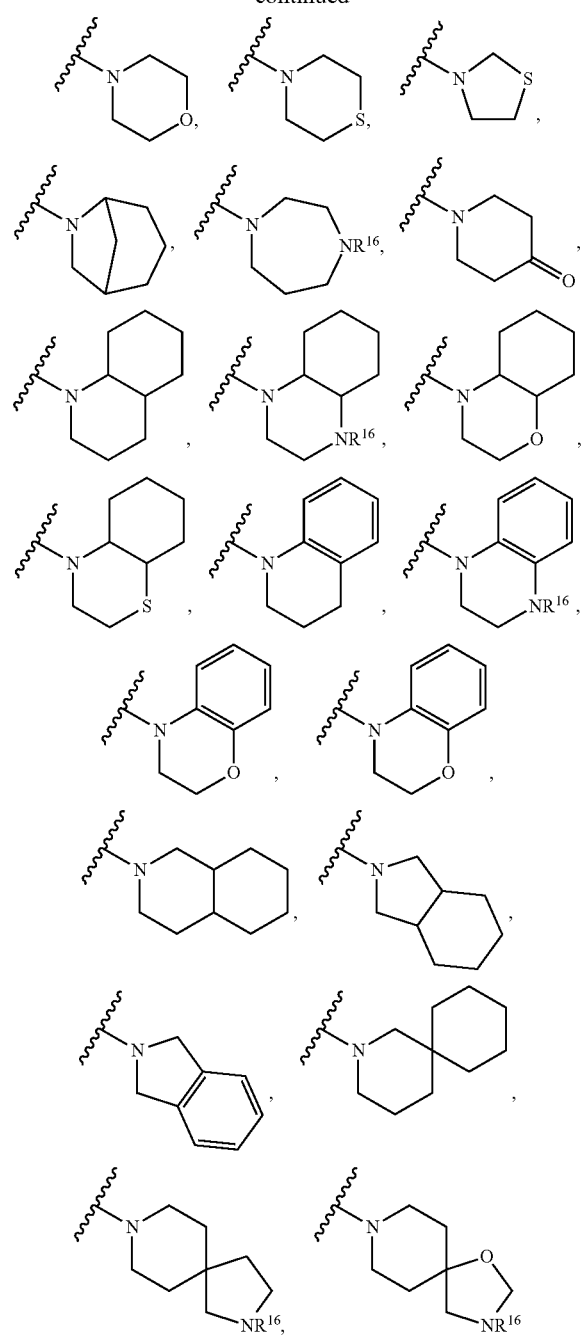

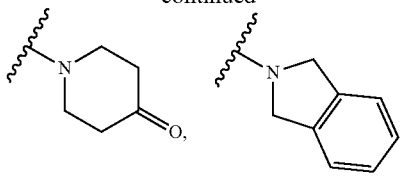

Herein, $R^{16}$ is hydrogen or substituted or unsubstituted alkyl.

Preferably, the following groups are exemplified.

[Formula 32]

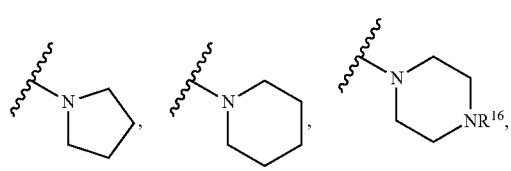

$R^X$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl, substituted or unsubstituted acyl, substituted or unsubstituted carbamoyl or substituted or unsubstituted amino.

m is an integer of 0 to 3. Preferable is 0 or 1.

X in the formula (III) and (IV) is —$CR^X$=, —CH= or —N=. Preferable is —CH=.

Y in the formula (III) and (IV) is —$CR^X$=, —CH= or —N=. Preferable is —CH=.

Ring C in the formula (V) is a monocyclic or bicyclic hetero ring and may include an aromatic hetero ring or a nonaromatic hetero ring. A substitutable arbitrary position in Ring C is substituted with $R^5$ (including hydrogen) and a substitutable arbitrary position other than a position which is substituted with $R^5$ may be substituted with 0 to 3 of $R^X$.

The constituent atom of the Ring C includes carbon atom, oxygen atom, nitrogen atom or sulfur atom. The bond constructing the Ring C includes a single bond or a double bond.

For example, the following rings are exemplified.

[Formula 33]

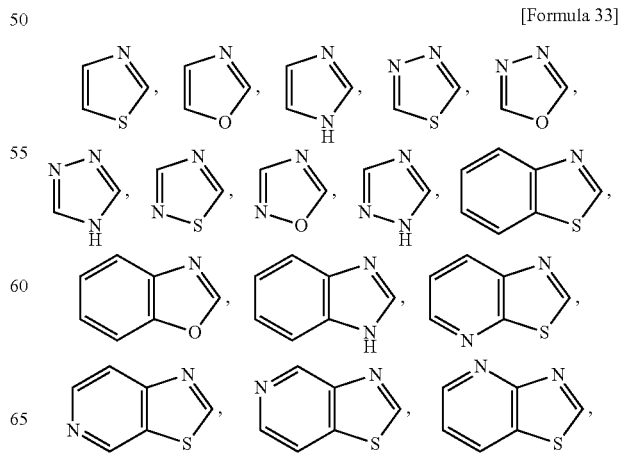

43
-continued
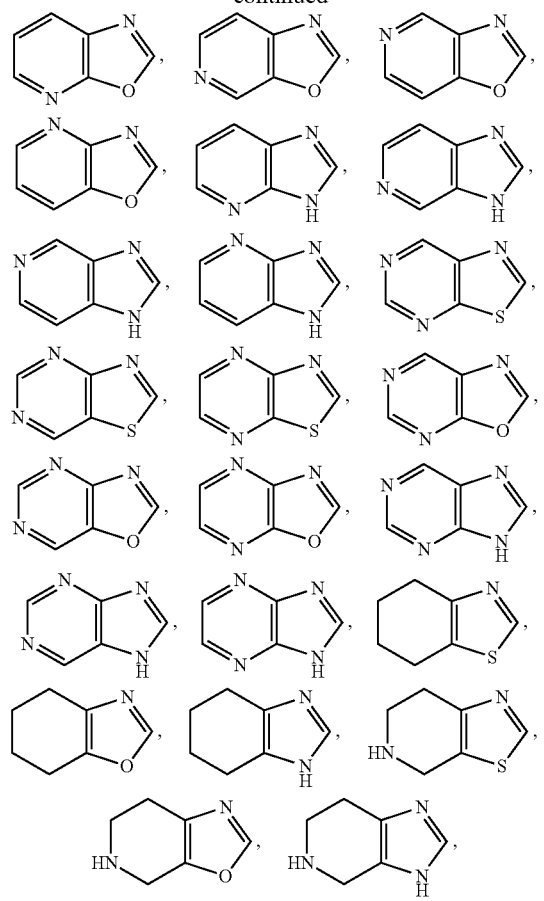
[Formula 34]
44
-continued
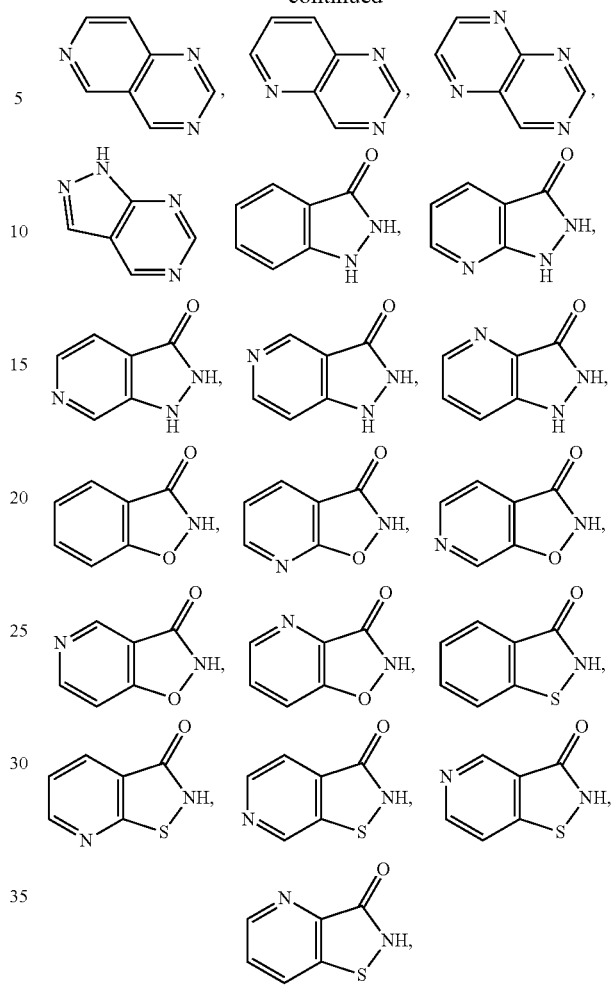
[Formula 35]
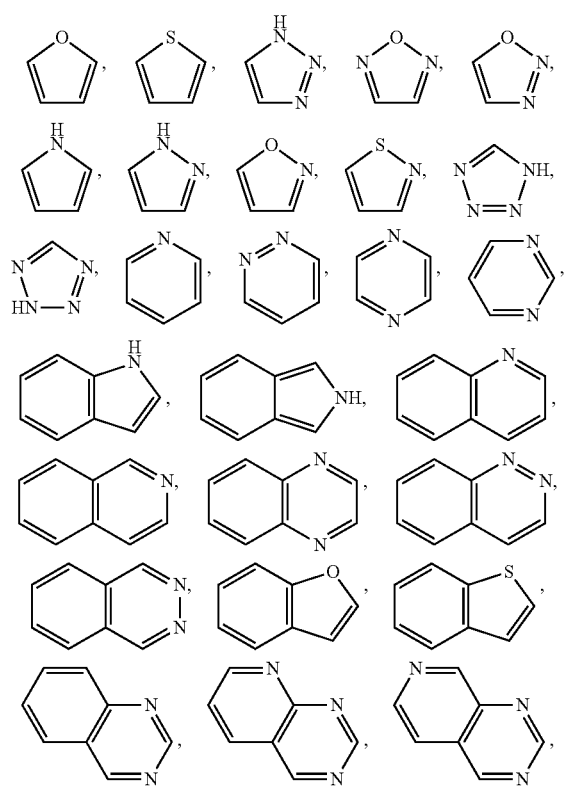
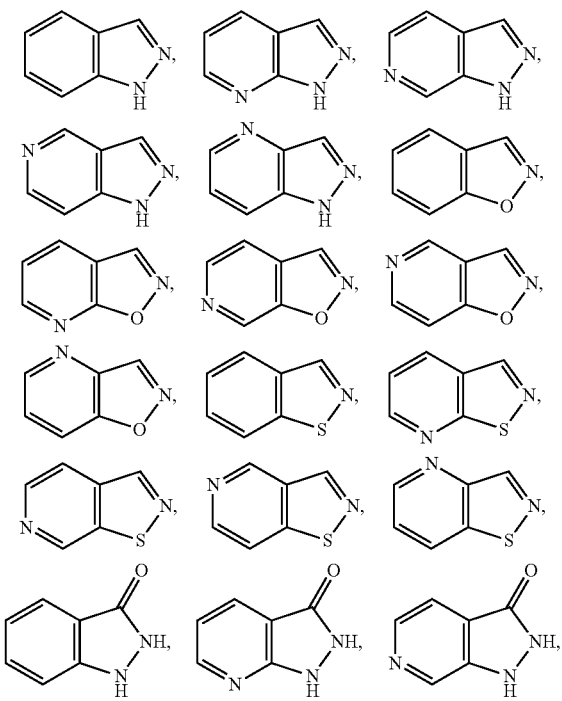

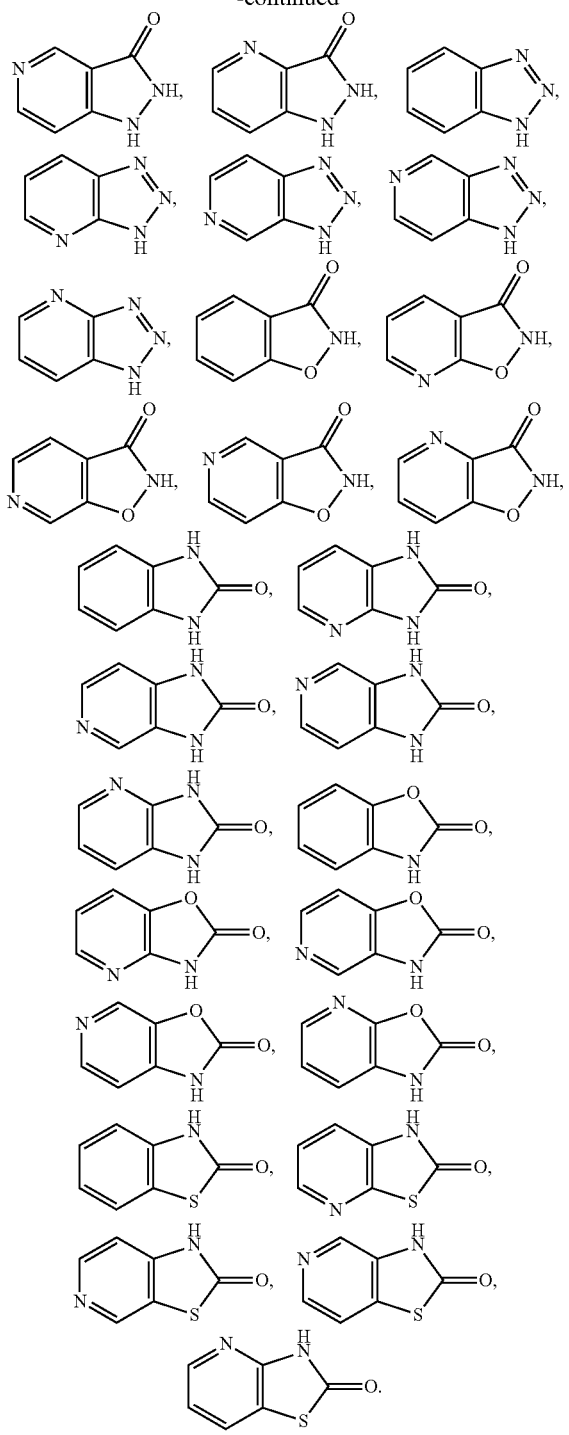

A substitutable arbitrary position in the above Ring C may be substituted with a group represented by the formula: —CH$_2$—C(=O)—NHR$^{4b}$, a group represented by the formula: —R$^5$ and a group represented by the formula: —R$^X$.

Hydrogen of —NH— in the above ring may be replaced by a group represented by the formula: —CH$_2$—C(=O)—NHR$^{4b}$, a group represented by the formula: —R$^5$ or a group represented by the formula: —R$^X$.

R$^{4b}$ in the formula (V) is substituted arylalkyl, wherein a substituent on a ring of the substituted arylalkyl is carboxy, substituted or unsubstituted carbamoyl, substituted or unsubstituted alkylsulfonyl or substituted or unsubstituted sulfamoyl, substituted heteroarylalkyl, wherein a substituent on a ring of the substituted heteroarylalkyl is carboxy, substituted or unsubstituted carbamoyl, substituted or unsubstituted alkylsulfonyl or substituted or unsubstituted sulfamoyl, substituted cycloalkylalkyl, wherein a substituent on a ring of the substituted cycloalkylalkyl is carboxy, substituted or unsubstituted carbamoyl, substituted or unsubstituted alkylsulfonyl or substituted or unsubstituted sulfamoyl, substituted cycloalkenylalkyl, wherein a substituent on a ring of the substituted cycloalkenylalkyl is carboxy, substituted or unsubstituted carbamoyl, substituted or unsubstituted alkylsulfonyl or substituted or unsubstituted sulfamoyl, substituted heterocyclealkyl, wherein a substituent on a ring of the substituted heterocyclealkyl is carboxy, substituted or unsubstituted carbamoyl, substituted or unsubstituted alkylsulfonyl or substituted or unsubstituted sulfamoyl or a group represented by the formula: —(CR$^7$R$^8$)n-C(=O)—R$^9$, wherein R$^7$ and R$^8$ are each independently hydrogen, halogen, hydroxy, carboxy, substituted or unsubstituted alkyl, substituted or unsubstituted alkyloxy, substituted or unsubstituted aryl, substituted or unsubstituted heteroaryl, substituted or unsubstituted cycloalkyl, substituted or unsubstituted cycloalkenyl or substituted or unsubstituted heterocycle, n is an integer of 1 to 10, R$^9$ is —OR$^{10}$ or —NR$^{11}$R$^{12}$, R$^{10}$ is hydrogen, substituted or unsubstituted alkyl, substituted or unsubstituted aryl, substituted or unsubstituted heteroaryl, substituted or unsubstituted cycloalkyl, substituted or unsubstituted cycloalkenyl or substituted or unsubstituted heterocycle, R$^{11}$ and R$^{12}$ are each independently hydrogen, substituted or unsubstituted alkyl, substituted or unsubstituted alkyloxy, substituted or unsubstituted aryloxy, substituted or unsubstituted heteroaryloxy, substituted or unsubstituted alkylsulfonyl, substituted or unsubstituted aryl, substituted or unsubstituted heteroaryl, substituted or unsubstituted cycloalkyl, substituted or unsubstituted cycloalkenyl or substituted or unsubstituted heterocycle.

Preferable is substituted arylalkyl, wherein a substituent on a ring of the substituted arylalkyl is carboxy, substituted or unsubstituted carbamoyl, substituted or unsubstituted alkylsulfonyl or substituted or unsubstituted sulfamoyl, substituted heteroarylalkyl, wherein a substituent on a ring of the substituted heteroarylalkyl is carboxy, substituted or unsubstituted carbamoyl, substituted or unsubstituted alkylsulfonyl or substituted or unsubstituted sulfamoyl or a group represented by the formula: —(CR$^7$R$^8$)n-C(=O)—R$^9$.

As a pharmaceutically acceptable salt of the present compound, the following salts can be included.

As a basic salt, example includes alkali metal salt such as sodium salt or potassium salt; alkaline earth metal salt such as calcium salt or magnesium salt; ammonium salt; aliphatic amine salt such as trimethylamine salt, triethylamine salt, dicyclohexylamine salt, ethanolamine salt, diethanolamine salt, triethanolamine salt, procaine salt, meglumine salt, diethanolamine salt or ethylenediamine salt; aralkylamine salt such as N,N-dibenzylethylenediamine salt or benethamine salt; heterocyclic aromatic amine salt such as pyridine salt, picoline salt, quinoline salt, or isoquinoline salt; quaternary ammonium salt such as tetramethylammonium salt, tetraethylammonium salt, benzyltrimethylammonium salt, benzyltriethylammonium salt, benzyltributylammonium salt, methyltrioctylammonium salt, or tetrabutylammonium salt; basic amino acid salt such as arginine salt or lysine salt or the like.

As an acidic salt, example includes inorganic acid salt such as hydrochloride, sulfate, nitrate, phosphate, carbonate, hydrogencarbonate, or perchlorate; organic acid salt such as acetate, propionate, lactate, maleate, fumarate, tartrate, malate, citrate or ascorbate; sulfonate such as methanesulfonate, isethionate, benzenesulfonate or p-toluenesulfonate; acidic amino acid salt such as aspartate or glutamate or the like.

The term "solvate" means a solvate of a compound of the present invention or a pharmaceutically acceptable salt thereof, and example includes alcohol (e.g., ethanol) solvate, hydrate or the like. Example of hydrate includes monohydrate, dihydrate or the like.

The term "inhibition", as used herein, means that the present compound inhibits work of EL.

The term "pharmaceutically acceptable", as used herein, means being not harmful for prevention or treatment.

A general method for producing the present compound is exemplified below. Also extraction, purification and the like may be conducted in a procedure performed in usual organic chemical experiment.

The compound represented by the Formula (I-1) can be synthesized by the following method.

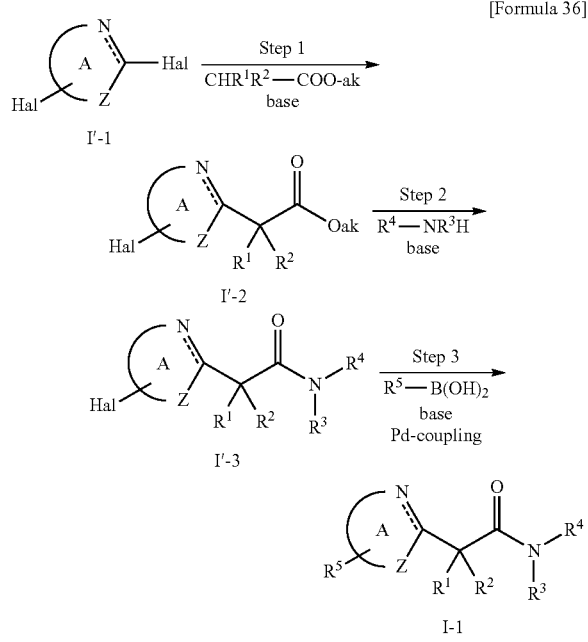

[Formula 36]

wherein each symbol in the above scheme has the same meaning as the above, and as to the compound represented by the Formula (I'-1), a known compound can be used, or a compound derived from a known compound by a usual method can be used. ak is C1 to C3 alkyl and Hal is halogen.

Step 1

Step 1 is a process for preparing the compound represented by the Formula (I'-2) which comprises reacting the compound represented by the Formula (I'-1) with the compound represented by the Formula: $CHR^1R^2$—COO-ak.

As a solvent, example includes N,N-dimethylformamide, dimethylsulfoxide, aromatic hydrocarbons (e.g., toluene, benzene, xylene or the like), saturated hydrocarbons (e.g., cyclohexane, hexane or the like), halogenated hydrocarbons (e.g., dichloromethane, chloroform, 1,2-dichloroethane or the like), ethers (e.g., tetrahydrofuran, diethylether, dioxane, 1,2-dimethoxyethane or the like), esters (e.g., methyl acetate, ethyl acetate or the like), ketones (e.g., acetone, methylethylketone or the like), nitriles (e.g., acetonitrile or the like), alcohols (e.g., methanol, ethanol, t-butanol or the like), water, a mixed solvent thereof or the like.

As a base, example includes metal hydrides (e.g., sodium hydride or the like), metal hydroxides (e.g., sodium hydroxide, potassium hydroxide, lithium hydroxide, barium hydroxide or the like), metal carbonates (e.g., sodium carbonate, calcium carbonate, cesium carbonate or the like), metal alkoxides (e.g., sodium methoxide, sodium ethoxide, potassium t-butoxide or the like), sodium hydrogen carbonate, metal sodium, metal amide, organic amines (e.g., triethylamine, diisopropylethylamine, DBU, 2,6-lutidine or the like), pyridine, alkyl lithiums (n-BuLi, sec-BuLi, tert-BuLi or the like) or the like.

Preferably, the reaction can be performed in a solvent of aromatic hydrocarbons (e.g., toluene, benzene, xylene or the like) or ethers (e.g., tetrahydrofuran, diethylether, dioxane, 1,2-dimethoxyethane or the like) with metal sodium or metal amide as a base. The reaction can be performed at −78 to 30° C. for 0.5 to 12 hours.

As a compound represented by the Formula: $CHR^1R^2$—COO-ak, example includes butyl acetate or ethyl acetate.

Step 2

Step 2 is a process for preparing the compound represented by the Formula (I'-3) which comprises reacting the compound represented by the Formula (I'-2) with the compound represented by the Formula: $R^1$—$NR^3H$.

As a solvent, a solvent described in Step 1 can be used. Preferably, N,N-dimethylformamide, dimethylsulfoxide or N-methyl-2-pyrorid on can be used. The reaction can be performed under the conditions which do not use a solvent by using microwave.

As a base, a base described in Step 1 can be used. Preferably, organic amines (e.g., triethylamine, diisopropylethylamine, DBU, pyridine, 2,6-lutidine or the like) can be used.

The reaction can be performed at a temperature at which a solvent being used is refluxed, for 0.5 to 12 hours.

The reaction can be performed at 80 to 200° C. for 5 minutes to 1 hour by using microwave. This reaction can be performed in a solvent described above or without any solvent.

As a compound represented by the Formula: $R^1$—$NR^3H$, example includes tert-butyl 3-(aminomethyl)benzoate hydrochloride or the like.

Step 3

Step 3 is a process for preparing the compound represented by the Formula (I-1) which comprises reacting the compound represented by the Formula (I'-3) with the compound represented by the Formula: $R^5$—$B(OH)_2$ in the presence of a palladium catalyst.

As a solvent, a solvent described in Step 1 can be used. Preferably, aromatic hydrocarbons (e.g., toluene, benzene, xylene or the like) or ethers (e.g., tetrahydrofuran, diethylether, dioxane, 1,2-dimethoxyethane or the like) can be used. The reaction can be performed under the conditions which do not use a solvent by using microwave.

As a base, a base described in Step 1 can be used. Preferably, metal carbonates (e.g., sodium carbonate, calcium carbonate, cesium carbonate or the like) or organic amines (e.g., triethylamine, diisopropylethylamine, DBU, 2,6-lutidine or the like) can be used. The reaction can be performed in the presence of palladium catalyst (e.g., Pd(PPh$_3$)$_4$, PdCl$_2$, Pd(OAc)$_2$, Pd(dba)$_2$ or the like) and phosphine ligand (e.g., PPh$_3$, BINAP or the like) at a temperature at which a solvent being used is refluxed, for 0.5 to 12 hours. The reaction can be performed at 80 to 200° C. for 5 minutes to 1 hour by using microwave. This reaction can be performed in a solvent described above or without any solvent.

As a compound represented by the Formula: $R^5$—$B(OH)_2$, example includes phenyl boronic acid or the like.

The compound represented by the Formula (II-1) can be synthesized by the same scheme as described above.

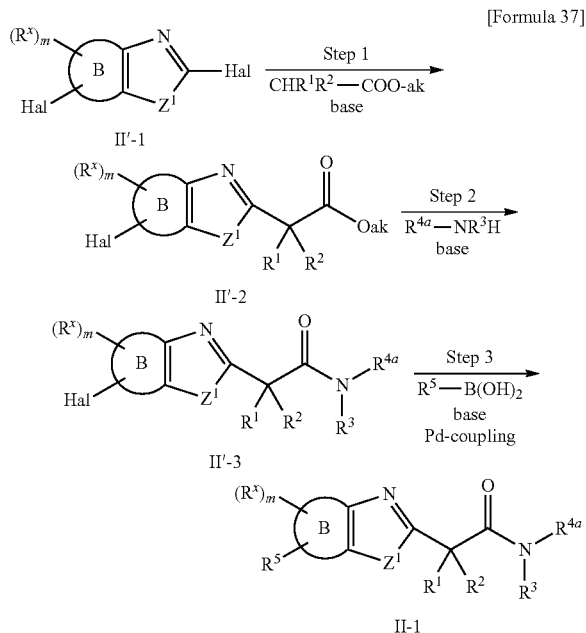

wherein each symbol in the above scheme has the same meaning as the above, and as to the compound represented by the Formula (II'-1), a known compound can be used, or a compound derived from a known compound by a usual method can be used. ak is C1 to C3 alkyl and Hal is halogen.

The compound represented by the Formula (III-1) can be synthesized by the same scheme as described above.

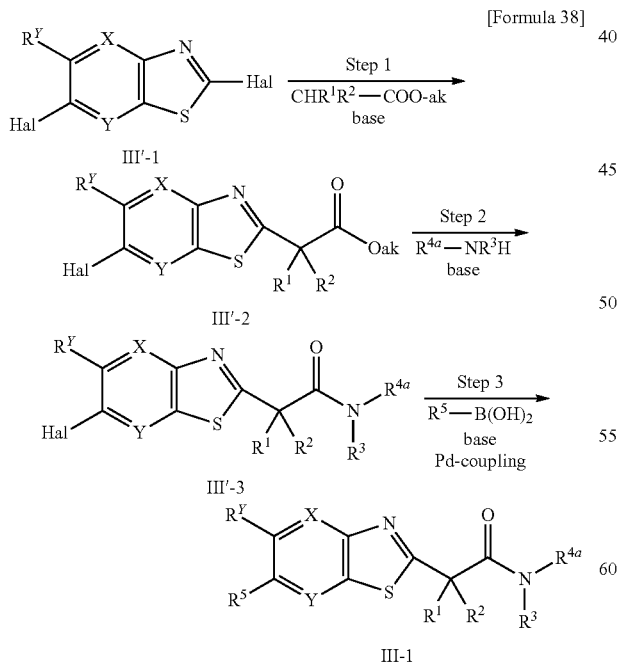

wherein each symbol in the above scheme has the same meaning as the above, and as to the compound represented by the Formula (III'-1), a known compound can be used, or a compound derived from a known compound by a usual method can be used. ak is C1 to C3 alkyl and Hal is halogen.

The compound represented by the Formula (IV-1) can be synthesized by the same scheme as described above.

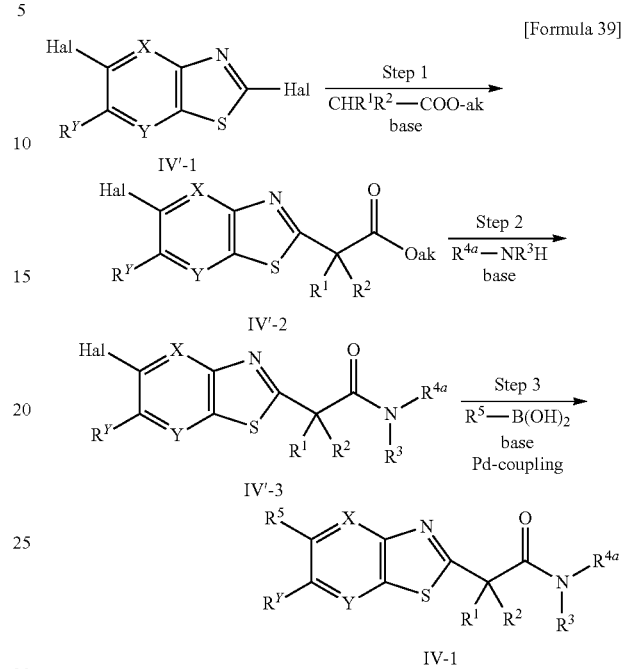

wherein each symbol in the above scheme has the same meaning as the above, and as to the compound represented by the Formula (IV'-1), a known compound can be used, or a compound derived from a known compound by a usual method can be used. ak is C1 to C3 alkyl and Hal is halogen.

The compound represented by the Formula (V-1) can be synthesized by the same scheme as described above.

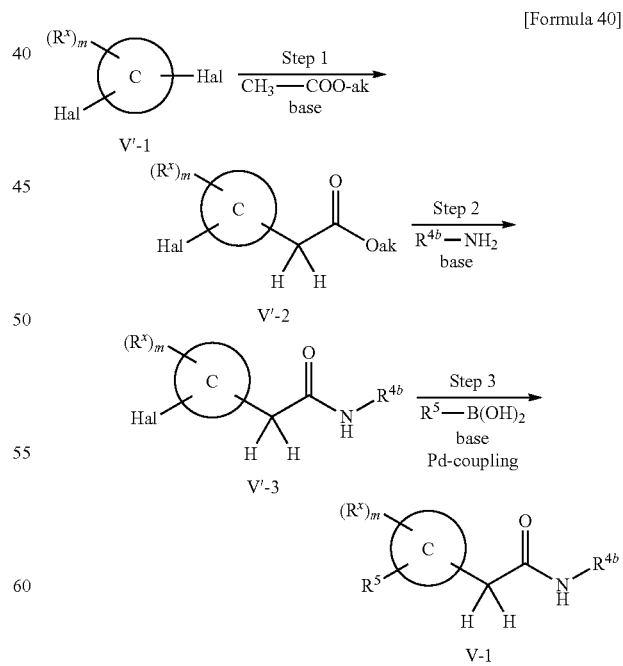

wherein each symbol in the above scheme has the same meaning as the above, and as to the compound represented by the Formula (V'-1), a known compound can be used, or a compound derived from a known compound by a usual method can be used. ak is C1 to C3 alkyl and Hal is halogen.

As an alternative general method for producing the present compound, the group represented by the Formula: —R$^5$ can be introduced before introduction of the group represented by the Formula: —C(R$^1$R$^2$)—CO—NR$^3$R$^4$.

For example, it is explained below by employing Step 4 to 6.

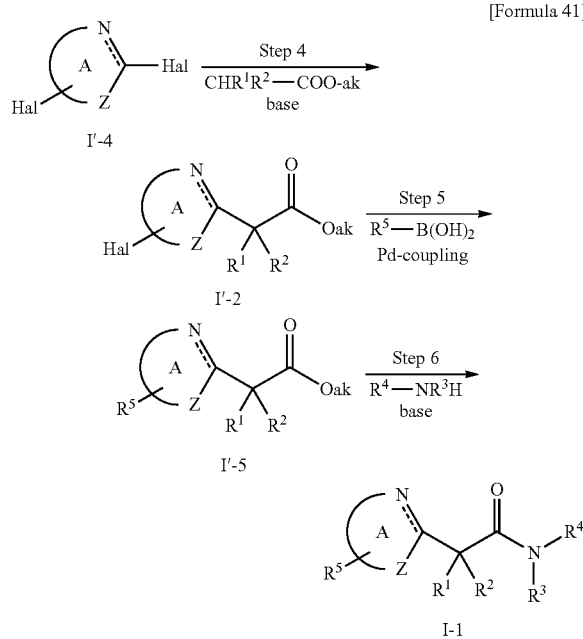

[Formula 41]

wherein each symbol in the above scheme has the same meaning as the above, and as to the compound represented by the Formula (I'-4), a known compound can be used, or a compound derived from a known compound by a usual method can be used. ak is C1 to C3 alkyl and Hal is halogen.

Step 4

Step 4 is a process for preparing the compound represented by the Formula (I'-2) which comprises reacting the compound represented by the Formula (I'-4) with the compound represented by the Formula: CHR$^1$R$^2$—COO-ak.

The reaction can be performed under the conditions described in the above Step 1.

Step 5

Step 5 is a process for preparing the compound represented by the Formula (I'-5) which comprises reacting the compound represented by the Formula (I'-2) with the compound represented by the Formula: R$^5$—B(OH)$_2$ in the presence of a palladium catalyst.

The reaction can be performed under the conditions described in the above Step 3.

Step 6

Step 6 is a process for preparing the compound represented by the Formula (I-1) which comprises reacting the compound represented by the Formula (I'-5) with the compound represented by the Formula: R$^4$—NR$^3$H.

The reaction can be performed under the conditions described in the above Step 2.

The compound represented by the Formula (II-1) can be synthesized by the same scheme as described above.

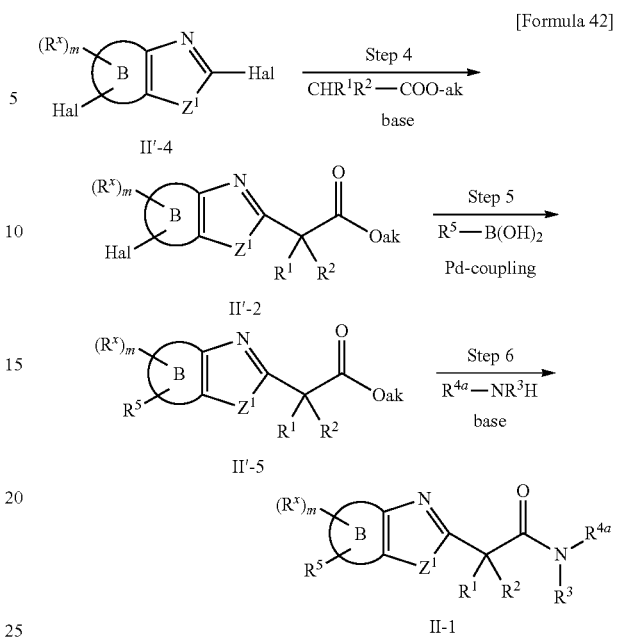

[Formula 42]

wherein each symbol in the above scheme has the same meaning as the above, and as to the compound represented by the Formula (II'-4), a known compound can be used, or a compound derived from a known compound by a usual method can be used. ak is C1 to C3 alkyl and Hal is halogen.

The compound represented by the Formula (III-1) can be synthesized by the same scheme as described above.

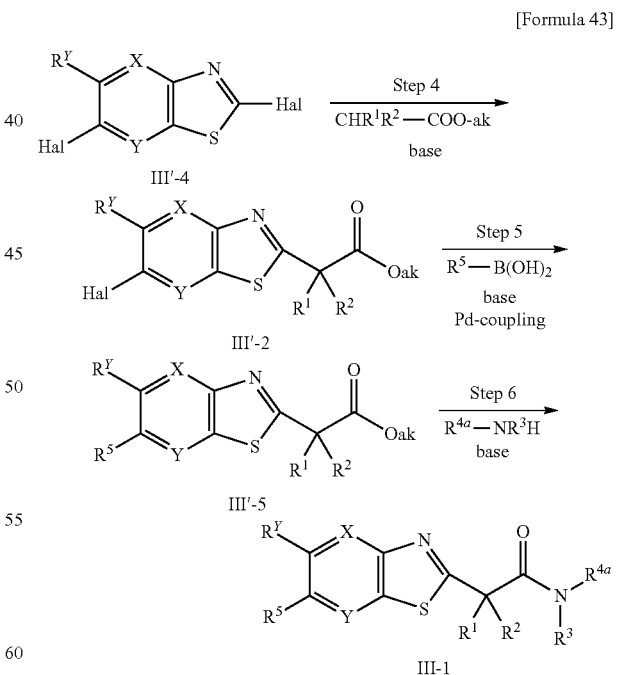

[Formula 43]

wherein each symbol in the above scheme has the same meaning as the above, and as to the compound represented by the Formula (III'-4), a known compound can be used, or a compound derived from a known compound by a usual method can be used. ak is C1 to C3 alkyl and Hal is halogen.

The compound represented by the Formula (IV-1) can be synthesized by the same scheme as described above.

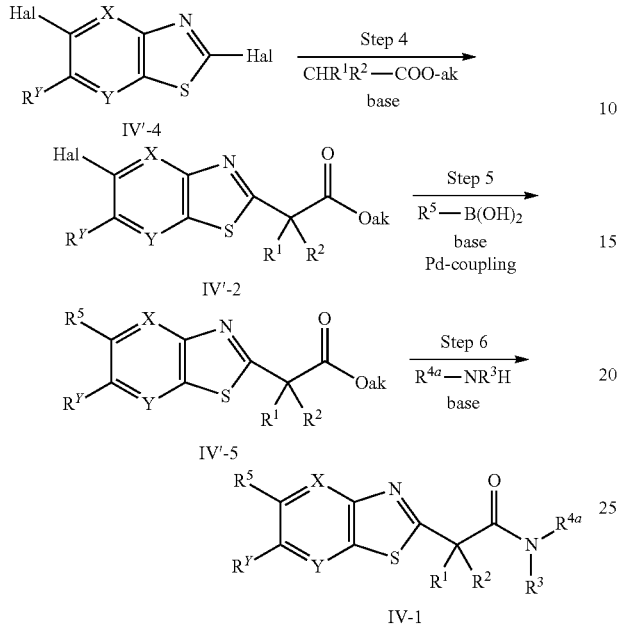

[Formula 44]

wherein each symbol in the above scheme has the same meaning as the above, and as to the compound represented by the Formula (IV'-4), a known compound can be used, or a compound derived from a known compound by a usual method can be used. ak is C1 to C3 alkyl and Hal is halogen.

The compound represented by the Formula (V-1) can be synthesized by the same scheme as described above.

[Formula 45]

wherein each symbol in the above scheme has the same meaning as the above, and as to the compound represented by the Formula (V'-4), a known compound can be used, or a compound derived from a known compound by a usual method can be used. ak is C1 to C3 alkyl and Hal is halogen.

The compound represented by the Formula (I-1) can be synthesized by the following method.

[Formula 46]

wherein each symbol in the above scheme has the same meaning as the above, and as to the compound represented by the Formula (I'-5), a known compound can be used, or a compound derived from a known compound by a usual method can be used. ak is C1 to C3 alkyl.

Step 7

Step 7 is a process for preparing the compound represented by the Formula (I'-6) which comprises hydrolyzing the compound represented by the Formula (I'-5).

As a solvent, a solvent described in Step 1 can be used. Preferably, alcohols (e.g., methanol, ethanol, t-butanol or the like) can be used.

As a base, a base described in Step 1 can be used. Preferably, metal hydroxides (e.g., sodium hydroxide, potassium hydroxide, lithium hydroxide, barium hydroxide or the like) can be used. The reaction can be performed at −20 to 90° C. for 0.5 to 24 hours.

Step 8

Step 8 is a process for preparing the compound represented by the Formula (I-1) which comprises reacting the compound represented by the Formula (I'-6) with the compound represented by the Formula: $R^4$—$NR^3H$.

The reaction can be performed under the conditions described in the above Step 2.

Preferably, a condensing agent (e.g., water soluble carbodiimide such as N,N-dicyclohexylcarbodiimide) and a catalyst such as hydroxybenzotriazole or hydroxysuccinimide can be used.

The compound represented by the Formula (II-1) can be synthesized by the same scheme as described above.

[Formula 47]

-continued

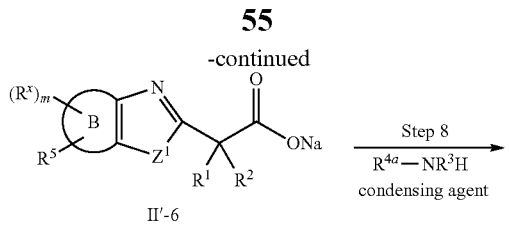
II'-6

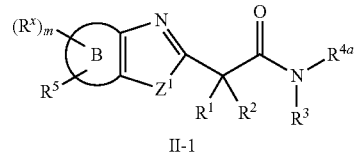
II-1 wherein each symbol in the above scheme has the same meaning as the above, and as to the compound represented by the Formula (II'-5), a known compound can be used, or a compound derived from a known compound by a usual method can be used. ak is C1 to C3 alkyl.

The compound represented by the Formula (III-1) can be synthesized by the same scheme as described above.

[Formula 48]

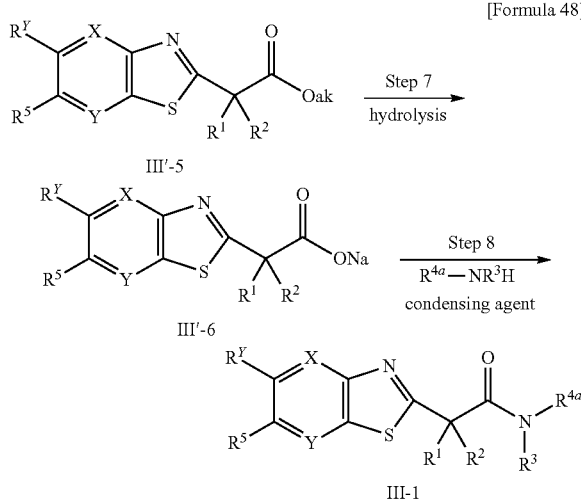
III'-5
III'-6
III-1 wherein each symbol in the above scheme has the same meaning as the above, and as to the compound represented by the Formula (III'-5), a known compound can be used, or a compound derived from a known compound by a usual method can be used. ak is C1 to C3 alkyl.

The compound represented by the Formula (IV-1) can be synthesized by the same scheme as described above.

[Formula 49]

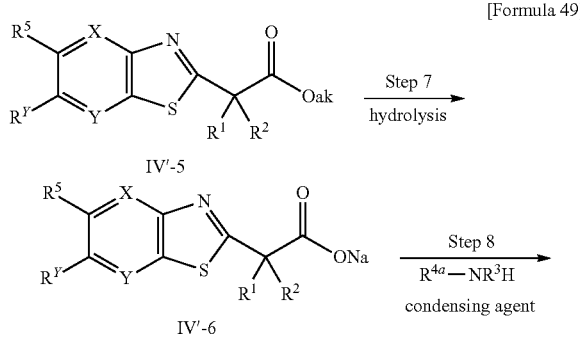
IV'-5
IV'-6

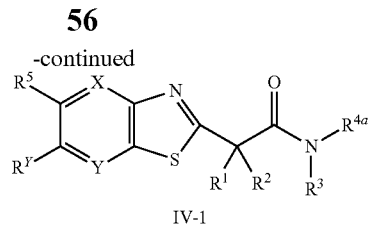
IV-1 wherein each symbol in the above scheme has the same meaning as the above, and as to the compound represented by the Formula (IV'-5), a known compound can be used, or a compound derived from a known compound by a usual method can be used. ak is C1 to C3 alkyl.

The compound represented by the Formula (V-1) can be synthesized by the same scheme as described above.

[Formula 50]

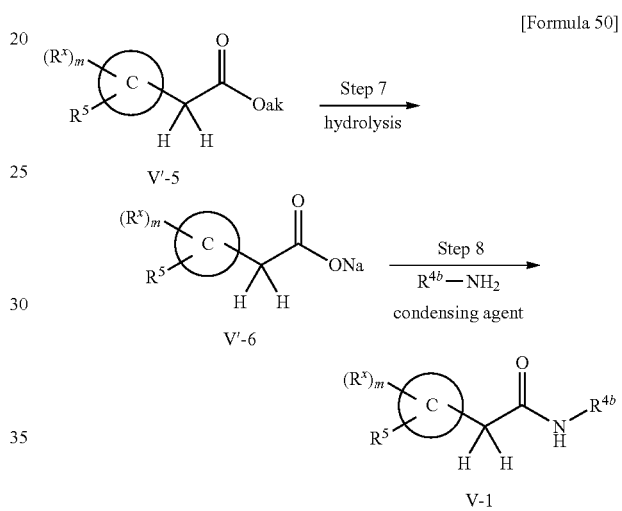
V'-5
V'-6
V-1 wherein each symbol in the above scheme has the same meaning as the above, and as to the compound represented by the Formula (V'-5), a known compound can be used, or a compound derived from a known compound by a usual method can be used. ak is C1 to C3 alkyl.

The compound represented by the Formula (I'-2) can be synthesized by the following method.

[Formula 51]

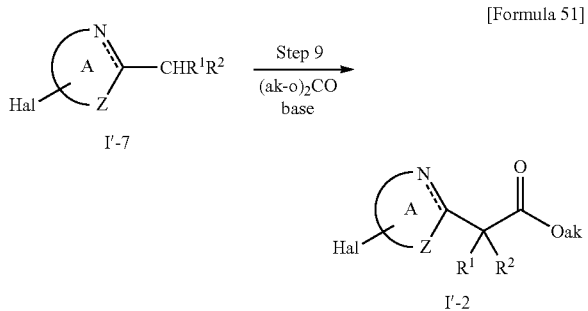
I'-7
I'-2 wherein each symbol in the above scheme has the same meaning as the above, and as to the compound represented by the Formula (I'-7), a known compound can be used, or a compound derived from a known compound by a usual method can be used. ak is C1 to C3 alkyl and Hal is halogen.

Step 9

Step 9 is a process for preparing the compound represented by the Formula (I'-2) which comprises reacting the compound represented by the Formula (I'-7) with the compound represented by the Formula: $(ak\text{-}O)_2CO$.

As a solvent, a solvent described in Step 1 can be used. Preferably, ethers (e.g., tetrahydrofuran, diethylether, dioxane or the like) can be used.

As a base, a base described in Step 1 can be used. Preferably, organic amines (e.g., triethylamine, diisopropylethylamine, DBU, 2,6-lutidine or the like), pyridine or alkyl lithiums (n-BuLi, sec-BuLi, tert-BuLi or the like) can be used.

The reaction can be performed at −78 to 30° C. for 0.5 to 24 hours.

As a compound represented by the Formula: $(ak\text{-}O)_2CO$, example includes diethyl carbonate or the like.

The compound represented by the Formula (II'-2) can be synthesized by the same scheme as described above.

[Formula 52]

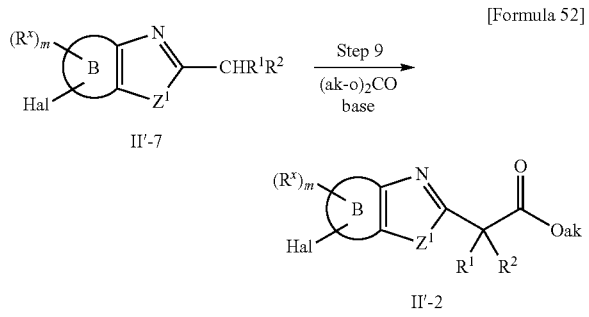

wherein each symbol in the above scheme has the same meaning as the above, and as to the compound represented by the Formula (II'-7), a known compound can be used, or a compound derived from a known compound by a usual method can be used. ak is C1 to C3 alkyl and Hal is halogen.

The compound represented by the Formula (III'-2) can be synthesized by the same scheme as described above.

[Formula 53]

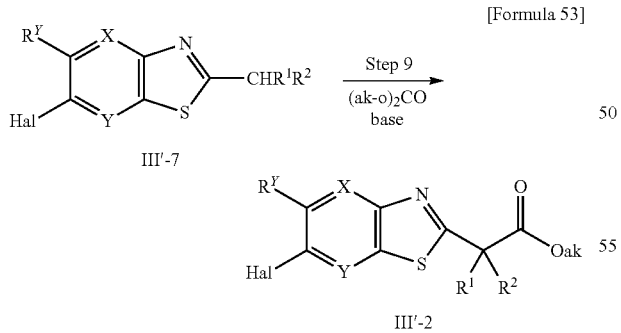

wherein each symbol in the above scheme has the same meaning as the above, and as to the compound represented by the Formula (III'-7), a known compound can be used, or a compound derived from a known compound by a usual method can be used. ak is C1 to C3 alkyl and Hal is halogen.

The compound represented by the Formula (IV'-2) can be synthesized by the same scheme as described above.

[Formula 54]

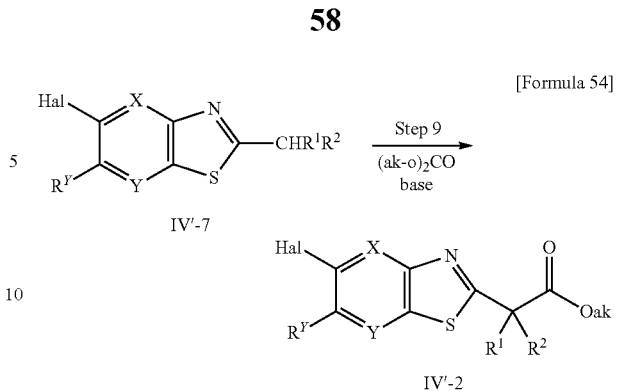

wherein each symbol in the above scheme has the same meaning as the above, and as to the compound represented by the Formula (IV'-7), a known compound can be used, or a compound derived from a known compound by a usual method can be used. ak is C1 to C3 alkyl and Hal is halogen.

The compound represented by the Formula (V'-2) can be synthesized by the same scheme as described above.

[Formula 55]

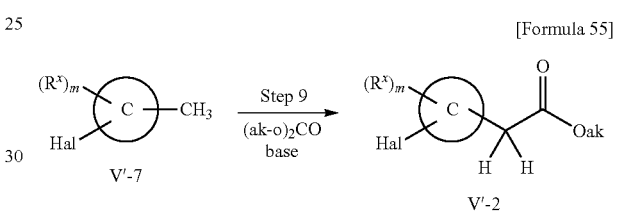

wherein each symbol in the above scheme has the same meaning as the above, and as to the compound represented by the Formula (V'-7), a known compound can be used, or a compound derived from a known compound by a usual method can be used. ak is C1 to C3 alkyl and Hal is halogen.

The compound represented by the Formula (III'-10) can be synthesized by the following method.

[Formula 56]

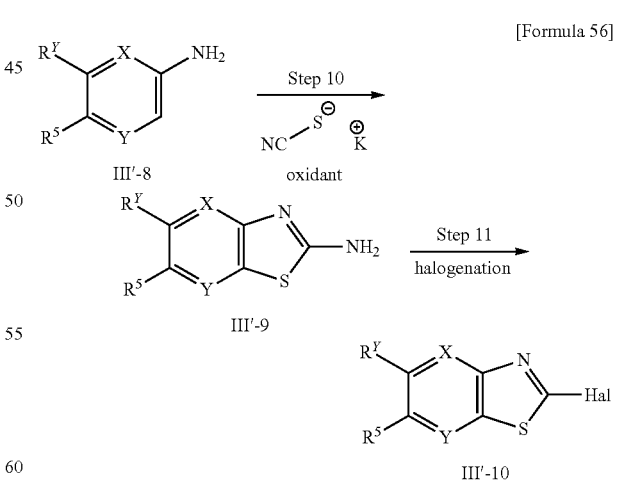

wherein each symbol in the above scheme has the same meaning as the above, and as to the compound represented by the Formula (III'-8), a known compound can be used, or a compound derived from a known compound by a usual method can be used. Hal is halogen.

Step 10

Step 10 is a process for preparing the compound represented by the Formula (III'-9) which comprises reacting the compound represented by the Formula (III'-8) with potassium thiocyanate.

As a solvent, a solvent described in Step 1 can be used. Preferably, halogenated hydrocarbons, acetic acid or water can be used.

As an oxidant, bromine or iodine can be used.

The reaction can be performed at −20 to 50° C. for 0.5 to 48 hours.

Step 11

Step 11 is a process for preparing the compound represented by the Formula (III'-10) which comprises halogenating the compound represented by the Formula (III'-9).

As a solvent, a solvent described in Step 1 can be used. Preferably, nitriles can be used.

As a halogenating agent, copper chloride (II) or copper bromide (II) can be used.

The reaction can be performed at −20 to 90° C. for 0.5 to 48 hours.

The compound represented by the Formula (IV'-10) can be synthesized by the same scheme as described above.

[Formula 57]

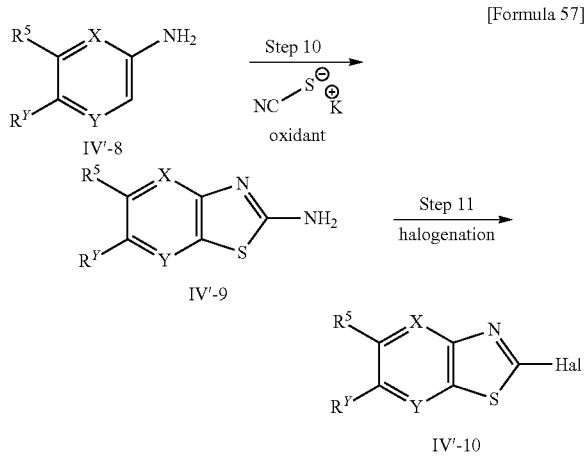

wherein each symbol in the above scheme has the same meaning as the above, and as to the compound represented by the Formula (IV'-8), a known compound can be used, or a compound derived from a known compound by a usual method can be used. Hal is halogen.

Various substituents in the present compound can be introduced by referring to (1) Alan R. Katriszly et al., Comprehensive Heterocyclic Chemistry (2) Alan R. Katriszly et al., Comprehensive Heterocyclic Chemistry II (3) RODD'S CHEMISTRY OF CARBON COMPOUNDS VOLUME IV HETEROCYCLIC COMPOUNDS or the like.

The present compound has excellent inhibitory activity on endothelial lipase. Therefore, it can be used for treatment or prevention of a disease concerning endothelial lipase, especially, disease such as lipid metabolism abnormality, hyperlipidemia, diabetes, obesity, arteriosclerosis, atherosclerosis and/or syndrome X. It is particularly useful in treatment or prevention of hyperlipidemia, arteriosclerosis or lipid metabolism abnormality.

A compound used in the present invention can be orally or parenterally administered. When administered orally, the compound used in the present invention can be used in any dose form including normal formulations, for example, solid formulations such as a tablet, powder, granule, capsule or the like; aqueous formulations; oleaginous suspensions; or liquid formulations such as syrup or elixir. When administered parenterally, the compound used in the present invention can be used as an aqueous or oleaginous suspension for injection or nasal solution. In preparation of such formulations, a conventional excipient, binder, lubricant, aqueous solvent, oleaginous solvent, emulsifying agent, suspending agent, preservative, stabilizer and the like can be optionally used. Especially, using in a form of an oral formulation is preferred.

A formulation of the compound used in the present invention can be produced by combining (e.g., mixing) a therapeutically effective amount of the compound used in the present invention with a pharmaceutically acceptable carrier or diluent. Formulation of the compound used in the present invention can be produced by a known method using a well-known easily available ingredient.

A dose of the compound used in the present invention is different depending on an administration method, an age, a weight and the condition of a patient, and a kind of a disease and, in the case of oral administration, usually about 0.05 mg to 3000 mg, preferably about 0.1 mg to 1000 mg per a day for adult person may be administered, if necessary, in divided doses. In addition, in the case of parenteral administration, about 0.01 mg to 1000 mg, preferably about 0.05 mg to 500 mg per a day for adult person may be administered. In administration, it can be used together with other therapeutic agents.

The present invention is further explained by the following Examples, which are not intended to limit the scope of the present invention.

The NMR spectrum or LC/MS data of the present compound and its intermediate was described below. LC/MS was measured under any one of the following three conditions.

Method A:

Luna 5μ C18(2) 100A, 50×4.6 mm (made by Phenomenex) was used for measurement.

A three minute linear gradient was run from 10:90-100:0 of acetonitrile/water (0.1% formic acid) with 3 ml/min of flow rate, and acetonitrile was passed for 1 minute.

Method C:

Shim-pack XR-ODS 50 L×3.0 (made by Shimazu) was used for measurement.

A three minute linear gradient was run from 10:90-100:0 of acetonitrile/water (0.1% formic acid) with 1.6 ml/min of flow rate, and acetonitrile was passed for 30 seconds.

Method D:

Shim-pack XR-ODS 50 L×3.0 (made by Shimazu) was used for measurement.

A eight minute linear gradient was run from 10:90-100:0 of acetonitrile/water (0.1% formic acid) with 1.6 ml/min of flow rate.

The terms used in the Examples are as follows.

NaHMDS: Sodium Bis(trimethylsilyl)amide
NMP: N-Methyl-2-pyrrolidone
TFA: Trifluoroacetic acid
THF: Tetrahydrofuran
DMF: Dimethylformamide
WSCD: 1-Ethyl-3-(3-dimethyl aminopropyl) carbodiimide
BOC: t-Butoxycarbonyl group
Bn: Benzyl group
LHMDS: lithium hexamethyldisilazide
HATU: O-(7-Azabenzotriazol-1-yl)-N,N,N',N'-tetramethyluronium hexafluorophosphate
$Pd_2(dba)_3$: BIS(Dibenzylideneacetone)palladium
MCPBA: META-Chloroperbenzoic acid
X-Phos: 2-Dicyclohexylphosphino-2',4',6'-tri-i-propyl-1,1'-biphenyl
NCS: N-Chlorosuccinimide
$Fe(acac)_3$: Ferric acetylacetonate
H-Gly-OtBu: Glycine tert-butyl ester

EXAMPLE 1

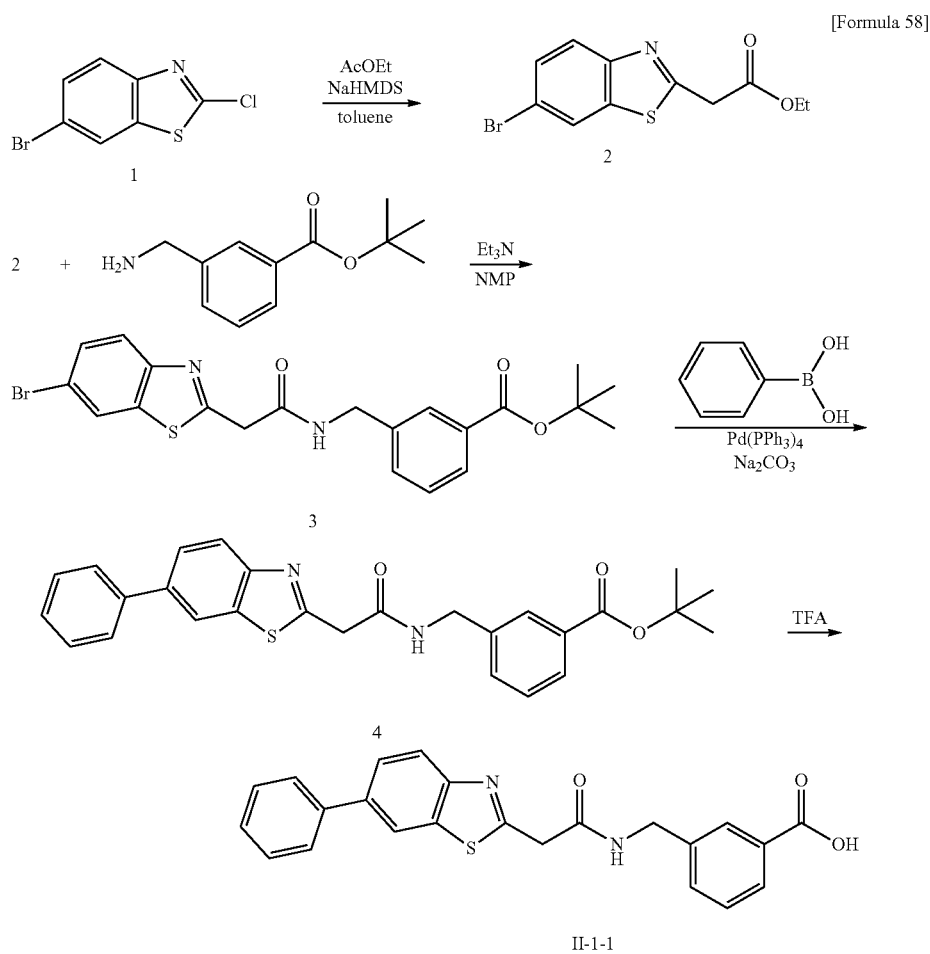

To a solution of 2M NaHMDS THF solution (111 mL, 211 mmol) in anhydrous toluene (375 mL) was added ethyl acetate (11.30 mL, 116 mmol) under nitrogen atmosphere at −60° C. for 10 minutes. It was stirred for 1 hour at −60° C. To the solution was dropped a solution of 6-bromo-2-chloro benzothiazole1 (25 g, 101 mmol) in an anhydrous toluene (125 ml). After dropping, it was stirred at 0° C. for 2 hours.

To the reaction mixture were added 1M hydrochloric acid and ethyl acetate. The mixture was extracted. The organic layer was washed with brine, dried with magnesium sulfate. The solvent was evaporated under reduced pressure. The residue was washed with a mixed solvent of hexane and diisopropyl ether to give Compound 2 (27.1 g, 90%) as a yellow solid.

Compound 2; $^1$H-NMR (CDCl$_3$) δ: 1.31 (t, J=7.2, Hz 3.0, 3H), 4.15 (s, 2H), 4.26 (q, J=7.2 Hz, 2H), 7.57 (dd, J=8.7, 1.8 Hz, 1H), 7.86 (d, J=9.0 Hz, 1H), 8.01 (d, J=1.8 Hz, 1H)

Compound 2 (5 g, 16.7 mmol) was dissolved in NMP (50 ml). To the solution were added tert-butyl 3-(aminomethyl) benzoate hydrochloride (4.9 g, 20 mmol) and Et$_3$N (3.5 ml, 25 mmol). The mixture was stirred at 170° C. for 15 minutes under microwave irradiation. To the reaction mixture were added 1M hydrochloric acid and ethyl acetate. After extraction, the organic layer was washed with brine and dried over magnesium sulfate. The solvent was evaporated under reduced pressure. The residue was purified with chromatography to give Compound 3 (4.9 g, 64%).

Compound 3; $^1$H-NMR (DMSO-d$_6$) δ: 1.51 (s, 9H), 4.14 (s, 2H) 4.40 (d, J=5.7 Hz, 2H), 7.45 (t, J=7.2 Hz, 1H) 7.54 (d, J=7.8 Hz, 1H), 7.64 (d, J=10.8 Hz, 1H), 7.76-7.82 (m, 3H), 7.89 (d, J=8.4 Hz, 1H), 8.36 (s, 1H), 8.95 (t, J=6.0 Hz) 1H)

To a solution of Compound 3 (60 mg, 0.13 mmol) in anhydrous 1,4-dioxane (4 mL) solution were added phenyl boronic acid (24 mg, 0.20 mmol), Pd(PPh$_3$)$_4$. (8 mg) and 2N Na$_2$CO$_3$ solution (200 µl). It was stirred at 140° C. for 15 minutes under microwave irradiation. To the reaction mixture was added 1M hydrochloric acid and ethyl acetate. After extraction, the organic layer was washed with saturated sodium bicarbonate solution and brine, respectively and dried over sodium sulfate. The solvent was evaporated under reduced pressure. The residue was purified with chromatography to give Compound 4 (37 mg, 62%).

Compound 4; $^1$H-NMR (DMSO-d$_6$) δ: 1.52 (s, 9H), 4.15 (s, 2H), 4.41 (d, J=6.1 Hz, 2H), 7.37-7.57 (m, 5H), 7.74-7.86 (m, 4H), 7.92 (s, 1H), 8.02 (d, J=8.6 Hz, 1H), 8.38 (d, J=1.5 Hz, 1H), 8.95 (t, J=6.1 Hz, 1H)

To a solution of Compound 4 (37 mg, 0.08 mmol) in dichloromethane (1 ml) was added trifluoroacetic acid (1 ml). It was stirred at room temperature for 2 hours. The solvent was evaporated under reduced pressure. It was crystallized with diethyl ether to give Compound (II-1-1) (29 mg 88%).

Compound (II-1-1); $^1$H-NMR (DMSO-d$_6$) δ: 4.15 (s, 2H), 4.41 (d, J=6.1 Hz, 2H) 7.37-7.57 (m, 5H), 7.74-7.86 (m, 4H), 7.92 (s, 1H), 8.02 (d, J=8.6 Hz, 1H), 8.38 (d, J=1.5 Hz, 1H), 8.95 (t, J=6.1 Hz, 1H), 12.96 (br s, 1H).

EXAMPLE 2

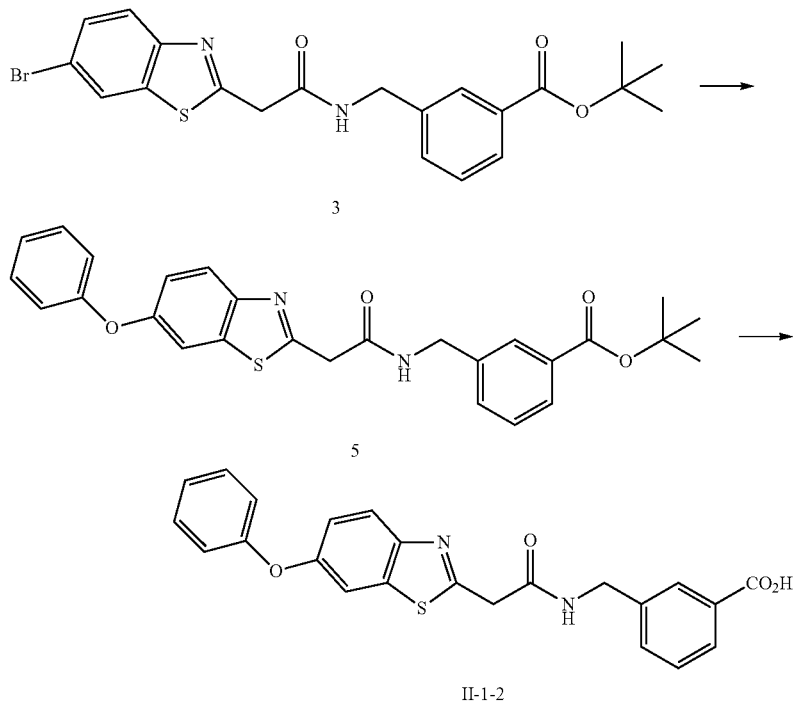

[Formula 59]

To a solution of Compound 3 (200 mg, 0.43 mmol) in ethyl acetate (3 mL) were added copper triflate benzene complex (22 mg, 0.043 mmol), naphtoic acid (149 mg, 0.87 mmol), phenol (82 mg, 0.87 mmol) and cesium carbonate (282 mg, 0.87 mmol). It was stirred for 140° C. for 3 hours under microwave irradiation. To the reaction mixture were added 1M hydrochloric acid and ethyl acetate. After extraction, the organic layer was washed with brine and dried over sodium sulfate. The solvent was evaporated under reduced pressure. The residue was purified with chromatography to give Compound 5 (26 mg, 13%).

Compound 5; $^1$H-NMR (DMSO-$d_6$) δ: 1.52 (s, 9H), 4.10 (s, 2H), 4.40 (d, J=6.1 Hz, 2H), 7.04 (d, J=8.1 Hz, 2H) 7.13-7.20 (m, 2H), 7.38-7.48 (m, 3H), 7.54 (d, J=7.6 Hz, 1H), 7.72 (d, J=2.5 Hz, 1H), 7.83 (d, J=7.6 Hz, 1H), 7.90 (s, 1H), 7.95 (d, J=8.6 Hz, 1H), 8.92 (t, J=5.8 Hz, 1H).

Compound (II-1-2) (23 mg, 100%) was obtained in accordance with the same manner as Example 1.

Compound (II-1-2); $^1$H-NMR (DMSO-$d_6$) δ: 4.10 (s, 2H), 4.40 (d, J=6.1 Hz, 2H) 7.04 (d, J=8.1 Hz, 2H), 7.13-7.20 (m, 2H), 7.38-7.48 (m, 3H), 7.54 (d, J=7.6 Hz, 1H) 7.72 (d, J=2.5 Hz, 1H), 7.83 (d, J=7.6 Hz, 1H), 7.90 (s, 1H), 7.95 (d, J=8.6 Hz, 1H), 8.92 (t, J=5.8 Hz, 1H), 12.96 (br s, 1H).

EXAMPLE 3

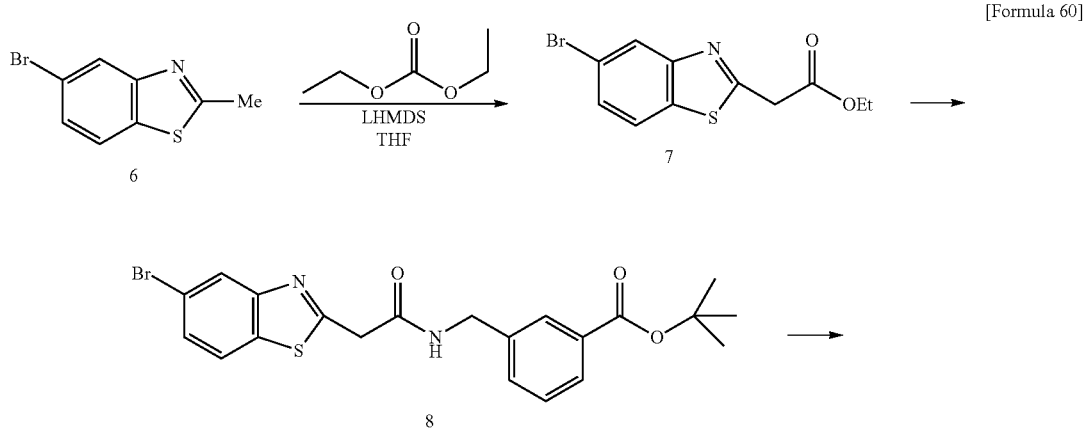

[Formula 60]

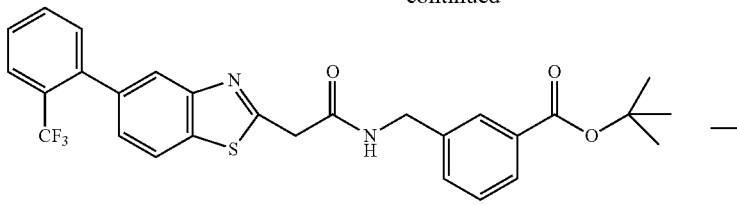

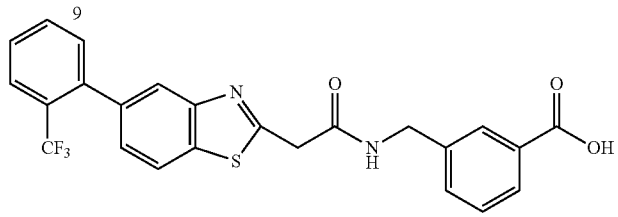

II-1-3

To a solution of 5-bromo-2-methylbenzothiazole 6 (6.5 g, 28.5 mmol) in anhydrous THF (260 mL) was dropped 1M LHMDS THF solution (59.8 mL, 59.8 mmol) at −60° C. under nitrogen atmosphere. After stirred at −60 to −78° C. for 80 minutes, diethyl carbonate (3.80 mL, 31.3 mmol) was added to the solution. It was stirred at 0° C. for 1 hour.

To the reaction mixture were added 1M hydrochloric acid and ethyl acetate. After extraction, the organic layer was washed with saturated sodium bicarbonate solution and brine, respectively and dried over sodium sulfate. The solvent was evaporated under reduced pressure. The residue was washed with hexane to give Compound 7 (7.19 g, 84%) as a brown solid.

Compound 7; $^1$H-NMR (CDCl$_3$) δ: 1.31 (t, J=7.1 Hz, 3H), 4.17 (s, 2H), 4.26 (q, J=7.1 Hz, 2H), 7.50 (dd, J=8.6, 2.0 Hz, 1H), 7.74 (d, J=8.6 Hz, 1H), 8.16 (d, J=2.0 Hz, 1H).

The compound 8 (984 mg, 43%) was obtained in accordance with the same manner as Example 1.

Compound 8; $^1$H-NMR (CDCl$_3$) δ: 1.58 (s, 9H), 4.11 (s, 2H) 4.55 (d, J=6.1 Hz, 2H), 7.37 (t, J=7.6 Hz, 1H) 7.45 (d, J=7.6 Hz, 1H), 7.50-7.53 (m, 2H), 7.73 (d, J=8.1 Hz, 1H), 7.89-7.90 (m, 2H), 8.14 (s, 1H).

The compound 9 (45 mg, 66%) was obtained in accordance with the same manner as Example 1.

Compound 9; $^1$H-NMR (CDCl$_3$) δ: 1.56 (s, 9H), 4.15 (s, 2H) 4.57 (d, J=6.1 Hz, 2H), 7.34-7.39 (m, 3H), 7.45-7.61 (m, 3H), 7.69 (s, 1H), 7.78 (d, J=7.6 Hz, 1H), 7.87-7.91 (m, 3H), 7.95 (s, 1H).

The compound (II-1-3) (29 mg, 88%) was obtained in accordance with the same manner as Example 1.

Compound (II-1-3); $^1$H-NMR (DMSO-d$_6$) δ: 4.17 (s, 2H), 4.41 (d, J=5.6 Hz, 2H), 7.36 (d, J=8.1 Hz, 1H), 7.44-7.50 (m, 2H), 7.55 (d, J=7.6 Hz, 1H), 7.65 (t, J=7.6 Hz, 1H), 7.76 (t, J=7.6 Hz, 1H), 7.82-7.91 (m, 4H), 8.12 (d, J=8.1 Hz, 1H), 8.94 (t, J=5.8 Hz, 1H), 12.95 (br s, 1H).

EXAMPLE 4

[Formula 61]

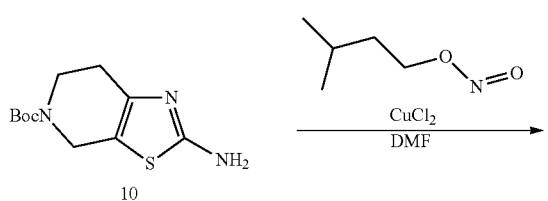

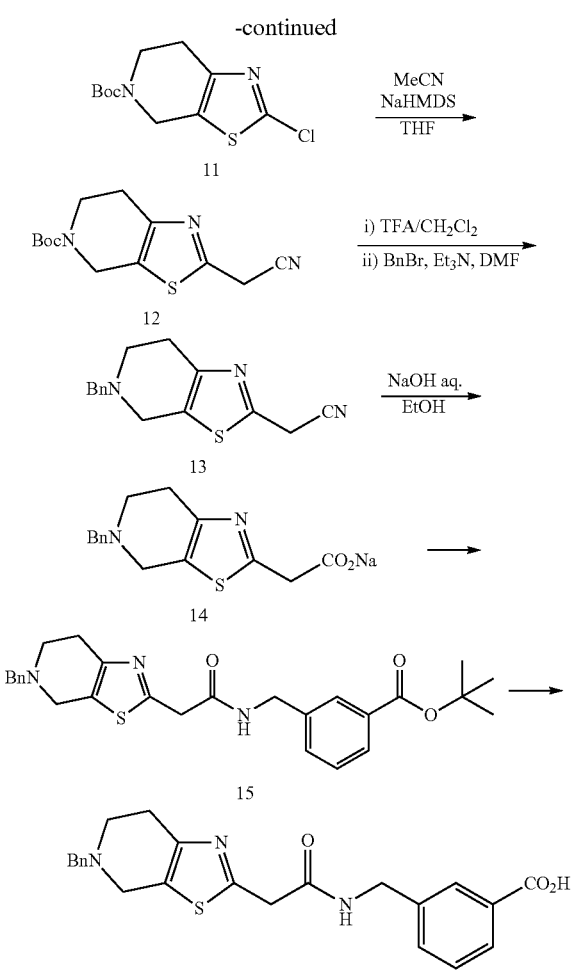

To a solution of copper chloride (II) (1.90 g, 14.10 mmol) in anhydrous dimethylformamide (5 ml) were dropped under ice-cooling isoamyl nitrite (2.37 ml, 17.62 mmol) and a suspension of Compound 10 (3 g, 11.75 mmol) in anhydrous dimethylformamide (10 ml), respectively. It was stirred at 50° C. for 2 hours. To the reaction mixture were added saturation ammonium chloride solution (50 ml) and ethyl acetate (50 ml). After extraction, the organic layer was washed with brine (40 ml) three times and dried over magnesium sulfate. The solvent was evaporated under reduced pressure. The residue was purified with silicagel chromatography (n-hexane:ethyl acetate=5:1) to give Compound 11 (1.62 g, 50%) as a white solid.

Compound 11; $^1$H-NMR (CDCl$_3$): δ (ppm) 1.49 (s, 9H), 2.82 (t, J=5.6 Hz, 2H), 3.73 (t, J=5.6 Hz, 2H), 4.55 (s, 2H).

1.9 M NaHMDS/THF solution (1.47 ml, 2.73 mmol) was diluted with absolute THF (1.5 ml) at −60° C. To the solution was dropped acetonitrile (95 μl, 1.82 mmol). It was stirred for 30 minutes. To the solution a solution of Compound 11 (250 mg, 0.91 mmol) in absolute THF (2 ml). It was stirred at room temperature for 1 hour. It was diluted with 2M HCl (3 ml) and extracted with ethyl acetate (5 ml). The oil layer was washed with brine (5 ml). The solvent was evaporated under reduced pressure. The residue was purified with silicagel chromatography (n-hexane:ethyl acetate=3:1) to give Compound 12 (150 mg, 59%) as red oil.

Compound 12; $^1$H-NMR (DMSO-d$_6$): δ (ppm) 1.42 (s, 9H), 2.75 (t, J=5.6 Hz, 2H), 3.63 (t, J=5.6 Hz, 2H), 4.50 (s, 2H), 4.58 (s, 2H)

To a solution of Compound 12 (120 mg, 0.430 mmol) in dichloromethane (1.2 ml) was added TFA (0.50 ml, 6.44 mmol) at 0° C. It was stirred for 2 hours. Dichloromethane and trifluoroacetic acid were evaporated under reduced pressure. The residue was dissolved in anhydrous DMF (1.5 ml). To the solution were added triethyl amine (0.12 ml, 0.86 mmol) and benzyl bromide (51 μl, 0.43 mmol). It was stirred at room temperature for 2.5 hours. The reaction mixture was diluted with sat. NaHCO$_3$ aq. (5 ml) and extracted with ethyl acetate (10 ml). The organic layer was washed with sat. NaHCO$_3$ aq. (5 ml). The solvent was evaporated under reduced pressure. The residue was purified with silicagel chromatography (chloroform:methanol=99:1) to give Compound 13 (77.5 mg, 67%) as yellow oil.

Compound 13; $^1$H-NMR (DMSO-d$_6$): δ (ppm) 2.73 (m, 2H), 2.89 (m, 2H), 3.64 (s, 2H), 3.70 (s, 2H) and 4.47 (s, 2H), 7.29-7.37 (m, 5H).

To a solution of Compound 13 (67 mg, 0.249 mmol) in ethanol was added 5M NaOH solution (0.15 ml, 0.746 mmol). It was heated under reflux and stirred for 1 hour. The solvent was evaporated under reduced pressure. Compound 14 (70 mg, 95%) was obtained as brown oil.

Compound 14; LC/MS Rt=0.60 min, MS:288.90, method:A

To a solution of Compound 14 (77 mg, 0.248 mmol) in DMF (1.5 ml) were added Et$_3$N (0.206 ml, 1.489 mmol), HOBt (67.1 mg, 0.496 mmol), WSCD HCl (95 mg, 0.496 mmol) and tert-butyl 3-(aminomethyl)benzoate hydrochloride (121 mg, 0.496 mmol). It was stirred overnight at room temperature. The reaction mixtures was diluted with H$_2$O (5 ml) and extracted with ethyl acetate (10 ml). The oil layer was washed with H$_2$O (5 ml) and brine (5 ml), respectively And dried over magnesium sulfate. The solvent was evaporated under reduced pressure. The residue was purified with silicagel chromatography (chloroform:methanol=50:1) to give Compound 15 (20 mg, 17%) as tan oil.

Compound 15; LC/MS Rt=2.38 min, MS:478.20, method:A

To a solution of Compound 15 (20 mg, 0.042 mmol) in dichloromethane (1.0 ml) was added TFA (500 μl, 6.49 mmol). It was stirred at room temperature for 1 hour. The solvent was evaporated under reduced pressure. The residue was purified with reverse phase chromatography (H$_2$O-MeCN, 5 to 95% MeCN/15 min) to give Compound (II-1-4) (8.7 mg, 49%) as a white solid.

Compound (II-1-4); $^1$H-NMR (DMSO-d$_6$) δ: 2.68-2.82 (m, 4H), 3.61 (s, 3H), 3.70 (s, 2H), 3.88 (s, 2H), 4.36 (d, J=5.6 Hz, 2H), 7.21-7.55 (m, 7H), 7.75-7.90 (m, 2H), 8.80 (t, J=5.6 Hz, 1H).

EXAMPLE 5

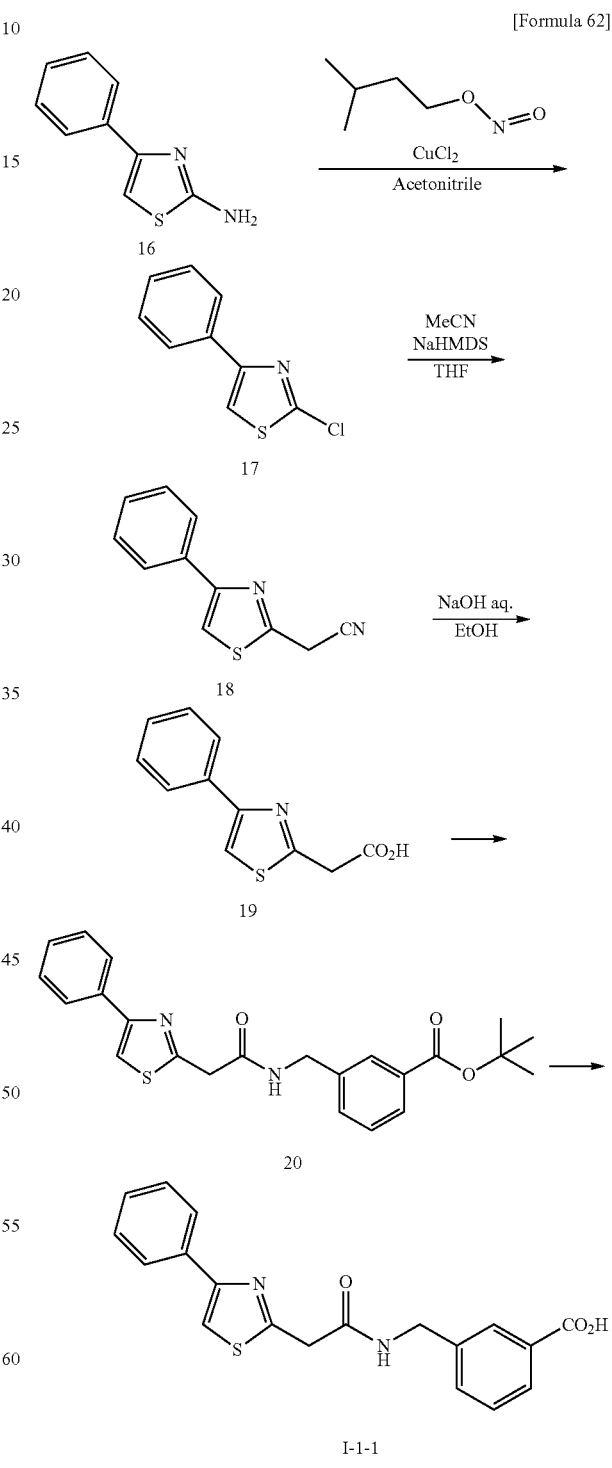

[Formula 62]

To a suspension of copper chloride (II) (9.15 g, 68.1 mmol) in anhydrous acetonitrile (100 ml) were dropped under ice-cooling isoamyl nitrite (11.46 ml, 85 mmol) and a suspension of Compound 16 (10 g, 56.7 mmol) in anhydrous acetonitrile (100 ml), respectively. It was stirred at 50° C. for 3 hours. The insoluble was filtered out. The solvent was evaporated under reduced pressure. To the residue were added ethyl acetate (200 ml) and 1M HCl (100 ml). The mixture was extracted. The organic layer was washed with brine (100 ml) and dried over magnesium sulfate. The solvent was evaporated under reduced pressure. The residue was purified with silicagel chromatography (n-hexane:ethyl acetate=99:1) to give Compound 17 (2.5 g, 23%) as a white solid.
Compound 17; $^1$H-NMR (DMSO-d$_6$): δ (ppm) 7.34-7.44 (m, 1H), 7.44-7.50 (m, 2H), 7.86-7.94 (m, 2H), 8.12 (s, 1H).

1.9 M NaHMDS/THF solution (8.07 ml, 15.33 mmol) was diluted with absolute THF (10 ml) at −60° C. To the solution was dropped acetonitrile (531 μl, 10.22 mmol). It was stirred for 30 minutes. To the mixture was dropped the solution of Compound 17 (1 g, 5.11 mmol) in absolute THF (10 ml). It was stirred for 1 hour at 0° C. The mixture was diluted with 2M HCl (10 ml) and extracted with ethyl acetate (50 ml). The oil layer was washed with brine (50 ml). The solvent was evaporated under reduced pressure. The residue was purified with silicagel chromatography (n-hexane:ethyl acetate=4:1) to give Compound 18 (740 mg, 72%) as a green solid.
Compound 18; $^1$H-NMR (DMSO-d$_6$): δ (ppm) 4.63 (s, 2H), 7.33-7.40 (m, 1H), 7.42-7.51 (m, 2H), 7.90-8.00 (m, 2H), 8.13 (s, 1H).

To a solution of Compound 18 (130 mg, 0.649 mmol) in EtOH (1.5 ml) was added 5 M NaOH solution (0.389 ml, 1.947 mmol). It was heated under reflux for 1 hour, diluted with 1M HCl aqueous solution (5 ml), and extracted with chloroform (10 ml) five times. The organic layer was dried over magnesium sulfate. The solvent was evaporated under reduced pressure. The residue was purified with silicagel chromatography (CHCl$_3$:MeOH:AcOH=10:1:0.1) to give Compound 19 (77.2 mg, 54%) as brown oil.
Compound 19; $^1$H-NMR (DMSO-d$_6$): δ (ppm) 4.13 (s, 2H), 7.30-7.37 (m, 1H), 7.39-7.47 (m, 2H), 7.90-7.97 (m, 2H), 8.04 (s, 1H), 12.81 (brs, 1H)

To a solution of Compound 19 (60 mg, 0.274 mmol) in DMF (1 ml) were added triethylamine (0.19 ml, 1.368 mmol), WSCD-HCl (79 mg, 0.410 mmol), HOBt (56 mg, 0.410 mmol) and tert-butyl 3-(aminomethyl)benzoate hydrochloride (133 mg, 0.547 mmol). It was stirred at room temperature for 12 hours. It was diluted with 1M HCl aqueous solution (2.0 ml) and extracted with ethyl acetate (10 ml). The oil layer was washed with H$_2$O (5 ml) and brine (5 ml), respectively and dried over magnesium sulfate. The solvent was evaporated under reduced pressure. The residue was purified with silicagel chromatography (n-hexane:ethyl acetate=1:1) to give Compound 20 (61.4 mg, 55%) as yellow amorphous.
Compound 20; $^1$H-NMR (DMSO-d$_6$) δ: 1.53 (s, 9H), 4.05 (s, 2H) 4.40 (d, J=5.6 Hz, 2H), 7.30-7.37 (m, 1H), 7.39-7.49 (m, 3H), 7.55 (d, J=7.6 Hz, 1H), 7.76-7.85 (m, 2H), 7.93 (d, J=7.6 Hz, 2H), 8.00 (s, 1H), 8.87 (t, J=5.6 Hz, 1H).

To a solution of Compound 20 (58 mg, 0.142 mmol) in dichloromethane (1.0 ml) was added TFA (0.328 ml, 4.26 mmol). It stirred at room temperature for 2 hours. The solvent was evaporated under reduced pressure. The obtained yellow solid was suspended in ethyl acetate (5 ml). It was stirred for 1 hour. The residue was filtered to give Compound (I-1-1) (33.3 mg, 67%) as a white solid.
Compound (I-1-1); $^1$H-NMR (DMSO-d$_6$) δ: 4.05 (s, 2H), 4.40 (d, J=6.1 Hz, 2H) 7.33 (dd J=7.1, 8.1 Hz, 1H), 7.40-7.49 (m, 3H), (d, J=7.6 Hz, 1H), 7.83 (d, J=7.6 Hz, 1H), 7.88-7.96 (m, 3H), 8.00 (s, 1H), 8.87 (t, J=6.1 Hz, 1H).

EXAMPLE 6

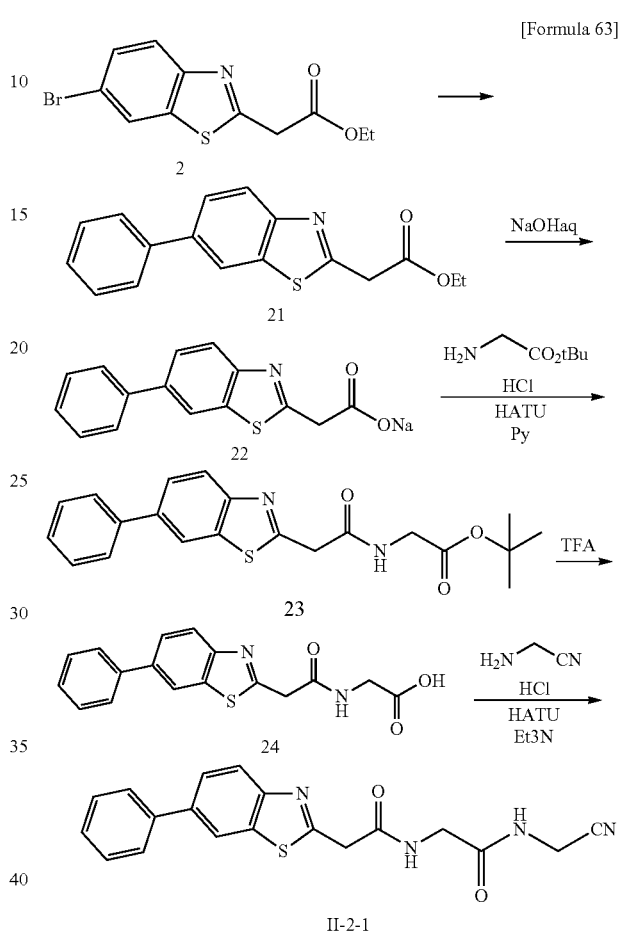

[Formula 63]

To a solution of Compound 2 (20 g, 67 mmol) in anhydrous 1,4-dioxane (200 mL) were added TETRAKIS(TRIPHENYLPHOSPHINE) PALLADIUM (0) (5.39 g, 4.66 mmol), PHENYLBORONIC ACID (9.75 g, 80 mmol) and K$_3$PO$_4$ (35.4 g, 167 mmol) at room temperature. It was heated under reflux for 6 hours. The reaction mixture was cooled to room temperature. To the mixture were added 1M hydrochloric acid and ethyl acetate. The mixture was extracted. The organic layer was washed with brine and dries over sodium sulfate. The solvent was evaporated under reduced pressure. The obtained residue was purified with chromatography to give Compound 21 (16.1 g, 81%) as a yellow solid.
Compound 21; $^1$H-NMR (CDCl$_3$) δ:1.31 (t, J=6.9 Hz, 3H), 4.19 (s, 2H), 4.27 (q, J=7.2 Hz, 2H), 7.38 (t, J=7.5 Hz, 1H), 7.48 (t, J=7.2 Hz, 2H), 7.63-7.73 (m, 3H), 8.06 (m, 2H)

To a solution of Compound 21 (5 g, 16.8 mmol) in anhydrous tetrahydrofran (35 mL) were added 2N NaOH solution (11 mL, 20 mmol). It was stirred at room temperature for 40 minutes. After the end of the reaction, n-hexane was added to the solution. The insoluble residue was collected by filtration. The obtained solid was washed with ethyl acetate. The obtained product was dried under reduced pressure to give Compound 22 (4.9 g, quant) as a yellows solid.

To a solution of Compound 22 (2 g, 6.87 mmol) in anhydrous dimethylformamide (20 ml) were added under nitrogen atmosphere tert-butyl 2-aminoacetate hydrochloride (1.38 g, 8.24 mmol), pyridine (2.78 ml, 34.3 mmol) and HATU (3.13 g, 8.24 mmol) at room temperature. It was stirred for 4 hours. To the reaction mixture were added 1M hydrochloric acid and ethyl acetate. The mixture was extracted. The organic layer was washed with brine and dried over sodium sulfate. The solvent was evaporated under reduced pressure. The obtained residue was purified with chromatography to give Compound 23 (1.63 g, 62%).

Compound 23; $^1$H-NMR (CDCl$_3$) δ: 1.46 (s, 9H), 4.01 (d, J=5.1 Hz, 2H), 4.13 (s, 2H), 7.38 (d, J=6.6 Hz, 1H), 7.48 (t, J=7.2 Hz, 2H), 7.64 (d, J=6.9 Hz, 2H), 7.72 (m, 1H), 8.06-8.10 (m, 2H)

To a solution of Compound 23 (1.6 g, 4.18 mmol) in anhydrous dichloromethane (5 mL) was added trifluoroacetic acid (5 ml). It was stirred at room temperature for 2 hours. The solvent was evaporated under reduced pressure. The obtained residue was crystallized with diethyl ether to give Compound 24 (1.12 g, 82%).

Compound 24; $^1$H-NMR (DMSO-d$_6$) δ: 3.85 (d, Hz J=5.7, 2H), 4.15 (s, 2H), 7.39 (d, J=6.9 Hz, 1H), 7.50 (t, J=7.8 Hz, 2H), 7.74-7.81 (m, 3H), 8.02 (d, J=8.7 Hz, 1H), 8.38 (s, 2H), 8.71 (m, 1H)

To a solution of Compound 24 (1.0 g, 3.06 mmol) in dimethylformamide (10 ml) were added at room temperature under nitrogen atmosphere 2-aminoacetonitrile hydrochloride (340 mg, 3.68 mmol), HATU (1.4 g, 3.68 mmol) and Et$_3$N (1.27 mL, 9.2 mmol). It was stirred for 3 hours. After the end of the reaction, 1M hydrochloric acid and ethyl acetate were added to the reaction mixture. It was extracted. The organic layer was washed with 10% sodium bicarbonate and water, respectively and dried over sodium sulfate. The solvent was evaporated under reduced pressure. The obtained residue was purified with chromatography to give Compound (II-2-1) (540 mg, 48%) as a white solid.

Compound (II-2-1); $^1$H-NMR (DMSO-d$_6$) δ: 3.84 (d, J=5.7 Hz, 2H), 4.17 (d, J=5.4 Hz, 4H) 7.39 (t, J=7.5 Hz, 1H), 7.50 (t, J=7.2 Hz, 2H), 8.02 (d, J=8.4 Hz, 1H), 8.38 (s, 1H), 8.69-8.75 (m, 2H)

EXAMPLE 7

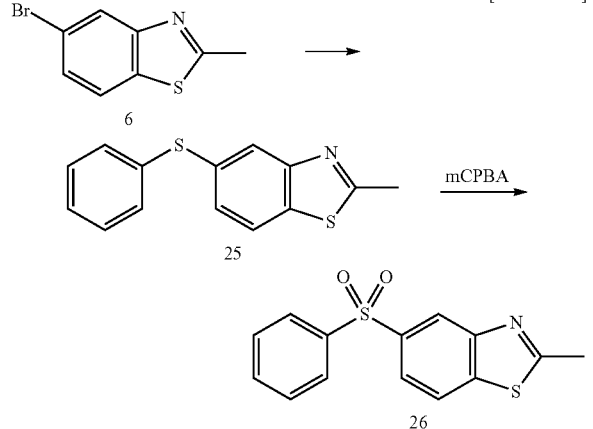

[Formula 64]

To a solution of 5-bromo-2-methylbenzothiazole 6 (1.3 g, 5.70 mmol) in 1,4-dioxane (13 mL) were added at room temperature under nitrogen atmosphere sodium salt of thiophenol (0.828 g, 6.27 mmol), xantphos (0.330 g, 0.570 mmol) and Pd$_2$(dba)$_3$ (0.261 g, 0.285 mmol). It was stirred for 30 minutes at 140° C. under microwave irradiation. The reaction mixture was poured into water and extracted with ethyl acetate. The obtained organic layer was washed with saturated aqueous sodium bicarbonate and brine, respectively and dried over magnesium sulfate. The solvent was evaporated under reduced pressure. The obtained residue was purified with silicagel chromatography (n-hexane:ethyl acetate) to give Compound 25 (2.34 g, 9.09 mmol, 87%) as a yellow liquid.

Compound 25; $^1$H-NMR (CDCl$_3$) δ: 2.82 (s, 3H), 7.25-7.39 (m, 6H), 7.74 (d, J=8.6 Hz, 1H), 7.89 (d, J=1.5 Hz, 1H).

To a solution of Compound 25 (2.34 g, 9.09 mmol) in dichloromathene (50 mL) was added little by little mCPBA (5.07 g, 19.09 mmol). It was stirred under ice-cooling for 2 hours. After the end of the reaction, the reaction mixture was poured into saturated aqueous sodium bicarbonate solution and extracted with ethyl acetate. The organic layer was washed with 10% aqueous sodium thiosulfate solution and brine, respectively and dried over sodium sulfate. The solvent was evaporated under reduced pressure. The obtained solid was washed with a mixed solvent of ethyl acetate and isopropyl ether to give Compound 26 (2.28 g, 7.88 mmol, 87%) as a white solid.

Compound 26; $^1$H-NMR (CDCl$_3$) δ: 2.86 (s, 3H), 7.48-7.58 (m, 3H), 7.89-7.99 (m, 4H), 8.52 (d, J=1.0 Hz, 1H).

EXAMPLE 8

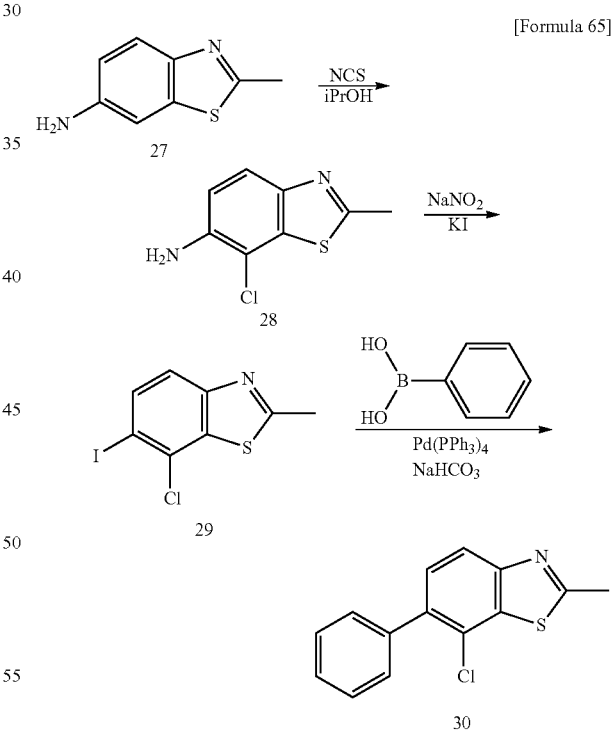

[Formula 65]

To a solution of Compound 27 (10.3 g, 62.7 mmol) in 2-propanol (300 mL) was added at room temperature under nitrogen atmosphere N-chloro succinimide (8.79 g, 65.9 mmol). It was stirred at room temperature for 2 hours. After the end of the reaction, the reaction mixture was cooled to room temperature and poured into saturated aqueous sodium bicarbonate. It was extracted twice with dichloromethane. The organic layer was washed with brine and dried over sodium sulfate. The solvent was evaporated under reduced pressure. The obtained residue was purified with silicagel chromatography (n-hexane:ethyl acetate) to give Compound 28 (4.95 g, 24.92 mmol, 40%) as a thin orange solid.

Compound 28; $^1$H-NMR (CDCl$_3$) δ: 2.77 (s, 3H), 4.11 (s, 2H), 6.88 (d, J=8.6 Hz, 1H), 7.63 (d, J=8.6 Hz, 1H).

A solution of Compound 28 (0.9 g, 4.53 mmol) in concentrated hydrochloric acid (5 mL) was diluted with water (5 ml). To the solution was dropped under ice-cooling a solution of sodium nitrite (344 mg, 4.98 mmol) in water (5 mL). It was stirred for 30 minutes. To the solution was dropped slowly a solution of potassium iodide (2707 mg, 16.31 mmol) in water (25 mL). It was stirred at room temperature for 1 hour. The reaction mixture was neutralized under ice-cooling with saturated aqueous sodium bicarbonate and extracted with chloroform. The organic layer was washed with a 10% aqueous solution of sodium thiosulfate and brine, respectively and dried over magnesium sulfate. The solvent was evaporated under reduced pressure. The obtained residue was purified with silicagel chromatography (n-hexane:ethyl acetate) to give Compound 29 (740 mg, 2.391 mmol, 53%) as a white solid.

Compound 29; LC/MS/Rt=2.54 min, MS:309.80 (M+1), method:C

To a solution of Compound 29 (740 mg, 2.391 mmol) in 1,4-dioxane (10 mL) and water (2.0 mL) at room temperature under nitrogen atmosphere phenyl boronic acid (364 mg, 2.99 mmol), tetrakis(triphenylphosphine)palladium (276 mg, 0.239 mmol) and sodium bicarbonate (502 mg, 5.98 mmol). After that, It was stirred at 100° C. for for 15 minutes under microwave irradiation. After the end of the reaction, ethyl acetate was added to the mixture. The organic layer was purified with silicagel chromatography (n-hexane:ethyl acetate) to give Compound 30 (588 mg, 2.264 mmol, 95%).

Compound 30; LC/MS/Rt=2.56 min, MS:260.0 (M+1), method:C

EXAMPLE 9

[Formula 66]

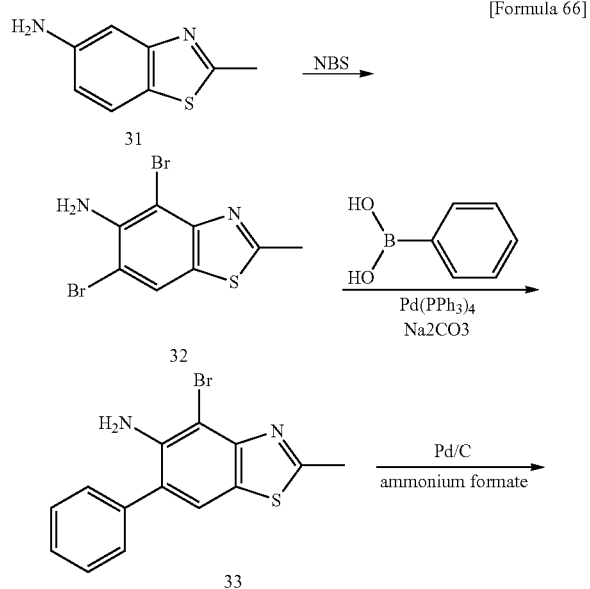

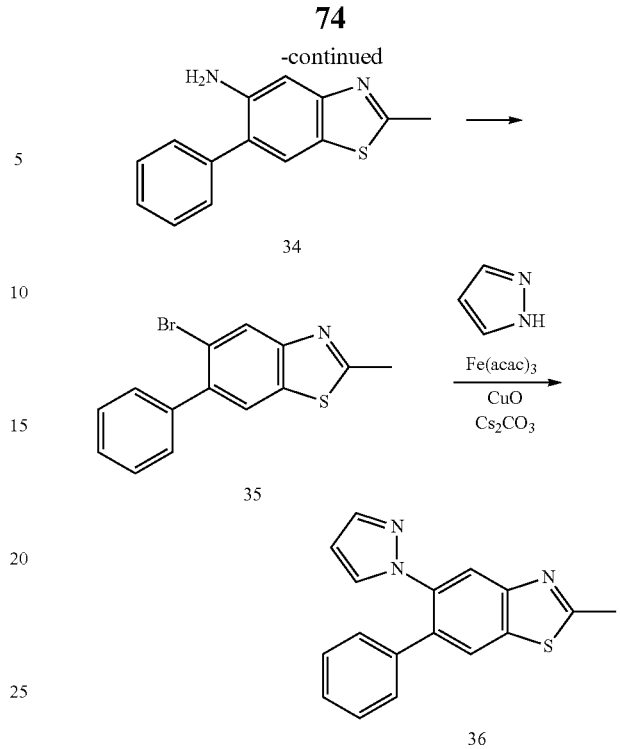

To a solution of 5-amino-2-methyl benzothiazole 31 (10 g, 60.9 mmol) in 2-propanol (200 mL) was added at room temperature under nitrogen atmosphere N-bromo succinimide (23.84 g, 134 mmol). It was stirred at 65° C. for 20 minutes. Furthermore, N-bromo succinimide (10.84 g, 60.9 mmol) was added to the reaction mixture. It was stirred at 65° C. for 30 minutes. The reaction mixture was poured into saturated aqueous sodium bicarbonate and extracted with dichloromethane. The organic layer was washed with brine and dried over sodium sulfate. The solvent was evaporated under reduced pressure. The obtained residue was purified with silicagel chromatography (n-hexane:ethyl acetate) to give Compound 32 (12.15 g, 37.7 mmol, 62%) as a solid.

Compound 32; $^1$H-NMR (CDCl$_3$) δ: 2.84 (s, 3H), 4.71 (br s, 2H), 7.84 (s, 1H).

To a solution of Compound 32 (12.15 g, 37.7 mmol) in 1,4-dioxane (120 mL) and water (30 mL) at room temperature under nitrogen atmosphere phenyl boronic acid (5.75 g, 47.2 mmol), tetrakis(triphenylphosphine)palladium (4.36 g, 3.77 mmol) and sodium carbonate (8.00 g, 75 mmol). Then, it was heated under reflux for 7 hours. After the end of the reaction, the mixture was poured into water and extracted with a mixed solvent of ethyl acetate and THF. The organic layer was washed with brine and dried over magnesium sulfate. The solvent was evaporated under reduced pressure. The obtained residue was crystallized with ethyl acetate and n-hexane to give Compound 33 (9.6 g, 30.1 mmol, 80%) as a solid.

Compound 33; $^1$H-NMR (DMSO-d$_6$) δ: 2.78 (s, 3H), 4.84 (br s, 2H), 7.41-7.53 (m, 5H), 7.65 (s, 1H).

To a solution of Compound 33 (8 g, 25.06 mmol) in THF (40 mL) and methanol (40 mL) were added at room temperature under nitrogen atmosphere Pd/C (10%, water) (13.34 g, 6.27 mmol). To the solution was added continuously ammonium formates (15.80 g, 251 mmol). The reaction mixture stirred at 50° C. for 2 hours. To the mixture was added Pd/C (10%, water) (13.34 g, 6.27 mmol). It was stirred at 50° C. for 4 hours. The reaction mixture was cooled to room temperature. To the mixture was added ethyl acetate. The reaction mixture was filtered with celite and concentrated under reduced pressure. The obtained residue was diluted with water. It was extracted with ethyl acetate. The organic layer was dried over magnesium sulfate. The solvent was evaporated under reduced pressure. The obtained solid was washed with ethyl acetate and n-hexane to give Compound 34 (3.16 g, 13.15 mmol, 53%) as a brown solid.

Compound 34; $^1$H-NMR (DMSO-$d_6$) δ: 2.72 (s, 3H), 4.86 (br s, 2H), 7.26 (s, 1H), 7.35-7.40 (m, 1H), 7.45-7.49 (m, 4H), 7.57 (s, 1H).

To a solution of isoamyl nitrite (1.707 mL, 12.17 mmol) in acetonitrile (40 mL) was added under ice-cooling and nitrogen atmosphere CuBr (1.397 g, 9.74 mmol). After that, Compound 34 (1.95 g, 8.11 mmol) was added to the solution little by little. It was stirred under ice-cooling for 20 minutes. After that, the mixture stirred at 50° C. for further 2 hours. The reaction mixture was poured into 0.1M HCl aqueous solution and extracted with ethyl acetate. The organic layer was washed with saturated aqueous sodium bicarbonate and brine, respectively and dried over magnesium sulfate. The solvent was evaporated under reduced pressure. The obtained residue was purified with silicagel chromatography (n-hexane:ethyl acetate) to give Compound 35 (1.005 g, 3.30 mmol, 41%) as a solid.

Compound 35; $^1$H-NMR (CDCl$_3$) δ: 2.86 (s, 3H), 7.40-7.46 (m, 5H), 7.76 (s, 1H), 8.25 (s, 1H).

To a solution of Compound 35 (400 mg, 1.315 mmol) in NMP (1 mL) at room temperature under nitrogen atmosphere pyrazole (134 mg, 1.972 mmol), Fe(acac)$_3$ (139 mg, 0.394 mmol), copper oxide (II) (20.92 mg, 0.263 mmol) and cesium carbonate (857 mg, 2.63 mmol). It was stirred at 180° C. for 30 minutes under microwave irradiation. Furthermore, it was stirred at 190° C. for 1 hour under microwave irradiation. The reaction mixture was poured into water and extracted with ethyl acetate. The organic layer was washed with brine and dried over sodium sulfate. The solvent was evaporated under reduced pressure. The obtained residue was purified with silicagel chromatography (n-hexane:ethyl acetate) to give Compound 36 (150 mg, 0.515 mmol, 39%).

Compound 36; LC/MS Rt=2.21 min, MS:292.050 (M+1), method:C

EXAMPLE 10

[Formula 67]

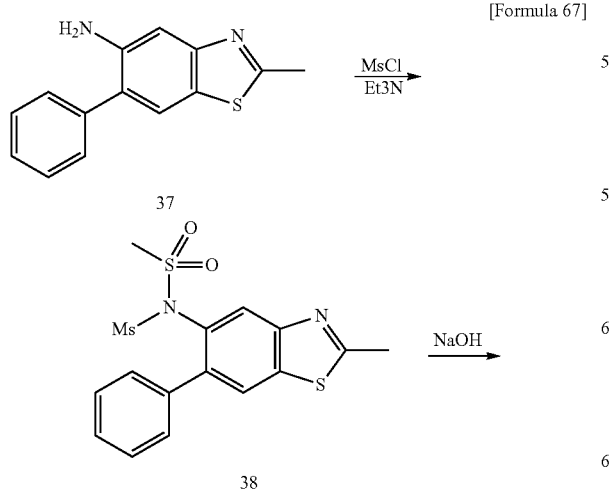

-continued

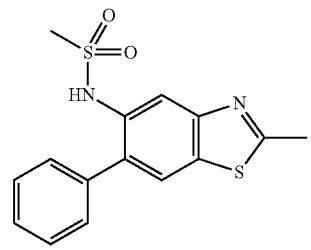

39

To a solution of Compound 37 (300 mg, 1.248 mmol) and triethyl amine (0.260 mL, 1.872 mmol) in dichloromethane (6 mL) was added under nitrogen atmosphere and ice-cooling methane sulfonyl chloride (0.107 mL, 1.373 mmol). It was stirred at room temperature for 5 hours. To the solution were added triethylamine (0.346 mL, 2.497 mmol) and methane sulfonyl chloride (0.146 mL, 1.872 mmol). It was stirred at room temperature for 12 hours. After the end of the reaction, the mixture was poured into 0.1M hydrochloric acid and extracted with ethyl acetate. The organic layer was washed with saturated aqueous sodium bicarbonate and brine, respectively and dried over magnesium sulfate. The solvent was evaporated under reduced pressure. Compound 38 (452 mg, 1.140 mmol, 91%) was obtained.

Compound 38; $^1$H-NMR (CDCl$_3$) δ: 2.88 (s, 3H), 3.01 (s, 6H), 7.42-7.50 (m, 3H), 7.60-7.61 (m, 2H), 7.87 (s, 1H), 7.95 (s, 1H).

To a solution of Compound 38 (452 mg, 1.140 mmol) in THF (4 mL) and the MeOH (2 mL) was added at room temperature 2M aqueous sodium hydroxide. It was stirred for 2 hours. The reaction mixture was concentrated under reduced pressure. The obtained residue was diluted with water, acidified with 10% aqueous citric acid and extracted with ethyl acetate. The organic layer was washed with brine and dried over magnesium sulfate. The solvent was evaporated under reduced pressure. The obtained residue was purified with silicagel chromatography (n-hexane:ethyl acetate) to give Compound 39 (290 mg, 0.911 mmol, 80%).

Compound 39; $^1$H-NMR (CDCl$_3$) δ: 2.86 (s, 3H), 2.93 (s, 3H), 6.50 (br s, 1H), 7.36-7.38 (m, 2H), 7.46-7.54 (m, 3H), 7.70 (s, 1H), 8.23 (s, 1H).

EXAMPLE 11

[Formula 68]

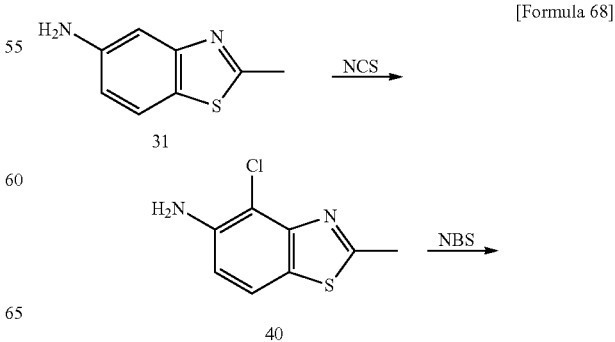

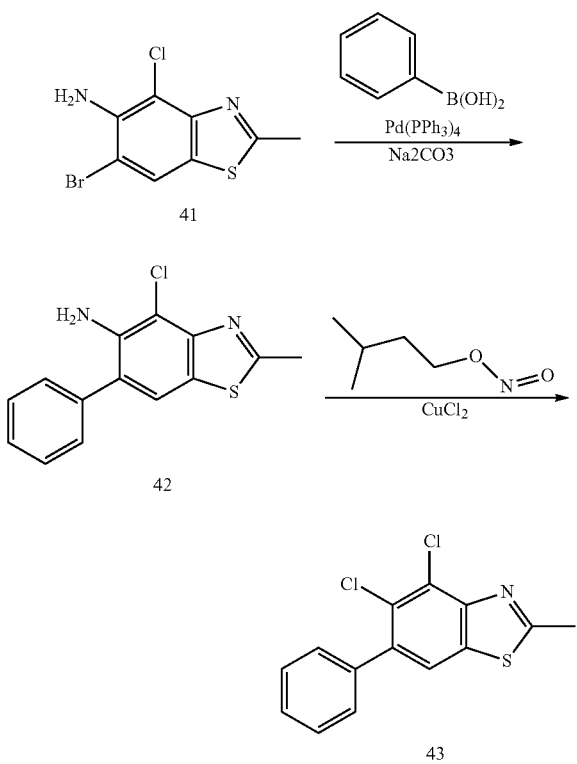

To a solution of Compound 31 (2.36 g, 14.37 mmol) in 2-propanol (35 mL) was added at room temperature under nitrogen atmosphere N-chloro succinimide (2.111 g, 15.81 mmol). It stirred for 20 minutes at 65° C. After the end of the reaction, it was cooled to room temperature. The reaction mixture was poured into saturated aqueous sodium bicarbonate and extracted twice with dichloromethane. The organic layer was washed with brine and dried over sodium sulfate. The solvent was evaporated under reduced pressure. The obtained residue was purified with silicagel chromatography (n-hexane:ethyl acetate) to give Compound 40 (1.73 g, 8, 71 mmol, 61%) as a thin orange solid.
Compound 40; $^1$H-NMR (CDCl$_3$) δ: 2.84 (s, 3H), 4.18 (d, J=1.0 Hz, 2H), 6.85 (d, J=8.6 Hz, 1H), 7.47 (d, J=8.1 Hz, 1H).

To a solution of Compound 40 (1.72 g, 8.66 mmol) in 2-propanol (35 mL) was added at room temperature under nitrogen atmosphere N-bromo succinimide (1.695 g, 9.52 mmol). It was stirred for 15 minutes at 65° C. After the end of the reaction, the mixture was cooled to room temperature and poured into saturated aqueous sodium bicarbonate. The mixture was extracted twice with chloroform. The organic layer was washed with brine and dried over magnesium sulfate. The solvent was evaporated under reduced pressure. The obtained residue was purified with silicagel chromatography (n-hexane:ethyl acetate) to give Compound 41 (1.93 g, 6.95 mmol, 80%) as a thin yellow solid.
Compound 41; $^1$H-NMR (CDCl$_3$) δ: 2.77 (s, 3H), 4.55 (br s, 2H), 7.94 (s, 1H).

To a solution of Compound 41 (0.96 g, 3.46 mmol) in 1,4-dioxane (10 mL) and water (2.0 mL) were added at room temperature under nitrogen atmosphere phenyl boronic acid (0.633 g, 5.19 mmol), tetrakis(triphenylphosphine)palladium (0) (0.400 g, 0.346 mmol) and sodium carbonate (0.916 g, 8.65 mmol). It was stirred for 20 minutes at 140° C. under microwave irradiation. After the end of the reaction, ethyl acetate was added to the reaction mixture. The organic layer was concentrated under reduced pressure. It was purified with silicagel chromatography (n-hexane ethyl acetate) to give Compound 42 (1.44 g, 5.24 mmol, 76%) as a yellows solid.
Compound 42; $^1$H-NMR (DMSO-d$_6$) δ: 2.78 (s, 3H), 4.88 (br s, 2H), 7.42-7.53 (m, 5H), 7.63 (s, 1H).

To a solution of isoamyl nitrite (0.515 mL, 3.82 mmol) in acetonitrile (14 mL) was added under ice-cooling and nitrogen atmosphere CuCl$_2$ (428 mg, 3.18 mmol). To the solution was gradually added Compound 42 (700 mg, 2.55 mmol). It was stirred under ice-cooling for 20 minutes. Furthermore, it was stirred at 50° C. for 2 hours. The reaction mixture was poured into 0.1M HCl aqueous solution and extracted with ethyl acetate. The organic layer was washed with saturated aqueous sodium bicarbonate and brine, respectively and dried over magnesium sulfate. The solvent was evaporated under reduced pressure. The obtained residue was purified with silicagel chromatography (n-hexane:ethyl acetate) to give Compound 43 (636 mg, 2.162 mmol, 85%) as a white solid.
Compound 43; $^1$H-NMR (CDCl$_3$) δ: 2.93 (s, 3H), 7.43-7.51 (m, 5H), 7.71 (s, 1H).

EXAMPLE 12

[Formula 69]

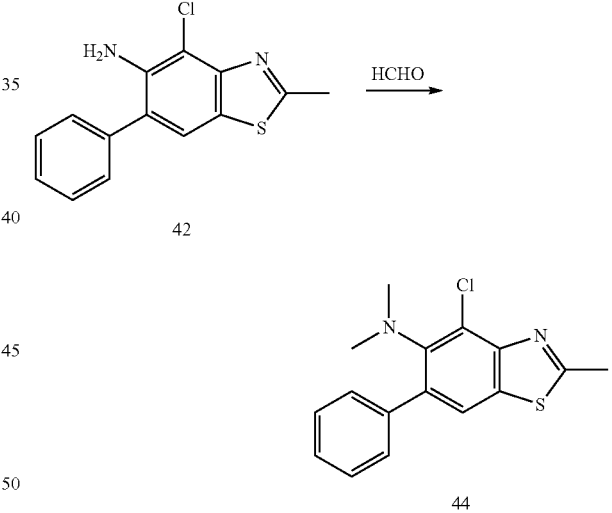

To a solution of Compound 42 (683 mg, 2.486 mmol) in formic acid (14 mL) was added at room temperature 35% formaldehyde solution (1.956 mL, 24.86 mmol). It was heated for 1 hour under reflux. The reaction mixture was cooled to room temperature and was made basic by slowly adding saturated aqueous sodium bicarbonate. The mixture was extracted with ethyl acetate. The organic layer was washed with water and brine, respectively and dried over magnesium sulfate. The solvent was evaporated under reduced pressure. The residue was purified with silicagel chromatography (n-hexane:ethyl acetate) to give Compound 44 (213 mg, 0.703 mmol, 28.3%) as a solid.

Compound 44; $^1$H-NMR (CDCl$_3$) δ: 2.68 (s, 6H), 2.88 (s, 3H), and 7.35-7.44 (m, 5H) and 7.56 (s, 1H).

EXAMPLE 13

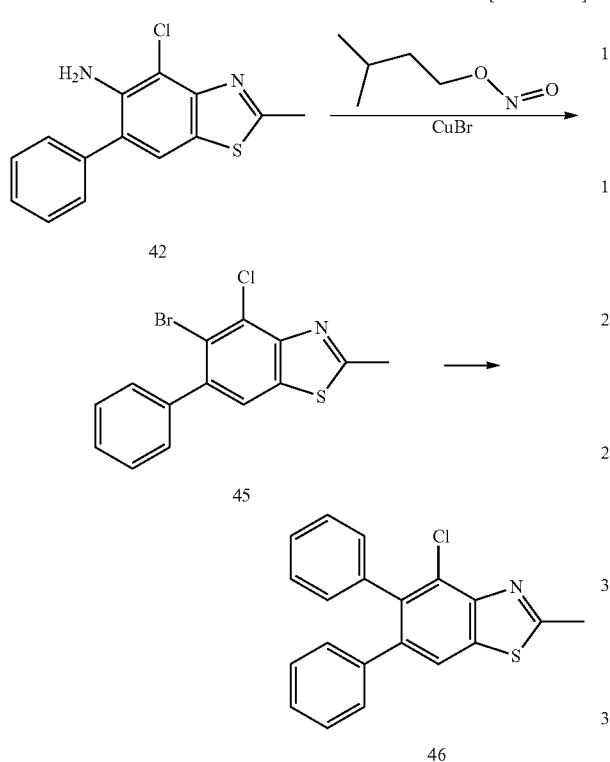

[Formula 70]

To a solution of isoamyl nitrite (0.416 mL, 2.96 mmol) in acetonitrile (11 mL) was added under ice-cooling and nitrogen atmosphere CuBr (340 mg, 2.371 mmol). After that, Compound 42 (543 mg, 1.976 mmol) was added little by little to the solution. It was stirred under ice-cooling for 20 minutes. Furthermore, it was stirred at 50° C. for 2 hours. The reaction mixture was poured into 0.1M HCl aqueous solution and extracted with ethyl acetate. The organic layer was washed with saturated aqueous sodium bicarbonate and brine, respectively and dried over magnesium sulfate. The solvent was evaporated under reduced pressure. The residue was purified with silicagel chromatography (n-hexane:ethyl acetate) to give Compound 45 (325 mg, 0.960 mmol, 49%) as a solid.

Compound 45; $^1$H-NMR (DMSO-d$_6$) δ: 2.87 (s, 3H) and 7.41-7.51 (m, 5H) and 8.07 (s, 1H).

To a solution of Compound 45 (120 mg, 0.354 mmol) in 1,4-dioxane (1.4 mL) and water (0.35 mL) were added at room temperature under nitrogen atmosphere tetrakis(triphenylphosphine)palladium(0) (20.47 mg, 0.018 mmol), phenyl boron acid (51.8 mg, 0.425 mmol) and sodium bicarbonate (74.4 mg, 0.886 mmol). It was stirred for 40 minutes at 130° C. under microwave irradiation. The reaction mixture was poured into water and extracted with ethyl acetate. The organic layer was washed with brine and dried over sodium sulfate. The solvent was evaporated under reduced pressure. The residue was purified with silicagel chromatography (n-hexane ethyl acetate) to give Compound 46 (107 mg, 0.319 mmol, 90%).

Compound 46; $^1$H-NMR (CDCl$_3$) δ: 2.93 (s, 3H), 7.06-7.28 (m, 10H), 7.77 (s, 1H).

EXAMPLE 14

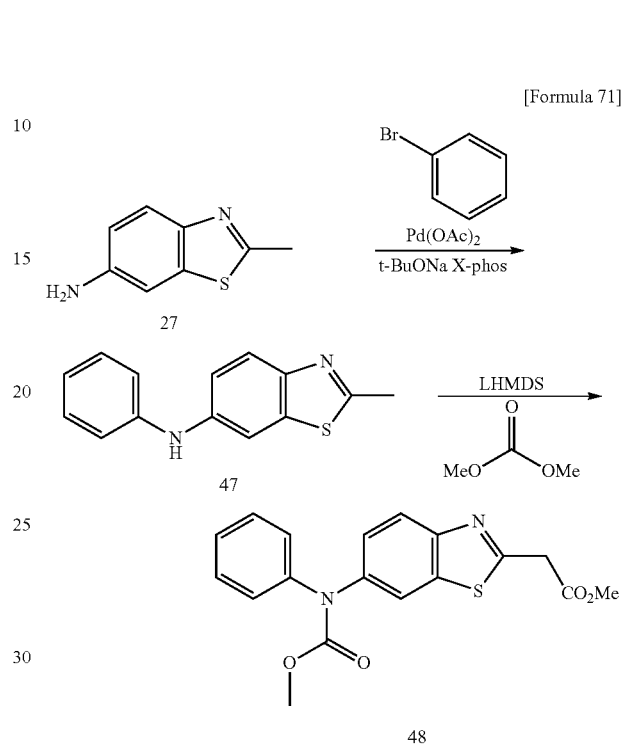

[Formula 71]

To a solution of 2-methylbenzo[d]thiazol-6-amine 27 (1 g, 6.09 mmol) in toluene (10 mL) and t-BuOH (2 mL) were added at room temperature under nitrogen atmosphere bromobenzene (1.004 g, 6.39 mmol), palladium acetate (0.068 g, 0.304 mmol), X-Phos (0.290 g, 0.609 mmol) and sodium tert-butoxide (0.819 g, 8.52 mmol). It was stirred for 30 minutes at 150° C. under microwave irradiation. The reaction mixture was poured into water and extracted with ethyl acetate. The organic layer was washed with saturated aqueous sodium bicarbonate and brine, respectively and dried over sodium sulfate. The solvent was evaporated under reduced pressure. The residue was purified with silicagel chromatography (n-hexane:ethyl acetate) to give Compound 47 (1.29 g, 5.37 mmol, 88%) as a solid.

Compound 47; $^1$H-NMR (CDCl$_3$) δ: 2.81 (s, 3H), 5.83 (br s, 1H), 6.97-7.01 (m, 1H), 7.10-7.17 (m, 3H), 7.29-7.34 (m, 2H), 7.53 (d, J=2.4 Hz, 1H), 7.83 (d, J=8.6 Hz, 1H).

To a solution of compound 47 (450 mg, 1.872 mmol) in THF (45 mL) was dropped at −60° C. under nitrogen atmosphere LHMDS (6.18 mL, 6.18 mmol). It was stirred for 30 minutes at −60° C. To the solution was added at −60° C. diethyl carbonate (0.347 mL, 4.12 mmol). The mixture was stirred at 0° C. for 1 hour. The reaction mixture was poured into 0.1M hydrochloric acid and extracted with ethyl acetate. The organic layer was washed with saturated aqueous sodium bicarbonate and brine, respectively and dried over sodium sulfate. The solvent was evaporated under reduced pressure. The residue was purified with silicagel chromatography (n-hexane:ethyl acetate) to give Compound 48 (503 mg, 1.411 mmol, 75%) as a brown liquid.

Compound 48; $^1$H-NMR (CDCl$_3$) δ: 3.77 (s, 3H), 3.78 (s, 3H), 4.16 (s, 2H), 7.22-7.27 (m, 3H), 7.33-7.37 (m, 3H), 7.79 (d, J=2.0 Hz, 1H), 7.94 (d, J=8.6 Hz, 1H).

EXAMPLE 15

[Formula 72]

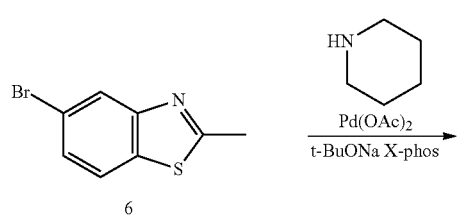

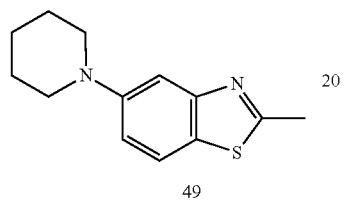

To a solution of 5-bromo-2-methylbenzothiazole 6 (300 mg, 1.315 mmol) in toluene (3.0 mL) and t-BuOH (0.6 mL) were added at room temperature under nitrogen atmosphere piperidine (224 mg, 2.63 mmol), palladium acetate (14.76 mg, 0.066 mmol), X-Phos (62.7 mg, 0.132 mmol) and sodium tert-butoxide (177 mg, 1.841 mmol). It was stirred for 20 minutes at 150° C. under microwave irradiation. The reaction mixture was poured into water and extracted with ethyl acetate. The organic layer was washed with brine and dried over magnesium sulfate. The solvent was evaporated under reduced pressure. The residue was purified with silicagel chromatography (n-hexane:ethyl acetate) to give Compound 49 (211 mg, 0.908 mmol, 69%).
Compound 49; $^1$H-NMR (CDCl$_3$) δ: 1.60-1.65 (m, 2H), 1.74-1.80 (m, 4H), 3.22 (t, J=5.6 Hz, 4H), 7.09 (dd, J=8.9, 2.3 Hz, 1H), 7.48 (d, J=2.5 Hz, 1H), 7.65 (t, J=4.6 Hz, 1H).

EXAMPLE 16

[Formula 73]

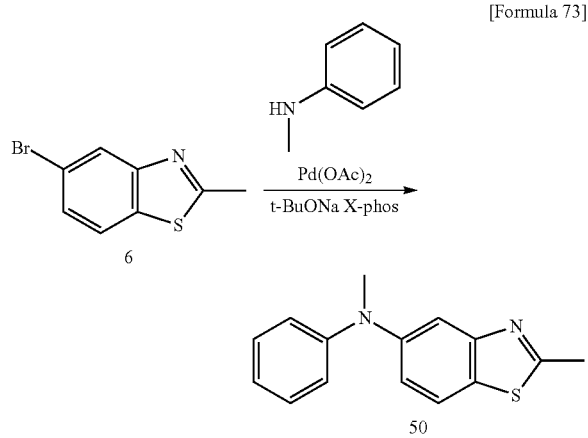

To a solution of 5-bromo-2-methylbenzothiazole 6 (1.2 g, 5.26 mmol) in toluene (10 mL) and t-BuOH (2 mL) were added at room temperature under nitrogen atmosphere N-methylaniline (620 mg, 5.79 mmol), palladium acetate (59.1 mg, 0.263 mmol), X-Phos (251 mg, 0.526 mmol) and sodium tert-butoxide (708 mg, 7.36 mmol). It was stirred for 20 minutes at 150° C. under microwave irradiation. The reaction mixture was poured into water and extracted with ethyl acetate. The organic layer was washed with brine and dried over magnesium sulfate. The solvent was evaporated under reduced pressure. The residue was purified with silicagel chromatography (n-hexane:ethyl acetate) to give Compound 50 (820 mg, 3.22 mmol, 61%).
Compound 50; $^1$H-NMR (CDCl$_3$) δ: 2.81 (s, 3H), 3.37 (s, 3H) 6.97 (t, J=7.4 Hz, 1H), 7.59 (d, J=2.0 Hz, 1H) 7.04-7.07 (m, 3H), 7.27-7.30 (m, 2H), 7.63 (d, J=8.6 Hz, 1H).

EXAMPLE 17

[Formula 74]

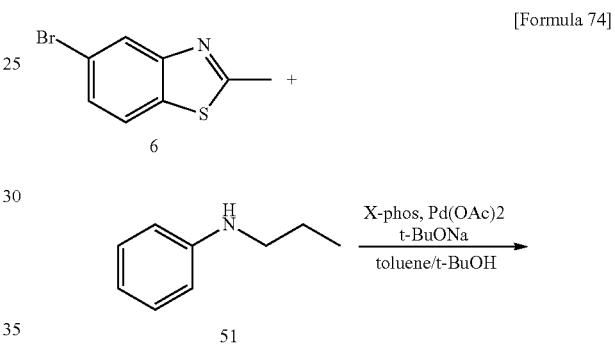

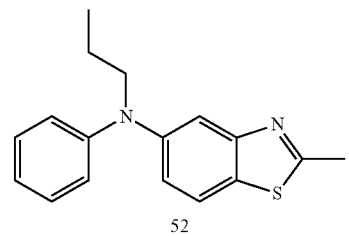

In a mixed solvent of toluene (10 mL) and t-BuOH (2 mL) were suspended under nitrogen atmosphere 5-bromo-2-methylbenzothiazole 6 (1.2 g, 5.26 mmol), N-propyl aniline 51 (0.782 g, 5.79 mmol), Pd(OAc)$_2$ (0.059 g, 0.263 mmol), X-phos (0.251 g, 0.526 mmol) and t-BuONa (0.708 g, 7.36 mmol). The obtained mixture was stirred at 150° C. for 30 minutes under microwave irradiation. To the reaction mixture were added Pd(OAc)$_2$ (0.059 g, 0.263 mmol) and X-phos (0.251 g, 0.526 mmol). It was stirred at 150° C. for 30 minutes under microwave irradiation. The reaction mixture was filtered with celite. Water and ethyl acetate were added. The mixture was extracted. The organic layer was washed with brine and dried over magnesium sulfate. The solvent was evaporated under reduced pressure. The residue was purified with column chromatography to give Compound 52 (1.29 g, 4.57 mmol).

Compound 52; $^1$H-NMR (CDCl$_3$) δ: 0.96 (t, J=7.6 Hz, 3H), 1.69-1.77 (m, 2H) and 2.82 (s, 3H), 3.72 (t, J=7.6 Hz, 2H), 6.96 (t, J=7.4 Hz, 1H), 7.02 (d, J=8.6 Hz, 3H), 7.25-7.29 (m, 2H), 7.58 (d, J=2.0 Hz, 1H), 7.62 (d, J=8.6 Hz, 1H).

EXAMPLE 18

[Formula 75]

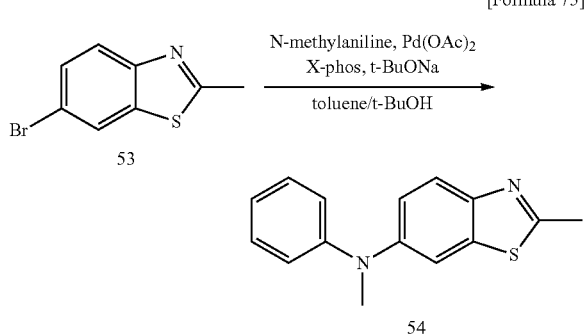

To a mixed solvent of toluene (9.2 mL) and t-BuOH (2.2 mL) were added under nitrogen atmosphere 6-bromo-2-methylbenzothiazole 53 (900 mg, 3.95 mmol), Pd(OAc)$_2$ (44.3 mg, 0.197 mmol), X-phos (188 mg, 0.395 mmol) and t-BuONa (531 mg, 5.52 mmol). To the obtained mixture was added N-methylaniline (0.470 ml, 4.34 mmol). It was stirred for 150° C. or 20 minutes under microwave irradiation. To the reaction mixture were added water and ethyl acetate. The mixture was extracted. The organic layer was washed with brine and dried over magnesium sulfate. The solvent was evaporated under reduced pressure. The residue was purified with column chromatography to give Compound 54 (868 mg, 3.41 mmol).

Compound 54; $^1$H-NMR (CDCl$_3$) δ: 2.82 (s, 3H), 3.38 (s, 3H) 6.97-7.08 (m, 3H), 7.15 (dd, J=8.9, 2.4 Hz, 1H), 7.27-7.35 (m, 2H), 7.44 (d, J=2.4 Hz, 1H), 7.83 (d, J=8.9 Hz, 1H)

EXAMPLE 19

[Formula 76]

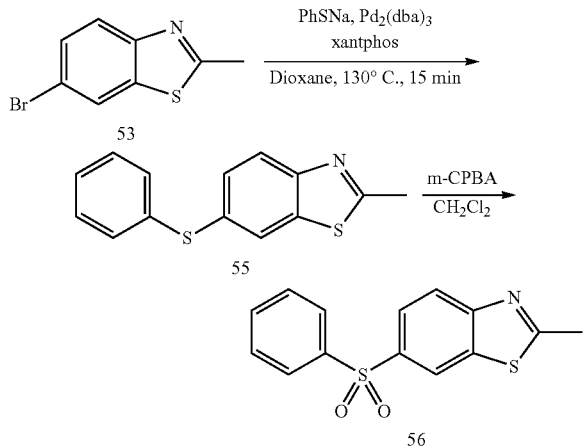

In dioxane (10 mL) were suspended under nitrogen atmosphere 6-bromo-2-methylbenzothiazole 53 (700 mg, 3.07 mmol), Pd$_2$(dba)$_3$ (141 mg, 0.153 mmol) and Xantphos (178 mg, 0.307 mmol). To the obtained mixture was added thiophenol sodium salt (487 mg, 3.68 mmol). It was stirred at 130° C. for 15 minutes under microwave irradiation. To the reaction mixture were added 0.1N hydrochloric acid and ethyl acetate. After extraction, the organic layer washed with saturated sodium bicarbonate aqueous solution and brine, respectively and dried over magnesium sulfate. The solvent was evaporated under reduced pressure. The residue was purified with column chromatography to give Compound 55 (587 mg, 2.28 mmol).

Compound 55; $^1$H-NMR (CDCl$_3$) δ: 2.85 (s, 3H), 7.24-7.39 (m, 5H), 7.46 (dd, J=8.6, 1.8 Hz, 1H), 7.83 (dd, J=1.8, 0.5 Hz, 1H), 7.89 (d, J=8.6 Hz, 1H).

To a solution of Compound 55 (586.6 mg, 2.279 mmol) in dichloromethane (12 mL) was added at 0° C. mCPBA (1452 mg, 5.47 mmol). It was stirred at 0° C. for 1 hour. To the reaction mixture was added saturated aqueous sodium bicarbonate and ethyl acetate. After extraction, the organic layer was washed 10% aqueous sodium thiosulfate and brine, respectively and dried over magnesium sulfate. The solvent was evaporated under reduced pressure. The residue was purified by crystallization to give Compound 56 (259 mg, 0.894 mmol).

Compound 56; $^1$H-NMR (CDCl$_3$) δ: 2.90 (s, 3H), 7.49-7.62 (m, 3H), 7.96-8.07 (m, 4H), 8.52 (dd, J=1.8, 0.6 Hz, 1H).

EXAMPLE 20

[Formula 77]

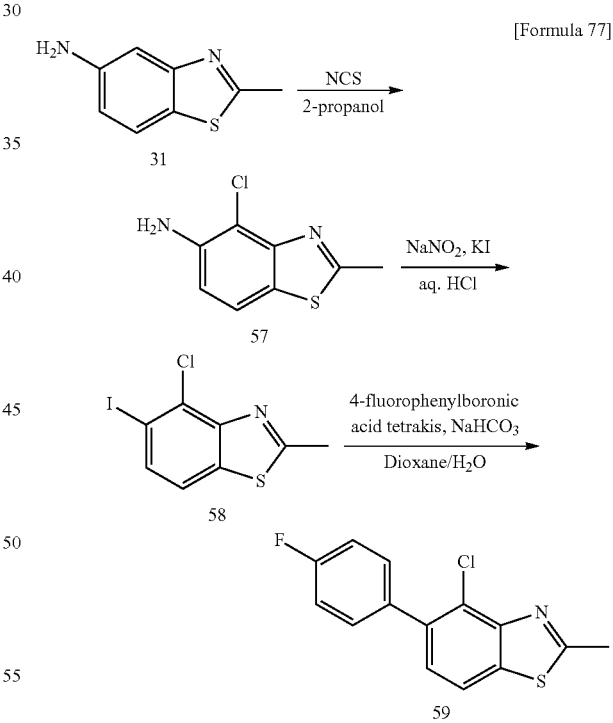

To a solution of 5-amino-2-methylbenzothiazole 31 (3 g, 18.27 mmol) in 2-propanol (30 mL) was added NCS (2.56 g, 19.18 mmol). It was stirred at room temperature for 1.5 hours. Water and ethyl acetate were added to the reaction mixture. After extraction, the organic layer was washed with brine and dried over magnesium sulfate. The solvent was evaporated under reduced pressure. The residue was purified with column chromatography to give Compound 57 (1.90 g, 9.56 mmol).

Compound 57; $^1$H-NMR (CDCl$_3$) δ: 2.86 (s, 3H), 4.20 (br s, 2H), 6.86 (d, J=8.6 Hz, 1H), 7.49 (d, J=8.6 Hz, 1H).

To a suspension of Compound 57 (1.90 g, 9.56 mmol) concentrated hydrochloric acid (10 mL) was dropped at 0° C. a solution of sodium nitrites (726 mg, 10.52 mmol) in H$_2$O (10 ml). It was stirred for 30 minutes at the same temperature. Potassium iodide (23.8 g, 143 mmol) aqueous solution (50 ml) was dropped to the reaction mixture at 0° C. It was stirred at the same temperature for 1 hour. The reaction mixture was neutralized with saturated aqueous sodium bicarbonate and extracted with chloroform. The organic layer was washed with 10% aqueous sodium thiosulfate and brine, respectively and dried over magnesium sulfate. The solvent was evaporated under reduced pressure. The residue was purified by crystallization to give Compound 58 (1.48 g, 4.79 mmol).
Compound 58; $^1$H-NMR (CDCl$_3$) δ: 2.91 (s, 3H), 7.48 (d, J=8.4 Hz, 1H), 7.81 (d, J=8.4 Hz, 1H).

In a mixed solvent of dioxane (8 mL) and H$_2$O (2 mL) were suspended under nitrogen atmosphere Compound 58 (799 mg, 2.58 mmol), 4-fluoro benzene boronic acid (542 mg, 3.87 mmol), tetrakis(triphenylphosphine) palladium (298 mg, 0.258 mmol) and sodium bicarbonate (542 mg, 6.45 mmol). The obtained mixture was stirred at 120° C. for 1 hour under microwave irradiation. To the reaction mixture were added water and ethyl acetate. After extraction, the organic layer was washed with saturated aqueous sodium bicarbonate and brine, respectively and dried over magnesium sulfate. The solvent was evaporated under reduced pressure. The residue was purified with column chromatography to give Compound 59 (464 mg, 1.67 mmol).
Compound 59; $^1$H-NMR (CDCl$_3$) δ: 2.93 (s, 3H), 7.14-7.21 (m, 2H), 7.34 (d, J=8.2 Hz, 1H), 7.45-7.52 (m, 2H), 7.77 (d, J=8.2 Hz, 1H).

EXAMPLE 21

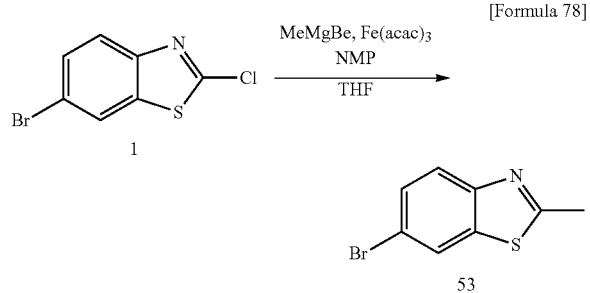

[Formula 78]

In a mixed solvent of THF (200 mL) and NMP (20 mL) were dissolved 6-bromo-2-chlorobenzothiazole 1 (15 g, 60.4 mmol) and Fe(acac)$_3$ (1.07 g, 3.02 mmol). To the obtained mixture was added at 0° C. 3M methyl magnesium bromide ethereal solution (24.14 ml, 72.4 mmol). It was stirred at room temperature for 1.5 hours. To the reaction mixture was added at 0° C. 3M methyl magnesium bromide ethereal solution (10.1 ml, 30.2 mmol). It was stirred at room temperatures for 1 hour. To the reaction mixture 1N aqueous hydrochloric acid and ethyl acetate. After extraction, the organic layer was washed with brine and dried over magnesium sulfate. The solvent was evaporated under reduced pressure. The residue was purified with column chromatography to give Compound 53 (10.6 g, 46.5 mmol).

Compound 53; $^1$H-NMR (CDCl$_3$) δ: 2.82 (s, 3H), 7.54 (dd, J=8.7, 2.0 Hz, 1H), 7.80 (d, J=8.7 Hz, 1H), 7.95 (d, J=2.0 Hz, 1H).

EXAMPLE 22

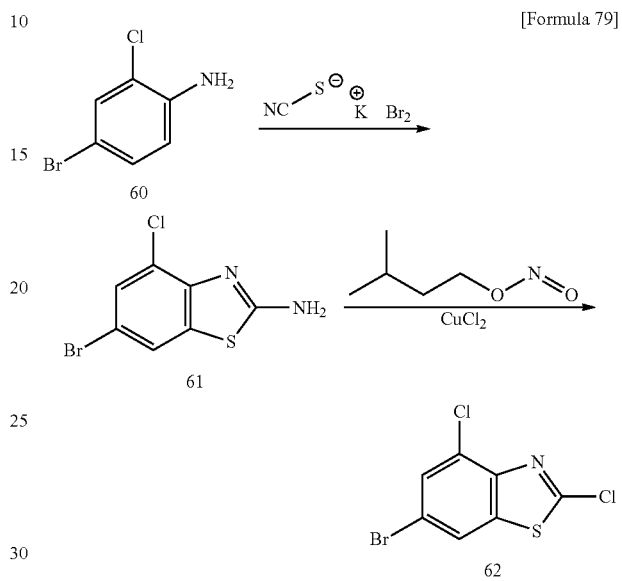

[Formula 79]

To a solution of 4-bromo-2-chloroaniline 60 (2.50 g, 12.11 mmol) in acetic acid (25 ml) was added at room temperature potassium thiocyanate (4.71 g, 48.4 mmol). To the mixture was dropped for 15 minutes a solutions of bromine (1.25 ml, 24.22 mmol) in acetic acid (5 ml). After the end of dropping, it was stirred at room temperature for 15 minutes and further stirred at 30° C. for 1 hour. After the end of the reaction, the mixture was neutralized with aqueous sodium hydroxide under ice-cooling and extracted with ethyl acetate. The organic layer was washed with saturated sodium bicarbonate solution and brine, respectively and dried over sodium sulfate. The solvent was evaporated under reduced pressure. To the residue was added ethyl acetate and di-isopropyl ether. The mixture was filtered to give Compound 61 (2.02 g, yield 43.3%) as a yellow solid.

Compound 61; $^1$H-NMR (DMSO-d$_6$) δ: 7.48 (dd, J=2.1, 0.9 Hz, 1H), 7.89 (dd, J=2.7, 1.8 Hz, 1H), 7.97 (brs, 2H).

To a suspension of copper chloride (II) (1.78 g, 13.20 mmol) in acetonitrile (29 ml) was added under ice-cooling and nitrogen atmosphere isopentyl nitrate (2.22 ml, 16.51 mmol). To the mixture was added for 10 minutes 2-amino-6-bromo-4-chlorobenzo[d]thiazole 61 (2.90 g, 11.00 mmol). It was stirred at room temperature for 10 minutes. The mixture was heated at 60° C. for 2 hours. After the end of the reaction, 2N HCl was added to the mixture. The mixture was extracted with ethyl acetate. The organic layer was washed with water and brine, respectively and dried over sodium sulfates. The solvent was evaporated under reduced pressure. The residue was purified with column chromatography (n-hexane:ethyl acetate=4:1) to give Compound 62 (1.60 g, yield 51.4%).

Compound 62; ¹H-NMR (DMSO-d₆) δ: 7.93 (d, J=1.8 Hz, 1H), 8.40 (d, J=1.8 Hz, 1H).

EXAMPLE 23

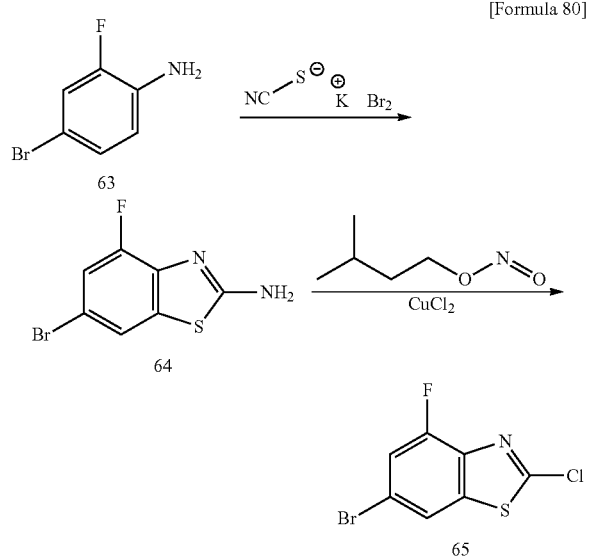

[Formula 80]

To a solution of 4-bromo-2-fluoroaniline 63 (5.0 g, 26.30 mmol) in acetic acid (50 ml) was added at room temperature potassium thiocyanate (10.23 g, 105.00 mmol). To the solution was dropped at room temperature for 15 minutes bromine (2.71 ml, 52.60 mmol) in acetic acid (12 ml). After the end of dropping, it was stirred at room temperature for 2 hours. After the end of the reaction, the mixture was neutralized with aqueous sodium hydroxide under ice-cooling and extracted with ethyl acetate. The organic layer was washed with saturated sodium bicarbonate solution and saturated NaCl solution and dried over sodium sulfate. The solvent was evaporated under reduced pressure. The obtained residue was purified with column chromatography (chloroform:methanol=20:1) to give Compound 64 (3.67 g, yield 56.1%) as a yellow solid.

Compound 64; ¹H-NMR (DMSO-d₆) δ: 7.35 (dd, J=10.5, 1.8 Hz, 1H), 7.77 (d, J=2.1 Hz, 1H), 7.84 (brs, 2H).

To a suspension of copper chloride (II) (645 mg, 4.80 mmol) in mixed solvent of acetonitrile (10 ml) and N-methyl-2-pyrrolidone (2 ml) was added under nitrogen atmosphere and ice-cooling isopentyl nitrate (0.81 ml, 6.00 mmol). To the suspension was added for 10 minutes 2-amino-6-bromo-4-fluorobenzo[d]thiazole 64 (988 mg, 4.00 mmol). It was stirred at room temperature for 10 minutes and then heated at 60° C. for 1 hour. After the end of the reaction, 2N HCl was added to the mixture. The mixture was extracted with ethyl acetate. The organic layer was washed with water and brine, respectively and dried over sodium sulfate. The solvent was evaporated under reduced pressure. The obtained residue was purified with column chromatography (chloroform) to give Compound 65 (3.67 g, yield 56.1%) as a yellow solid.

Compound 65; ¹H-NMR (DMSO-d₆) δ: 7.78 (dd, J=10.2, 1.8 Hz, 1H), 8.27 (dd, J=1.5, 0.6 Hz, 1H).

EXAMPLE 24

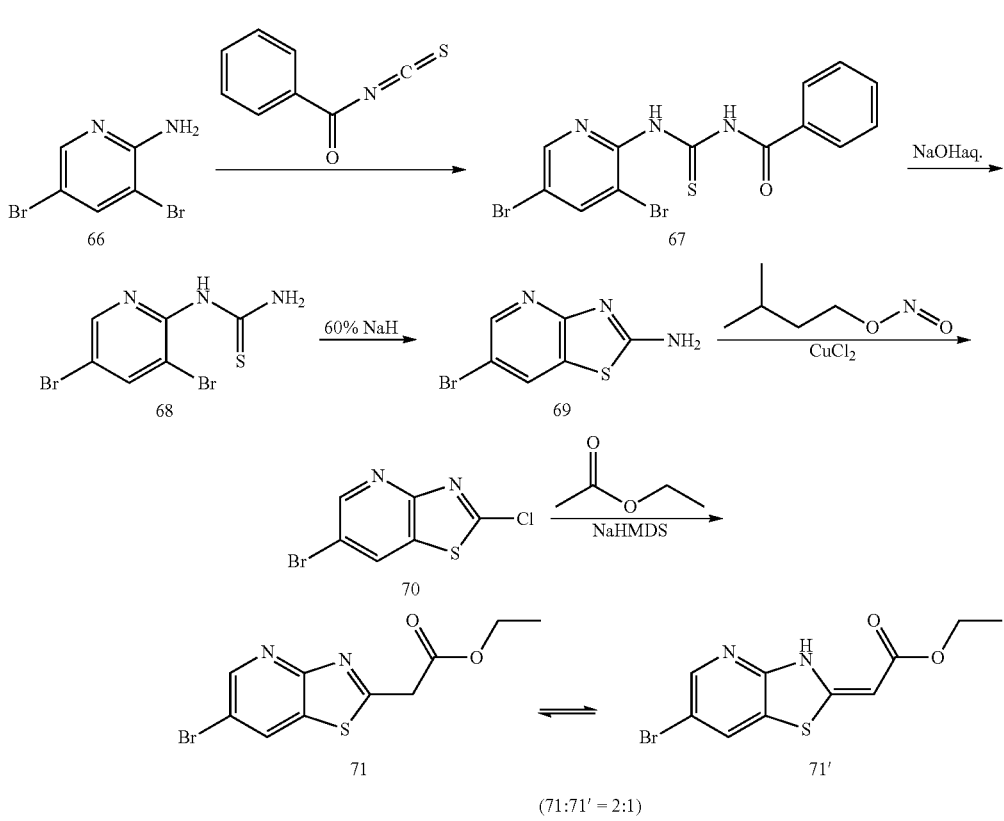

[Formula 81]

(71:71' = 2:1)

To a solution of 2-amino-3,5-dibromopyridine 66 (5.0 g, 19.85 mmol) in acetone (50 ml) was dropped under ice-cooling benzoyl isothiocyanate (3.83 ml, 28.5 mmol). It was stirred at room temperature for 18 hours. The precipitate solid was collected by filtration and washed with hexane. The obtained product was dried under reduced pressure to give Compound 67 (7.30 g, yield 83.0%) as a white solid.

Compound 67; $^1$H-NMR (DMSO-$d_6$) δ: 7.56 (t, J=7.8 Hz, 2H), 7.68 (t, J=5.7 Hz, 1H) 8.00 (d, J=7.5 Hz, 2H), 8.59 (d, J=1.5 Hz, 1H), 8.67 (d, J=2.1 Hz, 1H), 11.89 (s, 1H), 12.38 (s, 1H).

To a suspension of N-(3,5-dibromopyridin-2-ylcarbamothiyl)benzamide 67 (7.30 g, 17.59 mmol) in methanol (8 ml) was added 2N NaOH aqueous solution (70.3 ml, 175 mmol). It was heated under reflux for 1 hour. After the end of the reaction, the mixture was cooled to room temperature. The precipitate was collected by filtration and washed with water. The obtained product was dried under reduced pressure to give Compound 68 (5.10 g, yield 93%) as a white solid.

Compound 68; $^1$H-NMR (DMSO-$d_6$) δ: 8.43 (d, J=2.4 Hz, 1H), 8.52 (d, J=2.1 Hz, 1H), 8.61 (brs, 1H), 9.32 (brs, 1H), 9.69 (brs, 1H).

To a solution of 60% sodium hydride (2.03 g, 50.80 mmol) in dimethylformamide (75 ml) was added under ice-cooling for 15 minutes 1-(3,5-dibromopyridin-2-yl)thiourea 68 (5.10 g, 16.40 mmol). It was stirred for 15 minutes at room temperature and stirred for 3 hours at 80° C. After the end of the reaction, it was cooled. To the mixture were added saturated NH$_4$Cl and water. It was stirred for 30 minutes. The precipitate was collected by filtration and washed with water. The obtained product was dried under reduced pressure to give Compound 69 (3.0 g, yield 80%) as a yellow solid.

Compound 69; $^1$H-NMR (DMSO-$d_6$) δ: 8.11 (brs, 2H), 8.28 (dd, J=2.4, 0.9 Hz, 1H), 8.32 (dd, J=2.4, 0.9 Hz, 1H).

To a suspension of copper chloride (II) (2.10 g, 15.65 mmol) in N-methyl-2-pyrrolidone (30 ml) was added under nitrogen atmosphere and ice-cooling isopentyl nitrate (2.63 ml, 19.56 mmol). To the mixture was added for 10 minutes 6-bromothiazolo[4,5-b]pyridine-2-amine 69 (3.00 g, 13.04 mmol). It was stirred for 10 minutes at room temperature. Then it was stirred at 60° C. for 1 hour. After the end of the reaction, 2N HCl was added to the mixture. The mixture was extracted with ethyl acetate. The organic layer was washed with water and brine, respectively and dried over sodium sulfate. The solvent was evaporated under reduced pressure. The obtained residue was purified with column chromatography (chloroform:methanol=30:1) to give Compound 70 (1.50 g, yield 46.1%) as a yellow solid.

Compound 70; 1 H-NMR (DMSO-$d_6$) δ: 8.81 (d, J=2.4 Hz, 1H), 8.90 (d, J=2.4 Hz, 1H).

To a solution of 2M NaHMDS THF solution (0.464 ml, 0.882 mmol) in anhydrous toluene (2.5 ml) was dropped under nitrogen atmosphere at −60° C. for 10 minutes ethyl acetate (0.043 ml, 0.88 mmol). Then it was stirred at −60° C. for 1 hour. To the mixture was dropped a solution of 6-bromo-2-chlorothiazolo[4,5-b]pyridine 70 (100 mg, 0.401 mmol) in anhydrous THF (8 ml) and toluene (2.5 ml). After dropping, it was stirred at 0° C. for 2 hours.

To the reaction mixture was added saturated NH$_4$Cl aqueous solution and ethyl acetate. After extraction, the organic layer was washed with brine and dried over magnesium sulfate. The solvent was evaporated under reduced pressure. The obtained residue was purified with column chromatography (chloroform:methanol=20:1) to give the mixture of Compounds 71 and 71' as a yellow solid (107 mg, yield 89.0%).

Compound 71:71'(mix); $^1$H-NMR (DMSO-$d_6$) δ: 1.19 (t, J=6.3 Hz, 2H), 1.24 (t, J=6.3 Hz, 3H) 4.07 (q, J=6.8 Hz, 2H), 4.18 (q, J=6.8 Hz, 2H) 4.42 (s, 2H), 5.41 (s, 1H) 8.21 (d, J=2.1 Hz, 1H), 8.25 (d, J=2.1 Hz, 1H), 8.77 (d, J=2.1 Hz, 1H), 8.93 (d, J=2.1 Hz, 1H) 12.42 (brs, 1H).

EXAMPLE 25

[Formula 82]

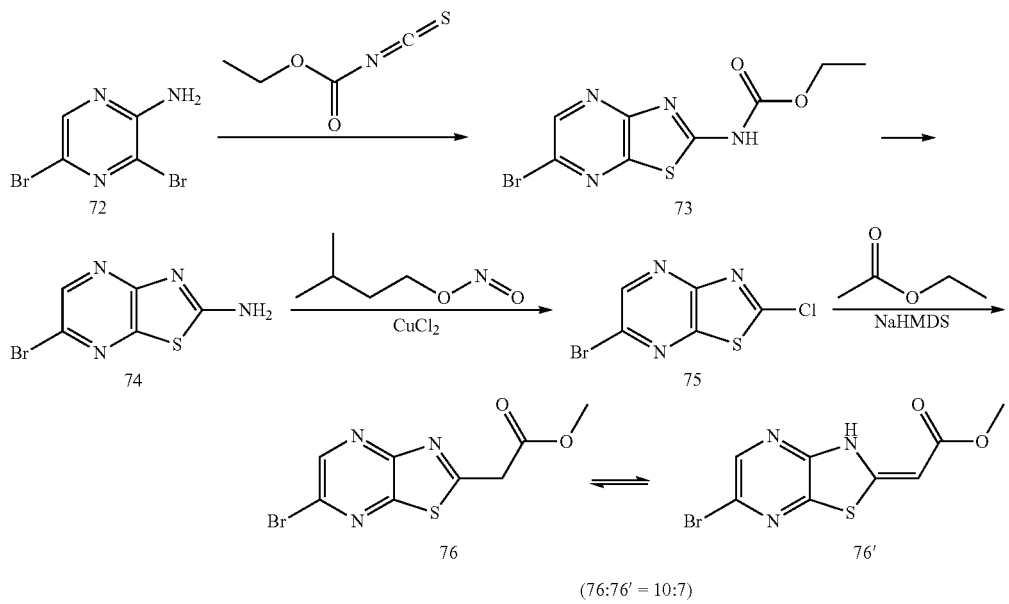

To a solution of 2-amino-3,5-dibromopyrazine 72 (497 mg, 1.96 mmol) in acetone (50 ml) was added isothianic acid ethyl ester (2.31 ml, 19.6 mmol). It was stirred for 10 minutes at 100° C. under reflux. To the mixture was added methanol (8 ml). It was stirred for 30 minutes at 80° C. It was cooled under ice-cooling. The precipitate was collected by filtration and washed with water:methanol (2:1). The obtained product was dried under reduced pressure to give Compound 73 (mg 487, yield 82.0%) as a brown solid.

Compound 73; $^1$H-NMR (DMSO-d$_6$) δ: 1.30 (t, J=7.2 Hz, 3H), 4.30 (q, J=1.2 Hz, 2H), 8.72 (d, J=1.2 Hz, 1H), 12.75 (brs, 1H).

To a suspension of ethyl 6-bromothiazolo[4,5-b]pyrazin-2-ylcarbamate 73 (480 mg, 1.58 mmol) in methanol (8 ml) was added 2N sodium hydroxide aqueous solution (7.91 ml, 15.83 mmol). It was heated for 5 hours under reflux. After the end of the reaction, the mixture was acidified with 2N HCl. Then the mixture was neutralized with saturated sodium bicarbonate and extracted with ethyl acetate. The organic layer was washed with saturated sodium bicarbonate solution and saturated NaCl aqueous solution and dried over sodium sulfate. The solvent was evaporated under reduced pressure. The precipitate was collected by filtration to give Compound 74 (334 mg, yield 91.0%) as a white yellow solid.

Compound 74; $^1$H-NMR (DMSO-d$_6$) δ: 8.37 (s, 1H), 8.59 (brs, 2H).

To a suspension of copper chloride (II) (2.17 g, 16.20 mmol) in N-methyl-2-pyrrolidone (30 ml) was added under nitrogen atmosphere and ice-cooling isopentyl nitrate (2.73 ml, 20.25 mmol). Then 2-amino-6-bromothiazolo[4,5-b]pyrazine 74 (3.12 g, 13.50 mmol) was added for 10 minutes to the mixture. It was stirred at room temperature for 10 minutes and further stirred at 60° C. for 1 hour. After the end of the reaction, 2N HCl was added to the mixture. The mixture was extracted with ethyl acetate. The organic layer was washed with water and brine, respectively and dried over sodium sulfate. The solvent was evaporated under reduced pressure. The obtained residue was purified with column chromatography (chloroform) to give Compound 75 (3.67 g, yield 56.1%) as a yellow solid.

Compound 75; $^1$H-NMR (DMSO-d$_6$) δ: 8.99 (d, J=0.9 Hz, 1H).

To a solution of 2M NaHMDS THF solution (3.700 ml, 7.03 mmol) in anhydrous toluene (8.0 ml) was dropped at −60° C. for 10 minutes under nitrogen atmosphere ethyl acetate (0.34 ml, 3.51 mmol). Then it was stirred at −60° C. for 1 hour. To the mixture was dropped a solution of 6-bromo-2-chlorothiazolo[4,5-b]pyrazine 75 (800 mg, 3.19 mmol) in anhydrous THF (8 ml) and toluene (8.0 ml). After dropping, it was stirred at −60° C. for 1 hour.

To the reaction mixture was added saturated NH$_4$Cl aqueous solution and ethyl acetate. After extraction, the organic layer was washed with brine and dried over magnesium sulfate. The solvent was evaporated under reduced pressure. The obtained residue was purified with column chromatography (chloroform:methanol=20:1) to give the mixture of Compounds 76 and 76' as a yellow solid (650 mg, yield 67.4%).

Compound 76, 76'(mix); $^1$H-NMR (DMSO-d$_6$) δ: 1.21 (t, J=6.4 Hz, 3H), 1.24 (t, J=6.4 Hz, 3H) 4.11 (q, J=6.4 Hz, 2H), 4.20 (q, J=6.4 Hz, 2H), 4.48 (s, 2H), 5.25 (s, 1H), 8.25 (s, 1H), 8.94 (s, 1H), 12.75 (brs, 1H).

EXAMPLE 26

[Formula 83]

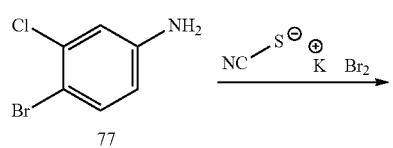

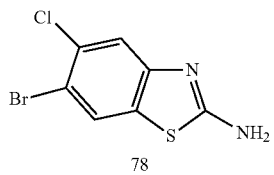

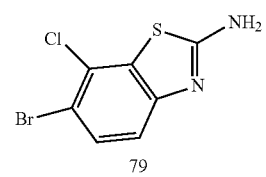

To a solution of Compound 77 (300 mg, 1.45 mmol) in acetic acid (20 ml) was added at room temperature potassium thiocyanate (565 mg, 5.81 mmol). To the mixture was slowly dropped under ice-cooling bromine (0.112 mL, 2.18 mmol) in acetic acid (4 ml). After dropping, the mixture was stirred at room temperature for 3 hours. After the end of the reaction, the mixture was neutralized under ice-cooling with aqueous sodium hydroxide and then extracted ethyl acetate. The organic layer was washed with saturated sodium bicarbonate aqueous solution and saturated NaCl aqueous solution and dried over sodium sulfate. The solvent was evaporated under reduced pressure. The obtained residue was purified with column chromatography (n-hexane:ethyl acetate=1:1) to give the mixture of Compounds 78 and 79 (79:79=1:1) as a white solid (190 mg).

Compound 78; $^1$H-NMR (DMSO-d$_6$) δ: 7.22 (d, J=8.11 Hz, 1H), 7.52 (s, 1H), 7.55 (d, J=8.11 Hz, 1H), 7.81 (s, 2H), 7.86 (s, 2H), 8.09 (s, 1H).

EXAMPLE 27

[Formula 84]

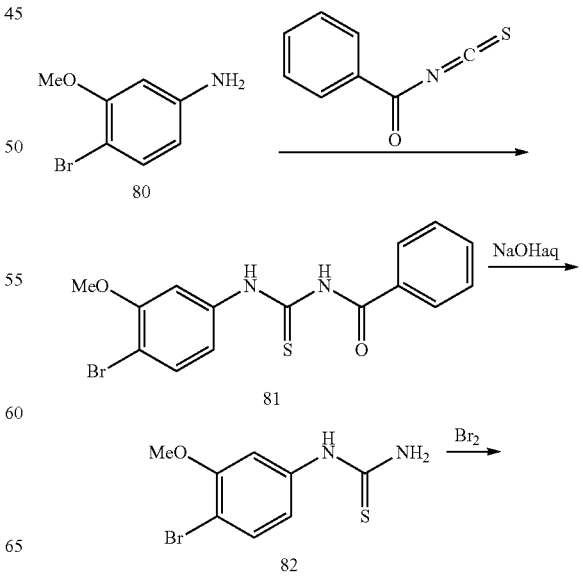

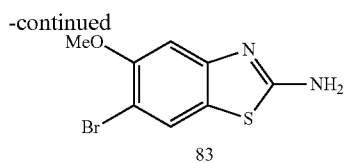

To a solution of Compound 80 (5 g, 24.8 mmol) in acetone (150 mL) was added under ice-cooling benzoyl isothiocyanate (3.83 mL, 28.5 mmol). It was stirred under ice-cooling for 60 minutes. The precipitate solid was collected by filtration and washed with diethyl ether. The obtained product was dried under reduced pressure to give Compound 81 (8.1 g, 90%) as a white solid.
Compound 81; $^1$H-NMR (DMSO-$d_6$) δ: 3.86 (s, 3H), 7.27 (m, 1H), 7.52-7.70 (m, 5H), 7.98 (d, J=8.11 Hz, 2H), 11.64 (s, 1H), 12.64 (s, 1H).

To a suspension of Compound 81 (8 g, 21.9 mmol) in methanol (80 ml) was added 2N NaOH aqueous solution (88 mL, 175 mmol). It was heated under reflux for 2 hours. After the end of the reaction, it was cooled to room temperature. MeOH was evaporated under reduced pressure. The precipitate solid was collected by filtration and washed with water. The obtained product was dried under reduced pressure to give Compound 82 (5.3 g, 93%) as a white solid.
Compound 82; $^1$H-NMR (DMSO-$d_6$) δ: 3.82 (s, 3H), 6.90 (dd, J=8.62, 2.03 Hz, 1H), 7.36 (d, J=2.03 Hz, 1H), 7.47 (d, J=8.62 Hz, 1H), 9.77 (s, 1H).

To a suspension of Compound 82 (5 g, 19.15 mmol) in acetic acid (75 ml) was slowly dropped under ice-cooling bromine (0.987 mL, 19.15 mmol) in acetic acid (75 mL). After dropping, it was stirred at room temperature for 1 hour. Then it was heated at 50° C. for further 1 hour. After the end of the reaction, the mixture was neutralized under ice-cooling with sodium hydroxide aqueous solution and extracted with ethyl acetate. The organic layer was washed with saturated sodium bicarbonate aqueous solution and saturated NaCl aqueous solution and dried over sodium sulfate. The solvent was evaporated under reduced pressure. The obtained residue was suspended in ethyl acetate (50 mL). The suspension stirred for 1 hour. The precipitate solid was collected by filtration to give Compound 83 (4.73 g, 95%) as a white solid.
Compound 83; $^1$H-NMR (DMSO-$d_6$) δ: 3.83 (s, 3H), 7.06 (s, 1H), 7.56 (brs, 2H), 7.83 (s, 1H).

EXAMPLE 28

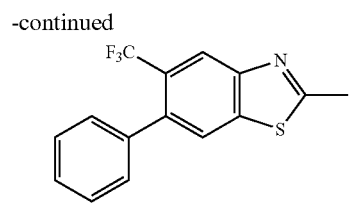

A solution of Compound 34 (350 mg, 1.46 mmol) in concentrated hydrochloric acid (2 mL) was diluted with water (2 mL). To the solution was dropped under ice-cooling an aqueous solution (2 mL) of sodium nitrite (111 mg, 1.60 mmol). It was stirred for 30 minutes. To the mixture was slowly dropped an aqueous solution (10 mL) of potassium iodide (3.63 g, 21.85 mmol). It was stirred at room temperature for 1 hour. The reaction mixture was neutralized under ice-cooling with sodium hydroxide solution and then extracted with chloroform. The organic layer was washed with 10% aqueous solution of sodium thiosulfate and brine, respectively and dried over magnesium sulfate. The solvent was evaporated under reduced pressure. The residue was purified with silica gel column chromatography (n-hexane:ethyl acetate=4:1) to give Compound 84 (360 mg, 70%) as a white solid.

Compound 84; $^1$H-NMR (DMSO-$d_6$) δ: 2.82 (s, 3H), 7.34-7.50 (m, 5H), 8.03 (s, 1H), 8.49 (s, 1H).

To a suspension of copper iodide (I) (191 mg, 1.00 mmol) in DMF (1.5 mL) was added 2,2-difluoro-2-(fluorosulfonyl) methyl acetate (0.403 mL, 3, 19 mmol). To the mixture was dropped a DMF solution (3 mL) of Compound 84 (320 mg, 0.911 mmol). It was stirred at 120° C. for 1 hour. The mixture was quenched with saturated aqueous ammonium chloride and extracted with ethyl acetate. The organic layer was washed with water and brine, respectively. The solvent was evaporated under reduced pressure. The residue was purified with silica gel column chromatography (n-hexane:ethyl acetate=4:1) to give Compound 85 (180 mg, 67%) as a white solid.

Compound 85; $^1$H-NMR (DMSO-$d_6$) δ: 2.87 (s, 3H), 7.35-7.40 (m, 2H), 7.43-7.48 (m, 3H), 8.13 (s, 1H), 8.32 (s, 1H).

EXAMPLE 29

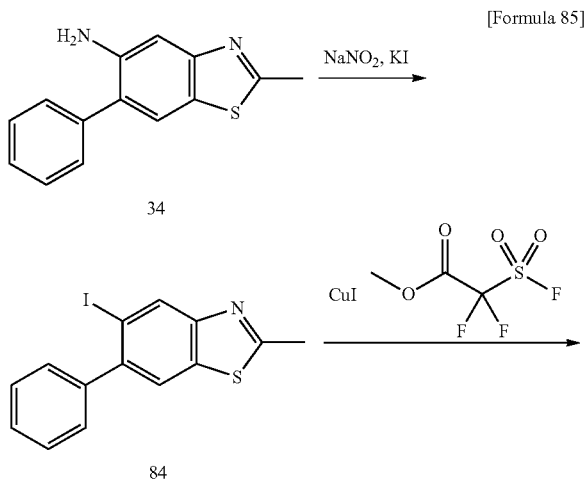

[Formula 85]

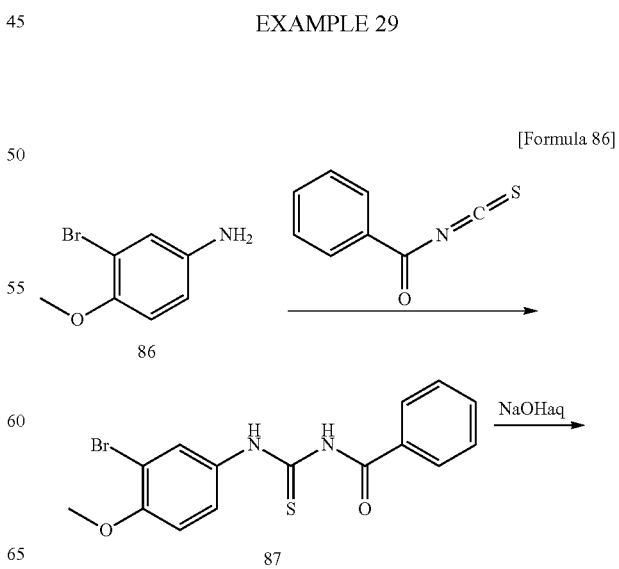

[Formula 86]

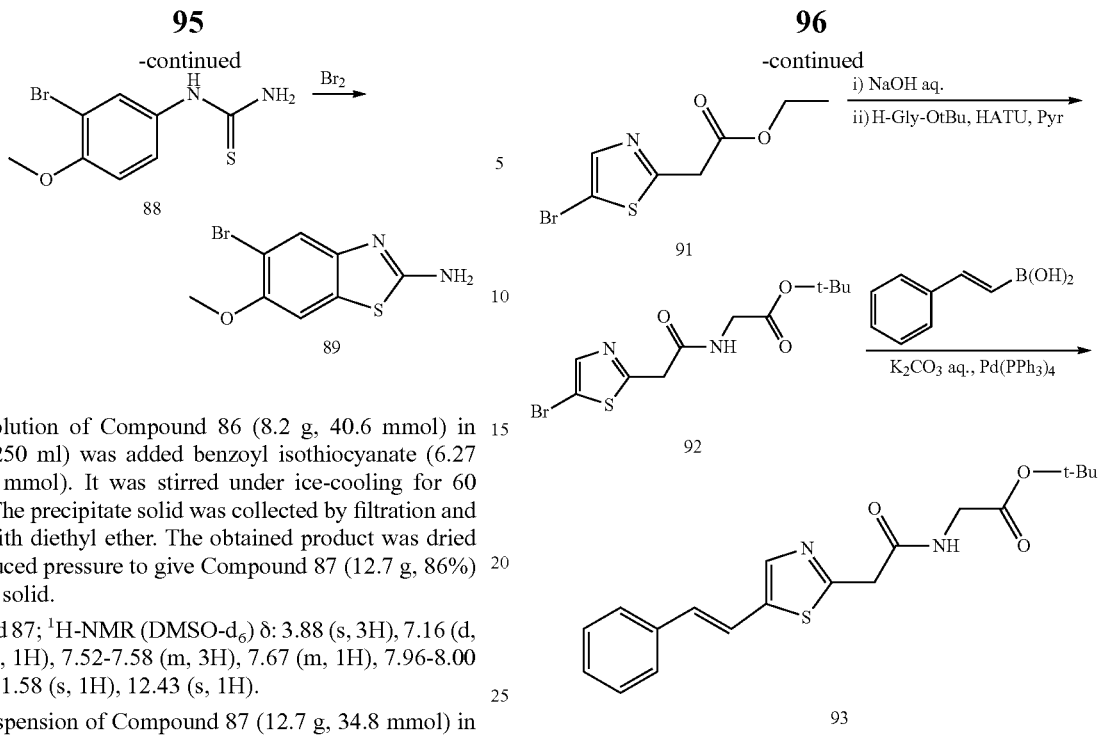

To a solution of Compound 86 (8.2 g, 40.6 mmol) in acetone (250 ml) was added benzoyl isothiocyanate (6.27 mL, 46.7 mmol). It was stirred under ice-cooling for 60 minutes. The precipitate solid was collected by filtration and washed with diethyl ether. The obtained product was dried under reduced pressure to give Compound 87 (12.7 g, 86%) as a white solid.

Compound 87; $^1$H-NMR (DMSO-$d_6$) δ: 3.88 (s, 3H), 7.16 (d, J=8.62 Hz, 1H), 7.52-7.58 (m, 3H), 7.67 (m, 1H), 7.96-8.00 (m, 3H), 11.58 (s, 1H), 12.43 (s, 1H).

To a suspension of Compound 87 (12.7 g, 34.8 mmol) in methanol (120 ml) was added 2N NaOH aqueous solution (139 mL, 278 mmol). It was heated for 2 hours under reflux. After the end of the reaction, it was cooled to room temperature. MeOH was evaporated under reduced pressure. The precipitate solid was collected by filtration and washed with water. The obtained product was dried under reduced pressure to give Compound 88 (8.72 g, 96%) as a white solid.

Compound 88; $^1$H-NMR (DMSO-$d_6$) δ: 3.82 (s, 3H), 7.07 (d, J=9.12 Hz, 1H), 7.27 (dd, J=9.12, 2.03 Hz, 1H), 7.64 (d, J=2.03 Hz, 1H), 9.54 (s, 1H).

To a suspension of Compound 88 (3 g, 11.49 mmol) in acetic acid (60 mL) was slowly dropped under ice-cooling an acetic acid solution (12 ml) of bromine (0.651 mL, 12.64 mmol). After dropping, the mixture was heated to 50 C and stirred for 4 hours. After the end of the reaction, the mixture was neutralized under ice-cooling with sodium hydroxide aqueous solution and extracted with ethyl acetate. The organic layer was washed with saturated sodium bicarbonate aqueous solution and saturated NaCl aqueous solution and dried over sodium sulfate. The solvent was evaporated under reduced pressure. The obtained residue was suspended in ethyl acetate (30 mL). The suspension stirred for 1 hour. The precipitate solid was collected by filtration to give Compound 89 (2.18 g, 73%) as a white solid.

Compound 89; $^1$H-NMR (DMSO-$d_6$) δ: 3.81 (s, 3H), 7.41 (brs, 2H), 7.50 (s, 1H), 7.51 (s, 1H).

EXAMPLE 30

[Formula 87]

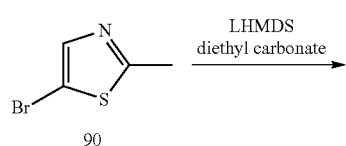

To 1M LHMDS/THF solution (18.5 mL, 18.5 mmol) was slowly dropped at −60° C. a solution of Compound 90 (1.5 g, 8.42 mmol) in THF (15 ml). It was stirred for 30 minutes. To the reaction mixture was added diethyl carbonate (1.23 mL, 10.11 mmol). It was stirred at 0° C. for 4 hours. After the end of the reaction, the reaction mixture was quenched with saturated aqueous ammonium chloride aqueous solution and extracted with ethyl acetate. The organic layer was washed with brine and dried over magnesium sulfate. The solvent was evaporated under reduced pressure. The residue was purified with silica gel column chromatography (n-hexane:ethyl acetate=4:1) to give Compound 91 (900 mg, 43%) as a yellow oil.

Compound 91; LC/MS/Rt=1.86 min, MS:251.85 (M+1), method:C

To a solution of Compound 91 (900 mg, 3.60 mmol) in THF (9.0 ml) and EtOH (4.5 ml) was added 2N NaOH aqueous solution (2.0 mL, 3.96 mmol). It was stirred at room temperature for 2 hours. After the end of the reaction, the solvent was evaporated under reduced pressure. The obtained residue was dissolved in DMF (9.0 mL). To the solution were added one by one H-Gly-OtBu hydrochloride salt (905 mg, 5.40 mmol), HATU (2.1 g, 5.40 mmol) and Pyridine (0.871 mL, 10.80 mmol). It was stirred at room temperature for 3 hours. After the end of the reaction, the mixture was quenched with 10% aqueous citric acid and extracted with ethyl acetate. The organic layer was washed with saturated sodium bicarbonate aqueous solution and saturated sodium chloride aqueous solution and dried over magnesium sulfate. The solvent was evaporated under reduced pressure. The residue was purified with silica gel column chromatography (n-hexane: ethyl acetate=1:1) to give Compound 92 (264 mg, 22%) as a yellow oil.

Compound 92; LC/MS/Rt=1.81 min, MS:336.95 (M+1), method:C

To a solution of Compound 92 (230 mg, 0.686 mmol) in dioxane (3 mL) were added (E)-styryl boronic acid (152 mg, 1.029 mmol), Pd(PPh$_3$)$_4$ (55.5 mg, 0.048 mmol) and 3M K$_2$CO$_3$ aq. (0.686 mL, 12.058 mmol). It was stirred at 120° C. for 25 minutes under microwave irradiation. After the end of the reaction, the insoluble was removed by celite filtration.

The obtained solution was extracted with ethyl acetate. The organic layer was washed with water and brine, respectively and dried over magnesium sulfate. The solvent was evaporated under reduced pressure. The residue was purified with silica gel column chromatography (n-hexane:ethyl acetate=1:1) to give Compound 93 (70 mg, 29%) as a yellow oil.

Compound 93; $^1$H-NMR (CDCl$_3$) δ: 1.47 (s, 9H), 3.96-3.99 (m, 4H), 6.86 (d, J=16.22 Hz, 1H), 7.16 (d, J=16.22 Hz, 1H), 7.28-7.40 (m, 3H), 7.44-7.50 (m, 3H), 7.68 (s, 1H).

The compounds shown below were prepared in accordance with the above example. The data of NMR or LC/MS were shown for each compounds.

TABLE 1

| No. | Structure | NMR(δ) | retention time | Mass | method |
|---|---|---|---|---|---|
| II-1-5 | 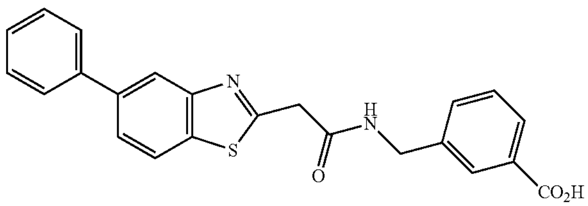 [SMILES: O=C(Cc1nc2cc(-c3ccccc3)ccc2s1)NCc1cccc(C(=O)O)c1] | 1H-NMR (DMSO-d6) δ: 4.16 (s, 2H), 4.41 (d, J = 6.1 Hz, 2H), 7.38-7.56 (m, 5H), 7.72-7.78 (m, 3H), 7.84 (d, J = 7.6 Hz, 1H), 7.91 (s, 1H), 8.14 (d, J = 8.1 Hz, 1H), 8.21 (d, J = 1.0 Hz, 1H), 8.94 (t, J = 5.8 Hz, 1H), 12.95 (br s, 1H). | | | |
| II-1-6 | 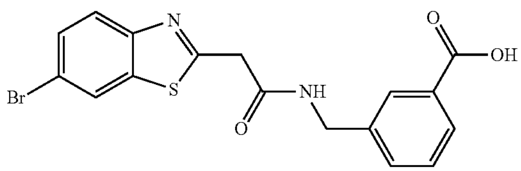 [SMILES: O=C(Cc1nc2ccc(Br)cc2s1)NCc1cccc(C(=O)O)c1] | 1H-NMR (DMSO-d6) δ: 4.14 (s, 2H), 4.40 (d, J = 5.6 Hz, 2H), 7.46 (t, J = 7.6 Hz, 1H), 7.54 (d, J = 7.6 Hz, 1H), 7.64 (dd, J = 8.6, 2.0 Hz, 1H), 7.83 (d, J = 7.6 Hz, 1H), 7.88-7.90 (m, 2H), 8.36 (d, J = 2.0 Hz, 1H), 8.94 (t, J = 5.8 Hz, 1H), 12.93 (br s, 1H). | | | |
| II-1-7 | 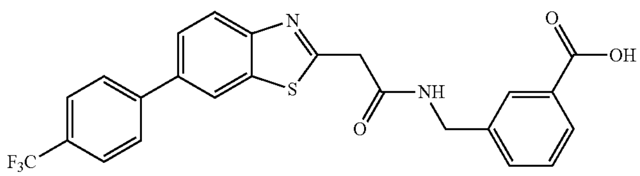 [SMILES: O=C(Cc1nc2ccc(-c3ccc(C(F)(F)F)cc3)cc2s1)NCc1cccc(C(=O)O)c1] | 1H-NMR (DMSO-d6) δ: 4.17 (s, 2H), 4.42 (d, J = 6.1 Hz, 2H), 7.47 (t, J = 7.6 Hz, 1H), 7.56 (d, J = 7.6 Hz, 1H), 7.82-7.88 (m, 4H), 7.91 (s, 1H), 7.99 (d, J = 8.1 Hz, 2H), 8.07 (d, J = 8.6 Hz, 1H), 8.49 (d, J = 2.0 Hz, 1H), 8.95 (t, J = 5.8 Hz, 1H), 12.96 (br s, 1H). | | | |
| II-1-8 | 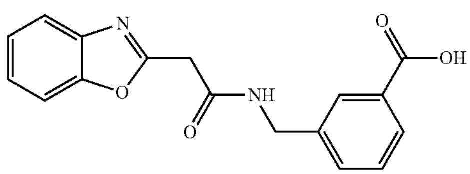 [SMILES: O=C(Cc1nc2ccccc2o1)NCc1cccc(C(=O)O)c1] | 1H-NMR (DMSO-d6) δ: 3.99 (s, 2H), 4.40 (d, J = 5.6 Hz, 2H), 7.34-7.41 (m, 2H), 7.47 (t, J = 7.6 Hz, 1H), 7.55 (d, J = 7.6 Hz, 1H), 7.68-7.73 (m, 2H), 7.84 (d, J = 7.6 Hz, 1H), 7.92 (s, 1H), 8.91 (t, J = 5.8 Hz, 1H), 12.97 (br s, 1H). | | | |
| II-1-9 | 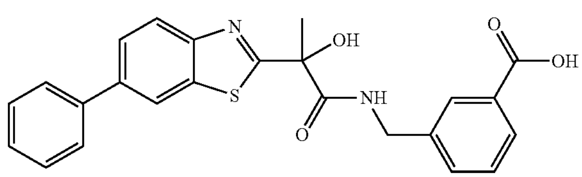 | 1H-NMR (DMSO-d6) δ: 1.84 (s, 3H), 4.35 (d, J = 6.6 Hz, 2H), 7.19 (brs, 1H), 7.39-7.42 (m, 2H), 7.46-7.53 (m, 3H), 7.75-7.87 (m, 5H), 8.05 (d, J = 8.7 Hz, 1H), 8.38 (d, J = 1.5 Hz, 1H), 8.82 (t, J = 5.7 Hz, 1H), 12.89 (brs, 1H). | | | |

TABLE 2

| No. | Structure | NMR(δ) | retention time | Mass | method |
|---|---|---|---|---|---|
| II-1-10 | 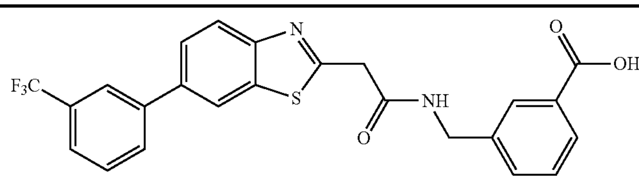 | 1H-NMR (DMSO-d6) δ: 4.17 (s, 2H), 4.42 (d, J = 5.6 Hz, 2H), 7.46 (t, J = 7.6 Hz, 1H), 7.55 (d, J = 7.6 Hz, 1H), 7.71-7.77 (m, 2H), 7.82-7.91 (m, 3H), 8.04-8.10 (m, 3H), 8.51 (s, 1H), 8.95 (t, J = 5.8 Hz, 1H), 12.97 (br s, 1H). | | | |

TABLE 2-continued

| No. | Structure | NMR(δ) | retention time | Mass | method |
|---|---|---|---|---|---|
| II-1-11 | 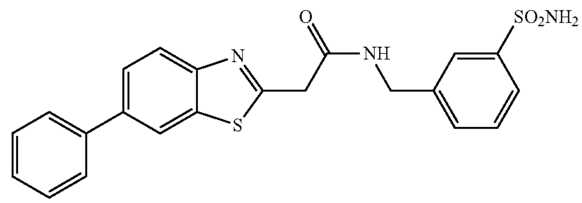 [SMILES: NS(=O)(=O)c1cccc(CNC(=O)Cc2nc3ccc(-c4ccccc4)cc3s2)c1] | 1H-NMR (DMSO-d6) δ: 4.16 (s, 2H), 4.43 (d, J = 5.5 Hz, 2H), 7.39 (t, J = 7.6 Hz, 3H), 7.51 (m, 4H), 7.76 (m, 5H), 8.03 (d, J = 8.4 Hz, 1H), 8.38 (s, 1H), 8.99 (s, 1H). | | | |
| II-1-12 | 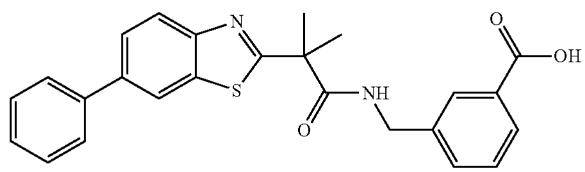 [SMILES: CC(C)(C(=O)NCc1cccc(C(=O)O)c1)c1nc2ccc(-c3ccccc3)cc2s1] | 1H-NMR (DMSO-d6) δ: 1.72 (s, 6H), 4.34 (d, J = 5.1 Hz, 2H), 7.40-7.53 (m,5H), 7.73-7.87 (m, 5H), 8.05 (d, J = 8.4 Hz, 1H), 8.38-8.42 (m, 2H), 12.89 (brs, 1H). | | | |
| II-1-13 | 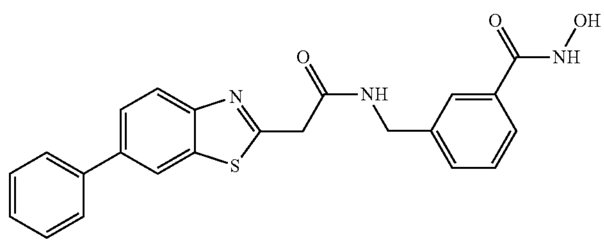 [SMILES: O=C(Cc1nc2ccc(-c3ccccc3)cc2s1)NCc1cccc(C(=O)NO)c1] | 1H-NMR (DMSO-d6) δ: 4.16 (s, 2H), 4.39 (d, J = 5.9 Hz, 2H), 7.52-7.37 (m, 5H), 7.62 (d, J = 7.4 Hz, 1H), 7.81-7.72 (m, 4H), 8.02 (d, J = 8.6 Hz, 1H), 8.38 (d, J = 1.5 Hz, 1H), 8.93 (d, J = 5.9 Hz, 1H), 9.04 (s, 1H), 11.21 (s, 1H). | | | |
| II-1-14 | 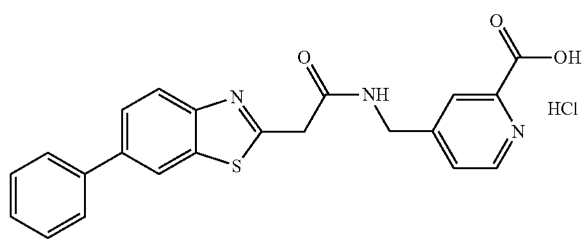 [SMILES: O=C(Cc1nc2ccc(-c3ccccc3)cc2s1)NCc1ccnc(C(=O)O)c1 ; Cl] | 1H-NMR (DMSO-d6) δ: 4.21 (s, 2H), 4.51 (d, J = 5.7 Hz, 2H), 7.39-7.50 (m, 3H), 7.65 (d, J = 5.4 Hz, 1H), 7.76-7.80 (m, 3H), 8.04-8.07 (m, 2H), 8.39 (s, 1H), 8.69 (d, J = 5.5 Hz, 1H), 9.12 (s, 1H). | | | |

TABLE 3

| No. | Structure | NMR(δ) | retention time | Mass | method |
|---|---|---|---|---|---|
| II-1-15 | 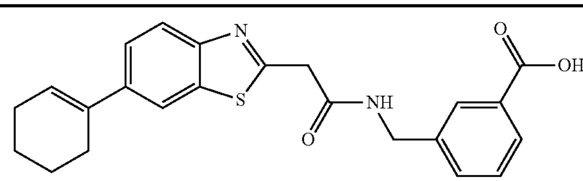 | 1H-NMR (DMSO-d6) δ: 1.59-1.65 (m, 2H), 1.72-1.78 (m, 2H), 2.18-2.24 (m, 2 H), 2.41-2.45 (m, 2H), 4.10 (s, 2H), 4.40 (d, J = 5.6 Hz, 2H), 6.26 (br s, 1H), 7.46 (t, J = 7.6 Hz, 1H), 7.53-7.57 (m, 2H), 7.81-7.90 (m, 3H), 8.05 (s, 1H), 8.91 (t, J = 5.6 Hz, 1H), 12.95 (br s, 1H) | | | |
| II-1-16 | 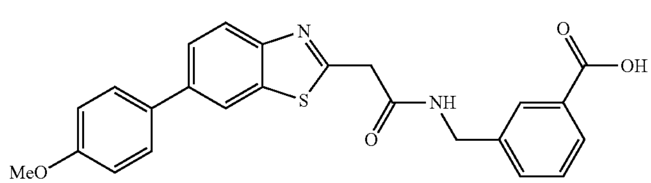 [SMILES: COc1ccc(-c2ccc3nc(CC(=O)NCc4cccc(C(=O)O)c4)sc3c2)cc1] | 1H-NMR (DMSO-d6) δ: 3.81 (s, 3H), 4.14 (s, 2H), 4.41 (d, J = 6.1 Hz, 2H), 7.05 (d, J = 8.6 Hz, 2H), 7.46 (t, J = 7.6 Hz, 1H), 7.55 (d, J = 7.6 Hz, 1H), 7.68-7.75 (m, 3H), 7.83 (d, J = 7.6 Hz, 1H), 7.91 (s, 1H), 7.98 (d, J = 8.1 Hz, 1H), 8.31 (d, J = 2.0 Hz, 1H), 8.93 (t, J = 5.8 Hz, 1H), 12.97 (br s, 1H). | | | |

TABLE 3-continued

| No. | Structure | NMR(δ) | retention time | Mass | method |
|---|---|---|---|---|---|
| II-1-17 | 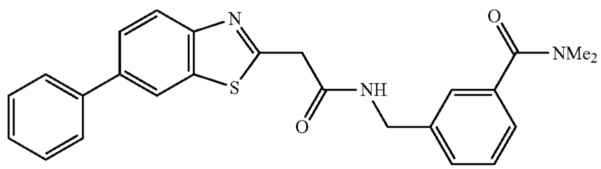 [SMILES: CN(C)C(=O)c1cccc(CNC(=O)Cc2nc3ccc(-c4ccccc4)cc3s2)c1] | 1H-NMR (DMSO-d6) δ: 2.85 (br s, 3H), 2.95 (br s, 3H), 4.15 (s, 2H), 4.39 (d, J = 6.1 Hz, 2H), 7.26-7.41 (m, 5H), 7.50 (t, J = 7.6 Hz, 2H), 7.75-7.81 (m, 3H), 8.01 (d, J = 8.1 Hz, 1H), 8.38 (s, 1H), 8.91 (t, J = 5.8 Hz, 1H). | | | |
| II-1-18 | 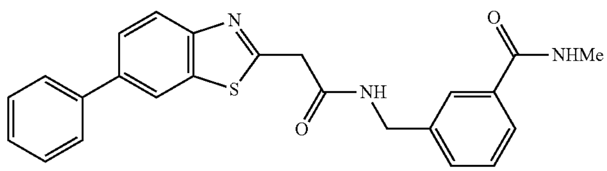 [SMILES: CNC(=O)c1cccc(CNC(=O)Cc2nc3ccc(-c4ccccc4)cc3s2)c1] | 1H-NMR (DMSO-d6) δ: 2.78 (d, J = 4.6 Hz, 3H), 4.15 (s, 2H), 4.39 (d, J = 5.6 Hz, 2H), 7.37-7.52 (m, 5H), 7.69-7.81 (m, 5H), 8.02 (d, J = 8.1 Hz, 1H), 8.38-8.42 (m, 2H), 8.91 (t, J = 5.8 Hz, 1H). | | | |
| II-1-19 | 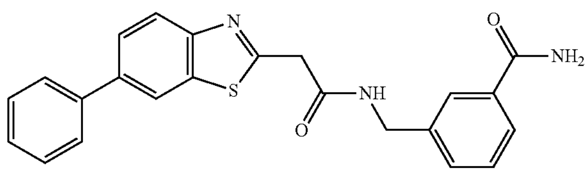 [SMILES: NC(=O)c1cccc(CNC(=O)Cc2nc3ccc(-c4ccccc4)cc3s2)c1] | 1H-NMR (DMSO-d6) δ: 4.16 (s, 2H), 4.40 (br s, 2H), 7.36-7.52 (m, 6H), 7.75-7.83 (m, 5H), 7.98 (br s, 1H), 8.03 (dd, J = 8.1, 3.5 Hz, 1H), 8.38 (s, 1H), 8.90 (br s, 1H). | | | |

TABLE 4

| No. | Structure | NMR(δ) | retention time | Mass | method |
|---|---|---|---|---|---|
| II-1-20 | 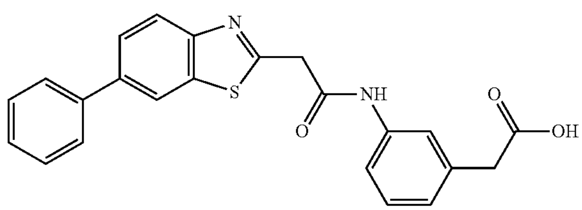 [SMILES: O=C(O)Cc1cccc(NC(=O)Cc2nc3ccc(-c4ccccc4)cc3s2)c1] | 1H-NMR (DMSO-d6) δ: 3.55 (s, 2H), 4.31 (s, 2H), 6.98 (d, J = 7.6 Hz, 1H), 7.27 (t, J = 7.8 Hz, 1H), 7.38-7.55 (m, 5H), 7.72-7.81 (m, 3H), 8.04 (d, J = 8.6 Hz, 1H), 8.40 (s, 1H), 10.46 (s, 1H), 12.35 (br s, 1H). | | | |
| II-1-21 | 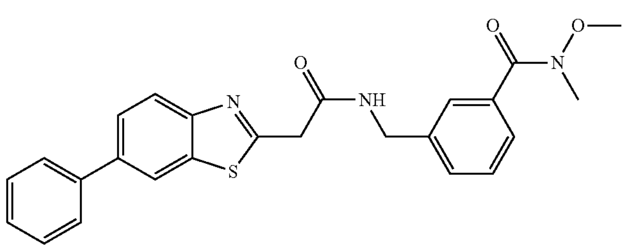 [SMILES: CON(C)C(=O)c1cccc(CNC(=O)Cc2nc3ccc(-c4ccccc4)cc3s2)c1] | 1H-NMR (DMSO-d6) δ: 3.22 (s, 3H), 3.49 (s, 3H), 4.15 (s, 2H), 4.40 (d, J = 5.4 Hz, 2H), 7.42-7.50 (m, 7H), 7.76-7.80 (m, 3H), 8.02 (d, J = 8.6 Hz, 1H), 8.38 (s, 1H), 8.92-8.95 (br m, 1H). | | | |
| II-1-22 | 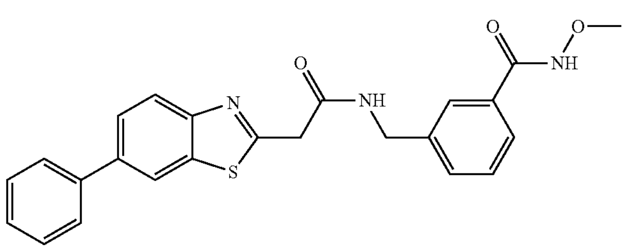 [SMILES: CONC(=O)c1cccc(CNC(=O)Cc2nc3ccc(-c4ccccc4)cc3s2)c1] | 1H-NMR (DMSO-d6) δ: 3.70 (s, 3H), 4.16 (s, 2H), 4.39 (d, J = 5.7 Hz, 2H), 7.40-7.49 (m, 5H), 7.61 (d, J = 7.1 Hz, 1H), 7.73-7.79 (m, 4H), 8.02 (d, J = 8.6 Hz, 1H), 8.38 (s, 1H), 8.90-8.93 (br m, 1H), 11.74 (s, 1H). | | | |

TABLE 4-continued

| No. | Structure | NMR(δ) | retention time | Mass | method |
|---|---|---|---|---|---|
| II-1-23 | 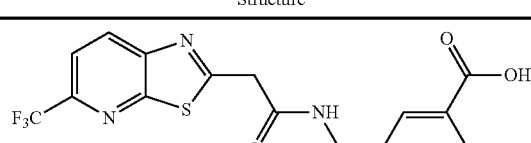 | 1H -NMR (DMSO-d6) δ: 4.29 (s, 2H), 4.44 (d, J = 6.0 Hz, 2H), 7.47 (t, J = 7.5 Hz, 1H), 7.56 (d, J = 7.8 Hz, 1H), 7.83 (d, J = 7.8 Hz, 1H), 7.90 (s, 1H), 8.06 (d, J = 8.4 Hz, 1H), 8.62 (d, J = 8.4 Hz, 1H), 9.01 (t, J = 5.7 Hz, 1H), 12.97 (brs, 1H) | | | |
| II-1-24 | 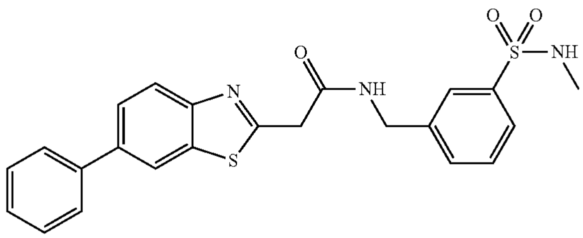 [SMILES: CNS(=O)(=O)c1cccc(CNC(=O)Cc2nc3ccc(-c4ccccc4)cc3s2)c1] | 1H-NMR (DMSO-d6) δ: 2.38 (d, J = 5.0 Hz, 3H), 4.16 (s, 2H), 4.44 (d, J = 6.2 Hz, 2H), 7.39-7.81 (m, 10H), 8.02 (d, J = 8.7 Hz, 1H), 8.37 (s, 1H), 8.97-9.01 (br m, 1H). | | | |

TABLE 5

| No. | Structure | NMR(δ) | retention time | Mass | method |
|---|---|---|---|---|---|
| II-1-25 | 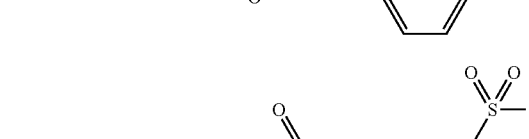 | 1H-NMR (DMSO-d6) δ: 2.54 (s, 6H), 4.16 (s, 2H), 4.46 (d, J = 5.9 Hz, 2H), 7.39 (t, J = 7.4 Hz, 1H), 7.50 (t, J = 7.5 Hz, 2H), 7.63-7.67 (m, 4H), 7.76-7.80 (m, 3H), 8.02 (d, J = 8.4 Hz, 1H), 8.38 (s, 1H), 8.98-9.00 (br m, 1H). | | | |
| II-1-26 | 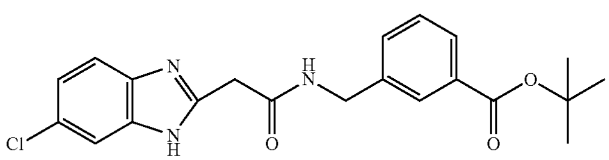 [SMILES: CC(C)(C)OC(=O)c1cccc(CNC(=O)Cc2nc3ccc(Cl)cc3[nH]2)c1] | 1H-NMR (CDCl3) δ: 1.55 (s, 9H), 3.97 (s, 2H), 4.48 (d, J = 5.6 Hz, 2H), 4.76 (br s, 2H), 7.18 (dd, J = 8.6, 2.0 Hz, 1H), 7.28-7.55 (m, 4H), 8.03-7.81 (m, 3H). | 1.84 | 400.30 (ES+) | C |
| II-1-27 | 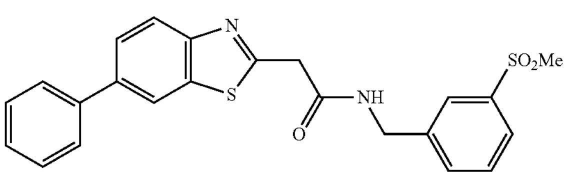 [SMILES: CS(=O)(=O)c1cccc(CNC(=O)Cc2nc3ccc(-c4ccccc4)cc3s2)c1] | 1H-NMR (DMSO-d6) δ: 3.19 (s, 3H), 4.17 (s, 2H), 4.47 (d, J = 6.1 Hz, 2H), 7.39 (t, J = 7.4 Hz, 1H), 7.50 (t, J = 7.6 Hz, 2H), 7.61-7.68 (m, 2H), 7.74-7.83 (m, 4H), 7.88 (s, 1H), 8.03 (d, J = 8.6 Hz, 1H), 8.38 (d, J = 1.5 Hz, 1H), 9.00 (t, J = 5.8 Hz, 1H). | | | |
| II-1-28 | 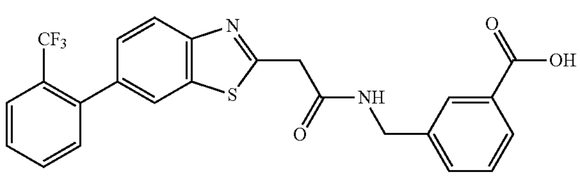 [SMILES: O=C(Cc1nc2ccc(-c3ccccc3C(F)(F)F)cc2s1)NCc1cccc(C(=O)O)c1] | 1H-NMR (DMSO-d6) δ: 4.17 (s, 2H), 4.41 (d, J = 6.1 Hz, 2H), 7.41-7.49 (m, 3H), 7.56 (d, J = 7.6 Hz, 1H), 7.65 (t, J = 7.9 Hz, 1H), 7.75 (t, J = 7.6 Hz, 1H), 7.82-7.88 (m, 2H), 7.92 (s, 1H), 8.00-8.02 (m, 2H), 8.95 (t, J = 5.6 Hz, 1H), 12.97 (br s, 1H). | | | |

TABLE 5-continued

| No. | Structure | NMR(δ) | retention time | Mass | method |
|---|---|---|---|---|---|
| II-1-29 | 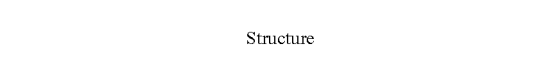 | 1H-NMR (DMSO-d6) δ: 4.14 (s, 2H), 4.53 (d, J = 5.7 Hz, 2H), 7.06 (d, J = 3.9 Hz, 1H), 7.39-7.81 (m, 7H), 8.00-8.03 (m, 1H), 8.39 (s, 1H), 9.06-9.09 (br m, 1H). | | | |

TABLE 6

| No. | Structure | NMR(δ) | retention time | Mass | method |
|---|---|---|---|---|---|
| II-1-30 | 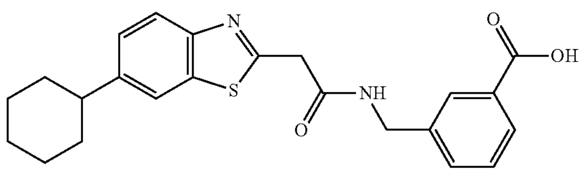 [SMILES: O=C(Cc1nc2ccc(C3CCCCC3)cc2s1)NCc1cccc(C(=O)O)c1] | 1H-NMR (DMSO-d6) δ: 1.24-1.82 (m, 10H), 2.60-2.67 (m, 1H), 4.09 (s, 2H), 4.39 (d, J = 6.1 Hz, 2H), 7.35 (dd, J = 8.4, 1.8 Hz, 1H), 7.45 (t, J = 7.6 Hz, 1H), 7.53 (d, J = 7.6 Hz, 1H), 7.81-7.90 (m, 4H), 8.90 (t, J = 5.8 Hz, 1H). | | | |
| II-1-31 | 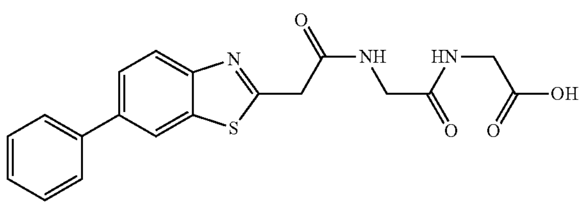 [SMILES: O=C(O)CNC(=O)CNC(=O)Cc1nc2ccc(-c3ccccc3)cc2s1] | 1H-NMR (DMSO-d6) δ: 3.80 (dd, J = 19.3, 5.6 Hz, 4H), 4.15 (s, 2H), 7.34-7.53 (m, 3H), 7.69-7.82 (m, 3H), 8.01 (d, J = 8.6 Hz, 1H), 8.28 (s, 1H), 8.38 (d, J = 10.0 Hz, 1H), 8.67 (s, 1H). | 1.64 | 384.00 (ES+) | C |
| II-1-32 | 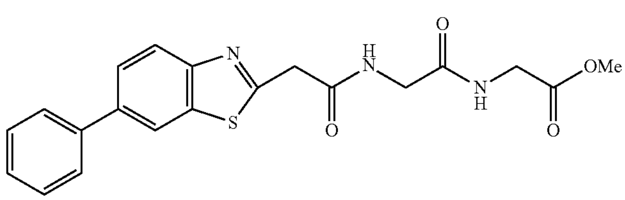 [SMILES: COC(=O)CNC(=O)CNC(=O)Cc1nc2ccc(-c3ccccc3)cc2s1] | 1H-NMR (CDCl3) δ: 3.74 (s, 3H), 4.08 (dd, J = 7.4, 5.8 Hz, 4H), 4.15 (s, 2H), 6.79 (s, 1H), 7.26 (s, 2H), 7.34-7.52 (m, 3H), 7.60-7.76 (m, 3H), 7.87 (s, 1H), 8.09-8.00 (m, 2H). | | | |
| II-1-33 | 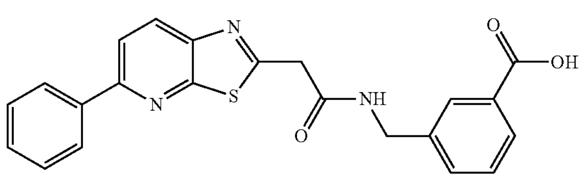 [SMILES: O=C(Cc1nc2ccc(-c3ccccc3)nc2s1)NCc1cccc(C(=O)O)c1] | 1H-NMR (DMSO-d6) δ: 4.20 (s, 2H), 4.42 (d, J = 6.0 Hz, 2H), 7.45-7.57 (m, 4H), 7.92 (s, 1H), 8.15-8.18 (m, 3H), 8.41 (d, J = 8.4 Hz, 1H), 8.97 (t, J = 5.7 Hz, 1H), 12.99 (brs, 1H). | | | |
| II-1-34 | 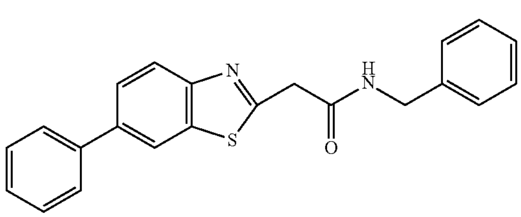 [SMILES: O=C(Cc1nc2ccc(-c3ccccc3)cc2s1)NCc1ccccc1] | 1H-NMR (CDCl3) δ: 4.13 (s, 2H), 4.53 (s, J = 5.7 Hz, 2H), 7.25-7.49 (m, 9H), 7.61-7.65 (m, 2H), 7.71 (d, J = 1.8, 8.7 Hz, 2H), 8.01 (d, J = 8.4 Hz, 1H), 8.06 (s, 1H) | | | |

TABLE 7

| No. | Structure | NMR(δ) | retention time | Mass | method |
|---|---|---|---|---|---|
| II-1-35 | 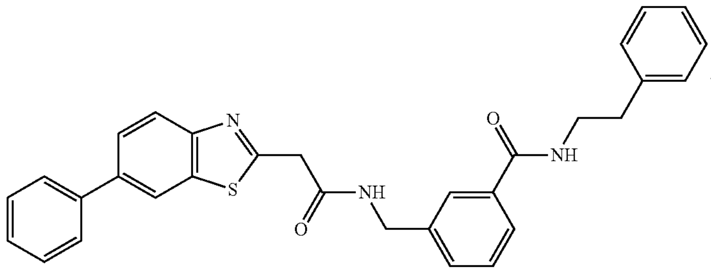 [SMILES: O=C(Cc1nc2ccc(-c3ccccc3)cc2s1)NCc1cccc(C(=O)NCCc2ccccc2)c1] | 1H-NMR (CDCl3) δ: 2.91 (t, J = 7.1 Hz, 2H), 3.66-3.72 (m, 2H), 4.13 (s, 2H), 4.54 (d, J = 6.1 Hz, 2H), 6.15 (s, 1H), 7.21-7.49 (m, 10H), 7.56-7.72 (m, 6H), 8.01 (d, J = 8.1 Hz, 1H), 8.06 (d, J = 1.5 Hz, 1H). | | | |
| II-1-36 | 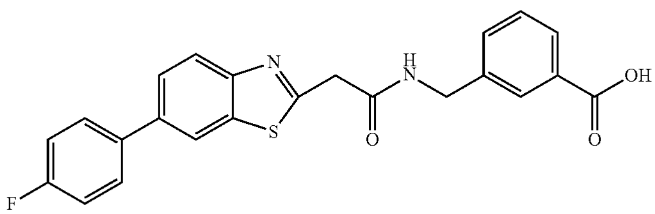 [SMILES: O=C(Cc1nc2ccc(-c3ccc(F)cc3)cc2s1)NCc1cccc(C(=O)O)c1] | | 1.93 | 421.42 (ES+) | A |
| II-1-37 | 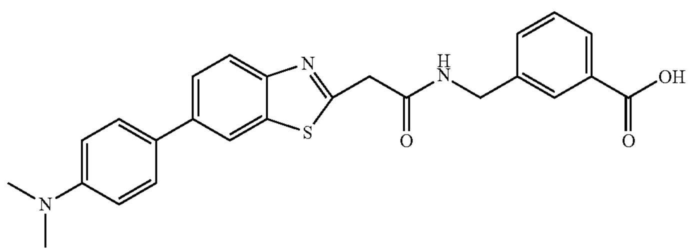 [SMILES: CN(C)c1ccc(-c2ccc3nc(CC(=O)NCc4cccc(C(=O)O)c4)sc3c2)cc1] | | 1.61 | 446.45 (ES+) | A |
| II-1-38 | 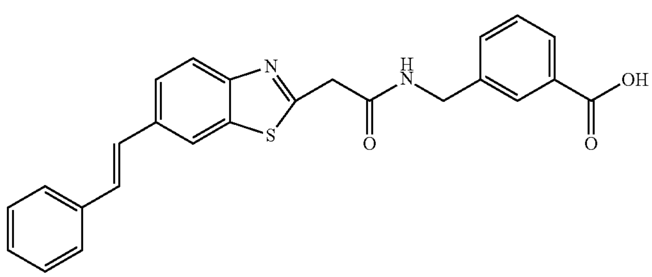 [SMILES: O=C(Cc1nc2ccc(/C=C/c3ccccc3)cc2s1)NCc1cccc(C(=O)O)c1] | | 2.07 | 429.45 (ES+) | A |
| II-1-39 | 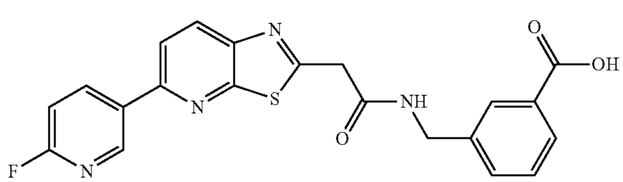 | 1H-NMR (DMSO-d6) δ: 4.22 (s, 2H), 4.42 (d, J = 5.7 Hz, 2H), 7.34 (dd, J = 8.4 Hz, 1H), 7.83 (d, J = 7.8 Hz, 1H), 7.92 (s, 1H), 8.21 (d, J = 8.4 Hz, 1H), 8.46 (d, J = 8.4 Hz, 1H), 8.69-8.76 (m, 1H), 8.69-8.76 (m, 1H), 8.98-9.01 (m, 2H), 12.81 (brs, 1H). | | | |

TABLE 8

| No. | Structure | NMR(δ) | retention time | Mass | method |
|---|---|---|---|---|---|
| II-1-40 | 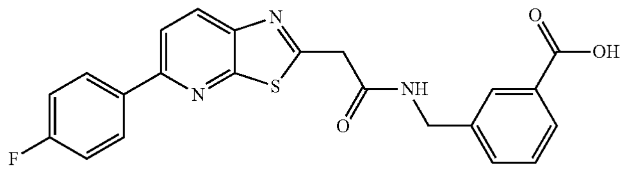 [SMILES: O=C(Cc1nc2ccc(-c3ccc(F)cc3)nc2s1)NCc1cccc(C(=O)O)c1] | 1H-NMR (DMSO-d6) δ: 4.189 (s, 2H), 4.43 (d, J = 6.9 Hz, 2H), 7.36 (t, J = 7.2 Hz, 2H), 7.56 (d, J = 7.8 Hz, 1H), 7.83 (d, J = 7.8 Hz, 1H), 7.92 (s, 1H), 8.13 (d, J = 8.4 Hz, 1H), 8.22 (d, J = 6.6 Hz, 1H), 6.23 (d, J = 6.6 Hz, 1H), 8.40 (d, J = 8.4 Hz, 1H), 8.99 (t, J = 6.0 Hz, 1H), 12.99 (brs, 1H), (s, 2H), 8.37 (d, J = 7.2 Hz, 1H), 12.53 (s, 1H) | | | |
| II-1-41 | 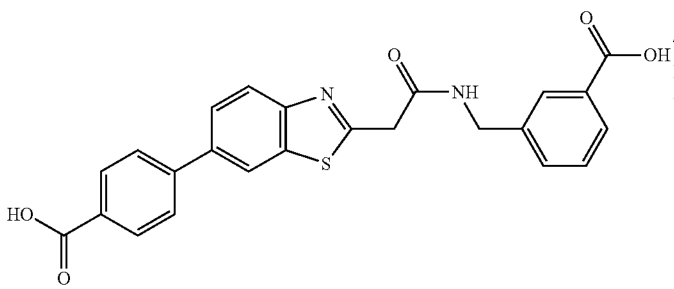 [SMILES: O=C(Cc1nc2ccc(-c3ccc(C(=O)O)cc3)cc2s1)NCc1cccc(C(=O)O)c1] | 1H-NMR (DMSO-d6) δ: 4.17 (s, 2H), 4.42 (d, J = 5.6 Hz, 2H), 7.47 (dd, J = 7.6, 8.1 Hz, 1H), 7.56 (d, J = 7.6 Hz, 1H), 7.80-7.93 (m, 5H), 8.00-8.08 (m, 3H), 8.48 (d, J = 1.5 Hz, 1H), 8.95 (t, J = 5.6 Hz, 1H), 12.99 (brs, 2H). | | | |
| II-1-42 | 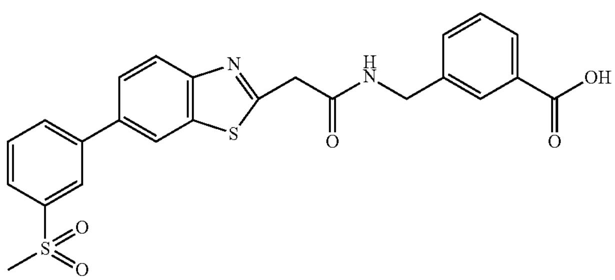 [SMILES: CS(=O)(=O)c1cccc(-c2ccc3nc(CC(=O)NCc4cccc(C(=O)O)c4)sc3c2)c1] | 1H-NMR (DMSO-d6) δ: 3.32 (s, 3H), 4.18 (s, 2H), 4.42 (d, J = 5.7 Hz, 2H), 7.47 (t, J = 7.5 Hz, 1H), 7.56 (d, J = 6.6 Hz, 1H), 7.75-7.96 (m, 5H), 8.10 (dd, J = 7.5, 15 Hz, 3H), 8.27 (s, 1H), 8.53 (s, 1H), 8.97 (m, 1H). | | | |
| II-1-43 | 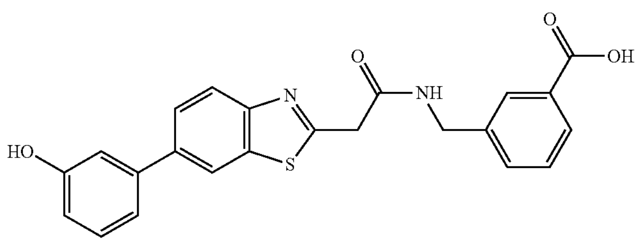 [SMILES: O=C(Cc1nc2ccc(-c3cccc(O)c3)cc2s1)NCc1cccc(C(=O)O)c1] | 1H-NMR (DMSO-d6) δ: 4.15 (s, 2H), 4.41 (d, J = 5.6 Hz, 2H), 6.80 (dd, J = 2.0, 7.6 Hz, 1H), 7.08-7.18 (m, 2H), 7.28 (dd, J = 7.6, 8.1 Hz, 1H), 7.47 (dd, J = 7.6, 8.1 Hz, 1H), 7.56 (d, J = 7.6 Hz, 1H), 7.71 (dd, J = 2.0, 8.1 Hz, 1H), 7.84 (d, J = 8.1 Hz, 1H), 7.91 (s, 1H), 8.00 (d, J = 8.6 Hz, 1H), 8.30 (d, J = 2.0 Hz, 1H), 8.94 (t, J = 5.6 Hz, 1H), 9.57 (brs, 1H), 13.00 (brs, 1H). | | | |
| II-1-44 | 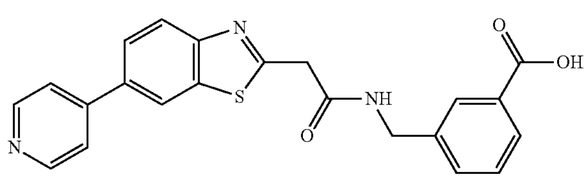 [SMILES: O=C(Cc1nc2ccc(-c3ccncc3)cc2s1)NCc1cccc(C(=O)O)c1] | 1H-NMR (DMSO-d6) δ: 4.18 (s, 2H), 4.41 (d, J = 5.6 Hz, 2H), 7.46 (t, J = 7.6 Hz, 1H), 7.55 (d, J = 7.6 Hz, 1H), 7.79-7.84 (m, 3H), 7.90-7.94 (m, 2H), 8.08 (d, J = 8.1 Hz, 1H), 8.57 (d, J = 1.5 Hz, 1H), 8.67 (d, J = 6.1 Hz, 2H), 8.96 (t, J = 5.8 Hz, 1H), 12.97 (br s, 1H). | | | |

TABLE 9

| No. | Structure | NMR(δ) | retention time | Mass | method |
|---|---|---|---|---|---|
| II-1-45 | 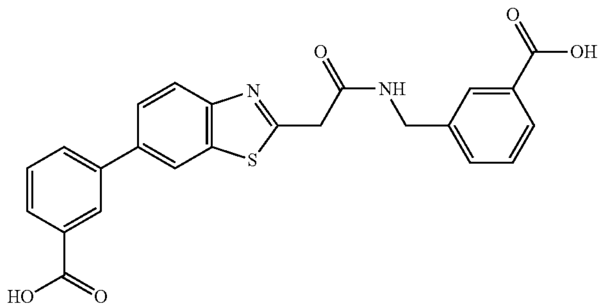 [SMILES: O=C(Cc1nc2ccc(-c3cccc(C(=O)O)c3)cc2s1)NCc1cccc(C(=O)O)c1] | 1H-NMR (DMSO-d6) δ: 4.16 (s, 2H), 4.42 (d, J = 6.1 Hz, 2H), 7.47 (dd, J = 7.6, 8.1 Hz, 1H), 7.56 (d, J = 7.6 Hz, 1H), 7.64 (dd, J = 7.6, 8.1 Hz, 1H), 7.79-7.86 (m, 2H), 7.91 (s, 1H), 7.96 (d, J = 7.6 Hz, 1H), 7.99-8.07 (m, 2H), 8.27 (m, 1H), 8.45 (d, J = 1.5 Hz, 1H), 8.95 (t, J = 6.1 Hz, 1H), 13.03 (brs, 2H). | | | |
| II-1-46 | 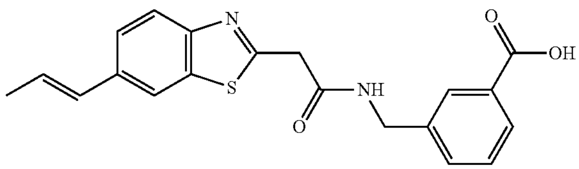 [SMILES: C/C=C/c1ccc2nc(CC(=O)NCc3cccc(C(=O)O)c3)sc2c1] | 1H-NMR (DMSO-d6) δ: 1.88 (d, J = 5.6 Hz, 3H), 4.10 (s, 2H), 4.40 (d, J = 5.6 Hz, 2H), 6.40 (dt, J = 16.9, 5.4 Hz, 1H), 6.53 (d, J = 16.2 Hz, 1H), 7.41-7.55 (m, 3H), 7.82-7.90 (m, 3H), 8.02 (s, 1H), 8.91 (t, J = 5.6 Hz, 1H), 12.95 (br s, 1H). | | | |
| II-1-47 | 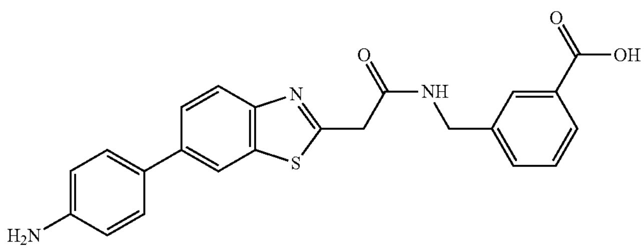 | 1H-NMR (DMSO-d6) δ: 4.17 (s, 2H), 4.41 (d, J = 6.1 Hz, 2H), 7.41-7.50 (m, 3H), 7.53-7.58 (m, 1H), 7.77-7.88 (m, 4H), 7.91 (s, 1H), 8.04 (d, J = 1.5 Hz, 1H), 8.99 (t, J = 6.1 Hz, 1H). | | | |
| II-1-48 | 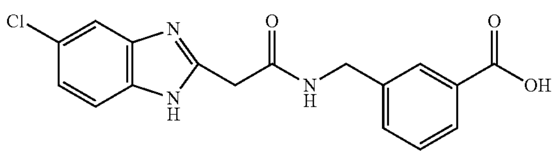 [SMILES: O=C(Cc1nc2cc(Cl)ccc2[nH]1)NCc1cccc(C(=O)O)c1] | 1H-NMR (DMSO-d6) δ: 4.11 (s, 2H), 4.42 (d, J = 6.1 Hz, 2H), 7.60-7.38 (m, 3H), 7.94-7.67 (m, 4H), 9.00 (t, J = 5.8 Hz, 1H). | | | |
| II-1-49 | 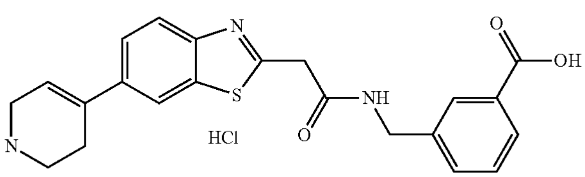 [SMILES: O=C(Cc1nc2ccc(C3=CCNCC3)cc2s1)NCc1cccc(C(=O)O)c1 ; Cl] | 1H-NMR (DMSO-d6) δ: 2.72 (m, 2H), 3.77 (m, 2H), 4.14 (s, 2H), 4.40 (d, J = 6.0 Hz, 2H) 6.31 ( (s, 1H), 7.48 (t, 7.5 Hz, 2H), 7.55 (d, J = 7.5 Hz, 1H), 7.82 (d, J = 7.5 Hz, 2H), 7.92 (-7.95 (m, 3H), 8.18 (d, J = 1.84 Hz, 1H) 8.99 (t, J = 6.0 Hz, 1H), 9.29 (brs, 1H). | | | |

TABLE 10

| No. | Structure | NMR(δ) | retention time | Mass | method |
|---|---|---|---|---|---|
| II-1-50 | 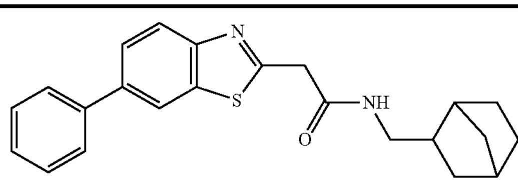 | | 2.66 | 377.05 (+)ESI | C |

TABLE 10-continued

| No. | Structure | NMR(δ) | retention time | Mass | method |
|---|---|---|---|---|---|
| II-1-51 | 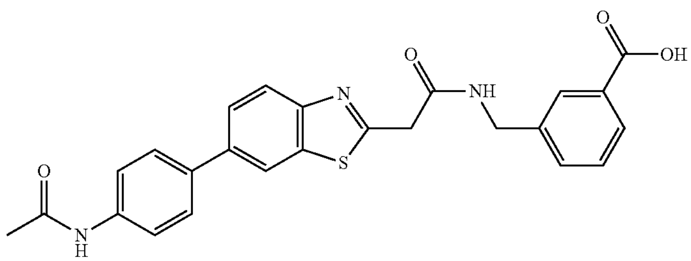 [SMILES: CC(=O)Nc1ccc(-c2ccc3nc(CC(=O)NCc4cccc(C(=O)O)c4)sc3c2)cc1] | 1H-NMR (DMSO-d6) δ: 2.07 (s, 3H), 4.14 (s, 2H), 4.41 (d, J = 5.6 Hz, 2H), 7.46 (dd, J = 7.6, 8.1 Hz, 1H), 7.52-7.58 (m, 1H), 7.70 (m, 4H), 7.76 (dd, J = 1.5, 8.6 Hz, 1H), 7.80-7.86 (m, 1H), 7.91 (s, 1H), 7.99 (d, J = 8.6 Hz, 1H), 8.33 (d, J = 1.5 Hz, 1H), 8.94 (t, J = 5.6 Hz, 1H), 10.05 (s, 1H), 12.94 (brs, 1H). | | | |
| II-1-52 | 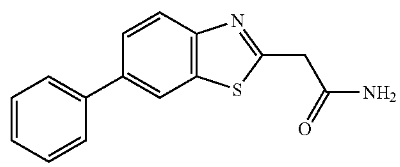 [SMILES: NC(=O)Cc1nc2ccc(-c3ccccc3)cc2s1] | 1H-NMR (DMSO-d6) δ: 4.04 (s, 2H), 7.25 (s, 1H), 7.39-7.41 (m, 1H), 7.50 (t, J = 7.6 Hz, 2H), 7.76-7.79 (m, 4H), 8.01 (d, J = 8.6 Hz, 1H), 8.38 (d, J = 1.8 Hz, 1H). | | | |
| II-1-53 | 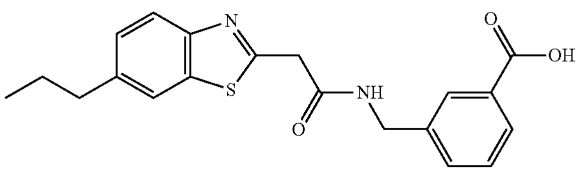 | 1H-NMR (DMSO-d6) δ: 0.90 (t, J = 7.1 Hz, 3H), 1.59-1.69 (m, 2H), 2.68 (t, J = 7.6 Hz, 2H), 4.09 (s, 2H), 4.39 (d, J = 6.1 Hz, 2H), 7.32 (d, J = 8.6 Hz, 1H), 7.45 (t, J = 7.6 Hz, 1H), 7.53 (d, J = 7.6 Hz, 1H), 7.81-7.90 (m, 4H), 8.91 (t, J = 6.1 Hz, 1H). | | | |
| II-1-54 | 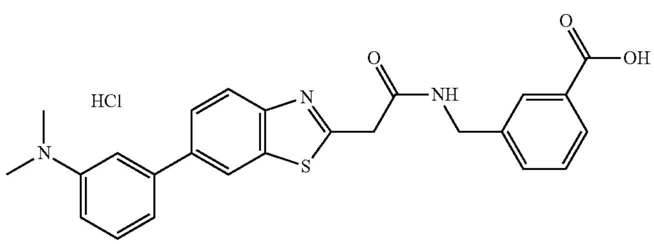 [SMILES: CN(C)c1cccc(-c2ccc3nc(CC(=O)NCc4cccc(C(=O)O)c4)sc3c2)c1 ; Cl] | 1H-NMR (DMSO-d6) δ: 3.14 (s, 6H), 4.17 (s, 2H), 4.41 (d, J = 5.6 Hz, 2H), 7.42-7.60 (m, 5H), 7.80-7.88 (m, 2H), 7.91 (s, 1H), 8.05 (d, J = 8.6 Hz, 1H), 8.43 (d, J = 1.5 Hz), 8.99 (t, J = 5.6 Hz, 1H). | | | |

TABLE 11

| No. | Structure | NMR(δ) | retention time | Mass | method |
|---|---|---|---|---|---|
| II-1-55 | 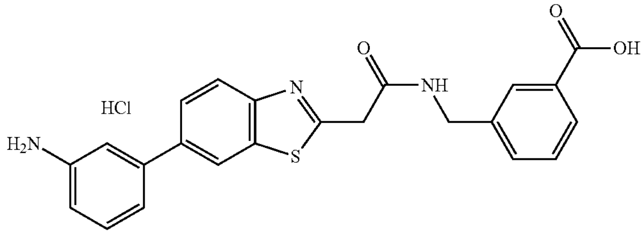 [SMILES: Nc1cccc(-c2ccc3nc(CC(=O)NCc4cccc(C(=O)O)c4)sc3c2)c1 ; Cl] | 1H-NMR (DMSO-d6) δ: 4.18 (s, 2H), 4.42 (d, J = 6.1 Hz, 2H), 7.36-7.42 (m, 1H), 7.47 (dd, J = 7.6, 8.1 Hz, 1H), 7.52-7.65 (m, 2H), 7.67-7.86 (m, 4H), 7.91 (brs, 1H), 8.07 (d, J = 8.1 Hz, 1H), 8.38 (d, J = 1.5 Hz, 1H), 9.01 (t, J = 6.1 Hz, 1H). | | | |

TABLE 11-continued

| No. | Structure | NMR(δ) | retention time | Mass | method |
|---|---|---|---|---|---|
| II-1-56 | 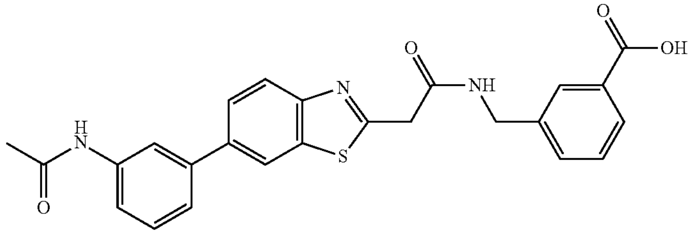 [SMILES: CC(=O)Nc1cccc(-c2ccc3nc(CC(=O)NCc4cccc(C(=O)O)c4)sc3c2)c1] | 1H-NMR (DMSO-d6) δ: 2.08 (s, 3H), 4.16 (s, 2H), 4.41 (d, J = 5.6 Hz, 2H), 7.34-7.50 (m, 3H), 7.52-7.61 (m, 2H), 7.71 (dd, J = 8.1, 2.0 Hz, 2H), 7.81-7.86 (m, 1H), 7.91 (s, 1H), 7.97 (s, 1H), 8.03 (d, J = 8.6 Hz, 1H), 8.30 (d, J = 1.5 Hz, 1H), 8.95 (t, J = 5.6 Hz, 1H), 10.05 (s, 1H), 12.96 (brs, 1H). | | | |
| II-1-57 | 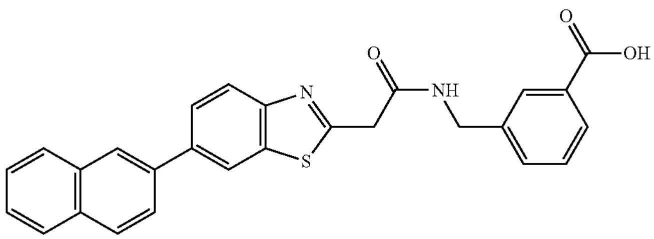 [SMILES: O=C(Cc1nc2ccc(-c3ccc4ccccc4c3)cc2s1)NCc1cccc(C(=O)O)c1] | 1H-NMR (DMSO-d6) δ: 4.17 (s, 2H), 4.42 (d, J = 5.6 Hz, 2H), 7.47 (dd, J = 7.6, 8.1 Hz, 1H), 7.51-7.60 (m, 3H), 7.80-7.87 (m, 1H), 7.89-7.99 (m, 4H), 8.00-8.10 (m, 3H), 8.33 (s, 1H), 8.54 (d, J = 1.5 Hz, 1H), 8.96 (t, J = 5.6 Hz, 1H), 12.97 (brs, 1H). | | | |
| II-1-58 | 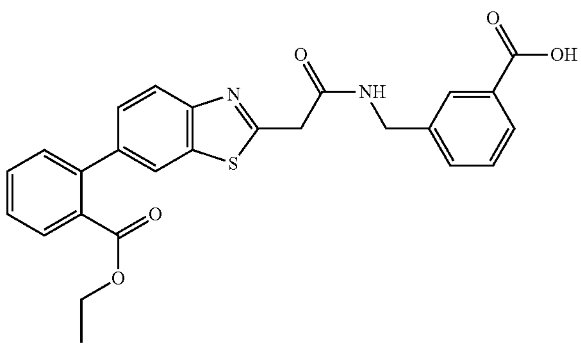 [SMILES: CCOC(=O)c1ccccc1-c1ccc2nc(CC(=O)NCc3cccc(C(=O)O)c3)sc2c1] | 1H-NMR (DMSO-d6) δ: 0.89 (t, J = 7.1 Hz, 3H), 4.02 (q, J = 7.1 Hz, 2H), 4.16 (s, 2H), 4.42 (d, J = 5.6 Hz, 2H), 7.37 (dd, J = 1.8, 8.4 Hz, 1H), 7.44-7.56 (m, 4H), 7.61-7.68 (m, 1H), 7.76-7.86 (m, 2H), 7.92 (s, 1H), 7.97 (d, J = 8.4 Hz, 1H), 8.00 (d, J = 1.5 Hz, 1H), 8.95 (t, J = 5.6 Hz, 1H), 12.96 (brs, 1H). | | | |
| II-1-59 | 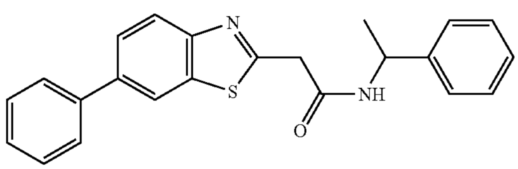 [SMILES: CC(NC(=O)Cc1nc2ccc(-c3ccccc3)cc2s1)c1ccccc1] | 1H-NMR (DMSO-d6) δ: 1.40 (d, J = 6.9 Hz, 3H), 4.12 (s, 2H), 4.97 (t, J = 7.3 Hz, 1H), 7.24-7.25 (m, 1H), 7.33-7.39 (m, 5H), 7.50 (t, J = 7.5 Hz, 2H), 7.75-7.79 (m, 3H), 8.01 (d, J = 8.6 Hz, 1H), 8.37 (s, 1H), 8.84 (d, J = 7.4 Hz, 1H). | | | |

TABLE 12

| No. | Structure | NMR(δ) | retention time | Mass | method |
|---|---|---|---|---|---|
| II-1-60 | 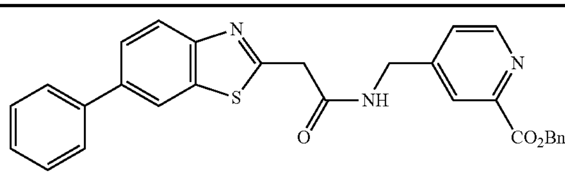 | 1H-NMR (DMSO)-d6) δ: 4.19 (s, 2H), 4.47 (d, J = 6.0 Hz, 2H), 5.37 (s, 2H), 7.34-7.58 (m, 9H), 7.75-7.80 (m, 3H), 8.02-8.04 (m, 2H), 8.37 (s, 1H), 8.66 (d, J = 5.2 Hz, 1H), 9.03-9.06 (br m, 1H). | | | |
| II-1-61 | 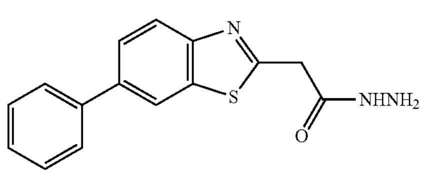 [SMILES: NNC(=O)Cc1nc2ccc(-c3ccccc3)cc2s1] | 1H-NMR (DMSO-d6) δ: 4.00 (s, 2H), 4.37 (d, J = 4.1 Hz, 2H), 7.39 (t, J = 7.4 Hz, 1H), 7.50 (t, J = 7.6 Hz, 2H), 7.74-7.80 (m, 3H), 8.00 (d, J = 8.1 Hz, 1H), 8.38 (d, J = 1.5 Hz, 1H), 9.47 (s, 1H). | | | |

TABLE 12-continued

| No. | Structure | NMR(δ) | retention time | Mass | method |
|---|---|---|---|---|---|
| II-1-62 | 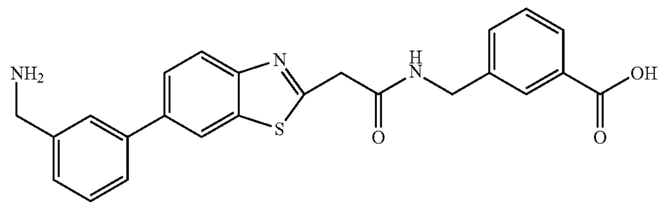 [SMILES: NCc1cccc(-c2ccc3nc(CC(=O)NCc4cccc(C(=O)O)c4)sc3c2)c1] | | 0.98 | 432.47 (ES+) | A |
| II-1-63 | 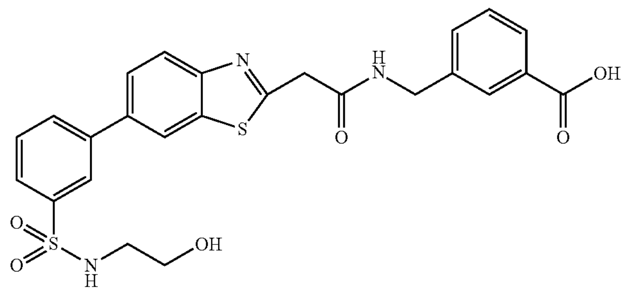 [SMILES: O=C(Cc1nc2ccc(-c3cccc(S(=O)(=O)NCCO)c3)cc2s1)NCc1cccc(C(=O)O)c1] | | 1.41 | 526.48 (ES+) | A |
| II-1-64 | 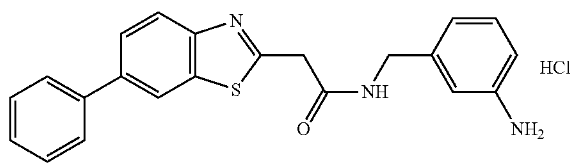 [SMILES: Nc1cccc(CNC(=O)Cc2nc3ccc(-c4ccccc4)cc3s2)c1 ; Cl] | 1H-NMR (DMSO-d6) δ: 4.16 (s, 2H), 4.36 (d, J = 5.2 Hz, 2H), 7.14-7.22 (m, 3H), 7.39-7.50 (m, 4H), 7.76-7.80 (m, 3H), 8.02 (d, J = 8.4 Hz, 1H), 8.39 (s, 1H), 8.99 (br s, 1H). | | | |

TABLE 13

| No. | Structure | NMR(δ) | retention time | Mass | method |
|---|---|---|---|---|---|
| II-1-65 | 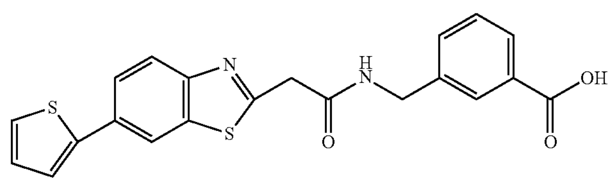 [SMILES: O=C(Cc1nc2ccc(-c3cccs3)cc2s1)NCc1cccc(C(=O)O)c1] | 1H-NMR (DMSO-d6) δ: 4.12 (s, 3H), 4.38 (d, J = 6.6 Hz, 2H), 7.44 (t, J = 7.8 Hz, 1H), 7.51-7.59 (m, 3H), 7.78 (dd, J = 8.1, 12 Hz, 2H), 7.88 (s, 1H), 7.94 (d, J = 8.4 Hz, 1H), 8.36 (s, 1H), 8.92 (m, 1H). | | | |
| II-1-66 | 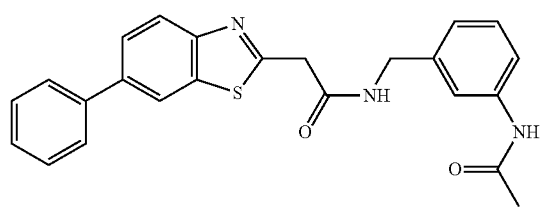 [SMILES: CC(=O)Nc1cccc(CNC(=O)Cc2nc3ccc(-c4ccccc4)cc3s2)c1] | 1H-NMR (DMSO-d6) δ: 2.01 (s, 3H), 4.13 (s, 2H), 4.30 (d, J = 5.9 Hz, 2H), 6.97 (d, J = 7.2 Hz, 1H), 7.24 (t, J = 8.3 Hz, 1H), 7.44 (dd, J = 25.3, 6.6 Hz, 5H), 7.76-7.79 (m, 3H), 8.01 (d, J = 8.6 Hz, 1H), 8.38 (s, 1H), 8.85-8.88 (br m, 1H), 9.92 (s, 1H). | | | |
| II-1-67 | 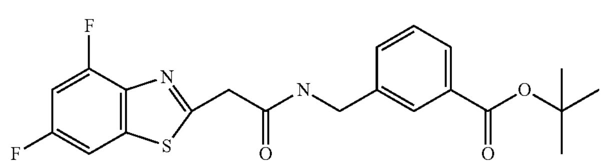 [SMILES: CC(C)(C)OC(=O)c1cccc(CNC(=O)Cc2nc3c(F)cc(F)cc3s2)c1] | 1H-NMR (CDCl3) δ: 1.57 (s, 9H), 4.11 (s, 2H), 4.54 (d, J = 5.7 Hz, 2H), 6.99 (t, J = 9.0 Hz, 1H), 7.18 (br-s, 1H), 7.35-7.41 (m, 2H), 7.47 (m, 1H), 7.87-7.91 (m, 2H). | | | |

TABLE 13-continued

| No. | Structure | NMR(δ) | retention time | Mass | method |
|---|---|---|---|---|---|
| II-1-68 | 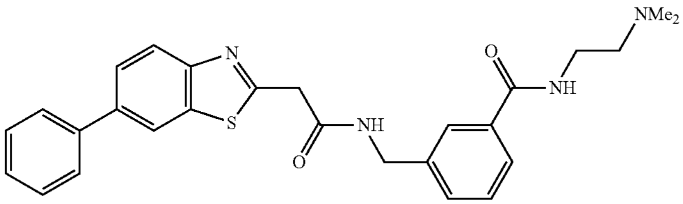 [SMILES: CN(C)CCNC(=O)c1cccc(CNC(=O)Cc2nc3ccc(-c4ccccc4)cc3s2)c1] | 1H-NMR (CDCl3) δ: 2.26 (s, 6H), 2.51 (t, J = 5.8 Hz, 2H), 3.51-3.52 (m, 2H), 4.14 (s, 2H), 4.57 (d, J = 5.6 Hz, 2H), 6.85 (s, 1H), 7.37-7.49 (m, 5H), 7.62-7.76 (m, 6H), 8.02 (d, J = 8.6 Hz, 1H), 8.06 (d, J = 1.5 Hz, 1H). | | | |
| II-1-69 | 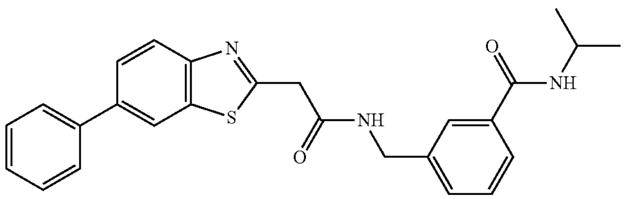 [SMILES: CC(C)NC(=O)c1cccc(CNC(=O)Cc2nc3ccc(-c4ccccc4)cc3s2)c1] | 1H-NMR (DMSO-d6) δ: 1.16 (d, J = 6.6 Hz, 6H), 4.02-4.15 (m, 3H), 4.39 (d, J = 5.6 Hz, 2H), 7.37-7.52 (m, 5H), 7.70-7.81 (m, 5H), 8.02 (d, J = 8.6 Hz, 1H), 8.19 (d, J = 8.1 Hz, 1H), 8.38 (d, J = 1.5 Hz, 1H), 8.90 (t, J = 5.8 Hz, 1H). | | | |

TABLE 14

| No. | Structure | NMR(δ) | retention time | Mass | method |
|---|---|---|---|---|---|
| II-1-70 | 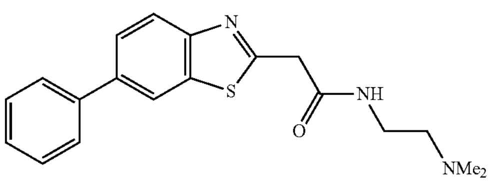 [SMILES: CN(C)CCNC(=O)Cc1nc2ccc(-c3ccccc3)cc2s1] | 1H-NMR (DMSO-d6) δ: 2.19 (s, 6H), 2.36 (t, J = 6.6 Hz, 2H), 3.22-3.23 (m, 2H), 4.07 (s, 2H), 7.39 (t, J = 7.4 Hz, 1H), 7.50 (t, J = 7.6 Hz, 2H), 7.74-7.80 (m, 3H), 8.00 (d, J = 8.1 Hz, 1H), 8.33 (br s, 1H), 8.38 (d, J = 1.5 Hz, 1H). | | | |
| II-1-71 | 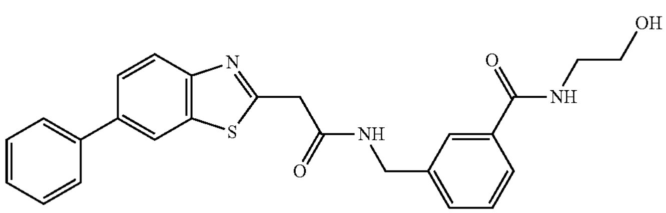 [SMILES: O=C(Cc1nc2ccc(-c3ccccc3)cc2s1)NCc1cccc(C(=O)NCCO)c1] | 1H-NMR (CDCl3) δ: 2.66 (br s, 1H), 3.59-3.63 (m, 2H), 3.82-3.83 (m, 2H), 4.14 (s, 2H), 4.55 (d, J = 6.1 Hz, 2H), 6.69 (br s, 1H), 7.36-7.49 (m, 5H), 7.62-7.75 (m, 6H), 8.01 (d, J = 8.1 Hz, 1H), 8.06 (d, J = 1.5 Hz, 1H). | | | |
| II-1-72 | 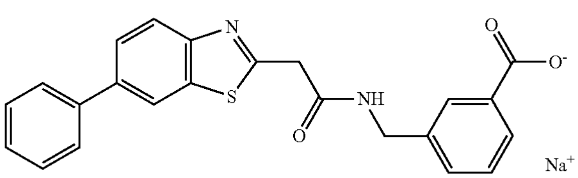 | 1H-NMR (DMSO-d6) δ: 4.15 (s, 2H), 4.34 (d, J = 5.7 Hz, 2H), 7.22 (d, J = 5.1 Hz, 2H), 7.39 (t, J = 7.2 Hz, 1H), 7.49 (d, J = 7.8 Hz, 2H), 7.74-7.83 (m, 5H), 8.02 (d, J = 8.4 Hz, 1H), 8.38 (d, J = 1.5 Hz, 1H), 8.93 (d, J = 6.3 Hz, 1H). | | | |
| II-1-73 | 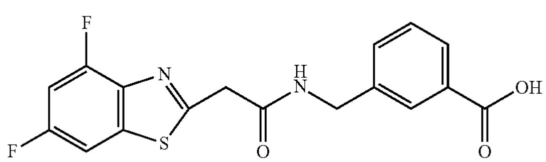 [SMILES: O=C(Cc1nc2c(F)cc(F)cc2s1)NCc1cccc(C(=O)O)c1] | 1H-NMR (DMSO)-d6) δ: 4.18 (s, 2H), 4.41 (d, J = 5.4 Hz, 2H), 7.40-7.57 (m, 3H), 7.82-7.89 (m, 3H), 8.96 (m, 1H), 12.86 (br-s, 1H) | | | |

TABLE 14-continued

| No. | Structure | NMR(δ) | retention time | Mass | method |
|---|---|---|---|---|---|
| II-1-74 | 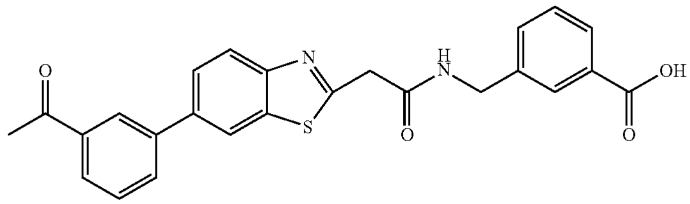 [SMILES: CC(=O)c1cccc(-c2ccc3nc(CC(=O)NCc4cccc(C(=O)O)c4)sc3c2)c1] | | 1.76 | 445.47 (ES+) | A |

TABLE 15

| No. | Structure | NMR(δ) | retention time | Mass | method |
|---|---|---|---|---|---|
| II-1-75 | 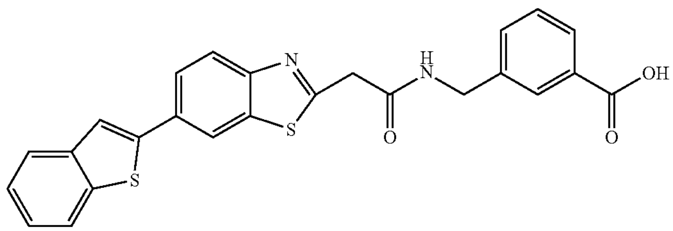 [SMILES: O=C(Cc1nc2ccc(-c3cc4ccccc4s3)cc2s1)NCc1cccc(C(=O)O)c1] | | 2.19 | 459.44 (ES+) | A |
| II-1-76 | 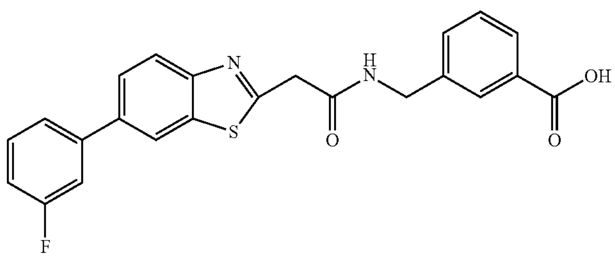 [SMILES: O=C(Cc1nc2ccc(-c3cccc(F)c3)cc2s1)NCc1cccc(C(=O)O)c1] | | 1.96 | 421.48 (ES+) | A |
| II-1-77 | 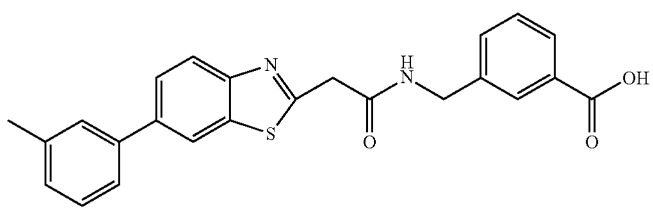 [SMILES: Cc1cccc(-c2ccc3nc(CC(=O)NCc4cccc(C(=O)O)c4)sc3c2)c1] | | 2.08 | 417.5 (ES+) | A |
| II-1-78 | 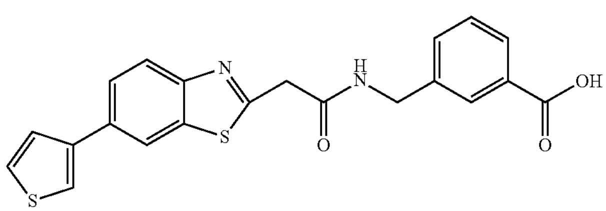 [SMILES: O=C(Cc1nc2ccc(-c3ccsc3)cc2s1)NCc1cccc(C(=O)O)c1] | | 1.86 | 409.39 (ES+) | A |
| II-1-79 | 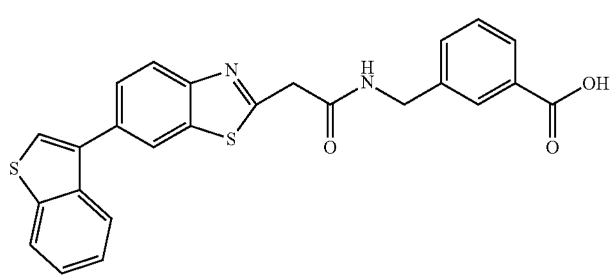 [SMILES: O=C(Cc1nc2ccc(-c3csc4ccccc34)cc2s1)NCc1cccc(C(=O)O)c1] | | 2.15 | 459.44 (ES+) | A |

TABLE 16

| No. | Structure | NMR (δ) | retention time | Mass | method |
|---|---|---|---|---|---|
| II-1-80 | 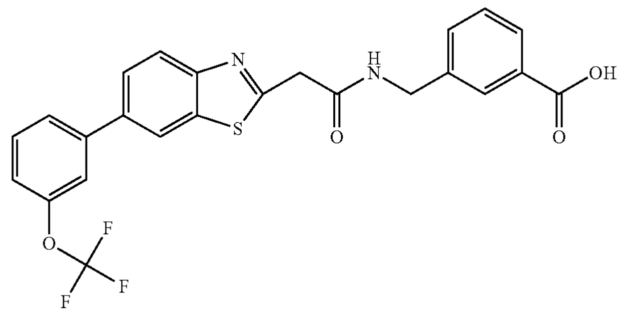 [SMILES: O=C(Cc1nc2ccc(-c3cccc(OC(F)(F)F)c3)cc2s1)NCc1cccc(C(=O)O)c1] | | 2.22 | 487.47 (ES+) | A |
| II-1-81 | 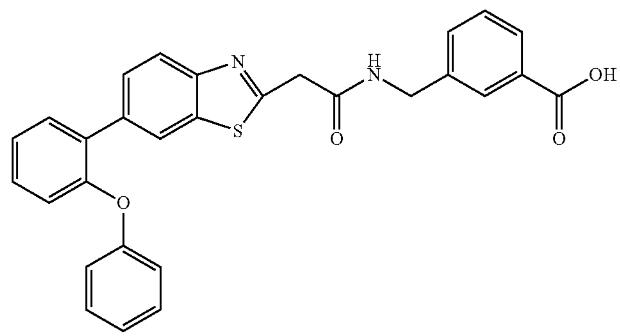 [SMILES: O=C(Cc1nc2ccc(-c3ccccc3Oc3ccccc3)cc2s1)NCc1cccc(C(=O)O)c1] | | 2.25 | 495.51 (ES+) | A |
| II-1-82 | 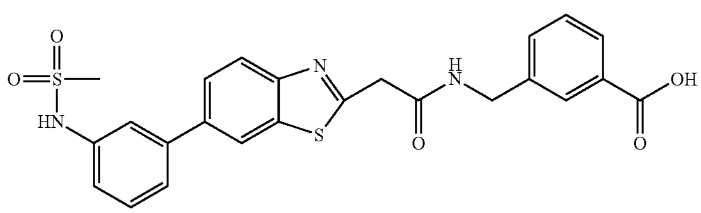 [SMILES: CS(=O)(=O)Nc1cccc(-c2ccc3nc(CC(=O)NCc4cccc(C(=O)O)c4)sc3c2)c1] | | 1.56 | 496.45 (ES+) | A |
| II-1-83 | 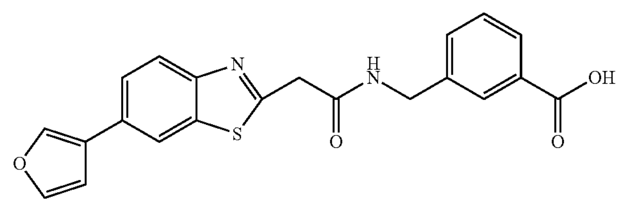 [SMILES: O=C(Cc1nc2ccc(-c3ccoc3)cc2s1)NCc1cccc(C(=O)O)c1] | | 1.72 | 393.41 (ES+) | A |
| II-1-84 | 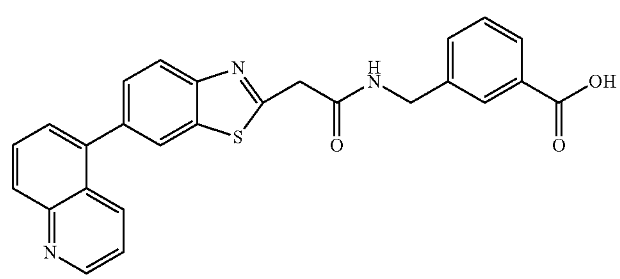 [SMILES: O=C(Cc1nc2ccc(-c3cccc4ncccc34)cc2s1)NCc1cccc(C(=O)O)c1] | | 1.26 | 454.43 (ES+) | A |

TABLE 17

| No. | Structure | NMR (δ) | retention time | Mass | method |
|---|---|---|---|---|---|
| II-1-85 | 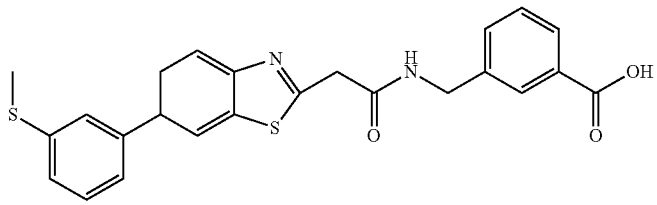 [SMILES: CSc1cccc(C2C=c3sc(CC(=O)NCc4cccc(C(=O)O)c4)nc3=CC2)c1] | | 2.07 | 449.46 (ES+) | A |
| II-1-86 | 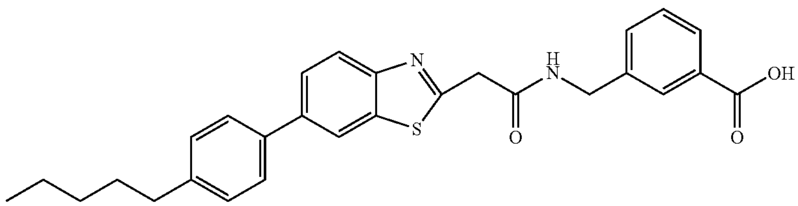 [SMILES: CCCCCc1ccc(-c2ccc3nc(CC(=O)NCc4cccc(C(=O)O)c4)sc3c2)cc1] | | 2.66 | 473.53 (ES+) | A |
| II-1-87 | 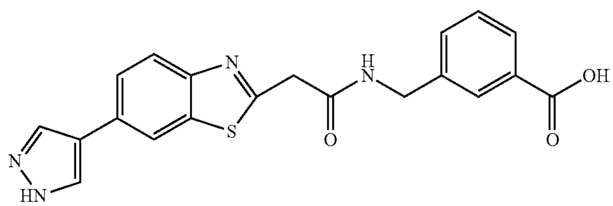 [SMILES: O=C(Cc1nc2ccc(-c3cn[nH]c3)cc2s1)NCc1cccc(C(=O)O)c1] | | 1.22 | 393.45 (ES+) | A |
| II-1-88 | 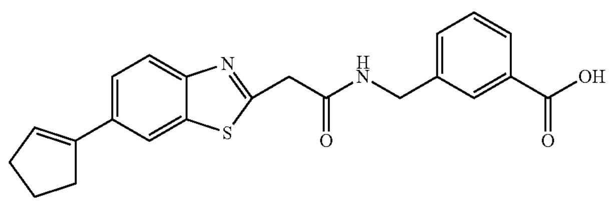 [SMILES: O=C(Cc1nc2ccc(C3=CCCC3)cc2s1)NCc1cccc(C(=O)O)c1] | | 2.04 | 393.44 (ES+) | A |
| II-1-89 | 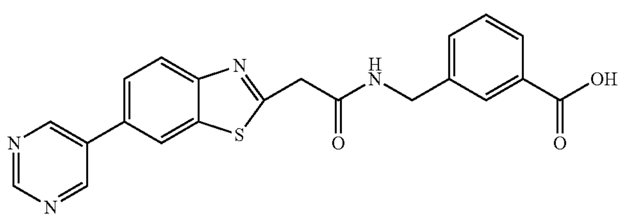 [SMILES: O=C(Cc1nc2ccc(-c3cncnc3)cc2s1)NCc1cccc(C(=O)O)c1] | | 1.26 | 405.42 (ES+) | A |

TABLE 18

| No. | Structure | NMR (δ) | retention time | Mass | method |
|---|---|---|---|---|---|
| II-1-90 | 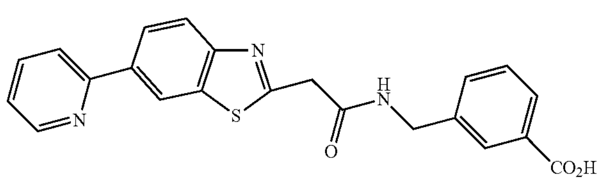 [SMILES: O=C(Cc1nc2ccc(-c3ccccn3)cc2s1)NCc1cccc(C(=O)O)c1] | | 1.29 | 404.2 (ES+) | A |

TABLE 18-continued

| No. | Structure | NMR (δ) | retention time | Mass | method |
|---|---|---|---|---|---|
| II-1-91 | 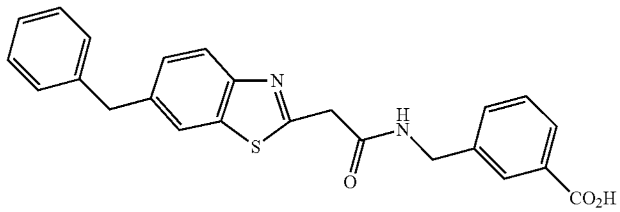 [SMILES: O=C(Cc1nc2ccc(Cc3ccccc3)cc2s1)NCc1cccc(C(=O)O)c1] | | 2 | 417.41 (ES+) | A |
| II-1-92 | 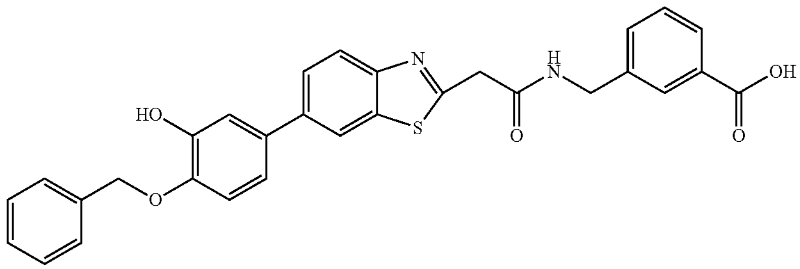 [SMILES: O=C(Cc1nc2ccc(-c3ccc(OCc4ccccc4)c(O)c3)cc2s1)NCc1cccc(C(=O)O)c1] | | 2.02 | 525.38 (ES+) | A |
| II-1-93 | 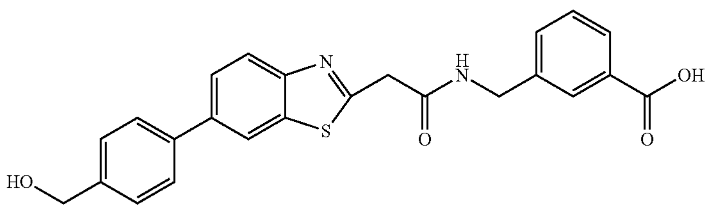 [SMILES: O=C(Cc1nc2ccc(-c3ccc(CO)cc3)cc2s1)NCc1cccc(C(=O)O)c1] | | 1.48 | 433.44 (ES+) | A |
| II-1-94 | 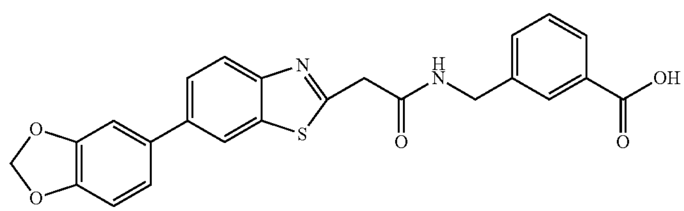 [SMILES: O=C(Cc1nc2ccc(-c3ccc4c(c3)OCO4)cc2s1)NCc1cccc(C(=O)O)c1] | | 1.88 | 447.41 (ES+) | A |

TABLE 19

| No. | Structure | NMR (δ) | retention time | Mass | method |
|---|---|---|---|---|---|
| II-1-95 | 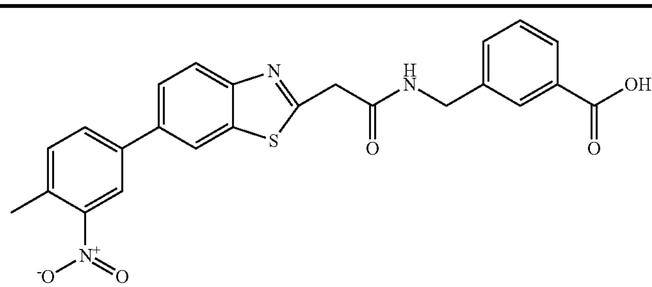 | | 2.03 | 462.45 (ES+) | A |
| II-1-96 | 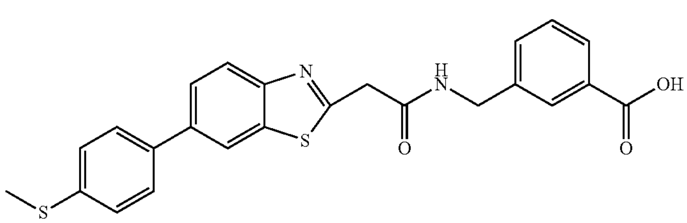 [SMILES: CSc1ccc(-c2ccc3nc(CC(=O)NCc4cccc(C(=O)O)c4)sc3c2)cc1] | | 2.08 | 449.41 (ES+) | A |

TABLE 19-continued
| No. | Structure | NMR (δ) | retention time | Mass | method |
|---|---|---|---|---|---|
| II-1-97 | 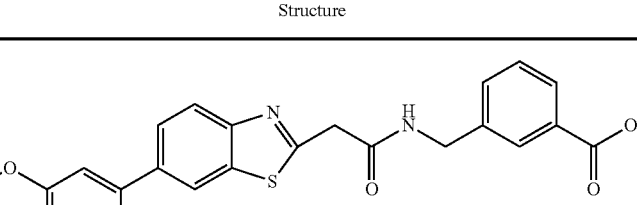 | | 1.77 | 493.49 (ES+) | A |
| II-1-98 | 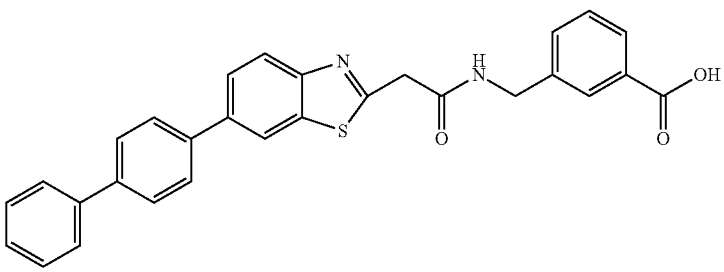 [SMILES: O=C(Cc1nc2ccc(-c3ccc(-c4ccccc4)cc3)cc2s1)NCc1cccc(C(=O)O)c1] | | 2.35 | 479.41 (ES+) | A |
| II-1-99 | 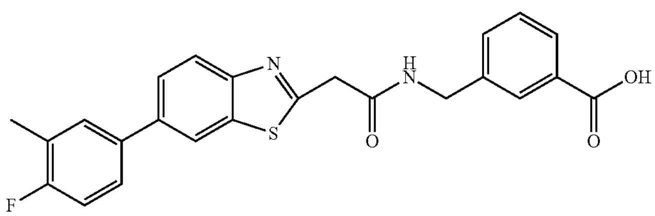 [SMILES: Cc1cc(-c2ccc3nc(CC(=O)NCc4cccc(C(=O)O)c4)sc3c2)ccc1F] | | 2.14 | 435.49 (ES+) | A |
TABLE 20
| No. | Structure | NMR (δ) | retention time | Mass | method |
|---|---|---|---|---|---|
| II-1-100 | 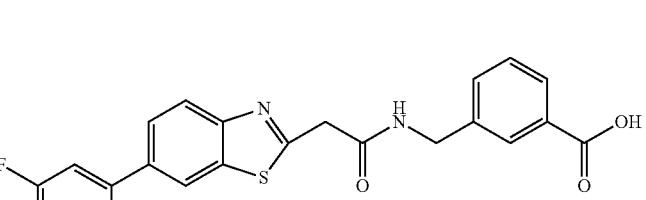 | | 1.76 | 463.44 (ES+) | A |
| II-1-101 | 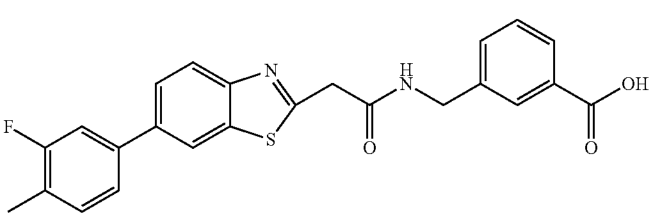 [SMILES: Cc1ccc(-c2ccc3nc(CC(=O)NCc4cccc(C(=O)O)c4)sc3c2)cc1F] | | 2.15 | 435.41 (ES+) | A |

TABLE 20-continued

| No. | Structure | NMR (δ) | retention time | Mass | method |
|---|---|---|---|---|---|
| II-1-102 | 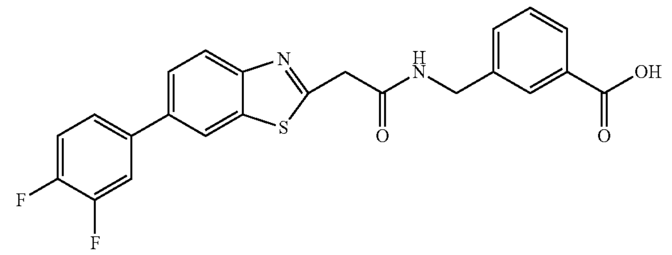 [SMILES: O=C(Cc1nc2ccc(-c3ccc(F)c(F)c3)cc2s1)NCc1cccc(C(=O)O)c1] | | 2.07 | 439.4 (ES+) | A |
| II-1-103 | 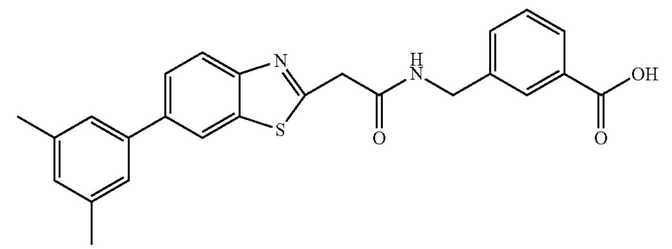 [SMILES: Cc1cc(C)cc(-c2ccc3nc(CC(=O)NCc4cccc(C(=O)O)c4)sc3c2)c1] | | 2.25 | 431.45 (ES+) | A |
| II-1-104 | 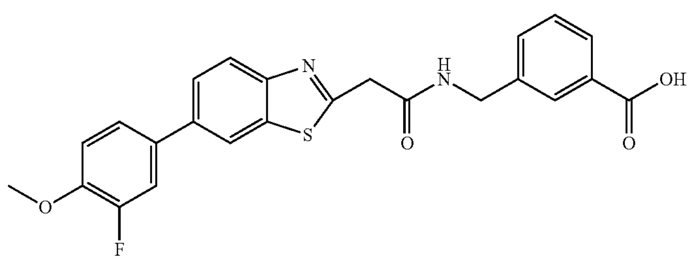 [SMILES: COc1ccc(-c2ccc3nc(CC(=O)NCc4cccc(C(=O)O)c4)sc3c2)cc1F] | | 1.91 | 451.48 (ES+) | A |

TABLE 21

| No. | Structure | NMR (δ) | retention time | Mass | method |
|---|---|---|---|---|---|
| II-1-105 | 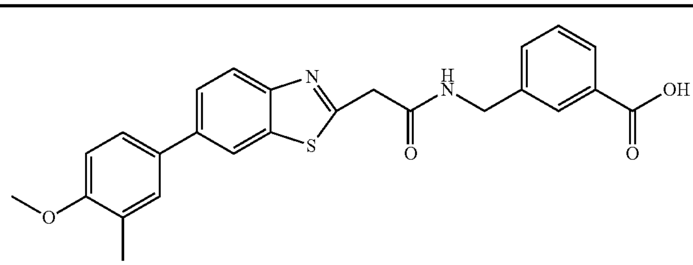 | | 2.1 | 447.46 (ES+) | A |
| II-1-106 | 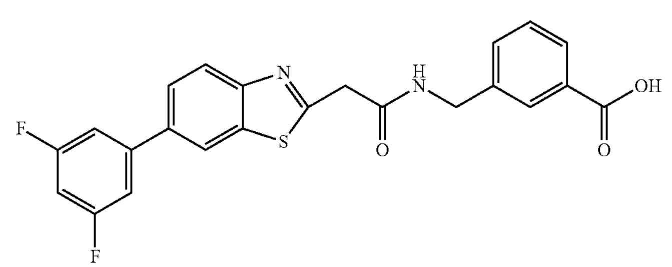 [SMILES: O=C(Cc1nc2ccc(-c3cc(F)cc(F)c3)cc2s1)NCc1cccc(C(=O)O)c1] | | 2.06 | 439.38 (ES+) | A |

TABLE 21-continued

| No. | Structure | NMR (δ) | retention time | Mass | method |
|---|---|---|---|---|---|
| II-1-107 | 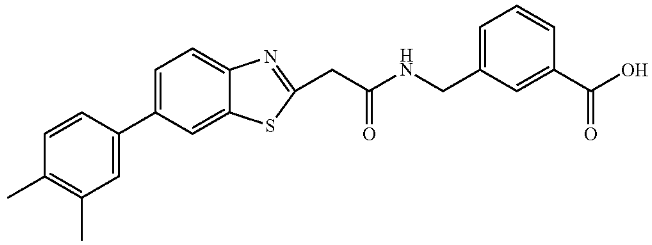 [SMILES: Cc1ccc(-c2ccc3nc(CC(=O)NCc4cccc(C(=O)O)c4)sc3c2)cc1C] | | 2.22 | 431.45 (ES+) | A |
| II-1-108 | 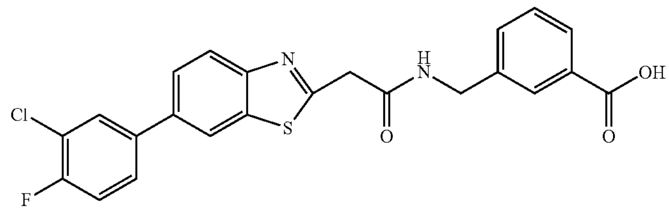 [SMILES: O=C(Cc1nc2ccc(-c3ccc(F)c(Cl)c3)cc2s1)NCc1cccc(C(=O)O)c1] | | 2.15 | 455.4 (ES+) | A |
| II-1-109 | 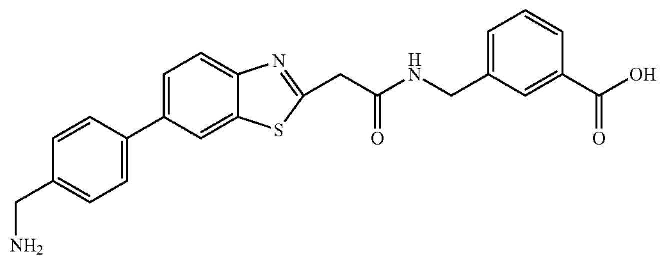 [SMILES: NCc1ccc(-c2ccc3nc(CC(=O)NCc4cccc(C(=O)O)c4)sc3c2)cc1] | | 0.95 | 432.53 (ES+) | A |

TABLE 22

| No. | Structure | NMR (δ) | retention time | Mass | method |
|---|---|---|---|---|---|
| II-1-110 | 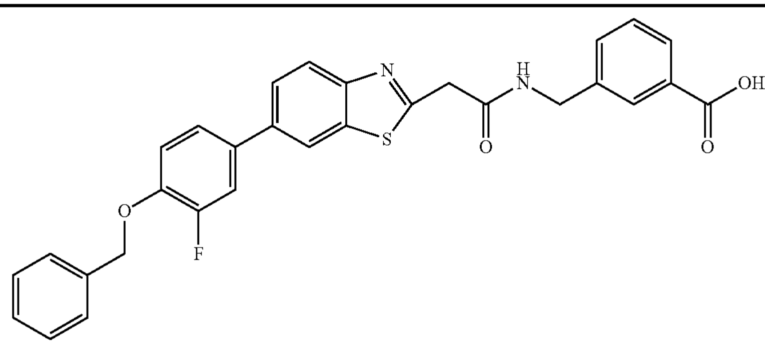 | | 2.3 | 527.5 (ES+) | A |
| II-1-111 | 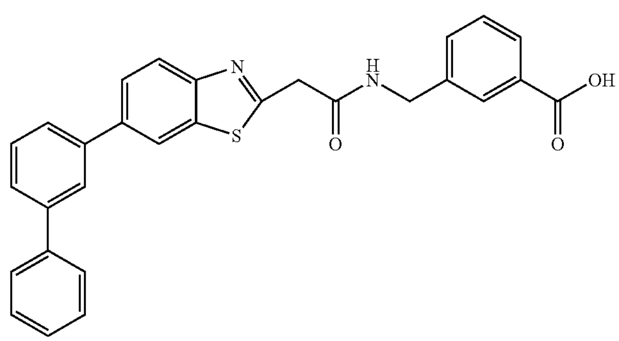 [SMILES: O=C(Cc1nc2ccc(-c3cccc(-c4ccccc4)c3)cc2s1)NCc1cccc(C(=O)O)c1] | | 2.35 | 479.43 (ES+) | A |

TABLE 22-continued

| No. | Structure | NMR (δ) | retention time | Mass | method |
|---|---|---|---|---|---|
| II-1-112 | 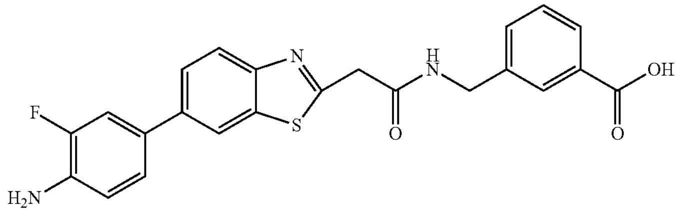 [SMILES: Nc1ccc(-c2ccc3nc(CC(=O)NCc4cccc(C(=O)O)c4)sc3c2)cc1F] | | 1.64 | 436.41 (ES+) | A |
| II-1-113 | 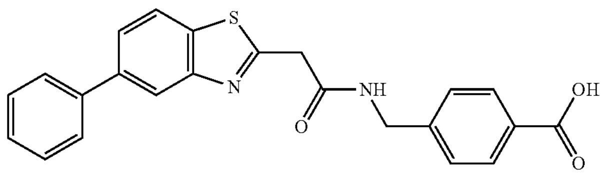 [SMILES: O=C(Cc1nc2cc(-c3ccccc3)ccc2s1)NCc1ccc(C(=O)O)cc1] | | 1.87 | 403.32 (ES+) | A |
| II-1-114 | 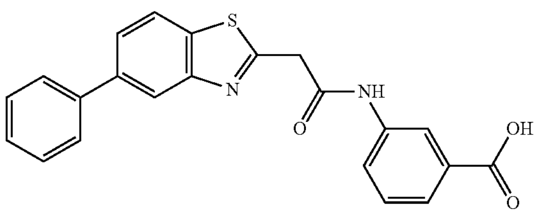 [SMILES: O=C(Cc1nc2cc(-c3ccccc3)ccc2s1)Nc1cccc(C(=O)O)c1] | | 1.99 | 389.34 (ES+) | A |

TABLE 23

| No. | Structure | NMR (δ) | retention time | Mass | method |
|---|---|---|---|---|---|
| II-1-115 | 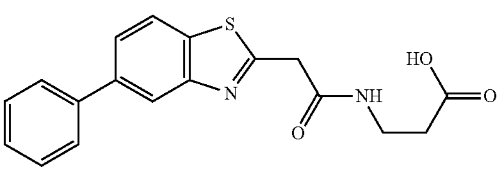 [SMILES: O=C(O)CCNC(=O)Cc1nc2cc(-c3ccccc3)ccc2s1] | | 1.63 | 341.29 (ES+) | A |
| II-1-116 | 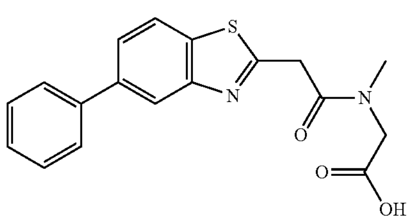 [SMILES: CN(CC(=O)O)C(=O)Cc1nc2cc(-c3ccccc3)ccc2s1] | (DMSO-d6) δ: 2.89 (1H, s), 3.16 (2H, s), 4.07 (1H, s), 4.26 (1H, s), 4.32 (1H, s), 4.42 (1H, s) 7.40 (1H, d, J = 7.1 Hz), 7.50 (2H, t, J = 7.2 Hz), 7.78 (3H, t, J = 11.2 Hz), 8.01 (1H, t, J = 7.2 Hz), 8.39 (1H, s). | | | |
| II-1-117 | 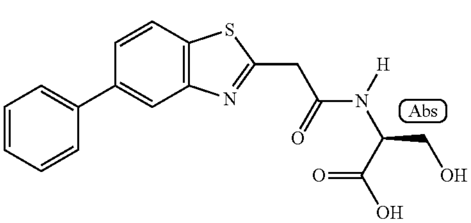 [SMILES: O=C(Cc1nc2cc(-c3ccccc3)ccc2s1)N[C@@H](CO)C(=O)O] | (DMSO-d6) δ: 1.97 (2H, s), 3.71 (2H, d, J = 22.7 Hz), 4.20 (1H, s), 4.34 (1H, ), 7.39 (1H, s), 7.50 s (2H, s), 7.77 (2H, t, J = 11.5 Hz), 8.01 (1H, d, J = 7.8 Hz), 8.38 (1H, s), 8.66 (1H, s). | | | |

TABLE 23-continued

| No. | Structure | NMR (δ) | retention time | Mass | method |
|---|---|---|---|---|---|
| II-1-118 | 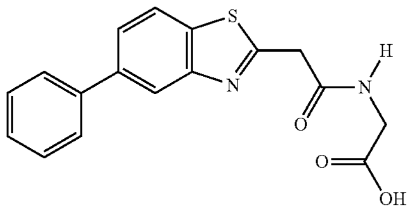 [SMILES: O=C(O)CNC(=O)Cc1nc2cc(-c3ccccc3)ccc2s1] | | 2.13 | 267.25 (ES+) | A |
| II-1-119 | 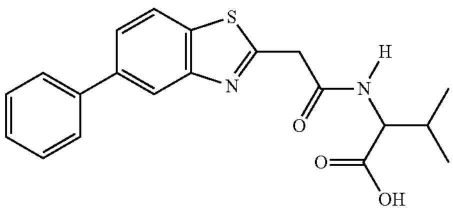 [SMILES: CC(C)C(NC(=O)Cc1nc2cc(-c3ccccc3)ccc2s1)C(=O)O] | (DMSO-d6) δ: 0.92 (6H, t, J = 5.1 Hz), 2.10 (1H, dd, J = 13.3, 7.2 Hz), 4.20 (2H, d, J = 9.3 Hz), 4.24 (1H, d, J = 8.8 Hz), 7.39 (1H, t, J = 7.3 Hz), 7.50 (2H, t, J = 7.6 Hz), 7.75 (2H, d, J = 7.6 Hz), 7.79 (1H, d, J = 8.6 Hz), 8.01 (1H, d, J = 8.6 Hz), 8.38 (1H, s), 8.59 (1H, d, J = 7.8 Hz). | | | |

TABLE 24

| No. | Structure | NMR (δ) | retention time | Mass | method |
|---|---|---|---|---|---|
| II-1-120 | 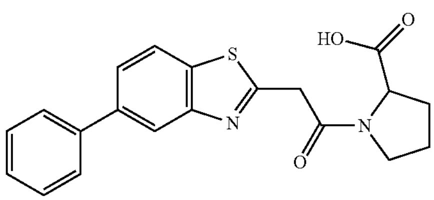 [SMILES: O=C(O)C1CCCN1C(=O)Cc1nc2cc(-c3ccccc3)ccc2s1] | (DMSO-d6) δ: 1.95 (2H, dd, J = 12.5, 5.9 Hz), 2.19 (1H, t, J = 8.7 Hz), 3.46 (2H, s), 3.69 (2H, dd, J = 12.5, 6.7 Hz), 4.31 (1H, d, J = 7.1 Hz), 4.35 (1H, d, J = 6.3 Hz), 7.39 (1H, t, J = 7.1 Hz), 7.50 (2H, t, J = 7.3 Hz), 7.77 (3H, t, J = 11.1 Hz), 8.01 (1H, t, J = 7.2 Hz), 8.38 (1H, s). | | | |
| II-1-121 | 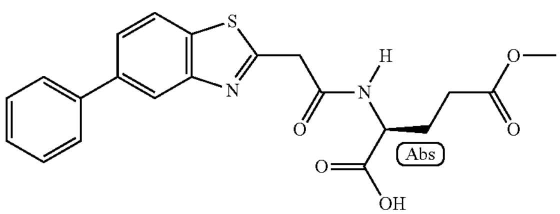 [SMILES: COC(=O)CC[C@H](NC(=O)Cc1nc2cc(-c3ccccc3)ccc2s1)C(=O)O] | (DMSO-d6) δ: 1.87 (1H, s), 2.05 (1H, s), 2.42 (2H, s), 3.59 (3H, s), 4.14 (2H, s), 4.30 (1H, s), 7.40 (1H, d, J = 7.3 Hz), 7.49 (2H, d, J = 6.8 Hz), 7.77 (3H, dd, J = 15.7, 7.6 Hz), 8.01 (1H, d, J = 9.1 Hz), 8.38 (1H, s), 8.72 (1H, d, J = 7.1 Hz). | | | |
| II-1-122 | 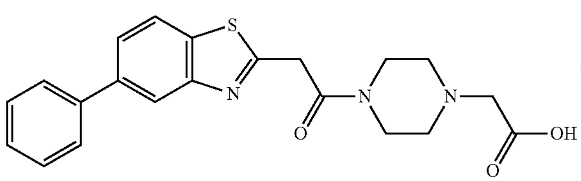 [SMILES: O=C(O)CN1CCN(C(=O)Cc2nc3cc(-c4ccccc4)ccc3s2)CC1] | (DMSO-d6) δ: 2.57 (4H, s), 3.19 (3H, s), 3.59 (7H, s), 4.37 (2H, s), 7.39 (1H, s), 7.50 (2H, s), 7.75 (3H, s), 8.02 (1H, s), 8.38 (1H, s). | | | |
| II-1-123 | 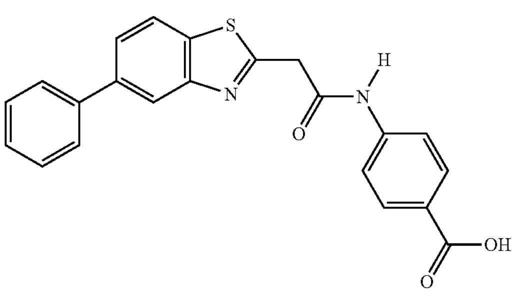 [SMILES: O=C(Cc1nc2cc(-c3ccccc3)ccc2s1)Nc1ccc(C(=O)O)cc1] | (DMSO-d6) δ: 2.57 (4H, s), 3.19 (3H, s), 3.59 (7H, s), 4.37 (2H, s), 7.39 (1H, s), 7.50 (2H, s), 7.75 (3H, s), 8.02 (1H, s), 8.38 (1H, s). | | | |

TABLE 24-continued

| No. | Structure | NMR (δ) | retention time | Mass | method |
|---|---|---|---|---|---|
| II-1-124 | 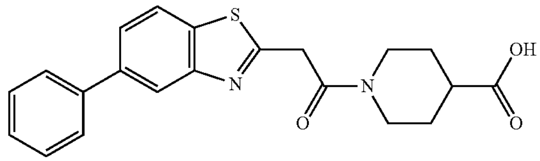 [SMILES: O=C(O)C1CCN(C(=O)Cc2nc3cc(-c4ccccc4)ccc3s2)CC1] | (DMSO-d6) δ: 1.48 (2H, dt, J = 47.4, 10.2 Hz), 1.85 (2H, d, J = 11.4 Hz), 2.01 (1H, s), 2.82 (1H, t, J = 12.9 Hz), 3.19 (1H, t, J = 13.8 Hz), 3.97 (1H, d, J = 16.7 Hz), 4.25 (1H, d, J = 13.1 Hz), 4.36 (2H, s), 7.39 (1H, s), 7.49 (2H, d, J = 7.8 Hz), 7.77 (3H, t, J = 11.2 Hz), 8.01 (1H, d, J = 8.6 Hz), 8.38 (1H, s). | | | |

TABLE 25

| No. | Structure | NMR (δ) | retention time | Mass | method |
|---|---|---|---|---|---|
| II-1-125 | 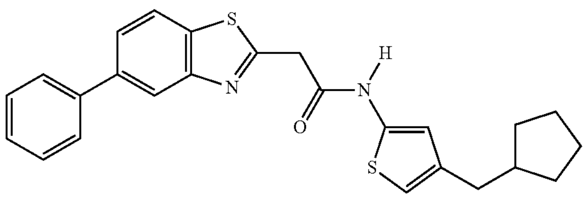 [SMILES: O=C(Cc1nc2cc(-c3ccccc3)ccc2s1)Nc1cc(CC2CCCC2)cs1] | (DMSO-d6) δ: 1.48 (2H, dt, J = 47.4, 10.2 Hz), 1.85 (2H, d, J = 11.4 Hz), 2.01 (1H, s), 2.82 (1H, t, J = 12.9 Hz), 3.19 (1H, t, J = 13.8 Hz), 3.97 (1H, d, J = 16.7 Hz), 4.25 (1H, d, J = 13.1 Hz), 4.36 (2H, s), 7.39 (1H, s), 7.49 (2H, d, J = 7.8 Hz), 7.77 (3H, t, J = 11.2 Hz), 8.01 (1H, d, J = 8.6 Hz), 8.38 (1H, s). | | | |
| II-1-126 | 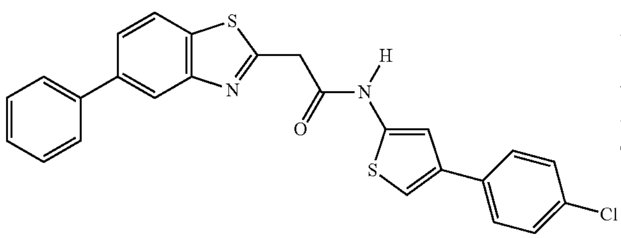 [SMILES: O=C(Cc1nc2cc(-c3ccccc3)ccc2s1)Nc1cc(-c2ccc(Cl)cc2)cs1] | (DMSO-d6) δ: 4.37 (2H, s), 7.09 (1H, s). 7.39 (2H, s), 7.46 (2H, d, J = 8.6 Hz), 7.49 (2H, d, J = 7.3 Hz), 7.68 (2H, d, J = 8.1 Hz), 7.76 (2H, d, J = 7.6 Hz), 7.81 (1H, d, J = 9.3 Hz), 8.05 (1H, d, J = 8.6 Hz), 8.42 (1H, s), 11.78 (1H, s). | | | |
| II-1-127 | 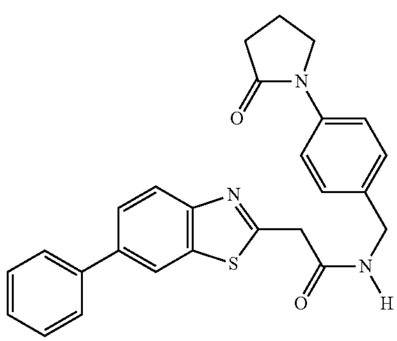 [SMILES: O=C(Cc1nc2ccc(-c3ccccc3)cc2s1)NCc1ccc(N2CCCC2=O)cc1] | (DMSO-d6) δ: 0.86 (1H, s), 1.99 (1H, s), 2.04 (2H, d, J = 8.3 Hz), 3.81 (2H, t, J = 6.6 Hz), 4.13 (2H, s), 4.32 (2H, d, J = 5.6 Hz), 7.29 (2H, d, J = 7.1 Hz), 7.40 (1H, d, J = 8.8 Hz), 7.49 (2H, d, J = 6.1 Hz), 7.60 (2H, d, J = 8.1 Hz), 7.73-7.81 (4H, m), 8.01 (1H, d, J = 8.3 Hz), 8.39 (1H, s), 8.85 (1H, s). | | | |
| II-1-128 | 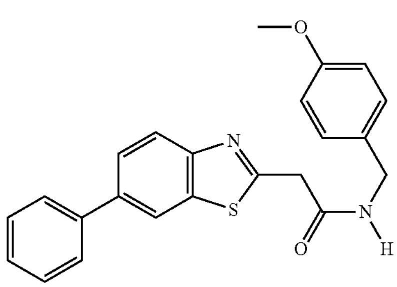 [SMILES: COc1ccc(CNC(=O)Cc2nc3ccc(-c4ccccc4)cc3s2)cc1] | | 2.19 | 389.29 (ES+) | A |

TABLE 25-continued

| No. | Structure | NMR (δ) | retention time | Mass | method |
|---|---|---|---|---|---|
| II-1-129 | 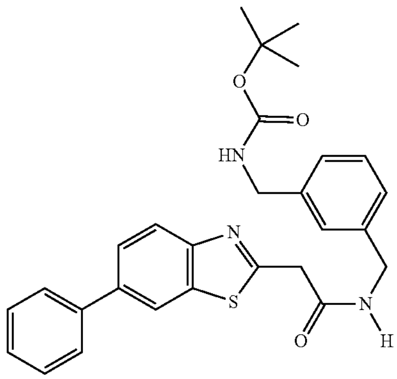 [SMILES: CC(C)(C)OC(=O)NCc1cccc(CNC(=O)Cc2nc3ccc(-c4ccccc4)cc3s2)c1] | (DMSO-d6) δ: 1.38 (9H, s), 4.12 (2H, s), 4.14 (2H, s), 4.33 (2H, d, J = 5.3 Hz), 5.75 (1H, s), 7.15 (3H, d, J = 11.6 Hz), 7.28 (1H, s), 7.39 (2H, s), 7.49 (2H, d, J = 7.3 Hz), 7.77 (3H, dd, J = 15.8, 8.0 Hz), 8.02 (1H, d, J = 7.8 Hz), 8.38 (1H, s), 8.88 (1H, s). | | | |

TABLE 26

| No. | Structure | NMR (δ) | retention time | Mass | method |
|---|---|---|---|---|---|
| II-1-130 | 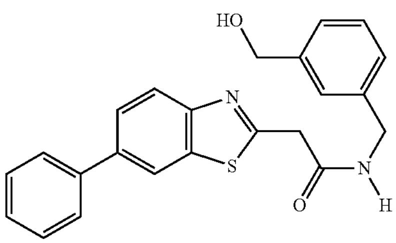 [SMILES: O=C(Cc1nc2ccc(-c3ccccc3)cc2s1)NCc1cccc(CO)c1] | (DMSO-d6) δ: 4.12 (2H, s), 4.25 (2H, d, J = 5.8 Hz), 5.75 (1H, s), 5.98 (2H, s), 6.78 (1H, d, J = 8.8 Hz), 6.86 (2H, d, J = 10.9 Hz), 7.40 (1H, s), 7.49 (2H, d, J = 7.6 Hz), 7.78 (3H, t, J = 12.4 Hz), 8.01 (1H, d, J = 7.8 Hz), 8.38 (1H, s), 8.80 (1H, s). | | | |
| II-1-131 | 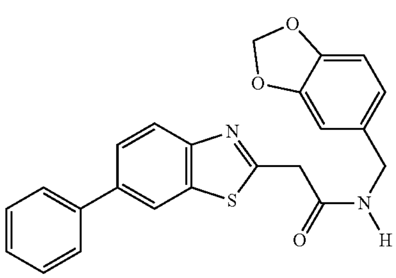 [SMILES: O=C(Cc1nc2ccc(-c3ccccc3)cc2s1)NCc1ccc2c(c1)OCO2] | | 2.16 | 403.31 (ES+) | A |
| II-1-132 | 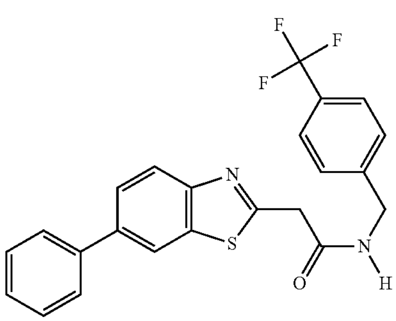 [SMILES: O=C(Cc1nc2ccc(-c3ccccc3)cc2s1)NCc1ccc(C(F)(F)F)cc1] | (DMSO-d6) δ: 4.22 (2H, s), 4.54 (2H, d, J = 5.3 Hz), 7.41 (1H, d, J = 6.8 Hz), 7.49 (3H, d, J = 6.8 Hz), 7.63 (1H, d, J = 7.1 Hz), 7.67 (1H, d, J = 7.8 Hz), 7.73 (3H, dd, J = 18.3, 8.7 Hz), 7.80 (1H, d, J = 8.6 Hz), 8.04 (1H, d, J = 8.3 Hz), 8.39 (1H, s), 8.97 (1H, s). | | | |

TABLE 26-continued

| No. | Structure | NMR (δ) | retention time | Mass | method |
|---|---|---|---|---|---|
| II-1-133 | 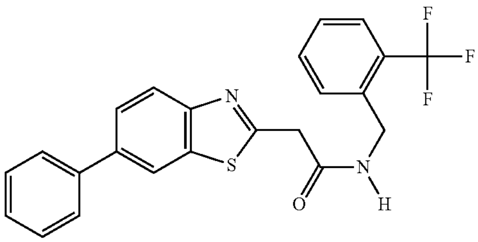 [SMILES: O=C(Cc1nc2ccc(-c3ccccc3)cc2s1)NCc1ccccc1C(F)(F)F] | (DMSO-d6) δ: 4.18 (2H, s), 4.45 (2H, d, J = 5.8 Hz), 7.41 (1H, d, J = 6.6 Hz), 7.52 (4H, dd, J = 17.4, 8.1 Hz), 7.71 (2H, d, J = 8.1 Hz), 7.76 (2H, d, J = 1.1 Hz), 7.80 (1H, d, J = 8.1 Hz), 8.03 (1H, d, J = 8.3 Hz), 8.39 (1H, s), 8.99 (1H, s). | | | |
| II-1-134 | 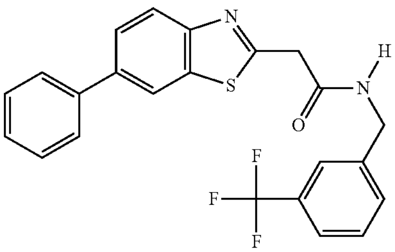 [SMILES: O=C(Cc1nc2ccc(-c3ccccc3)cc2s1)NCc1cccc(C(F)(F)F)c1] | (DMSO-d6) δ: 4.18 (2H, s), 4.46 (2H, d, J = 5.8 Hz), 7.40 (1H, t, J = 7.2 Hz), 7.50 (2H, t, J = 7.5 Hz), 7.61 (3H, d, J = 8.3 Hz), 7.67 (1H, s), 7.76 (2H, d, J = 7.8 Hz), 7.81 (1H, d, J = 8.6 Hz), 8.03 (1H, d, J = 8.6 Hz), 8.39 (1H, s), 8.99 (1H, s). | | | |

TABLE 27

| No. | Structure | NMR (δ) | retention time | Mass | method |
|---|---|---|---|---|---|
| II-1-135 | 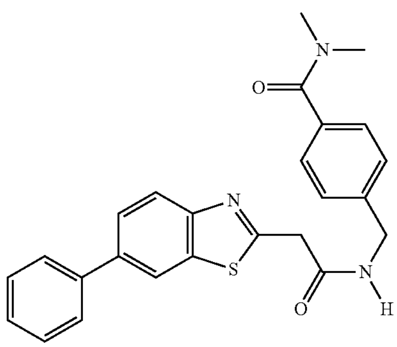 [SMILES: CN(C)C(=O)c1ccc(CNC(=O)Cc2nc3ccc(-c4ccccc4)cc3s2)cc1] | (DMSO-d6) δ: 2.84 (3H, s), 3.61 (3H, s), 4.18 (2H, s), 4.43 (2H, d, J = 29.8 Hz), 7.38 (2H, dd, J = 14.5, 5.7 Hz), 7.50 (2H, t, J = 7.7 Hz), 7.58 (1H, d, J = 8.8 Hz), 7.71 (2H, d, J = 9.3 Hz), 7.75 (2H, d, J = 7.6 Hz), 7.80 (1H, d, J = 10.6 Hz), 8.03 (1H, d, J = 8.3 Hz), 8.38 (1H, s), 9.00 (1H, s). | | | |
| II-1-136 | 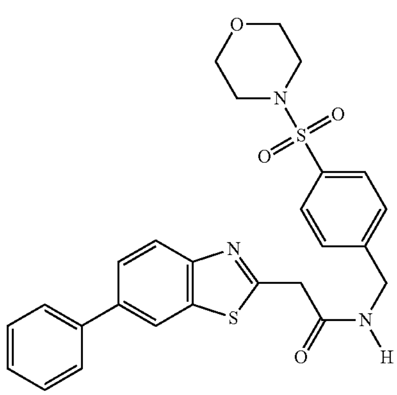 [SMILES: O=C(Cc1nc2ccc(-c3ccccc3)cc2s1)NCc1ccc(S(=O)(=O)N2CCOCC2)cc1] | (DMSO-d6) δ: 2.84 (4H, s), 3.61 (4H, s), 4.18 (2H, s), 4.47 (2H, s), 7.39 (1H, s), 7.49 (2H, d, J = 7.1 Hz), 7.59 (2H, d, J = 8.1 Hz), 7.71 (2H, d, J = 8.8 Hz), 7.76 (2H, d, J = 8.3 Hz), 7.80 (1H, d, J = 8.6 Hz), 8.03 (1H, d, J = 9.1 Hz), 8.39 (1H, s), 9.00 (1H, s). | | | |

TABLE 27-continued

| No. | Structure | NMR (δ) | retention time | Mass | method |
|---|---|---|---|---|---|
| II-1-137 | 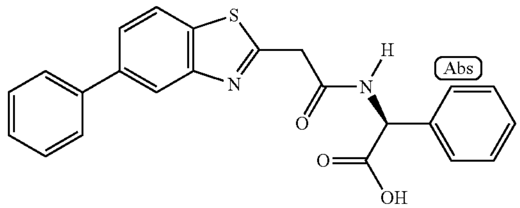 [SMILES: O=C(Cc1nc2cc(-c3ccccc3)ccc2s1)N[C@H](C(=O)O)c1ccccc1] | (DMSO-d6) δ: 4.22 (2H, s), 5.40 (1H, d, J = 6.8 Hz), 7.41 (7H, t, J = 8.6 Hz), 7.49 (2H, d, J = 6.8 Hz), 7.75 (2H, d, J = 7.1 Hz), 7.99 (1H, s), 8.37 (1H, s), 9.18 (1H, s). | | | |
| II-1-138 | 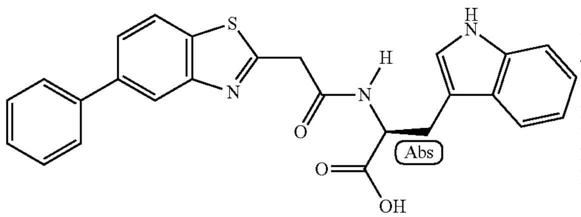 [SMILES: O=C(Cc1nc2cc(-c3ccccc3)ccc2s1)N[C@@H](Cc1c[nH]c2ccccc12)C(=O)O] | (DMSO-d6) δ: 3.10 (1H, d, J = 7.8 Hz), 3.22 (1H, d, J = 9.1 Hz), 4.12 (2H, d, J = 3.8 Hz), 4.56 (1H, d, J = 5.8 Hz), 6.96 (1H, t, J = 7.6 Hz), 7.05 (1H, t, J = 7.3 Hz), 7.18 (1H, s), 7.33 (1H, d, J = 7.8 Hz), 7.39 (1H, t, J = 7.5 Hz), 7.51 (3H, dd, J = 18.8, 7.7 Hz), 7.77 (3H, t, J = 9.9 Hz), 8.00 (1H, d, J = 8.8 Hz), 8.35 (1H, s), 8.73 (1H, d, J = 8.1 Hz), 10.87 (1H, s). | | | |
| II-1-139 | 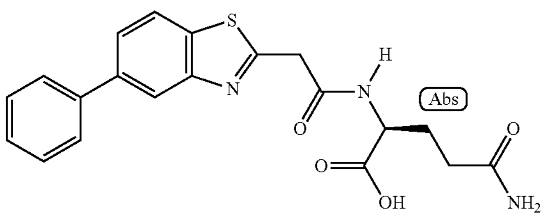 [SMILES: NC(=O)CC[C@H](NC(=O)Cc1nc2cc(-c3ccccc3)ccc2s1)C(=O)O] | (DMSO-d6) δ: 1.80 (1H, s), 1.99 (2H, s), 2.17 (2H, s), 4.14 (2H, s), 4.23 (1H, s), 6.78 (1H, s), 7.31 (1H, s), 7.39 (1H, s), 7.49 (2H, d, J = 6.8 Hz), 7.75 (3H, d, J = 7.8 Hz), 8.01 (1H, d, J = 7.8 Hz), 8.38 (1H, s), 8.72 (1H, s). | | | |

TABLE 28

| No. | Structure | NMR (δ) | retention time | Mass | method |
|---|---|---|---|---|---|
| II-1-140 | 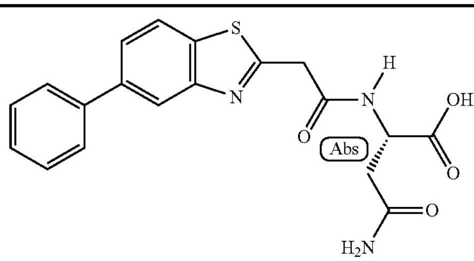 | (DMSO-d6) δ: 2.59 (1H, s), 4.14 (2H, s), 4.56 (1H, s), 6.93 (1H, s), 7.39 (2H, s), 7.49 (2H, d, J = 7.1 Hz), 7.77 (3H, t, J = 11.5 Hz), 8.01 (1H, d, J = 8.3 Hz), 8.37 (1H, s), 8.67 (1H, s). | | | |
| II-1-141 | 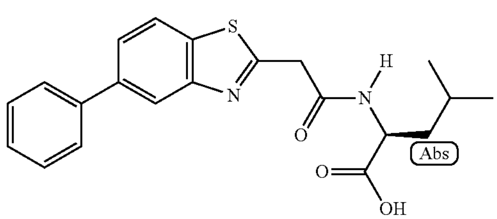 [SMILES: CC(C)C[C@H](NC(=O)Cc1nc2cc(-c3ccccc3)ccc2s1)C(=O)O] | (DMSO-d6) δ: 0.86 (3H, d, J = 6.1 Hz), 0.91 (3H, d, J = 6.6 Hz), 1.56 (2H, s), 1.68 (1H, s), 4.14 (2H, s), 4.28 (1H, s), 7.40 (1H, d, J = 6.8 Hz), 7.50 (2H, t, J = 7.8 Hz), 7.77 (3H, t, J = 11.4 Hz), 8.00 (1H, d, J = 8.1 Hz), 8.38 (1H, s), 8.68 (1H, d, J = 8.6 Hz). | | | |
| II-1-142 | 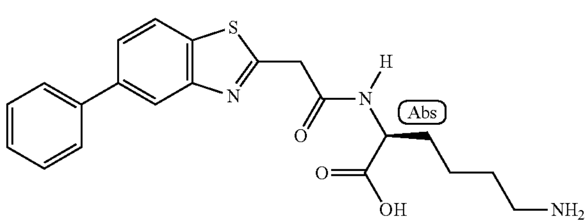 [SMILES: NCCCC[C@H](NC(=O)Cc1nc2cc(-c3ccccc3)ccc2s1)C(=O)O] | | 1.08 | 398.3 (ES+) | A |

TABLE 28-continued

| No. | Structure | NMR (δ) | retention time | Mass | method |
|---|---|---|---|---|---|
| II-1-143 | 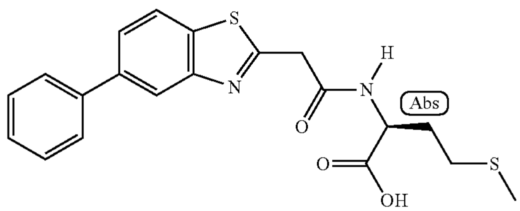 [SMILES: CSCC[C@H](NC(=O)Cc1nc2cc(-c3ccccc3)ccc2s1)C(=O)O] | (DMSO-d6) δ: 1.90 (2H, s), 2.04 (3H, s), 4.15 (2H, s), 4.39 (2H, s), 7.39 (1H, s), 7.49 (2H, d, J = 7.6 Hz), 7.74 (2H, s), 8.01 (1H, d, J = 7.1 Hz), 8.38 (1H, s), 8.73 (1H, s). | | | |
| II-1-144 | 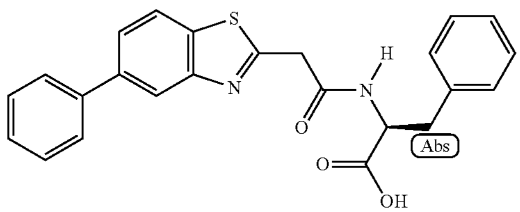 [SMILES: O=C(Cc1nc2cc(-c3ccccc3)ccc2s1)N[C@@H](Cc1ccccc1)C(=O)O] | (DMSO-d6) δ: 2.92 (1H, t, J = 11.6 Hz), 3.11 (1H, t, J = 7.2 Hz), 4.09 (2H, s), 4.50 (1H, d, J = 4.8 Hz), 7.19 (1H, s), 7.23 (4H, s), 7.40 (1H, d, J = 7.3 Hz), 7.50 (2H, t, J = 7.5 Hz), 7.77 (3H, t, J = 10.4 Hz), 8.00 (1H, d, J = 8.3 Hz), 8.36 (1H, s), 8.75 (1H, d, J = 8.3 Hz). | | | |

TABLE 29

| No. | Structure | NMR (δ) | retention time | Mass | method |
|---|---|---|---|---|---|
| II-1-145 | 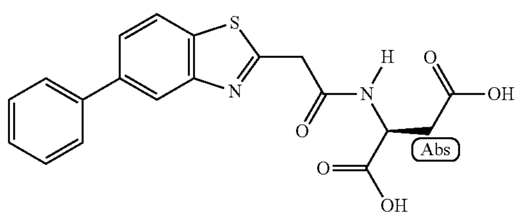 [SMILES: O=C(O)C[C@H](NC(=O)Cc1nc2cc(-c3ccccc3)ccc2s1)C(=O)O] | (DMSO-d6) δ: 2.70 (2H, dd, J = 17.7, 6.1 Hz), 4.15 (2H, s), 4.60 (1H, d, J = 6.3 Hz), 7.40 (1H, d, J = 7.3 Hz), 7.50 (2H, t, J = 7.6 Hz), 7.77 (3H, t, J = 11.7 Hz), 8.01 (1H, d, J = 8.3 Hz), 8.38 (1H, s), 8.79 (1H, d, J = 7.8 Hz). | | | |
| II-1-146 | 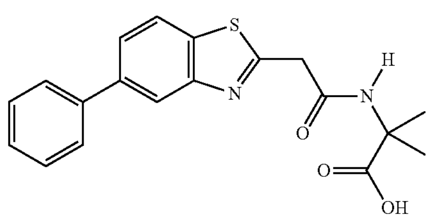 [SMILES: CC(C)(NC(=O)Cc1nc2cc(-c3ccccc3)ccc2s1)C(=O)O] | (DMSO-d6) δ: 1.40 (6H, s), 4.09 (2H, s), 7.40 (1H, d, J = 7.6 Hz) 7.50 (2H, t, J = 7.3 Hz), 7.77 (3H, t, J = 10.9 Hz) 8.01 (1H, d, J = 8.6 Hz), 8.38 (1H, s), 8.63 (1H, s). | | | |
| II-1-147 | 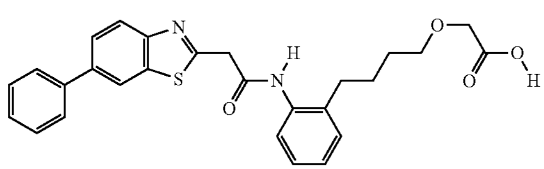 [SMILES: O=C(O)COCCCCc1ccccc1NC(=O)Cc1nc2ccc(-c3ccccc3)cc2s1] | | 2.12 | 475.39 (ES+) | A |
| II-1-148 | 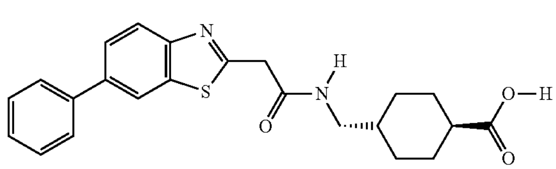 | | 1.84 | 409.33 (ES+) | A |

TABLE 29-continued
| No. | Structure | NMR (δ) | retention time | Mass | method |
|---|---|---|---|---|---|
| II-1-149 | 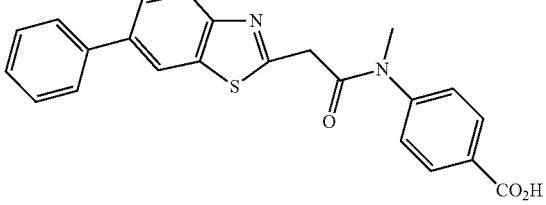 | | 2.29 | 403.25 (ES+) | A |
TABLE 30
| No. | Structure | NMR (δ) | retention time | Mass | method |
|---|---|---|---|---|---|
| II-1-150 | 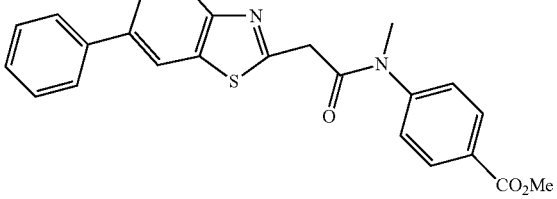 | | 1.54 | 417.31 (ES+) | A |
| II-1-151 | 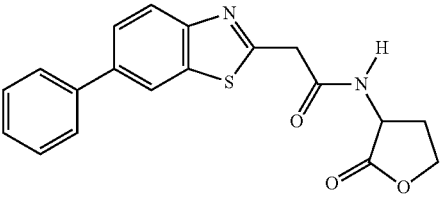 [SMILES: O=C(Cc1nc2ccc(-c3ccccc3)cc2s1)NC1CCOC1=O] | | 1.75 | 353.28 (ES+) | A |
| II-1-152 | 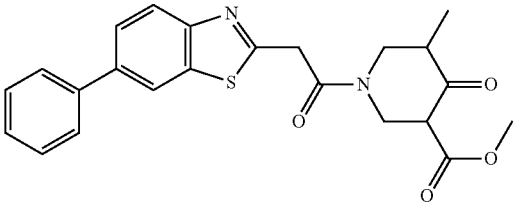 [SMILES: COC(=O)C1CN(C(=O)Cc2nc3ccc(-c4ccccc4)cc3s2)CC(C)C1=O] | | 2.38 | 423.51 (ES+) | A |
| II-1-153 | 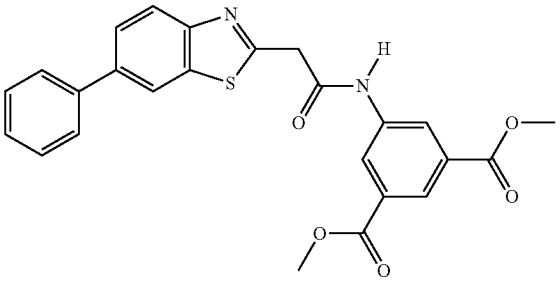 [SMILES: COC(=O)c1cc(NC(=O)Cc2nc3ccc(-c4ccccc4)cc3s2)cc(C(=O)OC)c1] | | 1.27 | 461.39 (ES+) | A |
| II-1-154 | 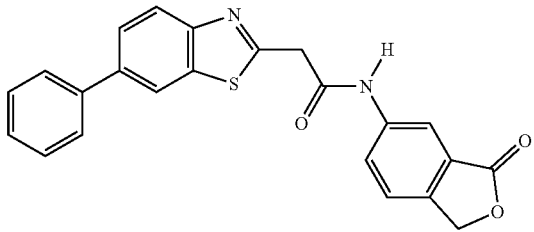 [SMILES: O=C(Cc1nc2ccc(-c3ccccc3)cc2s1)Nc1ccc2c(c1)C(=O)OC2] | | 2.05 | 401.29 (ES+) | A |

TABLE 31

| No. | Structure | NMR(δ) | retention time | Mass | method |
|---|---|---|---|---|---|
| II-1-155 | 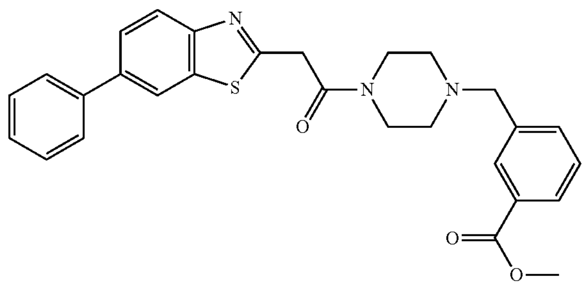 [SMILES: COC(=O)c1cccc(CN2CCN(C(=O)Cc3nc4ccc(-c5ccccc5)cc4s3)CC2)c1] | | 1.39 | 486.39 (ES+) | A |
| II-1-156 | 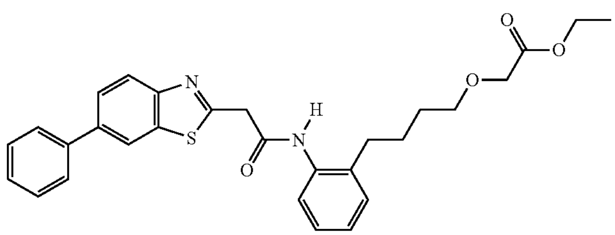 [SMILES: CCOC(=O)COCCCCc1ccccc1NC(=O)Cc1nc2ccc(-c3ccccc3)cc2s1] | | 2.53 | 503.43 (ES+) | A |
| II-1-157 | 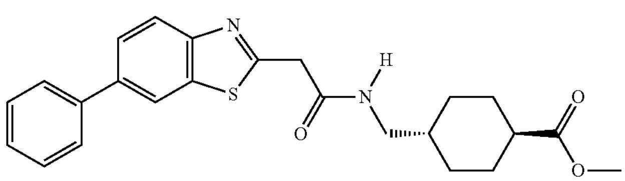 [SMILES: COC(=O)[C@H]1CC[C@H](CNC(=O)Cc2nc3ccc(-c4ccccc4)cc3s2)CC1] | | 2.19 | 423.39 (ES+) | A |
| II-1-158 | 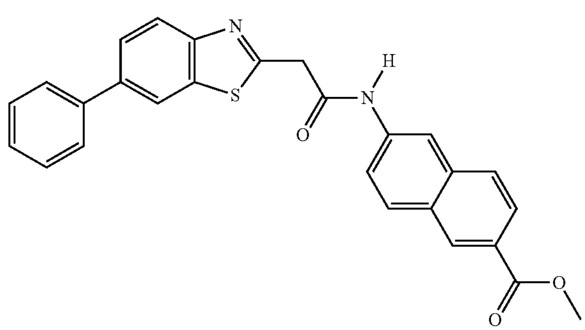 [SMILES: COC(=O)c1ccc2cc(NC(=O)Cc3nc4ccc(-c5ccccc5)cc4s3)ccc2c1] | | 2.53 | 453.38 (ES+) | A |
| II-1-159 | 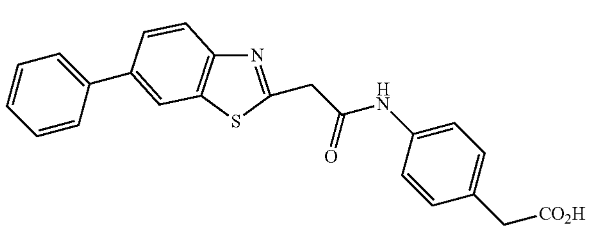 [SMILES: O=C(O)Cc1ccc(NC(=O)Cc2nc3ccc(-c4ccccc4)cc3s2)cc1] | (DMSO-d6) δ: 3.52 (2H, s), 4.31 (2H, s), 7.22 (2H, d, J = 8.8 Hz), 7.40 (1H, s), 7.50 (2H, s), 7.56 (2H, d, J = 8.1 Hz), 7.75 (3H, s), 8.03 (1H, s), 8.40 (1H, s), 10.45 (1H, s). | | | |

TABLE 32

| No. | Structure | NMR(δ) | retention time | Mass | method |
|---|---|---|---|---|---|
| II-1-160 | 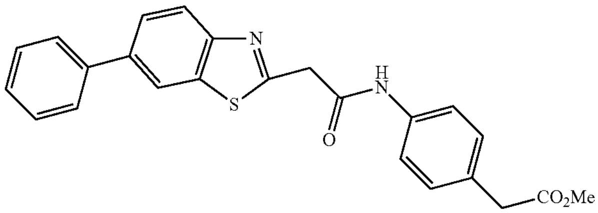 [SMILES: COC(=O)Cc1ccc(NC(=O)Cc2nc3ccc(-c4ccccc4)cc3s2)cc1] | | 2.23 | 417.45 (ES+) | A |
| II-1-161 | 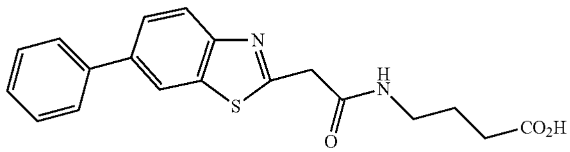 [SMILES: O=C(O)CCCNC(=O)Cc1nc2ccc(-c3ccccc3)cc2s1] | | 1.65 | 355.32 (ES+) | A |
| II-1-162 | 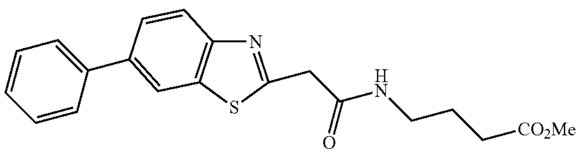 [SMILES: COC(=O)CCCNC(=O)Cc1nc2ccc(-c3ccccc3)cc2s1] | | 1.89 | 369.42 (ES+) | A |
| II-1-163 | 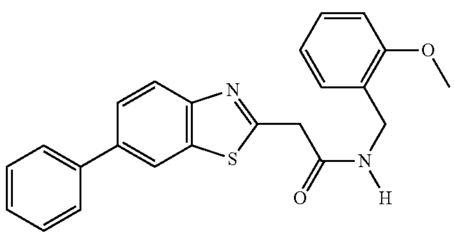 [SMILES: COc1ccccc1CNC(=O)Cc1nc2ccc(-c3ccccc3)cc2s1] | (DMSO-d6) δ: 2.82 (3H, s), 5.75 (1H, s), 7.40 (1H, d, J = 7.3 Hz), 7.49 (2H, t, J = 7.5 Hz), 7.76 (3H, t, J = 10.1 Hz), 7.97 (1H, d, J = 8.6 Hz), 8.35 (1H, s). | | | |
| II-1-164 | 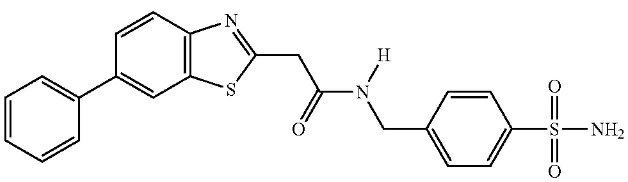 [SMILES: NS(=O)(=O)c1ccc(CNC(=O)Cc2nc3ccc(-c4ccccc4)cc3s2)cc1] | (DMSO-d6) δ: 4.17 (2H, s), 4.42 (2H, d, J = 6.1 Hz), 7.32 (2H, s), 7.40 (1H, d, J = 7.1 Hz), 7.50 (4H, t, J = 8.1 Hz), 7.78 (5H, dd, J = 16.5, 8.7 Hz), 8.03 (1H, d, J = 8.3 Hz), 8.39 (1H, s), 8.97 (1H, s). | | | |

TABLE 33

| No. | Structure | NMR(δ) | retention time | Mass | method |
|---|---|---|---|---|---|
| II-1-165 | 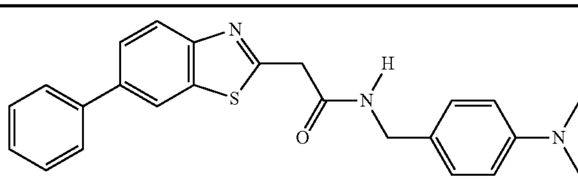 | (DMSO-d6) δ: 2.54 (2H, s), 2.98 (6H, s), 4.28 (2H, d, J = 5.3 Hz), 5.75 (1H, s), 7.04 (1H, s), 7.25 (2H, s), 7.40 (1H, d, J = 6.3 Hz), 7.50 (2H, t, J = 6.9 Hz), 7.75-7.82 (4H, m), 8.01 (1H, d, J = 8.3 Hz), 8.38 (1H, s), 8.80 (1H, s). | | | |
| II-1-166 | 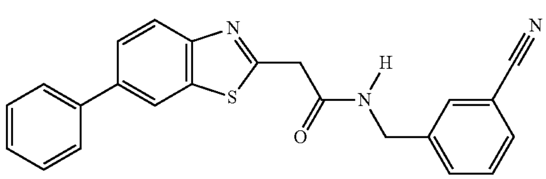 [SMILES: N#Cc1cccc(CNC(=O)Cc2nc3ccc(-c4ccccc4)cc3s2)c1] | (DMSO-d6) δ: 4.18 (2H, s), 4.42 (2H, d, J = 5.3 Hz), 7.40 (1H, t, J = 7.1 Hz), 7.50 (2H, t, J = 7.6 Hz), 7.56 (1H, t, J = 7.8 Hz), 7.66 (1H, d, J = 7.1 Hz), 7.73-7.81 (5H, m), 8.04 (1H, d, J = 8.6 Hz), 8.39 (1H, s), 8.95 (1H, s). | | | |

TABLE 33-continued

| No. | Structure | NMR(δ) | retention time | Mass | method |
|---|---|---|---|---|---|
| II-1-167 | 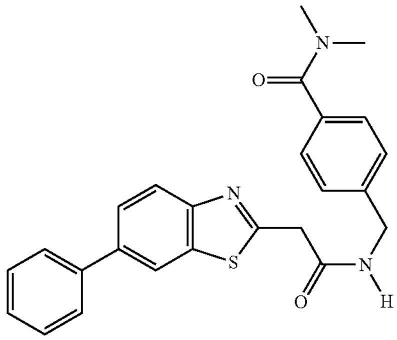 [SMILES: CN(C)C(=O)c1ccc(CNC(=O)Cc2nc3ccc(-c4ccccc4)cc3s2)cc1] | | 2.53 | 353.27 (ES+) | A |
| II-1-168 | 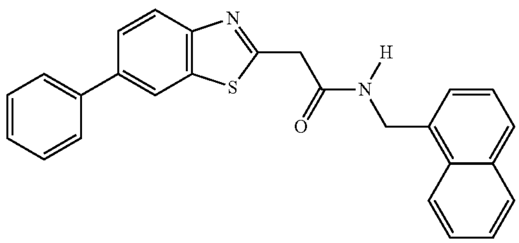 [SMILES: O=C(Cc1nc2ccc(-c3ccccc3)cc2s1)NCc1cccc2ccccc12] | | 2.47 | 409.49 (ES+) | A |
| II-1-169 | 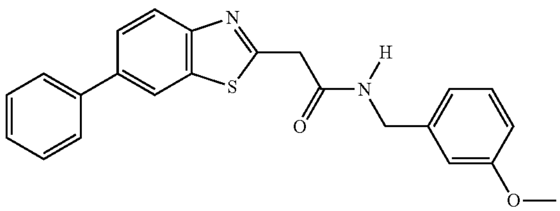 [SMILES: COc1cccc(CNC(=O)Cc2nc3ccc(-c4ccccc4)cc3s2)c1] | | 2.23 | 389.45 (ES+) | A |

TABLE 34

| No. | Structure | NMR(δ) | retention time | Mass | method |
|---|---|---|---|---|---|
| II-1-170 | 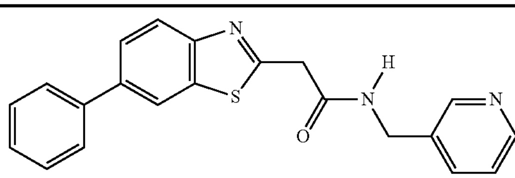 | | 2.47 | 360.25 (ES+) | A |
| II-1-171 | 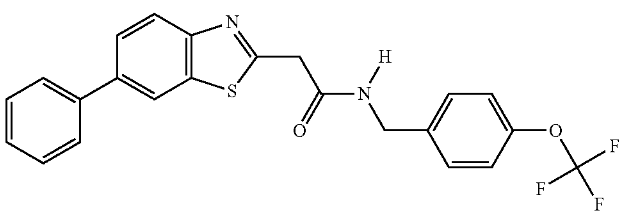 [SMILES: O=C(Cc1nc2ccc(-c3ccccc3)cc2s1)NCc1ccc(OC(F)(F)F)cc1] | | 1.26 | 442.39 (ES+) | A |
| II-1-172 | 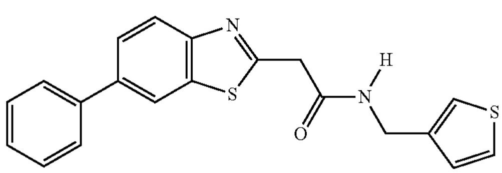 [SMILES: O=C(Cc1nc2ccc(-c3ccccc3)cc2s1)NCc1ccoc1] | | 2.3 | 365.38 (ES+) | A |

TABLE 34-continued

| No. | Structure | NMR(δ) | retention time | Mass | method |
|---|---|---|---|---|---|
| II-1-173 | 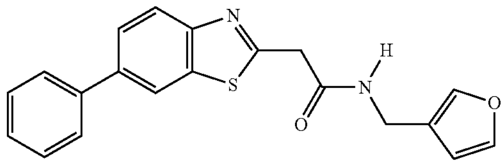 | | 2.07 | 348.38 (ES+) | A |
| II-1-174 | 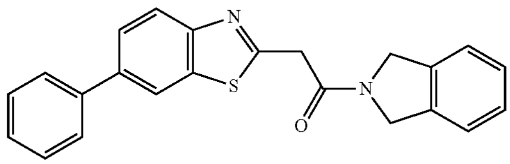 [SMILES: O=C(Cc1nc2ccc(-c3ccccc3)cc2s1)N1Cc2ccccc2C1] | | 2.31 | 371.28 (ES+) | A |

TABLE 35

| No. | Structure | NMR(δ) | retention time | Mass | method |
|---|---|---|---|---|---|
| II-1-175 | 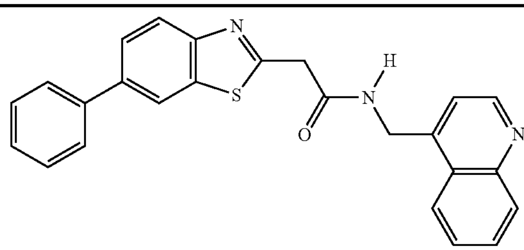 | | 1.52 | 410.42 (ES+) | A |
| II-1-176 | 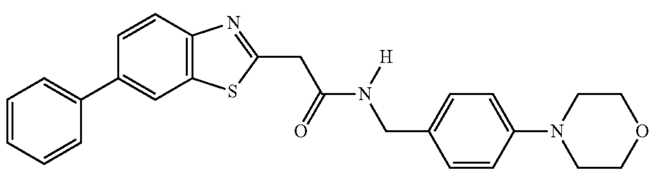 [SMILES: O=C(Cc1nc2ccc(-c3ccccc3)cc2s1)NCc1ccc(N2CCOCC2)cc1] | | 2.26 | 444.48 (ES+) | A |
| II-1-177 | 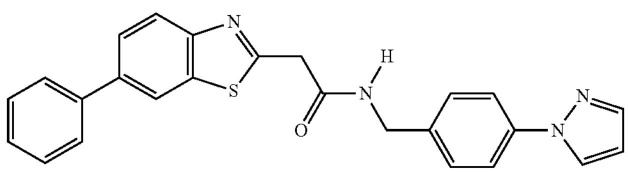 [SMILES: O=C(Cc1nc2ccc(-c3ccccc3)cc2s1)NCc1ccc(-n2cccn2)cc1] | | 2.3 | 425.36 (ES+) | A |
| II-1-178 | 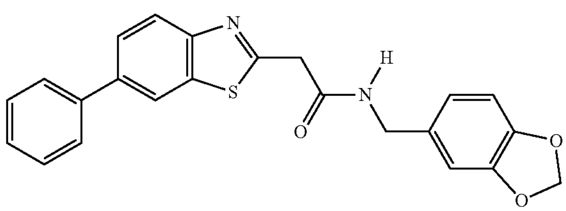 [SMILES: O=C(Cc1nc2ccc(-c3ccccc3)cc2s1)NCc1ccc2c(c1)OCO2] | | 2.19 | 403.28 (ES+) | A |
| II-1-179 | 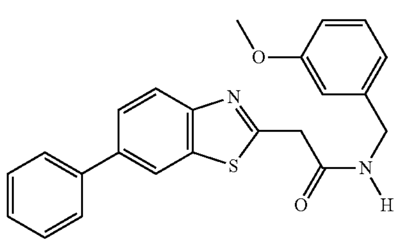 [SMILES: COc1cccc(CNC(=O)Cc2nc3ccc(-c4ccccc4)cc3s2)c1] | | 2.23 | 389.38 (ES+) | A |

TABLE 36

| No. | Structure | NMR(δ) | retention time | Mass | method |
|---|---|---|---|---|---|
| II-1-180 | 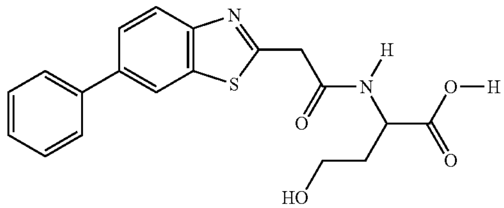 [SMILES: O=C(Cc1nc2ccc(-c3ccccc3)cc2s1)NC(CCO)C(=O)O] | | 1.51 | 371.38 (ES+) | A |
| II-1-181 | 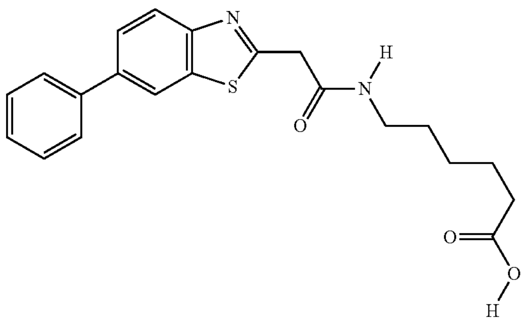 [SMILES: O=C(O)CCCCCNC(=O)Cc1nc2ccc(-c3ccccc3)cc2s1] | | 1.78 | 383.25 (ES+) | A |
| II-1-182 | 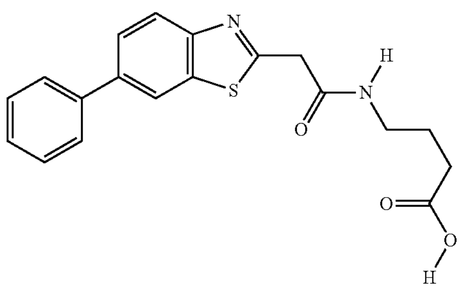 [SMILES: O=C(O)CCCNC(=O)Cc1nc2ccc(-c3ccccc3)cc2s1] | | 1.63 | 355.29 (ES+) | A |
| II-1-183 | 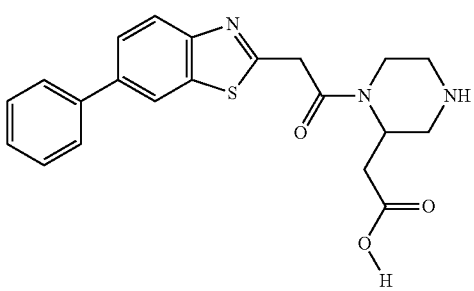 [SMILES: O=C(O)CC1CNCCN1C(=O)Cc1nc2ccc(-c3ccccc3)cc2s1] | | 1.19 | 396.38 (ES+) | A |
| II-1-184 | 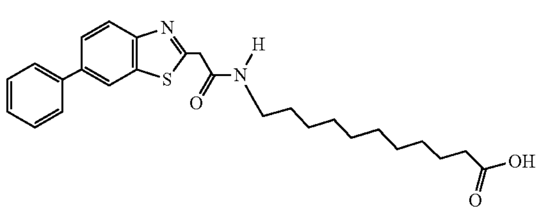 [SMILES: O=C(O)CCCCCCCCCCCNC(=O)Cc1nc2ccc(-c3ccccc3)cc2s1] | | 2.41 | 467.59 (ES+) | A |

TABLE 37

| No. | Structure | NMR(δ) | retention time | Mass | method |
|---|---|---|---|---|---|
| II-1-185 | 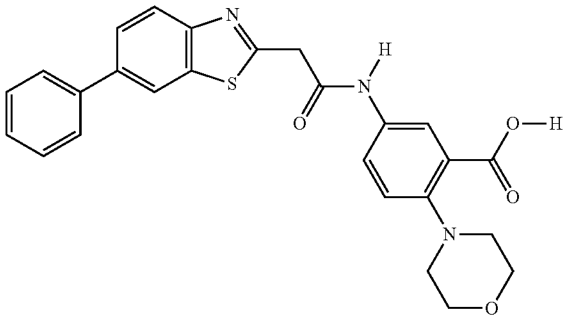 [SMILES: O=C(Cc1nc2ccc(-c3ccccc3)cc2s1)Nc1ccc(N2CCOCC2)c(C(=O)O)c1] | | 2.65 | 474.39 (ES+) | A |
| II-1-186 | 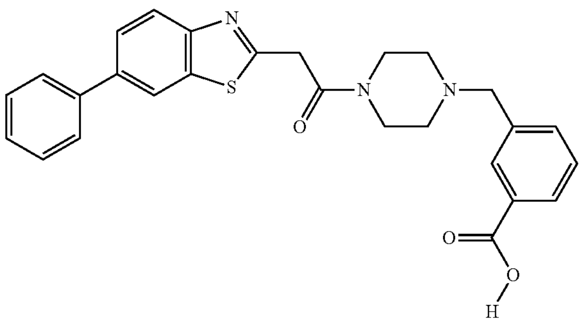 [SMILES: O=C(O)c1cccc(CN2CCN(C(=O)Cc3nc4ccc(-c5ccccc5)cc4s3)CC2)c1] | | 1.22 | 472.51 (ES+) | A |
| II-1-187 | 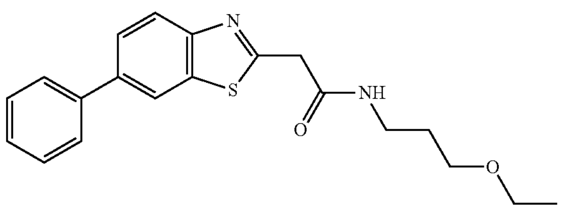 [SMILES: CCOCCCNC(=O)Cc1nc2ccc(-c3ccccc3)cc2s1] | | 0.23 | 354.47 (ES+) | A |
| II-1-188 | 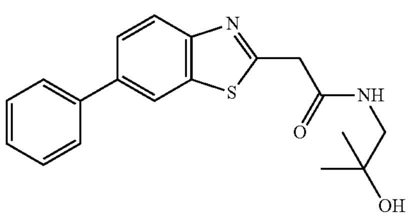 [SMILES: CC(C)(O)CNC(=O)Cc1nc2ccc(-c3ccccc3)cc2s1] | | 0.24 | 340.44 (ES+) | A |
| II-1-189 | 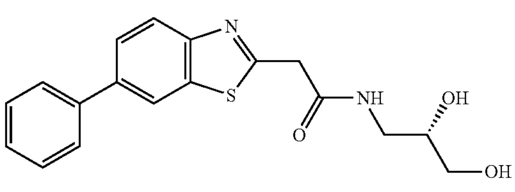 [SMILES: O=C(Cc1nc2ccc(-c3ccccc3)cc2s1)NC[C@H](O)CO] | | 1.5 | 342.41 (ES+) | A |

TABLE 38

| No. | Structure | NMR(δ) | retention time | Mass | method |
|---|---|---|---|---|---|
| II-1-190 | 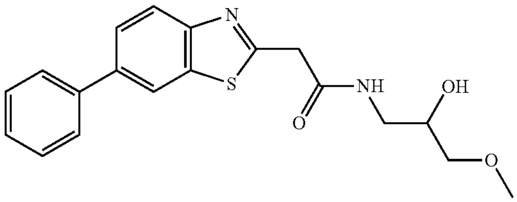 [SMILES: COCC(O)CNC(=O)Cc1nc2ccc(-c3ccccc3)cc2s1] | | 1.67 | 356.43 (ES+) | A |
| II-1-191 | 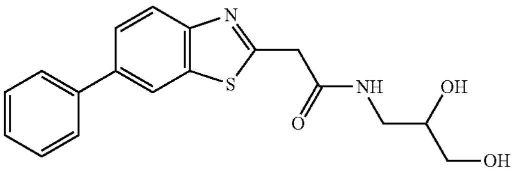 [SMILES: O=C(Cc1nc2ccc(-c3ccccc3)cc2s1)NCC(O)CO] | | 1.5 | 342.41 (ES+) | A |
| II-1-192 | 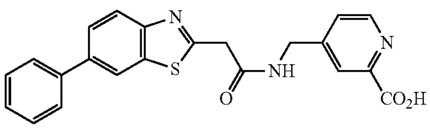 [SMILES: O=C(Cc1nc2ccc(-c3ccccc3)cc2s1)NCc1ccnc(C(=O)O)c1] | 1H-NMR (DMSO-d6) δ: 4.19 (s, 2H), 4.44 (d, J = 5.2 Hz, 2H), 7.36-7.52 (m, 4H), 7.76-7.79 (m, 3H), 7.96 (s, 1H), 8.04 (d, J = 8.4 Hz, 1H), 8.38 (s, 1H), 8.55 (d, J = 4.7 Hz, 1H), 9.05 (br s, 1H). | | | |
| II-1-193 | 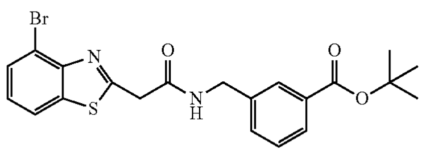 [SMILES: CC(C)(C)OC(=O)c1cccc(CNC(=O)Cc2nc3c(Br)cccc3s2)c1] | 1H-NMR (CDCl3) δ: 1.57 (s, 9H), 4.15 (s, 2H), 4.56 (d, J = 5.6 Hz, 2H), 7.21-7.42 (m, 2H), 7.47-7.54 (m, 1H), 7.64-7.69 (m, 1H), 7.75-7.94 (m, 4H). | | | |
| II-1-194 | 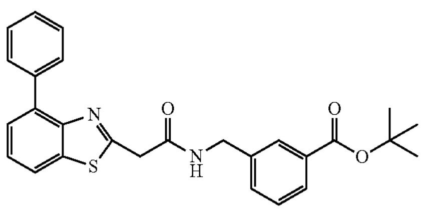 [SMILES: CC(C)(C)OC(=O)c1cccc(CNC(=O)Cc2nc3c(-c4ccccc4)cccc3s2)c1] | 1H-NMR (CDCl3) δ: 1.56 (s, 9H), 4.13 (s, 2H), 4.51 (s, 2H), 7.26-7.55 (m, 6H), 7.62-7.64 (m, 2H), 7.74 (d, J = 7.6 Hz, 1H), 7.85-7.89 (m, 3H), 8.27 (s, 1H). | 2.79 | 459.15 (ES+) | C |

TABLE 39

| No. | Structure | NMR(δ) | retention time | Mass | method |
|---|---|---|---|---|---|
| II-1-195 | 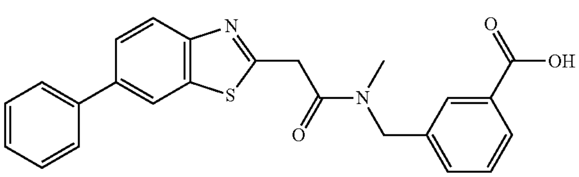 [SMILES: CN(Cc1cccc(C(=O)O)c1)C(=O)Cc1nc2ccc(-c3ccccc3)cc2s1] | | 4.09 | 417.25 (ES+) | D |
| II-1-196 | 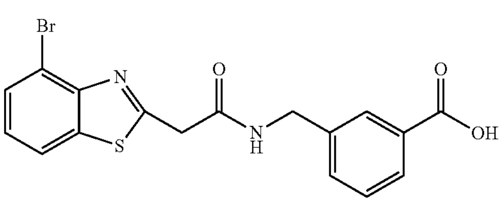 [SMILES: O=C(Cc1nc2c(Br)cccc2s1)NCc1cccc(C(=O)O)c1] | 1H-NMR (DMSO-d6) δ: 4.19 (s, 2H), 4.41 (d, J = 5.6 Hz, 2H), 7.34 (t, J = 7.9 Hz, 1H), 7.46 (t, J = 7.6 Hz, 1H), 7.55-7.57 (m, 1H), 7.73-7.74 (m, 1H), 7.83 (d, J = 7.6 Hz, 1H), 7.89 (s, 1H), 8.03-8.12 (m, 1H), 8.96 (t, J = 5.6 Hz, 1H), 12.94 (s, 1H). | 1.76 | 407.00 (ES+) | C |

TABLE 39-continued

| No. | Structure | NMR(δ) | retention time | Mass | method |
|---|---|---|---|---|---|
| II-1-197 | 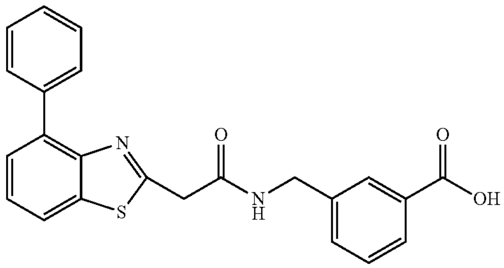 [SMILES: O=C(Cc1nc2c(-c3ccccc3)cccc2s1)NCc1cccc(C(=O)O)c1] | 1H-NMR (DMSO-d6) δ: 4.14 (s, 2H), 4.39 (d, J = 6.1 Hz, 2H), 7.40-7.58 (m, 7H), 7.84 (dd, J = 21.0, 14.4 Hz, 4H), 8.07 (d, J = 8.1 Hz, 1H), 8.90 (t, J = 5.8 Hz, 1H), 12.93 (s, 1H). | 2.1 | 403.05 (ES+) | C |
| II-1-198 | 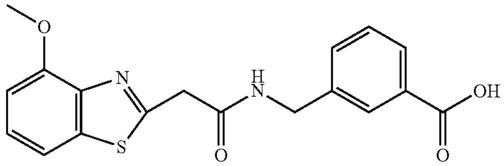 [SMILES: COc1cccc2sc(CC(=O)NCc3cccc(C(=O)O)c3)nc12] | 1H-NMR (DMSO-d6) δ: 3.94 (s, 3H), 4.10 (s, 2H), 7.02 (d, J = 8.1 Hz, 1H), 7.35 (t, J = 8.1 Hz, 1H), 7.46 (t, J = 7.5 Hz, 1H), 7.57 (dd, J = 7.5 Hz, 2H), 7.83 (d, J = 7.2 Hz, 1H), 7.89 (s, 1H), 8.92 (m, 1H), 12.94 (br-s, 1H). | | | |
| II-1-199 | 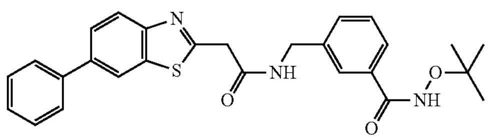 [SMILES: CC(C)(C)ONC(=O)c1cccc(CNC(=O)Cc2nc3ccc(-c4ccccc4)cc3s2)c1] | 1H-NMR (DMSO-d6) δ: 1.20 (s, 9H), 4.15 (s, 2H), 4.40 (d, J = 5.9 Hz, 2H), 7.39-7.52 (m, 5H), 7.69-7.76 (m, 5H), 8.02 (d, J = 8.6 Hz, 1H), 8.37 (d, J = 1.7 Hz, 1H), 8.90-8.94 (br m, 1H), 10.93 (s, 1H). | | | |

TABLE 40

| No. | Structure | NMR(δ) | retention time | Mass | method |
|---|---|---|---|---|---|
| II-1-200 | 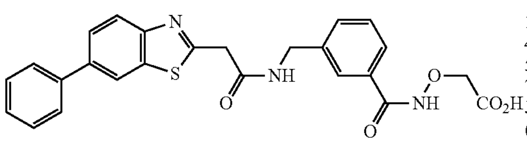 | 1H-NMR (DMS0-d6) δ: 4.15 (s, 2H), 4.39 (d, J = 5.5 Hz, 2H), 4.50 (s, 2H), 7.42-7.50 (m, 5H), 7.64 (d, J = 7.4 Hz, 1H), 7.76-7.79 (m, 4H), 8.02 (d, J = 8.4 Hz, 1H), 8.38 (s, 1H), 8.91 (br s, 1H). | | | |
| II-1-201 | 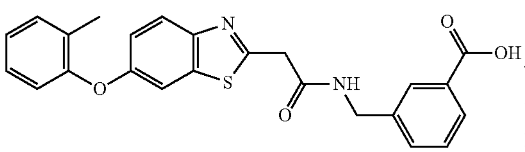 | 1H-NMR (DMSO-d6) δ: 2.20 (s, 3H), 4.08 (s, 2H), 4.39 (d, J = 5.6 Hz, 2H), 6.92 (d, J = 7.6 Hz, 1H), 7.10-7.13 (m, 2H), 7.23 (t, J = 7.1 Hz, 1H) 7.34 (d, J = 7.1 Hz, 1H), 7.45 (t, J = 7.6 Hz, 1H), 7.54-7.54 (m, 2H), 7.83 (d, J = 7.6 Hz, 1H), 7.90-7.92 (m, 2H), 8.89 (t, J = 5.8 Hz, 1H), 12.95 (br s, 1H). | | | |
| II-1-202 | 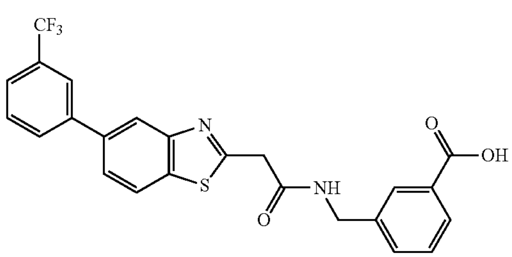 [SMILES: O=C(Cc1nc2cc(-c3cccc(C(F)(F)F)c3)ccc2s1)NCc1cccc(C(=O)O)c1] | 1H-NMR (DMSO-d6) δ: 4.18 (s, 2H), 4.42 (d, J = 5.6 Hz, 2H), 7.47 (t, J = 7.6 Hz, 1H), 7.56 (d, J = 7.6 Hz, 1H), 7.74-7.84 (m, 4H), 7.91 (s, 1H), 8.07-8.11 (m, 2H), 8.18 (d, J = 8.1 Hz, 1H), 8.32 (d, J = 1.5 Hz, 1H), 8.95 (t, J = 5.8 Hz, 1H), 12.95 (br s, 1H). | | | |

TABLE 40-continued

| No. | Structure | NMR(δ) | retention time | Mass | method |
|---|---|---|---|---|---|
| II-1-203 | 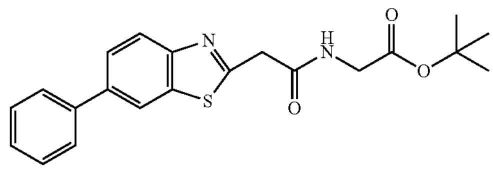 [SMILES: CC(C)(C)OC(=O)CNC(=O)Cc1nc2ccc(-c3ccccc3)cc2s1] | 1H-NMR (CDCl3) δ: 1.46 (s, 9H), 4.00 (d, J = 5.1 Hz, 2H), 4.12 (s, 2H), 7.33-7.42 (m, 1H), 7.43-7.50 (m, 2H), 7.54-7.66 (m, 3H), 7.71 (dd, J = 8.4, 1.8 Hz, 1H), 8.11-8.02 (m, 2H). | | | |
| II-1-204 | 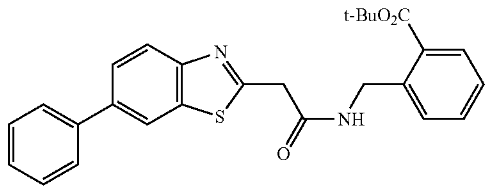 | 1H-NMR (DMSO-d6) δ: 1.54 (s, 9H), 4.18 (s, 2H), 4.62 (d, J = 5.5 Hz, 2H), 7.42-7.49 (m, 6H), 7.76-7.80 (m, 4H), 8.02 (d, J = 8.4 Hz, 1H), 8.39 (s, 1H), 8.75 (br s, 1H). | | | |

TABLE 41

| No. | Structure | NMR(δ) | retention time | Mass | method |
|---|---|---|---|---|---|
| II-1-205 | 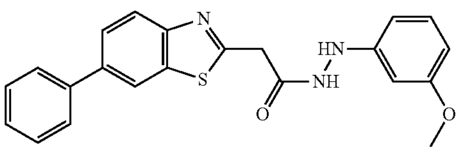 [SMILES: COc1cccc(NNC(=O)Cc2nc3ccc(-c4ccccc4)cc3s2)c1] | 1H-NMR (DMSO-d6) δ: 3.60 (s, 3H), 4.17 (s, 2H), 6.27-6.38 (m, 3H), 7.03 (t, J = 7.8 Hz, 1H), 7.50 (t, J = 7.2 Hz, 1H), 7.75-7.90 (m, 4H), 8.39 (d, J = 1.8 Hz, 1H), 10.11 (s, 1H). | | | |
| II-1-206 | 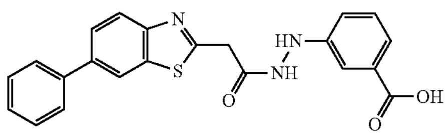 [SMILES: O=C(Cc1nc2ccc(-c3ccccc3)cc2s1)NNc1cccc(C(=O)O)c1] | 1H-NMR (DMS0-d6) δ: 4.19 (s, 2H), 6.99 (d, J = 6.3, 2.4 Hz, 1H), 737-7.41 (m, 2H), 7.50(t, J = 7.8 Hz, 2H), 7.52-7.82 (m, 3H), 8.06 (d, J = 8.7 Hz, 1H), 8.16 (d, J = 2.4 Hz, 1H), 8.39 (d, J = 2.4 Hz, 1H), 10.23(d, J = 2.4 Hz, 1H), 12.78(brs, 1H). | | | |
| II-1-207 | 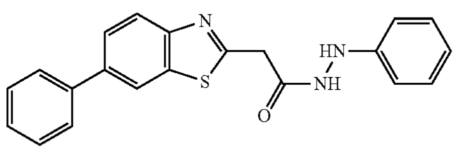 [SMILES: O=C(Cc1nc2ccc(-c3ccccc3)cc2s1)NNc1ccccc1] | 1H-NMR (DMSO-d6) δ: 4.18 (s, 2H), 6.68-6.80(m, 3H), 7.14(t, J = 7.2 Hz, 2H), 7.41 (t, J = 7.2 Hz, 1H), 7.53 (t, J = 7.2 Hz, 2H), 7.81 (dd, J = 8.4, 1.5 Hz, 1H), 7.89 (d, J = 2.4 Hz, 1H), 8.03 (d, J = 1.8 Hz, 1H), 10.12 (d, J = 2.7 Hz, 1H) | | | |
| II-1-208 | 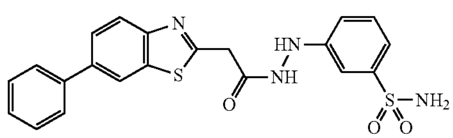 [SMILES: NS(=O)(=O)c1cccc(NNC(=O)Cc2nc3ccc(-c4ccccc4)cc3s2)c1] | 1H-NMR (DMSO-d6) δ: 4.20(s, 2H), 694 (dd, J = 8.1, 2.4 Hz, 1H), 7.17 (d, J = 7.8 Hz, 1H), 7.24-7.42 (m, 3H), 7.75 (d, J = 7.5 Hz, 2H), 7.81 (dd, J = 7.2, 1.5 Hz, 1H)., 8.05 (d, J = 8.4 Hz, 1H), 8.35 (d, J = 1.8 Hz, 1H), 8.39 (d, J = 1.8 Hz, 1H), 10.17 (d, J = 2.1 Hz, 1H) | | | |
| II-1-209 | 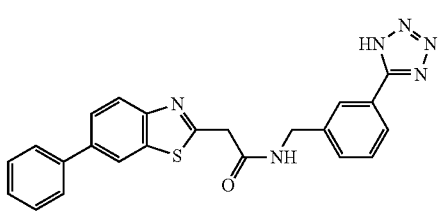 [SMILES: O=C(Cc1nc2ccc(-c3ccccc3)cc2s1)NCc1cccc(-c2nnn[nH]2)c1] | 1H-NMR (DMSO-d6) δ: 4.18 (s, 2H), 4.46 (d, J = 5.7 Hz, 2H), 7.39-7.42 (m, 1H), 7.48-7.61 (m, 4H), 7.74-7.81 (m, 3H), 7.93 (d, J = 7.2 Hz, 1H), 8.02 (d, J = 8.4 Hz, 2H), 8.38 (d, J = 1.5 Hz, 1H), 9.00 (br s, 1H). | | | |

TABLE 42

| No. | Structure | NMR(δ) | retention time | Mass | method |
|---|---|---|---|---|---|
| II-1-210 | 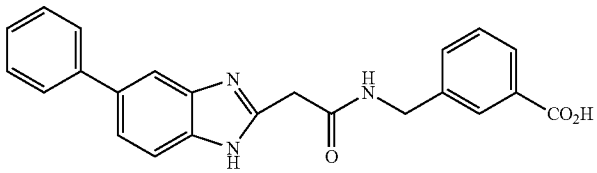 [SMILES: O=C(Cc1nc2cc(-c3ccccc3)ccc2[nH]1)NCc1cccc(C(=O)O)c1] | 1H-NMR (DMSO-d6) δ: 3.85 (s, 2H), 4.40 (d, J = 5.6 Hz, 2H), 7.93-7.28 (m, 12H), 8.83 (t, J = 6.1 Hz, 1H). | | | |
| II-1-211 | 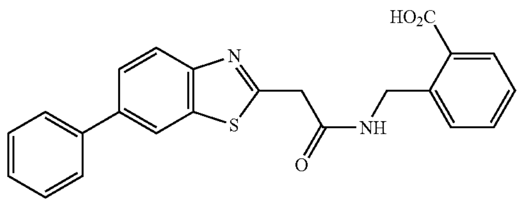 [SMILES: O=C(Cc1nc2ccc(-c3ccccc3)cc2s1)NCc1ccccc1C(=O)O] | 1H-NMR (DMSO-d6) δ: 4.19 (s, 2H), 4.69 (d, J = 5.7 Hz, 2H), 7.39-7.41 (m, 2H), 7.47-7.55 (m, 4H), 7.74-7.82 (m, 3H), 7.89 (dd, J = 7.7, 1.2 Hz, 1H), 8.03 (d, J = 8.4 Hz, 1H), 8.38 (d, J = 1.5 Hz, 1H), 8.77 (br s, 1H). | | | |
| II-1-212 | 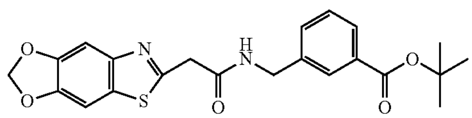 [SMILES: CC(C)(C)OC(=O)c1cccc(CNC(=O)Cc2nc3cc4c(cc3s2)OCO4)c1] | 1H-NMR (CDCl3) δ: 1.57 (s, 9H), 4.04 (s, 2H), 4.54 (d, J = 5.7 Hz, 2H), 6.06 (s, 2H), 7.21 (s, 1H), 7.33-7.41 (m, 2H), 7.44-7.47 (m, 1H), 7.59 (br-s, 1H), 7.87-7.90 (m, 2H) | | | |
| II-1-213 | 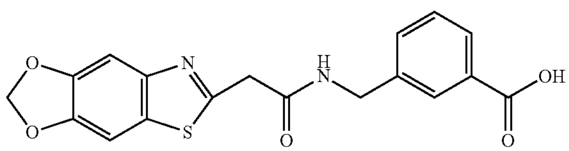 [SMILES: O=C(Cc1nc2cc3c(cc2s1)OCO3)NCc1cccc(C(=O)O)c1] | 1H-NMR (DMSO-d6) δ: 4.04 (s, 2H), 4.39 (d, J = 6.0 Hz, 2H), 6.1 (s, 2H), 7.46 (t, J = 8.4 Hz, 2H), 7.55 (t, J = 7.5 Hz, 2H), 7.83 (d, J = 7.5 Hz, 1H), 7.89 (s, 1H), 8.89 (m, 1H), 12.96 (br-s, 1H). | | | |
| II-1-214 | 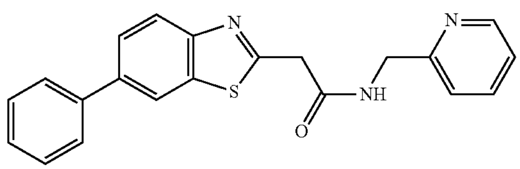 [SMILES: O=C(Cc1nc2ccc(-c3ccccc3)cc2s1)NCc1ccccn1] | 1H-NMR (DMSO-d6) δ: 4.19 (s, 2H), 4.45 (d, J = 5.9 Hz, 2H), 7.26-7.52 (m, 5H), 7.76-7.79 (m, 4H), 8.02 (d, J = 8.4 Hz, 1H), 8.39 (s, 1H), 8.52 (d, J = 4.4 Hz, 1H), 8.97 (br s, 1H). | | | |

TABLE 43

| No. | Structure | NMR(δ) | retention time | Mass | method |
|---|---|---|---|---|---|
| II-1-215 | 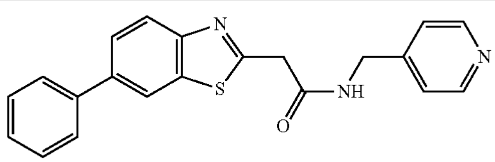 [SMILES: O=C(Cc1nc2ccc(-c3ccccc3)cc2s1)NCc1ccncc1] | 1H-NMR (DMSO-d6) δ: 4.19 (s, 2H), 4.36 (d, J = 5.9 Hz, 2H), 7.34-7.48 (m, 5H), 7.76-7.80 (m, 3H), 8.03 (d, J = 8.6 Hz, 1H), 8.39 (s, 1H), 8.51 (d, J = 5.5 Hz, 2H), 8.96 (br s, 1H). | | | |
| II-1-216 | 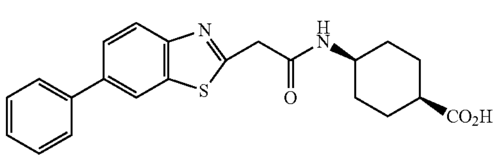 [SMILES: O=C(Cc1nc2ccc(-c3ccccc3)cc2s1)N[C@H]1CC[C@@H](C(=O)O)CC1] | 1H-NMR (DMSO-d6) δ: 1.43-1.68 (m, 6H), 1.78-1.92 (m, 2H), 2.34-2.43 (m, 1H), 3 71-3.82 (m, 1H), 4.06 (s, 2H), 7.34-7.53 (m, 3H), 7.70-7.81 (m, 3H), 8.00 (d, J = 8.1 Hz, 1H), 8.40-8.26 (m, 2H). | 3.69 | 394.95 (ES+) | C |

TABLE 43-continued

| No. | Structure | NMR(δ) | retention time | Mass | method |
|---|---|---|---|---|---|
| II-1-217 | 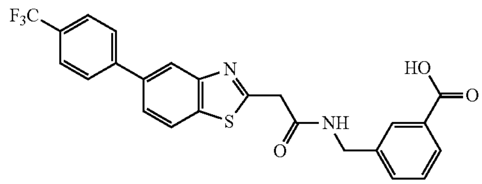 [SMILES: O=C(Cc1nc2cc(-c3ccc(C(F)(F)F)cc3)ccc2s1)NCc1cccc(C(=O)O)c1] | 1H NMR (DMSO-d6) δ: 4.18 (s, 2H), 4.41 (d, J = 6.1 Hz, 2H), 7.46 (t, J = 7.6 Hz, 1H), 7.55 (d, J = 7.6 Hz, 1H), 7.78-7.86 (m, 4H), 7.91 (s, 1H), 8.01 (d, J = 8.1 Hz, 2H), 8.20 (d, J = 8.1 Hz, 1H), 8.31 (d, J = 1.0 Hz, 1H), 8.94 (t, J = 5.8 Hz, 1H), 12.94 (br s, 1H). | | | |
| II-1-218 | 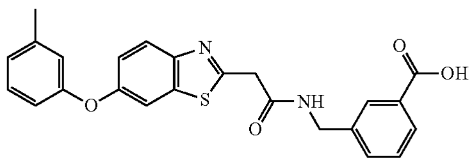 [SMILES: Cc1cccc(Oc2ccc3nc(CC(=O)NCc4cccc(C(=O)O)c4)sc3c2)c1] | 1H-NMR (DMSO-d6) δ: 2.29 (s, 3H), 4.11 (s, 2H), 4.40 (d, J = 5.6 Hz, 2H), 6.84 (t, J = 7.3 Hz, 2H), 6.97 (d, J = 7.1 Hz, 1H), 7.17 (d, J = 9.1 Hz, 1H), 7.27 (t, J = 7.6 Hz, 1H), 7.46 (t, J = 7.1 Hz, 1H), 7.55 (d, J = 8.1 Hz, 1H), 7.71 (s, 1H), 7.83 (d, J = 7.1 Hz, 1H), 7.90-7.96 (m, 2H), 8.93 (br s, 1H), 12.79 (br s, 1H). | | | |
| II-1-219 | 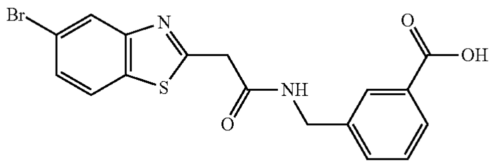 [SMILES: O=C(Cc1nc2cc(Br)ccc2s1)NCc1cccc(C(=O)O)c1] | 1H-NMR (DMSO-d6) δ: 4.16 (s, 2H), 4.40 (d, J = 5.6 Hz, 2H), 7.46 (t, J = 7.6 Hz, 1H), 7.54 (d, J = 8.1 Hz, 1H), 7.58 (dd, J = 8.6, 2.0 Hz, 1H), 7.83 (d, J = 7.6 Hz, 1H), 7.89 (s, 1H), 8.05 (d, J = 8.6 Hz, 1H), 8.17 (d, J = 2.0 Hz, 1H), 8.93 (t, J = 5.8 Hz, 1H), 12.94 (br s, 1H). | | | |

TABLE 44

| No. | Structure | NMR(δ) | retention time | Mass | method |
|---|---|---|---|---|---|
| II-1-220 | 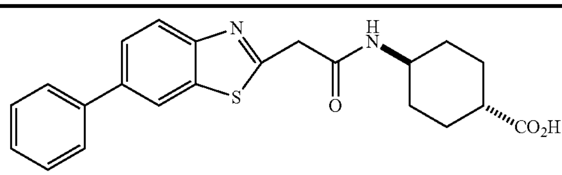 | 1H-NMR (DMSO-d6) δ: 1.12-1.45 (m, 4H), 1.81-1.98 (m, 4H), 2.10-2.24 (m, 1H), 3.45-3.66 (m, 1H), 4.03 (s, 2H), 7.39 (dd, J = 7.4, 3.7 Hz, 1H), 7.50 (t, J = 7.6 Hz, 2H), 7.83-7.70 (m, 3H), 8.00 (d, J = 8.6 Hz, 1H), 8.30 (d, J = 7.1 Hz, 1H), 8.37 (s, 1H). | 3.62 | 394.75 (ES+) | C |
| II-1-221 | 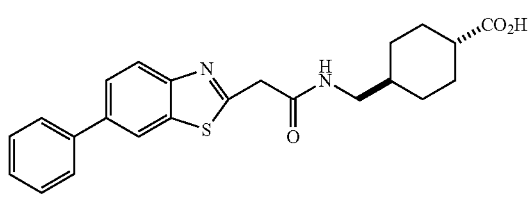 | 1H-NMR (DMSO-d6) δ: 0.83-2.19 (m, 10H), 2.98 (t, J = 6.1 Hz, 2H), 4.05 (s, 2H), 7.54-7.34 (m, 3H), 7.82-7.71 (m, 3H), 8.00 (d, J = 8.6 Hz, 1H), 8.32-8.37 (m, 2H). | 3.74 | 408.75 (ES+) | C |
| II-1-222 | 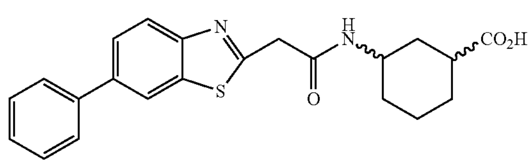 [SMILES: O=C(Cc1nc2ccc(-c3ccccc3)cc2s1)NC1CCCC(C(=O)O)C1] | 1H-NMR (DMSO-d6) δ: 1.01-1.44 (m, 4H), 1.68-2.10 (m, 5H), 2.24-2.36 (m, 1H), 4.03 (s, 2H, 7.34-7.53 (m, 3H), 7.71-7.82 (m, 3H), 8.00 (d, J = 8.1 Hz, 1H), 8.30-8.40 (m, 2H). | 3.72 | 394.75 (ES+) | C |

TABLE 44-continued

| No. | Structure | NMR(δ) | retention time | Mass | method |
|---|---|---|---|---|---|
| II-1-223 | 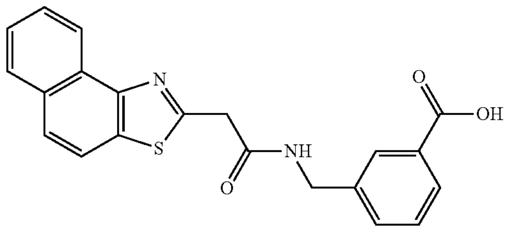 [SMILES: O=C(Cc1nc2c(ccc3ccccc32)s1)NCc1cccc(C(=O)O)c1] | 1H-NMR (DMSO-d6) δ: 4.26 (s, 2H), 4.43 (d, J = 6.1 Hz, 2H), 7.46 (t, J = 7.6 Hz, 1H), 7.56-7.64 (m, 2H), 7.70 (t, J = 6.8 Hz, 1H), 7.84 (d, J = 7.6 Hz, 1H), 7.91-7.93 (m, 2H), 8.07 (d, J = 8.1 Hz, 1H), 8.12 (d, J = 8.6 Hz, 1H), 8.64 (d, J = 8.1 Hz, 1H), 8.97 (t, J = 5.8 Hz, 1H), 12.95 (br s, 1H). | | | |
| II-1-224 | 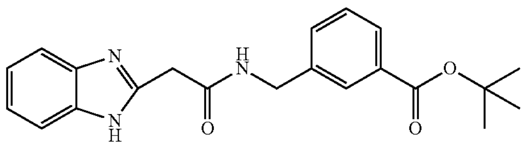 [SMILES: CC(C)(C)OC(=O)c1cccc(CNC(=O)Cc2nc3ccccc3[nH]2)c1] | 1H-NMR (DMSO-d6) δ: 1.54 (s, 9H), 3.82 (s, 2H), 4.38 (d, J = 5.6 Hz, 2H), 7.06-7.20 (m, 2H), 7.58, 7.40 (m, 4H), 7.78 (d, J = 7.6 Hz, 1H), 7.83 (s, 1H), 8.81 (t, J = 5.8 Hz, 1H), 12.26 (s, 1H). | | | |

TABLE 45

| No. | Structure | NMR(δ) | retention time | Mass | method |
|---|---|---|---|---|---|
| II-1-225 | 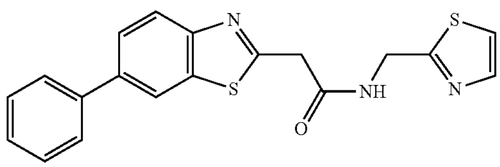 [SMILES: O=C(Cc1nc2ccc(-c3ccccc3)cc2s1)NCc1nccs1] | 1H-NMR (DMSO-d6) δ: 4.17 (s, 2H), 4.64 (d, J = 6.0 Hz, 2H), 7.39 (t, J = 7.4 Hz, 1H), 7.50 (t, J = 7.5 Hz, 2H), 7.64 (d, J = 3.2 Hz, 1H), 7.73-7.81 (m, 4H), 8.02 (d, J = 8.4 Hz, 1H), 8.39 (d, J = 1.5 Hz 1H), 9.25 (br s, 1H). | | | |
| II-1-226 | 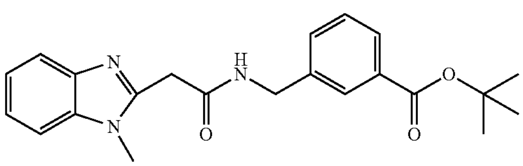 [SMILES: Cn1c(CC(=O)NCc2cccc(C(=O)OC(C)(C)C)c2)nc2ccccc21] | 1H-NMR (DMSO-d6) δ: 1.54 (s, 9H), 3.76 (s, 3H), 3.95 (s, 2H), 4.37 (d, J = 5.6 Hz, 2H), 7.26-7.12 (m, 2H), 7.58-7.41 (m, 4H), 7.78 (d, J = 7.6 Hz, 1H), 7.83 (s, 1H), 8.85 (t, J = 5.8 Hz, 1H). | | | |
| II-1-227 | 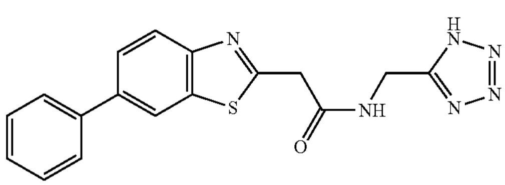 [SMILES: O=C(Cc1nc2ccc(-c3ccccc3)cc2s1)NCc1nnn[nH]1] | 1H NMR (DMSO-d6) δ: 4.17 (s, 2H), 4.64 (d, J = 5.5 Hz, 2H), 7.39-7.52 (m, 3H), 7.76-7.79 (m, 3H), 8.02 (d, J = 8.6 Hz, 1H), 8.39 (s, 2H), 9.10 (br s, 1H). | | | |
| II-1-228 | 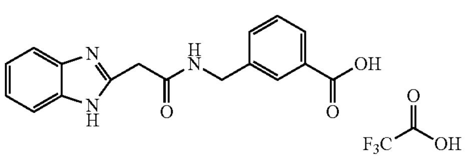 [SMILES: O=C(Cc1nc2ccccc2[nH]1)NCc1cccc(C(=O)O)c1 ; O=C(O)C(F)(F)F] | 1H-NMR (DMSO-d6) δ: 4.23 (s, 2H), 4.43 (d, J = 6.1 Hz, 2H), 7.54-1.44 (m, 3H), 7.58 (d, J = 7.6 Hz, 1H), 7.82-7.75 (m, 2H), 7.85 (d, J = 7.6 Hz, 1H), 7.92 (s, 1H), 9.06 (t, J = 5.6 Hz, 1H). | 0.97 | 309.65 (ES+) | C |
| II-1-229 | 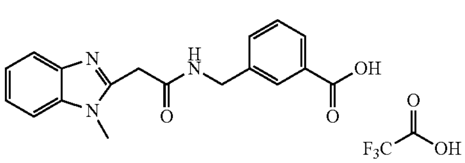 [SMILES: Cn1c(CC(=O)NCc2cccc(C(=O)O)c2)nc2ccccc21 ; O=C(O)C(F)(F)F] | 1H-NMR (DMSO-d6) δ: 3.92 (s, 3H), 4.28 (s, 2H), 4.42 (d, J = 6.1 Hz, 2H), 7.42-7.61 (m, 4H), 7.94-7.73 (m, 4H), 9.05 (t, J = 5.6 Hz, 1H). | 1.08 | 323.90 (ES+) | C |

TABLE 46

| No. | Structure | NMR(δ) | retention time | Mass | method |
|---|---|---|---|---|---|
| II-1-230 | 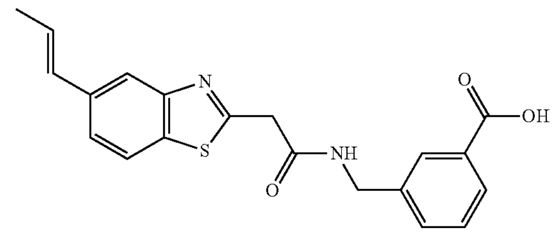 [SMILES: C/C=C/c1ccc2sc(CC(=O)NCc3cccc(C(=O)O)c3)nc2c1] | 1H-NMR (DMSO-d6) δ: 1.88 (d, J = 6.1 Hz, 3H), 4.11 (s, 2H), 4.40 (d, J = 4.5 Hz, 2H), 6.39-6.46 (m, 1H), 6.56 (d, J = 16.2 Hz, 1H), 7.46-7.55 (m, 3H), 7.82-8.02 (m, 4H), 8.93 (br s, 1H). | | | |
| II-1-231 | 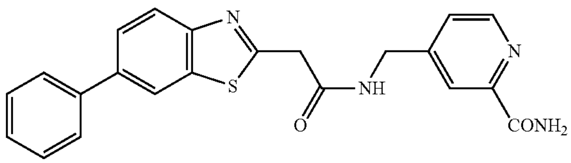 [SMILES: NC(=O)c1cc(CNC(=O)Cc2nc3ccc(-c4ccccc4)cc3s2)ccn1] | 1H-NMR (DMSO-d6) δ: 4.20 (s, 2H), 4.47 (d, J = 5.7 Hz, 2H), 7.43-7.57 (m, 5H), 7.76-7.79 (m, 3H), 8.03-8.08 (m, 3H), 8.38 (s, 1H), 8.57 (d, J = 4.9 Hz, 1H), 9.04 (br s, 1H). | | | |
| II-1-232 | 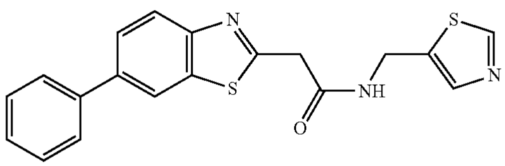 [SMILES: O=C(Cc1nc2ccc(-c3ccccc3)cc2s1)NCc1cncs1] | 1H-NMR (DMSO-d6) δ: 4.11 (s, 2H), 4.57 (d, J = 5.7 Hz, 2H), 7.39-7 42 (m, 1H), 7.50 (t, J = 7.5 Hz 2H), 7.74-7.81 (m, 4H), 8.01 (d, J = 8.6 Hz, 1H), 8.39 (d, J = 1.7 Hz, 1H), 8.98-9.02 (m, 2H). | | | |
| II-1-233 | 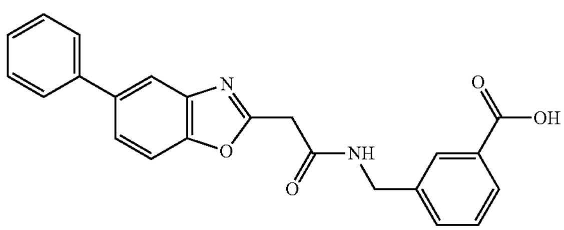 [SMILES: O=C(Cc1nc2cc(-c3ccccc3)ccc2o1)NCc1cccc(C(=O)O)c1] | 1H-NMR (DMSO-d6) δ: 4.02 (s, 2H), 4.41 (d, J = 6.1 Hz, 2H), 7.38 (t, J = 7.4 Hz, 1H), 7.48 (td, J = 7.6, 2.2 Hz, 3H), 7.57 (d, J = 7.6 Hz, 1H), 7.66-7.85 (m, 5H), 7. 95 (d, J = 14.7 Hz, 2H), 8.92 (t, J = 5.8 Hz, 1H), 12.97 (br s, 1H). | | | |
| II-1-234 | 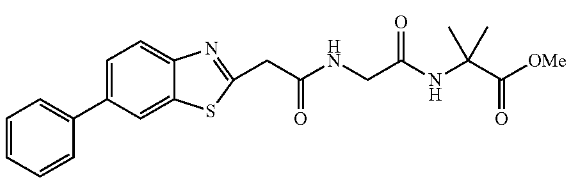 [SMILES: COC(=O)C(C)(C)NC(=O)CNC(=O)Cc1nc2ccc(-c3ccccc3)cc2s1] | 1H-NMR (CDCl3) δ: 1.54 (s, 6H), 3.71 (s, 3H), 4.00 (d, J = 5.1 Hz, 2H), 4.14 (s, 2H), 6.76 (br s, 1H), 7.34-7.51 (m, 3H), 7.59-7.86 (m, 4H), 8.08-8.02 (m, 2H). | | | |

TABLE 47

| No. | Structure | NMR(δ) | retention time | Mass | method |
|---|---|---|---|---|---|
| II-1-235 | 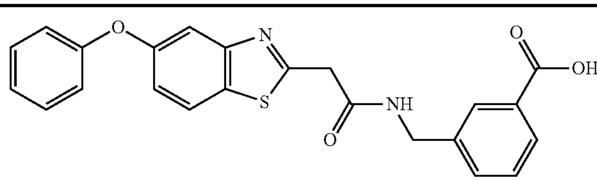 | 1H-NMR (DMSO-d6) δ: 4.12 (s, 2H), 4.39 (d, J = 6.1 Hz, 2H), 7.05 (d, J = 7.6 Hz, 2H), 7.14-7.18 (m, 2H), 7.38-7.55 (m, 5H), 7.83 (d, J = 7.6 Hz, 1H), 7.89 (s, 1H), 8.06 (d, J = 8.6 Hz, 1H), 8.91 (t, J = 5.8 Hz, 1H), 12.95 (br s, 1H). | | | |

TABLE 47-continued

| No. | Structure | NMR(δ) | retention time | Mass | method |
|---|---|---|---|---|---|
| II-1-236 | (6-hydroxy-benzothiazol-2-yl)-CH2-C(O)-NH-CH2-(3-carboxyphenyl) | 1H-NMR (DMSO-d6) δ: 4.05 (s, 2H), 4.39 (d, J = 6.1 Hz, 2H), 6.91 (dd, J = 8.6, 2.0 Hz, 1H), 7.28 (d, J = 2.0 Hz, 1H), 7.46 (t, J = 7.6 Hz, 1H), 7.54 (d, J = 7.6 Hz, 1H), 7.79 (d, J = 8.6 Hz, 1H), 7.83 (d, J = 7.6 Hz, 1H), 7.89 (s, 1H), 8.88 (t, J = 5.8 Hz, 1H), 9.61 (s, 1H), 12.90 (br s, 1H). | | | |
| II-1-237 | (5-hydroxy-benzothiazol-2-yl)-CH2-C(O)-NH-CH2-(3-carboxyphenyl) | 1H-NMR (DMSO-d6) δ: 4.02 (s, 2H), 4.38 (d, J = 6.0 Hz, 2H), 6.29 (dd, J = 8.3, 2.4 Hz), 7.32 (d, J = 2.4 Hz, 1H), 7.47 (t, J = 7.5 Hz, 1H), 7.54 (d, J = 7.8 Hz, 1H), 7.73 (d, J = 8.7 Hz, 1H), 7.81-7.84 (m, 1H), 7.89 (s, 1H), 8.88 (t, J = 5.7 Hz, 1H), 9.71 (s, 1H), 12.95 (brs, 1H). | | | |
| II-1-238 | (6-isopropoxy-benzothiazol-2-yl)-CH2-C(O)-NH-CH2-(3-carboxyphenyl) | 1H-NMR (DMSO-d6) δ: 1.30 (dd, J = 6.1, 1.5 Hz, 6H), 4.08 (s, 2H), 4.39 (d, J = 6.1 Hz, 2H), 4.67-4.73 (m, 1H), 7.02 (dd, J = 8.6, 2.0 Hz, 1H), 7.44-7.55 (m, 3H), 7.82-7.90 (m, 3H), 8.89 (t, J = 5.3 Hz, 1H), 12.94 (br s, 1H). | | | |
| II-1-239 | (6-phenyl-benzothiazol-2-yl)-CH2-C(O)-NH-CH2-(3-CH2CO2H-phenyl) | 1H-NMR (DMSO-d6) δ: 3.54 (s, 2H), 4.14 (s, 2H), 4.33 (d, J = 5.7 Hz, 2H), 7.15-7.18 (m, 3H), 7.28 (t, J = 7.8 Hz, 1H), 7.39 (t, J = 7.4 Hz, 1H), 7.50 (t, J = 7.5 Hz, 2H), 7.74-7.81 (m, 3H), 8.02 (d, J = 8.7 Hz, 1H), 8.38 (s, 1H), 8.86 (br s, 1H). | | | |

TABLE 48

| No. | Structure | NMR(δ) | retention time | Mass | method |
|---|---|---|---|---|---|
| II-1-240 | (6-phenyl-benzothiazol-2-yl)-CH2-C(O)-NH-CH2-(2-methylpyrimidin-4-yl) | 1H-NMR (DMSO-d6) δ: 2.59 (s, 3H), 4.21 (s, 2H), 4.38 (d, J = 5.7 Hz, 2H), 7.26 (d, J = 5.0 Hz, 1H), 7.39-7.42 (m, 1H), 7.50 (t, J = 7.6 Hz, 2H), 7.76-7.80 (m, 3H), 8.03 (d, J = 8.4 Hz, 1H), 8.39 (s, 1H), 8.64 (d, J = 5.4 Hz, 1H), 9.02 (br s, 1H). | | | |
| II-1-241 | (6-phenyl-benzothiazol-2-yl)-CH2-C(O)-NH-CH2-(3-OCF3-phenyl) | 1H-NMR (DMSO-d6) δ: 4.16 (s, 2H), 4.41 (d, J = 6.0 Hz, 2H), 7.26-7.52 (m, 7H), 7.74-7.82 (m, 3H), 8.01 (d, J = 8.6 Hz, 1H), 8.38 (d, J = 1.5 Hz, 1H), 8.94 (br s, 1H). | | | |

TABLE 48-continued

| No. | Structure | NMR(δ) | retention time | Mass | method |
|---|---|---|---|---|---|
| II-1-242 | 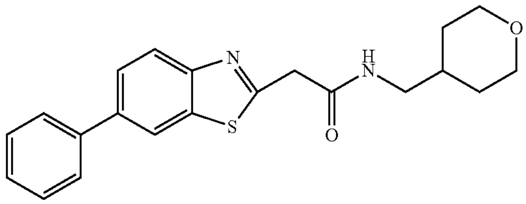 [SMILES: O=C(Cc1nc2ccc(-c3ccccc3)cc2s1)NCC1CCOCC1] | 1H-NMR (CDCl3) δ: 1.22-2.43 (m, 5H), 3.18-3.42 (m, 4H), 3.91-4.02 (m, 2H), 4.08 (s, 2H), 7 33-7.77 (m, 7H), 7.99-8.11 (m, 2H). | 3.7 | 367.05 (ES+) | C |
| II-1-243 | 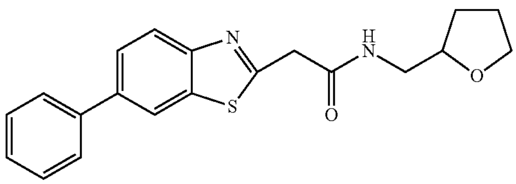 [SMILES: O=C(Cc1nc2ccc(-c3ccccc3)cc2s1)NCC1CCCO1] | 1H-NMR (CDCl3) δ: 2.06-1.47 (m, 5H), 2.84-4.08 (m, 6H), 7.28-7.52 (m, 4H), 7.57-7.77 (m, 3H), 7.98-8.13 (m, 2H). | 3.77 | 353.00 (ES+) | C |
| II-1-244 | 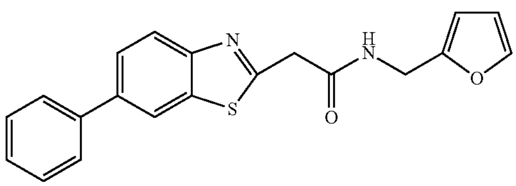 [SMILES: O=C(Cc1nc2ccc(-c3ccccc3)cc2s1)NCc1ccco1] | 1H-NMR (CDCl3) δ: 4.10, (s, 2H), 4.51 (d, J = 5.6 Hz, 2H), 6.24 (d, J = 3.0 Hz, 1H), 6.32 (t, J = 2.5 Hz, 1H), 7.32-7.67 (m, 7H), 7.72 (dd, J = 8.4, 1.8 Hz, 1H), 8.08-8.00 (m, 2H). | 4.18 | 349.15 (ES+) | C |

TABLE 49

| No. | Structure | NMR(δ) | retention time | Mass | method |
|---|---|---|---|---|---|
| II-1-245 | 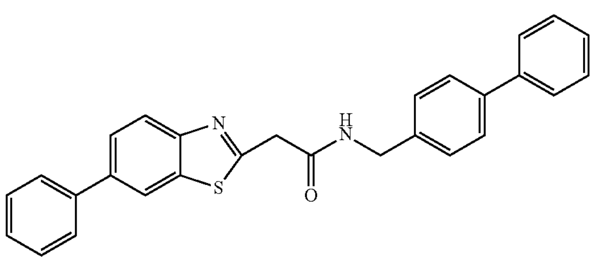 [SMILES: O=C(Cc1nc2ccc(-c3ccccc3)cc2s1)NCc1ccc(-c2ccccc2)cc1] | 1H-NMR (DMSO-d6) δ: 4.16 (s, 2H), 4.40 (d, J = 6.1 Hz, 2H), 7.30-7.54 (m, 8H), 7.59-7.68 (m, 4H), 7.72-7.82 (m, 3H), 8.03 (d, J = 8.6 Hz, 1H), 8.36-8.40 (m, 1H), 8.89 (t, J = 5.6 Hz, 1H). | 5.46 | 435.05 (ES+) | C |
| II-1-246 | 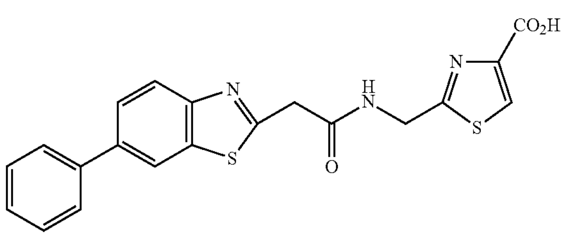 [SMILES: O=C(Cc1nc2ccc(-c3ccccc3)cc2s1)NCc1nc(C(=O)O)cs1] | | 1.83 | 410.00 (ES+) | C |

TABLE 50

| No. | Structure | NMR(δ) | retention time | Mass | method |
|---|---|---|---|---|---|
| II-2-2 | 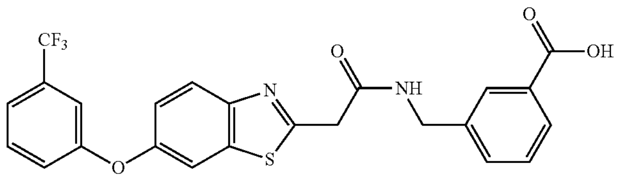 [SMILES: O=C(Cc1nc2ccc(Oc3cccc(C(F)(F)F)c3)cc2s1)NCc1cccc(C(=O)O)c1] | (DMSO-d6) δ: 4.13 (s, 2H), 4.40 (d, J = 5.58 Hz, 2H), 7.25-7.35 (m, 3H), 7.44-7.56 (m, 2H), 7.62 (m, 1H), 7.82-7.90 (m, 3H), 8.00 (d, J = 9.12 Hz, 1H), 8.93 (t, J = 5.58 Hz, 1H), 12.96 (brs, 1H). | | | |
| II-2-3 | 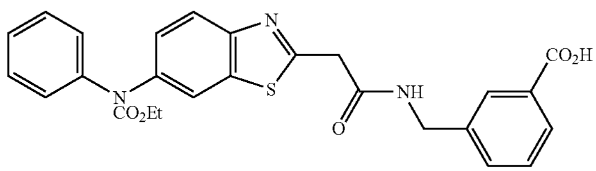 | (DMSO-d6) δ: 1.14 (t, J = 7.1 Hz, 3H), 4.10-4.15 (m, 4H), 4.39 (d, J = 6.1 Hz, 2H), 7.23 (t, J = 7.1 Hz, 1H), 7.29-7.39 (m, 5H), 7.45 (t, J = 7.6 Hz, 1H), 7.53 (d, J = 7.6 Hz, 1H), 7.82 (d, J = 7.6 Hz, 1H), 7.91 (t, J = 7.1 Hz, 2H), 8.03 (d, J = 2.0 Hz, 1H), 8.91 (t, J = 6.1 Hz, 1H), 12.98 (br s, 1H). | | | |
| II-2-4 | 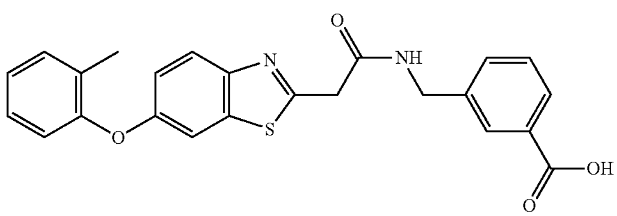 [SMILES: Cc1ccccc1Oc1ccc2nc(CC(=O)NCc3cccc(C(=O)O)c3)sc2c1] | (DMSO-d6) δ: 2.20 (s, 3H), 4.09 (s, 2H), 4.39 (d, J = 6.08 Hz, 2H), 6.93 (d, J = 8.11 Hz, 1H), 7.09-7.15 (m, 2H), 7.23 (m, 1H), 7.35 (d, J = 7.10 Hz, 1H), 7.46 (m, 1H), 7.53-7.56 (m, 2H), 7.83 (d, J = 7.60 Hz, 1H), 7.91 (m, 2H), 8.91 (t, J = 5.58 Hz, 1H), 12.96 (brs, 1H). | | | |
| II-2-5 | 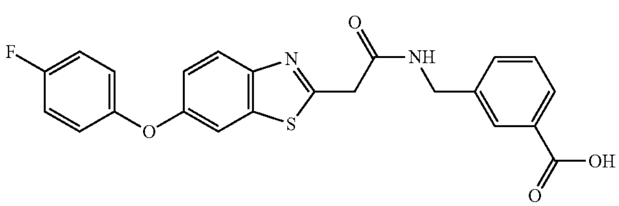 [SMILES: O=C(Cc1nc2ccc(Oc3ccc(F)cc3)cc2s1)NCc1cccc(C(=O)O)c1] | (DMSO-d6) δ: 4.10 (s, 2H), 4.40 (d, J = 5.58 Hz, 2H), 7.09-7.13 (m, 2H), 7.17 (dd, J = 8.62, 2.53 Hz, 1H), 7.20-7.28 (m, 2H), 7.43-7.57 (m, 2H), 7.69 (d, J = 2.53 Hz, 1H), 7.83 (d, J = 8.11 Hz, 1H), 7.88-7.97 (m, 2H), 8.92 (t, J = 5.83 Hz, 1H), 12.96 (brs, 1H). | | | |
| II-2-6 | 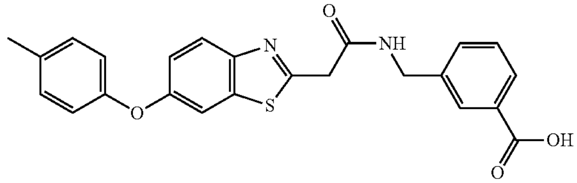 [SMILES: Cc1ccc(Oc2ccc3nc(CC(=O)NCc4cccc(C(=O)O)c4)sc3c2)cc1] | (DMSO-d6) δ: 2.30 (s, 3H), 4.09 (s, 2H), 4.39 (d, J = 5.58 Hz, 2H), 6.95 (d, J = 8.11 Hz, 2H), 7.15 (dd, J = 8.62, 2.53 Hz, 1H), 7.21 (d, J = 8.11 Hz, 2H), 7.46 (m, 1H), 7.54 (d, J = 7.60 Hz, 1H), 7.65 (d, J = 2.53 Hz, 1H), 7.83 (d, J = 7.60 Hz, 1H), 7.95-7.88 (m, 2H), 8.91 (t, J = 5.83 Hz, 1H), 12.95 (brs, 1H). | | | |

TABLE 51

| No. | Structure | NMR(δ) | retention time | Mass | method |
|---|---|---|---|---|---|
| II-2-7 | 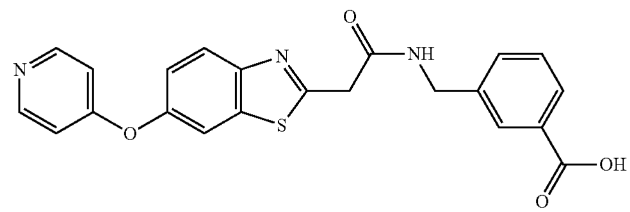 [SMILES: O=C(Cc1nc2ccc(Oc3ccncc3)cc2s1)NCc1cccc(C(=O)O)c1] | (DMSO-d6) δ: 4.14 (s, 2H), 4.41 (d, J = 5.58 Hz, 2H), 6.98-6.94 (m, 2H), 7.31 (dd, J = 8.87, 2.28 Hz, 1H), 7.46 (m, 1H), 7.55 (d, J = 7.60 Hz, 1H), 7.83 (d, J = 7.60 Hz, 1H), 7.91 (s, 1H), 7.96 (d, J = 2.03 Hz, 1H), 8.03 (d, J = 9.12 Hz, 1H), 8.47 (d, J = 5.07 Hz, 2H), 8.94 (t, J = 5.83 Hz, 1H), 12.96 (brs, 1H). | | | |
| II-2-8 | 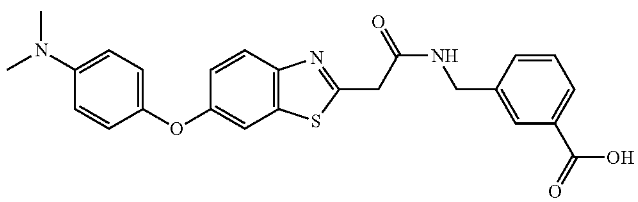 [SMILES: CN(C)c1ccc(Oc2ccc3nc(CC(=O)NCc4cccc(C(=O)O)c4)sc3c2)cc1] | (DMSO-d$_6$) δ: 2.88 (s, 6H), 4.07 (s, 2H), 4.39 (d, J = 5.58 Hz, 2H), 6.78 (d, J = 8.62 Hz, 2H), 6.96 (d, J = 9.12 Hz, 2H), 7.09 (dd, J = 8.62, 2.53 Hz, 1H), 7.42-7.56 (m, 3H), 7.81-7.90 (m, 3H), 8.90 (t, J = 5.83 Hz, 1H), 12.96 (brs, 1H). | | | |
| II-2-9 | 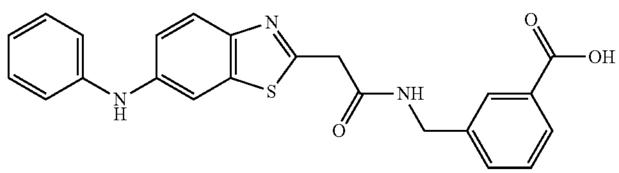 [SMILES: O=C(Cc1nc2ccc(Nc3ccccc3)cc2s1)NCc1cccc(C(=O)O)c1] | (DMSO-d6) δ: 4.03 (s, 2H), 4.39 (d, J = 5.6 Hz, 2H), 6.86 (t, J = 7.4 Hz, 1H), 7.11-7.19 (m, 3H), 7.26 (t, J = 7.9 Hz, 2H), 7.45 (t, J = 7.6 Hz, 1H), 7.54 (d, J = 7.6 Hz, 1H), 7.67 (d, J = 2.0 Hz, 1H), 7.77-7.83 (m, 2H), 7.90 (s, 1H), 8.36 (s, 1H), 8.88 (t, J = 5.8 Hz, 1H), 12.97 (br s, 1H). | | | |
| II-2-10 | 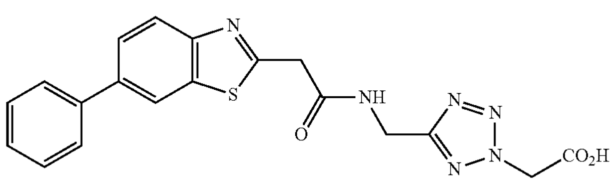 [SMILES: O=C(O)Cn1nnc(CNC(=O)Cc2nc3ccc(-c4ccccc4)cc3s2)n1] | 1H-NMR (DMSO-d6) δ: 4.16 (s, 2H), 4.64 (d, J = 6.1 Hz, 2H), 5.66 (s, 2H), 7.40 (d, J = 7.6 Hz, 1H), 7.50 (t, J = 7.6 Hz, 2H), 7.74-7.80 (m, 4H), 8.01 (d, J = 8.6 Hz, 1H), 8.38 (d, J = 1.5 Hz, 1H), 9.12 (s, 1H). | | | |
| II-2-11 | 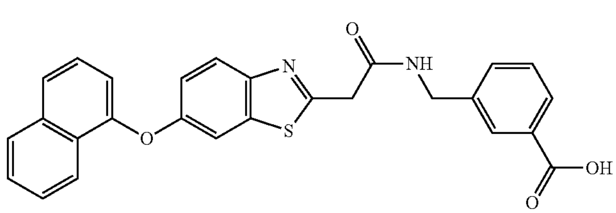 [SMILES: O=C(Cc1nc2ccc(Oc3cccc4ccccc34)cc2s1)NCc1cccc(C(=O)O)c1] | (DMSO-d$_6$) δ: 4.11 (s, 2H), 4.40 (d, J = 6.08 Hz, 2H), 7.02 (d, J = 7.10 Hz, 1H), 7.25 (dd, J = 8.62, 2.53 Hz, 1H), 7.43-7.63 (m, 5H), 7.73-7.85 (m, 3H), 7.89-8.03 (m, 3H), 8.12 (d, J = 8.11 Hz, 1H), 8.91 (t, J = 5.83 Hz, 1H), 12.95 (brs, 1H). | | | |

| No. | Structure | NMR(δ) | retention time | Mass | method |
|---|---|---|---|---|---|
| II-2-12 | 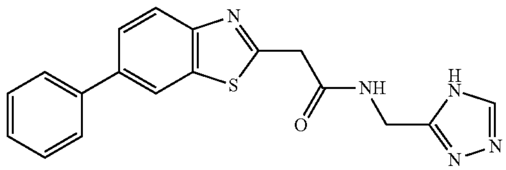 [SMILES: O=C(Cc1nc2ccc(-c3ccccc3)cc2s1)NCc1nnc[nH]1] | 1H-NMR (DMSO-d6) δ: 4.15 (s, 2H), 4.42 (d, J = 5.1 Hz, 2H), 7.44 (m, 3H), 7.77 (m, 3H), 8.01 (d, J = 8.6 Hz, 1H), 8.28-8.35 (m, 1H), 8.91 (s, 1H), 13.88 (s, 1H). | | | |
| II-2-13 | 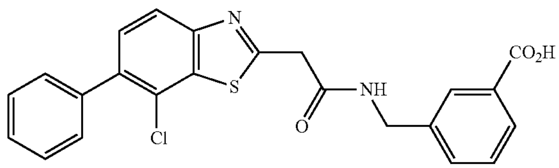 [SMILES: O=C(Cc1nc2ccc(-c3ccccc3)c(Cl)c2s1)NCc1cccc(C(=O)O)c1] | (DMSO-d6) δ: 4.21 (s, 2H), 4.42 (d, J = 5.6 Hz, 2H), 7.44-7.57 (m, 8H), 7.84 (d, J = 7.6 Hz, 1H), 7.91 (s, 1H), 8.01 (d, J = 8.6 Hz, 1H), 8.98 (t, J = 5.3 Hz, 1H), 12.96 (br s, 1H). | | | |
| II-2-14 | 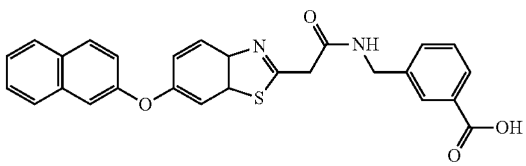 [SMILES: O=C(CC1=NC2C=CC(Oc3ccc4ccccc4c3)=CC2S1)NCc1cccc(C(=O)O)c1] | (DMSO-$d_6$) δ: 4.12 (s, 2H), 4.40 (d, J = 6.08 Hz, 2H), 7.25-7.57 (m, 7H), 7.80-7.85 (m, 3H), 7.90-7.94 (m, 2H), 7.99 (d, J = 9.12 Hz, 2H), 8.93 (t, J = 5.58 Hz, 1H), 12.96 (brs, 1H). | | | |
| II-2-15 | 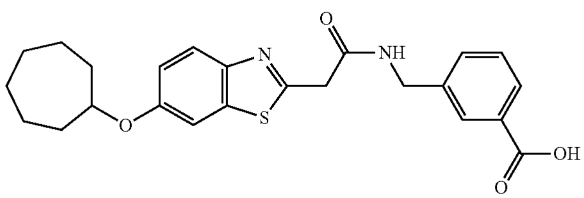 [SMILES: O=C(Cc1nc2ccc(OC3CCCCCC3)cc2s1)NCc1cccc(C(=O)O)c1] | (DMSO-$d_6$) δ: 1.41-1.78 (brm, 10H), 1.94-2.03 (m, 2H), 4.05 (s, 2H), 4.39 (d, J = 6.08 Hz, 2H), 4.54-4.60 (m, 1H), 7.03 (dd, J = 8.62, 2.53 Hz, 1H), 7.46 (t, J = 7.60 Hz, 1H), 7.52-7.59 (m, 2H), 7.78-7.85 (m, 2H), 7.90 (s, 1H), 8.88 (t, J = 5.58 Hz, 1H), 12.95 (s, 1H). | | | |
| II-2-16 | 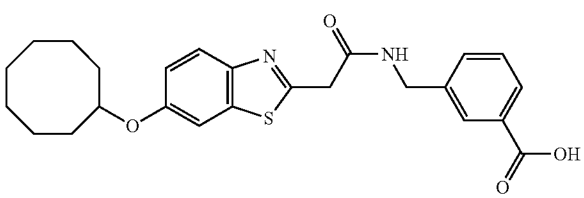 [SMILES: O=C(Cc1nc2ccc(OC3CCCCCCC3)cc2s1)NCc1cccc(C(=O)O)c1] | (DMSO-$d_6$) δ: 1.49-1.93 (brm, 14H), 4.05 (s, 2H), 4.39 (d, J = 5.58 Hz, 2H), 4.55 (brs, 1H), 7.02 (d, J = 7.10 Hz, 1H), 7.43-7.59 (m, 3H), 7.78-7.91 (m, 3H), 8.88 (t, J = 5.58 Hz, 1H), 12.95 (brs, 1H). | | | |

TABLE 53

| No. | Structure | NMR(δ) | retention time | Mass | method |
|---|---|---|---|---|---|
| II-2-17 | 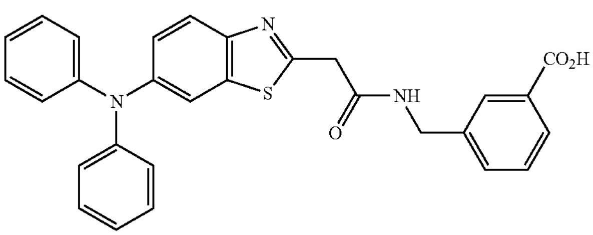 [SMILES: O=C(Cc1nc2ccc(N(c3ccccc3)c3ccccc3)cc2s1)NCc1cccc(C(=O)O)c1] | (DMSO-d6) δ: 4.07 (s, 2H), 4.39 (d, J = 5.6 Hz, 2H), 7.01-7.06 (m, 6H), 7.13 (dd, J = 8.9, 2.3 Hz, 1H), 7.31 (t, J = 7.6 Hz, 4H), 7.45 (t, J = 7.6 Hz, 1H), 7.53 (d, J = 7.6 Hz, 1H), 7.66 (d, J = 2.0 Hz, 1H), 7.81-7.89 (m, 3H), 8.90 (t, J = 5.8 Hz, 1H). | | | |

TABLE 53-continued

| No. | Structure | NMR(δ) | retention time | Mass | method |
|---|---|---|---|---|---|
| II-2-18 | 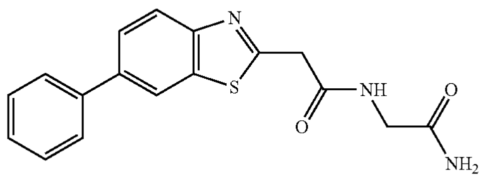 [SMILES: NC(=O)CNC(=O)Cc1nc2ccc(-c3ccccc3)cc2s1] | (DMSO-d6) δ: 3.72 (d, J = 5.6 Hz, 2H), 4.15 (s, 2H), 7.11 (s, 1H), 7.39 (t, J = 7.6 Hz, 1H), 7.46-7.52 (m, 3H), 7.74-7.81 (m, 3H), 8.01 (d, J = 8.1 Hz, 1H), 8.38 (d, J = 1.5 Hz, 1H), 8.58 (t, J = 5.3 Hz, 1H). | | | |
| II-2-19 | 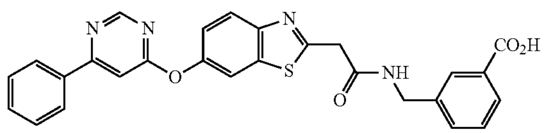 [SMILES: O=C(Cc1nc2ccc(Oc3cc(-c4ccccc4)ncn3)cc2s1)NCc1cccc(C(=O)O)c1] | (DMSO-d6) δ: 4.16 (s, 2H), 4.41 (d, J = 5.7 Hz, 2H), 7.78 (d, J = 0.9 Hz, 1H), 7.82-7.85 (m, 1H), 7.92 (s, 1H), 8.01-8.04 (m, 2H), 8.22-8.25 (m, 2H), 8.82 (d, J = 12 Hz, 1H), 8.95 (t, J = 5.4 Hz, 1H), 12.93 (brs, 1H). | | | |
| II-2-20 | 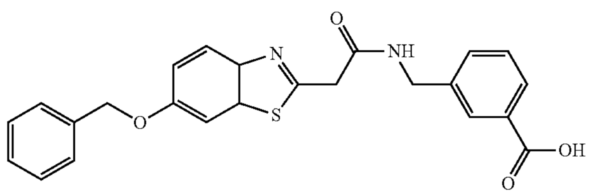 [SMILES: O=C(CC1=NC2C=CC(OCc3ccccc3)=CC2S1)NCc1cccc(C(=O)O)c1] | (DMSO-d6) δ: 4.07 (s, 2H), 4.39 (d, J = 6.08 Hz, 2H), 5.17 (s, 2H), 7.15 (dd, J = 9.12, 2.53 Hz, 1H), 7.31-7.56 (m, 7H), 7.72 (d, J = 2.53 Hz, 1H), 7.81-7.86 (m, 2H), 7.90 (s, 1H), 8.90 (t, J = 5.83 Hz, 1H) 12.96 (brs, 1H). | | | |
| II-2-21 | 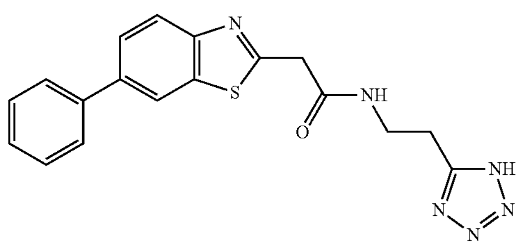 [SMILES: O=C(Cc1nc2ccc(-c3ccccc3)cc2s1)NCCc1nnn[nH]1] | 1H-NMR (DMSO-d6) δ: 3.08 (t, J = 6.6 Hz, 2H), 3.51-3.53 (m, 2H), 4.05 (s, 2H), 7 39-7.50 (m, 3H), 7.75-7.79 (m, 3H), 8.01 (d, J = 8.6 Hz, 1H), 8.38 (s, 1H), 8.56 (s, 1H), 16.04 (s, 1H). | | | |

TABLE 54

| No. | Structure | NMR(δ) | retention time | Mass | method |
|---|---|---|---|---|---|
| II-2-22 | 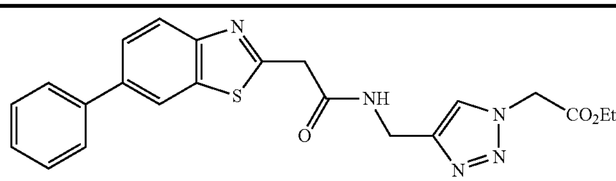 | (CDCl3) δ: 1.29 (t, J = 7.1 Hz, 3H), 4.09 (s, 2H), 4.26 (q, J = 7.1 Hz, 2H), 4.63 (d, J = 5.6 Hz, 2H), 5.12 (s, 2H), 7.38 (t, J = 7.4 Hz, 1H), 7.45-7.49 (m, 2H), 7.62-7.64 (m, 2H), 7.70-7.73 (m, 2H), 7.83 (br s, 1H), 8.03-8.06 (m, 2H). | | | |
| II-2-23 | 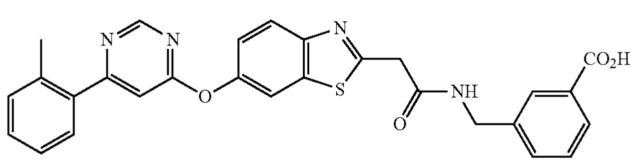 [SMILES: Cc1ccccc1-c1cc(Oc2ccc3nc(CC(=O)NCc4cccc(C(=O)O)c4)sc3c2)ncn1] | (DMSO-d6) δ: 2.41 (s, 3H), 4.15 (s, 2H), 4.41 (d, J = 5.7 Hz, 2H), 7.32-7 56 (m, 8H), 7.84 (d J = 7.5 Hz, 1H), 7.91 (s, 1H), 8.02 (d, J = 6.3 Hz, 1H), 8.04 (s, 1H), 8.82 (d, J = 0.9 Hz, 1H), 8.94 (t, J = 5.7 Hz, 1H), 12.96 (brs, 1H). | | | |

TABLE 54-continued

| No. | Structure | NMR(δ) | retention time | Mass | method |
|---|---|---|---|---|---|
| II-2-24 | 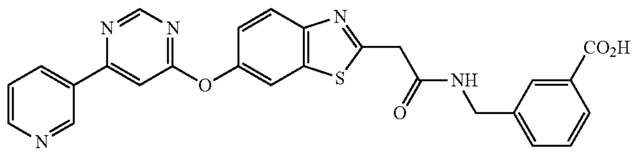 [SMILES: O=C(Cc1nc2ccc(Oc3cc(-c4cccnc4)ncn3)cc2s1)NCc1cccc(C(=O)O)c1] | (DMSO-d6) δ: 4.16 (s, 2H), 4.41 (d, J = 5.7 Hz, 2H), 7.38-7.62 (m, 5H), 7.82 (d J = 7.8 Hz, 1H), 7.91 (d, J = 6.9 Hz, 1H), 8.03 (dd, J = 5.7, 2.8 Hz, 2H), 857 (d, J = 2.8 Hz, 1H), 8.75 (d, J = 4.5 Hz, 1H), 8.86 (s, 1H), 8.95 (t, J = 5.7 Hz, 1H), 9.40 (s, 1H), 12.96 (brs, 1H). | | | |
| II-2-25 | 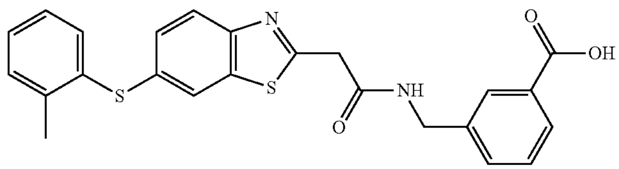 [SMILES: Cc1ccccc1Sc1ccc2nc(CC(=O)NCc3cccc(C(=O)O)c3)sc2c1] | (DMSO-d6) δ: 2.33 (s, 3H), 4.12 (s, 2H), 4.39 (d, J = 6.1 Hz, 2H), 7.19-7.35 (m, 5H), 7.46 (t, J = 7.6 Hz, 1H), 7.54 (d, J = 7.6 Hz, 1H), 7.83 (d, J = 7.6 Hz, 1H), 7.89-7.94 (m, 2H), 7.99 (d, J = 1.5 Hz, 1H), 8.93 (t, J = 6.1 Hz, 1H), 12.96 (br s, 1H). | | | |
| II-2-26 | 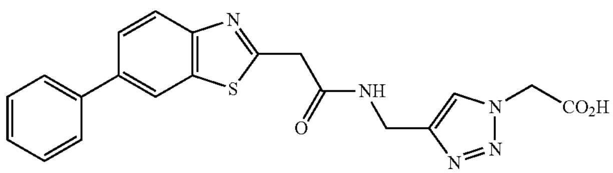 [SMILES: O=C(O)Cn1cc(CNC(=O)Cc2nc3ccc(-c4ccccc4)cc3s2)nn1] | (DMSO-d6) δ: 4.12 (s, 2H), 4.40 (d, J = 5.6 Hz, 2H), 5.24 (s, 2H), 7.39 (t, J = 7.4 Hz, 1H), 7.50 (t, J = 7.6 Hz, 2H), 7.74-7.80 (m, 3H), 7.96-8.02 (m, 2H), 8.37 (d, J = 2.0 Hz, 1H), 8.91 (t, J = 5.6 Hz, 1H). | | | |

TABLE 55

| No. | Structure | NMR(δ) | retention time | Mass | method |
|---|---|---|---|---|---|
| II-2-27 | 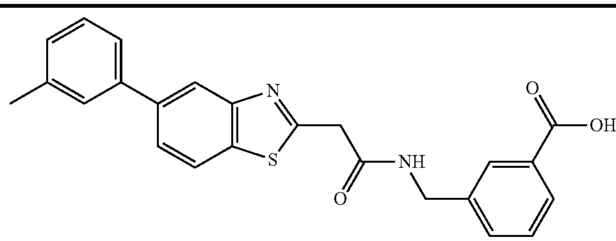 | (DMSO-d6) δ: 2.40 (s, 3H), 4.16 (s, 2H), 4.41 (d, J = 5.6 Hz, 2H), 7.21 (d, J = 7.6 Hz, 1H), 7.38 (t, J = 7.6 Hz, 1H), 7.47 (t, J = 7.9 Hz, 1H), 7.55-7.57 (m, 3H), 7.72 (dd, J = 8.4, 1.8 Hz, 1H), 7.83 (d, J = 7.6 Hz, 1H), 7.91 (s, 1H), 8.13 (d, J = 8.1 Hz, 1H), 8.19 (d, J = 1.5 Hz, 1H), 8.95 (t, J = 5.8 Hz, 1H), 12.95 (br s, 1H). | | | |
| II-2-28 | 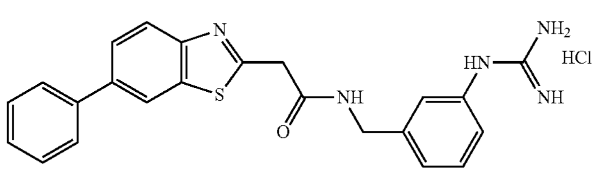 [SMILES: N=C(N)Nc1cccc(CNC(=O)Cc2nc3ccc(-c4ccccc4)cc3s2)c1 ; Cl] | 1H-NMR (DMSO-d6) δ: 4.17 (s, 2H), 4.38 (d, J = 6.1 Hz, 2H), 7.11-7.24 (m, 3H), 7.43-7.48 (m, 8H), 7.76-7.80 (m, 3H), 8.02 (d, J = 8.6 Hz, 1H), 8.40 (s, 1H), 8.96-8.99 (m, 1H), 9.95 (s, 1H). | | | |
| II-2-29 | 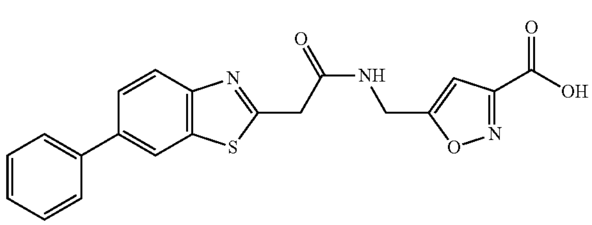 [SMILES: O=C(Cc1nc2ccc(-c3ccccc3)cc2s1)NCc1cc(C(=O)O)no1] | (DMSO-$d_6$) δ: 4.17 (s, 2H), 4.56 (d, J = 5.58 Hz, 2H), 6.76 (s, 1H), 7.39 (m, 1H), 7.47-7.53 (m, 2H), 7.73-7.82 (m, 3H), 8.03 (d, J = 8.11 Hz, 1H), 8.39 (d, J = 1.01 Hz, 1H), 9.08 (t, J = 5.83 Hz, 1H). | | | |

TABLE 55-continued

| No. | Structure | NMR(δ) | retention time | Mass | method |
|---|---|---|---|---|---|
| II-2-30 | 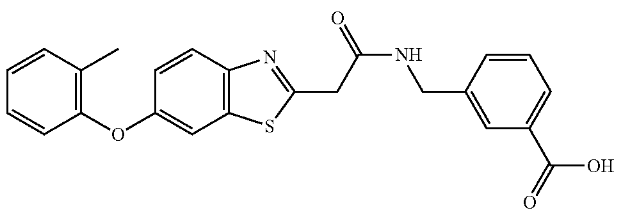 [SMILES: Cc1ccccc1Oc1ccc2nc(CC(=O)NCc3cccc(C(=O)O)c3)sc2c1] | (DMSO-d$_6$) δ: 2.20 (s, 3H), 4.09 (s, 2H), 4.39 (d, J = 6.08 Hz, 2H), 6.93 (d, J = 8.11 Hz, 1H), 7.08-7.15 (m, 2H), 7.23 (m, 1H), 7.34 (d, J = 7.60 Hz, 1H), 7.46 (m, 1H), 7.52-7.56 (m, 2H), 7.83 (d, J = 7.60 Hz, 1H), 7.88-7.94 (m, 2H), 8.91 (t, J = 5.83 Hz, 1H), 12.96 (s, 1H). | | | |
| II-2-31 | 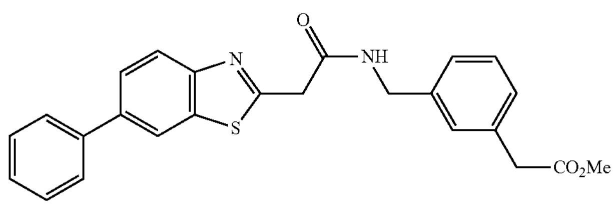 [SMILES: COC(=O)Cc1cccc(CNC(=O)Cc2nc3ccc(-c4ccccc4)cc3s2)c1] | 1H-NMR (DMSO-d6) δ: 3.62-3.67 (m, 5H), 4.17 (s, 2H), 4.36 (d, J = 6.0 Hz, 2H), 7.18-7.22 (m, 3H), 7.29-7.32 (m, 1H), 7.42-7.44 (m, 1H), 7.53 (t, J = 7.7 Hz, 2H), 7.78-7.82 (m, 3H), 8.04 (d, J = 8.6 Hz, 1H), 8.41 (s, 1H), 8.89-8.92 (m, 1H). | | | |

TABLE 56

| No. | Structure | NMR(δ) | retention time | Mass | method |
|---|---|---|---|---|---|
| II-2-32 | 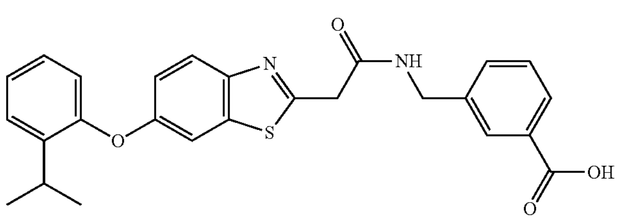 [SMILES: CC(C)c1ccccc1Oc1ccc2nc(CC(=O)NCc3cccc(C(=O)O)c3)sc2c1] | (DMSO-d6) δ: 1.19 (d, J = 6.59 Hz, 6H), 3.22 (m, 1H), 4.09 (s, 2H), 4.39 (d, J = 5.58 Hz, 2H), 6.90 (m, 1H), 7.10 (dd, J = 9.12, 2.53 Hz, 1H), 7.16-7.25 (m, 2H), 7.407.48- (m, 2H), 7.52-7.58 (m, 2H), 7.83 (d, J = 7.60 Hz, 1H), 7.88-7.94 (m, 2H), 8.91 (t, J = 5.83 Hz, 1H), 12.96 (brs, 1H). | | | |
| II-2-33 | 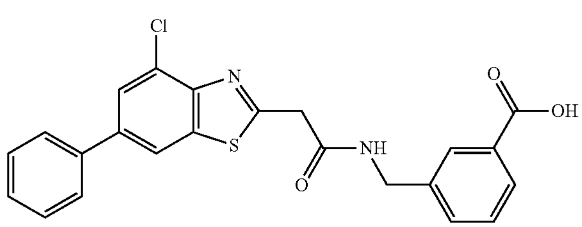 [SMILES: O=C(Cc1nc2c(Cl)cc(-c3ccccc3)cc2s1)NCc1cccc(C(=O)O)c1] | (DMSO-d6) δ: 4.22 (s, 2H), 4.43 (d, J = 5.7 Hz, 2H), 7.39-7.58 (m, 6H), 7.77-7.89 (m, 5H), 7.91 (s, 1H), 8.39 (d, J = 1.5 Hz, 1H), 8.98 (t, J = 5.7 Hz, 1H), 12.96 (brs, 1H). | | | |
| II-2-34 | 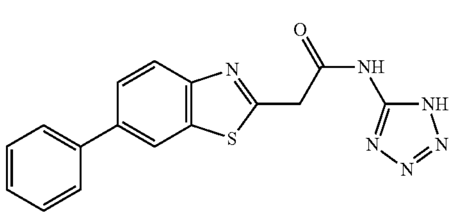 [SMILES: O=C(Cc1nc2ccc(-c3ccccc3)cc2s1)Nc1nnn[nH]1] | 1H-NMR (DMSO-d6) δ: 4.51 (s, 2H), 7.45-7.53 (m, 3H), 7.68-7.86 (m, 3H), 8.04-8 07 (m, 1H), 8.46 (s, 1H), 12.55 (s, 1H). | | | |

TABLE 56-continued

| No. | Structure | NMR(δ) | retention time | Mass | method |
|---|---|---|---|---|---|
| II-2-35 | 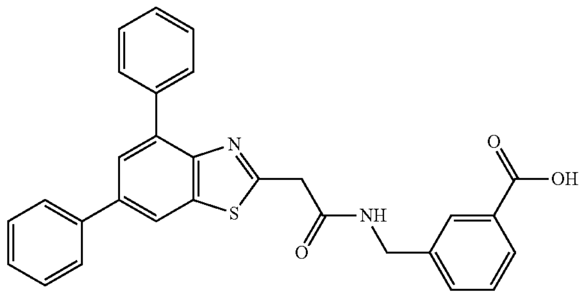 [SMILES: O=C(Cc1nc2c(-c3ccccc3)cc(-c3ccccc3)cc2s1)NCc1cccc(C(=O)O)c1] | (DMSO-d6) δ: 4.16 (s, 2H), 4.40 (d, J = 5.7 Hz, 2H), 7.38-7.55 (m, 9H), 7.82-7.85 (m, 4H), 7.89-7.91 (m, 3H), 8.38 (d, J = 1.5 Hz, 1H), 8.93 (t, J = 5.4 Hz 1H), 12.86 (brs, 1H). | | | |
| II-2-36 | 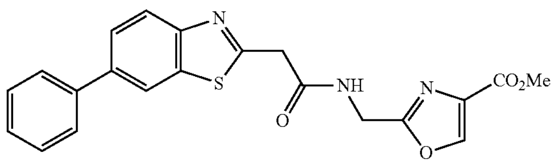 [SMILES: COC(=O)c1coc(CNC(=O)Cc2nc3ccc(-c4ccccc4)cc3s2)n1] | (CDCl3) δ: 3.92 (s, 3H), 4.16 (s, 2H), 4.71 (d, J = 5.6 Hz, 2H), 7.39 (t, J = 7.6 Hz, 1H), 7.48 (t, J = 7.4 Hz, 2H), 7.64 (d, J = 7.6 Hz, 2H), 7.74 (d, J = 8.6 Hz, 1H), 8.06-8.08 (m, 2H), 8.16 (br s, 1H), 8.19 (s, 1H). | | | |

TABLE 57

| No. | Structure | NMR(δ) | retention time | Mass | method |
|---|---|---|---|---|---|
| II-2-37 | 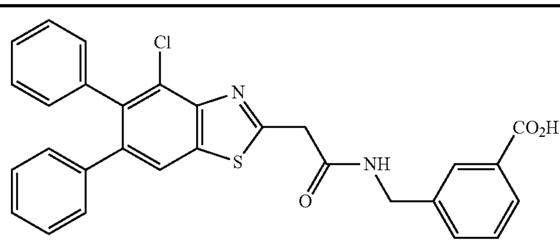 | (DMSO-d6) δ: 4.23 (s, 2H), 4.43 (d, J = 5.6 Hz, 2H), 7.09-7.59 (m, 13H), 7.84 (d, J = 7.6 Hz, 1H), 7.91 (s, 1H), 8.09 (s, 1H), 8.99 (t, J = 5.6 Hz, 1H). | | | |
| II-2-38 | 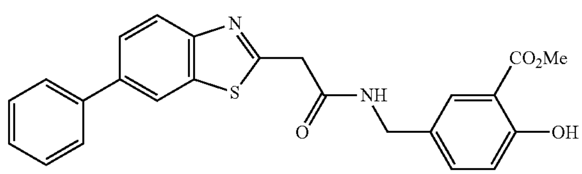 [SMILES: COC(=O)c1cc(CNC(=O)Cc2nc3ccc(-c4ccccc4)cc3s2)ccc1O] | 1H-NMR (DMSO-d6) δ: 3.90 (s, 3H), 4.17 (s, 2H), 4.31 (d, J = 5.7 Hz, 2H), 6.99 (d, J = 8.6 Hz, 1H), 7.45-7.52 (m, 4H), 7.73-7.96 (m, 4H), 8.04 (d, J = 8.4 Hz, 1H), 8.41-8.41 (m, 1H), 8.89-8.91 (m, 1H), 10.45 (s, 1H). | | | |
| II-2-39 | 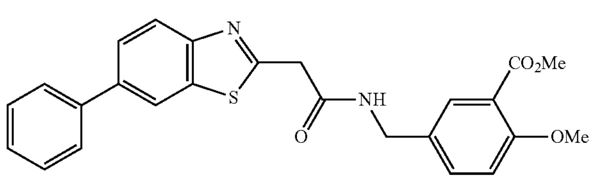 [SMILES: COC(=O)c1cc(CNC(=O)Cc2nc3ccc(-c4ccccc4)cc3s2)ccc1OC] | 1H-NMR (DMSO-d6) δ: 3.82 (s, 3H), 4.15 (s, 2H), 4.32 (d, J = 5.7 Hz, 2H), 7.11 (d, J = 8.7 Hz, 1H), 7.42-7.63 (m, 5H), 7.78-7.82 (m, 3H), 8.04 (d, J = 8.4 Hz, 1H), 8.40 (s, 1H), 8.88 (t, J = 5.8 Hz, 1H), 12.63 (s, 1H). | | | |
| II-2-40 | 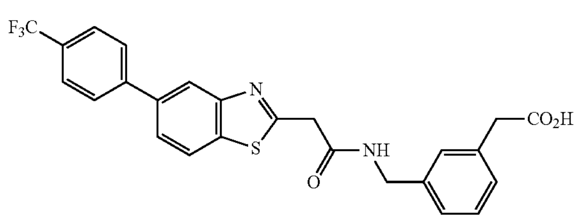 [SMILES: O=C(O)Cc1cccc(CNC(=O)Cc2nc3cc(-c4ccc(C(F)(F)F)cc4)ccc3s2)c1] | 1H-NMR (DMSO-d6) δ: 3.57 (s, 2H), 4.19 (s, 2H), 4.37 (d, J = 5.5 Hz, 2H), 7.19-7.31 (m, 5H), 7.83-7.88 (m, 3H), 8.04 (d, J = 8.1 Hz, 2H), 8.23 (d, J = 8.2 Hz, 2H), 8.34 (s, 1H), 8.92 (s, 1H), 12.39 (s, 1H). | | | |

TABLE 57-continued

| No. | Structure | NMR(δ) | retention time | Mass | method |
|---|---|---|---|---|---|
| II-2-41 | 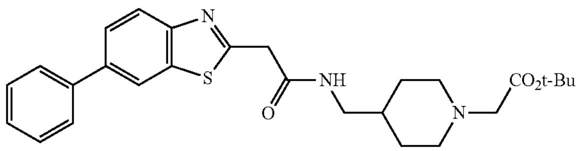 [SMILES: CC(C)(C)OC(=O)CN1CCC(CNC(=O)Cc2nc3ccc(-c4ccccc4)cc3s2)CC1] | 1H-NMR (CDCl3) δ: 1.38-1.45 (m, 11H), 1.67-1.69 (m, 3H), 2.17-2.19 (m, 2H), 2.94-2.97 (m, 2H), 3.11 (s, 2H), 3.23 (t, J = 6.3 Hz, 2H), 4.08 (s, 2H), 7.38-7.40 (m, 2H), 7.48 (t, J = 7.6 Hz, 2H), 7.64 (d, J = 7.6 Hz, 2H), 7.73 (dd, J = 8.6, 1.5 Hz, 1H), 8.05 (dd, J = 11.7, 5.1 Hz, 2H). | | | |

TABLE 58

| No. | Structure | NMR(δ) | retention time | Mass | method |
|---|---|---|---|---|---|
| II-2-42 | 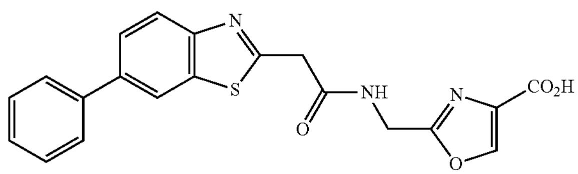 [SMILES: O=C(Cc1nc2ccc(-c3ccccc3)cc2s1)NCc1nc(C(=O)O)co1] | (DMSO-d6) δ: 4.17 (s, 2H), 4.50 (d, J = 5.6 Hz, 2H), 7.39 (t, J = 7.4 Hz, 1H), 7.50 (t, J = 7.6 Hz, 2H), 7.74-7 80 (m, 3H), 8.02 (d, J = 8.6 Hz, 1H), 8.38 (d, J = 1.0 Hz, 1H), 8.64 (s, 1H), 9.11 (br s, 1H). | | | |
| II-2-43 | 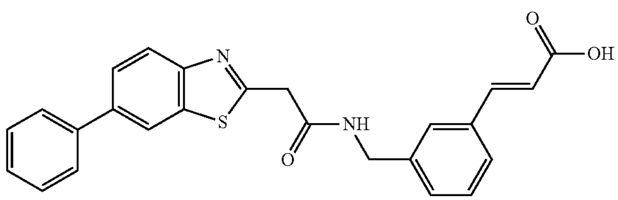 [SMILES: O=C(O)/C=C/c1cccc(CNC(=O)Cc2nc3ccc(-c4ccccc4)cc3s2)c1] | (DMSO-d6) δ: 4.17 (s, 2H), 4.38 (d, J = 5.7 Hz, 2H), 6.53 (d, J = 15.3 Hz, 1H), 7.35-7.42 (m, 3H), 7.52 (t, J = 7.5 Hz, 2H), 7.63 (d, J = 9.6 Hz, 2H), 7.74-7.81, (m, 3H), 8.04 (d, J = 5.4 Hz, 1H), 8.37 (t, J = 1.2 Hz, 1H), 8.89 (t. J = 5.7 Hz, 1H), 12.41 (brs, 1H). | | | |
| II-2-44 | 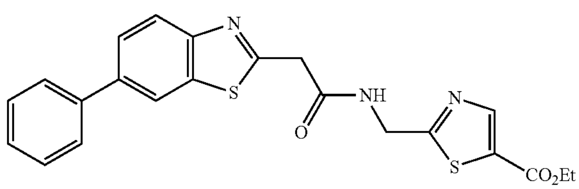 [SMILES: CCOC(=O)c1cnc(CNC(=O)Cc2nc3ccc(-c4ccccc4)cc3s2)s1] | (CDCl3) δ: 1.35 (t, J = 7.1 Hz, 3H), 4.17 (s, 2H), 4.34 (q, J = 7.1 Hz, 2H), 4.83 (d, J = 6.1 Hz, 2H), 7.39 (t, J = 7.4 Hz, 1H), 7.48 (t, J = 7.4 Hz, 2H), 7.64 (d, J = 7.1 Hz, 2H), 7.74 (dd, J = 8.6. 1.5 Hz, 1H), 8.04-8.08 (m, 2H), 8.29 (s, 1H), 8.32 (br s, 1H). | | | |
| II-2-45 | 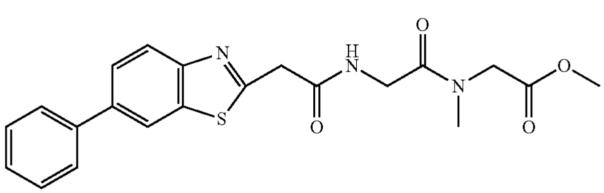 [SMILES: COC(=O)CN(C)C(=O)CNC(=O)Cc1nc2ccc(-c3ccccc3)cc2s1] | (DMSO-d6) δ: 3.01-3.06 (m, 3H), 3.74-3.78 (m, 3H), 4.11-4.22 (m, 6H), 7.38 (t, J = 7.2 Hz, 1H), 7.47 (t, J = 7.8 Hz, 2H), 7.63 (d, J = 7.5 Hz, 2H), 7.71 (dd, J = 9.0, 2.1 Hz, 2H), 8.02-8.10 (m, 2H) | | | |
| II-2-46 | 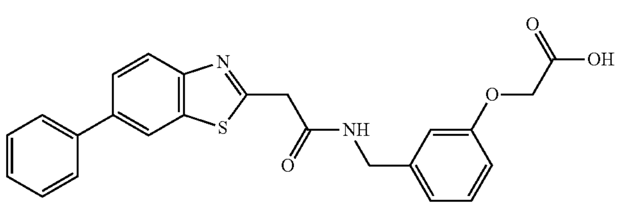 [SMILES: O=C(O)COc1cccc(CNC(=O)Cc2nc3ccc(-c4ccccc4)cc3s2)c1] | (DMSO-d6) δ: 4.15 (s, 2H), 4.32 (d, J = 5.7 Hz, 2H), 4.63 (s, 2H), 6.77-6.80 (m, 1H), 6.88-6.91 (m, 2H), 7.23 (t, J = 7.8 Hz, 1H), 7.39 (t, J = 7.5 Hz, 1H), 7.50 (t, J = 7.2 Hz, 2H), 7.74-7.81 (m, 3H), 8.03 (d, J = 5.7 Hz, 1H), 8.37 (d, J = 1.5 Hz, 1H), 8.85 (t, J = 5.7 Hz, 1H), 12.96 (brs, 1H). | | | |

TABLE 59

| No. | Structure | NMR(δ) | retention time | Mass | method |
|---|---|---|---|---|---|
| II-2-47 | 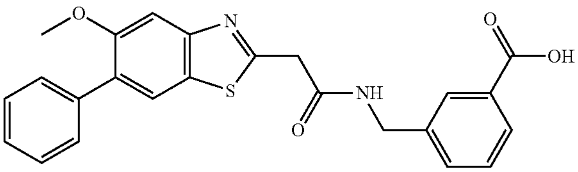 [SMILES: COc1cc2nc(CC(=O)NCc3cccc(C(=O)O)c3)sc2cc1-c1ccccc1] | (DMSO-d6) δ: 4.15 (s, 2H), 4.32 (d, J = 5.7 Hz, 2H), 4.64 (s, 2H), 6.77-6.81 (m, 1H), 6.88-6.91 (m, 2H), 7.24 (t, J = 7.5 Hz, 1H), 7.74-7.81 (m, 3H), 8.03 (d, J = 5.4 Hz, 1H), 8.38 (d, J = 1.5 Hz, 1H), 8.67 (t, J = 5.4 Hz, 1H), 12.96 (brs, 1H). | | | |
| II-2-48 | 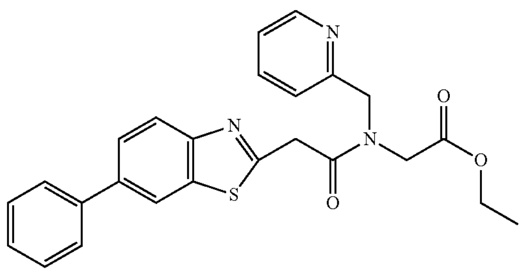 [SMILES: CCOC(=O)CN(Cc1ccccn1)C(=O)Cc1nc2ccc(-c3ccccc3)cc2s1] | (CDCl3) δ: 1.19-1.28 (m, 3H), 4.08-4.26 (m, 4H), 4.41 (d, J = 17 Hz, 2H), 4.83 (d, J = 23 Hz, 2H), 7.18-7.23 (m, 2H), 737-7.49 (m, 4H), 7.63-7.71 (m, 4H), 7.96-8.06 (m, 2H), 8.49-8.58 (m, 1H) | | | |
| II-2-49 | 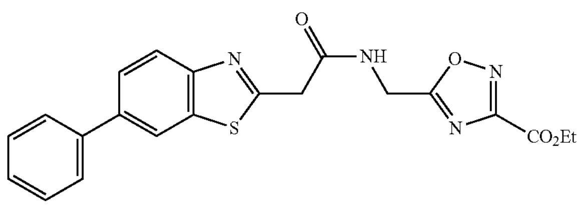 [SMILES: CCOC(=O)c1noc(CNC(=O)Cc2nc3ccc(-c4ccccc4)cc3s2)n1] | (DMSO-d$_6$) δ: 1.32 (t, J = 7.10 Hz, 3H) 4.40 (q, J = 7.10 Hz, 2H), 4.21 (s, 2H), 4.74 (d, J = 5.58 Hz, 2H), 7.39 (m, 1H), 7.50 (t, J = 7.60 Hz, 2H), 7.73-7.82 (m, 3H), 8.02 (d, J = 8.11 Hz, 1H). 8.39 (d, J = 1.01 Hz, 1H), 9.28 (t, J = 5.58 Hz, 1H). | | | |
| II-2-50 | 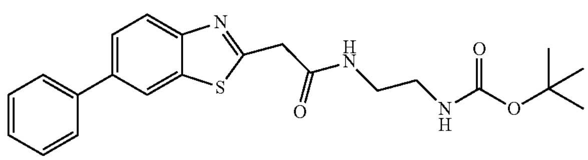 [SMILES: CC(C)(C)OC(=O)NCCNC(=O)Cc1nc2ccc(-c3ccccc3)cc2s1] | (CDCl3) δ: 1.40 (s, 9H), 3.30 (m, 2H), 4.07 (s, 2H), 4.96 (br-s, 1H), 7.38-7.50, (m, 4H), 7.62-7.73 (m, 3H), 8.05-8.08 (m, 2H) | | | |
| II-2-51 | 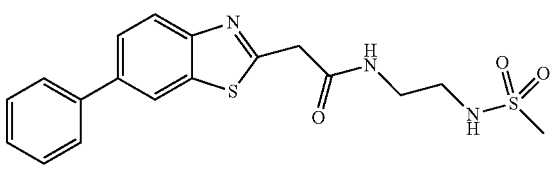 [SMILES: CS(=O)(=O)NCCNC(=O)Cc1nc2ccc(-c3ccccc3)cc2s1] | (CDCl3) δ: 2.91 (s, 3H), 3.04 (m, 2H), 3.24 (q, J = 6.0 Hz, 2H), 4.08 (s, 2H), 7.10 (br-s, 1H), 7.39 (t, J = 7.5 Hz, 1H), 7.50 (t, J = 8.1 Hz, 2H), 7.73-7.81 (m, 3H), 8.02 (d, J = 8.7 Hz, 1H), 8.38 (s, 1H), 8.47 (br-s, 1H) | | | |

TABLE 60

| No. | Structure | NMR(δ) | retention time | Mass | method |
|---|---|---|---|---|---|
| II-2-52 | 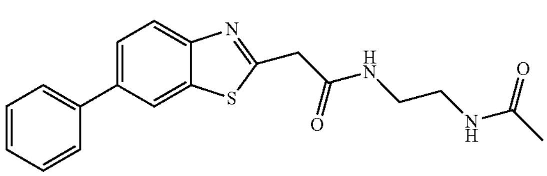 [SMILES: CC(=O)NCCNC(=O)Cc1nc2ccc(-c3ccccc3)cc2s1] | (DMSO-d6) δ: 1.80 (s, 3H), 3.11-3.18 (m, 4H), 4.06 (s, 2H), 7.39 (t, J = 6.6 Hz, 1H), 7.49 (t, J = 8.1 Hz, 2H), 7.73-7.80 (m, 3H), 7.91 (m, 1H), 8.06 (d, J = 8.4 Hz, 1H), 8.38 (s, 1H), 8.42 (m, 1H) | | | |

TABLE 60-continued
| No. | Structure | NMR(δ) | retention time | Mass | method |
|---|---|---|---|---|---|
| II-2-53 | 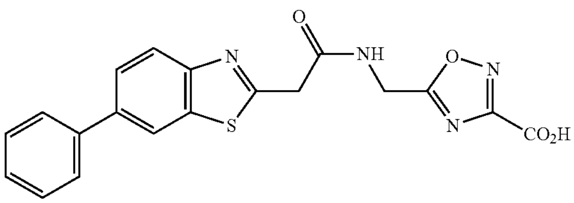 [SMILES: O=C(Cc1nc2ccc(-c3ccccc3)cc2s1)NCc1nc(C(=O)O)no1] | (DMSO-d6) δ: 3.57 (d, J = 5.07 Hz, 2H), 4.13 (s, 2H), 7.38 (m, 1H), 7.46-7.52 (m, 2H), 7.73-7.80 (m, 3H), 8.00 (d, J = 8.62 Hz, 1H), 8.18 (t, J = 5.07 Hz, 1H), 8.36 (d, J = 1.52 Hz, 1H). | | | |
| II-2-54 | 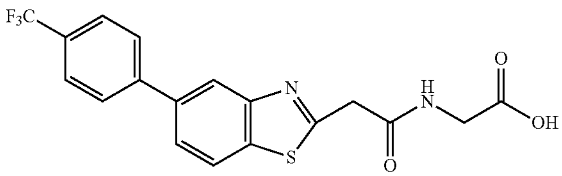 [SMILES: O=C(O)CNC(=O)Cc1nc2cc(-c3ccc(C(F)(F)F)cc3)ccc2s1] | (DMSO-d6) δ: 3.85 (d, J = 5.7 Hz, 2H), 4.18 (s, 2H), 7.78-7.86 (m, 4H), 7.98-8.02 (m, 3H), 8.20 (d, J = 8.4 Hz, 1H), 8.31 (s, 1H), 8.72 (m, 1H) | | | |
| II-2-55 | 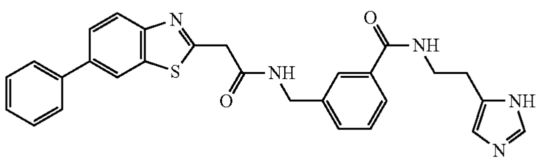 [SMILES: O=C(Cc1nc2ccc(-c3ccccc3)cc2s1)NCc1cccc(C(=O)NCCc2cnc[nH]2)c1] | 1H-NMR (DMSO-d6) δ: 2.57-2.97 (m, 2H), 3.46-3.50 (m, 2H), 4.16 (s, 2H), 4.40 (d, J = 5.6 Hz, 2H), 6.67-6.88 (m, 1H), 7.41-7.49 (m, 6H), 7.71- 7.80 (m, 5H), 8.02 (d, J = 8.1 Hz, 1H), 8.38 (s, 1H), 8.58-8.59 (m, 1H), 8.95-8.97 (m, 1H), 11.82-12.00 (m, 1H). | | | |
| II-2-56 | 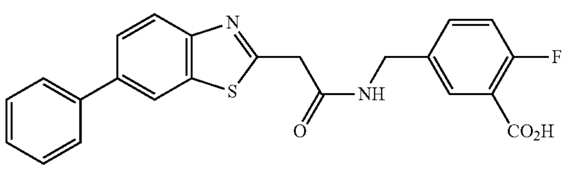 [SMILES: O=C(Cc1nc2ccc(-c3ccccc3)cc2s1)NCc1ccc(F)c(C(=O)O)c1] | 1H-NMR (DMSO-d6) δ: 4.17 (s, 2H), 4.39 (d, J = 5.7 Hz, 2H), 7.42-7 55 (m, 6H), 7 78-7.84 (m, 5H), 8.05 (d, J = 8.7 Hz, 1H), 8.40 (s, 1H), 8.96 (s, 1H), 13.30 (s, 1H). | | | |
TABLE 61
| No. | Structure | NMR(δ) | retention time | Mass | Method |
|---|---|---|---|---|---|
| II-2-57 | 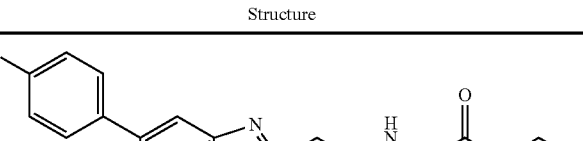 | | 2.12 | 432.95 | C |
| II-2-58 | 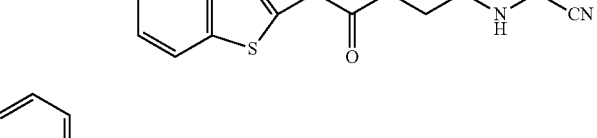 | (DMSO-d6) δ: 3.83 (s, 3H), 4.09 (s, 2H), 4.41 (d, J = 5.7 Hz, 2H), 7.33-7.38 (m, 1H), 7.41-7.56 (m, 6H), 7.79 (d, J = 5.7 Hz, 2H), 7.83 (d, J = 7.8 Hz, 1H), 7.91 (s, 1H), 8.91 (t, J = 5.7 Hz, 1H), 12.96 (brs. 1H). | | | |

TABLE 61-continued

| No. | Structure | NMR(δ) | retention time | Mass | Method |
|---|---|---|---|---|---|
| II-2-59 | 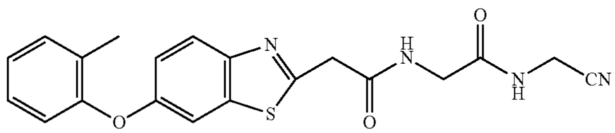 [SMILES: Cc1ccccc1Oc1ccc2nc(CC(=O)NCC(=O)NCC#N)sc2c1] | (DMSO-d6) δ: 2.20 (s, 3H), 3.81 (d, J = 6.0 Hz, 2H), 4.09 (s, 2H), 4.16 (d, J = 5.7 Hz, 2H), 6.93 (d, J = 7.8 Hz, 1H), 7.08-7.15 (m, 2H), 7.23 (t, J = 8.1 Hz, 1H), 7.34 (d, J = 7.2 Hz, 1H), 7.54 (s, 1H), 7.92 (d, J = 9.0 Hz, 1H), 8.66-8.69 (m, 2H) | | | |
| II-2-60 | 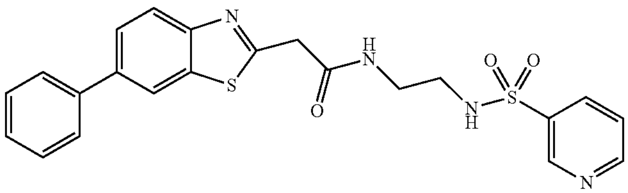 [SMILES: O=C(Cc1nc2ccc(-c3ccccc3)cc2s1)NCCNS(=O)(=O)c1cccnc1] | (DMSO-d6) δ: 2.89 (q, J = 6.0 Hz, 2H), 3.18 (q, J = 6.0 Hz, 2H), 4.03 (s, 2H), 7.39-7.81 (m, 6H), 7.99-8.02 (m, 2H), 8.19 (m, 1H), 8.37 (s, 1H), 8.43 (m, 1H), 8.82 (d, J = 6.0 Hz, 1H), 8.95 (s, 1H) | | | |
| II-2-61 | 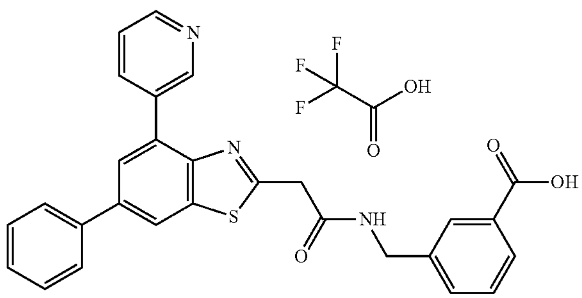 [SMILES: O=C(Cc1nc2c(-c3cccnc3)cc(-c3ccccc3)cc2s1)NCc1cccc(C(=O)O)c1 ; O=C(O)C(F)(F)F] | (DMSO-d6) δ: 4.20 (s, 2H), 4.41 (d, J = 5.7 Hz, 2H), 7.38-7.48 (m, 2H), 7.53 (t, J = 6.6 Hz, 3H), 7.8-7.92 (m, 5H), 8.04 (s, 1H), 8.32 (s, 1H), 8.71-8.89 (m, 2H), 8.95 (t, J = 5.7 Hz, 1H), 9.34 (s, 1H). | | | |

TABLE 62

| No. | Structure | NMR(δ) | retention time | Mass | method |
|---|---|---|---|---|---|
| II-2-62 | 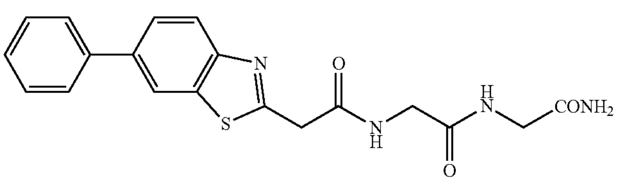 [SMILES: NC(=O)CNC(=O)CNC(=O)Cc1nc2ccc(-c3ccccc3)cc2s1] | (DMSO-d$_6$) δ: 3.66 (d, J = 6.08 Hz, 2H), 3.82 (d, J = 5.58 Hz, 2H), 4.17 (s, 2H), 7.09 (s, 1H), 7.25 (s, 1H), 7.39 (m, 1H), 7.47-7.52 (m, 2H), 7.73-7.81 (m, 3H), 8.01 (d, J = 8.62 Hz, 1H), 8.23 (t, J = 5.83 Hz, 1H), 8.38 (d, J = 1.01 Hz, 1H), 8.69 (t, J = 5.58 Hz, 1H). | | | |
| II-2-63 | 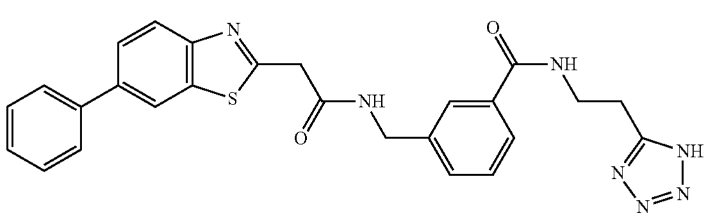 [SMILES: O=C(Cc1nc2ccc(-c3ccccc3)cc2s1)NCc1cccc(C(=O)NCCc2nnn[nH]2)c1] | 1H-NMR (DMSO-d6) δ: 3.10 (t, J = 7.1 Hz, 2H), 3.60-3.61 (m, 2H), 4.16 (s, 2H), 4.39 (d, J = 6.1 Hz, 2H), 7.37-7.51 (m, 5H), 7.75 (tt, J = 19.3, 6.5 Hz, 5H), 8.2 (d, J = 8.6 Hz, 1H), 8.38 (s, 1H), 8.64-8.65 (m, 1H), 8.92 (t, J = 5.6 Hz, 1H). | | | |

TABLE 62-continued

| No. | Structure | NMR(δ) | retention time | Mass | method |
|---|---|---|---|---|---|
| II-2-64 | 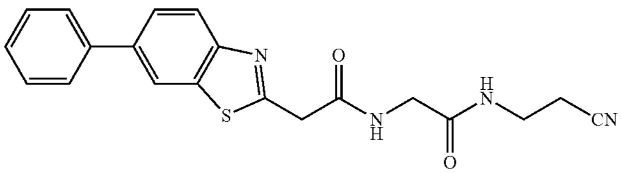 [SMILES: N#CCCNC(=O)CNC(=O)Cc1nc2ccc(-c3ccccc3)cc2s1] | (DMSO-d$_6$) δ: 2.65 (t, J = 6.34 Hz, 2H), 3.33 (dt, J = 6.34, 5.58 Hz, 2H), 3.79 (d, J = 6.08 Hz, 2H), 4.16 (s, 2H), 7.39 (m, 1H), 7.47-7.52 (m, 2H), 7.73-7.81 (m, 3H), 8.01 (d, J = 8.62 Hz, 1H), 8.34 (t, J = 5.58 Hz, 1H), 8.38 (d, J = 1.01 Hz, 1H), 8.67 (t, J = 5.58 Hz, 1H). | | | |
| II-2-65 | 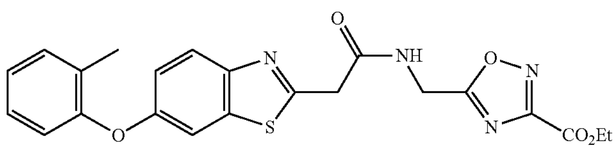 [SMILES: CCOC(=O)c1noc(CNC(=O)Cc2nc3ccc(Oc4ccccc4C)cc3s2)n1] | (DMSO-d$_6$) δ: 1.31 (t, J = 7.10 Hz, 3H), 2.20 (s, 3H), 4.14 (s, 2H), 4.40 (q, J = 7.27 Hz, 2H), 4.72 (d, J = 5.58 Hz, 2H), 6.93 (d, J = 8.11 Hz, 1H), 7.09-7.15 (m, 2H), 7.23 (m, 1H), 7.34 (d, J = 7.60 Hz, 1H), 7.54 (d, J = 2.53 Hz, 1H), 7.92 (d, J = 9.12 Hz, 1H), 9.25 (t, J = 5.58 Hz, 1H). | | | |
| II-2-66 | 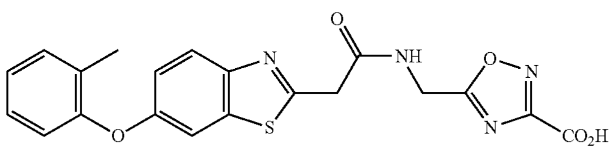 [SMILES: Cc1ccccc1Oc1ccc2nc(CC(=O)NCc3nc(C(=O)O)no3)sc2c1] | (DMSO-d$_6$) δ: 2.20 (s, 3H), 3.55 (d, J = 5.07 Hz, 2H), 4.06 (s, 2H), 6.92 (d, J = 8.11 Hz, 1H), 7.06-7.14 (m, 2H), 7.22 (m, 1H), 7.34 (d, J = 7.60 Hz, 1H), 7.53 (d, J = 2.53 Hz, 1H), 7.90 (d, J = 8.62 Hz, 1H), 8.15 (t, J = 5.07 Hz, 1H). | | | |

TABLE 63

| No. | Structure | NMR(δ) | retention time | Mass | method |
|---|---|---|---|---|---|
| II-2-67 | 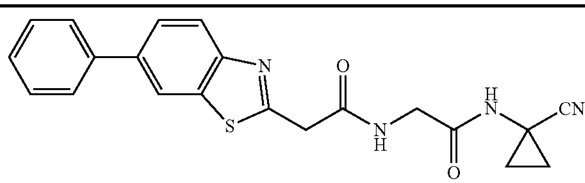 | (DMSO-d$_6$) δ: 1.13 (dd, J = 8.36, 5.32 Hz, 2H), 1.49 (dd, J = 8.36, 5.32 Hz, 2H), 3.78 (d, J = 5.58 Hz, 2H), 4.16 (s, 2H), 7.39 (m, 1H), 7.47-7.52 (m, 2H), 7.74-7.81 (m, 3H), 8.01 (d, J = 8.62 Hz, 1H), 8.38 (d, J = 1.01 Hz, 1H), 8.68 (t, J = 5.58 Hz, 1H), 8.92 (s, 1H). | | | |
| II-2-68 | 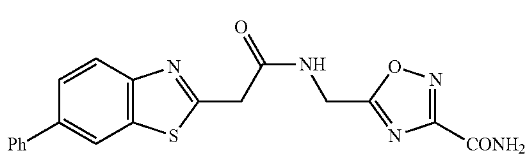 [SMILES: NC(=O)c1noc(CNC(=O)Cc2nc3ccc(-c4ccccc4)cc3s2)n1] | (DMSO-d$_6$) δ: 4.21 (s, 2H), 4.71 (d, J = 5.58 Hz, 2H), 7.39 (m, 1H), 7.47-7.52 (m, 2H), 7.73-7.82 (m, 3H), 8.02 (d, J = 8.62 Hz, 1H), 8.10 (brs, 1H), 8.31 (brs, 1H), 8.39 (d, J = 1.52 Hz, 1H), 9.26 (t, J = 5.58 Hz, 1H). | | | |
| II-2-69 | 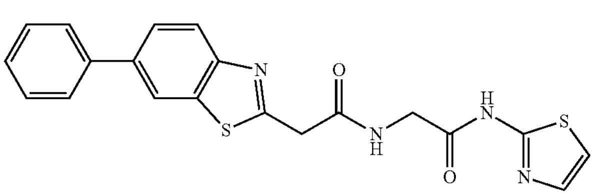 [SMILES: O=C(Cc1nc2ccc(-c3ccccc3)cc2s1)NCC(=O)Nc1nccs1] | (DMSO-d$_6$) δ: 4.10 (d, J = 6.08 Hz, 2H), 4.19 (s, 2H), 7.23 (d, J = 3.55 Hz, 1H), 7.39 (m, 1H), 7.46-7.53 (m, 3H), 7.73-7.82 (m, 3H), 8.04 (d, J = 8.62 Hz, 1H), 8.39 (s, 1H), 8.81 (t, J = 5.58 Hz, 1H), 12.21 (s, 1H). | | | |

TABLE 63-continued

| No. | Structure | NMR(δ) | retention time | Mass | method |
|---|---|---|---|---|---|
| II-2-70 | 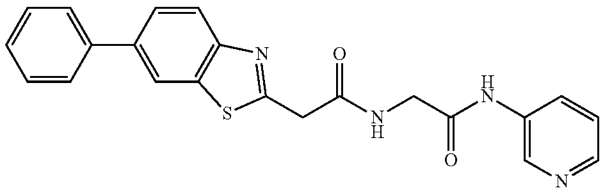 [SMILES: O=C(Cc1nc2ccc(-c3ccccc3)cc2s1)NCC(=O)Nc1cccnc1] | (DMSO-d₆) δ: 4.02 (d, J = 5.58 Hz, 2H), 4.20 (s, 2H), 7.34-7.41 (m, 2H), 7.47-7.52 (m, 2H), 10.27 (s, 1H), 7.73-7.81 (m, 3H), 8.00-8.04 (m, 2H), 8.28 (m, 1H), 8.39 (d, J = 1.52 Hz, 1H), 8.74 (d, J = 2.53 Hz, 1H), 8.79 (t, J = 5.83 Hz, 1H). | | | |
| II-2-71 | 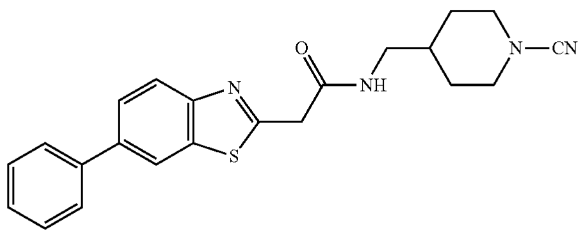 [SMILES: N#CN1CCC(CNC(=O)Cc2nc3ccc(-c4ccccc4)cc3s2)CC1] | 1H-NMR (DMSO-d6) δ: 1.19-1.24 (m, 2H), 1.57-1.68 (m, 3H), 2.99-3.03 (m, 4H), 3.36-3.39 (m, 2H), 4.05 (s, 2H), 7.39 (t, J = 7.4 Hz, 1H), 7.50 (t, J = 7.6 Hz, 2H), 7.76-7.78 (m, 3H), 8.00 (d, J = 8.6 Hz, 1H), 8.37-8.43 (m, 2H). | | | |

TABLE 64

| No. | Structure | NMR(δ) | retention time | Mass | method |
|---|---|---|---|---|---|
| II-2-72 | 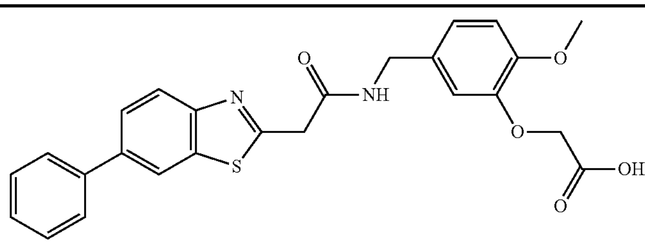 | (DMSO-d6) δ: 3.75 (s, 3H), 4.12 (s, 2H), 4.25 (d, J = 5.7 Hz, 2H), 6.84-6.95 (m, 3H), 7.37-7.41 (m, 3H), 7.74-7.53 (m, 3H), 8.02 (d, J = 5.7 Hz, 1H), 8.38 (d, J = 1.6 Hz, 1H), 8.79 (t, J = 5.7 Hz, 1H), 12.97 (brs, 1H). | | | |
| II-2-73 | 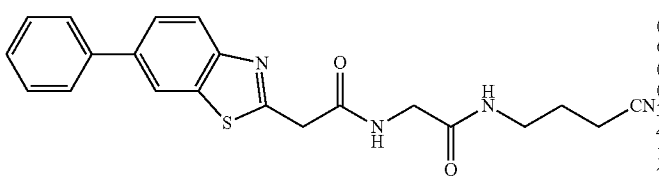 [SMILES: N#CCCCNC(=O)CNC(=O)Cc1nc2ccc(-c3ccccc3)cc2s1] | (DMSO-d₆) δ: 1.70 (tt, J = 6.25, 7.35 Hz, 2H), 2.48 (t, J = 7.35 Hz, 2H), 3.17 (dt, J = 6.25, 5.58 Hz, 2H), 3.75 (d, J = 5.58 Hz, 2H), 4.15 (s, 2.0H), 7.39 (m, 1.0H), 7.47-7.52 (m, 2.0H), 7.73-7.81 (m, 3.0H), 8.01 (d, J = 8.11 Hz, 1.0H), 8.04 (t, J = 5.58 Hz, 1.0H), 8.38 (t, J = 1.01 Hz, 1.0H), 8.64 (t, J = 5.58 Hz, 1.0H). | | | |
| II-2-74 | 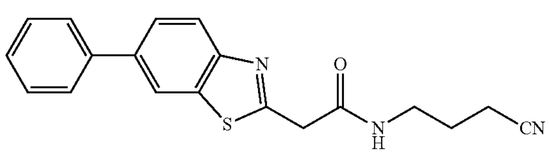 [SMILES: N#CCCCNC(=O)Cc1nc2ccc(-c3ccccc3)cc2s1] | (DMSO-d₆) δ: 1.75 (tt, J = 7.10, 6.59 Hz, 2H), 2.54 (t, J = 6.59 Hz, 2H), 3.21 (dt, J = 7.10, 5.58 Hz, 2H), 4.06 (s, 2H), 7.38 (m, 1H), 7.50 (m, 1H), 7.73-7.81 (m, 3H), 8.01 (d, J = 8.62 Hz, 1H), 8.38 (d, J = 1.01 Hz, 1H), 8.46 (t, J = 5.58 Hz, 1H). | | | |
| II-2-75 | 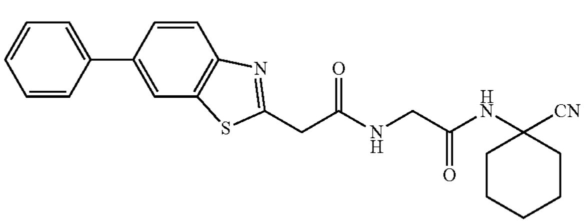 [SMILES: N#CC1(NC(=O)CNC(=O)Cc2nc3ccc(-c4ccccc4)cc3s2)CCCCC1] | (DMSO-d₆) δ: 1.21-1.70 (br m, 8H), 2.14-2.21 (m, 2H), 3.85 (d, J = 6.08 Hz, 2H), 4.16 (s, 2H), 7.39 (m, 1H), 7.47-7.52 (m, 2H), 7.73-7.81 (m, 3H), 8.01 (d, J = 8.11 Hz, 1H), 8.39 (d, J = 3.04 Hz, 2.0H), 8.65 (t, J = 5.58 Hz, 1.0H). | | | |

TABLE 64-continued

| No. | Structure | NMR(δ) | retention time | Mass | method |
|---|---|---|---|---|---|
| II-2-76 | 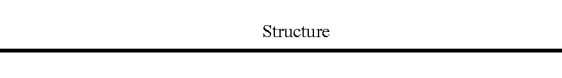 | 1H-NMR (DMSO-d6) δ: 1.21-1.23 (m, 2H), 1.55-1.59 (m, 1H), 1.76 (d, J = 12.2 Hz, 2H), 2.67 (t, J = 11.7 Hz, 2H), 2.83-2.84 (m, 3H), 3.06-3.07 (m, 2H), 3.55 (d, J = 11.2 Hz, 2H), 4.08 (s, 2H), 7.38-7.40 (m, 1H), 7.49-7.51 (m, 2H), 7.74-7.80 (m, 3H), 8.00-8.02 (m, 1H), 8.39-8.43 (m, 2H). | | | |

TABLE 65

| No. | Structure | NMR(δ) | retention time | Mass | method |
|---|---|---|---|---|---|
| II-2-77 | 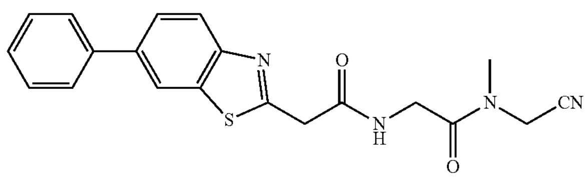 [SMILES: CN(CC#N)C(=O)CNC(=O)Cc1nc2ccc(-c3ccccc3)cc2s1] | (DMSO-d6) δ: 2.90-3.09 (m, 3H), 4.11 (d, J = 5.58 Hz, 2H), 4.19 (s, 2H), 4.40-4.67 (m, 2H), 7.39 (m, 1H), 7.47-7.52 (m, 2H), 7.73-7.81 (m, 3H), 8.01 (d, J = 8.62 Hz, 1H), 8.38 (d, J = 1.01 Hz, 1H), 8.62 (t, J = 5.58 Hz, 1H) | | | |
| II-2-78 | 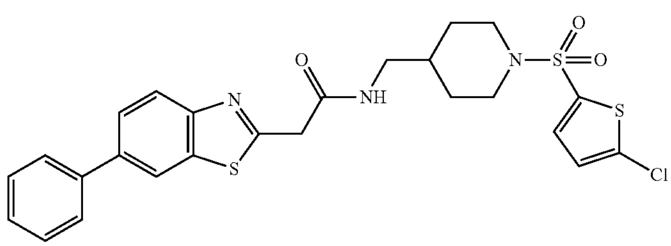 [SMILES: O=C(Cc1nc2ccc(-c3ccccc3)cc2s1)NCC1CCN(S(=O)(=O)c2ccc(Cl)s2)CC1] | 1H-NMR (DMSO-d6) δ: 1.22-1.25 (m, 2H), 1.43-1.55 (m, 1H), 1.74-1.76 (m, 2H), 2.39-2.42 (m, 2H), 3.03 (t, J = 6.1 Hz, 2H), 3.61 (d, J = 11.7 Hz, 2H), 4.06 (s, 2H), 7.36-7.40 (m, 2H), 7.48-7.54 (m, 3H), 7.76-7.78 (m, 3H), 8.00 (d, J = 8.6 Hz, 1H), 8.37-8.38 (m, 2H). | | | |
| II-2-79 | 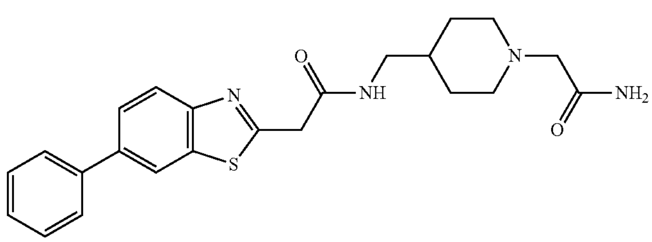 [SMILES: NC(=O)CN1CCC(CNC(=O)Cc2nc3ccc(-c4ccccc4)cc3s2)CC1] | 1H-NMR (DMSO-d6) δ: 1.22-1.25 (m, 2H), 1.38-1.42 (m, 1H), 1.63 (d, J = 11.2 Hz, 2H), 1.97-2.01 (m, 2H), 2.78-2.81 (m, 4H), 3.02 (t, J = 6.1 Hz, 2H), 4.07 (s, 2H), 7.09-7.11 (m, 2H), 7.39 (t, J = 7.4 Hz, 1H), 7.50 (t, J = 7.6 Hz, 2H), 7.74-7.80 (m, 3H), 8.00 (d, J = 8.6 Hz, 1H), 8.36-8.37 (m, 2H). | | | |
| II-2-80 | 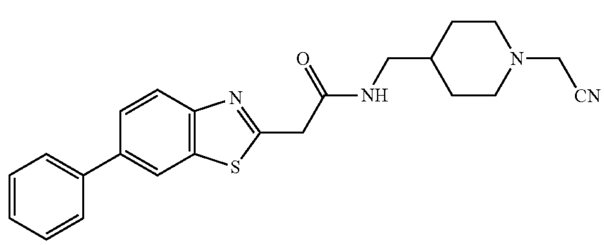 [SMILES: N#CCN1CCC(CNC(=O)Cc2nc3ccc(-c4ccccc4)cc3s2)CC1] | 1H-NMR (DMSO-d6) δ: 1.16-1.20 (m, 2H), 1.37-1.46 (m, 1H), 1.67-1.69 (m, 2H), 2.07-2.13 (m, 2H), 2.70-2.76 (m, 2H), 3.03 (t, J = 6.3 Hz, 2H), 3.68 (s, 2H), 4.04 (s, 2H), 7.39 (t, J = 7.4 Hz, 1H), 7.50 (t, J = 7.9 Hz, 2H), 7.74-7.80 (m, 3H), 8.00 (d, J = 8.6 Hz, 1H), 8.36-8.38 (m, 2H). | | | |

TABLE 65-continued

| No. | Structure | NMR(δ) | retention time | Mass | method |
|---|---|---|---|---|---|
| II-2-81 | 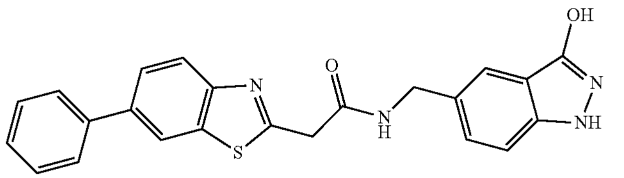 [SMILES: O=C(Cc1nc2ccc(-c3ccccc3)cc2s1)NCc1ccc2[nH]nc(O)c2c1] | 1H-NMR (DMSO-d6) δ: 4.13-4.15 (m, 2H), 4.39-4.40 (m, 2H), 7.23-7.26 (m, 2H), 7.43-7.50 (m, 4H), 7.75-7.80 (m, 3H), 8.02-8.04 (m, 1H), 8.38 (s, 1H), 8.86-8.87 (m, 1H), 10.54-10.67 (m, 1H), 11.29-11.34 (m, 1H). | | | |

TABLE 66

| No. | Structure | NMR(δ) | retention time | Mass | method |
|---|---|---|---|---|---|
| II-2-82 | 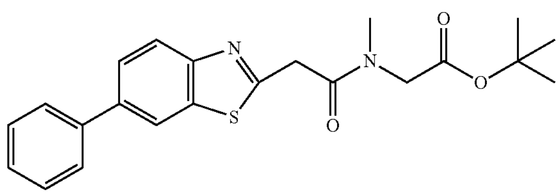 [SMILES: CN(CC(=O)OC(C)(C)C)C(=O)Cc1nc2ccc(-c3ccccc3)cc2s1] | (CDCl3) δ: 3.02-3.21 (m, 3H), 4.09-4.32 (m, 4H), 1.44-1.46 (m, 9H), 7.37 (m, 1H), 7.47 (t, J = 7.5 Hz, 2H), 7.63-7.71 (m, 3H), 8.02-8.07 (m, 2H) | | | |
| II-2-83 | 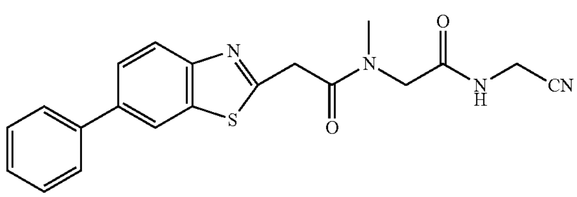 [SMILES: CN(CC(=O)NCC#N)C(=O)Cc1nc2ccc(-c3ccccc3)cc2s1] | (DMSO-d6) δ: 3.22 (s, 1H), 4.05 (s, 2H), 4.17-4.26 (m, 2H), 4.42 (s, 2H), 7.39 (m, 1H), 7.50 (t, J = 7.2 Hz, 2H), 7.74-7.81 (m, 3H), 8.01 (m, 1H), 8.38 (s, 1H), 8.66 (m, 1H) | | | |
| II-2-84 | 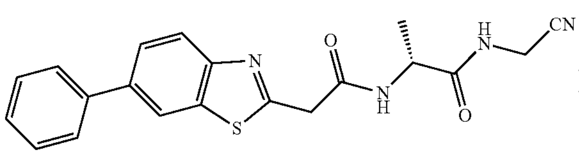 | 1H-NMR (DMSO-d6) δ: 1.27 (d, J = 3.5 Hz, 3H), 4.15-4.16 (m, 4H), 4.33-4.34 (m, 1H), 7.39-7.41 (m, 1H), 7.49-7.50 (m, 2H), 7.76-7.78 (m, 3H), 7.99-8.02 (m, 1H), 8.38 (s, 1H), 8.72-8.74 (m, 2H). | | | |
| II-2-85 | 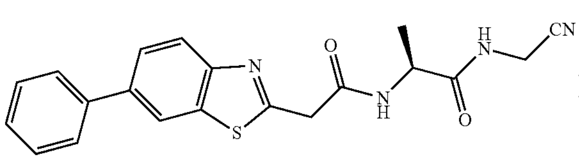 [SMILES: C[C@H](NC(=O)Cc1nc2ccc(-c3ccccc3)cc2s1)C(=O)NCC#N] | 1H-NMR (DMSO-d6) δ: 1.27 (d, J = 7.1 Hz, 3H), 4.14-4.16 (m, 4H), 4.33-4.35 (m, 1H), 7.38-7.40 (m, 1H), 7.50 (t, J = 7.6 Hz, 2H), 7.74-7.80 (m, 3H), 8.01 (d, J = 8.6 Hz, 1H), 8.38 (d, J = 1.5 Hz, 1H), 8.72-8.74 (m, 2H). | | | |

TABLE 66-continued

| No. | Structure | NMR(δ) | retention time | Mass | method |
|---|---|---|---|---|---|
| II-2-86 | (structure: 6-bromo-benzothiazol-2-yl-CH2-C(O)-NH-CH2-C(O)-O-tBu) | (CDCl3) δ: 1.46 (s, 9H), 4.00-4.14 (d, J = 5.1 Hz, 2H), 4.09 (s, 2H), 7.42 (br-s, 1H), 7.59 (m, J = 9.3 Hz, 1H), 7.88 (d, J = 8.7 Hz, 1H), 8.01 (s, 1H) | | | |

TABLE 67

| No. | Structure | NMR(δ) | retention time | Mass | method |
|---|---|---|---|---|---|
| II-2-87 | (6-phenyl-benzothiazol-2-yl-CH2-C(O)-NH-CH2-C≡CH) | (DMSO-d6) δ: 4.10-4.14 (m, 4H), 7.39-7.51 (m, 3H), 7.63-7.66 (m, 2H), 7.74 (m, 1H), 8.05-8.09 (m, 2H) | | | |
| II-2-88 | (6-bromo-benzothiazol-2-yl-CH2-C(O)-NH-CH2-C(O)-NH-CH2-CN) | (DMSO-d6) δ: 3.82 (2H, J = 6.0 Hz, dd), 4.15-4.17 (4H, m), 7.63 (1H, J = 9.3 Hz, d), 7.88 (d, J = 9.0 Hz, 1H), 8.36 (s, 1H), 8.68-8.74 (m, 2H) | | | |
| II-2-89 | (6-phenyl-benzothiazol-2-yl-CH2-C(O)-NH-CH2-C(O)-NH-CH(CH3)-CN) | (DMSO-d6) δ: 1.43 (d, J = 7.60 Hz, 3H), 3.77-3.88 (m, 2H), 4.16 (s, 2H), 4.79 (dq, J = 7.60, 7.10 Hz, 1H), 7.39 (m, 1H), 7.47-7.52 (m, 2H), 7.73-7.81 (m, 3H), 8.01 (d, J = 8.62 Hz, 1H), 8.38 (d, J = 1.52 Hz, 1H), 8.70 (t, J = 5.83 Hz, 1H), 8.75 (d, J = 7.10 Hz, 1H). | | | |
| II-2-90 | (6-phenyl-benzothiazol-2-yl-CH2-C(O)-NH-CH2-C(O)-NH-CH(CH3)-CN) | (DMSO-d6) δ: 1.43 (d, J = 7.60 Hz, 3H), 3.77-3.88 (m, 2H), 4.16 (s, 2H), 4.79 (dq, J = 7.60, 7.10 Hz, 1H), 7.39 (m, 1H), 7.47-7.52 (m, 2H), 7.73-7.81 (m, 3H), 8.01 (d, J = 8.62 Hz, 1H), 8.38 (d, J = 1.52 Hz, 1H), 8.70 (t, J = 5.83 Hz, 1H), 8.75 (d, J = 7.10 Hz, 1H). | | | |
| II-2-91 | (6-phenyl-benzothiazol-2-yl-CH2-C(O)-NH-CH2-C(O)-NH-pyridin-4-yl) | 1H-NMR (DMSO-d6) δ: 4.02 (d, J = 5.6 Hz, 2H), 4.20 (s, 2H), 7.39 (t, J = 7.4 Hz, 1H), 7.49-7.55 (m, 4H), 7.76-7.79 (m, 3H), 8.02 (d, J = 8.6 Hz, 1H), 8.39-8.44 (m, 3H), 8.80 (t, J = 5.6 Hz, 1H), 10.45 (s, 1H). | | | |

TABLE 68

| No. | Structure | NMR(δ) | retention time | Mass | method |
|---|---|---|---|---|---|
| II-2-92 | 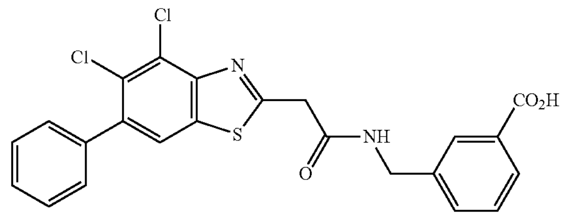 [SMILES: O=C(Cc1nc2c(Cl)c(Cl)c(-c3ccccc3)cc2s1)NCc1cccc(C(=O)O)c1] | (DMSO-d6) δ: 4.24 (s, 2H), 4.41 (d, J = 6.1 Hz, 2H), 7.41-7.53 (m, 7H), 7.82 (d, J = 7.6 Hz, 1H), 7.89 (s, 1H), 8.13 (s, 1H), 9.00 (t, J = 5.6 Hz, 1H). | | | |
| II-2-93 | 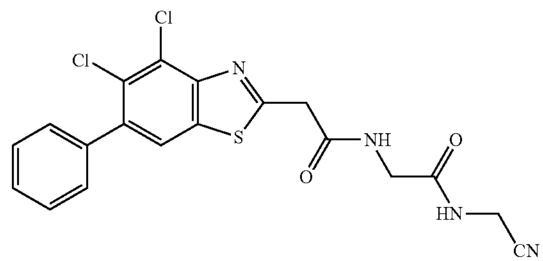 [SMILES: N#CCNC(=O)CNC(=O)Cc1nc2c(Cl)c(Cl)c(-c3ccccc3)cc2s1] | (DMSO-d6) δ: 3.84 (d, J = 5.6 Hz, 2H), 4.16 (d, J = 5.6 Hz, 2H), 4.25 (s, 2H), 7.45-7.52 (m, 5H), 8.14 (s, 1H), 8.70 (t, J = 5.3 Hz, 1H), 8.79 (t, J = 5.6 Hz, 1H). | | | |
| II-2-94 | 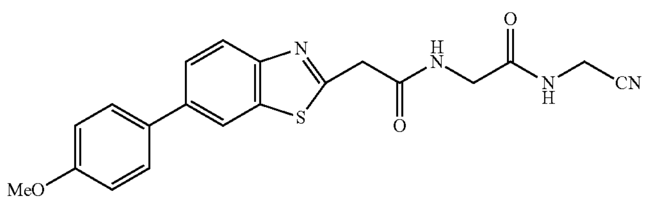 [SMILES: COc1ccc(-c2ccc3nc(CC(=O)NCC(=O)NCC#N)sc3c2)cc1] | | 1.8 | 394.95 (ES+) | C |
| II-2-95 | 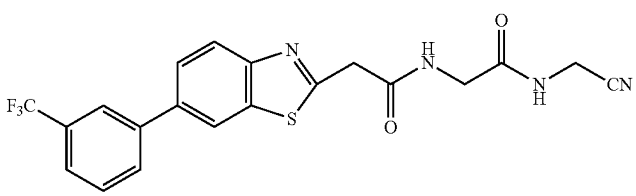 [SMILES: N#CCNC(=O)CNC(=O)Cc1nc2ccc(-c3cccc(C(F)(F)F)c3)cc2s1] | | 2.08 | 432.90 (ES+) | C |
| II-2-96 | 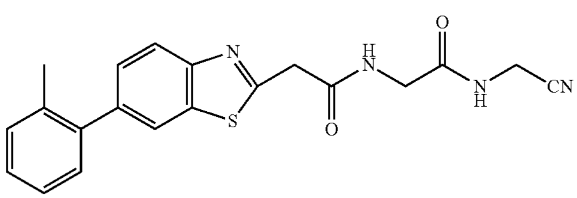 [SMILES: Cc1ccccc1-c1ccc2nc(CC(=O)NCC(=O)NCC#N)sc2c1] | (DMSO-d6) δ: 2.25 (3H, s), 3.83 (2H, J = 6.0 Hz, d), 4.16-4.18 (4H, m), 7.26-7.32 (m, 4H), 7.44 (d, J = 8.1 Hz, 1H), 8.03 (t, J = 8.4 Hz, 2H), 8.69-8.75 (m, 2H) | | | |

TABLE 69

| No. | Structure | NMR(δ) | retention time | Mass | method |
|---|---|---|---|---|---|
| II-2-97 | 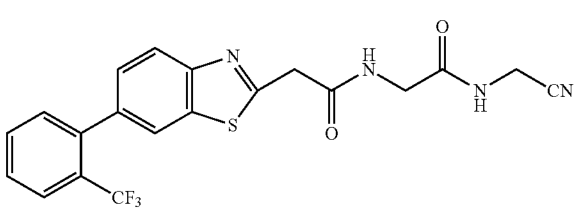 [SMILES: N#CCNC(=O)CNC(=O)Cc1nc2ccc(-c3ccccc3C(F)(F)F)cc2s1] | (DMSO-d6) δ: 3.83 (2H, J = 6.0 Hz, d), 4.16-4.18 (4H, m), 7.42 (1H, J = 9.3 Hz, d), 7.48 (1H, J = 7.5 Hz, d), 7.65-7.75 (m, 2H), 8.87 (d, J = 8.7 Hz, 1H), 1H), 7.98-8.04 (m, 2H), 8.69-8.74 (m, 2H) | | | |

TABLE 69-continued

| No. | Structure | NMR(δ) | retention time | Mass | method |
|---|---|---|---|---|---|
| II-2-98 | 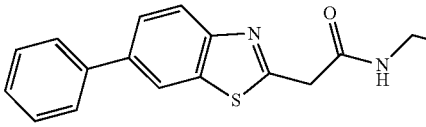 | 1H-NMR (DMSO-d6) δ: 1.37 (s, 9H), 2.98-3.00 (m, 2H), 3.09-3.11 (m, 2H), 3.75 (d, J = 6.1 Hz, 2H), 4.15 (s, 2H), 6.80-6.83 (m, 1H), 7.39-7.41 (m, 1H), 7.48-7.51 (m, 2H), 7.74-7.80 (m, 3H), 8.01-8.02 (m, 2H), 8.38 (d, J = 2.0 Hz, 1H), 8.60-8.63 (m, 1H). | | | |
| II-2-99 | 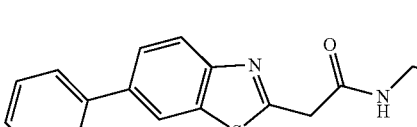 | 1H-NMR (DMSO-d6) δ: 2.12 (s, 6H), 2.27 (t, J = 6.8 Hz, 2H), 3.17 (q, J = 6.3 Hz, 2H), 3.75 (d, J = 6.1 Hz, 2H), 4.15 (s, 2H), 7.39-7.41 (m, 1H), 7.50 (t, J = 7.6 Hz, 2H), 7.76-7.79 (m, 3H), 7.84-7.87 (m, 1H), 8.01 (d, J = 8.6 Hz, 1H), 8.38 (d, J = 2.0 Hz, 1H), 8.62-8.64 (m, 1H). | | | |
| II-2-100 | 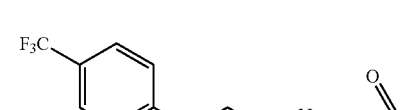 | (DMSO-d6) δ: 1.12 (dd, J = 8.11, 5.58 Hz, 2H), 1.49 (dd, J = 8.11, 5.58 Hz, 2H), 3.78 (d, J = 5.58 Hz, 2H), 4.18 (s, 2H), 7.78-7.87 (m, 3H), 8.01 (d, J = 8.62 Hz, 2H), 8.20 (d, J = 8.62 Hz, 1H), 8.31 (s, 1H), 8.69 (t, J = 5.58 Hz, 1H), 8.92 (s, 1H). | | | |
| II-2-101 | 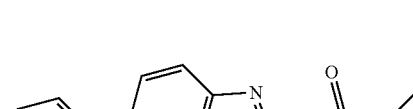 | 1H-NMR (DMSO-d6) δ: 2.38 (t, J = 7.1 Hz, 2H), 4.05 (s, 2H), 4.14 (d, J = 5.6 Hz, 2H), 7.40-7.41 (m, 1H), 7.50 (t, J = 7.6 Hz, 2H), 7.75-7.79 (m, 3H), 8.00 (d, J = 8.6 Hz, 1H), 8.37 (d, J = 1.5 Hz, 1H), 8.46-8.49 (m, 1H), 8.63-8.65 (m, 1H). | | | |

TABLE 70

| No. | Structure | NMR(δ) | retention time | Mass | method |
|---|---|---|---|---|---|
| II-2-102 | 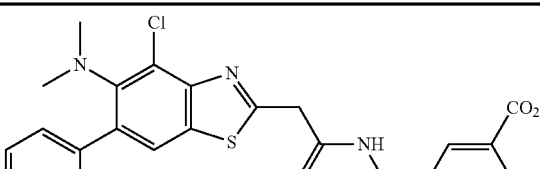 | (DMSO-d6) δ: 2.61 (s, 6H), 4.17 (s, 2H), 4.41 (d, J = 5.6 Hz, 2H), 7.38-7.49 (m, 6H), 7.55 (d, J = 7.6 Hz, 1H), 7.82-7.90 (m, 3H), 8.96 (t, J = 5.8 Hz, 1H). | | | |
| II-2-103 | 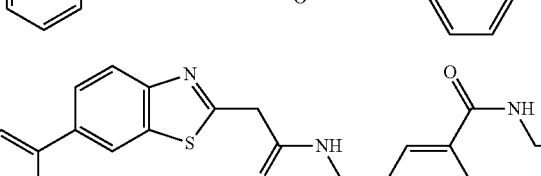 | (DMSO-d6) δ: 4.16 (s, 2H), 4.31 (d, J = 5.6 Hz, 2H), 4.41 (d, J = 6.1 Hz, 2H), 7.39 (t, J = 7.4 Hz, 1H), 7.45-7.53 (m, 4H), 7.74-7.83 (m, 5H), 8.02 (d, J = 8.6 Hz, 1H), 8.38 (d, J = 1.5 Hz, 1H), 8.94 (t, J = 5.8 Hz, 1H), 9.22 (t, J = 5.1 Hz, 1H). | | | |

TABLE 70-continued

| No. | Structure | NMR(δ) | retention time | Mass | method |
|---|---|---|---|---|---|
| II-2-104 | 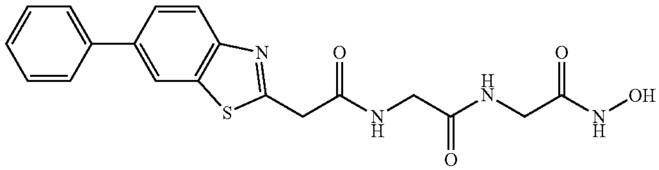 [SMILES: O=C(CNC(=O)CNC(=O)Cc1nc2ccc(-c3ccccc3)cc2s1)NO] | (DMSO-d6) δ: 3.65 (d, J = 5.58 Hz, 2H), 3.82 (d, J = 5.58 Hz, 2H), 4.16 (s, 2H), 7.39 (m, 1H), 7.47-7.52 (m, 2H), 7.73-7.81 (m, 3H), 8.01 (d, J = 8.62 Hz, 1H), 8.26 (t, J = 5.58 Hz, 1H), 8.38 (d, J = 1.52 Hz, 1H), 8.63 (t, J = 5.32 Hz, 1H), 8.83 (s, 1H), 10.48 (s, 1H). | | | |
| II-2-105 | 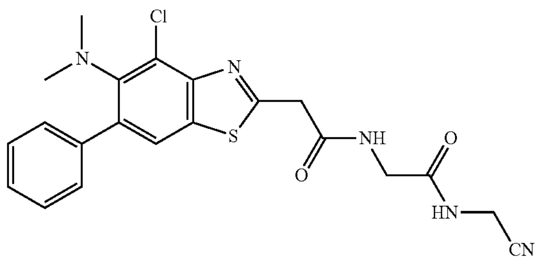 [SMILES: CN(C)c1c(-c2ccccc2)cc2sc(CC(=O)NCC(=O)NCC#N)nc2c1Cl] | (DMSO-d6) δ: 2.61 (s, 6H), 3.83 (d, J = 5.6 Hz, 2H), 4.15-4.18 (m, 4H), 7.37-7.49 (m, 5H), 7.86 (s, 1H), 8.69 (t, J = 5.6 Hz, 1H), 8.75 (t, J = 5.6 Hz, 1H). | | | |
| II-2-106 | 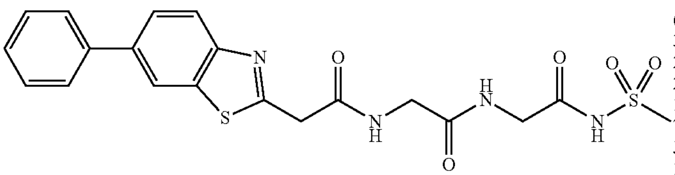 | (DMSO-d6) δ: 2.73 (s, 3H), 3.52 (d, J = 5.07 Hz, 2H), 3.80 (d, J = 6.08 Hz, 2H), 4.15 (s, 2H), 7.39 (m, 1H), 7.47-7.52 (m, 3H), 7.69-7.81 (m, 4H), 8.02 (d, J = 8.62 Hz, 1H), 8.38 (s, 1H), 8.67 (t, J = 5.58 Hz, 1H). | | | |

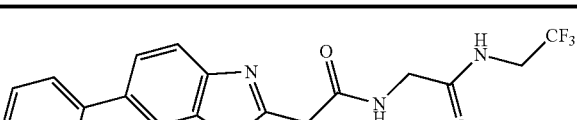

TABLE 71

| No. | Structure | NMR(δ) | retention time | Mass | method |
|---|---|---|---|---|---|
| II-2-107 | 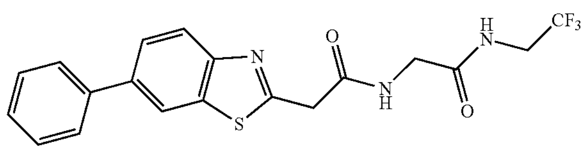 [SMILES: O=C(CNC(=O)Cc1nc2ccc(-c3ccccc3)cc2s1)NCC(F)(F)F] | 1H-NMR (DMSO-d6) δ: 3.86 (d, J = 5.6 Hz, 2H), 3.92-3.95 (m, 2H), 4.16 (s, 2H), 7.39-7.41 (m, 1H), 7.50 (t, J = 7.6 Hz, 2H), 7.74-7.81 (m, 3H), 8.01 (d, J = 8.6 Hz, 1H), 8.38 (d, J = 1.5 Hz, 1H), 8.62-8.64 (m, 1H), 8.69-8.72 (m, 1H). | | | |
| II-2-108 | 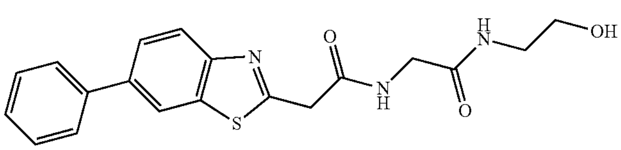 [SMILES: O=C(CNC(=O)Cc1nc2ccc(-c3ccccc3)cc2s1)NCCO] | 1H-NMR (DMSO-d6) δ: 3.15 (q, J = 5.9 Hz, 2H), 3.40-3.41 (m, 2H), 3.77 (d, J = 5.6 Hz, 2H), 4.15 (s, 2H), 4.67-4.69 (m, 1H), 7.39-7.41 (m, 1H), 7.50 (t, J = 7.6 Hz, 2H), 7.75-7.80 (m, 3H), 7.98-8.01 (m, 2H), 8.38 (d, J = 1.5 Hz, 1H), 8.59-8.62 (m, 1H). | | | |
| II-2-109 | 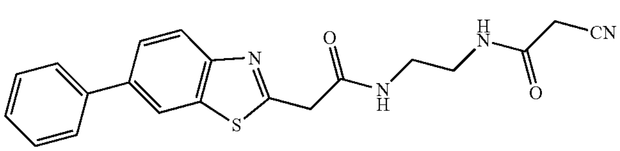 [SMILES: N#CCC(=O)NCCNC(=O)Cc1nc2ccc(-c3ccccc3)cc2s1] | 1H-NMR (DMSO-d6) δ: 3.18-3.20 (m, 4H), 3.61 (s, 2H), 4.06 (s, 2H), 7.39-7.41 (m, 1H), 7.50 (t, J = 7.6 Hz, 2H), 7.76-7.78 (m, 3H), 8.01 (d, J = 8.1 Hz, 1H), 8.34-8.41 (m, 3H). | | | |

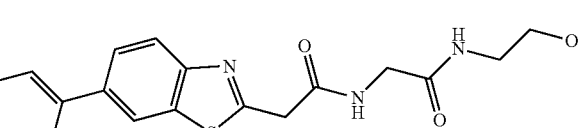

TABLE 71-continued

| No. | Structure | NMR(δ) | retention time | Mass | method |
|---|---|---|---|---|---|
| II-2-110 | 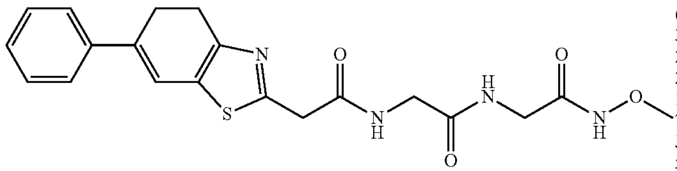 [SMILES: CONC(=O)CNC(=O)CNC(=O)Cc1nc2c(s1)C=C(c1ccccc1)CC2] | (DMSO-d₆) δ: 3.58 (s, 3H), 3.64 (d, J = 5.58 Hz, 2H), 3.83 (d, J = 5.58 Hz, 2H), 4.16 (s, 2H), 7.39 (m, 1H), 7.47-7.52 (m, 2H), 7.73-7.81 (m, 3H), 8.01 (d, J = 8.62 Hz, 1H), 8.29 (t, J = 5.58 Hz, 1H), 8.38 (s, 1H), 8.66 (t, J = 5.32 Hz, 1H), 11.07 (brs, 1H). | | | |
| II-2-111 | 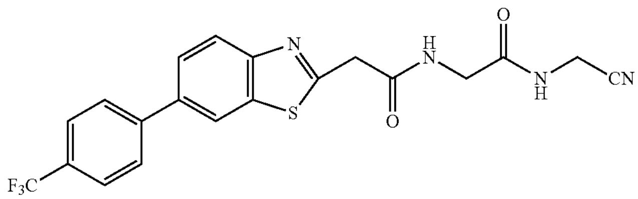 [SMILES: N#CCNC(=O)CNC(=O)Cc1nc2ccc(-c3ccc(C(F)(F)F)cc3)cc2s1] | (DMSO-d6) δ: 3.83 (2H, J = 6.0 Hz, d), 4.16-4.18 (4H, m), 7.83-7.88 (m, 3H), 8.50 (s, 1H), 8.69-8.75 (m, 2H) | | | |

TABLE 72

| No. | Structure | NMR(δ) | retention time | Mass | method |
|---|---|---|---|---|---|
| II-2-112 | 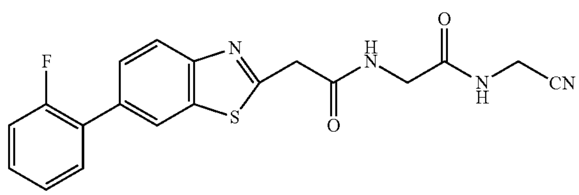 [SMILES: N#CCNC(=O)CNC(=O)Cc1nc2ccc(-c3ccccc3F)cc2s1] | (DMSO-d6) δ: 3.83 (2H, J = 6.0 Hz, d), 4.16-4.18 (4H, m), 7.31-7.38 (m, 2H), 7.44 (m, 1H), 7.58-7.68 (m, 2H), 8.03 (d, J = 8.1 Hz, 1H), 8.26 (s, 1H), 8.69-8.74 (m, 2H) | | | |
| II-2-113 | 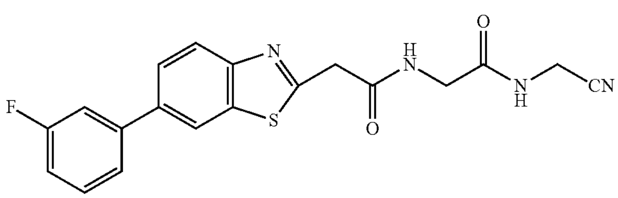 [SMILES: N#CCNC(=O)CNC(=O)Cc1nc2ccc(-c3cccc(F)c3)cc2s1] | (DMSO-d6) δ: 3.83 (2H, J = 6.0 Hz, d), 4.16-4.18 (4H, m), 7.23 (t, J = 9.3 Hz, 1H), 750-7.64 (m, 4H), 7.83 (d, J = 9.3 Hz, 1H), 8.02 (d, J = 8.4 Hz, 1H), 8.45 (s, 1H), 8.68-8.76 (m, 2H) | | | |
| II-2-114 | 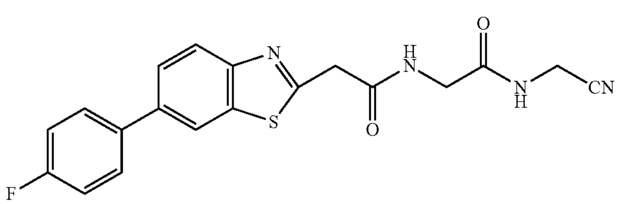 [SMILES: N#CCNC(=O)CNC(=O)Cc1nc2ccc(-c3ccc(F)cc3)cc2s1] | (DMSO-d6) δ: 3.83 (2H, J = 6.0 Hz, d), 4.16-4.18 (4H, m), 7.33 (t, J = 8.7 Hz, 1H), 7.76-7.80 (m, 3H), 8.01 (d, J = 8.4 Hz, 1H), 8.37 (s, 1H), 8.69-8.74 (m, 2H) | | | |
| II-2-115 | 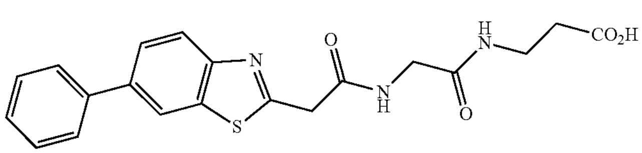 [SMILES: O=C(O)CCNC(=O)CNC(=O)Cc1nc2ccc(-c3ccccc3)cc2s1] | 1H-NMR (DMSO-d6) δ: 2.39 (t, J = 7.1 Hz, 2H), 3.26-3.30 (m, 2H), 3.74 (d, J = 5.6 Hz, 2H), 4.15 (s, 2H), 7.39-7.41 (m, 1H), 7.50 (t, J = 7.6 Hz, 2H), 7.74-7.80 (m, 3H), 8.01-8.03 (m, 2H), 8.38 (d, J = 1.5 Hz, 1H), 8.60-8.63 (m, 1H), 12.22-12.24 (m, 1H). | | | |

TABLE 72-continued

| No. | Structure | NMR(δ) | retention time | Mass | method |
|---|---|---|---|---|---|
| II-2-116 | 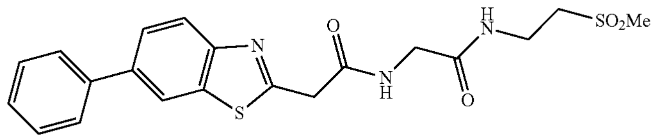 [SMILES: CS(=O)(=O)CCNC(=O)CNC(=O)Cc1nc2ccc(-c3ccccc3)cc2s1] | 1H-NMR (DMSO-d6) δ: 3.00 (s, 3H), 3.25 (t, J = 6.8 Hz, 2H), 3.49-3.51 (m, 2H), 3.76 (d, J = 5.6 Hz, 2H), 4.15 (s, 2H), 7.39 (t, J = 7.4 Hz, 1H), 7.50 (t, J = 7.6 Hz, 2H), 7.77 (td, J = 9.6, 3.5 Hz, 3H), 8.01 (d, J = 8.1 Hz, 1H), 8.24 (t, J = 5.6 Hz, 1H), 8.38 (d, J = 1.5 Hz, 1H), 8.67 (t, J = 5.8 Hz, 1H). | | | |

TABLE 73

| No. | Structure | NMR(δ) | retention time | Mass | method |
|---|---|---|---|---|---|
| II-2-117 | 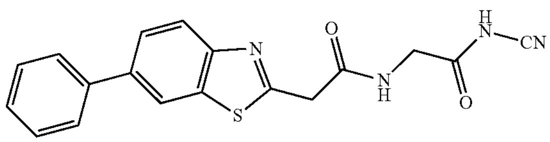 [SMILES: N#CNC(=O)CNC(=O)Cc1nc2ccc(-c3ccccc3)cc2s1] | 1H-NMR (DMSO-d6) δ: 3.96 (d, J = 5.6 Hz, 2H), 4.17 (s, 2H), 7.39 (t, J = 7.1 Hz, 1H), 7.50 (t, J = 7.6 Hz, 2H), 7.75-7.81 (m, 3H), 8.01 (d, J = 8.6 Hz, 1H), 8.39 (d, J = 1.5 Hz, 1H), 8.85 (t, J = 5.6 Hz, 1H). | | | |
| II-2-118 | 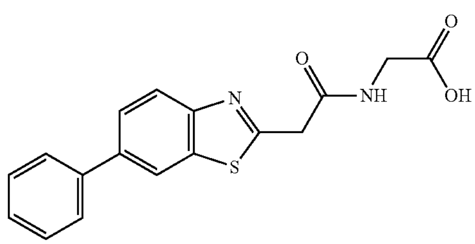 [SMILES: O=C(O)CNC(=O)Cc1nc2ccc(-c3ccccc3)cc2s1] | (DMSO-d$_6$) δ: 3.85 (d, J = 6.08 Hz, 2H), 4.15 (s, 2H), 7.39 (m, 1H), 7.47-7.52 (m, 2H), 7.73-7.81 (m, 3H), 8.01 (d, J = 8.11 Hz, 1H), 8.38 (d, J = 1.52 Hz, 1H), 8.71 (t, J = 5.83 Hz, 1H), 12.64 (brs, 1H). | | | |
| II-2-119 | 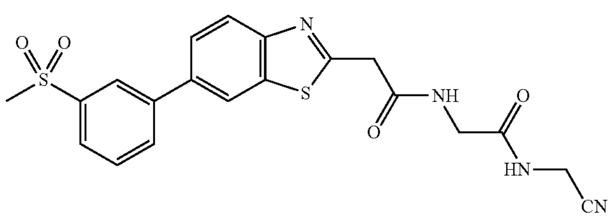 [SMILES: CS(=O)(=O)c1cccc(-c2ccc3nc(CC(=O)NCC(=O)NCC#N)sc3c2)c1] | (DMSO-d6) δ: 3.83 (d, J = 5.7 Hz, 2H), 4.16-4.19 (m, 2H), 7.78 (t, J = 7.8 Hz, 1H), 7.88-7.96 (m, 2H), 8.08 (d, J = 8.7 Hz, 1H), 8.13 (d, J = 7.8 Hz, 1H), 8.26 (s, 1H), 8.54 (s, 1H), 8.67-8.77 (m, 2H) | | | |
| II-2-120 | 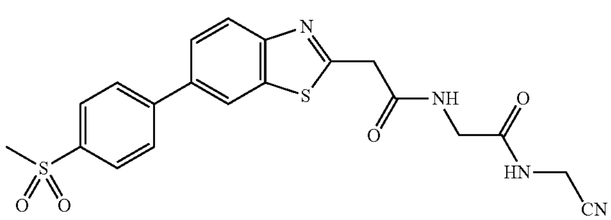 [SMILES: CS(=O)(=O)c1ccc(-c2ccc3nc(CC(=O)NCC(=O)NCC#N)sc3c2)cc1] | (DMSO-d6) δ: 3.27 (s, 3H), 3.84 (d, J = 5.7 Hz, 2H), 4.16-4.19 (m, 4H), 7.86-8.09 (m, 6H), 8.52 (d, J = 5.1 Hz, 1H), 8.63-8.81 (m, 2H) | | | |
| II-2-121 | 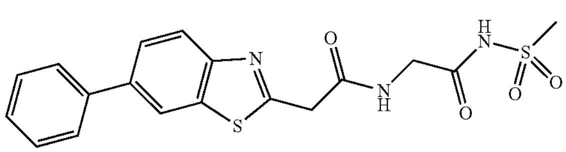 [SMILES: CS(=O)(=O)NC(=O)CNC(=O)Cc1nc2ccc(-c3ccccc3)cc2s1] | 1H-NMR (DMSO-d6) δ: 3.15 (s, 3H), 3.85-3.88 (m, 2H), 4.16 (s, 2H), 7.37-7.51 (m, 4H), 7.74-7.80 (m, 4H), 8.00-8.02 (m, 1H), 8.37-8.38 (m, 1H), 8.62-8.63 (m, 1H). | | | |

TABLE 74

| No. | Structure | NMR(δ) | retention time | Mass | method |
|---|---|---|---|---|---|
| II-2-122 | 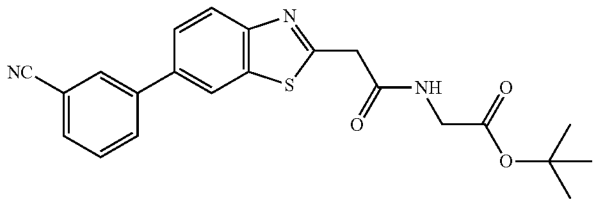 [SMILES: CC(C)(C)OC(=O)CNC(=O)Cc1nc2ccc(-c3cccc(C#N)c3)cc2s1] | (DMSO-d6) δ: 1.47 (s, 9H), 4.01 (d, J = 5.4 Hz, 2H), 4.08-4.16 (m, 2H), 7.48 (br-s, 1H), 7.58 (t, J = 7.5 Hz, 1H), 7.65-7.69 (m, 2H), 7.87 (d, J = 9.0 Hz, 1H), 7.91 (s, 1H), 8.05 (s, 1H), 8.12 (d, J = 8.4 Hz, 1H) | | | |
| II-2-123 | 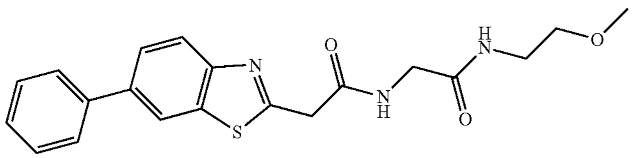 [SMILES: COCCNC(=O)CNC(=O)Cc1nc2ccc(-c3ccccc3)cc2s1] | 1H-NMR (DMSO-d6) δ: 3.24-3.25 (m, 5H), 3.34-3.36 (m, 1H), 3.77 (d, J = 6.1 Hz, 2H), 4.15 (s, 2H), 7.37-7.41 (m, 1H), 7.48-7.1 (m, 2H), 7.76-7.79 (m, 3H), 8.01-8.04 (m, 2H), 8.38 (d, J = 1.5 Hz, 1H), 8.62 (t, J = 5.8 Hz, 1H). | | | |
| II-2-124 | 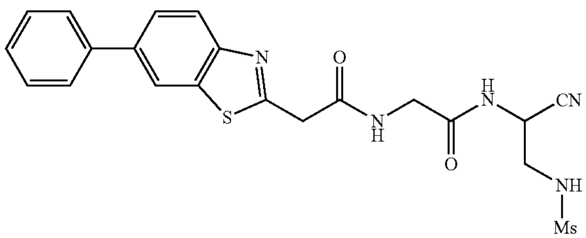 [SMILES: CS(=O)(=O)NCC(C#N)NC(=O)CNC(=O)Cc1nc2ccc(-c3ccccc3)cc2s1] | (CDCl3) δ: 2.95 (s, 3H), 3.55 (dd, J = 6.08, 5.58 Hz, 2H), 4.07 (d, J = 5.58 Hz, 2H), 4.15 (s, 2H), 4.97 (dt, J = 6.08, 6.59 Hz, 1H), 6.27 (t, J = 6.59 Hz, 1H), 7.31-7.44 (m, 3H), 7.55 (d, J = 7.60 Hz, 2H), 7.63 (dd, J = 8.11, 1.52 Hz, 1H), 7.91-7.99 (m, 3H), 8.10 (t, J = 5.58 Hz, 1H). | | | |
| II-2-125 | 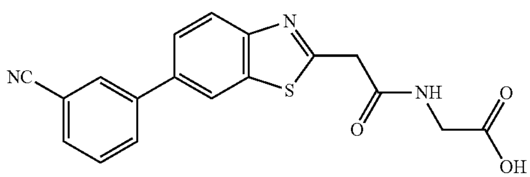 [SMILES: N#Cc1cccc(-c2ccc3nc(CC(=O)NCC(=O)O)sc3c2)c1] | (DMSO-d6) δ: 3.85 (d, J = 5.7 Hz, 2H), 4.17 (s, 2H), 7.70 (t, J = 7.5 Hz, 1H), 7.86 (t, J = 9.0 Hz, 2H), 8.04 (d, J = 8.7 Hz, 1H), 8.12 (d, J = 8.4 Hz, 1H), 8.50 (s, 1H), 8.73 (m, 1H), 12.61 (br-s, 1H) | | | |
| II-2-126 | 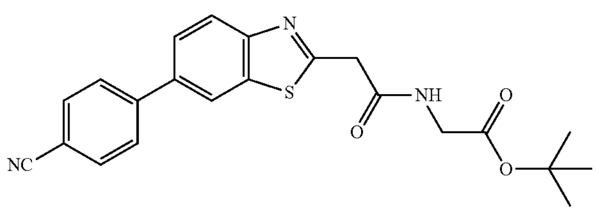 [SMILES: CC(C)(C)OC(=O)CNC(=O)Cc1nc2ccc(-c3ccc(C#N)cc3)cc2s1] | (DMSO-d6) δ: 1.47 (s, 9H), 4.01 (d, J = 5.4 Hz, 2H), 4.16 (s, 2H), 7.48 (br-s, 1H), 7.65-7.82 (m, 5H), 8.05-8.12 (m, 2H) | | | |

TABLE 75

| No. | Structure | NMR(δ) | retention time | Mass | method |
|---|---|---|---|---|---|
| II-2-127 | 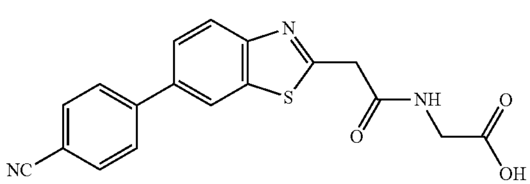 [SMILES: N#Cc1ccc(-c2ccc3nc(CC(=O)NCC(=O)O)sc3c2)cc1] | (DMSO-d6) δ: 3.85 (d, J = 6.0 Hz, 2H), 4.17 (s, 2H), 7.88 (d, J = 9.0 Hz, 1H), 7.89-7.97 (m, 4H), 8.06 (d, J = 8.4 Hz, 1H), 8.52 (s, 1H), 8.73 (s, 1H), 12.64 (br-s, 1H) | | | |

TABLE 75-continued

| No. | Structure | NMR(δ) | retention time | Mass | method |
|---|---|---|---|---|---|
| II-2-128 | 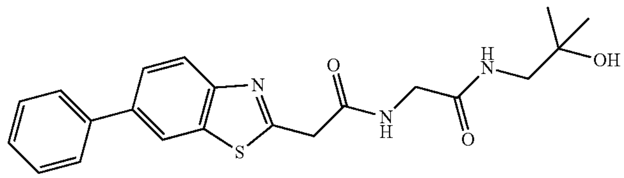 [SMILES: CC(C)(O)CNC(=O)CNC(=O)Cc1nc2ccc(-c3ccccc3)cc2s1] | 1H-NMR (DMSO-d6) δ: 1.04 (s, 6H), 3.05 (d, J = 6.1 Hz, 2H), 3.82 (d, J = 6.1 Hz, 2H), 4.15 (s, 2H), 4.44 (s, 1H), 7.39-7.41 (m, 1H), 7.50 (t, J = 7.6 Hz, 2H), 7.74-7.80 (m, 4H), 8.02 (d, J = 8.6 Hz, 1H), 8.38 (d, J = 1.5 Hz, 1H), 8.60-8.62 (m, 1H). | | | |
| II-2-129 | 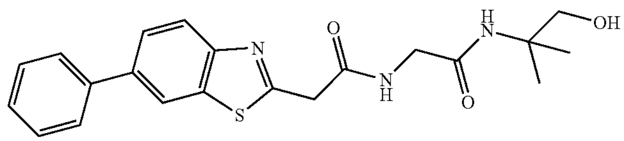 [SMILES: CC(C)(CO)NC(=O)CNC(=O)Cc1nc2ccc(-c3ccccc3)cc2s1] | 1H-NMR (DMSO-d6) δ: 1.18 (s, 7H), 3.39 (d, J = 6.1 Hz, 2H), 3.74 (d, J = 5.6 Hz, 2H), 4.15 (s, 2H), 4.79 (t, J = 5.8 Hz, 1H), 7.37-7.40 (m, 2H), 7.50 (t, J = 7.6 Hz, 2H), 7.76-7.79 (m, 3H), 8.01 (d, J = 8.6 Hz, 1H), 8.38 (d, J = 2.0 Hz, 1H), 8.49-8.52 (m, 1H). | | | |
| II-2-130 | 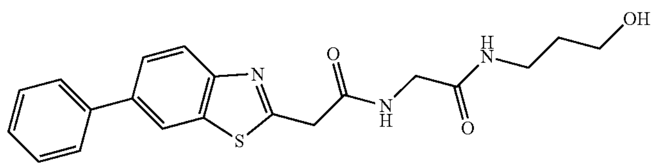 [SMILES: O=C(CNC(=O)Cc1nc2ccc(-c3ccccc3)cc2s1)NCCCO] | 1H-NMR (DMSO-d6) δ: 1.52-1.59 (m, 2H), 3.13-3.14 (m, 2H), 3.40-3.42 (m, 2H), 3.74 (d, J = 5.6 Hz, 2H), 4.15 (s, 2H), 4.43 (t, J = 5.3 Hz, 1H), 7.38-7.40 (m, 1H), 7.48-7.51 (m, 2H), 7.74-7.80 (m, 3H), 7.93 (t, J = 5.3 Hz, 1H), 8.01 (d, J = 8.6 Hz, 1H), 8.38 (d, J = 2.0 Hz, 1H), 8.62 (t, J = 5.6 Hz, 1H). | | | |
| II-2-131 | 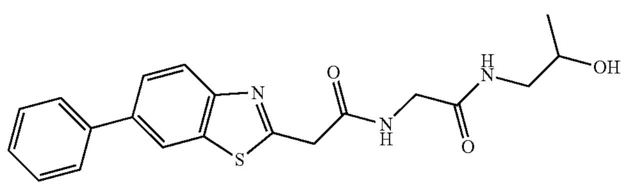 [SMILES: CC(O)CNC(=O)CNC(=O)Cc1nc2ccc(-c3ccccc3)cc2s1] | 1H-NMR (DMSO-d6) δ: 1.00-1.05 (m, 3H), 3.02-3.04 (m, 2H), 3.64-3.65 (m, 1H), 3.78 (,d J = 5.6 Hz, 2H), 4.15 (s, 2H), 4.67 (d, J = 4.6 Hz, 1H), 7.38-7.40 (m, 1H), 7.48-7.51 (m, 2H), 7.74-7.80 (m, 3H), 7.91 (t, J = 5.8 Hz, 1H), 8.01 (d, J = 8.1 Hz, 1H), 8.38 (d, J = 2.0 Hz, 1H), 8.61 (t, J = 5.8 Hz, 1H). | | | |

TABLE 76

| No. | Structure | NMR(δ) | retention time | Mass | method |
|---|---|---|---|---|---|
| II-2-132 | 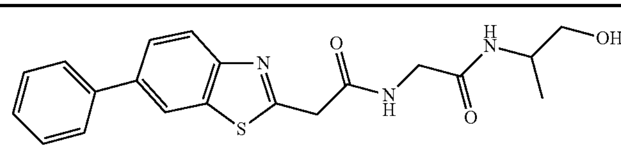 | 1H-NMR (DMSO-d6) δ: 1.03 (d, J = 6.6 Hz, 3H), 3.22-3.25 (m, 1H), 3.36-3.37 (m, 0H), 3.76-3.79 (m, 3H), 4.15 (s, 2H), 4.69 (t, J = 5.6 Hz, 1H), 7.37-7.41 (m, 1H), 7.48-7.51 (m, 2H), 7.73-7.77 (m, 5H), 8.01 (d, J = 8.1 Hz, 1H), 8.38 (d, J = 1.5 Hz, 1H), 8.57 (t, J = 5.6 Hz, 1H). | | | |

TABLE 76-continued

| No. | Structure | NMR(δ) | retention time | Mass | method |
|---|---|---|---|---|---|
| II-2-133 | 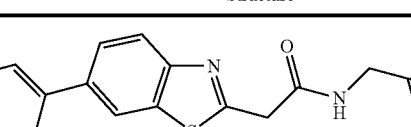 | (DMSO-d6) δ: 1.52-1.68 (m, 6H), 3.18 (t, J = 5.3 Hz, 4H), 3.81 (d, J = 5.6 Hz, 2H), 4.06 (s, 2H), 4.16 (d, J = 5.6 Hz, 2H), 7.14 (dd, J = 8.9, 2.3 Hz, 1H), 7.37 (d, J = 2.5 Hz, 1H), 7.80 (d, J = 8.6 Hz, 1H), 8.68 (t, J = 5.3 Hz, 2H). | | | |
| II-2-134 | 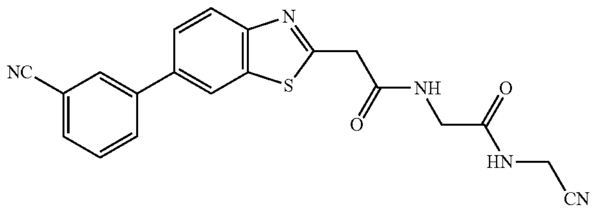 [SMILES: N#CCNC(=O)CNC(=O)Cc1nc2ccc(-c3cccc(C#N)c3)cc2s1] | (DMSO-d6) δ: 3.83 (d, J = 6.0 Hz, 2H), 4.16-4.18 (m, 4H), 7.70 (t, J = 8.1 Hz, 1H), 7.87 (t, J = 8.4 Hz, 2H), 8.05 (d, J = 8.7 Hz, 1H), 8.12 (d, J = 8.7 Hz, 1H), 8.26 (s, 1H), 8.50 (s, 1H). 8.69-8.75 (m, 2H) | | | |
| II-2-135 | 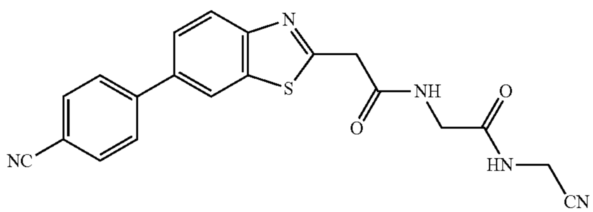 [SMILES: N#CCNC(=O)CNC(=O)Cc1nc2ccc(-c3ccc(C#N)cc3)cc2s1] | (DMSO-d6) δ: 3.83 (d, J = 6.0 Hz, 2H), 4.18 (s, 2H), 7.88 (d, J = 8.7 Hz, 1H), 7.90-8.04 (m, 4H), 8.06 (d, J = 8.4 Hz, 1H), 8.52 (s, 1H), 8.69-8.75 (m, 2H) | | | |
| II-2-136 | 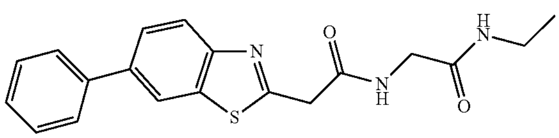 [SMILES: CCNC(=O)CNC(=O)Cc1nc2ccc(-c3ccccc3)cc2s1] | 1H-NMR (DMSO-d6) δ: 1.02 (t, J = 7.1 Hz, 3H), 3.10-3.12 (m, 2H), 3.73 (d, J = 5.6 Hz, 2H), 4.15 (s, 2H), 7.40-7.41 (m, 1H), 7.48-7.51 (m, 2H), 7.74-7.81 (m, 3H), 7.96-8.00 (m, 2H), 8.38 (d, J = 15 Hz, 1H), 8.61 (s, 1H). | | | |

TABLE 77

| No. | Structure | NMR(δ) | retention time | Mass | method |
|---|---|---|---|---|---|
| II-2-137 | 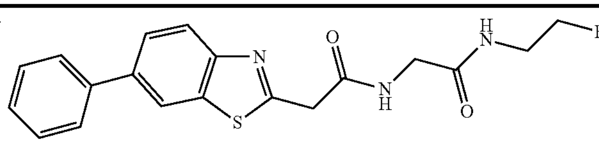 | 1H-NMR (DMSO-d6) δ: 3.36-3.37 (m, 1H), 3.42-3.44 (m, 1H), 3.79 (d, J = 5.6 Hz, 2H), 4.15 (s, 2H), 4.37 (t, J = 5.1 Hz, 1H), 4.49 (t, J = 5.1 Hz, 1H), 7.39 (t, J = 7.4 Hz, 1H), 7.50 (t, J = 7.6 Hz, 2H), 7.76-7.79 (m, 4H), 8.01 (d, J = 8.1 Hz, 1H), 8.23 (t, J = 5.6 Hz, 1H), 8.38 (d, J = 1.5 Hz, 1H), 8.65 (t, J = 5.8 Hz, 1H). | | | |
| II-2-138 | 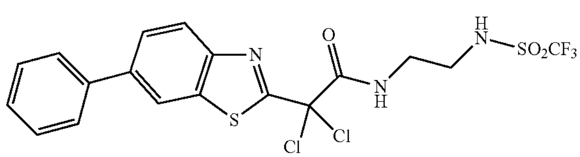 | 1H-NMR (DMSO-d6) δ: 3.29-3.36 (m, 4H), 7.43 (t, J = 7.4 Hz, 1H), 7.52 (t, J = 7.6 Hz, 2H), 7.78-7.79 (m, 2H), 7.93 (dd, J = 8.6, 2.0 Hz, 1H), 8.15 (d, J = 8.6 Hz, 1H), 8.53 (d, J = 1.5 Hz, 1H), 9.00 (t, J = 5.6 Hz, 1H), 9.57 (s, 1H). | | | |

TABLE 77-continued

| No. | Structure | NMR(δ) | retention time | Mass | method |
|---|---|---|---|---|---|
| II-2-139 | 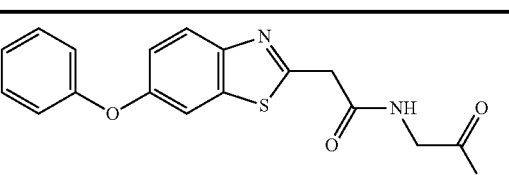 | (DMSO-d6) δ: 3.81 (d, J = 6.1 Hz, 2H), 4.08 (s, 2H), 4.16 (d, J = 5.6 Hz, 2H), 6.85 (t, J = 7.4 Hz, 1H), 7.11-7.17 (m, 3H), 7.26 (t, J = 7.6 Hz, 2H), 7.59 (d, J = 2.0 Hz, 1H), 7.86 (d, J = 8.6 Hz, 1 H), 8.33 (s, 1H), 8.66-8.69 (m, 2H). | | | |
| II-2-140 | 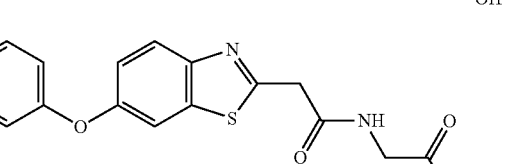 | (DMSO-d6) δ: 3.82 (d, J = 5.6 Hz, 2H), 4.11 (s, 2H), 4.17 (d, J = 5.6 Hz, 2H), 7.34 (t, J = 7.4 Hz, 1H), 7.44 (t, J = 7.6 Hz, 2H), 7.57-7.60 (m, 3H), 7.81 (s, 1H), 8.69 (t, J = 5.6 Hz, 2H). | | | |
| II-2-141 | 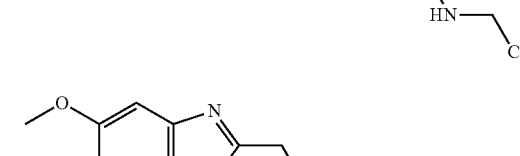 | (CDCl3) δ: 1.46 (s, 9H), 3.99 (d, J = 5.1 Hz, 2H), 4.07 (s, 2H), 7.04 (d, J = 7.8 Hz, 1H), 7.13-7.41 (m, 6H), 7.51 (m, 1H), 7.97 (d, J = 9.0 Hz, 1H) | | | |

TABLE 78

| No. | Structure | NMR(δ) | retention time | Mass | method |
|---|---|---|---|---|---|
| II-2-142 | 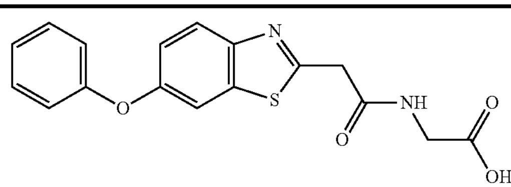 | (DMSO-d6) δ: 3.83 (d, J = 6.0 Hz, 2H), 4.10 (s, 2H), 7.04 (d, J = 8.1 Hz, 2H), 7.13-7.21 (m, 2H), 7.41 (t, J = 7.5 Hz, 2H), 7.73 (s, 1H), 7.95 (d, J = 9.0 Hz, 1H), 8.69 (m, 1H) | | | |
| II-2-143 | 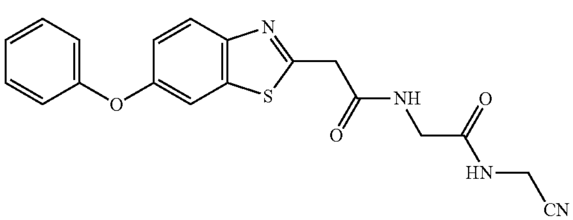 [SMILES: N#CCNC(=O)CNC(=O)Cc1nc2ccc(Oc3ccccc3)cc2s1] | (DMSO-d6) δ: 3.82 (d, J = 5.7 Hz, 2H), 4.11 (s, 2H), 4.16 (d, J = 5.1 Hz, 2H), 7.04 (d, J = 8.7 Hz, 2H), 7.15-7.20 (m, 2H), 7.40 (t, J = 7.8 Hz, 2H), 7.73 (s, 1H), 7.95 (d, J = 8.7 Hz, 1H), 8.68-8.71 (m, 2H) | | | |
| II-2-144 | 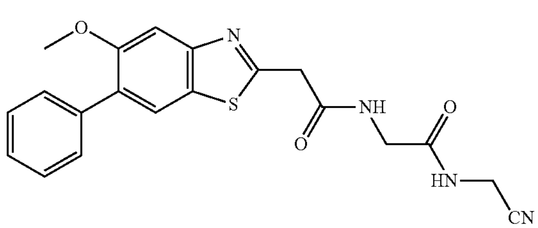 [SMILES: COc1cc2nc(CC(=O)NCC(=O)NCC#N)sc2cc1-c1ccccc1] | (DMSO-d6) δ: 3.81 (s, 2H), 3.84 (s, 2H), 4.13 (s, 2H), 4.18 (d, J = 5.7 Hz, 2H), 7.34-7.38 (m, 1H), 7.40-7.45 (m, 2H), 7.50-7.53 (m, 2H), 7.63 (s, 1H), 7.94 (s, 1H9, 8.68 (t, J = 6.0 Hz, 1H9, 8.71 (t, J = 6.0 Hz, 1H). | | | |

TABLE 78-continued

| No. | Structure | NMR(δ) | retention time | Mass | method |
|---|---|---|---|---|---|
| II-2-145 | 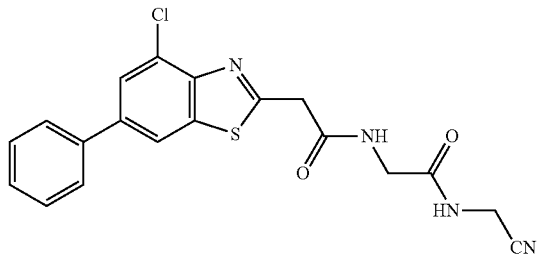 [SMILES: N#CCNC(=O)CNC(=O)Cc1nc2c(Cl)cc(-c3ccccc3)cc2s1] | (DMSO-d6) δ: 3.87 (d, J = 5.7 Hz, 2H), 4.19 (d, J = 5.5 Hz, 2H), 4.25 (s, 2H), 7.44-7.56 (m, 3H), 7.81 (d, J = 7.1 Hz, 2H), 7.92 (d, J = 1.7 Hz, 1H), 8.42 (d, J = 1.0 Hz, 1H), 8.71 (t, J = 5.5 Hz, 1H), 8.80 (t, J = 6.0 Hz, 1H). | | | |
| II-2-146 | 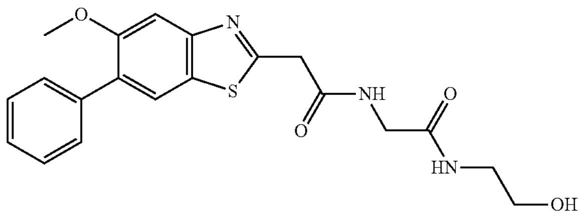 [SMILES: COc1cc2nc(CC(=O)NCC(=O)NCCO)sc2cc1-c1ccccc1] | (DMSO-d6) δ: 3.17 (q, J = 5.7 Hz, 2H), 3.42 (q, J = 5.7 Hz, 2H), 3.76 (d, J = 5.4 Hz, 2H), 4.12 (s, 2H), 4.69 (d, t = 5.4 Hz, 1H), 7.43 (t, J = 6.9 Hz, 2H), 7.50-7.53 (m, 2H), 7.98 (t, J = 5.7 Hz, 1H), 8.58 (t, J = 5.7 Hz, 1H). | | | |

TABLE 79

| No. | Structure | NMR(δ) | retention time | Mass | method |
|---|---|---|---|---|---|
| II-2-147 | 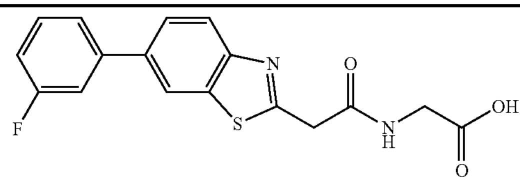 | (DMSO-d$_6$) δ: 3.85 (d, J = 5.58 Hz, 2H), 4.16 (s, 2H), 7.22 (m, 1H), 7.50-7.64 (m, 3H), 7.83 (m, 1H), 8.02 (d, J = 8.11 Hz, 1H), 8.45 (d, J = 1.01 Hz, 1H), 8.72 (t, J = 5.58 Hz, 1H), 12.64 (brs, 1H). | | | |
| II-2-148 | 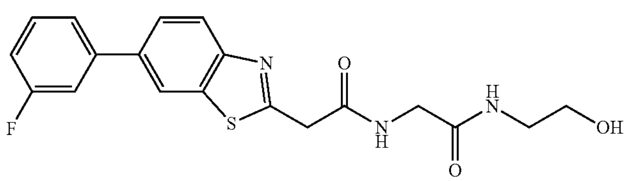 [SMILES: O=C(CNC(=O)Cc1nc2ccc(-c3cccc(F)c3)cc2s1)NCCO] | (DMSO-d$_6$) δ: 3.15 (dt, J = 6.08, 5.32 Hz, 2H), 3.41 (dt, J = 6.08, 5.32 Hz, 2H), 3.77 (d, J = 5.58 Hz, 2H), 4.16 (s, 2H), 4.68 (t, J = 5.32 Hz, 1H), 7.23 (m, 1H), 7.50-7.64 (m, 3H), 7.83 (m, 1H), 7.96 (t, J = 5.32 Hz, 1H), 8.02 (d, J = 8.62 Hz, 1H), 8.45 (s, 1H), 8.61 (t, J = 5.58 Hz, 1H). | | | |
| II-2-149 | 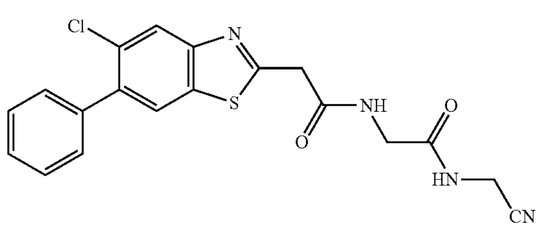 | (DMSO-d6) δ: 3.83 (d, J = 6.1 Hz, 2H), 4.16-4.19 (m, 4H), 7.43-7.50 (m, 5H), 8.15 (d, J = 5.1 Hz, 2H), 8.69 (t, J = 5.3 Hz, 1H), 8.75 (t, J = 5.6 Hz, 1H). | | | |
| II-2-150 | 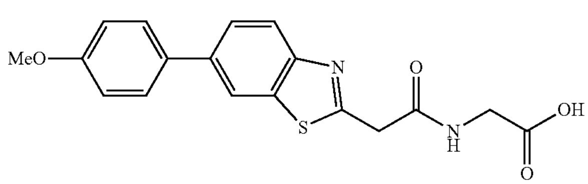 [SMILES: COc1ccc(-c2ccc3nc(CC(=O)NCC(=O)O)sc3c2)cc1] | (DMSO-d$_6$) δ: 3.81 (s, 3H), 3.84 (d, J = 5.58 Hz, 2H), 4.14 (s, 2H), 7.05 (d, J = 8.62 Hz, 2H), 7.69 (d, J = 8.62 Hz, 2H). 7.74 (dd, J = 8.62, 1.52 Hz, 1H), 7.97 (d, J = 8.62 Hz, 1H). 8.31 (d, J = 1.52 Hz, 1H), 8.70 (t, J = 5.58 Hz, 1H). 12.63 (brs, 1H). | | | |

TABLE 79-continued

| No. | Structure | NMR(δ) | retention time | Mass | method |
|---|---|---|---|---|---|
| II-2-151 | 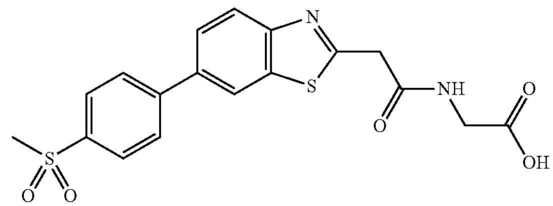 [SMILES: CS(=O)(=O)c1ccc(-c2ccc3nc(CC(=O)NCC(=O)O)sc3c2)cc1] | (DMSO-d6) δ: 3.28 (s, 3H), 3.86 (d, J = 6.0 Hz, 2H), 4.18 (s, 2H), 7.88 (dd, J = 8.7, 2.1 Hz, 1H), 8.03-8.08 (m, 5H), 8.52 (d, J = 1.8Hz, 1H), 8.73 (m, 1H) | | | |

TABLE 80

| No. | Structure | NMR(δ) | retention time | Mass | method |
|---|---|---|---|---|---|
| II-2-152 | 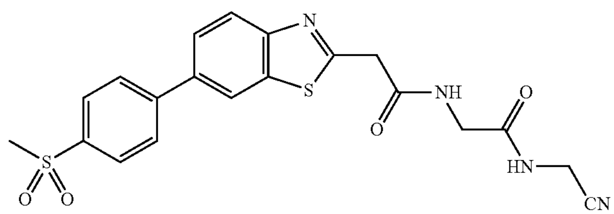 [SMILES: CS(=O)(=O)c1ccc(-c2ccc3nc(CC(=O)NCC(=O)NCC#N)sc3c2)cc1] | (DMSO-d6) δ: 3.27 (s, 3H), 3.84 (d, J = 4.2 Hz, 2H), 4.19 (s, 4H), 7.87 (d, J = 5.1 Hz, 1H), 7.90-8.08 (m, 5H), 8.52 (s, 1H), 8.70-8.75 (m, 2H) | | | |
| II-2-153 | 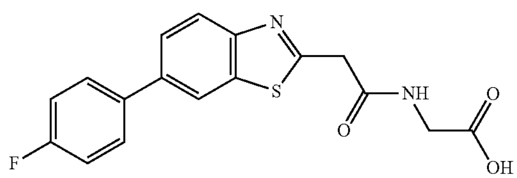 [SMILES: O=C(O)CNC(=O)Cc1nc2ccc(-c3ccc(F)cc3)cc2s1] | (DMSO-d6) δ: 3.85 (d, J = 5.7 Hz, 2H), 4.15 (s, 2H), 7.33 (t, J = 8.7 Hz, 2H), 7.75-7.79 (m, 3H), 8.01 (d, J = 8.4 Hz, 1H), 8.37 (s, 1H), 8.72 (m, 1H) | | | |
| II-2-154 | 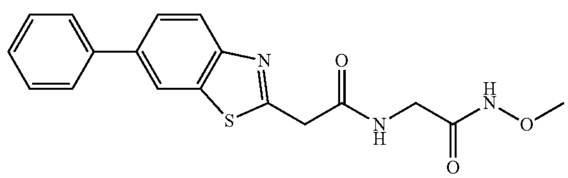 [SMILES: CONC(=O)CNC(=O)Cc1nc2ccc(-c3ccccc3)cc2s1] | (DMSO-$d_6$) δ: 3.60 (s, 3H), 3.69 (d, J = 5.07 Hz, 2H), 4.15 (s, 2H), 7.39 (m, 1H), 7.47-7.52 (m, 2H), 7.73-7.81 (m, 3H), 8.01 (d, J = 8.62 Hz, 1H), 8.38 (d, J = 1.52 Hz, 1H), 8.68 (t, J = 5.07 Hz, 1H), 11.20 (br s, 1H). | | | |
| II-2-155 | 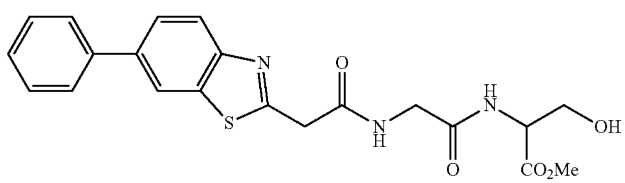 | (DMSO-$d_6$) δ: 3.59-3.73 (m, 5H), 3.82-3.93 (m, 2H), 4.15 (s, 2H), 4.38 (dt, J = 7.60, 5.07 Hz, 1H), 5.08 (t, J = 5.83 Hz, 1H), 7.39 (m, 1.0H) 7.47-7.52 (m, 2H), 7.73-7.81 (m, 3H), 8.01 (d, J = 8.62 Hz, 1H), 8.31 (d, J = 7.60 Hz, 1H), 8.38 (d, J = 1.01 Hz, 1H), 8.62 (t, J = 5.58 Hz, 1H). | | | |
| II-2-156 | 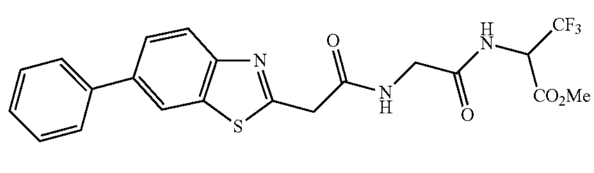 [SMILES: COC(=O)C(NC(=O)CNC(=O)Cc1nc2ccc(-c3ccccc3)cc2s1)C(F)(F)F] | 1H-NMR (DMSO-d6) δ: 3.76 (s, 3H), 3.93-3.95 (m, 2H), 4.16 (s, 2H), 5.45-5.47 (m, 1H), 7.37-7.41 (m, 1H), 7.48-7.51 (m, 2H), 7.76-7.79 (m, 3H), 8.01 (d, J = 8.6 Hz, 1H), 8.38 (d, J = 1.5 Hz, 1H), 8.70 (t, J = 5.8 Hz, 1H), 9.24 (d, J = 9.1 Hz, 1H). | | | |

TABLE 81

| No. | Structure | NMR(δ) | retention time | Mass | method |
|---|---|---|---|---|---|
| II-2-157 | 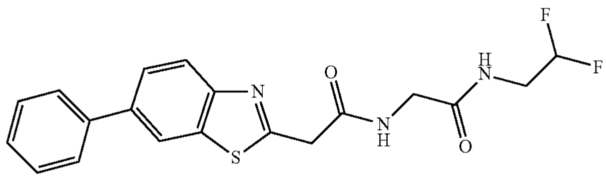 [SMILES: O=C(CNC(=O)Cc1nc2ccc(-c3ccccc3)cc2s1)NCC(F)F] | 1H-NMR (DMSO-d6) δ: 3.50-3.54 (m. 2H), 3.83 (d, J = 5.6 Hz, 2H), 4.16 (s, 2H), 5.87-6.15 (m, 1H), 7.37-7.41 (m, 1H), 7.48-7.51 (m, 2H), 7.75-7.79 (m, 3H), 8.01 (d, J = 8.6 Hz, 1H), 8.35-8.38 (m, 2H), 8.68 (t, J = 5.6 Hz, 1H). | | | |
| II-2-158 | 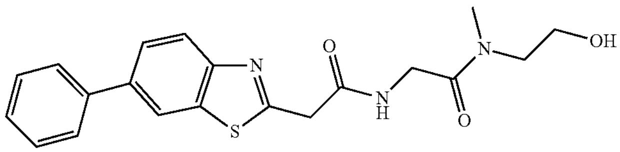 [SMILES: CN(CCO)C(=O)CNC(=O)Cc1nc2ccc(-c3ccccc3)cc2s1] | 1H-NMR (DMSO-d6) δ: 2.85 (s, 1.5H), 3.00 (s, 1.5H), 3.35-3.36 (m, 2H), 3.46-3.48 (m, 1H), 3.54-3.55 (m, 1H), 4.02 (d, J = 5.1 Hz, 1H), 4.10 (d, J = 5.1 Hz, 1H), 4.18 (d, J = 4.1 Hz, 2H), 4.66 (t, J = 5.6 Hz, 0.5H), 4.88 (t, J = 5.3 Hz, 0.5H), 7.39 (t, J = 7.4 Hz, 1H), 7.50 (t, J = 7.9 Hz, 2H), 7.74-7.80 (m, 3H), 8.01 (d, J = 8.6 Hz, 1H), 8.38 (d, J = 1.5 Hz, 1H), 8.46-8.47 (m, 1H). | | | |
| II-2-159 | 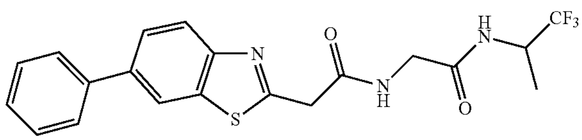 [SMILES: CC(NC(=O)CNC(=O)Cc1nc2ccc(-c3ccccc3)cc2s1)C(F)(F)F] | 1H-NMR (DMSO-d6) δ: 1.24 (d, J = 7.1 Hz, 3H), 3.80-3.89 (m, 2H), 4.16 (s, 2H), 4.58-4.62 (m, 1H), 7.38-7.40 (m, 1H), 7.50 (t, J = 7.6 Hz, 2H), 7.74-7.80 (m, 3H), 8.01 (d, J = 8.6 Hz, 1H), 8.38 (d, J = 1.5 Hz, 1H), 8.52 (d, J = 8.6 Hz, 1H), 8.66 (t, J = 5.8 Hz, 1H) | | | |
| II-2-160 | 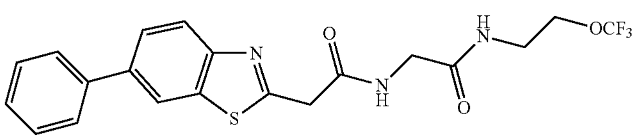 [SMILES: O=C(CNC(=O)Cc1nc2ccc(-c3ccccc3)cc2s1)NCCOC(F)(F)F] | 1H-NMR (DMSO-d6) δ: 3.40-3.41 (m, 2H), 3.79 (d, J = 6.1 Hz, 2H), 4.08 (t, J = 5.3 Hz, 2H), 4 15 (s, 2H), 7.39 (t, J = 7.4 Hz, 1H), 7.50 (t, J = 7.6 Hz, 2H), 7.74-7.80 (m, 3H), 8.01 (d, J = 8.1 Hz, 1H), 8.25 (t, J = 5.6 Hz, 1H), 8.38 (d, J = 1.5 Hz, 1H), 8.66 (t, J = 5.6 Hz, 1H). | | | |

TABLE 82

| No. | Structure | NMR(δ) | retention time | Mass | method |
|---|---|---|---|---|---|
| II-2-161 | 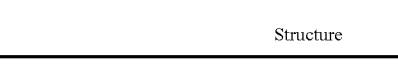 | (DMSO-$d_6$) δ: 3.15 (dt, J = 6.08, 6.08 Hz, 2H), 3.41 (dt, J = 5.58, 6.08 Hz, 2H), 3.76 (d, J = 5.58 Hz, 2H), 3.81 (s, 3H), 4.14 (s, 2H), 4.68 (t, J = 5.83 Hz, 1H), 7.05 (d, J = 8.62 Hz, 2H), 7.70 (d, J = 8.62 Hz, 2H), 7.74 (dd, J = 8.36, 1.77 Hz, 1H), 7.94-7.99 (m, 2H), 8.32 (d, J = 1.77 Hz, 1H), 8.60 (t, J = 5.58 Hz, 1H). | | | |

TABLE 82-continued

| No. | Structure | NMR(δ) | retention time | Mass | method |
|---|---|---|---|---|---|
| II-2-162 | 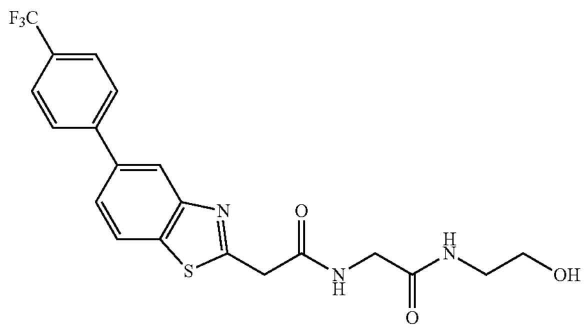 [SMILES: O=C(CNC(=O)Cc1nc2cc(-c3ccc(C(F)(F)F)cc3)ccc2s1)NCCO] | (DMSO-d$_6$) δ: 3.16 (dt, J = 6.08, 6.08 Hz, 2H), 3.41 (dt, J = 5.58, 6.08 Hz, 2H), 3.77 (d, J = 5.58 Hz, 2H), 4.18 (s, 2H), 4.69 (t, J = 6.08 Hz, 1H), 7.78-7.87 (m, 3H), 7.95-8.03 (m, 3H), 8.20 (d, J = 8.62 Hz, 1H), 8.32 (s, 1H), 8.62 (t, J = 5.58 Hz, 1H). | | | |
| II-2-163 | 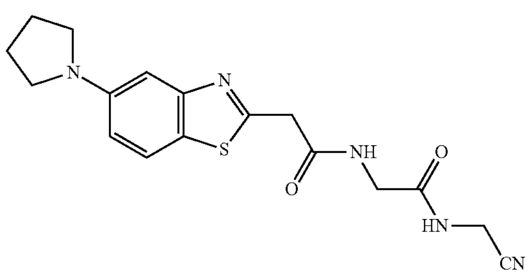 [SMILES: N#CCNC(=O)CNC(=O)Cc1nc2cc(N3CCCC3)ccc2s1] | (DMSO-d6) δ: 1.97-2.00 (m, 4H), 3.26-3.30 (m, 4H), 3.81 (d, J = 6.1 Hz, 2H), 4.04 (s, 2H), 4.17 (d, J = 5.6 Hz, 2H), 6.75 (dd, J = 8.6, 2.0 Hz, 1H). 6.99 (d, J = 2.0 Hz, 1H), 7.76 (d, J = 8.6 Hz, 1H), 8.65-8.69 (m, 2H). | | | |
| II-2-164 | 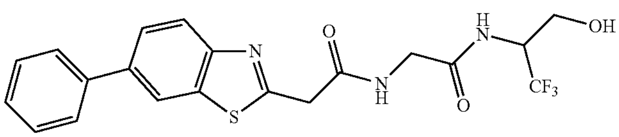 [SMILES: O=C(Cc1nc2ccc(-c3ccccc3)cc2s1)NCC(=O)NC(CO)C(F)(F)F] | 1H-NMR (DMSO-d6) δ: 3.60-3.66 (m, 2H), 3.86-3.94 (m, 2H), 4.16 (s, 2H), 4.53-4.56 (m, 1H), 5.18 (t, J = 5.8 Hz, 1H), 7.38-7.40 (m, 1H), 7.50 (t, J = 7.6 Hz, 2H), 7.74-7.80 (m, 3H), 8.01 (d, J = 8.6 Hz, 1H), 8.38 (d, J = 1 5 Hz, 1H), 8.50 (d, J = 9.1 Hz, 1H), 8.65 (t, J = 5.6 Hz, 1H). | | | |
| II-2-165 | 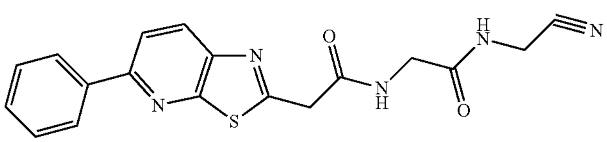 [SMILES: N#CCNC(=O)CNC(=O)Cc1nc2ccc(-c3ccccc3)nc2s1] | (DMSO-d6) δ: 3.84 (d, J = 5.7 Hz, 2H), 4.17 (d, J = 5.7 Hz, 2H), 4.21 (s, 2H), 7.47-7.56 (m, 3H), 8.12-8.18 (m, 3H), 8.41 (d, J = 8.4 Hz, 1H), 8.69 (t, J = 5.7 Hz, 1H), 8.77 (t, J = 5.7 Hz, 1H).. | | | |

TABLE 83

| No. | Structure | NMR(δ) | retention time | Mass | method |
|---|---|---|---|---|---|
| II-2-166 | 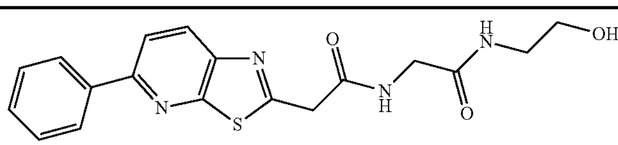 | (DMSO-d6) δ: 3.15 (q, J = 5.7 Hz, 2H), 3.42 (q, J = 5.7 Hz, 2H), 3.78 (d, J = 5.7 Hz, 2H), 419 (s, 2H), 4.68 (t, t = 5.7 Hz, 1H), 7.43-7.59 (m, 2H), 7.50-7.53 (m, 3H), 7.97 (t, J = 5.7 Hz, 1H), 8.11-8.19 (m, 3H), 8.40 (d, J = 5.7 Hz, 1H), 8.64 (t, J = 5.7 Hz, 1H). | | | |

TABLE 83-continued

| No. | Structure | NMR(δ) | retention time | Mass | method |
|---|---|---|---|---|---|
| II-2-167 | 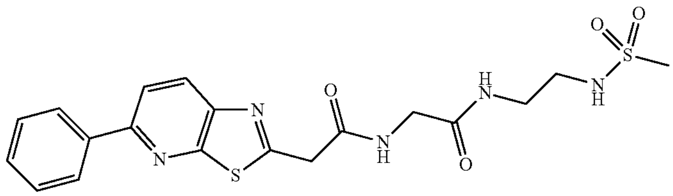 [SMILES: CS(=O)(=O)NCCNC(=O)CNC(=O)Cc1nc2ccc(-c3ccccc3)nc2s1] | (DMSO-d6) δ: 2.91 (s, 3H), 3.00 (q, J = 6.3 Hz, 2H), 3.20 (q, J = 6.3 Hz, 2H), 3.78 (d, J = 5.7 Hz, 2H), 419 (s, 2H), 7.06 (t, J = 6.0 Hz, 1H), 8.13-8.19 (m, 3H), 8.41 (d, J= 8.4 Hz, 1H), 8.67 (t, J = 5.7 Hz, 1H). | | | |
| II-2-168 | 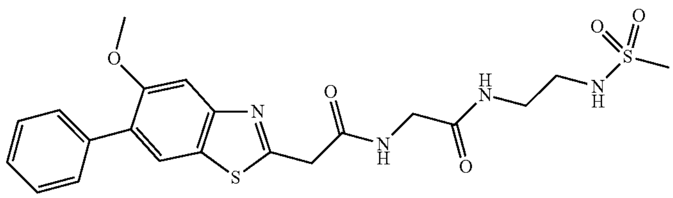 [SMILES: COc1cc2nc(CC(=O)NCC(=O)NCCNS(C)(=O)=O)sc2cc1-c1ccccc1] | (DMSO-d6) δ: 2.90 (s, 3H), 3.00 (q, J = 5.7 Hz, 2H), 3.76 (q, J = 5.7 Hz, 2H), 3.76 (d, J = 5.7 Hz, 2H), 3.84 (s, 2H), 4.12 (s, 1H), 7.05 (t, J = Hz, 1H), 7.32-7.37 (m, 3H), 7.40-7.45 (m, 2H), 7.62 (s, 1H), 7.94 (s, 1H), 8.05 (t, J = 5.7 Hz, 1H), 8.60 (t, J = 5.7 Hz, 1H). | | | |
| II-2-169 | 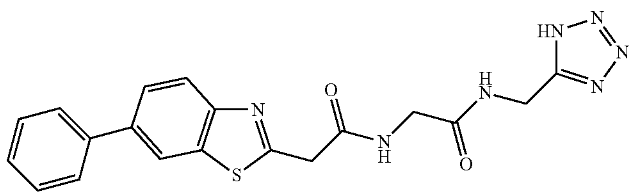 [SMILES: O=C(CNC(=O)Cc1nc2ccc(-c3ccccc3)cc2s1)NCc1nnn[nH]1] | 1H-NMR (DMSO-d6) δ: 3.86 (d, J = 5.6 Hz, 2H), 4.16 (s, 2H), 4.60 (d, J = 5.6 Hz, 2H), 7.39 (t, J = 7.6 Hz, 1H), 7.50 (t, J = 7.6 Hz, 2H), 7.77 (td, J = 9.1, 3.5 Hz, 3H), 8.01 (d, J = 8.6 Hz, 1H), 8.38 (d, J = 1.5 Hz, 1H), 8.66 (t, J = 5.6 Hz, 1H), 8.74 (t, J = 5.6 Hz, 1H). | | | |
| II-2-170 | 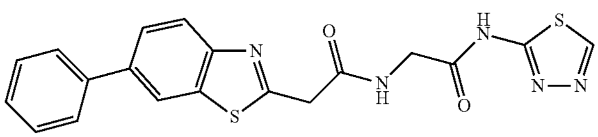 [SMILES: O=C(Cc1nc2ccc(-c3ccccc3)cc2s1)NCC(=O)Nc1nncs1] | (DMSO-d6) δ: 3.84 (d, J = 5.4 Hz, 2H), 4.11 (s, 2H), 7.26 (s, 1H), 7.39-7.51 (m, 3H), 7.77 (d, J = 7.2 Hz, 2H). 7.90 (s, 1H), 8.69 (m, 1H), 12.67 (br-s, 1H) | | | |

TABLE 84

| No. | Structure | NMR(δ) | retention time | Mass | method |
|---|---|---|---|---|---|
| II-2-171 | 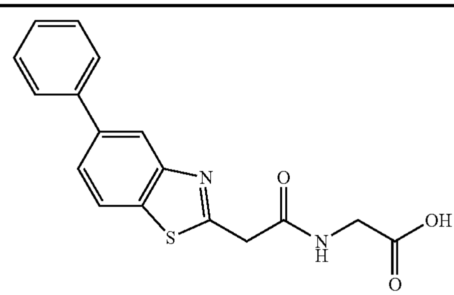 | (DMSO-d$_6$) δ: 3.85 (d, J = 5.58 Hz, 2H), 4.16 (s, 2H), 7.39 (m, 1H), 7.47-7.53 (m, 2H), 7.71-7.79 (m, 3H), 8.14 (d, J = 8.11 Hz, 1H), 8.21 (br s, 1H), 8.71 (t, J = 5.58 Hz, 1H), 12.64 (brs, 1H). | | | |
| II-2-172 | 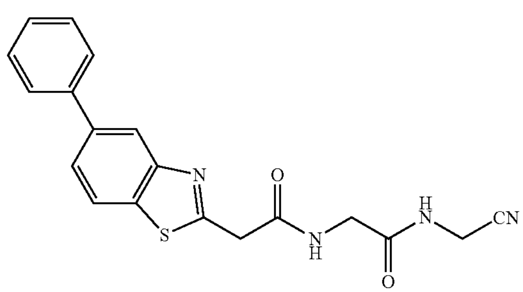 [SMILES: N#CCNC(=O)CNC(=O)Cc1nc2cc(-c3ccccc3)ccc2s1] | (DMSO-d$_6$) δ: 3.83 (d, J = 5.58 Hz, 2H), 4.15-4.19 (m, 4.0H), 7.40 (m, 1H), 7.47-7.53 (m, 2H), 7.72-7.79 (m, 3H), 8.14 (d, J = 8.11 Hz, 1H), 8.21 (d, J = 1.01 Hz, 1H), 8.69 (t, J = 5.32 Hz, 1H), 8.74 (t, J = 5.83 Hz, 1H). | | | |

TABLE 84-continued

| No. | Structure | NMR(δ) | retention time | Mass | method |
|---|---|---|---|---|---|
| II-2-173 | 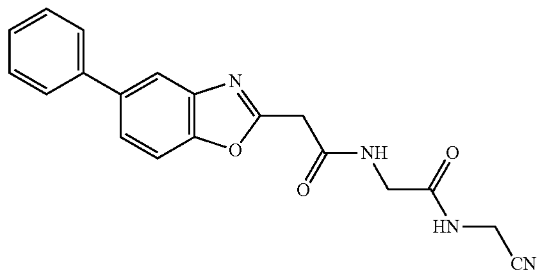 [SMILES: N#CCNC(=O)CNC(=O)Cc1nc2cc(-c3ccccc3)ccc2o1] | (DMSO-d6) δ: 3.83 (d, J = 6.1 Hz, 2H), 4.02 (s, 2H), 4.19 (d, J= 5.6 Hz, 2H), 7.38 (t. J = 6.8 Hz, 1H), 7.49 (t, J = 7.6 Hz, 2H), 7.66-7.73 (m, 3H), 7.78 (d, J = 8.1 Hz, 1H), 7.98 (s, 1H), 8.71 (q, J = 5.2 Hz, 2H). | | | |
| II-2-174 | 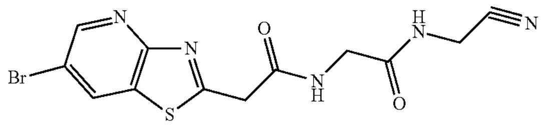 [SMILES: N#CCNC(=O)CNC(=O)Cc1nc2ncc(Br)cc2s1] | (DMSO-d6) δ: 3.84 (d, J = 5.7 Hz, 2H), 4.17 (d, J = 5.7 Hz, 2H), 4.23 (s, 2H), 8.71-8.61 (m, 2H), 8.79 (t, J = 5.7 Hz., 1H), 8.90 (d, J = 2.1 Hz, 1H). | | | |
| II-2-175 | 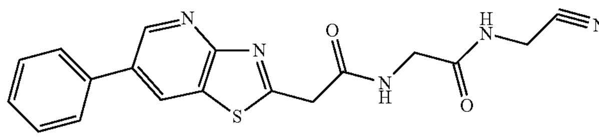 | (DMSO-d6) δ: 3.86 (d, J = 5.7 Hz, 2H), 4.19 (d, J = 5.7 Hz, 2H), 4.24 (s, 2H), 7.42-7.18 (m, 1H), 7.54-7.57 (m, 2H), 7.80-7.63 (m, 2H), 8.75-8.82 (m, 2H), 8.86 (d, J= 2.4 Hz, 1H), 8.86 (d, J = 2.4 Hz., 1H), 8.98 (d, J = 2.4 Hz, 1H). | | | |

TABLE 85

| No. | Structure | NMR(δ) | retention time | Mass | method |
|---|---|---|---|---|---|
| II-2-176 | 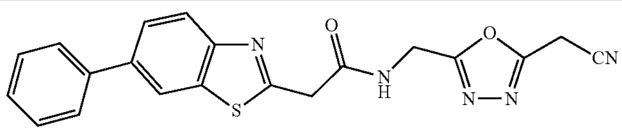 [SMILES: N#CCc1nnc(CNC(=O)Cc2nc3ccc(-c4ccccc4)cc3s2)o1] | 1H-NMR (DMSO-d6) δ: 4.17 (s, 2H), 4.62-4.63 (m, 4H), 7.38-7.40 (m, 1H), 7.49-7.51 (m, 2H), 7.75-7.80 (m, 3H), 8.02 (d, J = 8.1 Hz, 1H), 8.38 (d, J = 1.5 Hz, 1H), 9.17 (t, J = 5.8 Hz, 1H). | | | |
| II-2-177 | 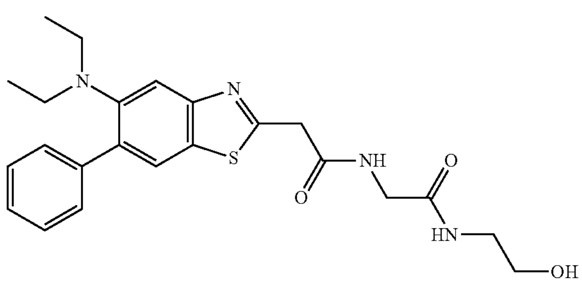 [SMILES: CCN(CC)c1cc2nc(CC(=O)NCC(=O)NCCO)sc2cc1-c1ccccc1] | (DMSO-d6) δ: 0.85 (t, J = 6.8 Hz, 6H), 2.87 (q, J = 7.1 Hz, 4H), 3.16 (q, J = 5.9 Hz, 2H), 3.41 (q, J = 5.7 Hz, 2H), 3.76 (d, J = 6.1 Hz, 2H), 4.10 (s, 2H), 4.68 (t, J = 5.6 Hz, 1H), 7.32 (t, J = 6.8 Hz, 1H), 7.42 (t, J = 7.6 Hz, 2H), 7.56 (d, J = 8.1 Hz, 2H), 7.63 (s, 1H), 7.82 (s, 1H), 7.96 (t, J = 5.1 Hz, 1H), 8.57 (t, J = 5.3 Hz, 1H). | | | |
| II-2-178 | 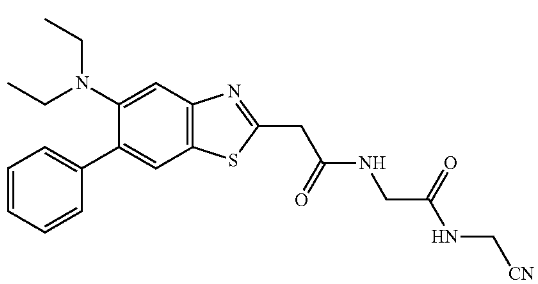 [SMILES: CCN(CC)c1cc2nc(CC(=O)NCC(=O)NCC#N)sc2cc1-c1ccccc1] | (DMSO-d6) δ: 0.85 (t, J = 6.3 Hz, 6H), 2.87 (q, J = 6.8 Hz, 4H), 3.82 (d, J = 5.1 Hz, 2H), 4.11 (s, 2H), 4.17 (d, J = 4.6 Hz, 2H), 7.30-7.44 (m, 3H), 7.55-7.64 (m, 6H), 7.84 (s, 1H), 8.67-8.71 (m, 2H). | | | |

TABLE 85-continued

| No. | Structure | NMR(δ) | retention time | Mass | method |
|---|---|---|---|---|---|
| II-2-179 | 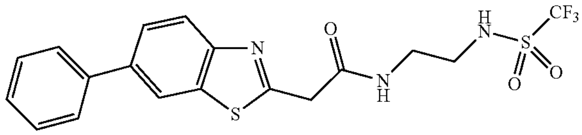 [SMILES: O=C(Cc1nc2ccc(-c3ccccc3)cc2s1)NCCNS(=O)(=O)C(F)(F)F] | 1H-NMR (DMSO-d6) δ: 3.23-3.28 (m, 4H), 4.08 (s, 2H), 7.38-7.40 (m, 1H), 7.48-7.51 (m, 2H), 7.76-7.79 (m, 3H), 8.01 (d, J = 8.6 Hz, 1H), 8.38 (d, J = 2.0 Hz, 1H), 8.52-8.53 (m, 1H), 9.52 (s, 1H). | | | |
| II-2-180 | 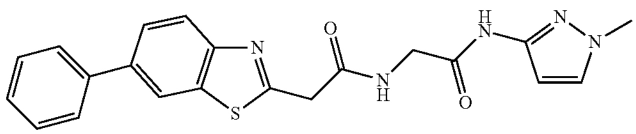 [SMILES: Cn1ccc(NC(=O)CNC(=O)Cc2nc3ccc(-c4ccccc4)cc3s2)n1] | 1H-NMR (DMSO-d6) δ: 3.73 (s, 3H), 3.94 (d, J = 6.1 Hz, 2H), 4.17 (s, 2H), 6.43 (d, J = 2.0 Hz, 1H), 7.37-7.41 (m, 1H), 7.49-7.53 (m, 3H), 7.76-7.79 (m, 3H), 8.05 (d, J = 8.6 Hz, 1H), 8.38 (d, J = 1.5 Hz, 1H), 8.69 (t, J = 5.6 Hz, 1H), 10.42 (s, 1H). | | | |

TABLE 86

| No. | Structure | NMR(δ) | retention time | Mass | method |
|---|---|---|---|---|---|
| II-2-181 | 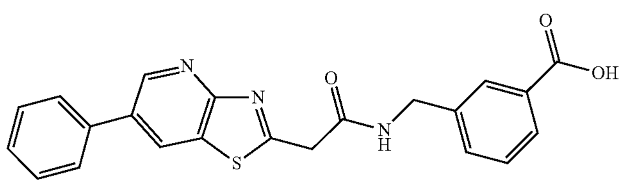 [SMILES: O=C(Cc1nc2ncc(-c3ccccc3)cc2s1)NCc1cccc(C(=O)O)c1] | (DMSO-d6) δ: 4.24 (s, 2H), 4.44 (d, J = 5.7 Hz, 2H), 7.44-7.54 (m, 5H), 8.61 (d, J = 2.1 Hz, 1H), 8.99 (t, J = 5.7 Hz., 1H), 1296 (brs, 1H). | | | |
| II-2-182 | 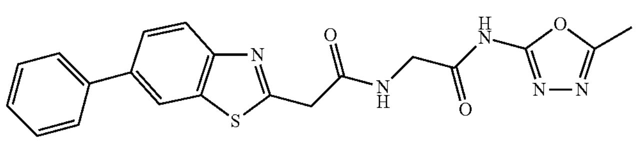 [SMILES: Cc1nnc(NC(=O)CNC(=O)Cc2nc3ccc(-c4ccccc4)cc3s2)o1] | 1H-NMR (DMSO-d6) δ: 2.45 (s, 2H), 4.03-4.05 (m, 2H), 4.18 (s, 2H), 7.39 (t, J = 7.4 Hz, 1H), 7.50 (t, J = 7.6 Hz, 2H), 7.75-7.81 (m, 3H), 8.02 (d, J = 8.6 Hz, 1H), 8.39 (d, J = 1.5 Hz, 1H), 8.80 (t, J = 5.6 Hz, 1H), 11.63-11.66 (m, 1H). | | | |
| II-2-183 | 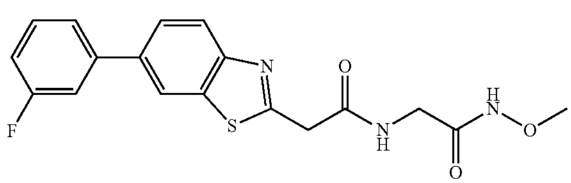 [SMILES: CONC(=O)CNC(=O)Cc1nc2ccc(-c3cccc(F)c3)cc2s1] | (DMSO-d$_6$) δ: 3.60 (s, 3H), 3.70 (d, J = 5.07 Hz, 2H), 4.16 (s, 2H), 7.23 (m, 1H), 7.50-7.64 (m, 3H), 7.84 (dd, J = 8.62. 1.01 Hz, 1H), 8.01 (d, J = 8.62 Hz, 1H), 8.45 (d, J = 1.01 Hz, 1H), 8.69 (t, J = 5.07 Hz, 1H), 11.25 (s, 1H). | | | |
| II-2-184 | 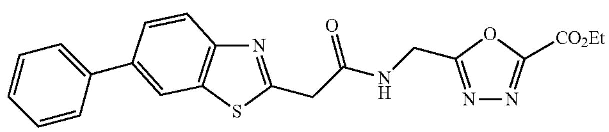 [SMILES: CCOC(=O)c1nnc(CNC(=O)Cc2nc3ccc(-c4ccccc4)cc3s2)o1] | 1H-NMR (DMSO-d6) δ: 1.32 (t, J = 7.1 Hz, 3H), 4.19 (s, 2H), 4.41 (q, J = 7.1 Hz, 2H ), 4.69 6.1 Hz, 2H), 7.39 (t, J = 7.4 Hz, 1H). 7.48-7.51 (m, 2H), 7.74-7.81 (m, 3H), 8.01 (d, J = 8.6 Hz, 1H), 8.39 (d, J = 2.0 Hz, 1H), 9.24 (t, J = 5.6 Hz, 1H). | | | |

TABLE 86-continued

| No. | Structure | NMR(δ) | retention time | Mass | method |
|---|---|---|---|---|---|
| II-2-185 | 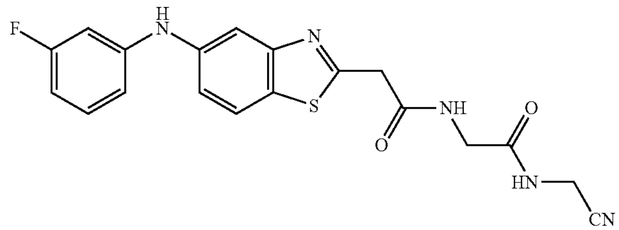 [SMILES: N#CCNC(=O)CNC(=O)Cc1nc2cc(Nc3cccc(F)c3)ccc2s1] | (DMSO-d6) δ: 3.82 (d, J = 5.6 Hz, 2H), 4.10 (s, 2H), 4.16 (d, J = 5.6 Hz, 2H), 6.60 (td, J = 8.4, 2.2 Hz, 1H), 6.83 (d, J = 11.7 Hz, 1H), 6.91 (dd, J = 8.1, 1.0 Hz, 1H), 7.18-7.28 (m, 2H), 7.64 (d, J = 1.5 Hz, 1H), 7.92 (d, J = 8.6 Hz, 1H), 8.58 (s, 1H), 8.66-8.71 (m, 2H). | | | |

TABLE 87

| No. | Structure | NMR(δ) | retention time | Mass | method |
|---|---|---|---|---|---|
| II-2-186 | 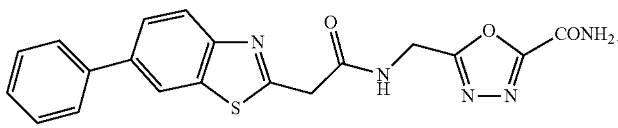 | 1H-NMR (DMSO-d6) δ: 4.19 (s, 2H), 4.66 (d, J = 6.1 Hz, 2H), 7.39 (t, J = 7.4 Hz, 1H), 7.50 (t, J = 7.6 Hz, 2H), 7.76-7.79 (m, 3H), 8.02 (d, J = 8.1 Hz, 1H), 8.21 (s, 1H), 8.38 (d, J = 1.5 Hz, 1H), 8.61 (s, 1H), 9.20 (t, J = 5.6 Hz, 1H). | | | |
| II-2-187 | 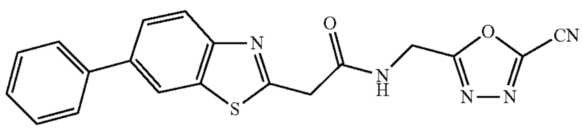 [SMILES: N#Cc1nnc(CNC(=O)Cc2nc3ccc(-c4ccccc4)cc3s2)o1] | 1H-NMR (DMSO-d6) δ: 4.18-4.21 (m, 2H), 4.73-4.74 (m, 2H), 7.41-7.50 (m, 3H), 7.74-7.81 (m, 3H), 8.01-8.02 (m, 1H), 8.39 (s, 1H), 9.24-9.25 (m, 1H). | | | |
| II-2-188 | 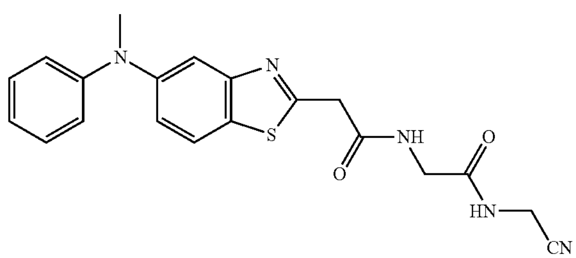 [SMILES: CN(c1ccccc1)c1ccc2sc(CC(=O)NCC(=O)NCC#N)nc2c1] | (CDCl3) δ: 3.40 (s, 3H), 4.07 (m, 4H), 4.14 (d, J = 6.1 Hz, 2H), 7.07-7.14 (m, 4H), 7.32-7.37 (m, 2H), 7.51 (d, J = 2.0 Hz, 1H), 7.56 (s, 1H), 7.65 (d, J = 8.6 Hz, 1H), 7.82 (s, 1H). | | | |
| II-2-189 | 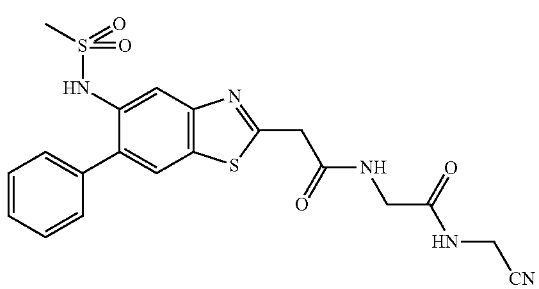 [SMILES: CS(=O)(=O)Nc1cc2nc(CC(=O)NCC(=O)NCC#N)sc2cc1-c1ccccc1] | (CDCl3) δ: 2.99 (s, 3H), 4.12-4.14 (m, 4H), 4.26 (d, J = 5.6 Hz, 2H), 6.57 (s, 1H), 7.37 (d, J = 7.6 Hz, 2H), 7.49-7.64 (m, 5H), 7.76 (s, 1H), 8.28 (s, 1H). | | | |
| II-2-190 | 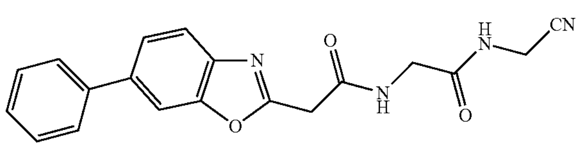 | (DMSO-d6) δ: 3.83 (d, J = 5.58 Hz, 2H), 4.03 (s, 2H), 4.18 (d, J = 5.58 Hz, 2H), 7.39 (m, 1H), 7.46-7.52 (m, 2H), 7.66-7.80 (m, 4H), 8.01 (s, 1H), 8.68-8.73 (m, 2H). | | | |

TABLE 88

| No. | Structure | NMR(δ) | retention time | Mass | method |
|---|---|---|---|---|---|
| II-2-191 | 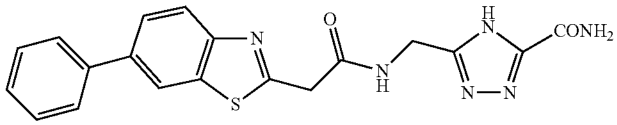 [SMILES: NC(=O)c1nnc(CNC(=O)Cc2nc3ccc(-c4ccccc4)cc3s2)[nH]1] | 1H-NMR (DMSO-d6) δ: 4.16 (s, 2H), 4.46 (d, J = 5.1 Hz, 2H), 7.38-7.40 (m, 1H), 7.50 (t, J = 7.6 Hz, 2H), 7.69-7.81 (m, 4H), 8.00-8.03 (m, 2H), 8.39 (s, 1H), 8.97 (s, 1H). | | | |
| II-2-192 | 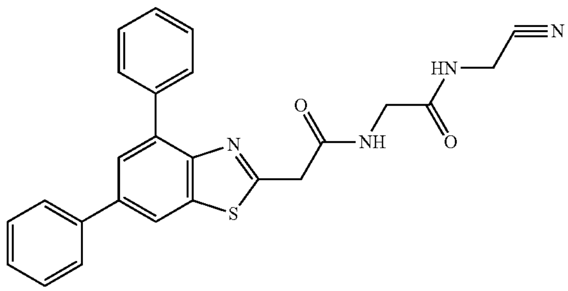 [SMILES: N#CCNC(=O)CNC(=O)Cc1nc2c(-c3ccccc3)cc(-c3ccccc3)cc2s1] | (DMSO-d6) δ: 3.83 (d, J = 5.7 Hz, 2H), 4.15 (d, J = 5.7 Hz, 2H), 4.17 (s, 2H), 7.38-7.52 (m, 6H), 7.62-7.82 (m, 5H), 8.39 (d, J = 1.5 Hz, 1H), 8.68 (t, J = 5.7 Hz, 1H), 8.71 (t, J = 5.7 Hz, 1H). | | | |
| II-2-193 | 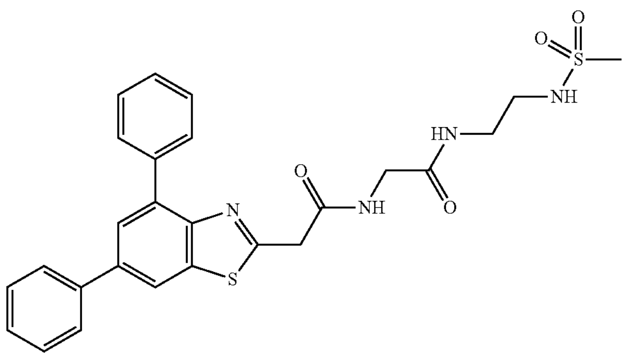 [SMILES: CS(=O)(=O)NCCNC(=O)CNC(=O)Cc1nc2c(-c3ccccc3)cc(-c3ccccc3)cc2s1] | (DMSO-d6) δ: 2.89 (s, 3H), 2.98 (q, J = 5.7 Hz, 2H), 3.76 (d, J = 5.7 Hz, 2H), 4.16 (s, 2H), 7.05 (t, J = 5.7 Hz, 6H), 7.81-7.92 (m, 5H), 2H), 8.04 (t, J = 5.7 Hz., 1H), 8.38 (d, J = 1.8 Hz, 1H), 8.60 (t, J = 5.7 Hz, 1H). | | | |
| II-2-194 | 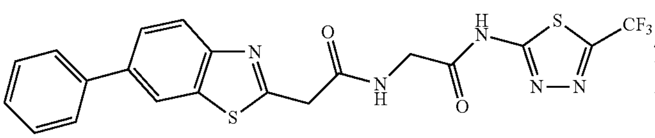 [SMILES: O=C(Cc1nc2ccc(-c3ccccc3)cc2s1)NCC(=O)Nc1nnc(C(F)(F)F)s1] | 1H-NMR (DMSO-d6) δ: 4.21-4.22 (m, 4H), 7.38-7.40 (m, 1H), 7.48-7.51 (m, 2H), 7.76-7.80 (m, 3H), 8.03 (d, J = 8.6 Hz, 1H), 8.39 (d, J = 1.5 Hz, 1H), 8.93 (t, J = 5.6 Hz, 1H), 13.42 (s, 1H). | | | |
| II-2-195 | 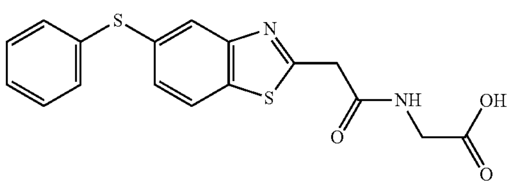 [SMILES: O=C(O)CNC(=O)Cc1nc2cc(Sc3ccccc3)ccc2s1] | (DMSO-d6) δ: 3.83 (d, J = 5.6 Hz, 2H), 4.13 (s, 2H), 7.30-7.40 (m, 6H), 7.86 (d, J = 1.0 Hz, 1H), 8.09 (d, J = 8.6 Hz, 1H), 8.70 (t, J = 5.6 Hz, 1H). | | | |

TABLE 89

| No. | Structure | NMR(δ) | retention time | Mass | method |
|---|---|---|---|---|---|
| II-2-196 | 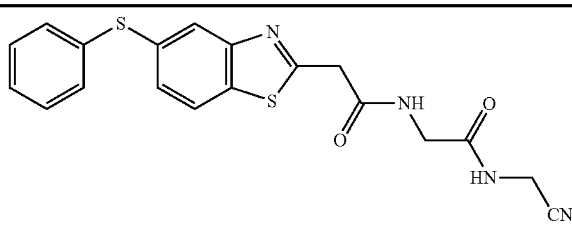 | (DMSO-d6) δ: 3.81 (d, J = 6.1 Hz, 2H), 4.14-4.16 (m, 4H), 7.32-7.41 (m, 6H), 7.87 (s, 1H), 8.09 (d, J = 8.6 Hz, 1H), 8.67 (t, J = 5.3 Hz, 1H), 8.72 (t, J = 5.8 Hz, 1H). | | | |

TABLE 89-continued

| No. | Structure | NMR(δ) | retention time | Mass | method |
|---|---|---|---|---|---|
| II-2-197 | 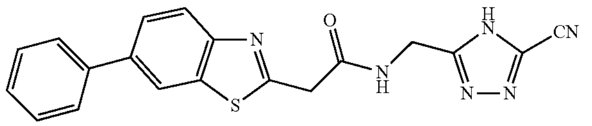 [SMILES: N#Cc1nnc(CNC(=O)Cc2nc3ccc(-c4ccccc4)cc3s2)[nH]1] | 1H-NMR (DMSO-d6) δ: 4.18 (s, 2H), 4.53 (d, J = 5.6 Hz, 2H), 7.39-7.52 (m, 3H), 7.76-7.80 (m, 3H), 8.02 (d, J = 8.6 Hz, 1H), 8.39 (d, J = 1.5 Hz, 1H), 9.11 (t, J = 5.6 Hz, 1H), 15.16 (s, 1H). | | | |
| II-2-198 | 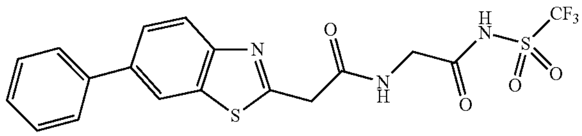 [SMILES: O=C(Cc1nc2ccc(-c3ccccc3)cc2s1)NCC(=O)NS(=O)(=O)C(F)(F)F] | 1H-NMR (DMSO-d6) δ: 3.71 (d, J= 5.6 Hz, 2H), 4.13 (s, 2H), 7.37-7.40 (m, 1H), 7.49 (t, J = 7.6 Hz, 2H), 7.75-7.79 (m, 3H), 8.01 (d, J = 8.6 Hz, 1H), 8.37-8.37 (m, 2H). | | | |
| II-2-199 | 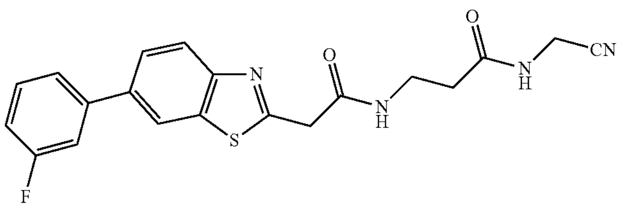 [SMILES: N#CCNC(=O)CCNC(=O)Cc1nc2ccc(-c3cccc(F)c3)cc2s1] | (DMSO-d$_6$) δ: 2.38 (t, J = 7.10 Hz, 2H), 3.34 (dt, J = 7.10, 5.32 Hz, 2H), 8.64 (t, J = 5.58, Hz, 1.0H), 4.05 (s, 2H), 7.22 (m, 1.0H), 7.50-7.64 (m, 3H), 7.83 (dd, J = 8.36, 1.77 Hz, 1H), 8.01 (d, J = 8.11 Hz, 1H), 8.43 (d, J = 1.01 Hz, 1H), 8.48 (t, J = 5.32 Hz, 1H). | | | |
| II-2-200 | 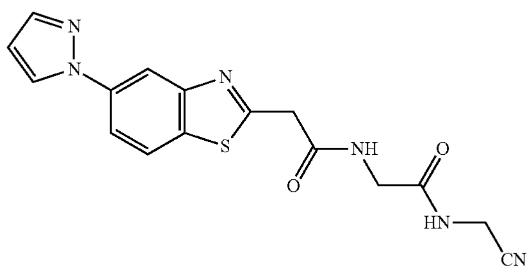 [SMILES: N#CCNC(=O)CNC(=O)Cc1nc2cc(-n3cccn3)ccc2s1] | (DMSO-d6) δ: 3.84 (d, J = 5.7 Hz, 2H), 4.16-4.18 (m, 4H), 6.59 (s, 1H), 7.79 (d, J = 2.1 Hz, 1H), 7.97 (dd, J = 8.4, 2.1 Hz, 1H), 8.18 (d, J = 8.7Hz, 1H), 8.40 (d, J = 2.4 Hz, 1H), 8.63 (d, J = 2.7 Hz, 1H), 8.67-8.78 (m, 2H) | | | |

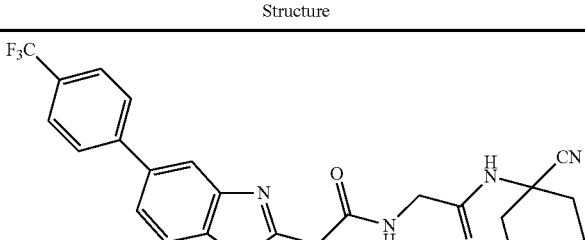

TABLE 90

| No. | Structure | NMR(δ) | retention time | Mass | method |
|---|---|---|---|---|---|
| II-2-201 | 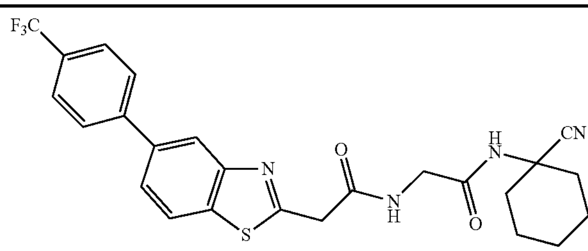 | (DMSO-d$_6$) δ: 1.21-1.70 (m, 8H), 2.13-2.21 (m, 2H), 3.85 (d, J = 5.58 Hz, 2H), 4.19 (s, 2H), 7.78-7.87 (m, 3H), 8.01 (d, J = 8.11 Hz, 2H), 8.20 (dd, J = 8.62, 1.52 Hz, 1H), 8.31 (d, J = 1.52 Hz, 1H), 8.40 (s, 1H), 8.66 (t, J = 5.58 Hz, 1H). | | | |
| II-2-202 | 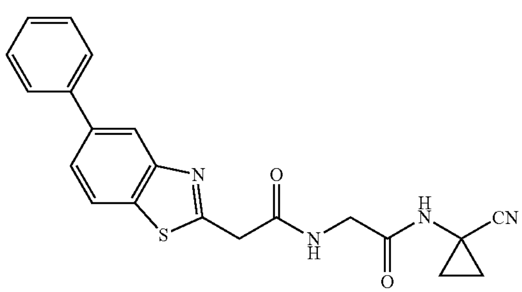 [SMILES: N#CC1(NC(=O)CNC(=O)Cc2nc3cc(-c4ccccc4)ccc3s2)CC1] | (DMSO-d$_6$) δ: 1.12 (dd, J = 8.11, 5.58 Hz, 2H), 1.49 (dd, J = 8.11, 5.58 Hz, 2H), 3.78 (d, J = 5.58 Hz, 2H), 4.16 (s, 2H), 7.40 (m, 1H), 7.48-7.53 (m, 2H), 7.71-7.79 (m, 3H), 8.14 (d, J = 8.11 Hz, 1H), 8.21 (d, J = 1.01 Hz, 1H), 8.68 (t, J = 5.58 Hz, 1H), 8.92 (s, 1H). | | | |

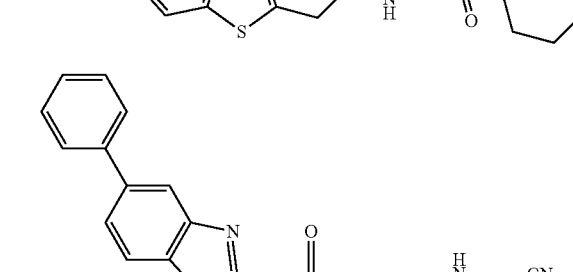

TABLE 90-continued

| No. | Structure | NMR(δ) | retention time | Mass | method |
|---|---|---|---|---|---|
| II-2-203 | 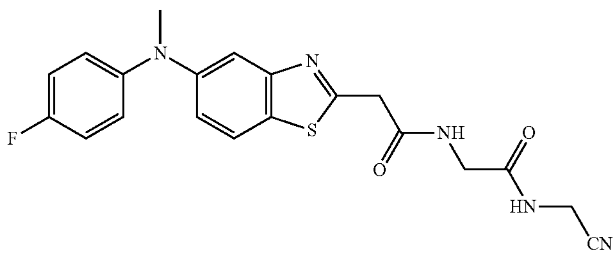 [SMILES: CN(c1ccc(F)cc1)c1ccc2sc(CC(=O)NCC(=O)NCC#N)nc2c1] | (DMSO-d6) δ: 3.30 (s, 3H), 3.81 (d, J = 5.6 Hz, 2H), 4.08 (s, 2H), 4.16 (d, J = 5.6 Hz, 2H), 7.00 (dd, J = 8.6, 2.0 Hz, 1H), 7.09-7.18 (m, 4H), 7.43 (d, J = 2.0 Hz, 1H), 7.86 (d, J = 8.6 Hz, 1H), 8.65-8.70 (m, 2H). | | | |
| II-2-204 | 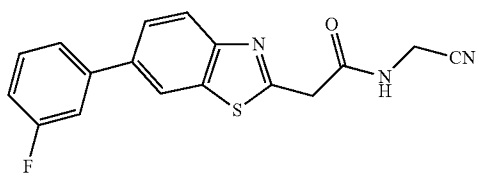 [SMILES: N#CCNC(=O)Cc1nc2ccc(-c3cccc(F)c3)cc2s1] | (DMSO-d$_6$) δ: 4.18 (s, 2H), 4.24 (d, J = 5.07 Hz, 2H), 7.22 (m, 1H), 7.51-7.64 (m, 3H), 7.85 (dd, J = 8.36, 1.52 Hz, 1H), 8.03 (d, J = 8.36 Hz, 1H), 8.47 (d, J = 1.52 Hz, 1H), 9.09 (t, J = 5.07 Hz, 1H) | | | |
| II-2-205 | 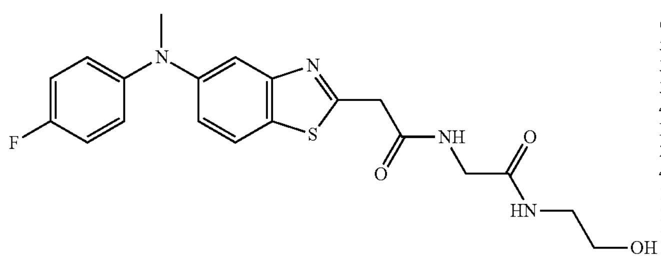 [SMILES: CN(c1ccc(F)cc1)c1ccc2sc(CC(=O)NCC(=O)NCCO)nc2c1] | (DMSO-d6) δ: 3.14 (q, J = 5.7 Hz, 2H), 3.29 (s, 3H), 3.40 (q, J = 5.4 Hz, 2H), 3.75 (d, J = 5.6 Hz, 2H), 4.07 (s, 2H), 4.67 (t, J = 5.3 Hz, 1H), 6.99 (dd, J = 8.9, 2.3 Hz, 1H), 7.09-7.18 (m, 4H), 7.44 (d, J = 2.0 Hz, 1H), 7.85 (d, J = 8.6 Hz, 1H), 7.95 (t, J = 5.1 Hz, 1H), 8.56 (t, J = 5.8 Hz, 1H). | | | |

TABLE 91

| No. | Structure | NMR(δ) | retention time | Mass | method |
|---|---|---|---|---|---|
| II-2-206 | 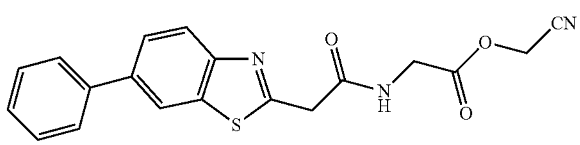 [SMILES: N#CCOC(=O)CNC(=O)Cc1nc2ccc(-c3ccccc3)cc2s1] | (DMSO-d$_6$) δ: 4.06 (d, J = 5.58 Hz, 2H), 4.17 (s, 2.0H), 5.03 (s, 2.0H), 7.37-7.52 (m, 3H), 7.74-7.81 (m, 3H), 8.02 (d, J = 8.62 Hz, 1H), 8.38 (d, J = 1.01 Hz, 1H), 8.92 (t, J = 5.83 Hz, 1H). | | | |
| II-2-207 | 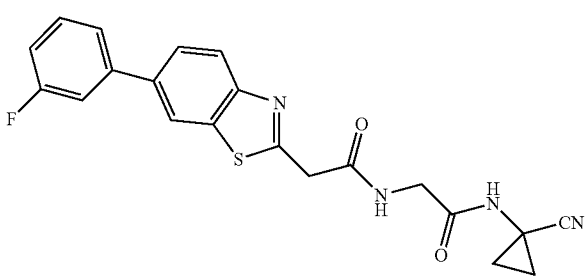 [SMILES: N#CC1(NC(=O)CNC(=O)Cc2nc3ccc(-c4cccc(F)c4)cc3s2)CC1] | (DMSO-d$_6$) δ: 1.12 (dd, J = 8.36, 5.32 Hz, 1.49 (dd, J = 8.36, 5.32 Hz, 2H), 3.78 (d, J = 6.08 Hz, 2H), 4.16 (s, 2H), 7.22 (m, 1H), 7.50-7.64 (m, 3H), 7.84 (dd, J = 8.62, 1.52 Hz, 1H), 8.02 (d, J = 8.11 Hz, 1H), 8.45 (d, J = 1.52 Hz, 1H), 8.68 (t, J = 6.08 Hz, 1H), 8.91 (s, 1H). | | | |

TABLE 91-continued

| No. | Structure | NMR(δ) | retention time | Mass | method |
|---|---|---|---|---|---|
| II-2-208 | 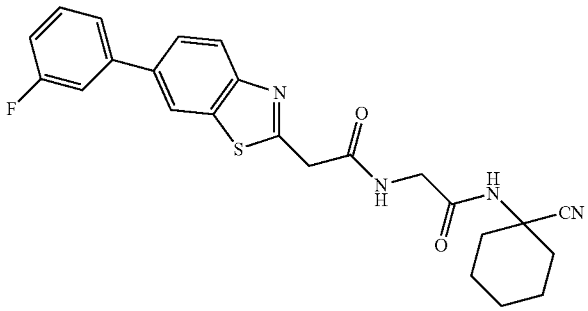 [SMILES: N#CC1(NC(=O)CNC(=O)Cc2nc3ccc(-c4cccc(F)c4)cc3s2)CCCCC1] | (DMSO-d$_6$) δ: 1.21-1.70 (m, 8H), 2.14-2.21 (m, 2H), 3.85 (d, J = 6.08 Hz, 2H), 4.17 (s, 2H), 7.22 (m, 1H), 7.50-7.64 (m, 3H), 7.84 (dd, J = 8.62, 2.03 Hz, 1H), 8.02 (d, J = 8.62 Hz, 1H), 8.40 (s, 1H), 8.45 (d, J = 2.03 Hz, 1H), 8.65 (t, J = 5.58 Hz, 1H). | | | |
| II-2-209 | 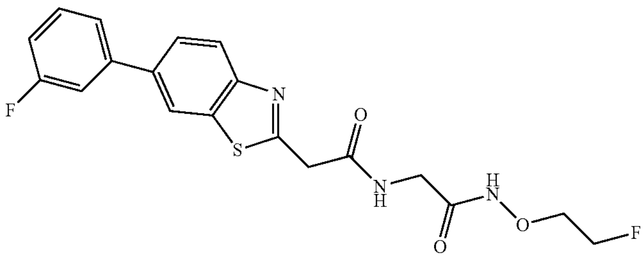 [SMILES: O=C(Cc1nc2ccc(-c3cccc(F)c3)cc2s1)NCC(=O)NOCCF] | (DMSO-d$_6$) δ: 3.71 (d, J = 5.07 Hz, 2H), 3.99 (t, J = 2.54 Hz, 1H), 4.06 (t, J = 2.54 Hz, 1H), 4.15 (s, 2H), 4.54 (t, J = 2.54 Hz, 1H), 4.66 (t, J = 2.54 Hz, 1H), 7.22 (m, 1H), 7.50-7.65 (m, 3H), 7.83 (dd, J = 8.62, 1.52 Hz, 1H), 8.02 (d, J = 8.62 Hz, 1H), 8.45 (d, J = 1.52 Hz, 1H), 8.69 (t, J = 5.07 Hz, 1H), 11.36 (s, 1.0H). | | | |
| II-2-210 | 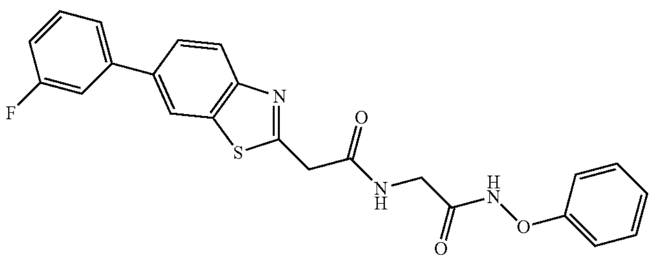 [SMILES: O=C(Cc1nc2ccc(-c3cccc(F)c3)cc2s1)NCC(=O)NOc1ccccc1] | (DMSO-d$_6$) δ: 3.90 (d, J = 5.07 Hz, 2H), 4.18 (s, 2H), 7.00-7.07 (m, 3H), 7.19-7.35 (m, 3H), 7.50-7.64 (m, 3H), 7.83 (dd, J = 8.62, 2.03 Hz, 1H), 8.00 (d, J = 8.62 Hz, 1H), 8.46 (d, J = 2.03 Hz, 1H), 8.84 (t, J = 5.07 Hz, 1H), 12.01 (s, 1H). | | | |

TABLE 92

| No. | Structure | NMR(δ) | retention time | Mass | method |
|---|---|---|---|---|---|
| II-2-211 | 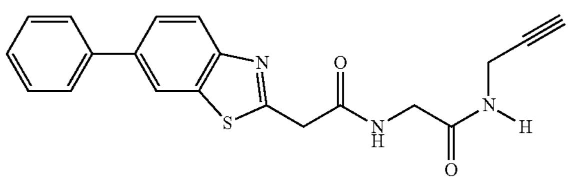 | (DMSO-d$_6$) δ: 3.13 (s, 1H), 3.79 (d, J = 5.6 Hz, 2H), 3.90 (m, 2H), 4.16 (s, 2H), 7.36-7.42 (m, 1H), 7.46-7.52 (m, 2H), 7.72-7.82 (m, 3H), 8.02 (d, J = 8.4 Hz, 1H), 8.38 (s, 1H), 8.40-8.48 (m, 1H), 8.65-8.70 (m, 1H). | | | |
| II-2-212 | 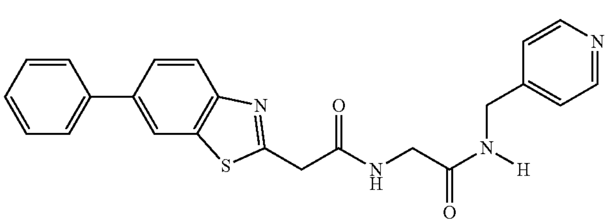 [SMILES: O=C(CNC(=O)Cc1nc2ccc(-c3ccccc3)cc2s1)NCc1ccncc1] | (DMSO-d$_6$) δ: 3.91 (d, J = 5.2 Hz, 2H), 4.19 (s, 2H), 4.60 (d, J = 5.6 Hz, 2H), 7.36-7.44 (m, 1H), 7.47-7.53 (m, 2H), 7.72-7.80 (m, 3H), 7.90 (d, J = 5.2 Hz, 1H), 8.00 (d, J = 8.4 Hz, 1H), 8.39 (s, 1H), 8.78-8.89 (m, 4H). | | | |

TABLE 92-continued

| No. | Structure | NMR(δ) | retention time | Mass | method |
|---|---|---|---|---|---|
| II-2-213 | 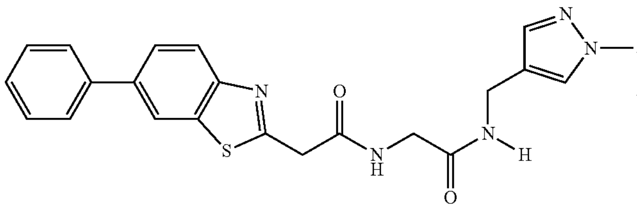 [SMILES: Cn1cc(CNC(=O)CNC(=O)Cc2nc3ccc(-c4ccccc4)cc3s2)cn1] | (DMSO-d$_6$) δ: 3.72-3.80 (m, 5H), 4.10-4.18 (m, 4H), 7.31 (s, 1H), 7.37-7.43 (m, 1H), 7.46-7.57 (m, 3H), 7.72-7.82 (m, 3H), 7.97-8.02 (m, 1H), 8.23-8.28 (m, 1H), 8.38 (s, 1H), 8.61-8.67 (m, 1H). | | | |
| II-2-214 | 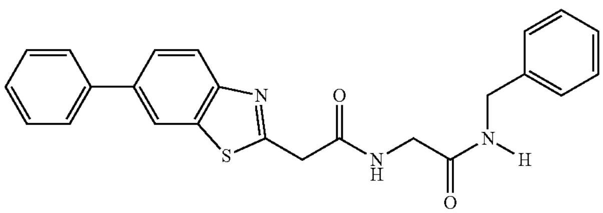 [SMILES: O=C(CNC(=O)Cc1nc2ccc(-c3ccccc3)cc2s1)NCc1ccccc1] | | 2.16 | 415.95 (ES+) | C |
| II-2-215 | 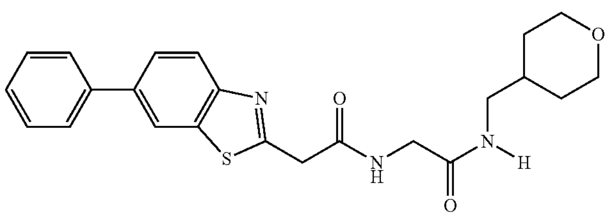 [SMILES: O=C(CNC(=O)Cc1nc2ccc(-c3ccccc3)cc2s1)NCC1CCOCC1] | (DMSO-d$_6$) δ: 1.05-1.18 (m, 2H), 1.48-1.68 (m, 3H), 2.96-3.02 (m, 2H), 3.21 (t, J = 11.2 Hz, 2H), 3.74-3.85 (m, 4H), 4.16 (s, 1H), 7.36-7.42 (m, 1H), 7.47-7.54 (m, 2H), 7.72-7.82 (m, 3H), 7.91-7.97 (m, 1H), 7.98-8.04 (m, 1H). | | | |

TABLE 93

| No. | Structure | NMR(δ) | retention time | Mass | method |
|---|---|---|---|---|---|
| II-2-216 | 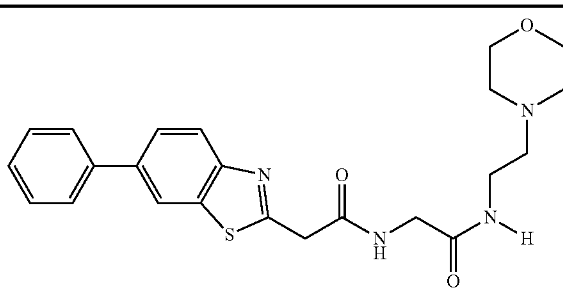 | | 1.29 | 439.05 (ES+) | C |
| II-2-217 | 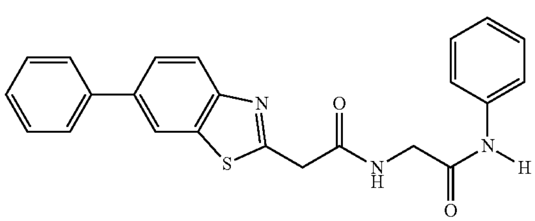 [SMILES: O=C(Cc1nc2ccc(-c3ccccc3)cc2s1)NCC(=O)Nc1ccccc1] | (DMSO-d$_6$) δ: 4.00 (d, J = 5.2 Hz, 2H), 4.21 (s, 2H), 7.02-7.08 (m, 1H), 7.28-7.35 (m, 2H), 7.35-7.42 (m, 1H), 7.46-7.53 (m, 2H), 7.59 (d, J = 7.6 Hz, 2H), 7.72-7.82 (m, 3H), 8.02 (d, J = 8.4 Hz, 1H), 8.39 (s, 1H), 8.73-8.79 (m, 1H), 10.05 (s, 1H). | | | |
| II-2-218 | 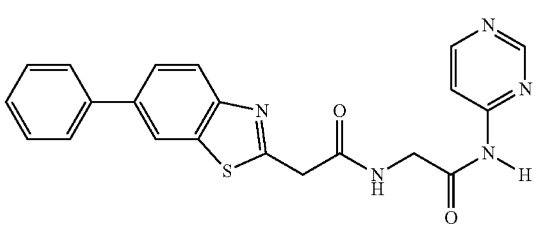 [SMILES: O=C(Cc1nc2ccc(-c3ccccc3)cc2s1)NCC(=O)Nc1ccncn1] | (DMSO-d$_6$) δ: 4.06 (d, J = 4.4 Hz, 2H), 4.21 (s, 2H), 7.37-7.43 (m, 1H), 7.47-7.53 (m, 2H), 7.73-7.82 (m, 3H), 8.02 (d, J = 7.6 Hz, 1H), 8.39 (s, 1H), 8.81-8.87 (m, 1H), 8.91 (s, 1H), 9.00 (s, 2H), 10.51 (s, 1H). | | | |

TABLE 93-continued

| No. | Structure | NMR(δ) | retention time | Mass | method |
|---|---|---|---|---|---|
| II-2-219 | 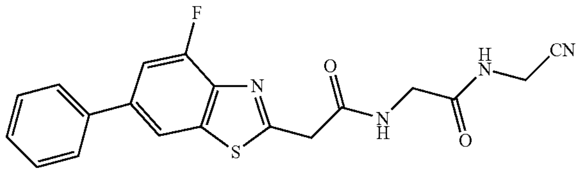 [SMILES: N#CCNC(=O)CNC(=O)Cc1nc2c(F)cc(-c3ccccc3)cc2s1] | (DMSO-d6) δ: 3.43 (d, J = 5.7 Hz, 2H), 4.17 (s, J = 5.7 Hz, 2H), 4.22 (s, 2H), 7.38-7.53 (m, 3H), 7.69 (d J = 13.2 Hz, 1H), 7.78 (d, J = 7.2 Hz, 2H), 8.26 (d, J = 0.9 Hz, 1H), 8.63 (t, J = 5.4 Hz, 1H), 8.67 (t, J = 5.4 Hz, 1H). | | | |
| II-2-220 | 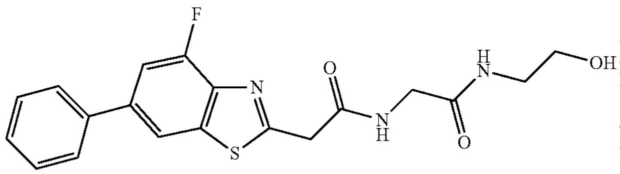 [SMILES: O=C(CNC(=O)Cc1nc2c(F)cc(-c3ccccc3)cc2s1)NCCO] | (DMSO-d6) δ: 3.16 (q, J = 5.7 Hz, 2H), 3.10 (q, J = 5.7 Hz, 2H), 3.78 (d, J = 5.7 Hz, 2H), 4.20 (s, 2H), 4.67 (t, J = 5.7 Hz, 1H), 741 (t, J = 5.7 Hz, 1H), 7.51 (t, J = 5.7 Hz, 2H), 7.67 (d, J = 12.0 Hz, 1H), 7.86 (d, J = 8.6 Hz, 2H), 7.95 (t, J = 1.8 Hz, 1H), 8.26 (d, J = 0.9 Hz, 1H), 8.63 (t, J = 5.7 Hz, 1H). | | | |

TABLE 94

| No. | Structure | NMR(δ) | retention time | Mass | method |
|---|---|---|---|---|---|
| II-2-221 | 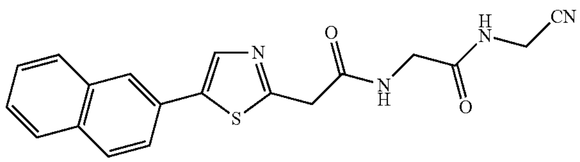 [SMILES: N#CCNC(=O)CNC(=O)Cc1ncc(-c2ccc3ccccc3c2)s1] | (DMSO-d$_6$) δ: 3.83 (s, 2H), 4.05 (s, 2H), 4.17 (s, 2H), 7.50-7.58 (m, 2H), 7.84 (dd, J = 8.62, 1.52 Hz, 1H), 7.91-8.00 (m, 3H), 8.17 (brs, 1H), 8.24 (s, 1H), 8.72 (brs, 2H). | | | |
| II-2-222 | 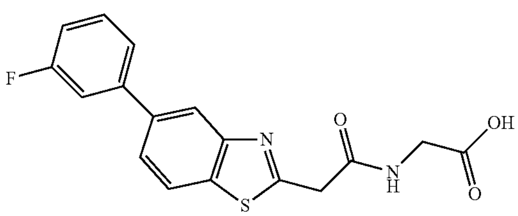 [SMILES: O=C(O)CNC(=O)Cc1nc2cc(-c3cccc(F)c3)ccc2s1] | (DMSO-d$_6$) δ: 3.85 (d, J = 6.08 Hz, 2H), 4.16 (s, 2H), 7.22 (m, 1H), 7.53 (m, 1H), 7.61-7.66 (m, 2H), 7.77 (dd, J = 8.62, 1.52 Hz, 1H), 8.16 (d, J = 8.62 Hz, 1H), 8.27 (d, J = 1.52 Hz, 1H), 8.71 (t, J = 5.83 Hz, 1H), 12.64 (s, 1H). | | | |
| II-2-223 | 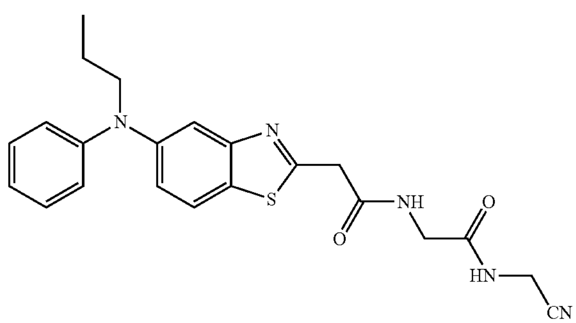 [SMILES: CCCN(c1ccccc1)c1ccc2sc(CC(=O)NCC(=O)NCC#N)nc2c1] | (DMSO-d6) δ: 0.93 (t, J = 7.4 Hz, 3H), 1.62-1.64 (m, 2H), 3.74 (t, J = 7.6 Hz, 2H), 3.84 (d, J = 5.9 Hz, 2H), 4.11 (s, 2H), 4.18 (d, J = 5.7 Hz, 2H), 6.90-7.04 (m, 3H), 7.09 (dd, J = 8.6, 2.3 Hz, 1H), 7.29 (t, J = 8.0 Hz, 2H), 7.53 (d, J = 2.4 Hz, 1H), 7.91 (d, J = 8.7 Hz, 1H), 8.63-8.74 (m, 2H). | | | |
| II-2-224 | 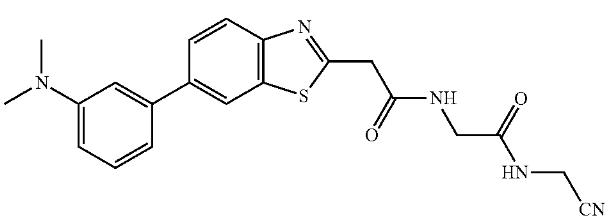 [SMILES: CN(C)c1cccc(-c2ccc3nc(CC(=O)NCC(=O)NCC#N)sc3c2)c1] | (CDCl3) δ: 3.03 (s, 6H), 3.76 (s, 2H), 4.08-4.15 (m, 4H), 6.80 (dd, J = 9.0, 2.4 Hz, 1H), 6.97-7.01 (m, 3H), 7.34 (t, J = 7.2 Hz, 1H), 7.74 (d, J = 15 Hz, 1H), 7.81 (br-s, 1H), 8.03-8.06 (m, 2H). | | | |

TABLE 94-continued

| No. | Structure | NMR(δ) | retention time | Mass | method |
|---|---|---|---|---|---|
| II-2-225 | 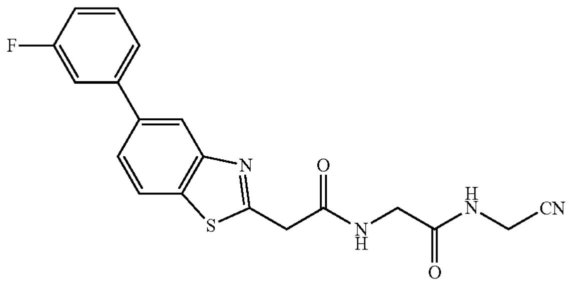 [SMILES: N#CCNC(=O)CNC(=O)Cc1nc2cc(-c3cccc(F)c3)ccc2s1] | (DMSO-d$_6$) δ: 3.83 (d, J = 5.58 Hz, 2H), 4.16-4.19 (m, 4H), 7.23 (m, 1H), 7.50-7.66 (m, 3H), 7.77 (dd, J = 8.62, 1.52 Hz, 1H), 8.16 (d, J = 8.62 Hz, 1H), 8.27 (d, J = 1.52 Hz, 1H), 8.69 (t, J = 5.58 Hz, 1H), 8.74 (t, J = 5.58 Hz, 1H). | | | |

TABLE 95

| No. | Structure | NMR(δ) | retention time | Mass | method |
|---|---|---|---|---|---|
| II-2-226 | 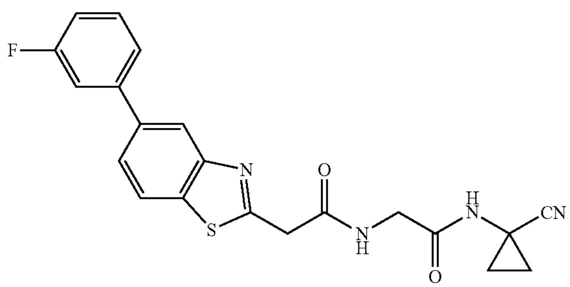 [SMILES: N#CC1(NC(=O)CNC(=O)Cc2nc3cc(-c4cccc(F)c4)ccc3s2)CC1] | (DMSO-d$_6$) δ: 1.12 (dd, J = 8.11, 5.83 Hz, 2H), 1.49 (dd, J = 8.11, 5.58 Hz, 2H), 3.78 (d, J = 5.83 Hz, 2H), 4.17 (s, 2H), 7.23 (m, 1H), 7.51-7.66 (m, 3H), 7.77 (dd, J = 8.36, 1.52 Hz, 1H), 8.16 (d, J = 8.36 Hz, 1H), 8.27 (d, J = 1.52 Hz, 1H), 8.69 (t, J = 5.83 Hz, 1H), 8.92 (s, 1H). | | | |
| II-2-227 | 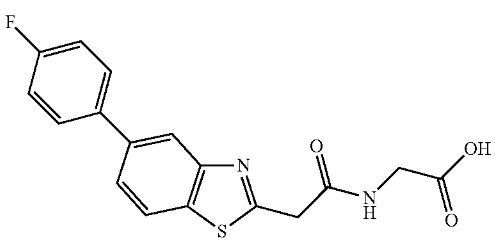 [SMILES: O=C(O)CNC(=O)Cc1nc2cc(-c3ccc(F)cc3)ccc2s1] | (DMSO-d$_6$) δ: 3.85 (d, J = 5.58 Hz, 2H), 4.16 (s, 2.0H), 7.32 (t, J = 8.61 Hz, 2H), 7.71 (dd, J = 8.11, 1.52 Hz, 1H), 7.79-7.84 (m, 2H), 8.14 (d, J = 8.11 Hz, 1H), 8.20 (d, J = 1.52 Hz, 1H), 8.71 (t, J = 5.83 Hz, 1H), 12.64 (s, 1H). | | | |
| II-2-228 | 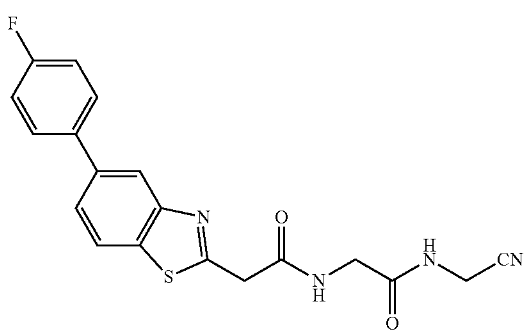 [SMILES: N#CCNC(=O)CNC(=O)Cc1nc2cc(-c3ccc(F)cc3)ccc2s1] | (DMSO-d$_6$) δ: 3.83 (d, J = 5.58 Hz, 2H), 4.15-4.19 (m, 4H), 7.33 (t, J = 8.87 Hz, 2H), 7.71 (dd, J = 8.62, 1.52 Hz, 1H), 7.79-7.84 (m, 2H), 8.14 (d, J = 8.62 Hz, 1H), 8.20 (d, J = 1.52 Hz, 1H), 8.69 (t, J = 5.58 Hz, 1H), 8.73 (t, J = 5.83 Hz, 1H). | | | |

TABLE 95-continued

| No. | Structure | NMR(δ) | retention time | Mass | method |
|---|---|---|---|---|---|
| II-2-229 | 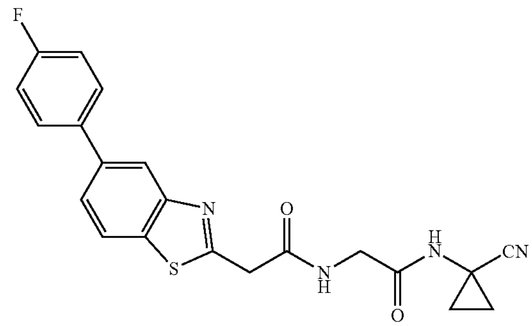 [SMILES: N#CC1(NC(=O)CNC(=O)Cc2nc3cc(-c4ccc(F)cc4)ccc3s2)CC1] | (DMSO-d$_6$) δ: 1.12 (dd, J = 8.36, 5.32 Hz, 2H), 1.49 (dd, J = 8.36. 5.32 Hz, 2H), 3.77 (d, J = 5.58 Hz, 2H), 4.16 (s, 2H), 7.29-7.35 (m, 2H), 7.71 (dd, J = 8.62, 1.52 Hz, 1H), 7.79-7.84 (m, 2H), 8.14 (d, J = 8.62 Hz, 1H), 8.20 (d, J = 1.52 Hz, 1H), 8.68 (t, J = 5.58 Hz, 1H), 8.91 (s, 1H). | | | |
| II-2-230 | 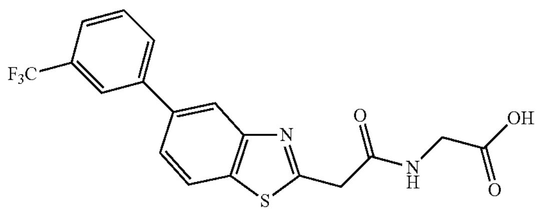 [SMILES: O=C(O)CNC(=O)Cc1nc2cc(-c3cccc(C(F)(F)F)c3)ccc2s1] | (DMSO-d$_6$) δ: 3.85 (d, J = 5.58 Hz, 2H), 4.17 (s, 2H), 7.71-7.83 (m, 3H), 8.07-8.12 (m, 2H), 8.19 (d, J = 8.11 Hz, 1H), 8.32 (d, J = 1.52 Hz, 1H), 8.72 (t, J = 5.83 Hz, 1H). | | | |

TABLE 96

| No. | Structure | NMR(δ) | retention time | Mass | method |
|---|---|---|---|---|---|
| II-2-231 | 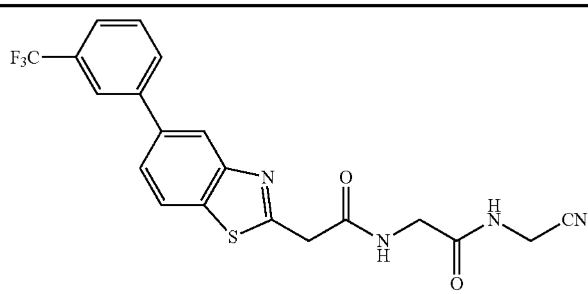 | (DMSO-d$_6$) δ: 3.84 (d, J = 6.08 Hz, 2H), 4.16-4.20 (m, 4H), 7.71-7.84 (m, 3H), 8.07-8.12 (m, 2H), 8.19 (d, J = 8.62 Hz, 1H), 8.32 (d, J = 1.52 Hz, 1H), 8.69 (t, J = 5.58 Hz, 1H), 8.74 (t, J = 5.83 Hz, 1H). | | | |
| II-2-232 | 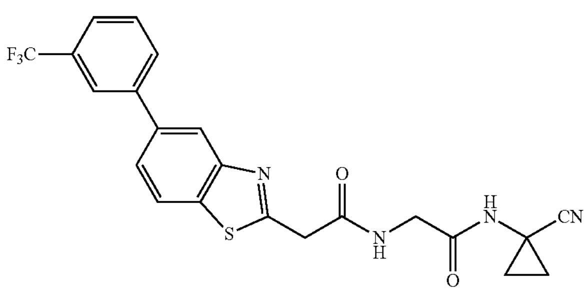 [SMILES: N#CC1(NC(=O)CNC(=O)Cc2nc3cc(-c4cccc(C(F)(F)F)c4)ccc3s2)CC1] | (DMSO-d$_6$) δ: 1.13 (dd, J = 8.11, 5.58 Hz, 2H), 1.49 (dd, J = 8.11, 5.58 Hz, 2H), 3.78 (d, J = 6.08 Hz, 2H), 4.18 (s, 2H), 7.71-7.84 (m, 3H), 8.06-8.12 (m, 2H), 8.19 (d, J = 8.62 Hz, 1H), 8.32 (d, J = 1.52 Hz, 1H), 8.69 (t, J = 5.58 Hz, 1H), 8.92 (s, 1H). | | | |
| II-2-233 | 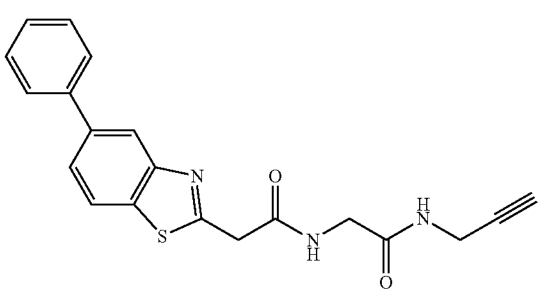 [SMILES: C#CCNC(=O)CNC(=O)Cc1nc2cc(-c3ccccc3)ccc2s1] | (DMSO-d$_6$) δ: 3.13 (t, J = 2.53 Hz, 1H), 3.78 (d, J = 6.08 Hz, 2H), 3.90 (dd, J = 5.58, 2.53 Hz, 2H), 4.16 (s, 2H), 7.40 (t, J = 7.35 Hz, 1H), 7.47-7.53 (m, 2H), 7.73 (dd, J = 8.62, 1.52 Hz, 1H), 7.77 (d, J = 7.10 Hz, 2H), 8.14 (d, J = 8.62 Hz, 1H), 8.22 (d, J = 1.52 Hz, 1H), 8.44 (t, J = 5.32 Hz, 1H), 8.67 (t, J = 5.83 Hz, 1H). | | | |

TABLE 96-continued

| No. | Structure | NMR(δ) | retention time | Mass | method |
|---|---|---|---|---|---|
| II-2-234 | 3-fluorophenyl-benzothiazole-CH2-C(O)-NH-CH2-C(O)-NH-CH2-C≡CH | (DMSO-d6) δ: 3.12 (t, J = 2.53 Hz, 1H), 3.78 (d, J = 5.58 Hz, 2H), 3.90 (dd, J = 5.58, 2.53 Hz, 2H), 4.16 (s, 2H), 7.22 (m, 1H), 7.50-7.64 (m, 3H), 7.84 (dd, J = 8.62, 1.77 Hz, 1H), 8.02 (d, J = 8.62 Hz, 1H), 8.40-8.46 (m, 2H), 8.67 (t, J = 5.83 Hz, 1H). | | | |
| II-2-235 | 3-MeO-phenyl-benzothiazole-CH2-C(O)-NH-CH2-COOH | (DMSO-d6) δ: 3.83-3.87 (m, 5H), 4.15 (s, 2H), 6.96 (m, 1H), 7.26-7.35 (m, 2H), 7.41 (t, J = 8.0 Hz, 1H), 7.80 (dd, J = 8.6, 1.8 Hz, 1H), 8.00 (d, J = 8.6 Hz, 1H), 8.40 (d, J = 1.5 Hz, 1H), 8.71 (t, J = 6.1 Hz, 1H). | | | |

TABLE 97

| No. | Structure | NMR(δ) | retention time | Mass | method |
|---|---|---|---|---|---|
| II-2-236 | 3-MeO-phenyl-benzothiazole-CH2-C(O)-NH-CH2-C(O)-NH-CH2-CN | (DMSO-d6) δ: 3.81-3.86 (m, 5H), 4.15-4.19 (m, 4H), 6.96 (dd, J = 8.1, 2.5 Hz, 1H), 7.27-7.34 (m, 2H), 7.41 (t, J = 7.8 Hz, 1H), 7.80 (dd, J = 8.5, 1.9 Hz, 1H), 8.01 (d, J = 8.6 Hz, 1H), 8.40 (d, J = 1.8 Hz, 1H), 8.65-8.77 (m, 2H). | | | |
| II-2-237 | 3-Cl-phenyl-benzothiazole-CH2-C(O)-NH-CH2-COOH | (DMSO-d6) δ: 3.85 (d, J = 5.7 Hz, 2H), 4.16 (s, 2H), 7.46 (m, 1H), 7.53 (t, J = 7.8 Hz, 1H), 7.72-7.76 (m, 1H), 7.81-7.85 (m, 2H), 8.02 (d, J = 8.4 Hz, 1H), 8.45 (d, J = 1.5 Hz, 1H), 8.72 (t, J = 5.8 Hz, 1H). | | | |
| II-2-238 | phenyl-benzothiazole-CH2-C(O)-NH-CH2-C(O)-N(Me)-CH2-C≡CH | (DMSO-d6) δ: 2.88 (s, 1H), 3.01 (s, 2H), 4.02-4.23 (m, 6H), 7.36-7.42 (m, 1H), 7.46-7.53 (m, 2H), 7.72-7.82 (m, 3H), 8.02 (d, J = 8.4 Hz, 1H), 8.38 (s, 1H), 8.53-8.59 (m, 1H). | | | |
| II-2-239 | phenyl-benzothiazole-CH2-C(O)-NH-CH2-C(O)-NH-(2-carbamoylphenyl) | (DMSO-d6) δ: 3.93 (d, J = 5.2 Hz, 2H), 4.30 (s, 2H), 7.11-7.18 (m, 1H), 7.35-7.43 (m, 1H), 7.46-7.56 (m, 3H), 7.72-7.87 (m, 5H), 8.03 (d, J = 8.4 Hz, 1H), 8.31-8.35 (m, 1H), 8.38 (m, 1H), 8.56 (d, J = 8.4 Hz, 1H), 9.09-9.13 (m, 1H), 12.21 (s, 1H). | | | |

TABLE 97-continued

| No. | Structure | NMR(δ) | retention time | Mass | method |
|---|---|---|---|---|---|
| II-2-240 | 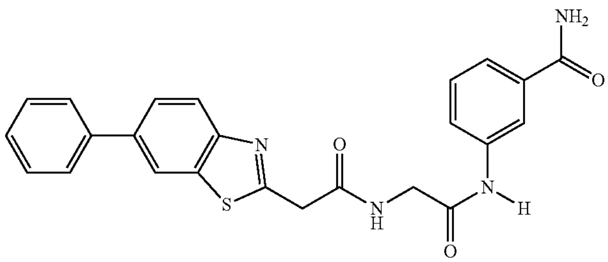 [SMILES: NC(=O)c1cccc(NC(=O)CNC(=O)Cc2nc3ccc(-c4ccccc4)cc3s2)c1] | (DMSO-d$_6$) δ: 4.01 (d, J = 4.8 Hz, 2H), 4.21 (s, 2H), 7.32-7.43 (m, 3H), 7.45-7.59 (m, 3H), 7.72-7.83 (m, 5H), 7.93-7.97 (m, 1H), 7.99-8.07 (m, 2H), 8.39 (s, 1H), 8.75-8.82 (m, 1H), 10.17 (s, 1H). | | | |

TABLE 98

| No. | Structure | NMR(δ) | retention time | Mass | method |
|---|---|---|---|---|---|
| II-2-241 | 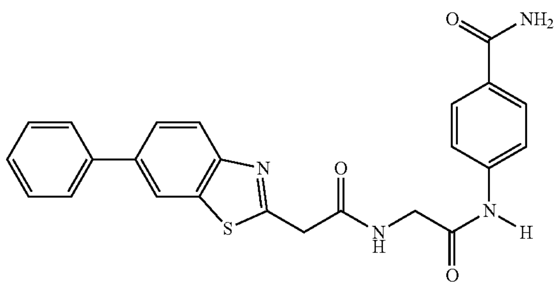 [SMILES: NC(=O)c1ccc(NC(=O)CNC(=O)Cc2nc3ccc(-c4ccccc4)cc3s2)cc1] | (DMSO-d$_6$) δ: 4.01 (d, J = 5.2 Hz, 2H), 4.20 (s, 2H), 7.22-7.28 (m, 1H), 7.37-7.43 (m, 1H), 7.45-7.54 (m, 2H), 7.65 (d, J = 8.4 Hz, 2H), 7.72-7.88 (m, 6H), 8.02 (d, 8.4 Hz, 1H), 8.39 (s, 1H), 8.75-8.82 (m, 1H), 10.27 (s, 1H). | | | |
| II-2-242 | 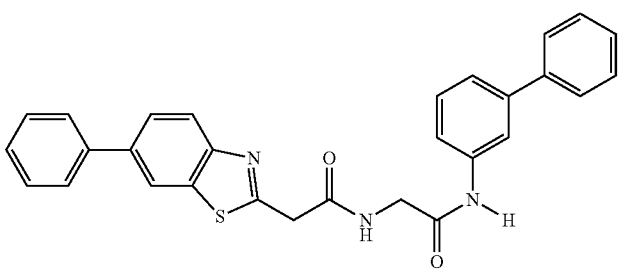 [SMILES: O=C(Cc1nc2ccc(-c3ccccc3)cc2s1)NCC(=O)Nc1cccc(-c2ccccc2)c1] | (DMSO-d$_6$) δ: 4.03 (d, J = 4.8 Hz, 2H), 4.22 (s, 2H), 7.32-7.54 (m, 8H), 7.56-7.63 (m, 3H), 7.72-7.82 (m, 3H), 7.92 (s, 1H), 8.02 (d, J = 8.8 Hz, 2H), 8.38 (s, 1H), 8.75-8.81 (m, 1H), 10.15 (s, 1H). | | | |
| II-2-243 | 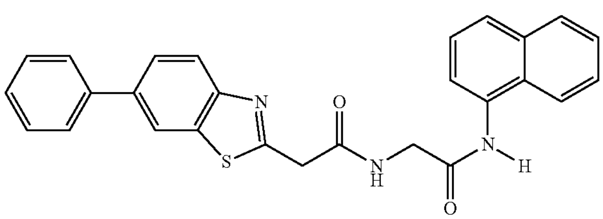 [SMILES: O=C(Cc1nc2ccc(-c3ccccc3)cc2s1)NCC(=O)Nc1cccc2ccccc12] | (DMSO-d$_6$) δ: 4.17 (d, J = 3.2 Hz, 2H), 4.24 (s, 2H), 7.35-7.43 (m, 1H), 7.45-7.56 (m, 4H), 7.64-7.69 (m, 1H), 7.72-7.82 (m, 3H), 7.94 (d, J = 7.2 Hz, 2H), 8.05-8.11 (m, 2H), 8.39 (s, 1H), 8.84-8.90 (m, 1H), 10.05 (s, 1H). | | | |
| II-2-244 | 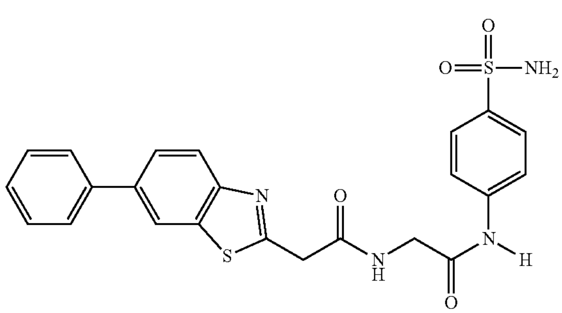 [SMILES: NS(=O)(=O)c1ccc(NC(=O)CNC(=O)Cc2nc3ccc(-c4ccccc4)cc3s2)cc1] | (DMSO-d$_6$) δ: 4.03 (d, J = 4.8 Hz, 2H), 4.21 (s, 2H), 7.27 (s, 2H), 7.35-7.43 (m, 1H), 7.45-7.54 (m, 2H), 7.71-7.83 (m, 7H), 8.02 (d, J = 8.4 Hz, 1H), 8.39 (s, 1H), 8.75-8.82 (m, 1H), 10.40 (s, 1H). | | | |

TABLE 98-continued

| No. | Structure | NMR(δ) | retention time | Mass method |
|---|---|---|---|---|
| II-2-245 | 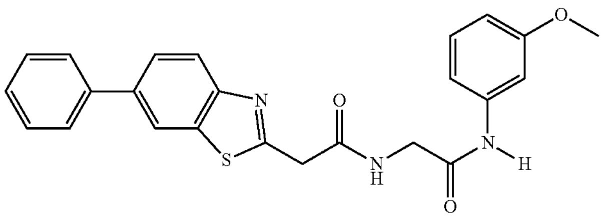 [SMILES: COc1cccc(NC(=O)CNC(=O)Cc2nc3ccc(-c4ccccc4)cc3s2)c1] | (DMSO-d$_6$) δ: 3.73 (s, 3H), 4.00 (d, J = 5.2 Hz, 2H), 4.21 (s, 2H), 6.64 (d, J = 7.6 Hz, 1H), 7.13 (d, J = 7.6 Hz, 1H), 7.18-7.26 (m, 1H), 7.31 (s, 1H), 7.35-7.42 (m, 1H), 7.45-7.53 (m, 2H), 7.72-7.82 (m, 3H), 8.02 (d, J = 8.4 Hz, 1H), 8.38 (s, 1H), 8.73-8.79 (m, 1H), 10.04 (s, 1H). | | |

TABLE 99

| No. | Structure | NMR(δ) | retention time | Mass method |
|---|---|---|---|---|
| II-2-246 | 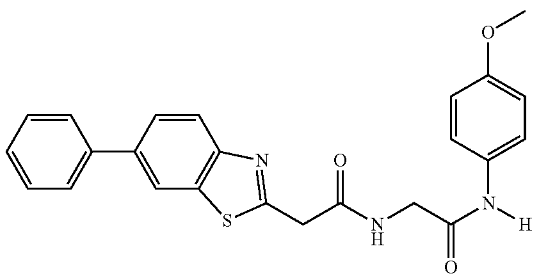 [SMILES: COc1ccc(NC(=O)CNC(=O)Cc2nc3ccc(-c4ccccc4)cc3s2)cc1] | (DMSO-d$_6$) δ: 3.39 (s, 3H), 3.97 (d, J = 4.4 Hz, 2H), 4.20 (s, 2H), 6.89 (d, J = 8.4 Hz, 2H), 7.36-7.43 (m, 1H), 7.45-7.53 (m, 4H), 7.72-7.82 (m, 3H), 8.01 (d, J = 8.4 Hz, 1H), 8.38 (s, 1H), 8.71-8.77 (m, 1H), 9.90 (s, 1H). | | |
| II-2-247 | 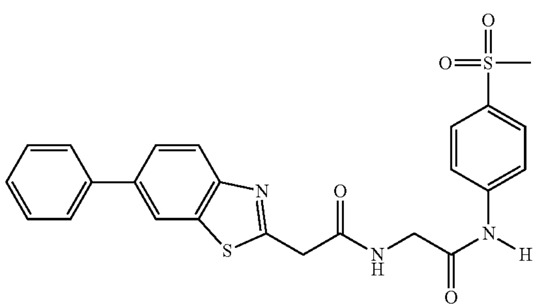 [SMILES: CS(=O)(=O)c1ccc(NC(=O)CNC(=O)Cc2nc3ccc(-c4ccccc4)cc3s2)cc1] | (DMSO-d$_6$) δ: 3.17 (s, 3H), 4.05 (d, J = 4.0 Hz, 2H), 4.21 (s, 2H), 7.37-7.43 (m, 1H), 7.46-7.53 (m, 2H), 7.72-7.90 (m, 7H), 8.02 (d, J = 7.6 Hz, 1H), 8.39 (s, 1H), 8.77-8.83 (m, 1H), 10.51 (s, 1H). | | |
| II-2-248 | 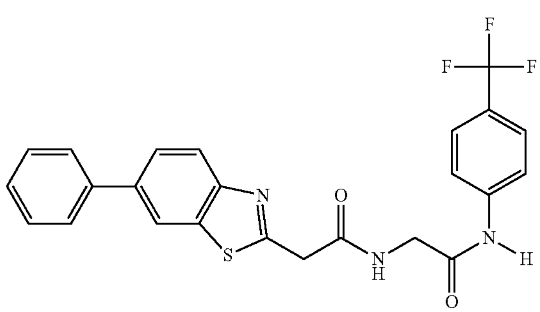 [SMILES: O=C(Cc1nc2ccc(-c3ccccc3)cc2s1)NCC(=O)Nc1ccc(C(F)(F)F)cc1] | (DMSO-d$_6$) δ: 4.03 (d, J = 5.2 Hz, 2H), 4.20 (s, 2H), 7.36-7.43 (m, 1H), 7.46-7.53 (m, 2H), 7.66-7.83 (m, 7H), 8.02 (d, J = 8.8 Hz, 1H), 8.39 (s, 1H), 8.76-8.82 (m, 1H), 10.43 (s, 1H). | | |
| II-2-249 | 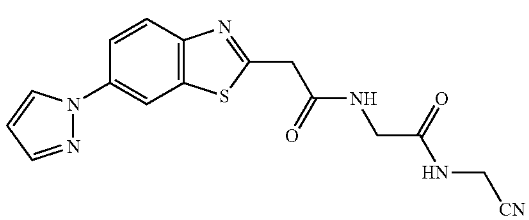 [SMILES: N#CCNC(=O)CNC(=O)Cc1nc2ccc(-n3cccn3)cc2s1] | (DMSO-d6) δ: 3.83 (d, J = 6.0 Hz, 2H), 4.16-4.18 (m, 4H), 6.58 (s, 1H), 7.79 (s, 1H), 8.00-8.06 (m, 2H), 8.54-8.57 (m, 2H), 8.68-8.74 (m, 2H) | | |

TABLE 99-continued

| No. | Structure | NMR(δ) | retention time | Mass | method |
|---|---|---|---|---|---|
| II-2-250 | 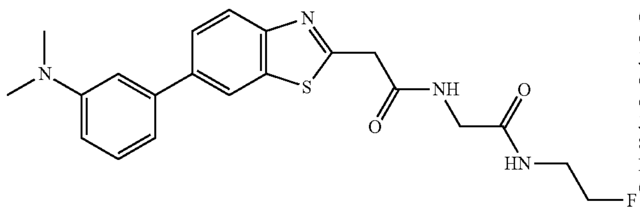 [SMILES: CN(C)c1cccc(-c2ccc3nc(CC(=O)NCC(=O)NCCF)sc3c2)c1] | (DMSO-d6) δ: 2.98 (s, 6H), 3.65 (s, 4H), 3.94 (d, J = 5.4 Hz, 2H), 4.15 (s, 2H), 6.75 (d, J = 9.6 Hz, 1H), 6.98-7.01 (m, 2H), 7.29 (t, J = 7.5 Hz, 1H), 7.77 (d, J = 8.4 Hz, 1H), 8.00 (d, J = 9.0 Hz, 1 H ), 8.36 (s, 1H), 8.82 (br-s, 1H) | | | |

TABLE 100

| No. | Structure | NMR(δ) | retention time | Mass | method |
|---|---|---|---|---|---|
| II-2-251 | 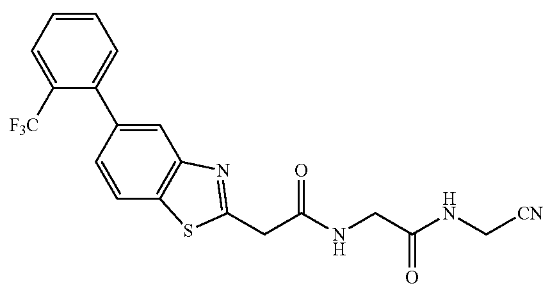 [SMILES: N#CCNC(=O)CNC(=O)Cc1nc2cc(-c3ccccc3C(F)(F)F)ccc2s1] | (DMSO-d$_6$) δ: 3.83 (d, J = 6.08 Hz, 2H), 4.18-4.15 (m, 4H), 7.36 (d, J = 7.60 Hz, 1H), 7.49 (d, J = 7.60 Hz, 1H), 7.65 (dd, J = 7.35, 7.60 Hz, 1H), 7.76 (dd, J = 7.35, 7.60 Hz, 1H), 7.85-7.89 (m, 2H), 8.13 (d, J = 8.11 Hz, 1H), 8.68 (t, J = 5.58 Hz, 1H), 8.74 (t, J = 5.58 Hz, 1H). | | | |
| II-2-252 | 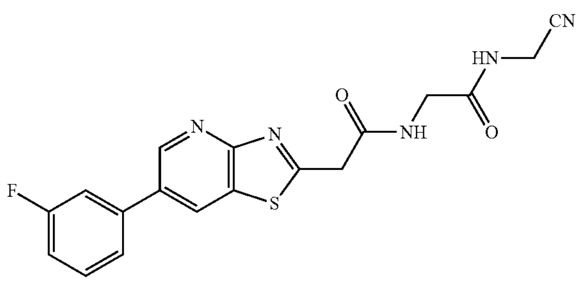 [SMILES: N#CCNC(=O)CNC(=O)Cc1nc2ncc(-c3cccc(F)c3)cc2s1] | (DMSO-d6) δ: 3.86 (d, J = 5.7 Hz, 2H), 4.18 (d, J = 5.4 Hz, 2H), 4.25 (s, 2H), 7.26-7.30 (m, 1H), 7.54-7.64 (m, 1H), 7.67-7.73 (m, 1H), 8.75-8.81 (m, 1H), 8.93 (d, J = 2.4 Hz, 2H), 9.02 (d, J = 2.41 Hz, 1H). | | | |
| II-2-253 | 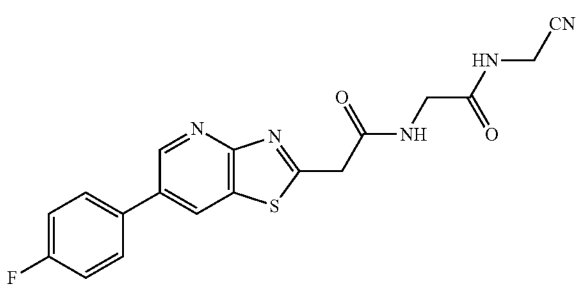 [SMILES: N#CCNC(=O)CNC(=O)Cc1nc2ncc(-c3ccc(F)cc3)cc2s1] | (DMSO-d6) δ: 3.86 (d, J = 5.7 Hz, 2H), 4.19 (d, J = 5.4 Hz, 4H), 4.25 (s, 2H), 7.34-7.41 (m, 2H), 7.85-7.89 (m, 2H), 8.75-8.82 (m, 2H), 8.86 (d, J = 2.4 Hz, 1H), 8.962 (d, J = 2.4 Hz, 1H). | | | |
| II-2-254 | 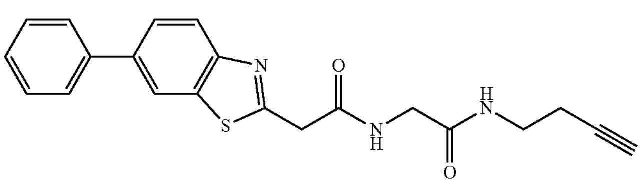 [SMILES: C#CCCNC(=O)CNC(=O)Cc1nc2ccc(-c3ccccc3)cc2s1] | (DMSO-d6) δ: 2.26-2.33 (m, 2H), 2.84 (s, 1H), 3.18-3.25 (m, 2H), 3.77 (d, J = 5.2 Hz, 2H), 4.16 (s, 2H), 7.36-7.43 (m, 1H), 7.46-7.53 (m, 2H), 7.72-7.82 (m, 3H), 8.02 (d, J = 8.8 Hz, 1H), 8.12-8.18 (m, 1H), 8.38 (s, 1H), 8.62-8.68 (m, 1H). | | | |

TABLE 100-continued

| No. | Structure | NMR(δ) | retention time | Mass | method |
|---|---|---|---|---|---|
| II-2-255 | 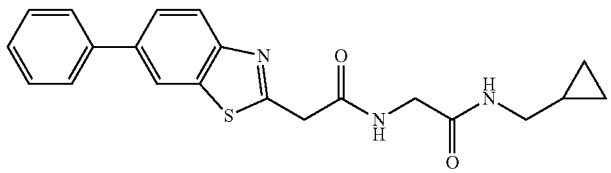 [SMILES: O=C(CNC(=O)Cc1nc2ccc(-c3ccccc3)cc2s1)NCC1CC1] | (DMSO-d6) δ: 0.13-0.19 (m, 2H), 0.37-0.43 (m, 2H), 0.86-0.93 (m, 1H), 2.94-3.02 (m, 2H), 3.77 (d, J = 5.2 Hz, 2H), 4.16 (s, 2H), 7.36-7.43 (m, 1H), 7.46-7.53 (m, 2H), 7.72-7.82 (m, 3H), 8.01 (d, J = 8.8 Hz, 2H), 8.38 (s, 1H), 8.60-8.66 (m, 1H). | | | |

TABLE 101

| No. | Structure | NMR(δ) | retention time | Mass | method |
|---|---|---|---|---|---|
| II-2-256 | 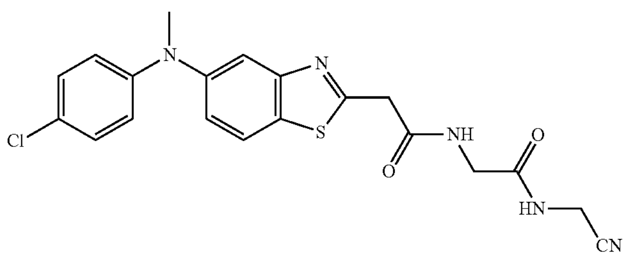 [SMILES: CN(c1ccc(Cl)cc1)c1ccc2sc(CC(=O)NCC(=O)NCC#N)nc2c1] | (DMSO-d6) δ: 3.82 (d, J = 6.1 Hz, 2H), 4.11 (s, 2H), 4.16 (d, J = 5.6 Hz, 2H), 6.94-6.97 (m, 2H), 7.16 (dd, J = 8.6, 2.5 Hz, 1H), 7.27-7.28 (m, 2H), 7.62 (d, J = 2.5 Hz, 1H), 7.96 (d, J = 8.6 Hz, 1H), 8.66-8.71 (m, 2H). | 2.1 | 428.00 (ES+) | C |
| II-2-257 | 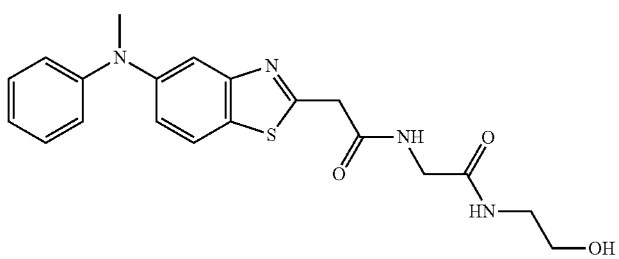 [SMILES: CN(c1ccccc1)c1ccc2sc(CC(=O)NCC(=O)NCCO)nc2c1] | (DMSO-d6) δ: 3.14 (q, J = 5.9 Hz, 2H), 3.40 (q, J = 5.9 Hz, 2H), 3.75 (d, J = 5.6 Hz, 2H), 4.08 (s, 2H), 4.67 (t, J = 5.6 Hz, 1H), 6.96 (t, J = 7.4 Hz, 1H), 7.03 (d, J = 7.6 Hz, 2H), 7.09 (dd, J = 8.9, 2.3 Hz, 1H), 7.29 (t, J = 8.1 Hz, 2H), 7.53 (d, J = 2.0 Hz, 1H), 7.89 (d, J = 8.6 Hz, 1H), 7.95 (t, J = 5.3 Hz, 1H), 8.56 (t, J = 5.6 Hz, 1H). | 1.75 | 398.95 (ES+) | C |
| II-2-258 | 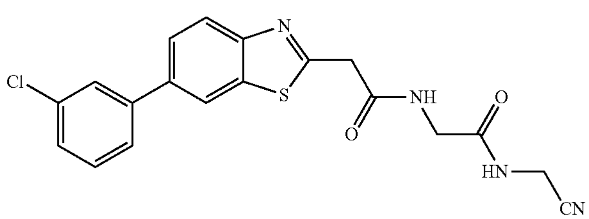 [SMILES: N#CCNC(=O)CNC(=O)Cc1nc2ccc(-c3cccc(Cl)c3)cc2s1] | (DMSO-d6) δ: 3.84 (d, J = 5.9 Hz, 2H), 4.15-4.20 (m, 4H), 7.44-7.47 (m, 1H), 7.53 (t, J = 7.8 Hz, 1H), 7.74 (dt, J = 7.6, 1.5 Hz, 1H), 7.81-7.85 (m, 2H), 8.03 (d, J = 8.4 Hz, 1H), 8.45 (d, J = 1.8 Hz, 1H), 8.65-8.78 (m, 2H) | | | |
| II-2-259 | 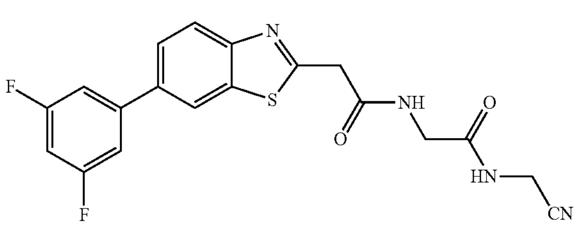 [SMILES: N#CCNC(=O)CNC(=O)Cc1nc2ccc(-c3cc(F)cc(F)c3)cc2s1] | (DMSO-d6) δ: 3.84 (d, J = 5.9 Hz, 2H), 4.15-4.20 (m, 4H), 7.26 (tt, J = 9.3, 2.3 Hz, 1H), 7.51-7.59 (m, 2H), 7.88 (dd, J = 8.6, 1.9 Hz, 1H), 8.03 (d, J = 8.6 Hz, 1H), 8.51 (d, J = 1.8 Hz, 1H), 8.65-8.78 (m, 2H). | | | |

TABLE 101-continued

| No. | Structure | NMR(δ) | retention time | Mass | method |
|---|---|---|---|---|---|
| II-2-260 | 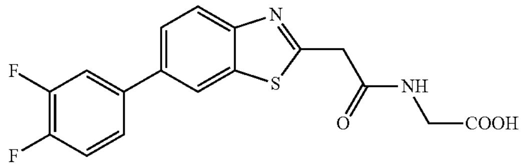 [SMILES: O=C(O)CNC(=O)Cc1nc2ccc(-c3ccc(F)c(F)c3)cc2s1] | (DMSO-d6) δ: 3.85 (d, J = 5.7 Hz, 2H), 4.16 (s, 2H), 7.49-7.67 (m, 2H), 7.78-7.92 (m, 2H), 8.02 (d, J = 8.6 Hz, 1H), 8.43 (d, J = 1.7 Hz, 1H), 8.72 (t, J = 5.8 Hz, 1H). | | | |

TABLE 102

| No. | Structure | NMR(δ) | retention time | Mass | method |
|---|---|---|---|---|---|
| II-2-261 | 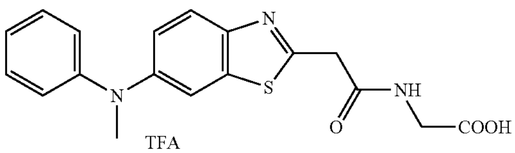 [SMILES: CN(c1ccccc1)c1ccc2nc(CC(=O)NCC(=O)O)sc2c1] | (DMSO-d6) δ: 3.32 (s, 3H), 3.83 (d, J = 5.7 Hz, 2H), 4.06 (s, 2H), 6.92-7.06 (m, 2H), 7.11 (dd, J = 8.9, 2.4 Hz, 1H), 7.27-7.32 (m, 3H), 7.66 (d, J = 2.2 Hz, 1H), 7.80 (d, J = 8.9 Hz, 1H), 8.66 (t, J = 5.5 Hz, 1H). | | | |
| II-2-262 | 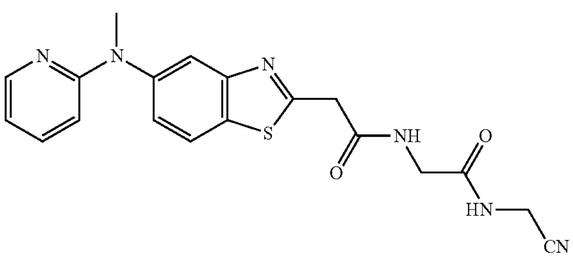 [SMILES: CN(c1ccc2sc(CC(=O)NCC(=O)NCC#N)nc2c1)c1ccccn1] | (DMSO-d6) δ: 3.45 (s, 3H), 3.82 (d, J = 6.1 Hz, 2H), 4.14-4.18 (m, 4H), 6.55 (d, J = 8.6 Hz, 1H), 6.69 (dd, J = 7.1, 5.1 Hz, 1H), 7.35 (dd, J = 8.6, 2.0 Hz, 1H), 7.43 (td, J = 7.9, 1.9 Hz, 1H), 7.85 (d, J = 2.0 Hz, 1H), 8.08 (d, J = 8.6 Hz, 1H), 8.17 (dd, J = 4.8, 1.3 Hz, 1H), 8.66-8.73 (m, 2H). | | | |
| II-2-263 | 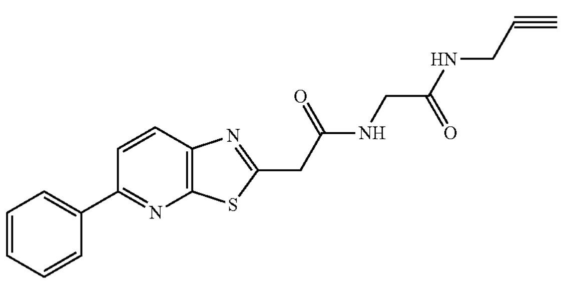 [SMILES: C#CCNC(=O)CNC(=O)Cc1nc2ccc(-c3ccccc3)nc2s1] | (DMSO-d6) δ: 3.80 (d, J = 6.0 Hz, 2H), 3.90 (d, J = 5.4 Hz, 2H), 4.20 (s, 2H), 7.47-7/56 (m, 3H), 8.12-8.18 (m, 3H), 8.39-8.42 (m, 2H), 8.69 (t, J = 5.4 Hz, 1H). | | | |
| II-2-264 | 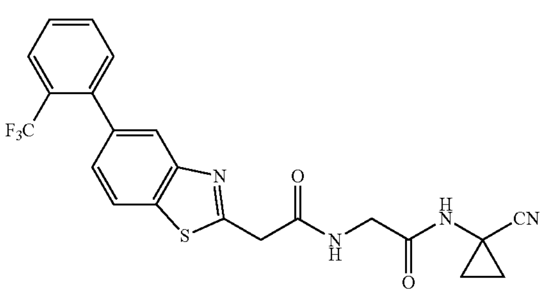 [SMILES: N#CC1(NC(=O)CNC(=O)Cc2nc3cc(-c4ccccc4C(F)(F)F)ccc3s2)CC1] | (DMSO-d6) δ: 1.12 (dd, J = 8.36, 5.32 Hz, 2H), 1.49 (dd, J = 8.36, 5.32 Hz, 2H), 3.77 (d, J = 5.58 Hz, 2H), 4.17 (s, 2H), 7.36 (d, J = 8.11 Hz, 1H), 7.49 (d, J = 7.60 Hz, 1H), 7.65 (dd, J = 8.11, 7.60 Hz, 1H), 7.76 (dd, J = 7.60, 8.11 Hz, 1H), 7.85-7.89 (m, 2H), 8.13 (d, J = 8.11 Hz, 1H), 8.69 (t, J = 5.58 Hz, 1H), 8.91 (s, 1H). | | | |

TABLE 102-continued

| No. | Structure | NMR(δ) | retention time | Mass | method |
|---|---|---|---|---|---|
| II-2-265 | 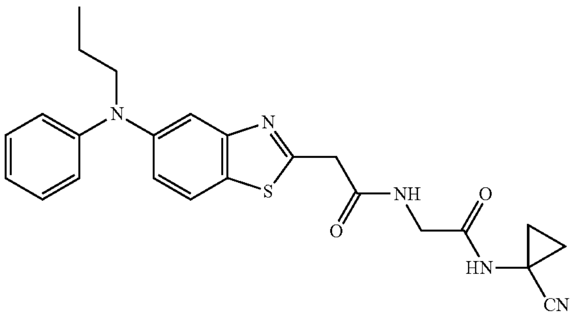 [SMILES: CCCN(c1ccccc1)c1ccc2sc(CC(=O)NCC(=O)NC3(C#N)CC3)nc2c1] | (CDCl3) δ: 0.97 (t, J = 7.4 Hz, 3H), 1.16-1.20 (m, 2H), 1.42-1.46 (m, 2H), 1.69-1.78 (m, 2H), 3.73 (t, J = 7.6 Hz, 2H), 4.00 (d, J = 6.1 Hz, 2H), 4.06 (s, 2H), 7.03-7.11 (m, 4H), 7.33 (t, J = 8.1 Hz, 2H), 7.53 (s, 1H), 7.62-7.69 (m, 3H). | | | |

TABLE 103

| No. | Structure | NMR(δ) | retention time | Mass | method |
|---|---|---|---|---|---|
| II-2-266 | 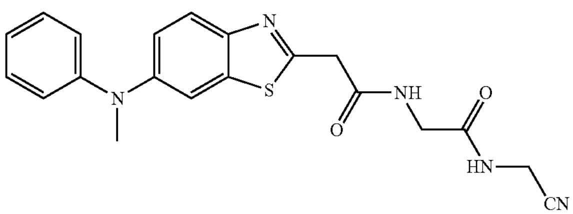 [SMILES: CN(c1ccccc1)c1ccc2nc(CC(=O)NCC(=O)NCC#N)sc2c1] | (DMSO-d6) δ: 3.82 (d, J = 5.9 Hz, 2H), 4.08 (s, 2H), 4.17 (d, J = 5.7 Hz, 2H), 6.93-7.06 (m, 3H), 7.11 (dd, J = 8.9, 2.4 Hz, 1H), 7.30 (t, J = 7.9 Hz, 2H), 7.66 (d, J = 2.4 Hz, 1H), 7.80 (d, J = 9.1 Hz, 1H), 8.68 (m, 2H). | 1.9 | 394.00 (ES+) | C |
| II-2-267 | 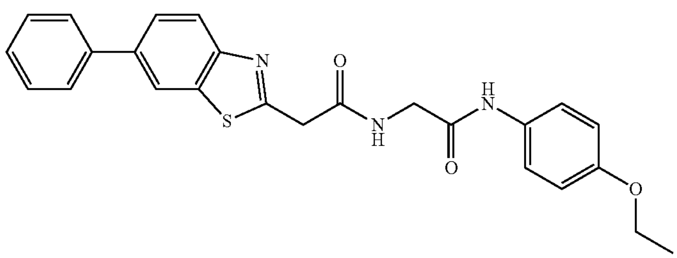 [SMILES: CCOc1ccc(NC(=O)CNC(=O)Cc2nc3ccc(-c4ccccc4)cc3s2)cc1] | (DMSO-d6) δ: 1.27-1.34 (m, 3H), 3.93-4.00 (m, 4H), 4.20 (s, 2H), 6.87 (d, J = 8.0 Hz, 2H), 7.36-7.43 (m, 1H), 7.46-7.53 (m, 4H), 7.72-7.82 (m, 3H), 8.02 (d, J = 8.4 Hz, 1H), 8.38 (s, 1H), 8.71-8.78 (m, 1H), 9.89 (s, 1H). | | | |
| II-2-268 | 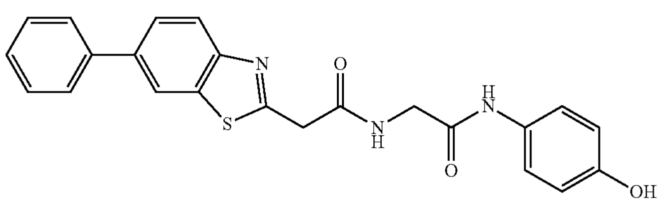 [SMILES: O=C(Cc1nc2ccc(-c3ccccc3)cc2s1)NCC(=O)Nc1ccc(O)cc1] | (DMSO-d6) δ: 3.94 (d, J = 4.8 Hz, 2H), 4.19 (s, 2H), 6.71 (d, J = 8.4 Hz, 2H), 7.33-7.43 (m, 3H), 7.45-7.53 (m, 2H), 7.72-7.82 (m, 3H), 8.01 (d, J = 8.0 Hz, 1H), 8.38 (s, 1H), 8.70-8.76 (m, 1H), 9.22 (s, 1H), 9.78 (s, 1H). | | | |
| II-2-269 | 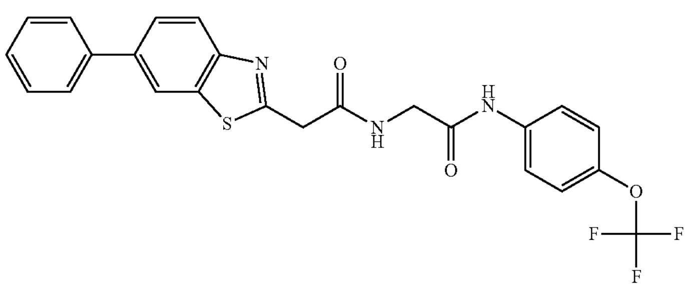 [SMILES: O=C(Cc1nc2ccc(-c3ccccc3)cc2s1)NCC(=O)Nc1ccc(OC(F)(F)F)cc1] | (DMSO-d6) δ: 4.01 (d, J = 3.2 Hz, 2H), 4.20 (s, 2H), 7.33 (d, J = 8.0 Hz, 2H), 7.36-7.43 (m, 1H), 7.46-7.53 (m, 2H), 7.66-7.82 (m, 5H), 8.02 (d, J = 8.8 Hz, 1H), 8.38 (s, 1H), 8.76-8.82 (m, 1H), 10.27 (s, 1H). | | | |

TABLE 103-continued

| No. | Structure | NMR(δ) | retention time | Mass | method |
|---|---|---|---|---|---|
| II-2-270 | 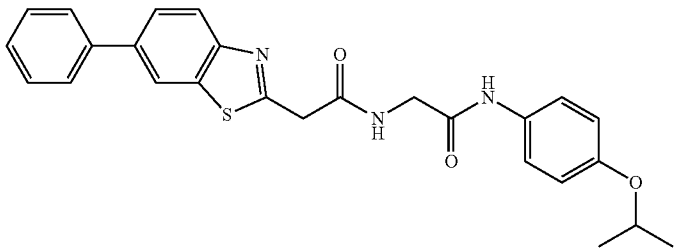 [SMILES: CC(C)Oc1ccc(NC(=O)CNC(=O)Cc2nc3ccc(-c4ccccc4)cc3s2)cc1] | (DMSO-d6) δ: 1.23 (d, J = 5.6 Hz, 6H), 3.96 (d, J = 4.0 Hz, 2H), 4.20 (s, 2H), 4.48-4.55 (m, 1H), 6.86 (d, J = 8.4 Hz, 2H), 7.36-7.43 (m, 1H), 7.46-7.53 (m, 4H), 7.72-7.82 (m, 3H), 8.01 (d, J = 8.4 Hz, 1H), 8.38 (s, 1H), 8.71-8.78 (m, 1H), 9.89 (s, 1H). | | | |

TABLE 104

| No. | Structure | NMR(δ) | retention time | Mass | method |
|---|---|---|---|---|---|
| II-2-271 | 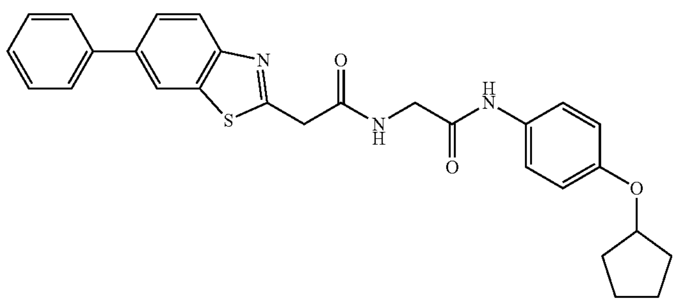 [SMILES: O=C(Cc1nc2ccc(-c3ccccc3)cc2s1)NCC(=O)Nc1ccc(OC2CCCC2)cc1] | (DMSO-d6) δ: 1.51-1.92 (m, 8H), 3.96 (d, J = 5.2 Hz, 2H), 4.19 (s, 2H), 4.71-4.78 (m, 1H), 6.85 (d, J = 8.4 Hz, 2H), 7.36-7.53 (m, 5H), 7.72-7.82 (m, 3H), 8.01 (d, J = 8.4 Hz, 1H), 8.39 (s, 1H), 8.70-8.77 (m, 1H), 9.87 (s, 1H). | | | |
| II-2-272 | 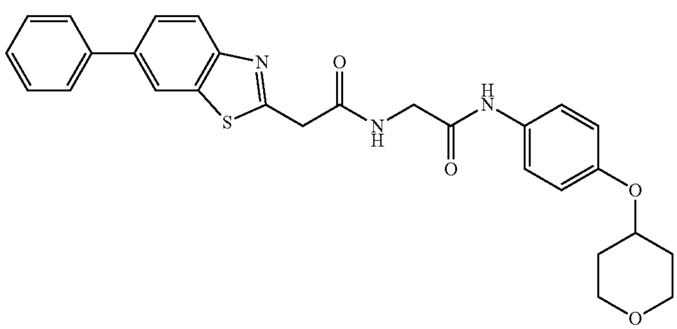 [SMILES: O=C(Cc1nc2ccc(-c3ccccc3)cc2s1)NCC(=O)Nc1ccc(OC2CCOCC2)cc1] | (DMSO-d6) δ: 1.50-1.59 (m, 2H), 1.90-1.98 (m, 2H), 3.41-3.50 (m, 2H), 3.78-3.88 (m, 2H), 3.96 (d, J = 4.8 Hz, 2H), 4.20 (s, 2H), 4.44-4.53 (m, 1H), 6.93 (d, J = 8.4 Hz, 2H), 7.36-7.43 (m, 1H), 7.45-7.52(m, 4H), 7.72-7.82 (m, 3H), 8.01 (d, J = 8.4 Hz, 1H), 8.38 (s, 1H), 8.71-8.78 (m, 1H), 9.90 (s, 1H). | | | |
| II-2-273 | 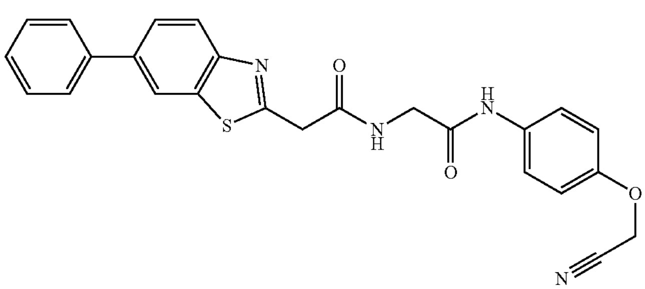 [SMILES: N#CCOc1ccc(NC(=O)CNC(=O)Cc2nc3ccc(-c4ccccc4)cc3s2)cc1] | (DMSO-d6) δ: 3.98 (d, J = 4.8 Hz, 2H), 4.20 (s, 2H), 5.13 (s, 2H), 7.04 (d, J = 8.4 Hz, 2H), 7.36-7.43 (m, 1H), 7.46-7.52 (m, 2H), 7.52-7.60 (m, 2H), 7.72-7.82 (m, 3H), 8.02 (d, J = 8.0 Hz, 1H), 8.39 (s, 1H), 8.72-8.79 (m, 1H), 10.02 (s, 1H). | | | |

TABLE 104-continued

| No. | Structure | NMR(δ) | retention time | Mass | method |
|---|---|---|---|---|---|
| II-2-274 | 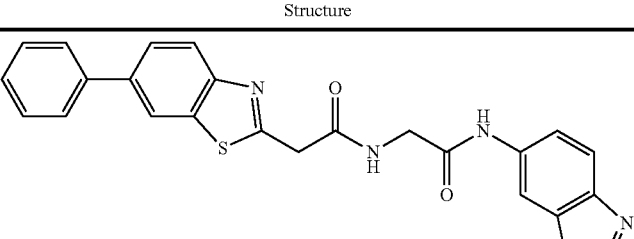 | (DMSO-d6) δ: 4.04 (d, J = 5.2 Hz, 2H), 4.22 (s, 2H), 7.36-7.52 (m, 4H), 7.70-7.82 (m, 4H), 8.02 (d, J = 8.4 Hz, 1H), 8.22 (s, 1H), 8.38 (s, 1H), 8.66 (s, 1H), 8.74-8.83 (m, 1H), 10.36 (s, 1H). | | | |
| II-2-275 | 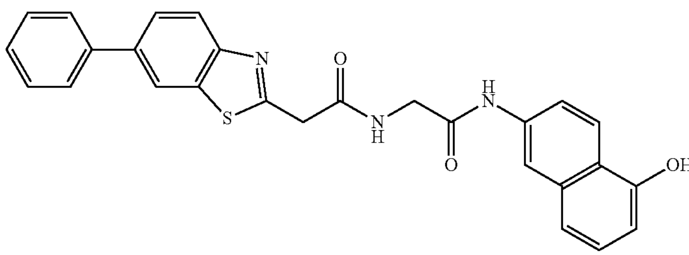 [SMILES: O=C(Cc1nc2ccc(-c3ccccc3)cc2s1)NCC(=O)Nc1ccc2c(O)cccc2c1] | (DMSO-d6) δ: 4.05 (d, J = 4.8 Hz, 2H), 4.23 (s, 2H), 6.77 (d, J = 6.8 Hz, 1H), 7.19-7.29 (m, 2H), 7.35-7.43 (m, 1H), 7.45-7.56 (m, 3H), 7.71-7.82 (m, 3H), 7.99-8.11 (m, 2H), 8.18 (s, 1H), 8.39 (s, 1H), 8.77-8.83 (m, 1H), 10.07 (s, 1H), 10.20 (s, 1H). | | | |

TABLE 105

| No. | Structure | NMR(δ) | retention time | Mass | method |
|---|---|---|---|---|---|
| II-2-276 | 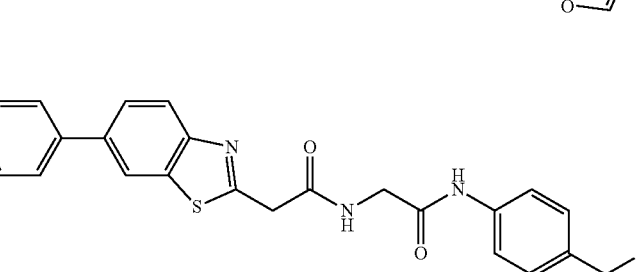 | (DMSO-d6) δ: 2.02 (s, 3H), 3.97 (d, J = 4.8 Hz, 2H), 4.20 (s, 2H), 7.35-7.45(m, 1H), 7.47-7.53 (m, 6H), 7.72-7.82 (m, 3H), 8.02 (d, J = 8.8 Hz, 1H), 8.38 (s, 1H), 8.72-8.78 (m, 1H), 9.88 (s, 1H), 9.97 (s, 1H). | | | |
| II-2-277 | 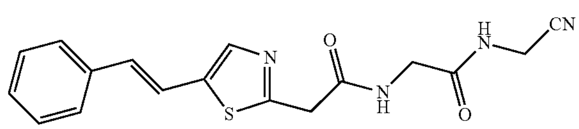 [SMILES: N#CCNC(=O)CNC(=O)Cc1ncc(/C=C/c2ccccc2)s1] | (DMSO-d₆) δ: 3.81 (d, J = 6.08 Hz, 2H), 3.98 (s, 2H), 4.16 (d, J = 5.58 Hz, 2H), 6.94 (d, J = 16.22 Hz, 1H), 7.28 (m, 1H), 7.34-7.40 (m, 2.0 H), 7.45 (d, J = 16.22 Hz, 1H), 7.56-7.59 (m, 2H), 7.76 (s, 1H), 8.64 (t, J = 5.83 Hz, 1H), 8.68 (t, J = 5.58 Hz, 1H). | | | |
| II-2-278 | 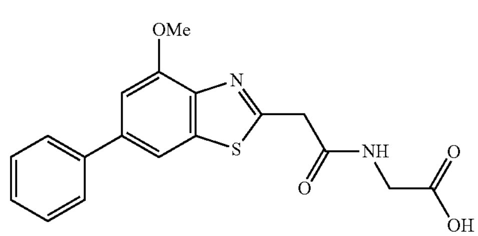 [SMILES: COc1cc(-c2ccccc2)cc2sc(CC(=O)NCC(=O)O)nc12] | (DMSO-d6) δ: 3.83 (d, J = 6.0 Hz, 2H), 4.04 (s, 3H), 4.13 (s, 2H), 4.17 (d, J = 5.7 Hz, 2H), 7.27 (s, 1H), 7.39-7.52 (m, 3H), 7.77 (d, J = 7.5 Hz, 2H), 7.91 (s, 1H), 8.67-8.73 (m, 2H) | | | |

TABLE 105-continued

| No. | Structure | NMR(δ) | retention time | Mass | method |
|---|---|---|---|---|---|
| II-2-279 | 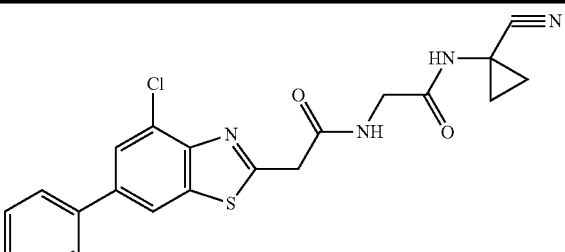 | (DMSO-d6) δ: 1.12 (dd, J = 8.1, 5.1 Hz, 2H), 1.49 (dd, J = 8.1, 5.5 Hz, 2H), 3.78 (d, J = 5.7 Hz, 2H), 4.22 (s, 2H), 7.39-7.44 (m, 1H), 7.48-7.54 (m, 2H), 7.77-7.97 (m, 2H), 7.88 (d, J = 1.8 Hz, 1H), 8.39 (d, J = 1.8 Hz, 1H), 8.71 (t, J = 5.4 Hz, 1H), 8.91 (s, 1H). | | | |
| II-2-280 | 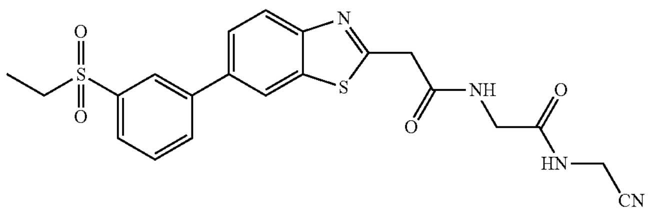 [SMILES: CCS(=O)(=O)c1cccc(-c2ccc3nc(CC(=O)NCC(=O)NCC#N)sc3c2)c1] | (DMSO-d6) δ: 1.15 (t, J = 7.3 Hz, 3H), 3.41 (q, J = 7.3 Hz, 2H), 3.84 (d, J = 5.9 Hz, 2H), 4.15-4.21 (m, 4H), 7.79 (t, J = 7.7 Hz, 1H), 7.86-7.93 (m, 2H), 8.07 (d, J = 8.4 Hz, 1H), 8.15 (m, 1H), 8.21 (m, 1H), 8.54 (d, J = 1.7 Hz, 1H), 8.65-8.79 (m, 2H). | | | |

TABLE 106

| No. | Structure | NMR(δ) | retention time | Mass | method |
|---|---|---|---|---|---|
| II-2-281 | 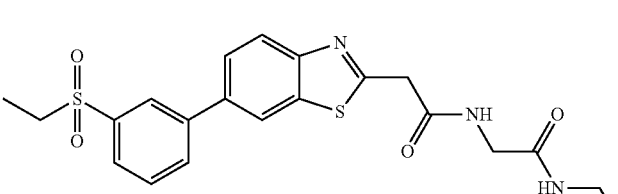 | (DMSO-d6) δ: 1.12 (dd, J = 8.1, 5.1 Hz, 2H), 1.49 (dd, J = 8.1, 5.5 Hz, 2H), 3.76 (d, J = 5.7 Hz, 2H), 4.07 (s, 2H), 6.92-7.15 (m, 4H), 7.30 (t, J = 7.6 Hz, 2H), 7.66 (d, J = 2.4 Hz, 1H), 7.80 (d, J = 8.9 Hz, 1H), 8.63 (t, J = 5.5 Hz, 1H), 8.90 (s, 1H). | | | |
| II-2-282 | 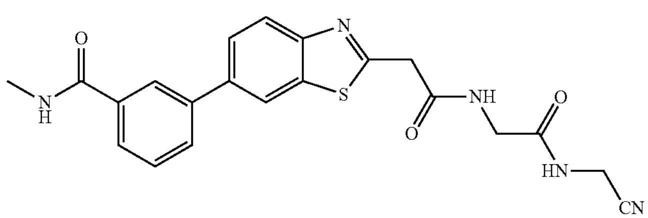 [SMILES: CNC(=O)c1cccc(-c2ccc3nc(CC(=O)NCC(=O)NCC#N)sc3c2)c1] | (DMSO-d6) δ: 2.83 (d, J = 4.5 Hz, 3H), 3.84 (d, J = 5.9 Hz, 2H), 4.15-4.21 (m, 4H), 7.58 (t, J = 7.7 Hz, 1H), 7.81-7.94 (m, 3H), 8.05 (d, J = 8.6 Hz, 1H), 8.21 (brs, 1H), 8.46 (d, J = 1.8 Hz, 1H), 8.58 (q, J = 4.7 Hz, 1H), 8.67-8.77 (m, 2H). | | | |
| II-2-283 | 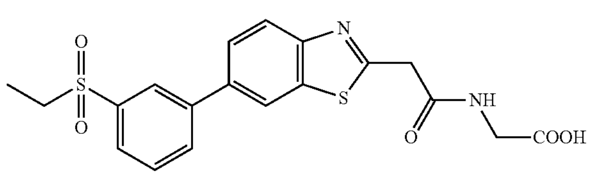 [SMILES: CCS(=O)(=O)c1cccc(-c2ccc3nc(CC(=O)NCC(=O)O)sc3c2)c1] | (DMSO-d6) δ: 1.15 (t, J = 7.3 Hz, 3H), 3.41 (q, J = 7.3 Hz, 2H), 3.86 (d, J = 5.9 Hz, 2H), 4.18 (s, 2H), 7.79 (t, J = 7.6 Hz, 1H), 7.88-7.91 (m, 2H), 8.07 (d, J = 8.6 Hz, 1H), 8.15 (d, J = 7.9 Hz, 1H), 8.21 (s, 1H), 8.54 (d, J = 1.7 Hz, 1H), 8.73 (t, J = 5.7 Hz, 1H). | | | |

TABLE 106-continued

| No. | Structure | NMR(δ) | retention time | Mass | method |
|---|---|---|---|---|---|
| II-2-284 | 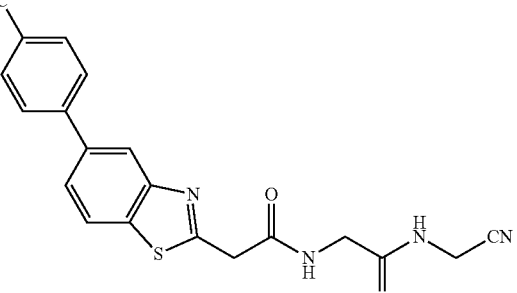 | (DMSO-d6) δ: 3.83 (d, J = 6.0 Hz, 2H), 4.04 (s, 3H), 4.13 (s, 2H), 4.17 (d, J = 5.7 Hz, 2H), 7.27 (s, 1H), 7.39-7.52 (m, 3H), 7.77 (d, J = 7.5 Hz, 2H), 7.91 (s, 1H), 8.67-8.73 (m, 2H) | | | |
| II-2-285 | 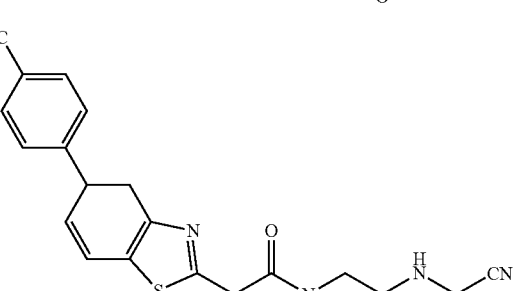 | (DMSO-$d_6$) δ: 3.85 (d, J = 6.08 Hz, 2H), 4.17 (s, 2H), 7.81 (dd, J = 8.11, 1.52 Hz, 1H), 7.93-8.03 (m, 4H), 8.20 (d, J = 8.11 Hz, 1H), 8.33 (d, J = 1.52 Hz, 1H), 8.72 (t, J = 5.58 Hz, 1H). | | | |

TABLE 107

| No. | Structure | NMR(δ) | retention time | Mass | method |
|---|---|---|---|---|---|
| II-2-286 | 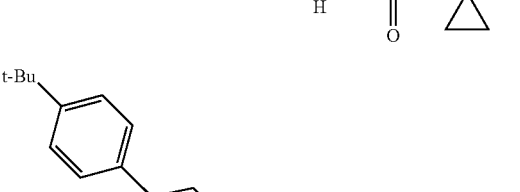 | (DMSO-$d_6$) δ: 3.83 (d, J = 5.58 Hz, 2H), 4.16-4.19 (m, 4H), 7.81 (dd, J = 8.11, 1.52 Hz, 1H), 7.94-8.02 (m, 4H), 8.20 (d, J = 8.11 Hz, 1H), 8.33 (d, J = 1.52 Hz, 1H), 8.69 (t, J = 5.32 Hz, 1H), 8.74 (t, J = 5.83 Hz, 1.0H). | | | |
| II-2-287 | 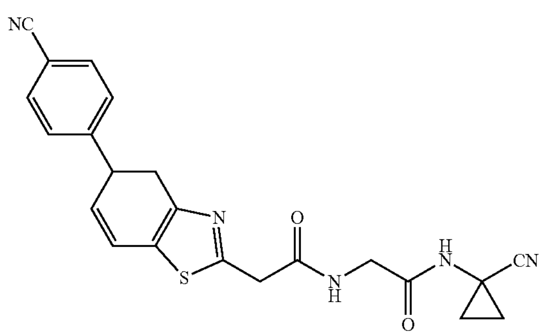 [SMILES: N#Cc1ccc(C2C=Cc3sc(CC(=O)NCC(=O)NC4(C#N)CC4)nc3C2)cc1] | (DMSO-$d_6$) δ: 1.12 (dd, J = 8.11, 5.58 Hz, 2H), 1.49 (dd, J = 8.11, 5.58 Hz, 2H), 3.78 (d, J = 5.58 Hz, 2H), 4.18 (s, 2H), 7.81 (dd, J = 8.11, 1.52 Hz, 1H), 7.94-8.03 (m, 4H), 8.20 (d, J = 8.11 Hz, 1H), 8.33 (d, J = 1.52 Hz, 1H), 8.69 (t, J = 5.58 Hz, 1H), 8.91 (s, 1H). | | | |
| II-2-288 | 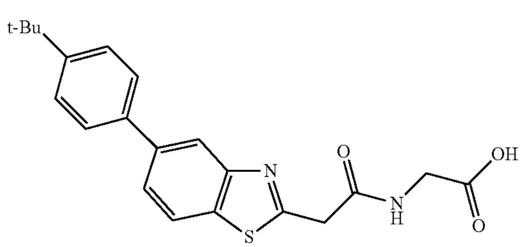 [SMILES: CC(C)(C)c1ccc(-c2ccc3sc(CC(=O)NCC(=O)O)nc3c2)cc1] | (DMSO-$d_6$) δ: 1.33 (s, 9H), 3.85 (d, J = 5.58 Hz, 2H), 4.15 (s, 2H), 7.51 (d, J = 8.11 Hz, 2H), 7.67-7.73 (m, 3H), 8.12 (d, J = 8.11 Hz, 1H), 8.19 (d, J = 1.52 Hz, 1H), 8.71 (t, J = 5.83 Hz, 1H). | | | |

TABLE 107-continued

| No. | Structure | NMR(δ) | retention time | Mass | method |
|---|---|---|---|---|---|
| II-2-289 | F₃C-O-[phenyl]-[benzothiazole]-CH₂-C(O)-NH-CH₂-C(O)-OH | (DMSO-d₆) δ: 3.85 (d, J = 6.08 Hz, 2H), 4.17 (s, 2H), 7.48 (d, J = 8.62 Hz, 2H), 7.74 (dd, J = 8.62, 1.52 Hz, 1H), 7.90 (d, J = 8.62 Hz, 2.0 H), 8.17 (d, J = 8.62 Hz, 1H), 8.25 (d, J= 1.52 Hz, 1H), 8.72 (t, J = 5.83 Hz, 1H), 12.64 (brs, 1H). | | | |
| II-2-290 | t-Bu-[phenyl]-[benzothiazole]-CH₂-C(O)-NH-CH₂-C(O)-NH-[1-cyanocyclopropyl] | (DMSO-d₆) δ: 1.12 (dd, J = 8.36, 5.32 Hz, 2H), 1.33 (s, 9H), 1.49 (dd, J = 8.36, 5.32 Hz, 2H), 3.77 (d, J = 6.08 Hz, 2H), 4.16 (s, 2H), 7.51 (d, J = 8.62 Hz, 2H), 7.73-7.67 (m, 3H), 8.12 (d, J = 8.11 Hz, 1H), 8.19 (d, J = 1.52 Hz, 1H), 8.67 (t, J = 5.58 Hz, 1H), 8.91 (s, 1H). | | | |

TABLE 108

| No. | Structure | NMR(δ) | retention time | Mass | method |
|---|---|---|---|---|---|
| II-2-291 | F₃C-O-[phenyl]-[benzothiazole]-CH₂-C(O)-NH-CH₂-C(O)-NH-CH₂-CN | (DMSO-d₆) δ: 3.83 (d, J = 5.58 Hz, 2H), 4.15-4.19 (m, 4H), 7.49 (d, J = 8.62 Hz, 2H), 7.75 (dd, J = 8.11, 1.52 Hz, 1H), 7.90 (d, J = 9.12 Hz, 2H), 8.17 (d, J = 8.11 Hz, 1H), 8.25 (d, J = 1.52 Hz, 1H), 8.69 (t, J = 5.83 Hz, 1H), 8.74 (t, J = 5.58 Hz, 1H). | | | |
| II-2-292 | F₃C-O-[phenyl]-[benzothiazole]-CH₂-C(O)-NH-CH₂-C(O)-NH-[1-cyanocyclopropyl] | (DMSO-d₆) δ: 1.12 (dd, J = 8.36, 5.32 Hz, 2H), 1.49 (dd, J = 8.36, 5.32 Hz, 2H), 3.78 (d, J = 6.08 Hz, 2H), 4.17 (s, 2H), 7.49 (d, J = 8.62 Hz, 2H), 7.75 (dd, J = 8.11, 1.52 Hz, 1H), 7.90 (d, J = 8.62 Hz, 2H), 8.17 (d, J = 8.11 Hz, 1H), 8.25 (d, J = 1.52 Hz, 1H), 8.68 (t, J = 5.83 Hz, 1H), 8.92 (s, 1H). | | | |

TABLE 108-continued
| No. | Structure | NMR(δ) | retention time | Mass | method |
|---|---|---|---|---|---|
| II-2-293 | 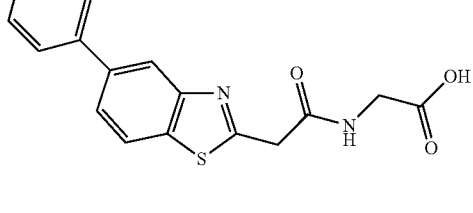 | (DMSO-d$_6$) δ: 2.08 (s, 3H), 3.85 (d, J = 6.08 Hz, 2H), 4.15 (s, 2H), 7.68-7.74 (m, 5H), 8.11 (d, J = 8.62 Hz, 1H), 8.18 (d, J = 1.52 Hz, 1H), 8.71 (t, J = 5.58 Hz, 1H), 10.05 (s, 1H). | | | |
| II-2-294 | 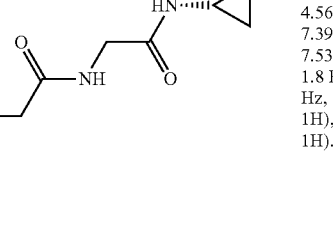 | (DMSO-d6) δ: 0.86-1.12 (m, 3H), 3.82 (dd, J = 5.7, 3.3 Hz, 2H), 4.22 (s, 2H), 4.56 and 4.81 (m, 1H), 7.39-7.44 (m, 1H), 7.48-7.53 (m, 2H), 7.88 (d, J = 1.8 Hz, 1H), 8.17 (d, J = 8.9 Hz, 1H), 8.63 (t, J = 1.8 Hz, 1H), 8.67 (d, J = 1.8 Hz, 1H). | | | |
| II-2-295 | 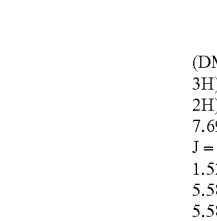 | (DMSO-d$_6$) δ: 2.07 (s, 3H), 3.83 (d, J = 6.08 Hz, 2H), 4.14-4.19 (m, 4H), 7.69-7.73 (m, 5H), 8.11 (d, J = 8.62 Hz, 1H), 8.18 (d, J = 1.52 Hz, 1H), 8.69 (t, J = 5.58 Hz, 1H), 8.73 (t, J = 5.58 Hz, 1H), 10.05 (s, 1H). | | | |
TABLE 109
| No. | Structure | NMR(δ) | retention time | Mass | method |
|---|---|---|---|---|---|
| II-2-296 | 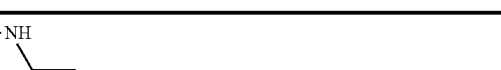 | (DMSO-d$_6$) δ: 1.12 (dd, J = 8.11, 5.58 Hz, 2H), 1.49 (dd, J = 8.11, 5.58 Hz, 2H), 2.07 (s, 3H), 3.77 (d, J = 5.58 Hz, 2H), 4.15 (s, 2H), 7.67-7.74 (m, 5H), 8.11 (d, J = 8.62 Hz, 1H), 8.18 (d, J = 1.01 Hz, 1H), 8.67 (t, J = 5.83 Hz, 1H), 8.92 (s, 1H), 10.05 (s, 1H). | | | |

TABLE 109-continued

| No. | Structure | NMR(δ) | retention time | Mass | method |
|---|---|---|---|---|---|
| II-2-297 | 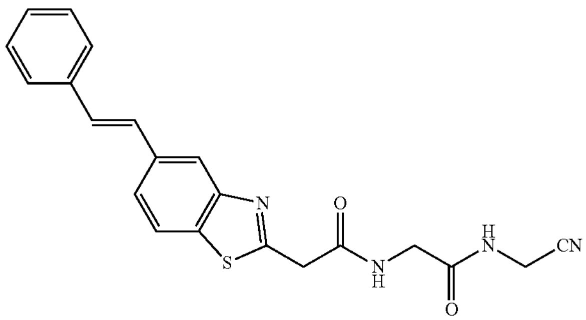 [SMILES: N#CCNC(=O)CNC(=O)Cc1nc2cc(/C=C/c3ccccc3)ccc2s1] | (DMSO-d$_6$) δ: 3.83 (d, J = 5.58 Hz, 2H), 4.14-4.19 (m, 4H), 7.29 (m, 1H), 7.38-7.42 (m, 4H), 7.64 (d, J = 7.60 Hz, 2H), 7.73 (dd, J = 8.62, 1.15 Hz, 1H), 8.05 (d, J = 8.62 Hz, 1H), 8.15 (d, J = 1.15 Hz, 1H), 8.69 (t, J = 5.58 Hz, 1H), 8.73 (t, J = 5.83 Hz, 1H). | | | |
| II-2-298 | 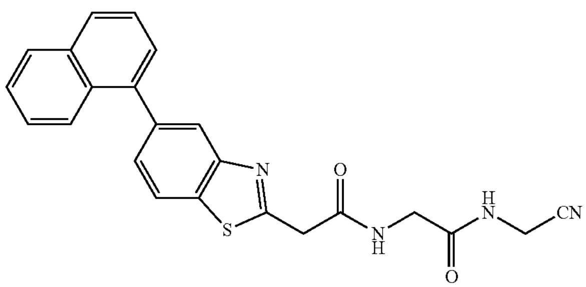 [SMILES: N#CCNC(=O)CNC(=O)Cc1nc2cc(-c3cccc4ccccc34)ccc2s1] | (DMSO-d$_6$) δ: 3.84 (d, J = 5.58 Hz, 2H), 4.17 (d, J = 5.58 Hz, 2.0 H), 4.20 (s, 2H), 7.65-7.47 (m, 5H), 7.83 (d, J = 8.62 Hz, 1H), 7.98-8.05 (m, 3H), 8.21 (d, J = 8.11 Hz, 1H), 8.69 (t, J = 5.32 Hz, 1H), 8.75 (t, J = 5.83 Hz, 1H). | | | |
| II-2-299 | 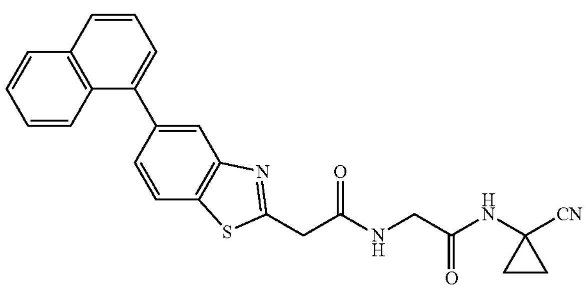 [SMILES: N#CC1(NC(=O)CNC(=O)Cc2nc3cc(-c4cccc5ccccc45)ccc3s2)CC1] | (DMSO-d6) δ: 1.13 (dd, J = 8.36, 5.32 Hz, 2H), 1.49 (dd, J = 8.36, 5.32 Hz, 2H), 3.79 (d, J = 5.58 Hz, 2H), 4.19 (s, 2H), 7.47-7.65 (m, 5H), 7.83 (d, J = 8.11 Hz, 1H), 7.98-8.05 (m, 3H), 8.21 (d, J = 8.11 Hz, 1H), 8.70 (t, J = 5.83 Hz, 1H), 8.92 (s, 1H). | | | |
| II-2-300 | 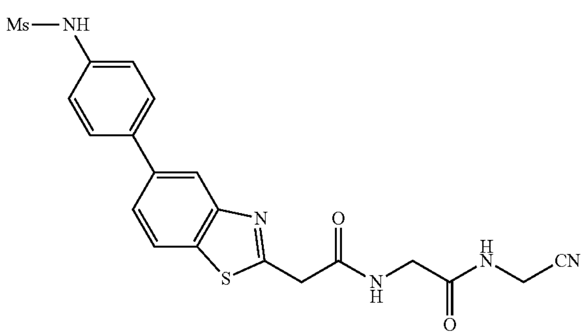 | 3.04 (s, 3H), 3.83 (d, J = 5.58 Hz, 2.0H), 4.15-4.19 (m, 4.0H), 7.33 (d, J = 8.62 Hz, 2H), 7.71 (dd, J = 8.11, 1.52 Hz, 1H), 7.76 (d, J = 8.62 Hz, 2H), 8.12 (d, J = 8.11 Hz, 1H), 8.19 (d, J = 1.52 Hz, 1H), 8.68 (t, J = 5.58 Hz, 1H), 8.73 (t, J = 5.83 Hz, 1H), 9.87 (s, 1H). | | | |

TABLE 110

| No. | Structure | NMR(δ) | retention time | Mass | method |
|---|---|---|---|---|---|
| II-2-301 | 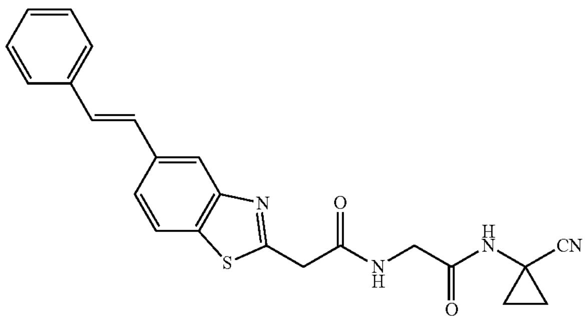 [SMILES: N#CC1(NC(=O)CNC(=O)Cc2nc3cc(/C=C/c4ccccc4)ccc3s2)CC1] | (DMSO-d6) δ: 1.12 (dd, J = 8.36, 5.32 Hz, 2H), 1.49 (dd, J = 8.36, 5.32 Hz, 2H), 3.77 (d, J = 5.58 Hz, 2H), 4.14 (s, 2H), 7.29 (m, 1H), 7.35-7.45 (m, 4H), 7.64 (d, J = 7.60 Hz, 2H), 7.73 (dd, J = 8.62, 1.52 Hz, 1H), 8.05 (d, J = 8.62 Hz, 1H), 8.14 (d, J = 1.52 Hz, 1H), 8.67 (t, J = 5.58 Hz, 1H), 8.91 (s, 1H). | | | |
| II-2-302 | 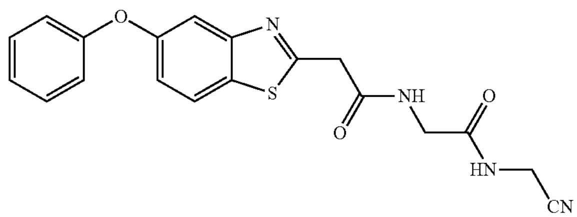 [SMILES: N#CCNC(=O)CNC(=O)Cc1nc2cc(Oc3ccccc3)ccc2s1] | (DMSO-d6) δ: 3.82 (d, J = 5.7 Hz, 2H), 4.13 (s, 2H), 4.16 (d, J = 5.7 Hz, 2H), 7.05 (d, J = 9.7 Hz, 2H), 7.13-7.20 (m, 2H), 7.37-7.44 (m, 2H), 7.52 (d, J = 2.4 Hz, 1H), 8.07 (d, J = 8.7 Hz, 1H), 8.64-8.74 (m, 2H). | | | |
| II-2-303 | 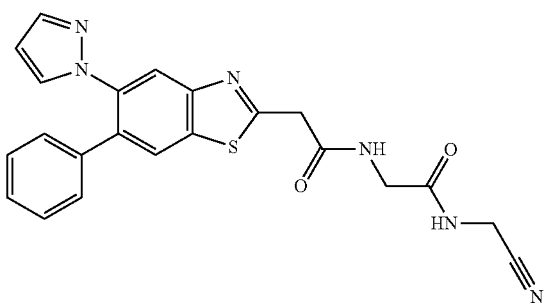 [SMILES: N#CCNC(=O)CNC(=O)Cc1nc2cc(-n3cccn3)c(-c3ccccc3)cc2s1] | (DMSO-d6) δ: 3.84 (d, J = 5.6 Hz, 2H), 4.17 (d, J = 5.6 Hz, 2H), 4.22 (s, 2H), 6.32 (t, J = 2.0 Hz, 1H), 7.07-7.11 (m, 2H), 7.28-7.31 (m, 3H), 7.55 (d, J = 2.0 Hz, 1H), 7.60 (d, J = 1.5 Hz, 1H), 8.05 (s, 1H), 8.24 (s, 1H), 8.69 (t, J = 5.6 Hz, 1H), 8.75 (t, J = 5.8 Hz, 1H). | | | |
| II-2-304 | 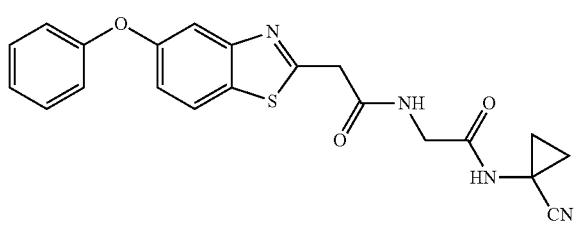 [SMILES: N#CC1(NC(=O)CNC(=O)Cc2nc3cc(Oc4ccccc4)ccc3s2)CC1] | (DMSO-d6) δ: 1.11 (dd, J = 8.2, 5.5 Hz, 2H), 1.48 (dd, J = 8.2, 5.4 Hz, 2H), 3.76 (d, J = 5.7 Hz, 2H), 4.13 (s, 2H), 7.06 (d, J = 5.4 Hz, 2H), 7.13-7.20 (m, 2H), 7.37-7.45 (m, 2H), 7.51 (d, J = 2.4 Hz, 1H), 8.08 (d, J = 8.7 Hz, 1H), 8.66 (t, J = 5.5 Hz, 1H), 8.90 (s, 1H). | | | |
| II-2-305 | 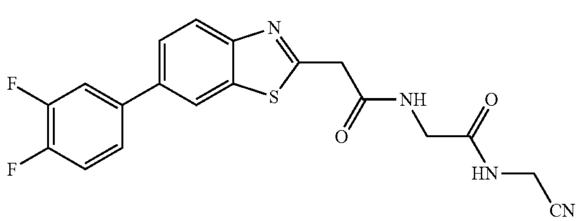 [SMILES: N#CCNC(=O)CNC(=O)Cc1nc2ccc(-c3ccc(F)c(F)c3)cc2s1] | (DMSO-d6) δ: 3.83 (d, J = 5.7 Hz, 2H), 4.14-4.20 (m, 4H), 7.50-7.67 (m, 2H), 7.79-7.93 (m, 2H), 8.02 (d, J = 8.6 Hz, 1H), 8.43 (d, J = 1.7 Hz, 1H), 8.65-8.77 (m, 2H). | | | |

TABLE 111

| No. | Structure | NMR(δ) | retention time | Mass | method |
|---|---|---|---|---|---|
| II-2-306 | 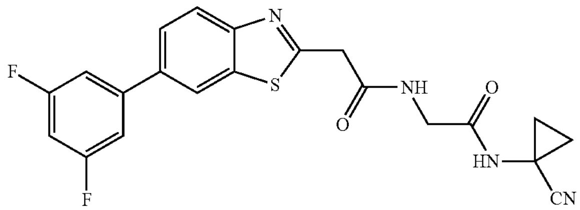 [SMILES: N#CC1(NC(=O)CNC(=O)Cc2nc3ccc(-c4cc(F)cc(F)c4)cc3s2)CC1] | (DMSO-d6) δ: 1.12 (dd, J = 8.4, 5.5 Hz, 2H), 1.50 (dd, J = 8.4, 5.4 Hz, 2H), 3.78 (d, J = 5.9 Hz, 2H), 4.17 (s, 2H), 7.26 (tt, J = 9.2, 2.2 Hz, 1H), 7.51-7.60 (m, 2H), 7.88 (dd, J = 8.6, 1.8 Hz, 1H), 8.03 (d, J = 8.6 Hz, 1H), 8.51 (d, J = 1.8 Hz, 1H), 8.69 (t, J = 5.6 Hz, 1H), 8.92 (s, 1H). | | | |
| II-2-307 | 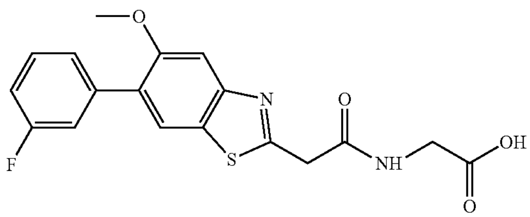 [SMILES: COc1cc2nc(CC(=O)NCC(=O)O)sc2cc1-c1cccc(F)c1] | (DMSO-d$_6$) δ: 3.84 (d, J = 6.08 Hz, 2H), 3.86 (s, 3H), 4.12 (s, 2H), 7.19 (m, 1H), 7.33-7.39 (m, 2H), 7.46 (m, 1H), 7.65 (s, 1H), 8.00 (s, 1H), 8.68 (t, J = 5.58 Hz, 1H), 12.63 (s, 1H). | | | |
| II-2-308 | 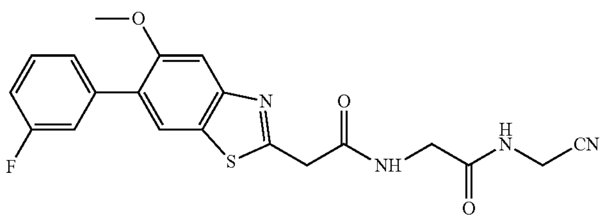 [SMILES: COc1cc2nc(CC(=O)NCC(=O)NCC#N)sc2cc1-c1cccc(F)c1] | (DMSO-d$_6$) δ: 3.84 (d, J = 5.05 Hz, 2H), 3.87 (s. 3H), 4.14 (s, 2H), 4.18 (d, J = 5.56 Hz, 2H), 7.20 (m, 1H), 7.337-.51 (m, 2H), 7.65 (s, (s, 1H), 8.66-8.73 (m, 2H). | | | |
| II-2-309 | 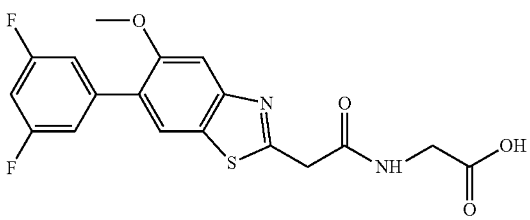 [SMILES: COc1cc2nc(CC(=O)NCC(=O)O)sc2cc1-c1cc(F)cc(F)c1] | (DMSO-d$_6$) δ: 3.85 (d, J = 5.88 Hz, 2H), 3.88 (s, 3H), 4.13 (s, 2H), 7.19-7.32 (m, 3H), 7.66 (s, 1H), 8.06 (s, 1H), 8.69 (t, J = 5.79 Hz, 1H), 12.64 (s, 1H) | | | |
| II-2-310 | 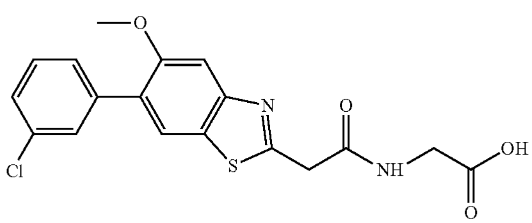 [SMILES: COc1cc2nc(CC(=O)NCC(=O)O)sc2cc1-c1cccc(Cl)c1] | (DMSO-d$_6$) δ: 3.82-3.88 (m, 5H), 4.13 (s, 2H), 7.40-7.59 (m, 4H), 7.65 (s, 1H), 8.00 (s, 1H), 8.69 (t, J = 5.58 Hz, 1H). | | | |

TABLE 112

| No. | Structure | NMR(δ) | retention time | Mass | method |
|---|---|---|---|---|---|
| II-2-311 | 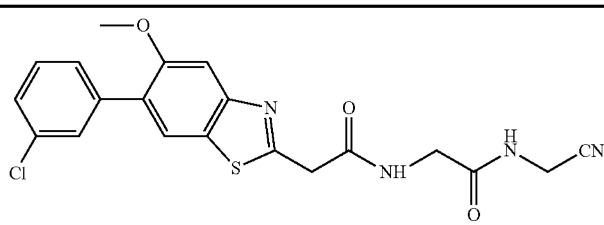 | (DMSO-d$_6$) δ: 3.83 (d, J = 5.71 Hz, 2H), 3.86 (s, 3H), 4.14 (s, 2H), 4.18 (d, J = 5.54 Hz, 2H), 7.40-7.52 (m, 3H), 7.57 (m, 1.0H), 7.65 (s, 1H), 8.00 (s, 1H), 8.65-8.75 (m, 2H). | | | |

TABLE 112-continued

| No. | Structure | NMR(δ) | retention time | Mass | method |
|---|---|---|---|---|---|
| II-2-312 | 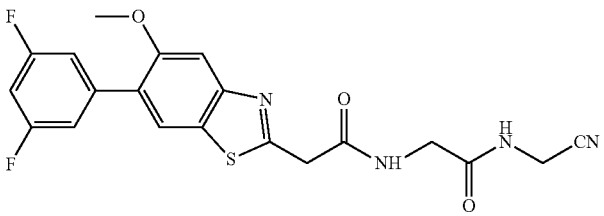 | (DMSO-d6) δ: 3.83 (d, J = 5.37 Hz, 2H), 3.88 (s, 3H), 4.15 (s, 2H), 4.17 (d, J = 5.37 Hz, 2H), 7.19-7.31 (m, 3H), 7.66 (s, 1H), 8.06 (s, 1H), 8.64-8.76 (m, 2H). | | | |
| II-2-313 | 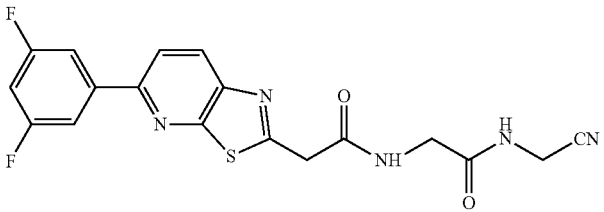 [SMILES: N#CCNC(=O)CNC(=O)Cc1nc2ccc(-c3cc(F)cc(F)c3)nc2s1] | (DMSO-d6) δ: 3.84 (d, J = 5.7 Hz, 2H), 4.17 (d, J = 5.7 Hz, 2H), 4.23 (s, 2H), 8.71-8.61 (m, 3H), 8.89 (d, J = 2.1 Hz, 1H). | | | |
| II-2-314 | 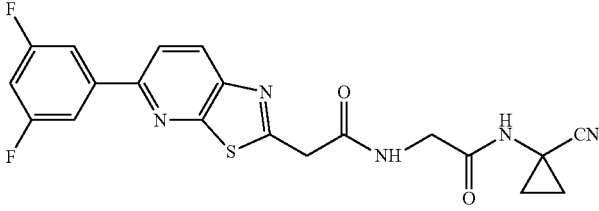 [SMILES: N#CC1(NC(=O)CNC(=O)Cc2nc3ccc(-c4cc(F)cc(F)c4)nc3s2)CC1] | (DMSO-d6) δ: 1.13 (dd, J = 8.7, 5.7 Hz, 2H), 1.49 (dd, J = 8.7, 5.7 Hz, 2H), 3.77 (d, J = 5.7 Hz, 2H), 4.22 (s, 2H), 7.33-7.39 (m, 1H), 7.81-7.92 (m, 2H), 8.25 (d, J = 8.1 Hz, 1H), 8.45 (d, J = 8. Hz, 1H), 8.71 (t, J = 5.4 Hz, 1H), 8.92 (s, 1H). | | | |
| II-2-315 | 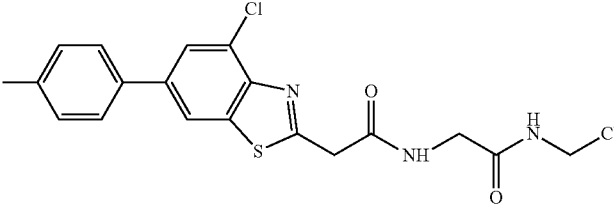 | (DMSO-d6) δ: 3.85 (d, J = 5.7 Hz, 2H), 4.16 (d, J = 5.7 Hz, 2H), 4.23 (s, 2H), 7.30-7.36 (m, 2H), 7.88 (d, J = 1.8 Hz, 1H), 8.37 (d, J = 1.8 Hz, 1H), 8.68 (t, J = 5.7 Hz, 1H), 8.76 (t, J = 5.7 Hz, 1H). | | | |

TABLE 113

| No. | Structure | NMR(δ) | retention time | Mass | method |
|---|---|---|---|---|---|
| II-2-316 | 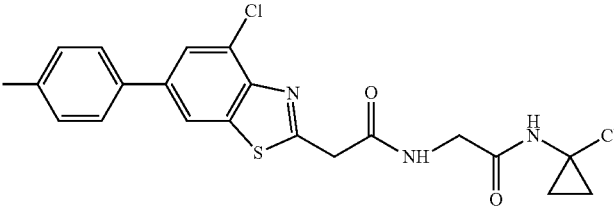 | (DMSO-d6) δ: 1.13 (dd, J = 8.7, 5.7 Hz, 2H), 1.50 (dd, J = 8.7, 5.7 Hz, 2H), 3.79 (d, J = 5.7 Hz, 2H), 4.21 (s, 2H), 7.30-7.36 (m, 2H), 7.81-7.56 (m, 2H), 7.88 (d, J = 1.4 Hz, 1H), 8.37 (d, J = 1.4 Hz, 1H), 8.71 (t, J = 5.7 Hz, 1H), 8.91 (s, 1H). | | | |
| II-2-317 | 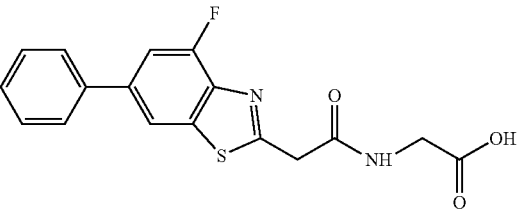 [SMILES: O=C(O)CNC(=O)Cc1nc2c(F)cc(-c3ccccc3)cc2s1] | (DMSO-d6) δ: 3.86 (d, J = 5.7 Hz, 2H), 4.20 (s, 2H), 7.38-7.48 (m, 1H), 7.47-7.52 (m, 2H), 7.66 (d, J = 1.8 Hz, 1H), 7.77-7.79 (m, 2H), 8.26 (d, J = 5.4 Hz, 1H), 8.74 (t, J = 5.7 Hz, 1H), 12.66 (brs, 1H). | | | |

TABLE 113-continued

| No. | Structure | NMR(δ) | retention time | Mass | method |
|---|---|---|---|---|---|
| II-2-318 | 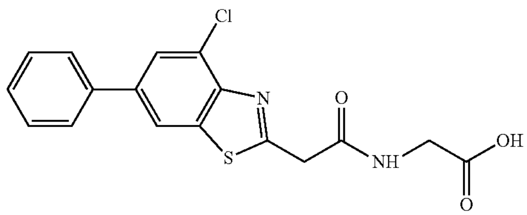 | (DMSO-d6) δ: 3.87 (d, J = 5.7 Hz, 2H), 4.22 (s, 2H), 7.39-7.53 (m, 1H), 7.77 (d, J = 5.4 Hz, 2H), 7.89 (d, J = 1.8 Hz, 1H), 8.39 (d, J = 1.4 Hz, 1H), 8.75 (t, J = 5.7 Hz, 1H), 12.66 (brs, 1H). | | | |
| II-2-319 | 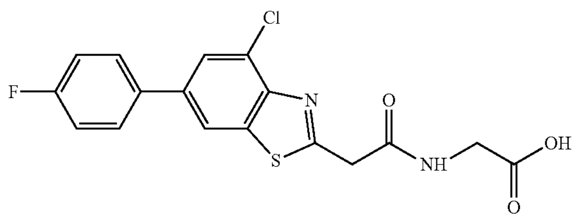 [SMILES: O=C(O)CNC(=O)Cc1nc2c(Cl)cc(-c3ccc(F)cc3)cc2s1] | (DMSO-d6) δ: 3.86 (d, J = 5.7 Hz, 2H), 4.21 (s, 2H), 7.30-7.69 (m, 1H), 7.81-7.83 (m, 2H), 7.89 (d, J = 1.8 Hz, 1H), 8.37 (d, J = 1.8 Hz, 1H), 8.75 (t, J = 5.7 Hz, 1H), 12.63 (brs, 1H). | | | |
| II-2-320 | 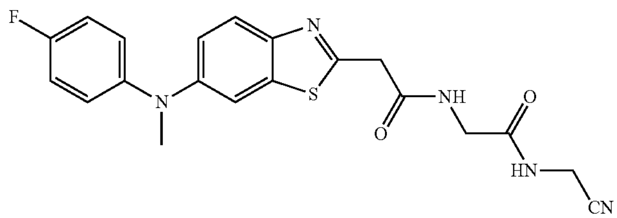 [SMILES: CN(c1ccc(F)cc1)c1ccc2nc(CC(=O)NCC(=O)NCC#N)sc2c1] | (DMSO-d6) δ: 3.29 (s, 3H), 3.81 (d, J = 6.0 Hz, 2H), 4.06 (s, 2H), 4.16 (d, J = 5.5 Hz, 2H), 7.00 (dd, J = 8.7, 2.4 Hz, 1H), 7.07-7.22 (m, 4H), 7.56 (d, J = 2.4 Hz, 1H), 7.76 (d, J = 8.9 Hz, 1H), 8.63-8.71 (m, 2H). | | | |

TABLE 114

| No. | Structure | NMR(δ) | retention time | Mass | method |
|---|---|---|---|---|---|
| II-2-321 | 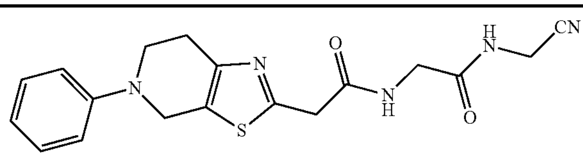 | (DMSO-d$_6$) δ: 2.80 (t, J = 5.83 Hz, 2H), 3.65 (t, J = 5.83 Hz, 2H), 3.78 (d, J = 5.58 Hz, 2H), 3.91 (s, 2H), 4.15 (d, J = 5.58 Hz, 2H), 4.46 (s, 2H), 6.76 (t, J = 7.35 Hz, 1H), 7.02 (d, J = 8.11 Hz, 2H), 7.21 (dd, J = 8.11, 7.35 Hz, 2H), 8.58 (t, J = 5.83 Hz, 1H), 8.64 (t, J = 5.58 Hz, 1H). | | | |
| II-2-322 | 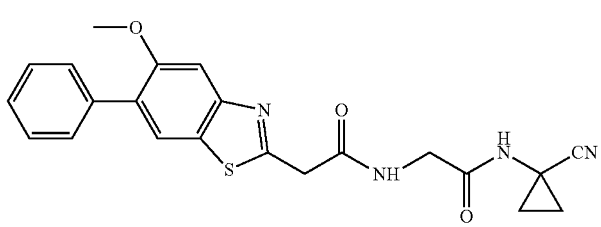 [SMILES: COc1cc2nc(CC(=O)NCC(=O)NC3(C#N)CC3)sc2cc1-c1ccccc1] | (DMSO-d$_6$) δ: 1.13 (dd, J = 8.36, 5.32 Hz, 2H), 1.50 (dd, J = 8.36, 5.32 Hz, 2H), 3.77 (d, J = 6.08 Hz, 2H), 3.84 (s, 3H), 4.12 (s, 2H), 7.35 (m, 1H), 7.40-7.46 (m, 2H), 7.52 (d, J = 7.10 Hz, 2H), 7.63 (s, 1H), 7.94 (s, 1H), 8.64 (t, J = 5.83 Hz, 1H), 8.91 (s, 1H). | | | |
| II-2-323 | 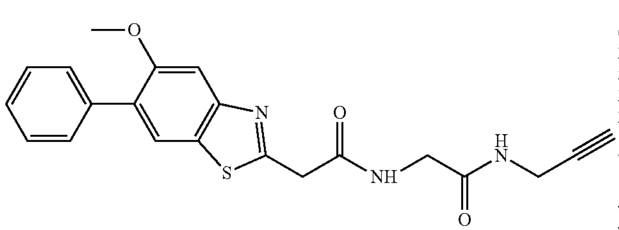 [SMILES: C#CCNC(=O)CNC(=O)Cc1nc2cc(OC)c(-c3ccccc3)cc2s1] | (DMSO-d$_6$) δ: 3.13 (t, J = 2.53 Hz, 1H), 3.78 (d, J = 5.58 Hz, 2H), 3.85 (s, 3H), 3.91 (dd, J = 5.58, 2.53 Hz, 2H), 4.12 (s, 2H), 7.35 (m, 1H), 7.40-7.45 (m, 2H), 7.48-7.54 (m, 2H), 7.63 (s, 1H), 7.94 (s, 1H), 8.43 (t, J = 5.58 Hz, 1H), 8.64 (t, J = 5.58 Hz, 1H). | | | |

TABLE 114-continued

| No. | Structure | NMR(δ) | retention time | Mass | method |
|---|---|---|---|---|---|
| II-2-324 | 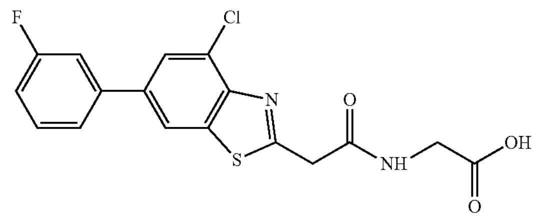 [SMILES: O=C(O)CNC(=O)Cc1nc2c(Cl)cc(-c3cccc(F)c3)cc2s1] | (DMSO-d6) δ: 3.86 (d, J = 5.7 Hz, 2H), 4.22 (s, 2H), 7.22-7.28 (m, 1H), 7.63-7.69 (m, 2H), 7.95 (d, J = 1.4 Hz, 1H), 8.45 (d, J = 1.4 Hz, 1H), 8.76 (t, J = 5.4 Hz, 1H), 12.66 (brs, 1H). | | | |
| II-2-325 | 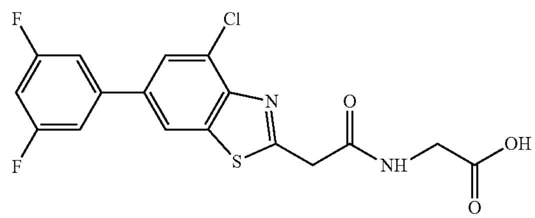 [SMILES: O=C(O)CNC(=O)Cc1nc2c(Cl)cc(-c3cc(F)cc(F)c3)cc2s1] | (DMSO-d6) δ: 3.87 (d, J = 5.7 Hz, 2H), 4.23 (s, 2H), 7.22-7.32 (m, 1H), 7.58-7.26 (m, 2H), 8.02 (d, J = 1.2 Hz, 1H), 8.50 (d, J = 0.9 Hz, 1H), 8.76 (t, J = 5.4 Hz, 1H), 12.66 (brs, 1H). | | | |

TABLE 115

| No. | Structure | NMR(δ) | retention time | Mass | method |
|---|---|---|---|---|---|
| II-2-326 | 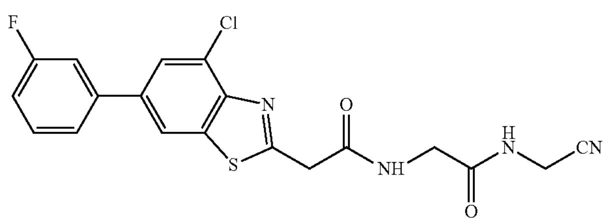 [SMILES: N#CCNC(=O)CNC(=O)Cc1nc2c(Cl)cc(-c3cccc(F)c3)cc2s1] | (DMSO-d6) δ: 3.85 (d, J = 5.7 Hz, 2H), 4.17 (d, J = 5.4 Hz, 2H), 4.24 (s, 2H), 7.22-7.28 (m, 1H), 7.64-7.69 (m, 2H), 7.95 (s, 1H), 8.45 (s, 1H), 8.69 (t, J = 5.4 Hz, 1H), 8.78 (t, J = 5.4 Hz, 1H). | | | |
| II-2-327 | 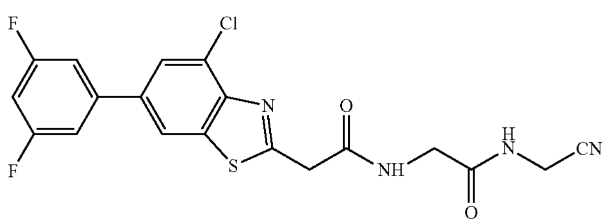 [SMILES: N#CCNC(=O)CNC(=O)Cc1nc2c(Cl)cc(-c3cc(F)cc(F)c3)cc2s1] | (DMSO-d6) δ: 3.85 (d, J = 5.7 Hz, 2H), 4.17 (d, J = 5.4 Hz, 2H), 4.24 (s, 2H), 7.44-7.28 (m, 1H), 7.50-7.58 (m, 1H), 7.64-7.69 (m, 2H), 7.95 (s, 1H), 8.45 (s, 1H), 8.69 (t, J = 5.4 Hz, 1H), 8.78 (t, J = 5.4 Hz, 1H). | | | |
| II-2-328 | 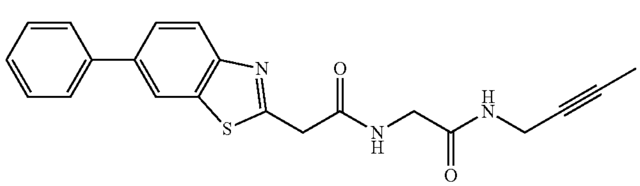 [SMILES: CC#CCNC(=O)CNC(=O)Cc1nc2ccc(-c3ccccc3)cc2s1] | (DMSO-d6) δ: 1.77 (s, 3H), 3.78 (d, J = 5.2 Hz, 2H), 3.83-3.89 (m, 2H), 4.16 (s, 2H), 7.36-7.43 (m, 1H), 7.46-7.53 (m, 2H), 7.72-7.82 (m, 3H), 8.02 (d, J = 8.4 Hz, 1H), 8.33-8.40 (m, 2H), 8.62-8.68 (m, 1H). | | | |
| II-2-329 | 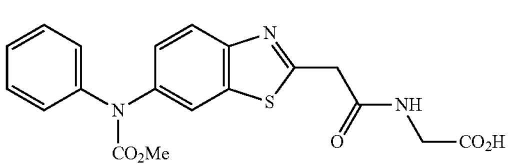 [SMILES: COC(=O)N(c1ccccc1)c1ccc2nc(CC(=O)NCC(=O)O)sc2c1] | (DMSO-d6) δ: 3.65 (s, 3H), 3.82 (d, J = 5.6 Hz, 2H), 4.12 (s, 2H), 7.24 (t, J = 7.1 Hz, 1H), 7.31-7.41 (m, 5H), 7.91 (d, J = 8.6 Hz, 1H), 8.06 (d, J = 2.0 Hz, 1H), 8.67 (t, J = 5.6 Hz, 1H), 12.63 (br s, 1H). | | | |

TABLE 115-continued
| No. | Structure | NMR(δ) | retention time | Mass | method |
|---|---|---|---|---|---|
| II-2-330 | 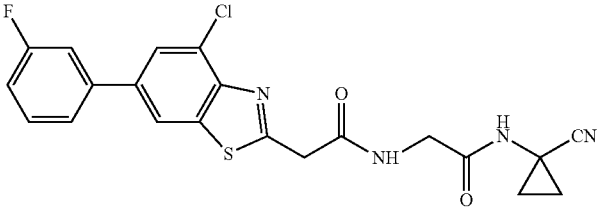 [SMILES: N#CC1(NC(=O)CNC(=O)Cc2nc3c(Cl)cc(-c4cccc(F)c4)cc3s2)CC1] | (DMSO-d6) δ: 3.65 (s, 3H), 3.81 (d, J = 5.6 Hz, 2H), 4.13 (s, 2H), 4.16 (d, J = 5.6 Hz, 2H), 7.24 (t, J = 7.1 Hz, 1H), 7.31-7.41 (m, 5H), 7.92 (d, J = 8.6 Hz, 1H), 8.06 (d, J = 2.0 Hz, 1H), 8.65-8.71 (m, 2H). | | | |
TABLE 116
| No. | Structure | NMR(δ) | retention time | Mass | method |
|---|---|---|---|---|---|
| II-2-331 | 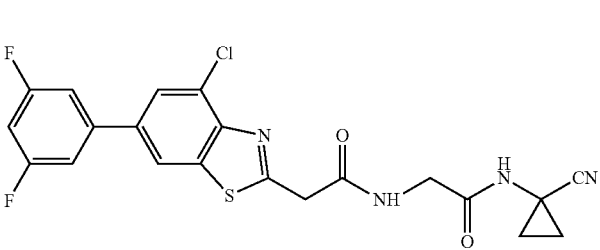 | (DMSO-d6) δ: 1.12 (dd, J = 7.8 Hz, 2H), 1.48 (dd, J = 7.8 Hz, 2H), 3.78 (d, J = 5.4 Hz, 2H), 4.22 (s, 2H), 4.24 (s, 2H), 7.22-7.28 (m, 1H), 7.64-7.69 (m, 2H), 7.95 (d, J = 1.8 Hz, 1H), 8.45 (d, J = 1.8 Hz, 1H), 8.71 (t, J = 5.4 Hz, 1H), 8.91 (s, 1H). | | | |
| II-2-332 | 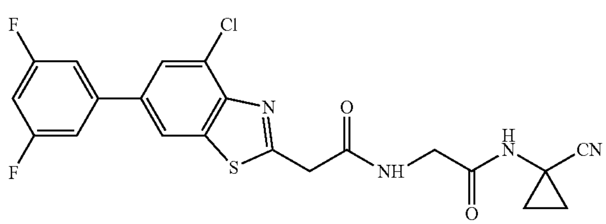 [SMILES: N#CC1(NC(=O)CNC(=O)Cc2nc3c(Cl)cc(-c4cc(F)cc(F)c4)cc3s2)CC1] | (DMSO-d6) δ: 1.12 (dd, J = 7.8 Hz, 2H), 1.48 (dd, J = 7.8 Hz, 2H), 3.78 (d, J = 5.4 Hz, 2H), 4.22 (s, 2H), 4.24 (s, 2H), 7.22-7.28 (m, 1H), 7.64-7.69 (m, 2H), 7.95 (d, J = 1.8 Hz, 1H), 8.71 (t, J = 5.4 Hz, 1H), 8.91 (s, 1H). | | | |
| II-2-333 | 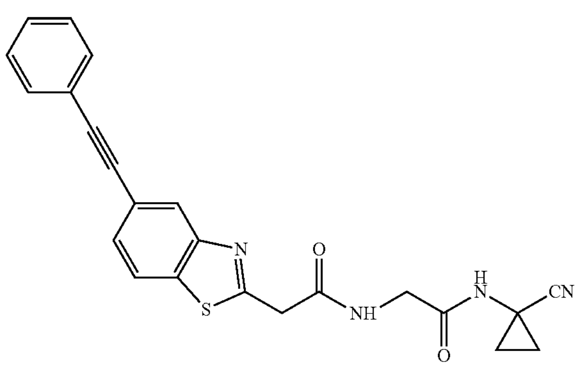 [SMILES: N#CC1(NC(=O)CNC(=O)Cc2nc3cc(C#Cc4ccccc4)ccc3s2)CC1] | (DMSO-d$_6$) δ: 1.12 (dd, J = 8.36, 5.32 Hz, 2H), 1.49 (dd, J = 8.36, 5.32 Hz, 2H), 3.77 (d, J = 6.08 Hz, 2H), 4.17 (s, 2H), 7.42-7.47 (m, 3H), 7.56-7.63 (m, 3H), 8.11-8.15 (m, 2H), 8.69 (t, J = 5.58 Hz, 1H), 8.91 (s, 1H). | | | |

TABLE 116-continued

| No. | Structure | NMR(δ) | retention time | Mass | method |
|---|---|---|---|---|---|
| II-2-334 | 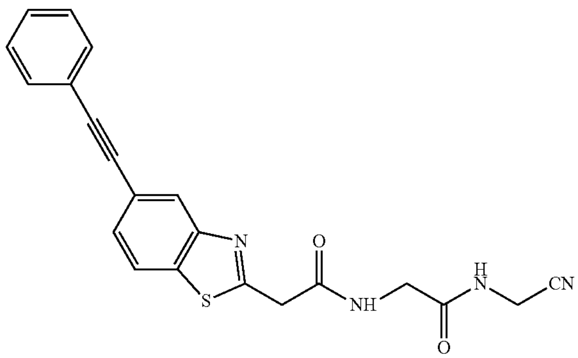 [SMILES: N#CCNC(=O)CNC(=O)Cc1nc2cc(C#Cc3ccccc3)ccc2s1] | (DMSO-d$_6$) δ: 3.83 (d, J = 5.58 Hz, 2H), 4.15-4.19 (m, 4H), 7.42-7.48 (m, 3H), 7.56-7.63 (m, 3H), 8.10-8.15 (m, 2H), 8.68 (t, J = 5.32 Hz, 1H), 8.74 (t, J = 5.83 Hz, 1H). | | | |
| II-2-335 | 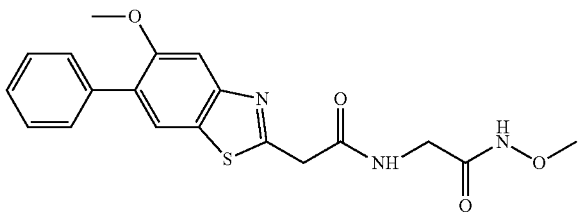 [SMILES: CONC(=O)CNC(=O)Cc1nc2cc(OC)c(-c3ccccc3)cc2s1] | (DMSO-d$_6$) δ: 3.61 (s, 3H), 3.69 (d, J = 5.07 Hz, 2H), 3.84 (s, 3H), 4.11 (s, 2H), 7.35 (m, 1H), 7.40-7.46 (m, 2H), 7.49-7.53 (m, 2H), 7.62 (s, 1H), 7.94 (s, 1H), 8.66 (t, J = 5.07 Hz, 1H), 11.26 (brs, 1H). | | | |

TABLE 117

| No. | Structure | NMR(δ) | retention time | Mass | method |
|---|---|---|---|---|---|
| II-2-336 | 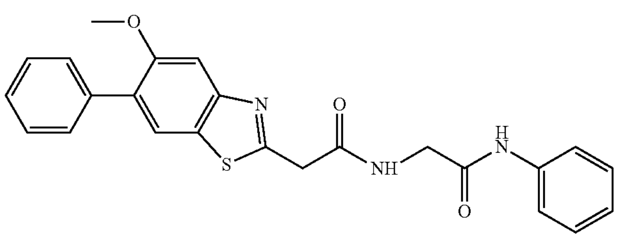 [SMILES: COc1cc2nc(CC(=O)NCC(=O)Nc3ccccc3)sc2cc1-c1ccccc1] | (DMSO-d$_6$) δ: 3.84 (s, 3H), 3.98 (d, J = 5.58 Hz, 2H), 4.16 (s, 2H), 7.05 (m, 1H), 7.28-7.63 (m, 10H), 7.94 (s, 1H), 8.71 (t, J = 5.58 Hz, 1H), 10.01 (s, 1H). | | | |
| II-2-337 | 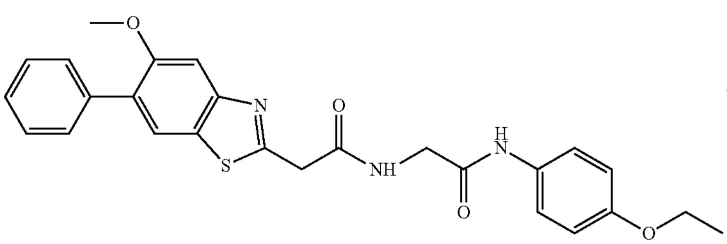 [SMILES: CCOc1ccc(NC(=O)CNC(=O)Cc2nc3cc(OC)c(-c4ccccc4)cc3s2)cc1] | (DMSO-d$_6$) δ: 1.30 (t, J = 6.84 Hz, 3H), 3.83 (s, 3H), 3.92-4.01 (m, 4H), 4.16 (s, 2H), 6.87 (d, J = 8.62 Hz, 2H), 7.32-7.53 (m, 7H), 7.61 (s, 1H), 7.94 (s, 1H), 8.70 (t, J = 5.32 Hz, 1H), 9.86 (s, 1H). | | | |
| II-2-338 | 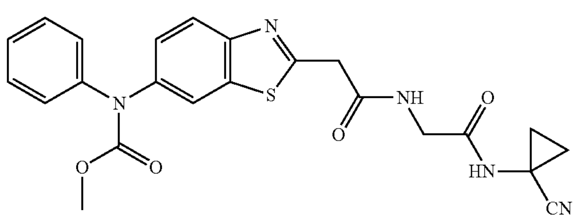 [SMILES: COC(=O)N(c1ccccc1)c1ccc2nc(CC(=O)NCC(=O)NC3(C#N)CC3)sc2c1] | (DMSO-d6) δ: 1.11 (dd, J = 8.4, 5.3 Hz, 2H), 1.48 (dd, J = 8.4, 5.3 Hz, 2H), 3.65 (s, 3H), 3.75 (d, J = 5.6 Hz, 2H), 4.12 (s, 2H), 7.24 (t, J = 7.1 Hz, 1H), 7.31-7.41 (m, 5H), 7.91 (d, J = 8.6 Hz, 1H), 8.06 (d, J = 2.0 Hz, 1H), 8.64 (t, J = 5.8 Hz, 1H), 8.89 (s, 1H). | | | |

TABLE 117-continued

| No. | Structure | NMR(δ) | retention time | Mass | method |
|---|---|---|---|---|---|
| II-2-339 | 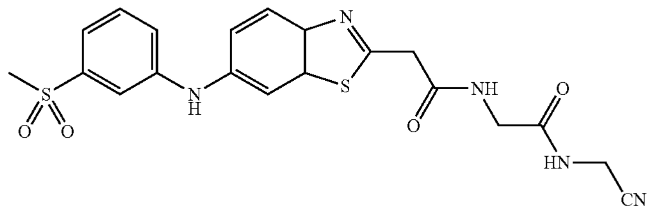 [SMILES: CS(=O)(=O)c1cccc(NC2=CC3SC(CC(=O)NCC(=O)NCC#N)=NC3C=C2)c1] | (DMSO-d6) δ: 3.19 (s, 3H), 3.82 (d, J = 6.1 Hz, 2H), 4.08 (s, 2H), 4.16 (d, J = 5.6 Hz, 2H), 7.25 (dd, J = 8.6, 2.0 Hz, 1H), 7.32 (d, J = 7.6 Hz, 1H), 7.40 (dd, J = 7.9, 1.8 Hz, 1H), 7.48-7.54 (m, 2H), 7.80 (d, J = 2.5 Hz, 1H), 7.86 (d, J = 9.1 Hz, 1H), 8.65-8.70 (m, 2H), 8.82 (s, 1H). | | | |
| II-2-340 | 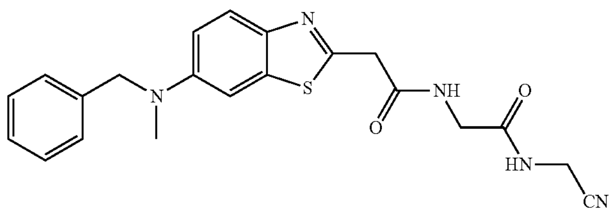 [SMILES: CN(Cc1ccccc1)c1ccc2nc(CC(=O)NCC(=O)NCC#N)sc2c1] | (DMSO-d6) δ: 3.06 (s, 3H), 3.80 (d, J = 5.9 Hz, 2H), 4.00 (s, 2H), 4.16 (d, J = 5.7 Hz, 2H), 4.65 (s, 2H), 6.96 (dd, J = 9.1, 2.4 Hz, 1H), 7.17-7.35 (m, 6H), 7.69 (d, J = 9.1 Hz, 1H), 8.60-8.69 (m, 2H). | | | |

TABLE 118

| No. | Structure | NMR(δ) | retention time | Mass | method |
|---|---|---|---|---|---|
| II-2-341 | 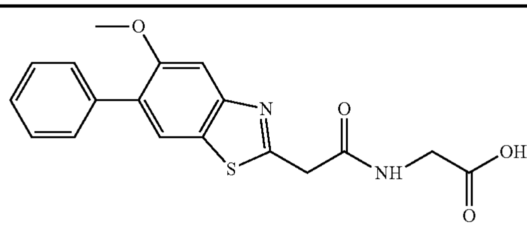 | (DMSO-d$_6$) δ: 3.82-3.86 (m, 5H), 4.12 (s, 2H), 7.35 (m, 1H), 7.40-7.53 (m, 4H), 7.63 (s, 1H), 7.94 (s, 1H), 8.67 (t, J = 5.58 Hz, 1H), 12.62 (s, 1H). | | | |
| II-2-342 | 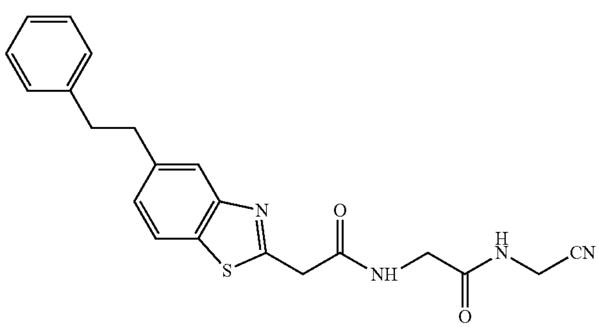 [SMILES: N#CCNC(=O)CNC(=O)Cc1nc2cc(CCc3ccccc3)ccc2s1] | (DMSO-d$_6$) δ: 3.06-2.92 (m, 4H), 3.81 (d, J = 5.58 Hz, 2H), 4.11 (s, 2H), 4.16 (d, J = 5.58 Hz, 2H), 7.14-7.31 (m, 6.0H), 7.77 (s, 1H), 7.93 (d, J = 8.11 Hz, 1H), 8.64-8.72 (m, 2H). | | | |
| II-2-343 | 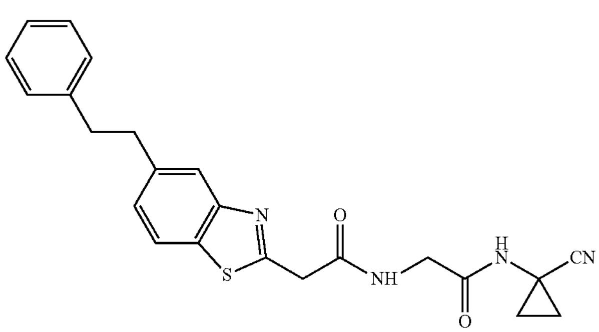 [SMILES: N#CC1(NC(=O)CNC(=O)Cc2nc3cc(CCc4ccccc4)ccc3s2)CC1] | (DMSO-d$_6$) δ: 1.12 (dd, J = 8.11, 5.58 Hz, 2H), 1.49 (dd, J = 8.11, 5.58 Hz, 2H), 2.92-3.07 (m, 4H), 3.76 (d, J = 5.58 Hz, 2H), 4.10 (s, 2H), 7.14-7.31 (m, 6H), 7.77 (s, 1H), 7.93 (d, J = 8.11 Hz, 1H), 8.64 (t, J = 5.58 Hz, 1H), 8.90 (s, 1H). | | | |

TABLE 118-continued

| No. | Structure | NMR(δ) | retention time | Mass | method |
|---|---|---|---|---|---|
| II-2-344 | 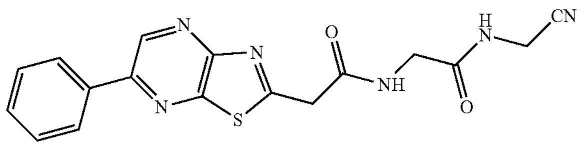 [SMILES: N#CCNC(=O)CNC(=O)Cc1nc2ncc(-c3ccccc3)nc2s1] | (DMSO-d6) δ: 3.87 (d, J = 5.7 Hz, 2H), 4.16 (d, J = 5.4 Hz, 2H), 4.31 (s, 2H), 7.54-7.62 (m, 3H), 8.22 (d, J = 8.1 Hz, 1H), 8.73 (t, J = 5.7 Hz, 1H), 8.83 (t, J = 5.7 Hz, 1H), 9.366 (s, 1H). | | | |
| II-2-345 | 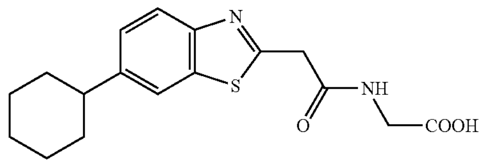 [SMILES: O=C(O)CNC(=O)Cc1nc2ccc(C3CCCCC3)cc2s1] | (DMSO-d6) δ: 1.20-1.55 (m, 5H), 1.66-1.91 (m, 5H), 2.64 (m, 1H), 3.83 (d, J = 5.9 Hz, 2H), 4.09 (s, 2H), 7.36 (dd, J = 8.4, 1.7 Hz, 1H), 7.84 (d, J = 8.4 Hz, 1H), 7.89 (d, J = 1.7 Hz, 1H), 8.66 (t, J = 5.8 Hz, 1H). | | | |

TABLE 119

| No. | Structure | NMR(δ) | retention time | Mass | method |
|---|---|---|---|---|---|
| II-2-346 | 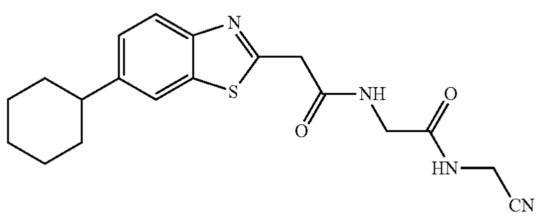 [SMILES: N#CCNC(=O)CNC(=O)Cc1nc2ccc(C3CCCCC3)cc2s1] | (DMSO-d6) δ: 1.22-1.56 (m, 5H), 1.66-1.91 (m, 5H), 2.64 (m, 1H), 3.81 (d, J = 5.9 Hz, 2H), 4.10 (s, 2H), 4.16 (d, J = 5.5 Hz, 2H), 7.36 (dd, J = 8.6, 1.7 Hz, 1H), 7.84 (d, J = 8.6 Hz, 1H), 7.89 (d, J = 1.5 Hz, 1H), 8.62-8.72 (m, 2H). | | | |
| II-2-347 | 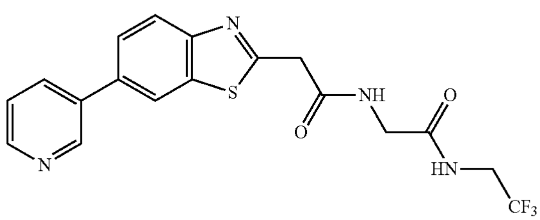 [SMILES: O=C(CNC(=O)Cc1nc2ccc(-c3cccnc3)cc2s1)NCC(F)(F)F] | (DMSO-d6) δ: 3.86 (d, J = 6.1 Hz, 2H), 3.89-3.98 (m, 2H), 4.18 (s, 2H), 7.57 (dd, J = 8.1, 5.1 Hz, 1H), 7.87 (dd, J = 8.6, 2.0 Hz, 1H), 8.06 (d, J = 8.6 Hz, 1H), 8.23 (dt, J = 8.1, 2.0 Hz, 1H), 8.49 (d, J = 1.5 Hz, 1H), 8.61-8.65 (m, 2H), 8.71 (t, J = 5.8 Hz, 1H), 9.01 (d, J = 2.0 Hz, 1H). | | | |
| II-2-348 | 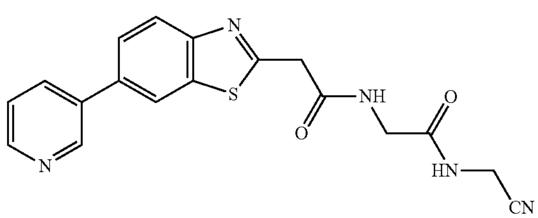 [SMILES: N#CCNC(=O)CNC(=O)Cc1nc2ccc(-c3cccnc3)cc2s1] | (DMSO-d6) δ: 3.83 (d, J = 5.6 Hz, 2H), 4.16-4.18 (m, 4H), 7.52 (dd, J = 8.1, 4.6 Hz, 1H), 7.86 (dd, J = 8.4, 1.8 Hz, 1H), 8.06 (d, J = 8.6 Hz, 1H), 8.17 (dt, J = 7.9, 1.9 Hz, 1H), 8.48 (d, J = 2.0 Hz, 1H), 8.60 (dd, J = 4.6, 1.5 Hz, 1H), 8.68 (t, J = 5.6 Hz, 1H), 8.73 (t, J = 5.8 Hz, 1H), 8.98 (d, J = 2.0 Hz, 1H). | | | |
| II-2-349 | 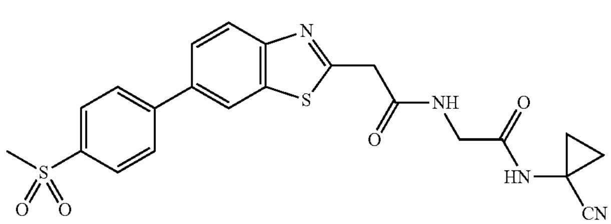 [SMILES: CS(=O)(=O)c1ccc(-c2ccc3nc(CC(=O)NCC(=O)NC4(C#N)CC4)sc3c2)cc1] | (DMSO-d6) δ: 1.12 (dd, J = 8.1, 5.6 Hz, 2H), 1.49 (dd, J = 8.1, 5.6 Hz, 2H), 3.27 (s, 3H), 3.78 (d, J = 6.1 Hz, 2H), 4.18 (s, 2H), 7.88 (dd, J = 8.4, 1.8 Hz, 1H), 8.03-8.07 (m, 5H), 8.52 (d, J = 2.0 Hz, 1H), 8.69 (t, J = 5.8 Hz, 1H), 8.91 (s, 1H). | | | |

TABLE 119-continued

| No. | Structure | NMR(δ) | retention time | Mass | method |
|---|---|---|---|---|---|
| II-2-350 | 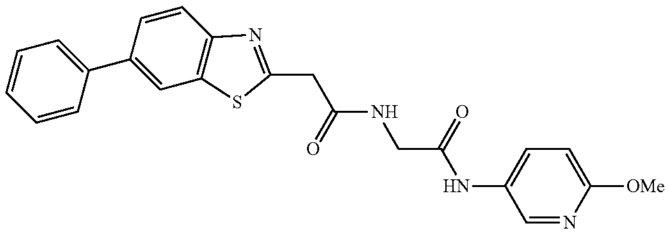 [SMILES: COc1ccc(NC(=O)CNC(=O)Cc2nc3ccc(-c4ccccc4)cc3s2)cn1] | (DMSO-d6) δ: 3.81 (s, 3H), 3.98 (d, J = 5.4 Hz, 2H), 4.20 (s, 2H), 6.81 (d, J = 9.0 Hz, 1H), 7.39 (t, J = 6.9 Hz, 1H), 7.50 (t, J = 7.2 Hz, 2H), 7.74-7.90 (m, 5H), 8.01 (d, J = 8.4 Hz, 1H), 8.34-8.39 (2H, m), 8.76 (1H, m), 10.07 (s, 1H) | | | |

TABLE 120

| No. | Structure | NMR(δ) | retention time | Mass | method |
|---|---|---|---|---|---|
| II-2-351 | 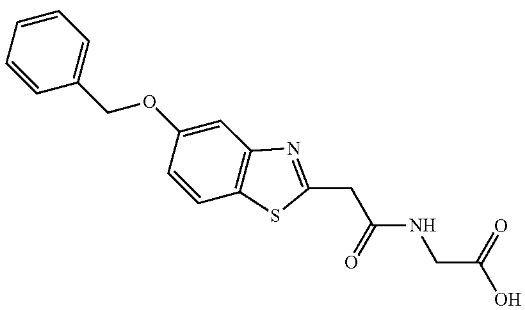 [SMILES: O=C(O)CNC(=O)Cc1nc2cc(OCc3ccccc3)ccc2s1] | (DMSO-d6) δ: 3.82 (d, J = 6.0 Hz, 2H), 4.08 (s, 2H), 5.20 (s, 2H), 7.13 (d, J = 9.0 Hz, 1H), 7.32-7.50 (m, 5H), 7.56 (s, 1H), 7.92 (d, J = 9.0 Hz, 1H), 8.66 (m, 1H) | | | |
| II-2-352 | 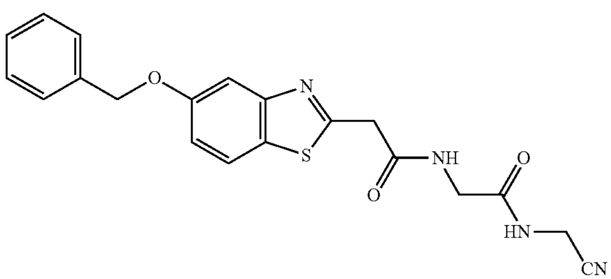 [SMILES: N#CCNC(=O)CNC(=O)Cc1nc2cc(OCc3ccccc3)ccc2s1] | (DMSO-d6) δ: 3.81 (d, J = 5.7 Hz, 2H), 4.09 (s, 2H), 4.16 (d, J = 5.4 Hz, 2H), 5.20 (s, 2H), 7.13 (d, J = 9.0 Hz, 1H), 7.33-7.50 (m, 5H), 7.56 (s, 1H), 7.92 (d, J = 9.0 Hz, 1H), 8.67-8.69 (m, 2H) | | | |
| II-2-353 | 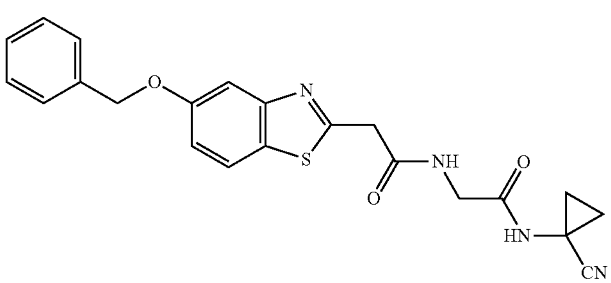 [SMILES: N#CC1(NC(=O)CNC(=O)Cc2nc3cc(OCc4ccccc4)ccc3s2)CC1] | (DMSO-d6) δ: 1.09-1.14 (m, 2H), 1.46-1.51 (m, 2H), 3.75 (d, J = 6.3 Hz, 2H), 4.09 (s, 2H), 5.20 (s, 2H), 7.13 (d, J = 9.0 Hz, 1H), 7.33-7.57 (m, 6H), 7.93 (d, J = 9.0 Hz, 1H), 8.62 (m, 1H), 8.67-8.69 (m, 2H) | | | |

TABLE 120-continued

| No. | Structure | NMR(δ) | retention time | Mass | method |
|---|---|---|---|---|---|
| II-2-354 | 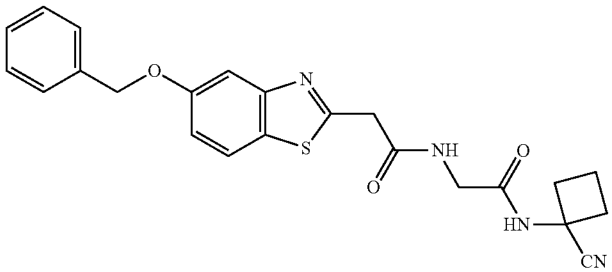 [SMILES: N#CC1(NC(=O)CNC(=O)Cc2nc3cc(OCc4ccccc4)ccc3s2)CCC1] | (DMSO-d6) δ: 1.97-2.03 (m, 2H), 2.25-2.32 (m, 2H), 2.55-2.59 (m, 2H), 3.81 (d, J = 5.7 Hz, 2H), 4.09 (s, 2H), 5.20 (s, 2H), 7.12 (d, J = 9.0 Hz, 1H), 7.33-7.56 (m, 6H), 7.92 (d, J = 9.0 Hz, 1H), 8.62 (m, 1H), 8.92 (s, 1H). | | | |
| II-2-355 | 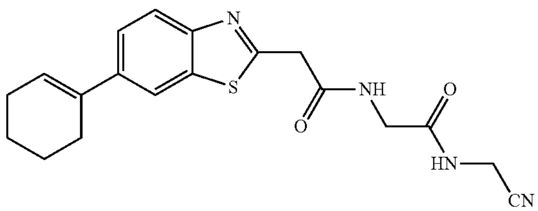 [SMILES: N#CCNC(=O)CNC(=O)Cc1nc2ccc(C3=CCCCC3)cc2s1] | (DMSO-d6) δ: 1.62 (m, 2H), 1.75 (m, 2H), 2.22 (m, 2H), 2.43 (m, 2H), 3.82 (d, J = 5.9 Hz, 2H), 4.11 (s, 2H), 4.16 (d, J = 5.4 Hz, 2H), 6.26 (m, 1H), 7.56 (dd, J = 8.6, 1.8 Hz, 1H), 7.86 (d, J = 8.6 Hz, 1H), 8.06 (d, J = 1.5 Hz, 1H), 8.64-8.73 (m, 2H). | | | |

TABLE 121

| No. | Structure | NMR(δ) | retention time | Mass | method |
|---|---|---|---|---|---|
| II-2-356 | 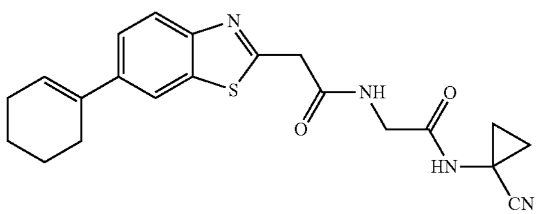 [SMILES: N#CC1(NC(=O)CNC(=O)Cc2nc3ccc(C4=CCCCC4)cc3s2)CC1] | (DMSO-d6) δ: 1.12 (dd, J = 8.2, 5.5 Hz, 2H), 1.49 (dd, J = 8.1, 5.4 Hz, 2H), 1.62 (m, 2H), 1.76 (m, 2H), 2.21 (m, 2H), 2.44 (m, 2H), 3.76 (d, J = 5.7 Hz, 2H), 4.11 (s, 2H), 6.26 (s, 1H), 7.56 (dd, J = 8.6, 1.8 Hz, 1H), 7.86 (d, J = 8.6 Hz, 1H), 8.06 (d, J = 1.5 Hz, 1H), 8.65 (t, J = 5.5 Hz, 1H), 8.90 (s, 1H). | | | |
| II-2-357 | 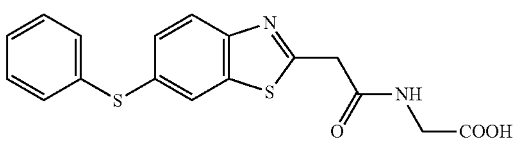 [SMILES: O=C(O)CNC(=O)Cc1nc2ccc(Sc3ccccc3)cc2s1] | (DMSO-d6) δ: 3.83 (d, J = 5.7 Hz, 2H), 4.14 (s, 2H), 7.26-7.40 (m, 5H), 7.45 (dd, J = 8.5, 1.9 Hz, 1H), 7.95 (d, J = 8.4 Hz, 1H), 8.15 (d, J = 1.8 Hz, 1H), 8.70 (t, J = 5.7 Hz, 1H). | | | |
| II-2-358 | 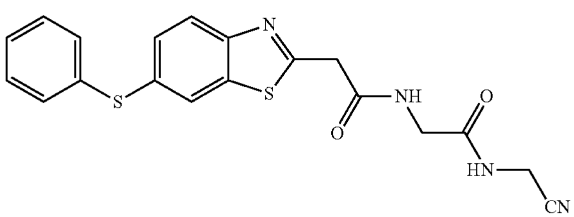 [SMILES: N#CCNC(=O)CNC(=O)Cc1nc2ccc(Sc3ccccc3)cc2s1] | (DMSO-d6) δ: 3.82 (d, J = 5.9 Hz, 2H), 4.13-4.19 (m, 4H), 4.26-7.40 (m, 5H), 7.45 (dd, J = 8.5, 1.9 Hz, 1H), 7.95 (d, J = 8.6 Hz, 1H), 8.15 (d, J = 1.5 Hz, 1H), 8.64-8.76 (m, 2H). | | | |
| II-2-359 | 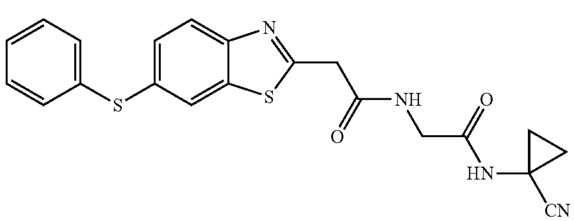 [SMILES: N#CC1(NC(=O)CNC(=O)Cc2nc3ccc(Sc4ccccc4)cc3s2)CC1] | (DMSO-d6) δ: 1.12 (dd, J = 8.2, 5.5 Hz, 2H), 1.49 (dd, J = 8.1, 5.5 Hz, 2H), 3.76 (d, J = 5.7 Hz, 2H), 4.14 (s, 2H), 7.26-7.41 (m, 5H), 7.45 (dd, J = 8.5, 1.9 Hz, 1H), 7.95 (d, J = 8.6 Hz, 1H), 8.15 (d, J = 1.8 Hz, 1H), 8.67 (t, J = 5.4 Hz, 1H), 8.90 (s, 1H). | | | |

TABLE 121-continued

| No. | Structure | NMR(δ) | retention time | Mass | method |
|---|---|---|---|---|---|
| II-2-360 | 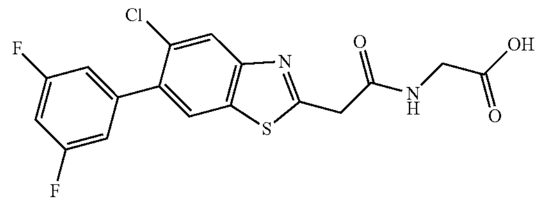 [SMILES: O=C(O)CNC(=O)Cc1nc2cc(Cl)c(-c3cc(F)cc(F)c3)cc2s1] | (DMSO-d$_6$) δ: 3.85 (d, J = 5.58 Hz, 2H), 4.19 (s, 2H), 7.38-7.22 (m, 3H), 8.19 (s, 1H), 8.22 (s, 1H), 8.73 (t, J = 5.58 Hz, 1H), 12.64 (brs, 1H). | | | |

TABLE 122

| No. | Structure | NMR(δ) | retention time | Mass | method |
|---|---|---|---|---|---|
| II-2-361 | 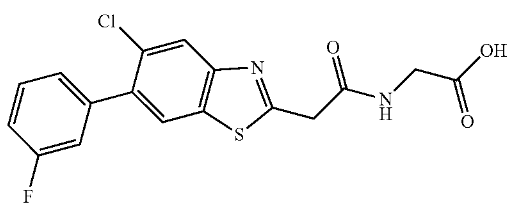 [SMILES: O=C(O)CNC(=O)Cc1nc2cc(Cl)c(-c3cccc(F)c3)cc2s1] | (DMSO-d$_6$) δ: 3.85 (d, J = 6.08 Hz, 2H), 4.18 (s, 2H), 7.26-7.37 (m, 3.0H), 7.54 (m, 1H), 8.17 (s, 1H), 8.19 (s, 1H), 8.73 (t, J = 5.58 Hz, 1H), 12.65 (brs, 1H). | | | |
| II-2-362 | 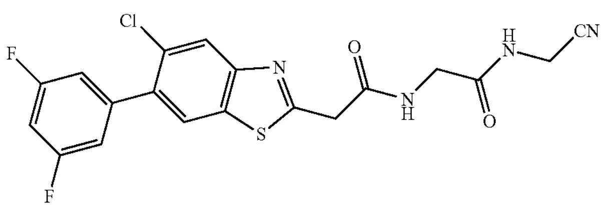 [SMILES: N#CCNC(=O)CNC(=O)Cc1nc2cc(Cl)c(-c3cc(F)cc(F)c3)cc2s1] | (DMSO-d$_6$) δ: 3.83 (d, J = 6.08 Hz, 2H) 4.16 (d, J = 5.58 Hz, 2H), 4.20 (s, 2H), 7.23-7.38 (m, 3H), 8.19 (s, 1H), 8.22 (s, 1H), 8.68 (t, J = 5.32 Hz, 1H), 8.75 (t, J = 5.83 Hz, 1H). | | | |
| II-2-363 | 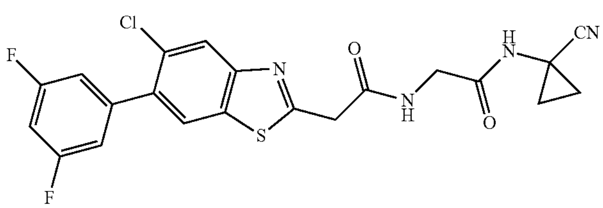 [SMILES: N#CC1(NC(=O)CNC(=O)Cc2nc3cc(Cl)c(-c4cc(F)cc(F)c4)cc3s2)CC1] | (DMSO-d$_6$) δ: 1.12 (dd, J = 8.36, 5.32 Hz, 2H), 1.49 (dd, J = 8.36, 5.32 Hz, 2H), 3.78 (d, J = 5.58 Hz, 2H), 4.20 (s, 2H), 7.23-7.38 (m, 3H), 8.19 (s, 1H), 8.22 (s, 1H), 8.70 (t, J = 5.58 Hz, 1H), 8.91 (s, 1H). | | | |
| II-2-364 | 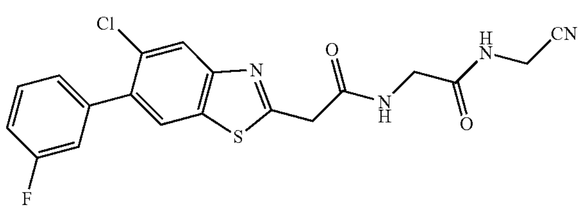 [SMILES: N#CCNC(=O)CNC(=O)Cc1nc2cc(Cl)c(-c3cccc(F)c3)cc2s1] | (DMSO-d$_6$) δ: 3.83 (d, J = 6.08 Hz, 2H), 4.16 (d, J = 5.58 Hz, 2H), 4.19 (s, 2H), 7.25-7.37 (m, 3H), 7.54 (m, 1H), 8.17 (s, 1H), 8.19 (s, 1H), 8.68 (t, J = 5.58 Hz, 1H), 8.74 (t, J = 5.58 Hz, 1H). | | | |
| II-2-365 | 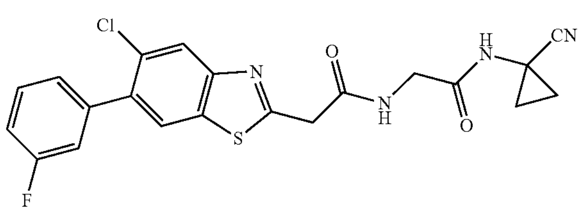 [SMILES: N#CC1(NC(=O)CNC(=O)Cc2nc3cc(Cl)c(-c4cccc(F)c4)cc3s2)CC1] | (DMSO-d$_6$) δ: 1.12 (dd, J = 8.36, 5.32 Hz, 2H), 1.49 (dd, J = 8.36, 5.32 Hz, 2H), 3.77 (d, J = 5.58 Hz, 2H), 4.19 (s, 2H), 7.25-7.37 (m, 3H), 7.53 (m, 1H), 8.17 (s, 1H), 8.19 (s, 1H), 8.69 (t, J = 5.58 Hz, 1H), 8.91 (s, 1H). | | | |

TABLE 123
| No. | Structure | NMR(δ) | retention time | Mass | method |
|---|---|---|---|---|---|
| II-2-366 | 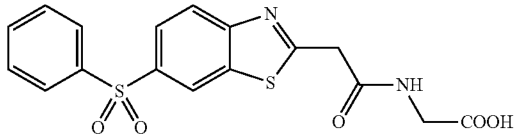 [SMILES: O=C(O)CNC(=O)Cc1nc2ccc(S(=O)(=O)c3ccccc3)cc2s1] | (DMSO-d6) δ: 3.84 (d, J = 5.7 Hz, 2H), 4.21 (s, 2H), 7.59-7.73 (m, 3H), 7.95-8.03 (m, 3H), 8.12 (d, J = 8.7 Hz, 1H), 8.72 (t, J = 5.6 Hz, 1H), 8.86 (d, J = 1.8 Hz, 1H), 12.65 (br s, 1H). | | | |
| II-2-367 | 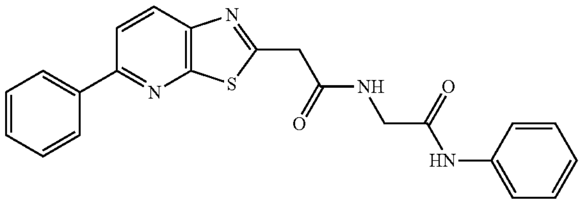 [SMILES: O=C(Cc1nc2ccc(-c3ccccc3)nc2s1)NCC(=O)Nc1ccccc1] | | 1.9 | 403 | C |
| II-2-368 | 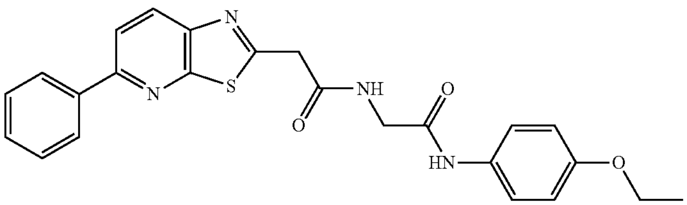 [SMILES: CCOc1ccc(NC(=O)CNC(=O)Cc2nc3ccc(-c4ccccc4)nc3s2)cc1] | (DMSO-d6) δ: 1.30 (t, J = 6.9 Hz, 3H), 3.94-3.98 (m, 4H), 4.23 (s, 2H), 6.87 (d, J = 9.0 Hz, 2H), 7.46-7.54 (m, 5H), 8.15 (t, J = 8.7 Hz, 3H), 8.40 (t, J = 8.4 Hz, 1H), 8.76 (1H, m), 9.88 (s, 1H) | | | |
| II-2-369 | 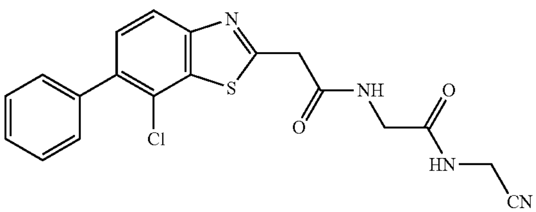 [SMILES: N#CCNC(=O)CNC(=O)Cc1nc2ccc(-c3ccccc3)c(Cl)c2s1] | (DMSO-d6) δ: 3.85 (d, J = 6.1 Hz, 2H), 4.17 (d, J = 5.6 Hz, 2H), 4.22 (s, 2H), 7.44-7.56 (m, 6H), 8.01 (d, J = 8.6 Hz, 1H), 8.69 (t, J = 5.3 Hz, 1H), 8.77 (t, J = 5.6 Hz, 1H) | | | |
| II-2-370 | 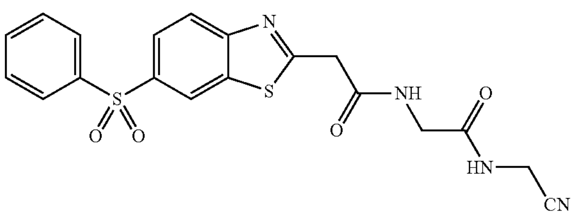 [SMILES: N#CCNC(=O)CNC(=O)Cc1nc2ccc(S(=O)(=O)c3ccccc3)cc2s1] | (DMSO-d6) δ: 3.82 (d, J = 5.7 Hz, 2H), 4.15 (d, J = 5.5 Hz, 2H), 4.22 (s, 2H), 7.57-7.73 (m, 3H), 7.95-8.03 (m, 3H), 8.13 (d, J = 8.4 Hz, 1h), 8.62-8.78 (m, 2H), 8.86 (m, 1H). | | | |
TABLE 124
| No. | Structure | NMR(δ) | retention time | Mass | method |
|---|---|---|---|---|---|
| II-2-371 | 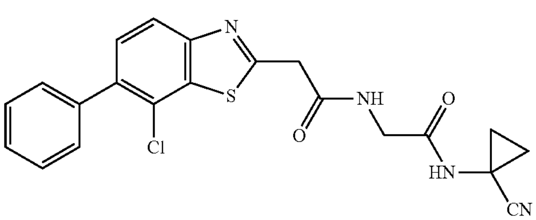 [SMILES: N#CC1(NC(=O)CNC(=O)Cc2nc3ccc(-c4ccccc4)c(Cl)c3s2)CC1] | (DMSO-d6) δ: 1.13 (dd, J = 8.4, 5.3 Hz, 2H), 1.49 (dd, J = 8.4, 5.3 Hz, 2H), 3.79 (d, J = 5.6 Hz, 2H), 4.21 (s, 2H), 7.44-7.56 (m, 6H), 8.00 (d, J = 8.1 Hz, 1H), 8.71 (t, J = 5.8 Hz, 1H), 8.92 (s, 1H). | | | |

TABLE 124-continued

| No. | Structure | NMR(δ) | retention time | Mass | method |
|---|---|---|---|---|---|
| II-2-372 | 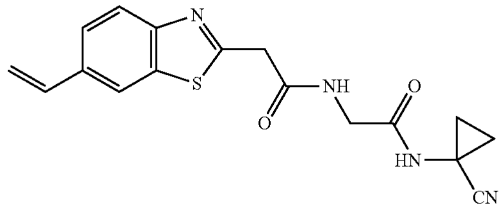 [SMILES: C=Cc1ccc2nc(CC(=O)NCC(=O)NC3(C#N)CC3)sc2c1] | (DMSO-d6) δ: 1.12 (dd, J = 8.4, 5.3 Hz, 2H), 1.49 (dd, J = 8.4, 5.3 Hz, 2H), 3.76 (d, J = 5.6 Hz, 2H), 4.12 (s, 2H), 5.33 (d, J = 10.6 Hz, 1H), 5.93 (d, J = 17.7 Hz, 1H), 6.85 (dd, J = 17.5, 10.9 Hz, 1H), 7.63 (dd, J = 8.6, 1.5 Hz, 1H), 7.90 (d, J = 8.6 Hz, 1H), 8.15 (s, 1H), 8.66 (t, J = 5.8 Hz, 1H), 8.90 (s, 1H). | | | |
| II-2-373 | 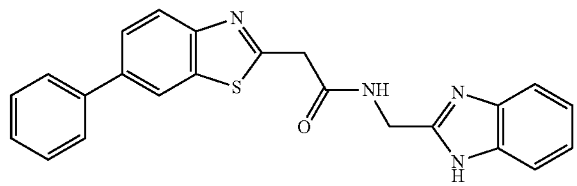 [SMILES: O=C(Cc1nc2ccc(-c3ccccc3)cc2s1)NCc1nc2ccccc2[nH]1] | (DMSO-d6) δ: 4.21 (s, 2H), 4.57 (d, J = 5.6 Hz, 2H), 7.12-7.18 (m, 2H), 7.37-7.57 (m, 5H), 7.74-7.80 (m, 3H), 8.02 (d, J = 8.6 Hz, 1H), 8.38 (d, J = 1.5 Hz, 1H), 9.05 (t, J = 5.6 Hz, 1H), 12.30 (s, 1H). | | | |
| II-2-374 | 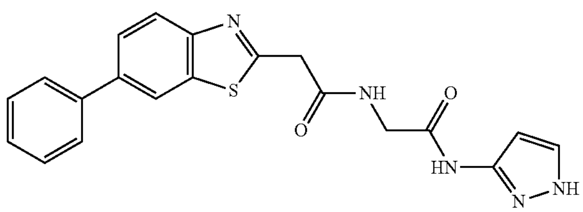 [SMILES: O=C(Cc1nc2ccc(-c3ccccc3)cc2s1)NCC(=O)Nc1cc[nH]n1] | (DMSO-d6) δ: 4.21 (s, 2H), 4.53 (d, J = 9.0 Hz, 2H), 5.72 (s, 2H), 5.96 (d, J = 9.0 Hz, 1H), 7.39 (m, 1H), 7.50 (t, J = 7.5 Hz, 2H), 7.74-7.81 (m, 3H), 8.0-8.04 (2H, m), 8.38 (s, 1H), 8.80 (m, 1H) | | | |
| II-2-375 | 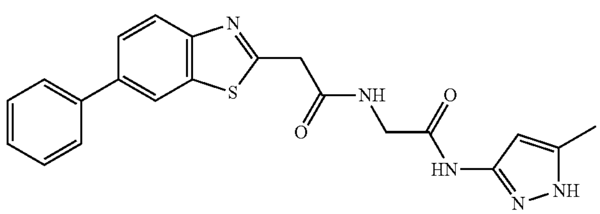 [SMILES: Cc1cc(NC(=O)CNC(=O)Cc2nc3ccc(-c4ccccc4)cc3s2)n[nH]1] | | 1.95 | 406 | C |

TABLE 125

| No. | Structure | NMR(δ) | retention time | Mass | method |
|---|---|---|---|---|---|
| II-2-376 | 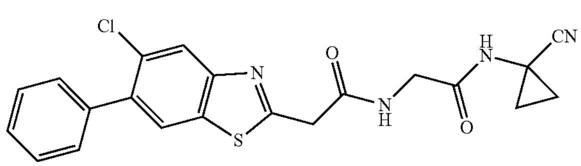 [SMILES: N#CC1(NC(=O)CNC(=O)Cc2nc3cc(Cl)c(-c4ccccc4)cc3s2)CC1] | (DMSO-d$_6$) δ: 1.12 (dd, J = 8.11, 5.58 Hz, 2H), 1.49 (dd, J = 8.11, 5.58 Hz, 2H), 3.77 (d, J = 5.58 Hz, 2H), 4.18 (s, 2H), 7.40-7.52 (m, 5H), 8.146 (s, 1H), 8.154 (s, 1H), 8.69 (t, J = 5.58 Hz, 1H), 8.91 (s, 1H). | | | |

TABLE 125-continued

| No. | Structure | NMR(δ) | retention time | Mass | method |
|---|---|---|---|---|---|
| II-2-377 | 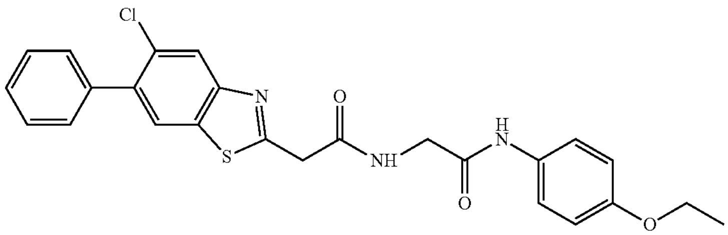 [SMILES: CCOc1ccc(NC(=O)CNC(=O)Cc2nc3cc(Cl)c(-c4ccccc4)cc3s2)cc1] | (DMSO-d$_6$) δ: 1.30 (t, J = 6.84 Hz, 3H), 3.93-4.01 (m, 4H), 4.22 (s, 2H), 6.84-6.89 (m, 2H), 7.42-7.52 (m, 7H), 8.15 (s, 2H), 8.74 (t, J = 5.58 Hz, 1H), 9.87 (s, 1H). | | | |
| II-2-378 | 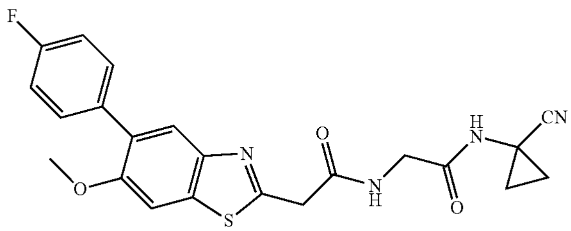 [SMILES: COc1cc2sc(CC(=O)NCC(=O)NC3(C#N)CC3)nc2cc1-c1ccc(F)cc1] | (DMSO-d$_6$) δ: 1.12 (dd, J = 8.11, 5.58 Hz, 2H), 1.49 (dd, J = 8.11, 5.58 Hz, 2H), 3.83 (s, 3H), 4.09 (s, 2H), 7.23-7.29 (m, 2H), 7.53-7.59 (m, 2H), 7.79 (s, 1H), 7.80 (s, 1H), 8.64 (t, J = 5.58 Hz, 1H), 8.90 (s, 1H). | | | |
| II-2-379 | 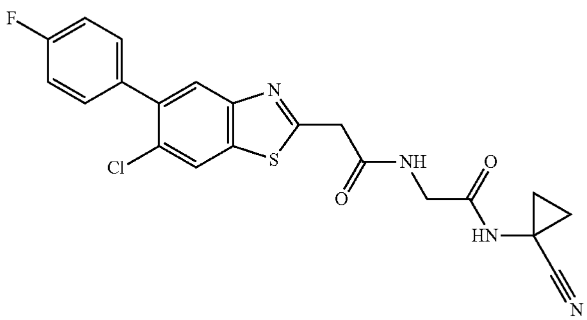 [SMILES: N#CC1(NC(=O)CNC(=O)Cc2nc3cc(-c4ccc(F)cc4)c(Cl)cc3s2)CC1] | (DMSO-d6) δ: 1.12 (dd, J = 8.1, 5.6 Hz, 2H), 1.49 (dd, J = 8.4, 5.3 Hz, 2H), 3.77 (d, J = 5.6 Hz, 2H), 4.17 (s, 2H), 7.30-7.34 (m, 2H), 7.51-7.56 (m, 2H), 7.93 (s, 1H), 8.36 (s, 1H), 8.68 (t, J = 5.8 Hz, 1H), 8.91 (s, 1H). | | | |
| II-2-380 | 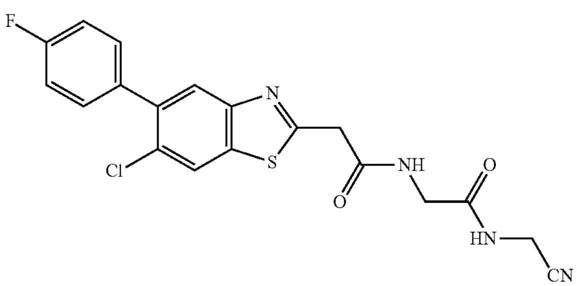 [SMILES: N#CCNC(=O)CNC(=O)Cc1nc2cc(-c3ccc(F)cc3)c(Cl)cc2s1] | (DMSO-d6) δ: 3.83 (d, J = 6.1 Hz, 2H), 4.15-4.18 (m, 4H), 7.32 (t, J = 8.9 Hz, 2H), 7.52-7.55 (m, 2H), 7.94 (s, 1H), 8.36 (s, 1H), 8.68 (t, J = 5.3 Hz, 1H), 8.74 (t, J = 5.8 Hz, 1H). | | | |

TABLE 126

| No. | Structure | NMR(δ) | retention time | Mass | method |
|---|---|---|---|---|---|
| II-2-381 | 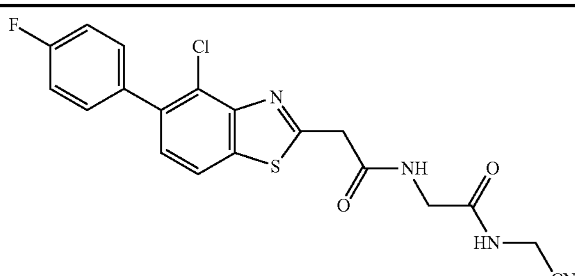 | (DMSO-d6) δ: 3.84 (d, J = 5.9 Hz, 2H), 4.16 (d, J = 5.7 Hz, 2H), 4.23 (s, 2H), 7.34 (m, 2H), 7.45 (d, J = 8.2 Hz, 1H), 7.51-7.57 (m, 2H), 8.11 (d, J = 8.2 Hz, 1H), 8.68 (t, J = 5.8 Hz, 1H), 8.77 (t, J = 5.7 Hz, 1H). | | | |

TABLE 126-continued
| No. | Structure | NMR(δ) | retention time | Mass | method |
|---|---|---|---|---|---|
| II-2-382 | 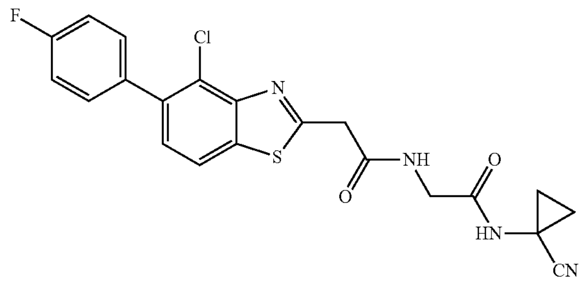 [SMILES: N#CC1(NC(=O)CNC(=O)Cc2nc3c(Cl)c(-c4ccc(F)cc4)ccc3s2)CC1] | (DMSO-d6) δ: 1.12 (dd, J = 8.2, 5.5 Hz, 2H), 1.49 (dd, J = 8.2, 5.4 Hz, 2H), 3.78 (d, J = 5.7 Hz, 2H), 4.22 (s, 2H), 7.34 (t, J = 9.0 Hz, 2H), 7.44 (d, J = 8.2 Hz, 1H), 7.51-7.59 (m, 2H), 8.11 (d, J = 8.2 Hz, 1H), 8.72 (t, J = 5.5 Hz, 1H), 8.91 (s, 1H). | | | |
| II-2-383 | 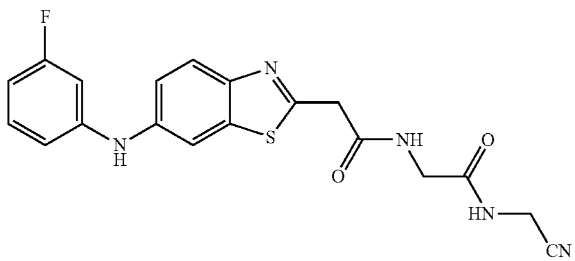 [SMILES: N#CCNC(=O)CNC(=O)Cc1nc2ccc(Nc3cccc(F)c3)cc2s1] | (DMSO-d6) δ: 3.82 (d, J = 5.7 Hz, 2H), 4.07 (s, 2H), 4.17 (d, J = 5.7 Hz, 2H), 6.61 (td, J = 8.7, 2.4 Hz, 1H), 6.81-6.94 (m, 2H), 7.18-7.30 (m, 2H), 7.77 (d, J = 2.2 Hz, 1H), 7.83 (d, J = 8.7 Hz, 1H), 8.60 (s, 1H), 8.63-8.72 (m, 2H). | | | |
| II-2-384 | 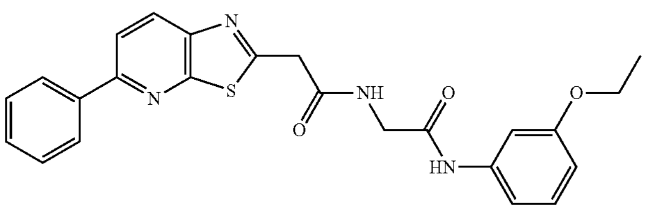 [SMILES: CCOc1cccc(NC(=O)CNC(=O)Cc2nc3ccc(-c4ccccc4)nc3s2)c1] | | 2.07 | 447.3 | C |
| II-2-385 | 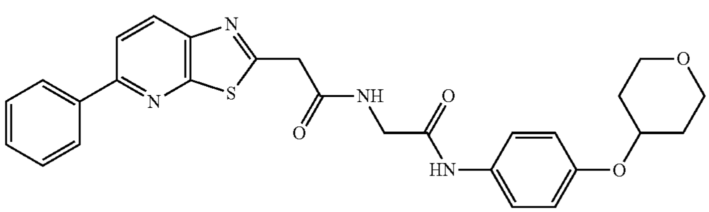 [SMILES: O=C(Cc1nc2ccc(-c3ccccc3)nc2s1)NCC(=O)Nc1ccc(OC2CCOCC2)cc1] | (DMSO-d6) δ: 1.52-1.58 (m, 2H), 1.92-1.99 (m, 2H), 3.46 (t, J = 10.8 Hz, 2H), 3.80-3.86 (m, 2H), 3.96 (d, J = 5.4 Hz, 2H), 4.23 (s, 2H), 4.48 (m, 1H), 6.93 (d, J = 9.3 Hz, 2H), 7.46-7.56 (m, 5H), 8.15 (t, J = 7.2 Hz, 3H), 8.39 (d, J = 8.4 Hz, 1H), 8.74 (m, 1H), 9.88 (s, 1H). | | | |
TABLE 127
| No. | Structure | NMR(δ) | retention time | Mass | method |
|---|---|---|---|---|---|
| II-2-386 | 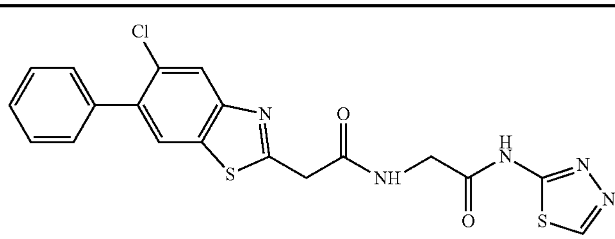 | (DMSO-d$_6$) δ: 4.15 (d, J = 5.58 Hz, 2H), 4.22 (s, 2H), 7.40-7.52 (m, 5H), 8.15 (s, 1H), 8.18 (s, 1H), 8.87 (t, J = 5.58 Hz, 1H), 9.18 (s, 1H), 12.68 (s, 1H). | | | |

TABLE 127-continued

| No. | Structure | NMR(δ) | retention time | Mass | method |
|---|---|---|---|---|---|
| II-2-387 | 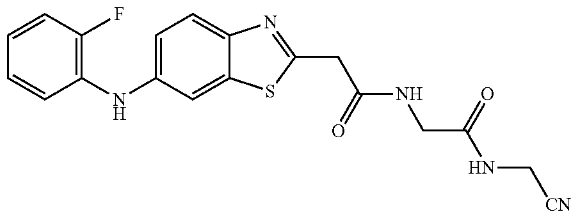 [SMILES: N#CCNC(=O)CNC(=O)Cc1nc2ccc(Nc3ccccc3F)cc2s1] | (DMSO-d6) δ: 3.81 (d, J = 6.1 Hz, 2H), 4.04 (s, 2H), 4.16 (d, J = 6.1 Hz, 2H), 6.96 (dd, J = 12.9, 6.3 Hz, 1H), 7.11 (t, J = 8.1 Hz, 1H), 7.16 (dd, J = 8.6, 2.5 Hz, 1H), 7.23 (dd, J = 11.7, 8.1 Hz, 1H), 7.33 (t, J = 8.1 Hz, 1H), 7.53 (d, J = 2.0 Hz, 1H), 7.78 (d, J = 8.6 Hz, 1H), 8.14 (s, 1H), 8.62-8.69 (m, 2H). | | | |
| II-2-388 | 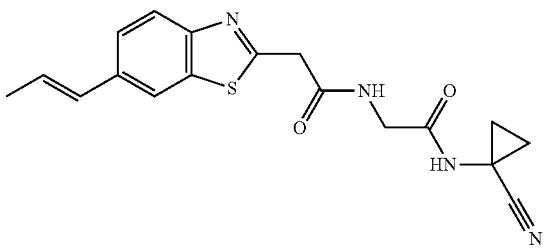 [SMILES: C/C=C/c1ccc2nc(CC(=O)NCC(=O)NC3(C#N)CC3)sc2c1] | (DMSO-d6) δ: 1.12 (dd, J = 8.4, 5.3 Hz, 2H), 1.49 (dd, J = 8.4, 5.3 Hz, 2H), 1.88 (d, J = 6.1 Hz, 3H), 3.76 (d, J = 5.6 Hz, 2H), 4.10 (s, 2H), 6.35-6.43 (m, 1H), 6.53 (d, J = 16.7 Hz, 1H), 7.53 (dd, J = 8.6, 1.5 Hz, 1H), 7.85 (d, J = 8.6 Hz, 1H), 8.02 (s, 1H), 8.64 (t, J = 5.6 Hz, 1H), 8.89 (s, 1H). | | | |
| II-2-389 | 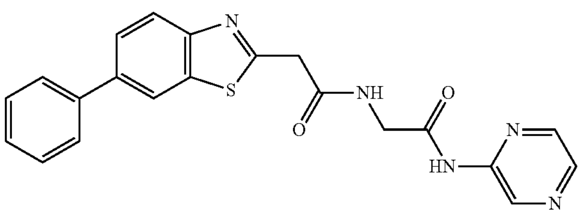 [SMILES: O=C(Cc1nc2ccc(-c3ccccc3)cc2s1)NCC(=O)Nc1cnccn1] | (DMSO-d6) δ: 4.00 (d, J = 5.7 Hz, 2H), 4.20 (s, 2H), 7.39-7.52 (m, 3H), 7.74-7.81 (m, 3H), 8.03 (d, J = 8.4 Hz, 1H), 8.37-8.42 (m, 3H), 8.78 (br-s, 1H), 9.31 (s, 1H), 10.88 (s, 1H) | | | |
| II-2-390 | 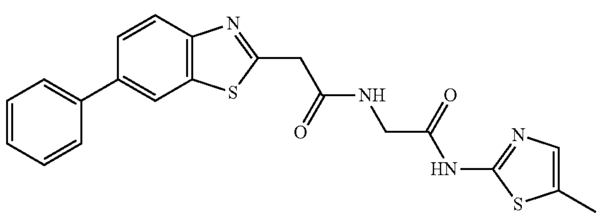 [SMILES: Cc1cnc(NC(=O)CNC(=O)Cc2nc3ccc(-c4ccccc4)cc3s2)s1] | (DMSO-d6) δ: 2.34 (s, 3H), 4.07 (d, J = 5.7 Hz, 2H), 4.19 (s, 2H), 7.15 (s, 1H), 7.38-7.52 (m, 3H), 7.74-7.81 (m, 3H), 8.04 (d, J = 8.7 Hz, 1H), 8.38 (s, 1H), 8.79 (m, 1H), 12.00 (s, 1H) | | | |

TABLE 128

| No. | Structure | NMR(δ) | retention time | Mass | method |
|---|---|---|---|---|---|
| II-2-391 | 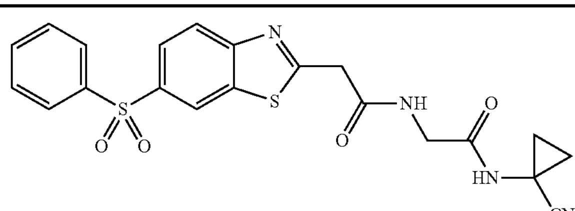 | (DMSO-d6) δ: 1.11 (dd, J = 8.4, 5.3 Hz, 2H), 1.48 (dd, J = 8.4, 5.3 Hz, 2H), 3.76 (d, J = 5.6 Hz, 2H), 4.21 (s, 2H), 7.59-7.72 (m, 3H), 7.96-8.01 (m, 3H), 8.12 (d, J = 8.6 Hz, 1H), 8.68 (t, J = 5.6 Hz, 1H), 8.86 (d, J = 1.5 Hz, 1H), 8.89 (s, 1H). | | | |

TABLE 128-continued

| No. | Structure | NMR(δ) | retention time | Mass | method |
|---|---|---|---|---|---|
| II-2-392 | 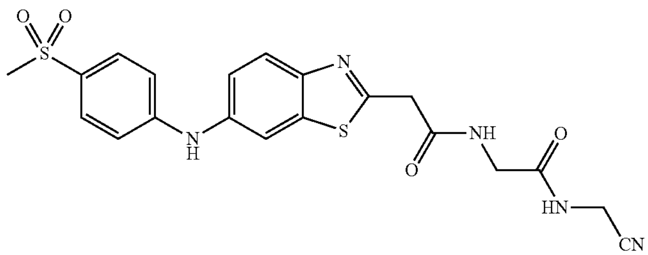 [SMILES: CS(=O)(=O)c1ccc(Nc2ccc3nc(CC(=O)NCC(=O)NCC#N)sc3c2)cc1] | (DMSO-d6) δ: 3.11 (s, 3H), 3.82 (d, J = 5.6 Hz, 2H), 4.09 (s, 2H), 4.16 (d, J = 5.6 Hz, 2H), 7.18 (d, J = 9.1 Hz, 2H), 7.29 (dd, J = 8.9, 2.3 Hz, 1H), 7.71 (d, J = 9.1 Hz, 2H), 7.87-7.92 (m, 2H), 8.69 (q, J = 6.1 Hz, 2H), 9.05 (s, 1H). | | | |
| II-2-393 | 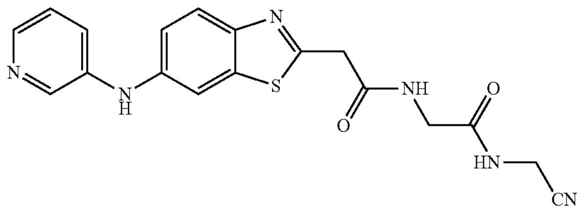 [SMILES: N#CCNC(=O)CNC(=O)Cc1nc2ccc(Nc3cccnc3)cc2s1] | (DMSO-d6) δ: 3.81 (d, J = 6.1 Hz, 2H), 4.06 (s, 2H), 4.16 (d, J = 5.6 Hz, 2H), 7.20 (dd, J = 8.9, 2.3 Hz, 1H), 7.26 (dd, J = 8.1, 4.6 Hz, 1H), 7.52-7.54 (m, 1H), 7.74 (d, J = 2.5 Hz, 1H), 7.82 (d, J = 8.6 Hz, 1H), 8.06 (d, J = 4.6 Hz, 1H), 8.39 (d, J = 3.0 Hz, 1H), 8.56 (s, 1H), 8.67 (t, J = 4.6 Hz, 2H). | | | |
| II-2-394 | 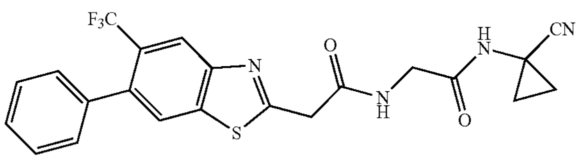 | 1H-NMR (DMSO-d6) δ: 1.12 (dd, J = 8.36, 5.32 Hz, 2H), 1.49 (dd, J = 8.36, 5.32 Hz, 2H), 3.78 (d, J = 5.58 Hz, 2H), 4.23 (s, 2H), 7.35-7.39 (m, 2H), 7.45-7.48 (m, 3H), 8.16 (s, 1H), 8.36 (s, 1H), 8.71 (t, J = 5.58 Hz, 1H), 8.92 (s, 1H). | | | |
| II-2-395 | 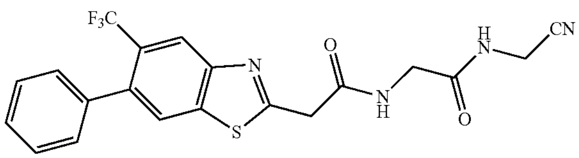 [SMILES: N#CCNC(=O)CNC(=O)Cc1nc2cc(C(F)(F)F)c(-c3ccccc3)cc2s1] | 1H-NMR (DMSO-d6) δ: 3.84 (d, J = 6.08 Hz, 2H), 4.16 (d, J = 5.58 Hz, 2H), 4.24 (s, 2H), 7.37-7.38 (m, 2H), 7.43-7.50 (m, 3H), 8.16 (s, 1H), 8.36 (s, 1H), 8.69 (t, J = 5.58 Hz, 1H), 8.77 (t, J = 5.83 Hz, 1H). | | | |

TEST EXAMPLE 1

Evaluation Method of Human Endothelial Lipase (EL) Inhibitory Activity Using Human High-Density Lipoprotein (HDL)

After the present compound dissolved in DMSO was added to become 0.5% DMSO to the reaction buffer consisting of 20 mM tris hydrochloric acid (pH7.4), bovine serum albumin (0.5%), calcium chloride (4 mM), sodium chloride (150 mM) and human HDL (2 mg/ml), the EL enzyme was added (total volume was 20 μl).

After 4-hour reaction at 37° C., non-esterified fatty acid (NEFA) generated from HDL by EL was measured with a commercially available assay kit and the amount of NEFA was used as an index of enzyme activity. Considering the enzyme activity without the inhibitor as a control value, the inhibition rate of each concentration of the present compound was calculated, and 50% inhibitory concentration (IC50 value) was calculated from an inhibition curve.

The result of Test Example 1 is shown below.
Compound (II-1-1): IC50=0.23 μM
Compound (II-1-11): IC50=0.56 μM
Compound (II-1-17): IC50=1.3 μM
Compound (II-1-190): IC50=2.1 μM
Compound (II-1-202): IC50=0.29 μM
Compound (II-1-246): IC50=0.28 μM
Compound (II-2-1): IC50=0.11 μM
Compound (II-2-291): IC50=0.056 μM
Compound (II-2-211): IC50=0.032 μM
Compound (II-2-67): IC50=0.029 μM
Compound (II-2-131): IC50=0.092 μM
Compound (II-2-144): IC50=0.029 μM The present compound selectively inhibits endothelial lipase as shown in Test Example 1, and has high selectivity for hepatic lipase (HL) and lipoprotein lipase (LPL). Selectivity was analyzed by the following tests.

TEST EXAMPLE 2

Evaluation Method of Human Hepatic Lipase (HL) Inhibitory Activity Using Human Very Low-Density Lipoprotein (VLDL)

After an inhibitor dissolved in DMSO was added to become 0.5% DMSO to the reaction buffer consisting of 20 mM tris hydrochloric acid (pH7.4), bovine serum albumin (0.5%), calcium chloride (4 mM), sodium chloride (150 mM) and human VLDL (0.5 mg/ml), the HL enzyme was added (total volume was 20 μl).

After 4-hour reaction at 37° C., non-esterified fatty acid (NEFA) generated from VLDL by HL was measured with a commercially available assay kit and the amount of NEFA was used as an index of enzyme activity. Considering the enzyme activity without the inhibitor as a control value, the inhibition rate of each concentration of an inhibitor was calculated, and 50% inhibitory concentration (IC50 value) was calculated from an inhibition curve.

TEST EXAMPLE 3

Evaluation Method of Human Lipoprotein Lipase (LPL) Inhibitory Activity Using Human Very Low-Density Lipoprotein (VLDL)

After an inhibitor dissolved in DMSO was added to become 0.5% DMSO to the reaction buffer consisting of 20 mM tris hydrochloric acid (pH7.4), bovine serum albumin (0.5%), calcium chloride (4 mM), sodium chloride (150 mM) and human VLDL (0.5 mg/ml), the LPL enzyme was added (total volume was 20 μl).

After 4-hour reaction at 37° C., non-esterified fatty acid (NEFA) generated from HDL by LPL was measured with a commercially available assay kit and the amount of NEFA was used as an index of enzyme activity. Considering the enzyme activity without the inhibitor as a control value, the inhibition rate of each concentration of an inhibitor was calculated, and 50% inhibitory concentration (IC50 value) was calculated from an inhibition curve.

The results of Test Example 2 and 3 indicated that the present compound inhibited the endothelial lipase selectively and had high selectivity for hepatic Lipase (HL) and lipoprotein lipase (LPL).

Serum HDL cholesterol elevating effect can be examined as follows.

Pharmacological Test on HDL Elevating Effect

The C57BL/6J mice at 8-25-weeks old were divided into 5-9 animals per group and administered test compound (20-200 mg/kg/day) orally. To the control group, 0.5% methyl cellulose solution (10 mL/kg) of the vehicle was administered orally. The blood was collected from tail vein before and 24-hour after the administration of compound, and serum HDL cholesterol concentration was measured with [koresutesuto] N HDL (Daiiti chemical Ltd.). The animals were separated into groups so that the mean value of weight and serum HDL cholesterol level become almost equal between each examination groups. The efficacy of the test compound was shown as the rate of changes compared to the values before administration (the HDL cholesterol elevating rate; % Initial), and significant differences against the values of control groups were evaluated.

Usefulness for medicaments can be analyzed by the following examinations etc.

CYP3A4 Fluorescent MBI Test

The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethyl-chmarin (HFC) emitting fluorescent light.

The reaction conditions were as follows: substrate, 5.6 μmol/L 7-BFC; pre-reaction time, 0 or 30 minutes; reaction time, 15 minutes; reaction temperature, 25° C. (room temperature); CYP3A4 content (enzyme expressed in *Escherichia coli*), at pre-reaction 62.5 μmol/mL, at reaction 6.25 μmol/mL (at 10-fold dilution); test drug concentration, 0.625, 1.25, 2.5, 5, 10, 20 μmol/L (six points).

An enzyme in a K-Pi buffer (pH 7.4) and a test drug solution were added as a pre-reaction solution to a 96-well plate at the composition of the pre-reaction, a part of it was transferred to another 96-well plate so that it was 1/10 diluted with a substrate and a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. When a difference between $IC_{50}$ values is 5 μM or more, this was defined as (+) and, when the difference is 3 μM or less, this was defined as (−).

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 μmol/L ethoxyresorufin (CYP1A2), 100 μmol/L tolbutamide (CYP2C9), 50 μmol/L S-mephenitoin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 μmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2C9 metabolite), mephenyloin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate.

Solubility Test

The solubility of a compound was determined under a condition in which 1% DMSO was added. 10 mM compound solution was prepared using DMSO, and then 6 μL of the compound solution was added to 594 μL of artificial intestinal juice in pH 6.8 (to 250 mL of 0.2 mol/L potassium dihydrogen phosphate reagent solution was added 118 mL of 0.2 mol/L NaOH reagent solution and water to provide a final volume of 1000 mL). After standing at 25 degrees Celsius for 16 hours, the mixed solution was filtrated with suction. The filtrate was diluted twice with methanol/water (1/1), and then a concentration in the filtration was measured with HPLC or LC/MS/MS by the absolute calibration method.

Metabolism Stability Test

Using commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%.

BA Test

Materials and methods for studies on oral absorption
(1) Animals: SD Rats
(2) Animal Husbandry:
Rats had free access to solid food and sterilized bottled tap water.
(3) Setting of Dose and Group Compositions:
orally or intravenously administered at a predetermined dose; Group compositions were as shown below (Dose depends on the compound)
Oral: 1 to 30 mg/kg (n=2 to 3)
Intravenous: 0.5 to 10 mg/kg (n=2 to 3)
(4) Preparation for Dosing Formulation:
for oral administration, in a solution or a suspension state; for intravenous administration, in a solubilized state
(5) Dosing Procedure:
In oral administration study, the test suspension was dosed to the stomach of rats by using a gavage tube In intravenous administration study, the test solution was dosed to rats via tail vein using a syringe with a needle.
(6) Evaluation Items:
Blood was collected at each time point, and plasma concentration of the test substance was determined by a LC/MS/MS system.
(7) Data Analysis:
Regarding the transition of the plasma concentration, area under the plasma concentration-time curve (AUC) was calculated by means of WinNonlin® program, respectively. Bioavailability (BA) was calculated by using AUC values in oral administration study and in intravenous administration study.

FORMULATION EXAMPLE 1

A hard gelatin capsule is prepared by using the following ingredients:

|  | Dose (mg/capsule) |
| --- | --- |
| Active ingredient | 250 |
| Starch (dry) | 200 |
| Magnesium stearate | 10 |
| Total | 460 mg |

FORMULATION EXAMPLE 2

A tablet is prepared by using the following ingredients:

|  | Dose (mg/tablet) |
| --- | --- |
| Active ingredient | 250 |
| Cellulose (microcrystal) | 400 |
| Silicon dioxide (fumed) | 10 |
| Stearic acid | 5 |
| Total | 665 mg |

The ingredients are mixed, and compressed to form tables each weighing 665 mg.

FORMULATION EXAMPLE 3

An aerosol solution containing the following ingredients is prepared:

|  | Weight |
| --- | --- |
| Active ingredient | 0.25 |
| Ethanol | 25.75 |
| Propellant 22 (chlorodifluoromethane) | 74.00 |
| Total | 100.00 |

The active ingredient and ethanol are mixed, and the mixture is added to part of propellant 22, cooled to −30° C., and transferred to a packing machine. Then, a necessary amount is supplied to a stainless steel container, and diluted with the remaining propellant. A bubble unit is attached to the container.

FORMULATION EXAMPLE 4

A tablet containing 60 mg of the active ingredient is prepared in the following manner:

| Active ingredient | 60 mg |
| --- | --- |
| Starch | 45 mg |
| Microcrystalline cellulose | 35 mg |
| Polyvinylpyrrolidone (10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. An aqueous solution containing polyvinylpyrrolidone is mixed with obtained powder and then the mixture is passed through a No. 14 mesh U.S. sieve. Granules obtained in this manner are dried at 50° C. and passed through a No. 18 mesh U.S.

sieve. The sodium carboxymethyl starch, magnesium stearate and talc that are passed through a No. 60 mesh U.S. sieve in advance, are added to the granules, mixed, and then compressed by a tableting machine to obtain tablets each weighing 150 mg.

FORMULATION EXAMPLE 5

A capsule containing 80 mg of the active ingredient is prepared in the following manner:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, starch, cellulose, and magnesium stearate are mixed, and passed through a No. 45 mesh U.S. sieve, and filled into a hard gelatin capsule in 200 mg quantities.

FORMULATION EXAMPLE 6

Suppository containing 225 mg of the active ingredient is prepared in the following manner:

| | |
|---|---|
| Active ingredient | 225 mg |
| Saturated fatty acid glyceride | 2000 mg |
| Total | 2225 mg |

The active ingredient is passed through a No. 60 mesh U.S. sieve, and suspended in saturated fatty acid glyceride that is melted by heating least necessarily in advance. Then, the resultant mixture is put into an apparent 2 g mold, and cooled.

FORMULATION EXAMPLE 7

A suspension containing 50 mg of the active ingredient is prepared in the following manner:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Pigment | q.v. |
| Purified water to total | 5 mL |

The active ingredient is passed through a No. 45 mesh U.S. sieve, and mixed with sodium carboxymethyl cellulose and syrup to form a smooth paste. The benzoic acid solution and the flavor diluted with part of water are added, and stirred. Then a sufficient amount of water is added to achieve required volume.

FORMULATION EXAMPLE 8

An intravenous formulation is prepared in the following manner:

| | |
|---|---|
| Active ingredient | 100 mg |
| Saturated fatty acid glyceride | 1000 mL |

The solution of the above ingredients is intravenously administered to a patient usually at a speed of 1 mL per minute.

[Industrial Applicability]

As is apparent from the above test examples, the compounds according to the present invention show inhibitory activity on endothelial lipase. Therefore, the compounds according to the present invention are very useful as therapeutic agents for lipid metabolism abnormality, hyperlipidemia or arteriosclerosis.

The invention claimed is:

1. A compound represented by formula (II):

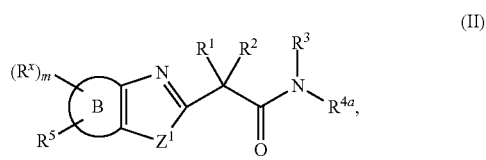

its pharmaceutically acceptable salt,
wherein
$Z^1$ is —S—,
Ring B is benzene,
$R^1$ and $R^2$ are each independently hydrogen, halogen, cyano, nitro, carboxy, or substituted or unsubstituted alkyl,
$R^3$ is hydrogen,
$R^{4a}$ is a group represented by the formula: —$(CR^7R^8)$n—C(=O)—$R^9$, wherein $R^7$ and $R^8$ are each independently hydrogen, halogen, hydroxy, carboxy or substituted or unsubstituted alkyl, n is an integer of 1 to 3, $R^9$ is —$NR^{11}R^{12}$, $R^{11}$ and $R^{12}$ are each independently hydrogen, substituted or unsubstituted alkyl, substituted or unsubstituted alkyloxy, substituted or unsubstituted aryloxy, substituted or unsubstituted heteroaryloxy, substituted or unsubstituted alkylsulfonyl, substituted or unsubstituted aryl, substituted or unsubstituted heteroaryl, substituted or unsubstituted cycloalkyl, substituted or unsubstituted cycloalkenyl or, substituted or unsubstituted heterocycle,
$R^5$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl, substituted or unsubstituted acyl, substituted or unsubstituted carbamoyl, or substituted or unsubstituted amino,
$R^x$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl, substituted or unsubstituted acyl, substituted or unsubstituted carbamoyl or, substituted or unsubstituted amino, m is an integer of 0 to 3.

2. The compound of claim 1, its pharmaceutically acceptable salt, wherein the compound represented by formula (II) is a compound represented by formula (III):

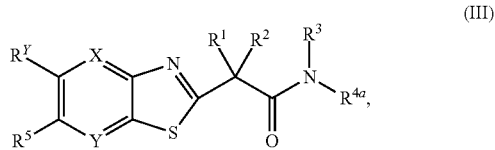

(III)

wherein X and Y are each —CH=, and $R^Y$ is hydrogen or $R^X$.

3. The compound of claim 1, its pharmaceutically acceptable salt, wherein the compound represented by formula (II) is a compound represented by formula (IV):

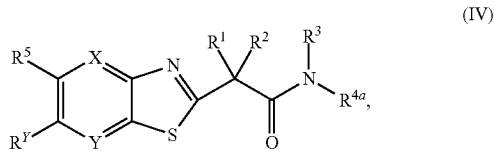

(IV)

wherein X and Y are each —CH=, and $R^Y$ is hydrogen or $R^X$.

4. The compound of claim 1, its pharmaceutically acceptable salt, wherein $R^1$, $R^2$, $R^7$, and $R^8$ are hydrogen.

5. The compound of claim 1, its pharmaceutically acceptable salt, wherein $R^{12}$ is substituted or unsubstituted alkyl.

6. The compound of claim 1, its pharmaceutically acceptable salt, wherein $R^{11}$ is hydrogen.

7. The compound of claim 1, its pharmaceutically acceptable salt, wherein n is 1.

8. The compound of claim 1, its pharmaceutically acceptable salt, wherein $R^7$ and $R^8$ are hydrogen.

9. The compound of claim 1, its pharmaceutically acceptable salt, wherein $R^1$ and $R^2$ are hydrogen.

10. The compound of claim 1, its pharmaceutically acceptable salt, wherein $R^5$ is substituted or unsubstituted aryl, substituted or unsubstituted heteroaryl, substituted or unsubstituted cycloalkyl, substituted or unsubstituted cycloalkenyl, substituted or unsubstituted heterocycle, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocycleoxy, substituted or unsubstituted arylthio, substituted or unsubstituted heteroarylthio, substituted or unsubstituted cycloalkylthio, substituted or unsubstituted cycloalkenylthio, substituted or unsubstituted heterocyclethio, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclesulfonyl, or substituted or unsubstituted amino.

11. The compound of claim 1, its pharmaceutically acceptable salt, wherein $R^5$ is substituted or unsubstituted aryl, substituted or unsubstituted heteroaryl, substituted or unsubstituted aryloxy, substituted or unsubstituted heteroaryloxy, substituted or unsubstituted arylthio, substituted or unsubstituted heteroarylthio, substituted or unsubstituted arylsulfonyl, substituted or unsubstituted heteroarylsulfonyl, or substituted or unsubstituted amino.

12. The compound of claim 1, its pharmaceutically acceptable salt, wherein $R^5$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocycle, substituted or unsubstituted alkyloxy, substituted or unsubstituted aryloxy, substituted or unsubstituted arylsulfonyl, or substituted or unsubstituted acyl.

13. A pharmaceutical composition, comprising the compound of claim 1 or its pharmaceutically acceptable salt.

14. The compound of claim 1, its pharmaceutically acceptable salt, wherein $R^{12}$ is substituted or unsubstituted cycloalkyl.

* * * * *

UNITED STATES PATENT AND TRADEMARK OFFICE
CERTIFICATE OF CORRECTION

PATENT NO. : 8,957,219 B2
APPLICATION NO. : 13/124788
DATED : February 17, 2015
INVENTOR(S) : Koji Masuda et al.

It is certified that error appears in the above-identified patent and that said Letters Patent is hereby corrected as shown below:

In the Claims

Column 332, Line 22, "its pharmaceutically acceptable salt" should read -- or its pharmaceutically acceptable salt --.

Column 333, Lines 24-25, "its pharmaceutically acceptable salt" should read -- or its pharmaceutically acceptable salt --.

Column 333, Lines 38-39, "its pharmaceutically acceptable salt" should read -- or its pharmaceutically acceptable salt --.

Column 334, Lines 1-2, "its pharmaceutically acceptable salt" should read -- or its pharmaceutically acceptable salt --.

Column 334, Lines 3-4, "its pharmaceutically acceptable salt" should read -- or its pharmaceutically acceptable salt --.

Column 334, Lines 5-6 "its pharmaceutically acceptable salt" should read -- or its pharmaceutically acceptable salt --.

Column 334, Lines 7-8, "its pharmaceutically acceptable salt" should read -- or its pharmaceutically acceptable salt --.

Column 334, Lines 9-10, "its pharmaceutically acceptable salt" should read -- or its pharmaceutically acceptable salt --.

Column 334, Lines 11-12, "its pharmaceutically acceptable salt" should read -- or its pharmaceutically acceptable salt --.

Signed and Sealed this
Fifteenth Day of September, 2015

Michelle K. Lee
*Director of the United States Patent and Trademark Office*

Column 334, Lines 13-14, "its pharmaceutically acceptable salt" should read -- or its pharmaceutically acceptable salt --.

Column 334, Lines 29-30, "its pharmaceutically acceptable salt" should read -- or its pharmaceutically acceptable salt --.

Column 334, Lines 37-38, "its pharmaceutically acceptable salt" should read -- or its pharmaceutically acceptable salt --.

Column 334, Lines 48-49, "its pharmaceutically acceptable salt" should read -- or its pharmaceutically acceptable salt --.